(12) United States Patent
Kahne et al.

(10) Patent No.: US 11,261,201 B2
(45) Date of Patent: Mar. 1, 2022

(54) TRNA SYNTHETASE INHIBITORS

(71) Applicant: President and Fellows of Harvard College, Cambridge, MA (US)

(72) Inventors: Daniel E. Kahne, Brookline, MA (US); Vadim Baidin, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/961,516

(22) PCT Filed: Jan. 11, 2019

(86) PCT No.: PCT/US2019/013305
§ 371 (c)(1),
(2) Date: Jul. 10, 2020

(87) PCT Pub. No.: WO2019/140265
PCT Pub. Date: Jul. 18, 2019

(65) Prior Publication Data
US 2021/0053997 A1    Feb. 25, 2021

Related U.S. Application Data

(60) Provisional application No. 62/616,979, filed on Jan. 12, 2018.

(51) Int. Cl.
*C07F 5/02*    (2006.01)
*A61P 31/04*    (2006.01)
(Continued)

(52) U.S. Cl.
CPC .............. *C07F 5/027* (2013.01); *A61P 31/04* (2018.01); *C07C 211/27* (2013.01); *C07C 211/40* (2013.01); *C07C 215/28* (2013.01); *C07D 209/04* (2013.01); *C07D 213/38* (2013.01); *C07D 213/643* (2013.01); *C07D 215/06* (2013.01); *C07D 215/12* (2013.01); *C07D 221/04* (2013.01); *C07D 221/20* (2013.01); *C07D 231/12* (2013.01); *C07D 231/56* (2013.01); *C07D 239/26* (2013.01); *C07D 239/34* (2013.01); *C07D 261/08* (2013.01); *C07D 267/10* (2013.01); *C07D 295/13* (2013.01); *C07D 307/14* (2013.01); *C07D 307/79* (2013.01); *C07D 307/87* (2013.01); *C07D 309/04* (2013.01); *C07D 311/74* (2013.01); *C07D 317/58* (2013.01); *C07D 319/08* (2013.01); *C07D 327/06* (2013.01); *C07D 471/04* (2013.01); *C07D 471/08* (2013.01); *C07D 493/08* (2013.01); *C07D 495/04* (2013.01); *C07D 498/08* (2013.01)

(58) Field of Classification Search
CPC ... C07C 211/27; C07C 211/40; C07C 215/28; C07C 2603/28; C07C 2601/02; C07C 2601/14; C07C 2601/16; C07C 2601/08; C07C 2603/74; C07C 2602/38; C07C 311/55; C07C 317/18; C07C 317/28; C07C 323/12; C07C 233/36; C07C 235/14; C07C 235/06; C07C 237/06; C07C 237/20; C07C 275/40; C07C 275/50; C07C 311/16; C07C 311/35; C07C 229/46; C07C 229/38; C07C 229/34; C07C 229/36; C07C 259/06; C07C 219/28; C07C 215/42; C07C 215/18; C07C 215/50; C07C 215/20; C07C 217/58; C07C 217/48; C07C 217/76; C07C 225/12; C07C 211/35; C07C 211/38; C07C 211/49; C07D 209/04; C07D 213/38; C07D 213/643; C07D 215/06; C07D 215/12; C07D 221/04; C07D 221/20; C07D 231/12; C07D 231/56; C07D 239/26; C07D 239/34; C07D 261/08; C07D 267/10; C07D 295/13; C07D 307/14; C07D 307/79; C07D 307/87; C07D 309/04; C07D 311/74; C07D 317/58; C07D 319/08; C07D 327/06; C07D 471/04; C07D 471/08; C07D 493/08; C07D 495/04; C07D 498/08; C07D 333/20; C07D 498/04; C07D 213/64; C07D 491/08; C07D 209/08; C07D 319/20; C07D 311/58; C07D 319/16; C07F 5/025; C07F 5/027; A61P 31/04
See application file for complete search history.

(56) References Cited

U.S. PATENT DOCUMENTS 3,310,469 A    3/1967    Marvin et al.
2004/0224981 A1    11/2004    Janjic et al.
(Continued)

FOREIGN PATENT DOCUMENTS

WO    WO 2007/017267    *    2/2007
WO    WO-2013/086131 A1    6/2013
(Continued)

OTHER PUBLICATIONS

"Pubchem CID 55193860" Create Date: Jan. 24, 2012, Date Accessed: May 13, 2019; p. 3.
(Continued)

*Primary Examiner* — Alicia L Otton
(74) *Attorney, Agent, or Firm* — Foley Hoag LLP

(57) ABSTRACT

Disclosed herein are secondary amine compounds that inhibit tRNA synthetase. The compounds of the invention are useful in inhibiting tRNA synthetase in Gram-negative bacteria and are useful in killing Gram-negative bacteria. The secondary amine compounds of the invention are also useful in the treatment of tuberculosis.

27 Claims, 1 Drawing Sheet

(51) Int. Cl.

| | | |
|---|---|---|
| *C07C 211/27* | (2006.01) | |
| *C07C 211/40* | (2006.01) | |
| *C07C 215/28* | (2006.01) | |
| *C07D 209/04* | (2006.01) | |
| *C07D 213/38* | (2006.01) | |
| *C07D 213/643* | (2006.01) | |
| *C07D 215/06* | (2006.01) | |
| *C07D 215/12* | (2006.01) | |
| *C07D 221/04* | (2006.01) | |
| *C07D 221/20* | (2006.01) | |
| *C07D 231/12* | (2006.01) | |
| *C07D 231/56* | (2006.01) | |
| *C07D 239/26* | (2006.01) | |
| *C07D 239/34* | (2006.01) | |
| *C07D 261/08* | (2006.01) | |
| *C07D 267/10* | (2006.01) | |
| *C07D 295/13* | (2006.01) | |
| *C07D 307/14* | (2006.01) | |
| *C07D 307/79* | (2006.01) | |
| *C07D 307/87* | (2006.01) | |
| *C07D 309/04* | (2006.01) | |
| *C07D 311/74* | (2006.01) | |
| *C07D 317/58* | (2006.01) | |
| *C07D 319/08* | (2006.01) | |
| *C07D 327/06* | (2006.01) | |
| *C07D 471/04* | (2006.01) | |
| *C07D 471/08* | (2006.01) | |
| *C07D 493/08* | (2006.01) | |
| *C07D 495/04* | (2006.01) | |
| *C07D 498/08* | (2006.01) | |

(56) References Cited

U.S. PATENT DOCUMENTS

| | | |
|---|---|---|
| 2006/0287317 A1 | 12/2006 | Smith et al. |
| 2012/0058133 A1 | 3/2012 | Whitman et al. |
| 2021/0053997 A1 | 2/2021 | Kahne et al. |

FOREIGN PATENT DOCUMENTS

| | | |
|---|---|---|
| WO | WO-2017/018803 A1 | 2/2017 |
| WO | WO-2019/140254 A1 | 7/2019 |
| WO | WO-2019/140265 A1 | 7/2019 |

OTHER PUBLICATIONS

International Search Report and Written Opinion for International Application No. PCT/US2019/13305 dated Jun. 10, 2019.
Chinnapattu et al., "Synthesis and biological evaluation of adamantane-based aminophenols as a novel class of antiplasmodial agents," Bioorganic & medicinal chemistry letters, 25(4):952-955 (2015).
International Search Report and Written Opinion for International Application No. PCT/US2019/013290 dated May 14, 2019.
Simmons et al., "Nickel-Catalyzed Reduction of Secondary and Tertiary Amides," Org. Lett. 19(7):1910-1913 (2017).

* cited by examiner

Resistant colonies(frequency) and averages from 8 independent populations of $10^8$ cells each after 36 h
| 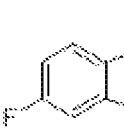 | 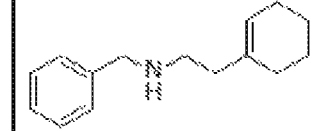 | Both (adjusted for dose equivalence) |
|---|---|---|
| 64 ($6 \times 10^{-7}$) | 2 ($2 \times 10^{-8}$) | 0 |
| 50 ($5 \times 10^{-7}$) | 2 ($2 \times 10^{-8}$) | 0 |
| 77 ($8 \times 10^{-7}$) | 3 ($3 \times 10^{-8}$) | 0 |
| 56 ($6 \times 10^{-7}$) | 3 ($3 \times 10^{-8}$) | 0 |
| 55 ($6 \times 10^{-7}$) | 4 ($4 \times 10^{-8}$) | 0 |
| 53 ($5 \times 10^{-7}$) | 3 ($3 \times 10^{-8}$) | 0 |
| 54 ($5 \times 10^{-7}$) | 4 ($4 \times 10^{-8}$) | 0 |
| 80 ($8 \times 10^{-7}$) | 21 ($2 \times 10^{-7}$) | 0 |
| 61 ($6 \times 10^{-7}$) | 5 ($5 \times 10^{-8}$) | 0 |

TRNA SYNTHETASE INHIBITORS

CROSS-REFERENCE TO RELATED APPLICATION

This application is the U.S. National Stage of International Application No. PCT/US2019/13305, filed Jan. 11, 2019, which designates the U.S, published in English, and claims the benefit of U.S. Provisional Application No. 62/616,979, filed Jan. 12, 2018. The entire teachings of the above applications are incorporated herein by reference.

GOVERNMENT SUPPORT

This invention was made with government support under U19 AI109764 from the National Institute of Allergy and Infectious Disease. The government has certain rights in the invention.

BACKGROUND OF THE INVENTION

Gram-negative bacteria are intrinsically resistant to many small molecules owing to the presence of an outer membrane, which acts as a permeability barrier. tRNA synthetases are involved in protein biosynthesis so that inhibition thereof may be expected to lead to a cessation of cell growth. Thus, for instance, the compound mupirocin, produced by the organism *Pseudomonas fluorescens*, is an antibacterial agent and is used as the active ingredient in the product Bactroban, marketed by GlaxoSmithKline. However, mupirocin is only effective against Gram-positive, but not Gram-negative bacteria. Mupirocin has been shown to be an inhibitor of the isoleucyl tRNA synthetase. Each tRNA synthetase represents a separate target for drug discovery. tRNA synthetase inhibitors which are selective for bacterial cells over mammalian cells are of considerable therapeutic interest as they have the potential to be used as antibacterial agents. Thus, there remains a need to develop compounds having inhibitory activity toward tRNA synthetase in Gram-negative bacteria.

SUMMARY OF THE INVENTION

In certain aspects, the invention provides a compound of formula (I):

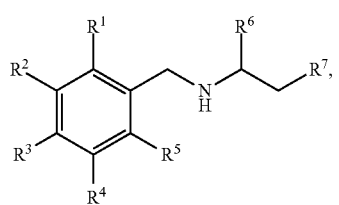

or a pharmaceutically acceptable salt thereof;
wherein:
each of $R^1$, $R^2$, $R^3$, $R^4$, and $R^5$ is independently selected from H, OH, —$NH_2$, halide, sulfonamido, $(C_1-C_6)$alkylsulfonyl, —OC(O)(($C_1-C_8$)alkyl), —C(O)O(($C_1-C_5$)alkyl), —C(O)OH, optionally substituted —NHC(O)(aryl), —C(O)$NH_2$, —B(OH)$_2$, tri(($C_1-C_8$)alkyl)silyl, optionally substituted ($C_1-C_8$)alkyl, optionally substituted ($C_1-C_8$)alkoxy, optionally substituted ($C_1-C_8$)aminoalkyl, optionally substituted ($C_1-C_8$)hydroxy-alkyl, optionally substituted ($C_1-C_8$)haloalkyl, optionally substituted ($C_1-C_8$)haloalkoxy, optionally substituted aryl, optionally substituted heteroaryl, optionally substituted aryloxy, optionally substituted arylalkoxy, optionally substituted heteroaryloxy, optionally substituted heteroarylalkoxy, optionally substituted ($C_3-C_{10}$)cycloalkyl, optionally substituted ($C_3-C_{10}$)cycloalkoxy, optionally substituted ($C_2-C_9$)heterocycloalkyl, optionally substituted ($C_2-C_9$)heterocycloalkoxy, ($H_3CSO_2$)($C_1-C_8$)alkylene, optionally substituted ($R^b_2NSO_2$)($C_1-C_8$)alkylene, optionally substituted di(($C_1-C_8$)alkyl)amino, —NH—$CH_2$—$R^8$, —O—$CH_2$—$R^8$, and —O—$CH_2CH_2$—O—$R^9$;

or $R^1$ and $R^2$, $R^2$ and $R^3$, $R^3$ and $R^4$, or $R^4$ and $R^5$, taken together with the intervening atoms, form an optionally substituted aryl, heteroaryl, cycloalkyl, or heterocycloalkyl group;

$R^6$ is H or ($C_1-C_6$)alkyl;

$R^7$ is optionally substituted ($C_3-C_{10}$)cycloalkyl or ($C_3-C_{10}$)cycloalkenyl;

$R^8$ is selected from —C(O)(($C_2-C_9$)heterocycloalkyl), —C(O)NH(($C_1-C_8$)alkyl), —C(O)NH(aryl($C_1-C_8$)alkyl), —C(O)NH(($C_3-C_8$)cycloalkyl), —C(O)NH(($C_3-C_8$)cycloalkyl($C_1-C_8$)alkyl), —C(O)N($CH_3$)(($C_3-C_8$) cycloalkyl), —C(O)N($CH_3$)(aryl($C_1-C_8$)alkyl), —C(O)NHC(O)NH(($C_3-C_8$)cycloalkyl), —C(O)NHC(O)NH(($C_1-C_8$)alkyl), —C(O)NHC(O)$NH_2$, optionally substituted heteroaryl wherein the heteroaryl is not 4-pyridinyl, benzimidazole or thiazole, optionally substituted aryloxy($C_1-C_8$)alkyl, ($C_3-C_8$)cycloalkyl, ($C_2-C_9$)heterocycloalkyl, ($C_2-C_9$)heterocycloalkyl($C_2-C_8$)alkyl, heteroaryl ($C_1-C_8$)alkyl, ($C_2-C_8$)alkoxy, ($C_3-C_8$)hydroxyalkyl, ($C_1-C_8$)alkoxy($C_1-C_8$)alkyl, ($C_1-C_8$)haloalkoxy($C_1-C_8$)alkyl, ($C_1-C_8$)thioalkoxy($C_1-C_8$)alkyl, ($CH_3SO_2$)($C_1-C_8$)alkyl, and (($C_1-C_8$)alkylC(O))($C_1-C_8$)alkyl;

$R^9$ is selected from ($C_3-C_{10}$)cycloalkyl, ($C_3-C_{10}$)cycloalkyl($C_1-C_8$)alkyl, ($C_1-C_8$)haloalkyl, ($C_1-C_3$)hydroxyalkyl, ($C_1-C_8$)alkyl, ($C_1-C_8$)alkoxy($C_1-C_8$)alkyl, and optionally substituted aryl; and $R^b$, independently for each occurrence, is selected from H, optionally substituted ($C_1-C_8$)alkyl, optionally substituted ($C_1-C_8$)haloalkyl, optionally substituted ($C_1-C_8$)hydroxyalkyl, optionally substituted ($C_3-C_{10}$)cycloalkyl, optionally substituted ($C_3-C_{10}$)cycloalkyl($C_1-C_8$)alkyl, optionally substituted aryl, and optionally substituted aryl($C_1-C_8$) alkyl;

further wherein:

at least one of $R^1$, $R^2$, $R^3$, $R^4$, and $R^5$ is selected from ($C_3-C_8$)alkyl, ($C_2-C_8$)hydroxyalkyl, ($C_1-C_8$)aminoalkyl, straight chain ($C_2-C_8$)alkoxy, ($C_1-C_8$)haloalkoxy, ($C_1-C_8$)cycloalkyl, optionally substituted aryl, optionally substituted heteroaryl, optionally substituted aryloxy, ($C_6-C_{10}$)cycloalkoxy, —OC(O)(($C_1-C_8$)alkyl), —NHC(O)(aryl), ($H_3CSO_2$)($C_1-C_8$)alkylene, optionally substituted ($R^b_2NSO_2$)($C_1-C_8$)alkylene, di(($C_1-C_8$)alkyl)amino, —NH—$CH_2$—$R^8$, —O—$CH_2$—$R^8$, and —O—$CH_2CH_2$—O—$R^9$.

In other aspects, the invention provides a compound of formula (II'):

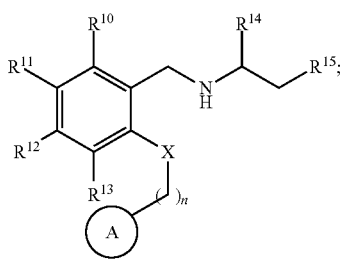

or a pharmaceutically acceptable salt thereof;
wherein:
X is O or S;
each of $R^{10}$, $R^{11}$, $R^{12}$, and $R^{13}$ is independently selected from H, OH, —$NH_2$, halide, sulfonamido, $(C_1$-$C_6)$ alkylsulfonyl, —OC(O)(($C_1$-$C_8$)alkyl), —C(O)O(($C_1$-$C_8$)alkyl), —C(O)OH, optionally substituted —NHC(O)(aryl), —C(O)$NH_2$, —B(OH)$_2$, tri(($C_1$-$C_8$)alkyl) silyl, optionally substituted $(C_1$-$C_8)$alkyl, optionally substituted $(C_3$-$C_8)$alkoxy, optionally substituted $(C_1$-$C_8)$aminoalkyl, optionally substituted $(C_1$-$C_8)$hydroxyalkyl, optionally substituted $(C_1$-$C_8)$haloalkyl, optionally substituted $(C_1$-$C_8)$haloalkoxy, optionally substituted aryl, optionally substituted heteroaryl, optionally substituted aryloxy, optionally substituted arylalkoxy, optionally substituted heteroaryloxy, optionally substituted heteroarylalkoxy, optionally substituted $(C_3$-$C_{10})$cycloalkyl, optionally substituted $(C_3$-$C_{10})$cycloalkoxy, optionally substituted $(C_2$-$C_9)$heterocycloalkyl, optionally substituted $(C_2$-$C_9)$heterocycloalkoxy, $(H_3CSO_2)(C_1$-$C_8)$alkylene, $(H_2NSO_2)(C_1$-$C_8)$alkylene, optionally substituted di(($C_1$-$C_8$)alkyl)amino;
or $R^{10}$ and $R^{11}$, $R^{11}$ and $R^{12}$, or $R^{12}$ and $R^{13}$, taken together with the intervening atoms, form an aryl, heteroaryl, cycloalkyl, or heterocycloalkyl group;
$R^{14}$ is H or $(C_1$-$C_6)$alkyl;
$R^{15}$ is optionally substituted $(C_3$-$C_{10})$cycloalkyl or $(C_3$-$C_{10})$cycloalkenyl;

represents a heterocyclic group substituted by oxo (═O) and optionally substituted by one or more additional substituents; and
n is an integer from 1-3.
In further aspects, the invention provides a compound of formula (III'):

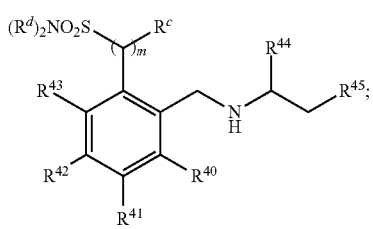

or a pharmaceutically acceptable salt thereof;
wherein:
each of $R^{40}$, $R^{41}$, $R^{42}$, and $R^{43}$ is independently selected from H, OH, —$NH_2$, halide, sulfonamido, $(C_1$-$C_6)$ alkylsulfonyl, —OC(O)(($C_1$-$C_8$)alkyl), —C(O)O(($C_1$-$C_8$)alkyl), —C(O)OH, optionally substituted —NHC(O)(aryl), —C(O)$NH_2$, —B(OH)$_2$, tri(($C_1$-$C_8$)alkyl) silyl, optionally substituted $(C_1$-$C_8)$alkyl, optionally substituted $(C_1$-$C_8)$alkoxy, optionally substituted $(C_1$-$C_8)$aminoalkyl, optionally substituted $(C_1$-$C_8)$hydroxyalkyl, optionally substituted $(C_1$-$C_8)$haloalkyl, optionally substituted $(C_1$-$C_8)$haloalkoxy, optionally substituted aryl, optionally substituted heteroaryl, optionally substituted aryloxy, optionally substituted arylalkoxy, optionally substituted heteroaryloxy, optionally substituted heteroarylalkoxy, optionally substituted $(C_3$-$C_{10})$cycloalkyl, optionally substituted $(C_3$-$C_{10})$cycloalkoxy, optionally substituted $(C_2$-$C_9)$heterocycloalkyl, optionally substituted $(C_2$-$C_9)$heterocycloalkoxy, $(H_3CSO_2)(C_1$-$C_8)$alkylene, $(H_2NSO_2)(C_1$-$C_8)$alkylene, optionally substituted di(($C_1$-$C_8$)alkyl)amino;
or $R^{40}$ and $R^{41}$, $R^{41}$ and $R^{42}$, or $R^{42}$ and $R^{43}$, taken together with the intervening atoms, form an aryl, heteroaryl, cycloalkyl, or heterocycloalkyl group;
$R^{44}$ is H or $(C_1$-$C_6)$alkyl;
$R^{45}$ is optionally substituted $(C_3$-$C_{10})$cycloalkyl or $(C_3$-$C_{10})$cycloalkenyl;
$R^c$, independently for each occurrence, is selected from H, $(C_1$-$C_8)$alkyl, $(C_1$-$C_8)$haloalkyl, $(C_1$-$C_8)$alkoxyl, $(C_1$-$C_8)$hydroxyalkyl, $(C_3$-$C_{10})$cycloalkyl, $(C_3$-$C_{10})$cycloalkyl($C_1$-$C_8)$alkyl, aryl, and aryl($C_1$-$C_8$) alkyl;
$R^d$, independently for each occurrence, is selected from H, optionally substituted —C(O)($C_1$-$C_8)$alkyl, optionally substituted —C(O)NH—$(C_3$-$C_{10})$cycloalkyl, optionally substituted $(C_1$-$C_8)$alkyl, optionally substituted $(C_1$-$C_8)$haloalkyl, optionally substituted $(C_1$-$C_8)$hydroxyalkyl, optionally substituted $(C_3$-$C_{10})$cycloalkyl, optionally substituted heterocyclyl, optionally substituted $(C_3$-$C_{10})$cycloalkyl($C_1$-$C_8)$alkyl, optionally substituted aryl, and optionally substituted aryl($C_1$-$C_8$) alkyl, or
two $R^d$ are taken together with the nitrogen atom to which they are attached to form an optionally substituted 5-6-membered heterocyclyl; and m is an integer from 1-3.
The invention further provides compounds, or pharmaceutically acceptable salts thereof, of the compounds listed in Table 1.
In other aspects, the invention provides pharmaceutical compositions comprising a compound of any one of claims 1-38, in combination with a pharmaceutically acceptable carrier.
In certain aspects, the invention provides methods of treating a bacterial infection in a subject, comprising administering to the subject a therapeutically effective amount of a compound of the invention, i.e., a compound of formula (I), formula (II), formula (IT), formula (III), formula (III'), or a compound pictured in Table 1, or a pharmaceutical composition comprising the compound.
The invention further provides methods of treating a bacterial infection in a subject, comprising administering to the subject a therapeutically effective amount of a compound of formula (IV'):

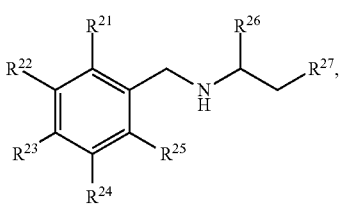

(IV')

or a pharmaceutically acceptable salt thereof;
wherein:
each of $R^{21}$, $R^{22}$, $R^{23}$, $R^{24}$, and $R^{25}$ is independently selected from H, OH, —$NH_2$, halide, sulfonamido, ($C_1$-$C_6$)alkylsulfonyl, —OC(O)(($C_1$-$C_8$)alkyl), —C(O)O(($C_1$-$C_8$)alkyl), —C(O)OH, optionally substituted —NHC(O)(aryl), —C(O)$NH_2$, —B(OH)$_2$, optionally substituted —S—($C_1$-$C_6$)alkyl; tri(($C_1$-$C_8$)alkyl)silyl, optionally substituted ($C_1$-$C_8$)alkyl, optionally substituted ($C_1$-$C_8$)alkoxy, optionally substituted ($C_1$-$C_8$) aminoalkyl, optionally substituted ($C_1$-$C_8$)hydroxyalkyl, optionally substituted ($C_1$-$C_8$)haloalkyl, optionally substituted ($C_1$-$C_8$)haloalkoxy, optionally substituted aryl, optionally substituted heteroaryl, optionally substituted aryloxy, optionally substituted arylalkoxy, optionally substituted heteroaryloxy, optionally substituted heteroarylalkoxy, optionally substituted ($C_3$-$C_{10}$) cycloalkyl, optionally substituted ($C_3$-$C_{10}$)cycloalkoxy, optionally substituted ($C_2$-$C_9$)heterocycloalkyl, optionally substituted ($C_2$-$C_9$)heterocycloalkoxy, ($H_3CSO_2$)($C_1$-$C_8$)alkylene, optionally substituted ($R^e_2NSO_2$)($C_1$-$C_8$)alkylene, optionally substituted di(($C_1$-$C_8$)alkyl)amino, —NH—$CH_2$—$R^{28}$, —O—$CH_2$—$R^{28}$, and —O—$CH_2CH_2$—O—$R^{29}$;
or $R^{21}$ and $R^{22}$, $R^{22}$ and $R^{23}$, $R^{23}$ and $R^{24}$, or $R^{24}$ and $R^{25}$, taken together with the intervening atoms, form an optionally substituted aryl, heteroaryl, cycloalkyl, or heterocycloalkyl group;
$R^{26}$ is H or ($C_1$-$C_6$)alkyl;
$R^{27}$ is optionally substituted ($C_3$-$C_{10}$)cycloalkyl or ($C_3$-$C_{10}$)cycloalkenyl;
$R^{28}$ is selected from H, —C(O)(($C_2$-$C_9$)heterocycloalkyl), —C(O)NH(($C_1$-$C_8$)alkyl), —C(O)NH(aryl($C_1$-$C_8$)alkyl), —C(O)NH(($C_3$-$C_8$)cycloalkyl), —C(O)NH(($C_3$-$C_8$)cycloalkyl($C_1$-$C_8$)alkyl), —C(O)N($CH_3$)(($C_3$-$C_8$)cycloalkyl), —C(O)N($CH_3$)(aryl($C_1$-$C_8$)alkyl), —C(O)NHC(O)NH(($C_3$-$C_8$)cycloalkyl), —C(O)NHC(O)NH(($C_1$-$C_8$)alkyl), —C(O)NHC(O)$NH_2$, optionally substituted heteroaryl, optionally substituted aryl, optionally substituted aryloxy($C_1$-$C_8$)alkyl, ($C_3$-$C_8$)cycloalkyl, ($C_2$-$C_9$)heterocycloalkyl, ($C_2$-$C_9$)heterocycloalkyl($C_2$-$C_8$)alkyl, heteroaryl($C_1$-$C_8$)alkyl, ($C_1$-$C_8$) alkoxy, ($C_2$-$C_8$)hydroxyalkyl, ($C_1$-$C_8$)alkoxy($C_1$-$C_8$)alkyl, ($C_1$-$C_8$)haloalkoxy($C_1$-$C_8$)alkyl, ($C_1$-$C_8$) thioalkoxy($C_1$-$C_8$)alkyl, ($CH_3SO_2$)($C_1$-$C_8$)alkyl, and (($C_1$-$C_8$)alkylC(O))($C_1$-$C_8$)alkyl;
$R^{29}$ is selected from ($C_3$-$C_{10}$)cycloalkyl, ($C_3$-$C_{10}$)cycloalkyl($C_1$-$C_8$)alkyl, ($C_1$-$C_8$)haloalkyl, ($C_1$-$C_8$)hydroxyalkyl, ($C_1$-$C_8$)alkyl, ($C_1$-$C_8$)alkoxy($C_1$-$C_8$)alkyl, and optionally substituted aryl; and
$R^e$, independently for each occurrence, is selected from H, optionally substituted —C(O)($C_1$-$C_8$)alkyl, optionally substituted —C(O)NH—($C_3$-$C_{10}$)cycloalkyl, optionally substituted ($C_1$-$C_8$)alkyl, optionally substituted ($C_1$-$C_8$)haloalkyl, optionally substituted ($C_1$-$C_8$)hydroxyalkyl, optionally substituted ($C_3$-$C_{10}$)cycloalkyl, optionally substituted heterocyclyl, optionally substituted ($C_3$-$C_{10}$)cycloalkyl($C_1$-$C_8$)alkyl, optionally substituted aryl, and optionally substituted aryl($C_1$-$C_8$) alkyl, or
two $R^e$ are taken together with the nitrogen atom to which they are attached to form an optionally substituted 5-6-membered heterocyclyl;
further wherein:
if $R^{26}$ is ($C_1$-$C_6$)alkyl and $R^{27}$ is ($C_6$)cycloalkyl, then $R^{21}$ and $R^{25}$ are not OH, —OC(O)(($C_1$-$C_8$)alkyl), optionally substituted ($C_1$-$C_8$)alkoxy, optionally substituted ($C_1$-$C_8$) haloalkoxy, optionally substituted aryloxy, optionally substituted arylalkoxy, optionally substituted heteroaryloxy, optionally substituted heteroarylalkoxy, optionally substituted ($C_3$-$C_{10}$)cycloalkoxy, optionally substituted ($C_2$-$C_9$) heterocycloalkoxy, —O—$CH_2$—$R^{28}$, or —O—$CH_2CH_2$—O—$R^{29}$.

In certain aspects, the invention provides methods of treating tuberculosis, comprising administering to a subject in need thereof a therapeutically effective amount of a compound of the invention, i.e., a compound of formula (I), formula (II), formula (II'), formula (III), formula (III'), or a compound pictured in Table 1, or a pharmaceutical composition comprising the compound.

The invention further provides methods of treating tuberculosis, comprising administering to a subject in need thereof a therapeutically effective amount of a compound of formula (V'):

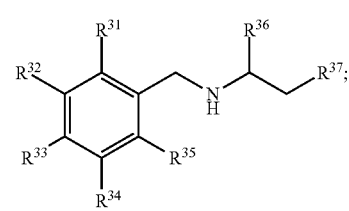

(V')

or a pharmaceutically acceptable salt thereof;
wherein:
each of $R^{31}$, $R^{32}$, $R^{33}$, $R^{34}$, and $R^{35}$ is independently selected from from H, OH, —$NH_2$, halide, sulfonamido, ($C_1$-$C_6$)alkylsulfonyl, —OC(O)(($C_1$-$C_8$)alkyl), —C(O)O(($C_1$-$C_8$)alkyl), —C(O)OH, optionally substituted —NHC(O)(aryl), —C(O)$NH_2$, —B(OH)$_2$, optionally substituted —S—($C_1$-$C_6$)alkyl; tri(($C_1$-$C_8$) alkyl)silyl, optionally substituted ($C_1$-$C_8$)alkyl, optionally substituted ($C_1$-$C_8$)alkoxy, optionally substituted ($C_1$-$C_8$)aminoalkyl, optionally substituted ($C_1$-$C_8$)hydroxyalkyl, optionally substituted ($C_1$-$C_8$)haloalkyl, optionally substituted ($C_1$-$C_8$)haloalkoxy, optionally substituted aryl, optionally substituted heteroaryl, optionally substituted aryloxy, optionally substituted arylalkoxy, optionally substituted heteroaryloxy, optionally substituted heteroarylalkoxy, optionally substituted ($C_3$-$C_{10}$)cycloalkyl, optionally substituted ($C_3$-$C_{10}$)cycloalkoxy, optionally substituted ($C_2$-$C_9$)heterocycloalkyl, optionally substituted ($C_2$-$C_9$) heterocycloalkoxy, ($H_3CSO_2$)($C_1$-$C_8$)alkylene, optionally substituted ($R^f_2NSO_2$)($C_1$-$C_8$)alkylene, optionally substituted di(($C_1$-$C_8$)alkyl)amino, —NH—$CH_2$—$R^{38}$, —O—$CH_2$—$R^{38}$, and —O—$CH_2CH_2$—O—$R^{39}$;

or $R^{31}$ and $R^{32}$, $R^{32}$ and $R^{33}$, $R^{33}$ and $R^{34}$, or $R^{34}$ and $R^{35}$, taken together with the intervening atoms, form an optionally substituted aryl, heteroaryl, cycloalkyl, or heterocycloalkyl group;

$R^{36}$ is H or $(C_1$-$C_6)$alkyl;

$R^{37}$ is optionally substituted $(C_3$-$C_{10})$cycloalkyl or $(C_3$-$C_{10})$cycloalkenyl;

$R^{38}$ is selected from H, —C(O)((C$_2$-C$_9$)heterocycloalkyl), —C(O)NH((C$_1$-C$_8$)alkyl), —C(O)NH(aryl(C$_1$-C$_8$)alkyl), —C(O)NH((C$_3$-C$_8$)cycloalkyl), —C(O)NH((C$_3$-C$_8$)cycloalkyl(C$_1$-C$_8$)alkyl), —C(O)N(CH$_3$)((C$_3$-C$_8$)cycloalkyl), —C(O)N(CH$_3$)(aryl(C$_1$-C$_8$)alkyl), —C(O)NHC(O)NH((C$_3$-C$_8$)cycloalkyl), —C(O)NHC(O)NH((C$_1$-C$_8$)alkyl), —C(O)NHC(O)NH$_2$, optionally substituted heteroaryl, optionally substituted aryl, optionally substituted aryloxy(C$_1$-C$_8$)alkyl, (C$_3$-C$_8$)cycloalkyl, (C$_2$-C$_9$)heterocycloalkyl, (C$_2$-C$_9$)heterocycloalkyl(C$_2$-C$_8$)alkyl, heteroaryl(C$_1$-C$_8$)alkyl, (C$_1$-C$_8$)alkoxy, (C$_2$-C$_8$)hydroxyalkyl, (C$_1$-C$_8$)alkoxy(C$_1$-C$_8$)alkyl, (C$_1$-C$_8$)haloalkoxy(C$_1$-C$_8$)alkyl, (C$_1$-C$_8$)thioalkoxy(C$_1$-C$_8$)alkyl, (CH$_3$SO$_2$)(C$_1$-C$_8$)alkyl, and ((C$_1$-C$_8$)alkylC(O))(C$_1$-C$_8$)alkyl;

$R^{39}$ is selected from $(C_3$-$C_{10})$cycloalkyl, $(C_3$-$C_{10})$cycloalkyl$(C_1$-$C_8)$alkyl, $(C_1$-$C_8)$haloalkyl, $(C_1$-$C_8)$hydroxyalkyl, $(C_1$-$C_8)$alkyl, $(C_1$-$C_8)$alkoxy$(C_1$-$C_8)$alkyl, and optionally substituted aryl; and $R^f$, independently for each occurrence, is selected from H, optionally substituted —C(O)(C$_1$-C$_8$)alkyl, optionally substituted —C(O)NH—(C$_3$-C$_{10}$)cycloalkyl, optionally substituted (C$_1$-C$_8$)alkyl, optionally substituted (C$_1$-C$_8$)haloalkyl, optionally substituted (C$_1$-C$_8$)hydroxyalkyl, optionally substituted (C$_3$-C$_{10}$)cycloalkyl, optionally substituted heterocyclyl, optionally substituted (C$_3$-C$_{10}$)cycloalkyl(C$_1$-C$_8$)alkyl, optionally substituted aryl, and optionally substituted aryl(C$_1$-C$_8$) alkyl, or two $R^f$ are taken together with the nitrogen atom to which they are attached to form an optionally substituted 5-6-membered heterocyclyl.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 1 shows that the compounds of the invention, such as B1, can be used in combination with other tRNA synthetase inhibitors in order to overcome antibiotic resistance.

DETAILED DESCRIPTION OF THE INVENTION

The present invention is based on the discovery of a class of compounds with surprising antibacterial activity. A description of example embodiments of the invention follows.

Definitions

"Alkyl" means an optionally substituted saturated aliphatic branched or straight-chain monovalent hydrocarbon radical having the specified number of carbon atoms. Thus, "$(C_1$-$C_6)$ alkyl" means a radical having from 1-6 carbon atoms in a linear or branched arrangement. "$(C_1$-$C_6)$alkyl" includes methyl, ethyl, propyl, butyl, pentyl and hexyl.

"Alkylene" means an optionally substituted saturated aliphatic branched or straight-chain divalent hydrocarbon radical having the specified number of carbon atoms.

Thus, "$(C_1$-$C_6)$alkylene" includes a divalent saturated aliphatic radical having from 1-6 carbon atoms in a linear arrangement, e.g., —[(CH$_2$)$_n$]—, where n is an integer from 1 to 6, "$(C_1$-$C_6)$alkylene" includes methylene, ethylene, propylene, butylene, pentylene and hexylene. "$(C_1$-$C_6)$alkylene" also includes a divalent saturated radical having from 1-6 carbon atoms in a branched arrangement, for example: —[(CH$_2$CH$_2$CH$_2$CH$_2$CH(CH$_3$))]—, —[(CH$_2$CH$_2$CH$_2$CH$_2$C(CH$_3$)$_2$)]—, —[(CH$_2$C(CH$_3$)$_2$CH(CH$_3$))]—, and the like. Where indicated, alkylene is optionally and independently substituted with one or more substituents independently selected from halo, $(C_1$-$C_6)$alkyl, —OH, =O, $(C_1$-$C_6)$alkoxy, and $(C_1$-$C_6)$haloalkyl.

"Aryl" or "aromatic" means an aromatic monocyclic or polycyclic (e.g. bicyclic or tricyclic) carbocyclic ring system. In one embodiment, "aryl" is a 6-12 membered monocylic or bicyclic system. Aryl systems include, but not limited to, phenyl, naphthyl, fluorenyl, indenyl, azulenyl, and anthracenyl. In certain preferred embodiments, "aryl" is phenyl.

"Carbocyclyl" means a cyclic group with only ring carbon atoms. "Carbocyclyl" includes 3-12 membered saturated or unsaturated aliphatic cyclic hydrocarbon rings or 6-12 membered aryl rings. A carbocyclyl moiety can be monocyclic, fused bicyclic, bridged bicyclic, spiro bicyclic, or polycyclic.

Monocyclic carbocyclyls are saturated or unsaturated aliphatic cyclic hydrocarbon rings or aromatic hydrocarbon rings having the specified number of carbon atoms. Monocyclic carbocyclyls include cycloalkyl, cycloalkenyl, cycloalkynyl and phenyl.

A fused bicyclic carbocyclyl has two rings which have two adjacent ring atoms in common. The first ring is a monocyclic carbocyclyl and the second ring is a monocyclic carbocyclyl or a monocyclic heterocyclyl.

A bridged bicyclic carbocyclyl has two rings which have three or more adjacent ring atoms in common. The first ring is a monocyclic carbocyclyl and the second ring is a monocyclic carbocyclyl or a monocyclic heterocyclyl. In some preferred embodiments, a bridged bicyclic carbocylyl is adamantyl.

A spiro bicyclic carbocyclyl has two rings which have only one ring atom in common. The first ring is a monocyclic carbocyclyl and the second ring is a monocyclic carbocyclyl or a monocyclic heterocyclyl.

Polycyclic carbocyclyls have more than two rings (e.g., three rings resulting in a tricyclic ring system) and adjacent rings have at least one ring atom in common. The first ring is a monocyclic carbocyclyl and the remainder of the ring structures are monocyclic carbocyclyls or monocyclic heterocyclyls. Polycyclic ring systems include fused, bridged and spiro ring systems. A fused polycyclic ring system has at least two rings that have two adjacent ring atoms in common. A spiro polycyclic ring system has at least two rings that have only one ring atom in common. A bridged polycyclic ring system has at least two rings that have three or more adjacent ring atoms in common.

"Cycloalkyl" means a saturated aliphatic cyclic hydrocarbon ring. Thus, "$(C_3$-$C_7)$cycloalkyl" means a hydrocarbon radical of a (3-7 membered) saturated aliphatic cyclic hydrocarbon ring. A $C_3$-$C_7$cycloalkyl includes, but is not limited to cyclopropyl, cyclobutyl, cyclopentyl, cyclohexyl and cycloheptyl.

"Cycloalkene" means an aliphatic cyclic hydrocarbon ring having one or more double bonds in the ring.

"Cycloalkyne" means an aliphatic cyclic hydrocarbon ring having one or more triple bonds in the ring.

"Hetero" refers to the replacement of at least one carbon atom member in a ring system with at least one heteroatom selected from N, S, and O. "Hetero" also refers to the replacement of at least one carbon atom member in a acyclic system. A hetero ring system or a hetero acyclic system may have 1, 2, 3 or 4 carbon atom members replaced by a heteroatom.

"Heterocyclyl" means a cyclic 4-12 membered saturated or unsaturated aliphatic or aromatic ring containing 1, 2, 3, 4 or 5 heteroatoms independently selected from N, O or S. When one heteroatom is S, it can be optionally mono- or di-oxygenated (i.e. —S(O)— or —S(O)$_2$—). The heterocylyl can be monocyclic, fused bicyclic, bridged bicyclic, spiro bicyclic or polycyclic.

"Saturated heterocyclyl" means an aliphatic heterocyclyl group without any degree of unsaturation (i.e., no double bond or triple bond). It can be monocyclic, fused bicyclic, bridged bicyclic, spiro bicyclic or polycyclic.

Examples of monocyclic saturated heterocyclyls include, but are not limited to, azetidine, pyrrolidine, piperidine, piperazine, azepane, hexahydropyrimidine, tetrahydrofuran, tetrahydropyran, morpholine, thiomorpholine, thiomorpholine 1,1-dioxide, tetrahydro-2H-1,2-thiazine, tetrahydro-2H-1,2-thiazine 1,1-dioxide, isothiazolidine, isothiazolidine 1,1-dioxide.

A fused bicyclic heterocyclyl has two rings which have two adjacent ring atoms in common. The first ring is a monocyclic heterocyclyl and the second ring is a monocyclic carbocycle (such as a cycloalkyl or phenyl) or a monocyclic heterocyclyl. For example, the second ring is a ($C_3$-$C_6$)cycloalkyl, such as cyclopropyl, cyclobutyl, cyclopentyl and cyclohexyl. Alternatively, the second ring is phenyl. Examples of fused bicyclic heterocyclyls include, but are not limited to, octahydrocyclopenta[c]pyrrolyl, indoline, isoindoline, 2,3-dihydro-1H-benzo[d]imidazole, 2,3-dihydrobenzo[d]oxazole, 2,3-dihydrobenzo[d]thiazole, octahydrobenzo[d]oxazole, octahydro-1H-benzo[d]imidazole, octahydrobenzo[d]thiazole, octahydrocyclopenta[c]pyrrole, 3-azabicyclo[3.1.0]hexane, and 3-azabicyclo[3.2.0]heptane.

A spiro bicyclic heterocyclyl has two rings which have only one ring atom in common. The first ring is a monocyclic heterocyclyl and the second ring is a monocyclic carbocycle (such as a cycloalkyl or phenyl) or a monocyclic heterocyclyl. For example, the second ring is a ($C_3$-$C_6$) cycloalkyl. Alternatively, the second ring is phenyl. Example of spiro bicyclic heterocyclyl includes, but are not limited to, azaspiro[4.4]nonane, 7-azaspiro[4.4]nonane, azaspiro[4.5]decane, 8-azaspiro[4.5]decane, azaspiro[5.5]undecane, 3-azaspiro[5.5]undecane and 3,9-diazaspiro[5.5]undecane.

A bridged bicyclic heterocyclyl has two rings which have three or more adjacent ring atoms in common. The first ring is a monocyclic heterocyclyl and the other ring is a monocyclic carbocycle (such as a cycloalkyl or phenyl) or a monocyclic heterocyclyl.

Examples of bridged bicyclic heterocylyls include, but are not limited to, azabicyclo[3.3.1]nonane, 3-azabicyclo[3.3.1]nonane, azabicyclo[3.2.1]octane, 3-azabicyclo[3.2.1] octane, 6-azabicyclo[3.2.1]octane and azabicyclo[2.2.2]octane, 2-azabicyclo[2.2.2]octane.

Polycyclic heterocyclyls have more than two rings, one of which is a heterocyclyl (e.g., three rings resulting in a tricyclic ring system) and adjacent rings having at least one ring atom in common. Polycyclic ring systems include fused, bridged and spiro ring systems. A fused polycyclic ring system has at least two rings that have two adjacent ring atoms in common. A spiro polycyclic ring system has at least two rings that have only one ring atom in common. A bridged polycyclic ring system has at least two rings that have three or more adjacent ring atoms in common.

"Heteroaryl" or "heteroaromatic ring" means a 5-12 membered monovalent heteroaromatic monocyclic or bicylic ring radical. A heretoaryl contains 1, 2, 3 or 4 heteroatoms independently selected from N, O, and S. Heteroaryls include, but are not limited to furan, oxazole, thiophene, 1,2,3-triazole, 1,2,4-triazine, 1,2,4-triazole, 1,2,5-thiadiazole 1,1-dioxide, 1,2,5-thiadiazole 1-oxide, 1,2,5-thiadiazole, 1,3,4-oxadiazole, 1,3,4-thiadiazole, 1,3,5-triazine, imidazole, isothiazole, isoxazole, pyrazole, pyridazine, pyridine, pyridine-N-oxide, pyrazine, pyrimidine, pyrrole, tetrazole, and thiazole. Bicyclic heteroaryl rings include, but are not limited to, bicyclo[4.4.0] and bicyclo[4.3.0]fused ring systems such as indolizine, indole, isoindole, indazole, benzimidazole, benzthiazole, purine, quinoline, isoquinoline, cinnoline, phthalazine, quinazoline, quinoxaline, 1,8-naphthyridine, and pteridine.

In certain embodiments, where indicated, a group such as alkylene, adamantyl, naphthyl, or aryl may be optionally substituted. Exemplary substituents include halo, ($C_1$-$C_6$) alkyl, —OH, =O, ($C_1$-$C_6$)alkoxy, ($C_1$-$C_6$)alkoxy-($C_1$-$C_6$) alkylene, ($C_1$-$C_6$)haloalkyl, ($C_1$-$C_6$)haloalkoxy, and —C(O)—($C_1$-$C_6$)alkyl.

In certain embodiments, where indicated, a phenyl group may have two adjacent substituents that, taken together with the intervening atoms, form an optionally substituted heteroaryl, aryl, cycloalkyl, or heterocycloalkyl ring. By way of example, a phenyl group having two adjacent substituents that, taken together with the intervening atoms, form a pyridinyl group can have the structure

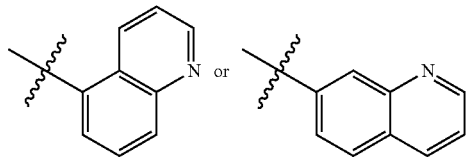 [SMILES: *c1cccc2ncccc12 ; *c1ccc2cccnc2c1]

or any positional isomer thereof. In another example, a phenyl group having two adjacent substituents that, taken together with the intervening atoms, form a tetrahydropyranyl group can have the structure

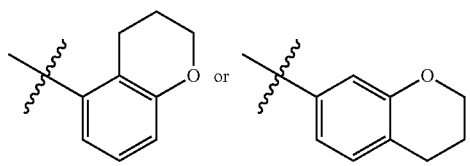 [SMILES: *c1cccc2c1CCCO2 ; *c1ccc2c(c1)OCCC2]

or any positional isomer thereof.

"Halogen" and "halo" are interchangeably used herein and each refers to fluorine, chlorine, bromine, or iodine.

"Alkoxy" means an alkyl radical attached through an oxygen linking atom. "$(C_1-C_6)$-alkoxy" includes methoxy, ethoxy, propoxy, butoxy, pentoxy and hexoxy.

Haloalkyl includes mono, poly, and perhaloalkyl groups where each halogen is independently selected from fluorine, chlorine, and bromine.

"Pharmaceutically acceptable carrier" means non-therapeutic components that are of sufficient purity and quality for use in the formulation of a composition of the invention that, when appropriately administered to an animal or human, typically do not produce an adverse reaction, and that are used as a vehicle for a drug substance (i.e. a compound of the present invention).

Pharmaceutically acceptable salts of the compounds of the present invention are also included. For example, an acid salt of a compound of the present invention containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, triethiodide, and trifluoroacetate salts.

Salts of the compounds of the present invention containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acids such as lysine and arginine.

tRNA Synthetase Inhibitor Compounds

In certain aspects, the invention provides a compound of formula (I):

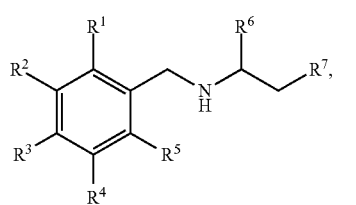

(I)

or a pharmaceutically acceptable salt thereof;
wherein:
each of $R^1$, $R^2$, $R^3$, $R^4$, and $R^5$ is independently selected from H, OH, —$NH_2$, halide, sulfonamido, $(C_1-C_6)$alkylsulfonyl, —OC(O)(($C_1-C_8$)alkyl), —C(O)O(($C_1$-$C_8$)alkyl), —C(O)OH, optionally substituted —NHC(O)(aryl), —C(O)$NH_2$, —B(OH)$_2$, tri(($C_1-C_8$)alkyl)silyl, optionally substituted ($C_1-C_8$)alkyl, optionally substituted ($C_1-C_8$)alkoxy, optionally substituted ($C_1-C_8$)aminoalkyl, optionally substituted ($C_1-C_8$)hydroxyalkyl, optionally substituted ($C_1-C_8$)haloalkyl, optionally substituted ($C_1-C_8$)haloalkoxy, optionally substituted aryl, optionally substituted heteroaryl, optionally substituted aryloxy, optionally substituted arylalkoxy, optionally substituted heteroaryloxy, optionally substituted heteroarylalkoxy, optionally substituted ($C_3-C_{10}$)cycloalkyl, optionally substituted ($C_3$-$C_{10}$)cycloalkoxy, optionally substituted ($C_2-C_9$)heterocycloalkyl, optionally substituted ($C_2-C_9$)heterocycloalkoxy, ($H_3CSO_2$)($C_1-C_8$)alkylene, optionally substituted ($R^b_2NSO_2$)($C_1-C_8$)alkylene, optionally substituted di(($C_1-C_8$)alkyl)amino, —NH—$CH_2$—$R^8$, —O—$CH_2$—$R^8$, and —O—$CH_2CH_2$—O—$R^9$;

or $R^1$ and $R^2$, $R^2$ and $R^3$, $R^3$ and $R^4$, or $R^4$ and $R^5$, taken together with the intervening atoms, form an optionally substituted aryl, heteroaryl, cycloalkyl, or heterocycloalkyl group;

$R^6$ is H or ($C_1-C_6$)alkyl;

$R^7$ is optionally substituted ($C_3-C_{10}$)cycloalkyl or ($C_3$-$C_{10}$)cycloalkenyl;

$R^8$ is selected from —C(O)(($C_2-C_9$)heterocycloalkyl), —C(O)NH(($C_1-C_8$)alkyl), —C(O)NH(aryl($C_1-C_8$)alkyl), —C(O)NH(($C_3-C_8$)cycloalkyl), —C(O)NH(($C_3$-$C_8$)cycloalkyl($C_1-C_8$)alkyl), —C(O)N($CH_3$)(($C_3-C_8$)cycloalkyl), —C(O)N($CH_3$)(aryl($C_1-C_8$)alkyl), —C(O)NHC(O)NH(($C_3-C_8$)cycloalkyl), —C(O)NHC(O)NH(($C_1-C_8$)alkyl), —C(O)NHC(O)$NH_2$, optionally substituted heteroaryl wherein the heteroaryl is not 4-pyridinyl, benzimidazole or thiazole, optionally substituted aryloxy($C_1-C_8$)alkyl, ($C_3-C_8$)cycloalkyl, ($C_2$-$C_9$)heterocycloalkyl, ($C_2-C_9$)heterocycloalkyl($C_2-C_8$)alkyl, heteroaryl($C_1-C_8$)alkyl, ($C_2-C_8$)alkoxy, ($C_3-C_8$)hydroxyalkyl, ($C_1-C_8$)alkoxy($C_1-C_8$)alkyl, ($C_1-C_8$)haloalkoxy($C_1-C_8$)alkyl, ($C_1-C_8$)thioalkoxy($C_1-C_8$)alkyl, ($CH_3SO_2$)($C_1-C_8$)alkyl, and (($C_1-C_8$)alkylC(O))($C_1-C_8$)alkyl;

$R^9$ is selected from ($C_3-C_{10}$)cycloalkyl, ($C_3-C_{10}$)cycloalkyl($C_1-C_8$)alkyl, ($C_1-C_8$)haloalkyl, ($C_1-C_8$)hydroxyalkyl, ($C_1-C_8$)alkyl, ($C_1-C_8$)alkoxy($C_1-C_8$)alkyl, and optionally substituted aryl; and $R^b$, independently for each occurrence, is selected from H, optionally substituted ($C_1-C_8$)alkyl, optionally substituted ($C_1-C_8$)haloalkyl, optionally substituted ($C_1-C_8$)hydroxyalkyl, optionally substituted ($C_3-C_{10}$)cycloalkyl, optionally substituted ($C_3-C_{10}$)cycloalkyl($C_1-C_8$)alkyl, optionally substituted aryl, and optionally substituted aryl($C_1-C_8$) alkyl;

further wherein:

at least one of $R^1$, $R^2$, $R^3$, $R^4$, and $R^5$ is selected from ($C_3-C_8$)alkyl, ($C_2-C_8$)hydroxyalkyl, ($C_1-C_8$)aminoalkyl, straight chain ($C_2-C_8$)alkoxy, ($C_1-C_8$)haloalkoxy, ($C_4-C_8$)cycloalkyl, optionally substituted aryl, optionally substituted heteroaryl, optionally substituted aryloxy, ($C_6-C_{10}$)cycloalkoxy, —OC(O)(($C_1-C_8$)alkyl), —NHC(O)(aryl), ($H_3CSO_2$)($C_1-C_8$)alkylene, optionally substituted ($R^b_2NSO_2$)($C_1-C_8$)alkylene, di(($C_1-C_8$)alkyl)amino, —NH—$CH_2$—$R^8$, —O—$CH_2$—$R^8$, and —O—$CH_2CH_2$—O—$R^9$.

In certain embodiments, $R^6$ is $(C_1-C_6)$alkyl, for example, methyl.

Alternatively, $R^6$ may be H.

In certain embodiments, $R^7$ is optionally substituted cyclohexyl or cyclohexenyl.

In some preferred embodiments, $R^7$ is optionally substituted cyclohexyl.

In certain embodiments, four of $R^1$, $R^2$, $R^3$, $R^4$, and $R^5$ are H. For example, $R^2$, $R^3$, $R^4$, and $R^5$ may each be H.

In certain embodiments, $R^1$ is selected from the group consisting of $(C_3-C_8)$alkyl, $(C_2-C_8)$hydroxyalkyl, $(C_1-C_8)$aminoalkyl, $(C_4-C_8)$cycloalkyl, aryl, heteroaryl, $(CH_3SO_2)(C_1-C_8)$alkyl, and $di((C_1-C_8)$alkyl)amino. In some preferred embodiments, $R^1$ is selected from the group consisting of aryl and heteroaryl.

In some embodiments, $R^1$ represents optionally substituted $(R^b{}_2NSO_2)(C_1-C_8)$alkylene.

Alternatively, $R^1$ may be selected from the group consisting of straight chain $(C_2-C_8)$alkoxy, $(C_1-C_8)$haloalkoxy, aryloxy, —OC(O)$((C_1-C_8)$alkyl), —O—CH$_2$—R$^8$, and —O—CH$_2$CH$_2$—O—R$^9$. For example, $R^1$ may be selected from the group consisting of straight chain $(C_2-C_8)$alkoxy, $(C_1-C_8)$haloalkoxy, and aryloxy. In other embodiments, $R^1$ is selected from the group consisting of —O—CH$_2$—R$^8$ and —O—CH$_2$CH$_2$—O—R$^9$. In some preferred embodiments, $R^1$ is —O—CH$_2$—R$^8$ and $R^8$ is optionally substituted heteroaryl wherein the heteroaryl is not 4-pyridinyl, benzimidazole or thiazole.

In further aspects, the invention provides a compound of formula (IF):

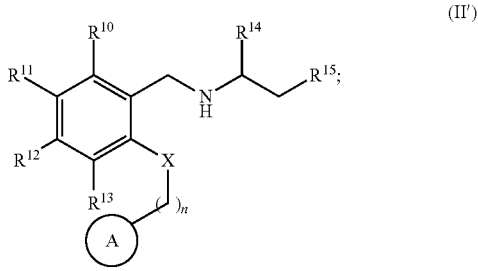

or a pharmaceutically acceptable salt thereof;
wherein:
X is O or S;
each of $R^{10}$, $R^{11}$, $R^{12}$, and $R^{13}$ is independently selected from H, OH, —NH$_2$, halide, sulfonamido, $(C_1-C_6)$alkylsulfonyl, —OC(O)$((C_1-C_8)$alkyl), —C(O)O$((C_1-C_8)$alkyl), —C(O)OH, optionally substituted —NHC(O)(aryl), —C(O)NH$_2$, —B(OH)$_2$, tri$((C_1-C_8)$alkyl)silyl, optionally substituted $(C_1-C_8)$alkyl, optionally substituted $(C_1-C_8)$alkoxy, optionally substituted $(C_1-C_8)$aminoalkyl, optionally substituted $(C_1-C_8)$hydroxyalkyl, optionally substituted $(C_1-C_8)$haloalkyl, optionally substituted $(C_1-C_8)$haloalkoxy, optionally substituted aryl, optionally substituted heteroaryl, optionally substituted aryloxy, optionally substituted arylalkoxy, optionally substituted heteroaryloxy, optionally substituted heteroarylalkoxy, optionally substituted $(C_3-C_{10})$cycloalkyl, optionally substituted $(C_3-C_{10})$cycloalkoxy, optionally substituted $(C_2-C_9)$heterocycloalkyl, optionally substituted $(C_2-C_9)$heterocycloalkoxy, $(H_3CSO_2)(C_1-C_8)$alkylene, $(H_2NSO_2)(C_1-C_8)$alkylene, optionally substituted $di((C_1-C_8)$alkyl)amino;
or $R^{10}$ and $R^{11}$, $R^{11}$ and $R^{12}$, or $R^{12}$ and $R^{13}$, taken together with the intervening atoms, form an aryl, heteroaryl, cycloalkyl, or heterocycloalkyl group;

$R^{14}$ is H or $(C_1-C_6)$alkyl;
$R^{15}$ is optionally substituted $(C_3-C_{10})$cycloalkyl or $(C_3-C_{10})$cycloalkenyl;

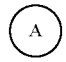

represents a heterocyclic group substituted by oxo (=O) and optionally substituted by one or more additional substituents; and
n is an integer from 1-3.

In further aspects, the invention provides a compound of formula (II):

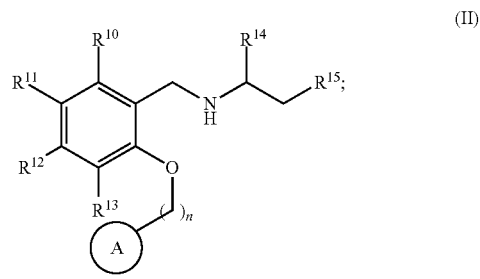

or a pharmaceutically acceptable salt thereof;
wherein:
each of $R^{10}$, $R^{11}$, $R^{12}$, and $R^{13}$ is independently selected from H, OH, —NH$_2$, halide, sulfonamido, $(C_1-C_6)$alkylsulfonyl, —OC(O)$((C_1-C_8)$alkyl), —C(O)O$((C_1-C_8)$alkyl), —C(O)OH, optionally substituted —NHC(O)(aryl), —C(O)NH$_2$, —B(OH)$_2$, tri$((C_1-C_8)$alkyl)silyl, optionally substituted $(C_1-C_8)$alkyl, optionally substituted $(C_1-C_8)$alkoxy, optionally substituted $(C_1-C_8)$aminoalkyl, optionally substituted $(C_1-C_8)$hydroxyalkyl, optionally substituted $(C_1-C_8)$haloalkyl, optionally substituted $(C_1-C_8)$haloalkoxy, optionally substituted aryl, optionally substituted heteroaryl, optionally substituted aryloxy, optionally substituted arylalkoxy, optionally substituted heteroaryloxy, optionally substituted heteroarylalkoxy, optionally substituted $(C_3-C_{10})$cycloalkyl, optionally substituted $(C_3-C_{10})$cycloalkoxy, optionally substituted $(C_2-C_9)$heterocycloalkyl, optionally substituted $(C_2-C_9)$heterocycloalkoxy, $(H_3CSO_2)(C_1-C_8)$alkylene, $(H_2NSO_2)(C_1-C_8)$alkylene, optionally substituted $di((C_1-C_8)$alkyl)amino;
or $R^{10}$ and $R^{11}$, $R^{11}$ and $R^{12}$, or $R^{12}$ and $R^{13}$, taken together with the intervening atoms, form an aryl, heteroaryl, cycloalkyl, or heterocycloalkyl group;
$R^{14}$ is H or $(C_1-C_6)$alkyl;
$R^{15}$ is optionally substituted $(C_3-C_{10})$cycloalkyl or $(C_3-C_{10})$cycloalkenyl;

represents a heterocyclic group substituted by oxo (=O) and optionally substituted by one or more additional substituents; and
n is an integer from 1-3.

In certain embodiments of the compounds of formula (II) and (II'), at least three of $R^{10}$, $R^{11}$, $R^{12}$, and $R^{13}$ are H. For example, $R^{10}$, $R^{11}$, $R^{12}$, and $R^{13}$ may each be H.

In certain embodiments, $R^{14}$ is H. Alternatively, $R^{14}$ may be $(C_1-C_6)$alkyl, e.g., methyl.

In certain embodiments, $R^{15}$ is optionally substituted cyclohexyl or cyclohexenyl. In some preferred embodiments, $R^{15}$ is optionally substituted cyclohexyl.

In certain embodiments,

represents optionally substituted oxazolidinone.

For example,

may represent

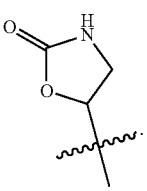

Alternatively,

may represent

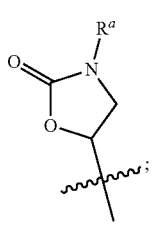

and $R^a$ may represent $(C_3-C_{10})$cycloalkyl or $(C_1-C_8)$alkyl.

In further aspects, the invention provides a compound of formula (III'):

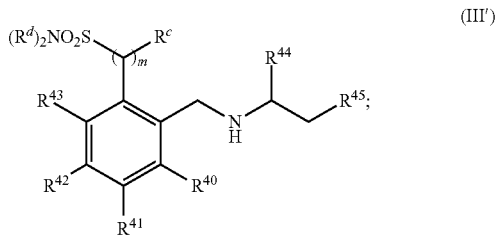

or a pharmaceutically acceptable salt thereof;

wherein:

each of $R^{40}$, $R^{41}$, $R^{42}$, and $R^{43}$ is independently selected from H, OH, —$NH_2$, halide, sulfonamido, $(C_1-C_6)$alkylsulfonyl, —OC(O)(($C_1-C_8$)alkyl), —C(O)O(($C_1-C_8$)alkyl), —C(O)OH, optionally substituted —NHC(O)(aryl), —C(O)$NH_2$, —B(OH)$_2$, tri(($C_1-C_8$)alkyl)silyl, optionally substituted $(C_1-C_8)$alkyl, optionally substituted $(C_1-C_8)$alkoxy, optionally substituted $(C_1-C_8)$aminoalkyl, optionally substituted $(C_1-C_8)$hydroxyalkyl, optionally substituted $(C_1-C_8)$haloalkyl, optionally substituted $(C_1-C_8)$haloalkoxy, optionally substituted aryl, optionally substituted heteroaryl, optionally substituted aryloxy, optionally substituted arylalkoxy, optionally substituted heteroaryloxy, optionally substituted heteroarylalkoxy, optionally substituted $(C_3-C_{10})$cycloalkyl, optionally substituted $(C_3-C_{10})$cycloalkoxy, optionally substituted $(C_2-C_9)$heterocycloalkyl, optionally substituted $(C_2-C_9)$heterocycloalkoxy, $(H_3CSO_2)(C_1-C_8)$alkylene, $(H_2NSO_2)(C_1-C_8)$alkylene, optionally substituted di(($C_1-C_8$)alkyl)amino;

or $R^{40}$ and $R^{41}$, $R^{41}$ and $R^{42}$, or $R^{42}$ and $R^{43}$, taken together with the intervening atoms, form an aryl, heteroaryl, cycloalkyl, or heterocycloalkyl group;

$R^{44}$ is H or $(C_1-C_6)$alkyl;

$R^{45}$ is optionally substituted $(C_3-C_{10})$cycloalkyl or $(C_3-C_{10})$cycloalkenyl;

$R^c$, independently for each occurrence, is selected from H, $(C_1-C_8)$alkyl, $(C_1-C_8)$haloalkyl, $(C_1-C_8)$alkoxyl, $(C_1-C_3)$hydroxyalkyl, $(C_3-C_{10})$cycloalkyl, $(C_3-C_{10})$cycloalkyl($C_1-C_8$)alkyl, aryl, and aryl($C_1-C_8$) alkyl;

$R^d$, independently for each occurrence, is selected from H, optionally substituted —C(O)alkyl, optionally substituted —C(O)NH—$(C_3-C_{10})$cycloalkyl, optionally substituted $(C_1-C_8)$alkyl, optionally substituted $(C_1-C_8)$haloalkyl, optionally substituted $(C_1-C_8)$hydroxyalkyl, optionally substituted $(C_3-C_{10})$cycloalkyl, optionally substituted heterocyclyl, optionally substituted $(C_3-C_{10})$cycloalkyl($C_1-C_8$)alkyl, optionally substituted aryl, and optionally substituted aryl($C_1-C_8$) alkyl, or two $R^d$ are taken together with the nitrogen atom to which they are attached to form an optionally substituted 5-6-membered heterocyclyl; and m is an integer from 1-3.

In other aspects, the invention provides a compound of formula (III):

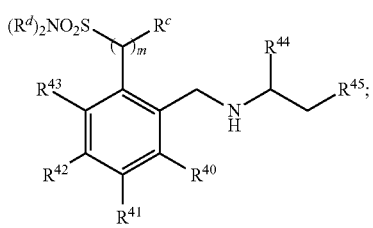

(III)

or a pharmaceutically acceptable salt thereof;
wherein:
each of $R^{40}$, $R^{41}$, $R^{42}$, and $R^{43}$ is independently selected from H, OH, —NH$_2$, halide, sulfonamido, (C$_1$-C$_6$) alkylsulfonyl, —OC(O)((C$_1$-C$_8$)alkyl), —C(O)O((C$_1$-C$_8$)alkyl), —C(O)OH, optionally substituted —NHC(O)(aryl), —C(O)NH$_2$, —B(OH)$_2$, tri((C$_1$-C$_8$)alkyl) silyl, optionally substituted (C$_1$-C$_8$)alkyl, optionally substituted (C$_1$-C$_8$)alkoxy, optionally substituted (C$_1$-C$_8$)aminoalkyl, optionally substituted (C$_1$-C$_8$)hydroxyalkyl, optionally substituted (C$_1$-C$_8$)haloalkyl, optionally substituted (C$_1$-C$_8$)haloalkoxy, optionally substituted aryl, optionally substituted heteroaryl, optionally substituted aryloxy, optionally substituted arylalkoxy, optionally substituted heteroaryloxy, optionally substituted heteroarylalkoxy, optionally substituted (C$_3$-C$_{10}$)cycloalkyl, optionally substituted (C$_3$-C$_{10}$)cycloalkoxy, optionally substituted (C$_2$-C$_9$)heterocycloalkyl, optionally substituted (C$_2$-C$_9$) heterocycloalkoxy, (H$_3$CSO$_2$)(C$_1$-C$_8$)alkylene, (H$_2$NSO$_2$)(C$_1$-C$_8$)alkylene, optionally substituted di((C$_1$-C$_8$)alkyl)amino;
or $R^{40}$ and $R^{41}$, $R^{41}$ and $R^{42}$, or $R^{42}$ and $R^{43}$, taken together with the intervening atoms, form an aryl, heteroaryl, cycloalkyl, or heterocycloalkyl group;
$R^{44}$ is H or (C$_1$-C$_6$)alkyl;
$R^{45}$ is optionally substituted (C$_3$-C$_{10}$)cycloalkyl or (C$_3$-C$_{10}$)cycloalkenyl;
$R^c$, independently for each occurrence, is selected from H, (C$_1$-C$_8$)alkyl, (C$_1$=h-C$_8$)haloalkyl, (C$_1$-C$_8$)alkoxyl, (C$_1$-C$_8$)hydroxyalkyl, (C$_3$-C$_{10}$)cycloalkyl, (C$_3$-C$_{10}$)cycloalkyl(C$_1$-C$_8$)alkyl, aryl, and aryl(C$_1$-C$_8$) alkyl;
$R^d$, independently for each occurrence, is selected from H, optionally substituted (C$_1$-C$_8$)alkyl, optionally substituted (C$_1$-C$_8$)haloalkyl, optionally substituted (C$_1$-C$_8$) hydroxyalkyl, optionally substituted (C$_3$-C$_{10}$)cycloalkyl, optionally substituted (C$_3$-C$_{10}$)cycloalkyl(C$_1$-C$_8$) alkyl, optionally substituted aryl, and optionally substituted aryl(C$_1$-C$_8$) alkyl; and m is an integer from 1-3.

In certain embodiments of the compounds of formula (III), at least three of $R^{40}$, $R^{41}$, $R^{42}$, and $R^{43}$ are H. For example, $R^{40}$, $R^{41}$, $R^{42}$, and $R^{43}$ may each be H.

In certain embodiments, $R^{44}$ is H. Alternatively, $R^{44}$ may be (C$_1$-C$_6$)alkyl, e.g., methyl.

In certain embodiments, $R^{45}$ is optionally substituted cyclohexyl or cyclohexenyl.

In some preferred embodiments, $R^{45}$ is optionally substituted cyclohexyl.

In certain embodiments, $R^c$ is H.

In certain embodiments, $R^d$, independently for each occurrence, is selected from H and (C$_1$-C$_8$)alkyl, preferably H. In other embodiments, each $R^d$ is methyl. In certain embodiments, one $R^d$ is methyl or ethyl and the other $R^d$ is H.

In certain embodiments, one $R^d$ is optionally substituted —C(O)alkyl, such as —C(O)CH(NH$_2$)CH$_2$CHMe$_2$. In other embodiments, one $R^d$ is —C(O)NH—(C$_3$-C$_{10}$)cycloalkyl, such as —C(O)NH-cyclohexyl, optionally substituted with methyl.

In certain embodiments, one $R^d$ is optionally substituted (C$_1$-C$_8$)alkyl, such as —CH$_2$CH(OH)CH$_2$OH. In other embodiments, one $R^d$ is —CH$_2$CH(OH)CH$_2$OH and the other $R^d$ is methyl. In certain embodiments, one $R^d$ is —CH$_2$C(O)NHCH$_2$COOH. In some embodiments, one $R^d$ is —CH$_2$CH$_2$OMe. In certain embodiments, one $R^d$ is —CH$_2$COOH. In other embodiments, one $R^d$ is —CH(Me)COOH. In other embodiments, one $R^d$ is —CH$_2$-heterocyclyl, such as —CH$_2$-furanyl.

In certain embodiments, one $R^d$ is optionally substituted cycloalkyl, such as 3-COOHcyclobutyl. In other embodiments, one $R^d$ is optionally substituted aryl, such as 3-(B(OH$_3$))-phenyl. In certain embodiments, one $R^d$ is optionally substituted heterocyclyl, such as N-methylpiperidinyl.

In certain embodiments, both $R^d$ are taken together with the nitrogen atom to which they are attached to form an optionally substituted 5-6-membered heterocyclyl, such as an N-methylpiperizinyl.

In some aspects, the invention provides a compound, or a pharmaceutically acceptable salt thereof, selected from Table 1:

TABLE 1

Compounds of the Invention

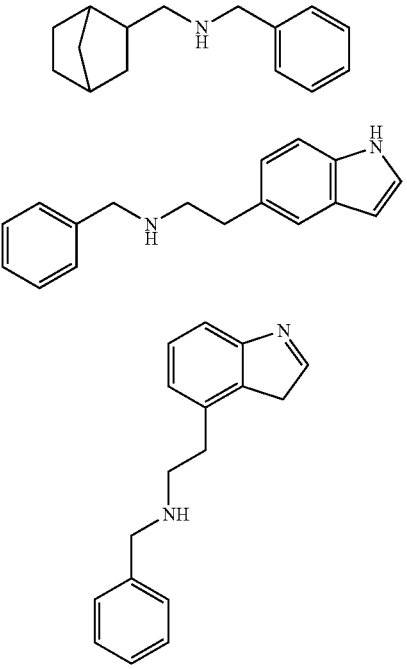

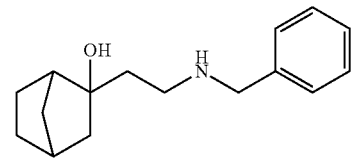 [SMILES: OC1(CCNCc2ccccc2)CC2CCC1C2]

TABLE 1-continued

Compounds of the Invention

TABLE 1-continued

Compounds of the Invention

TABLE 1-continued
Compounds of the Invention
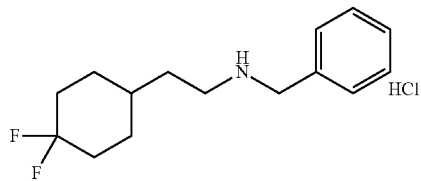 [SMILES: FC1(F)CCC(CCNCc2ccccc2)CC1 ; Cl]
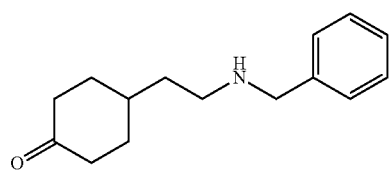 [SMILES: O=C1CCC(CCNCc2ccccc2)CC1]
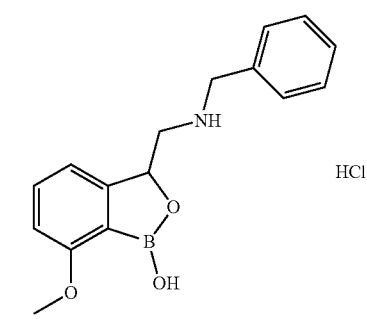 [SMILES: COc1cccc2c1B(O)OC2CNCc1ccccc1 ; Cl]
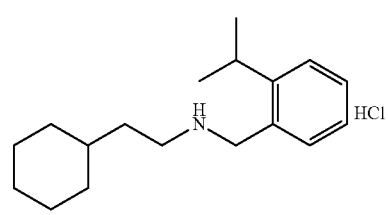 [SMILES: CC(C)c1ccccc1CNCCC1CCCCC1 ; Cl]
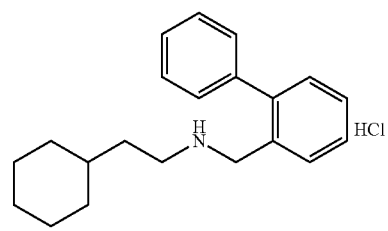 [SMILES: c1ccc(-c2ccccc2CNCCC2CCCCC2)cc1 ; Cl]
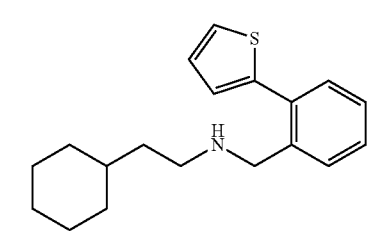 [SMILES: c1csc(-c2ccccc2CNCCC2CCCCC2)c1]
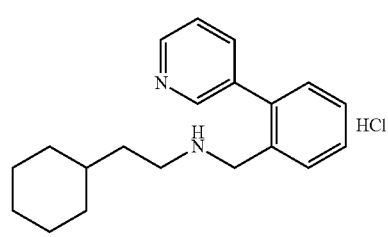 [SMILES: c1cncc(-c2ccccc2CNCCC2CCCCC2)c1 ; Cl]
TABLE 1-continued
Compounds of the Invention
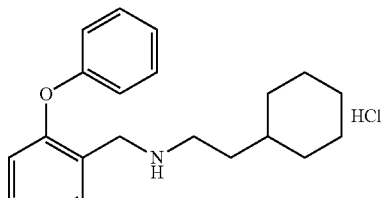
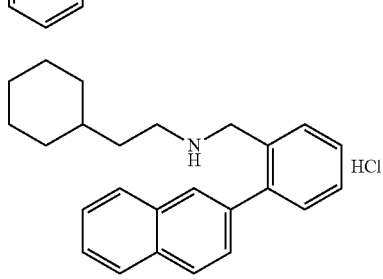
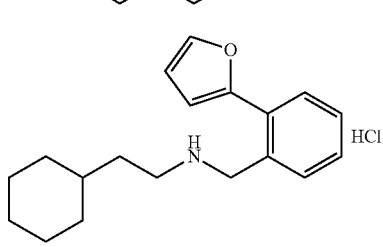
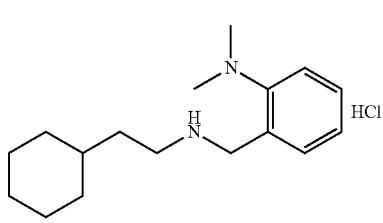 [SMILES: CN(C)c1ccccc1CNCCC1CCCCC1 ; Cl]
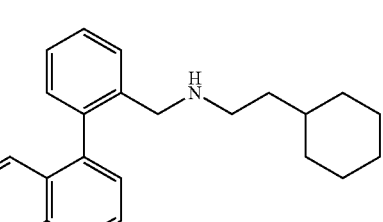
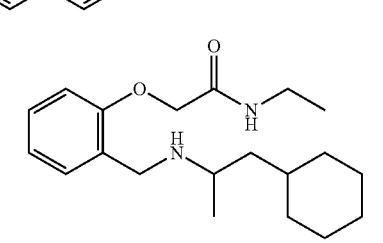
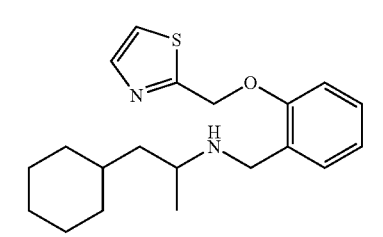 [SMILES: CC(CC1CCCCC1)NCc1ccccc1OCc1nccs1]

TABLE 1-continued
Compounds of the Invention
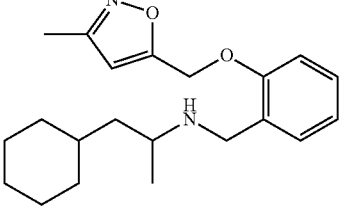
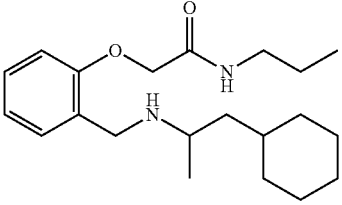 [SMILES: CCCNC(=O)COc1ccccc1CNC(C)CC1CCCCC1]
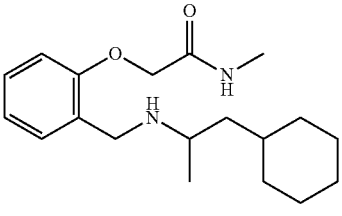 [SMILES: CNC(=O)COc1ccccc1CNC(C)CC1CCCCC1]
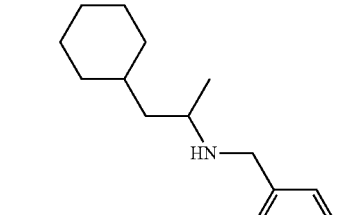
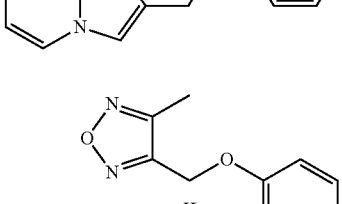
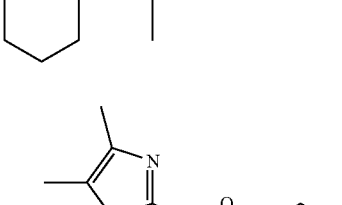
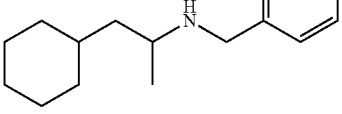
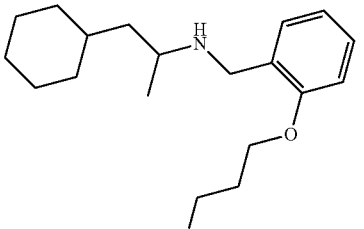
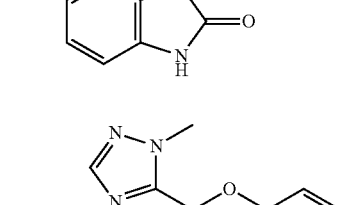
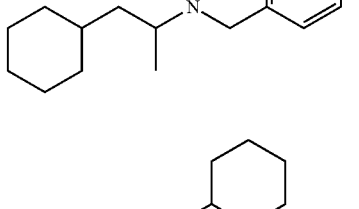
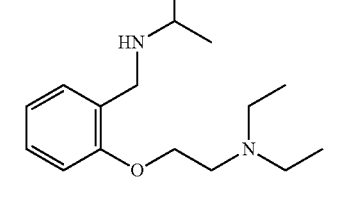
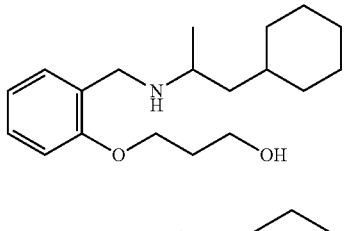
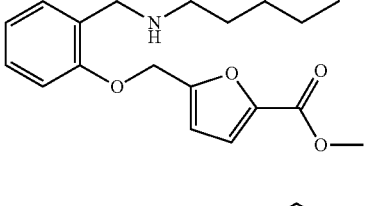
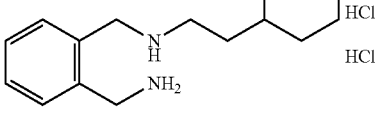

TABLE 1-continued

Compounds of the Invention

TABLE 1-continued

Compounds of the Invention

TABLE 1-continued
Compounds of the Invention
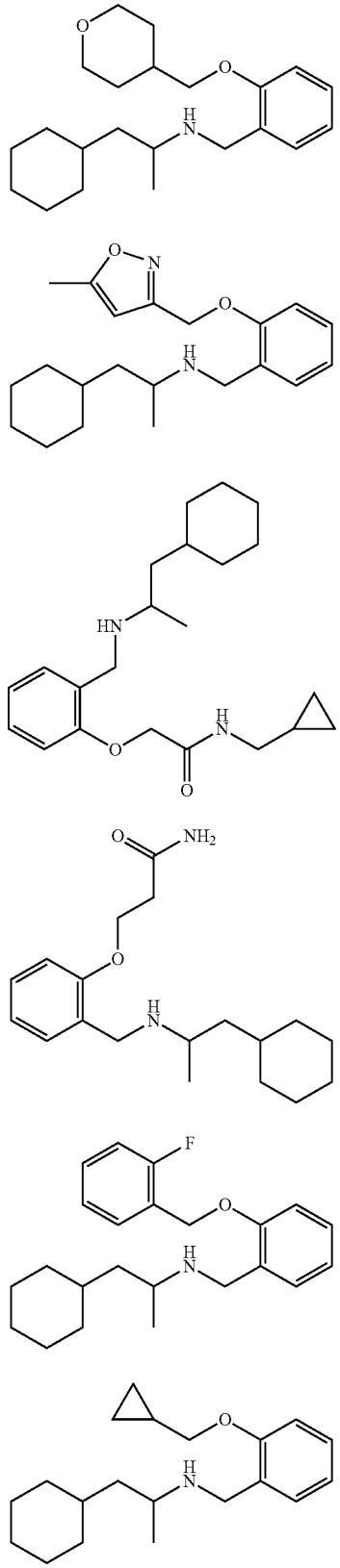
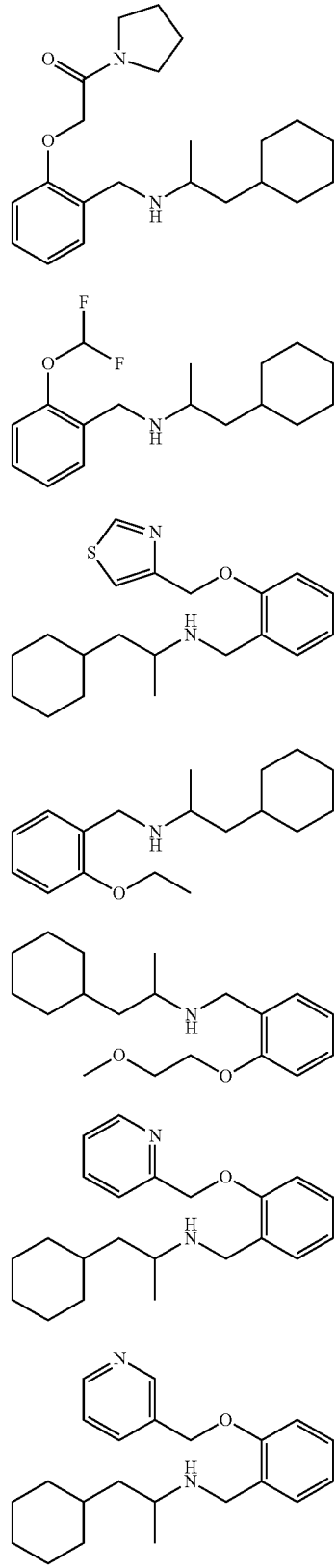

TABLE 1-continued
Compounds of the Invention
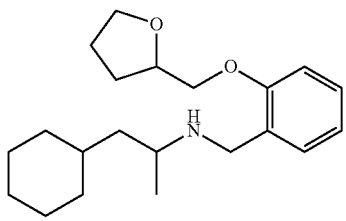 [SMILES: CC(CC1CCCCC1)NCc1ccccc1OCC1CCCO1]
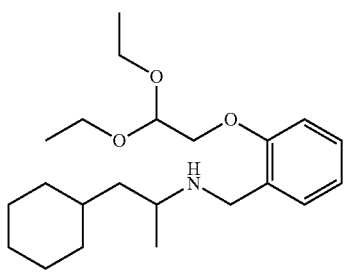 [SMILES: CCOC(COc1ccccc1CNC(C)CC1CCCCC1)OCC]
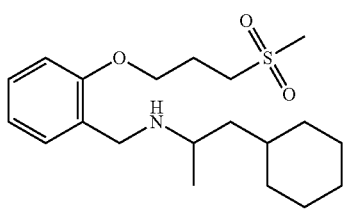 [SMILES: CC(CC1CCCCC1)NCc1ccccc1OCCCS(C)(=O)=O]
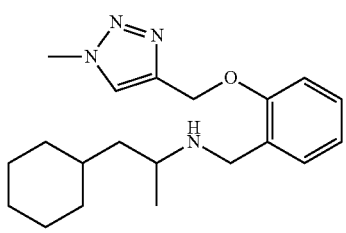 [SMILES: CC(CC1CCCCC1)NCc1ccccc1OCc1cn(C)nn1]
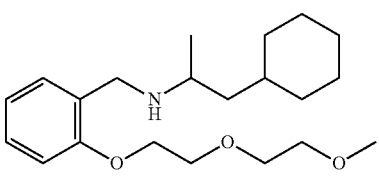 [SMILES: COCCOCCOc1ccccc1CNC(C)CC1CCCCC1]
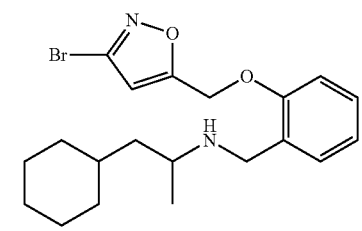 [SMILES: CC(CC1CCCCC1)NCc1ccccc1OCc1cc(Br)no1]
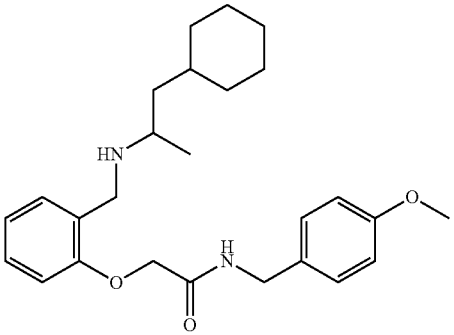 [SMILES: COc1ccc(CNC(=O)COc2ccccc2CNC(C)CC2CCCCC2)cc1]
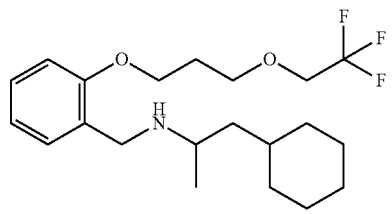 [SMILES: CC(CC1CCCCC1)NCc1ccccc1OCCCOCC(F)(F)F]
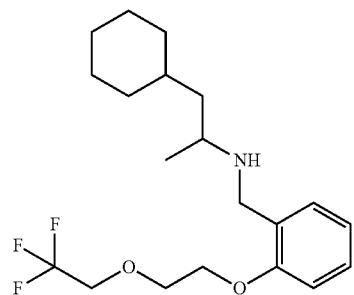 [SMILES: CC(CC1CCCCC1)NCc1ccccc1OCCOCC(F)(F)F]
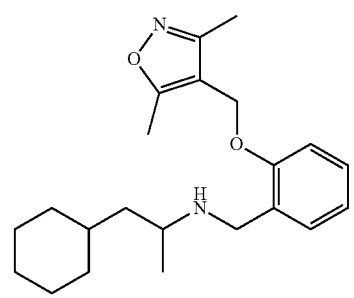 [SMILES: Cc1noc(C)c1COc1ccccc1CNC(C)CC1CCCCC1]
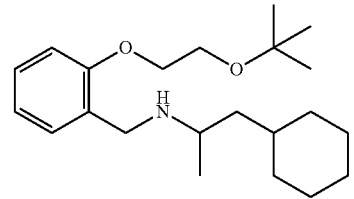 [SMILES: CC(CC1CCCCC1)NCc1ccccc1OCCOC(C)(C)C]
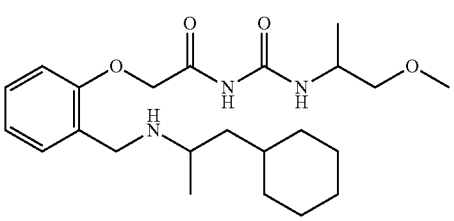 [SMILES: COCC(C)NC(=O)NC(=O)COc1ccccc1CNC(C)CC1CCCCC1]

TABLE 1-continued
Compounds of the Invention
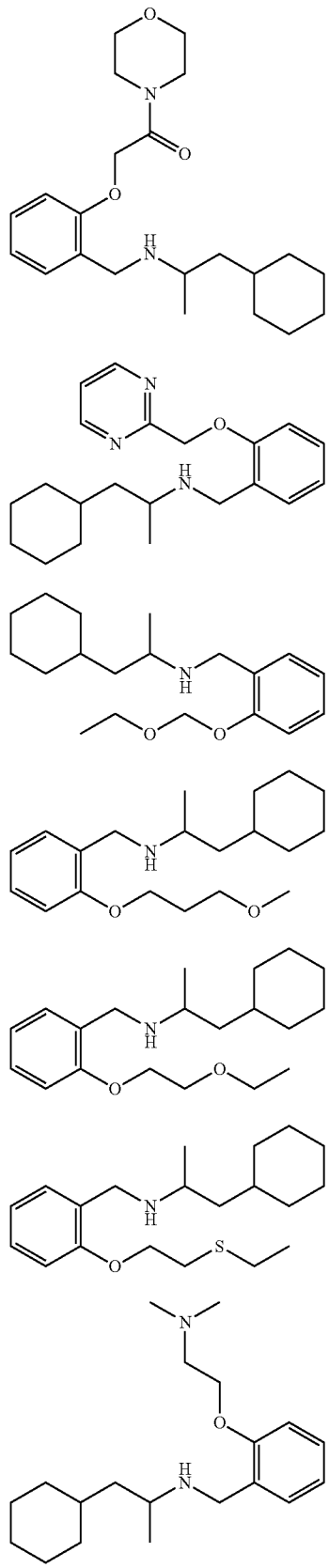
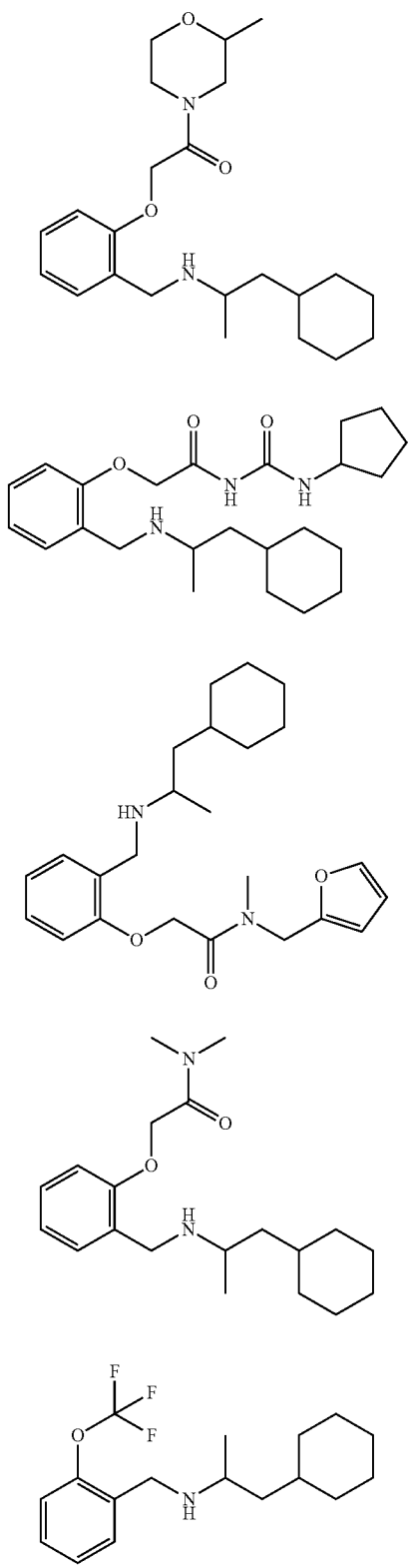

TABLE 1-continued
Compounds of the Invention
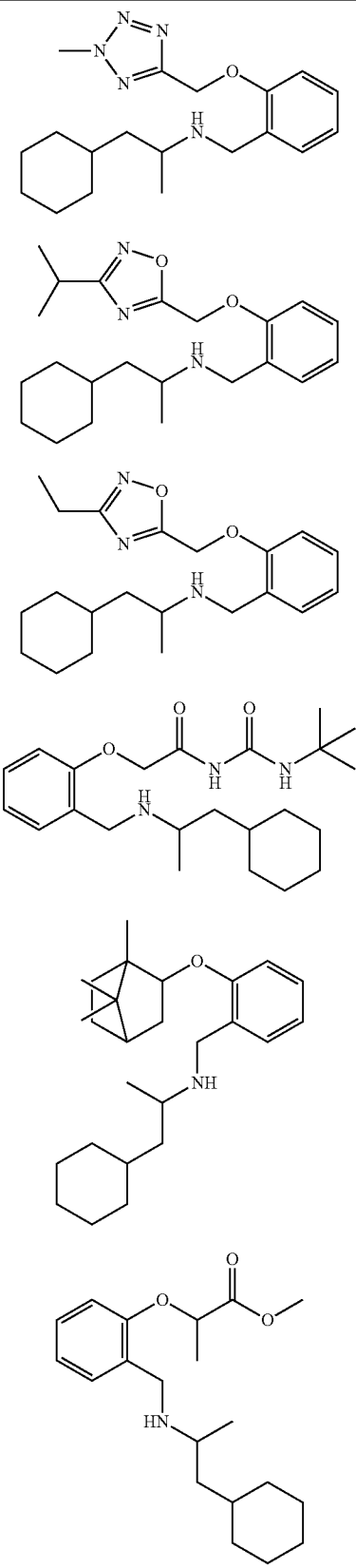
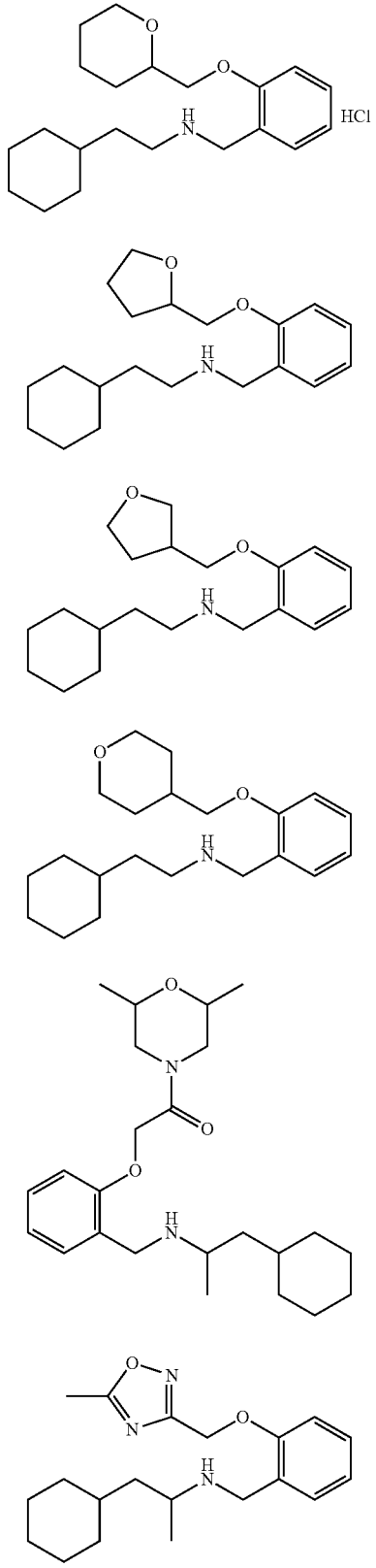

TABLE 1-continued

Compounds of the Invention

TABLE 1-continued
Compounds of the Invention
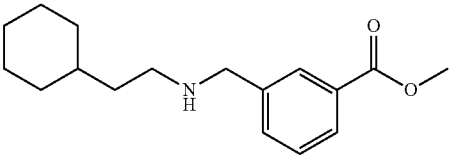 [SMILES: COC(=O)c1cccc(CNCCC2CCCCC2)c1]
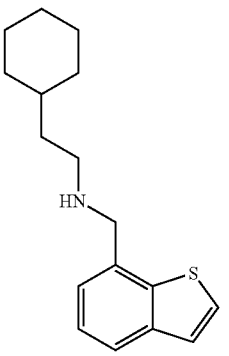 [SMILES: c1cc(CNCCC2CCCCC2)c2sccc2c1]
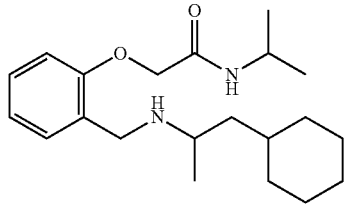 [SMILES: CC(C)NC(=O)COc1ccccc1CNC(C)CC1CCCCC1]
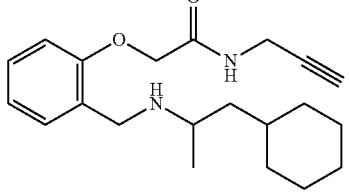
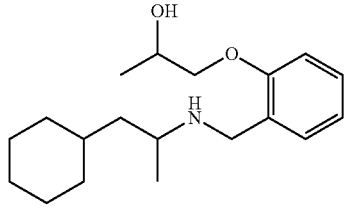 [SMILES: CC(O)COc1ccccc1CNC(C)CC1CCCCC1]
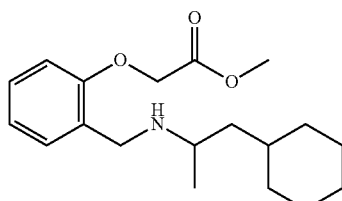
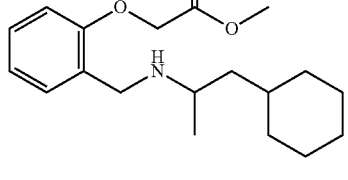
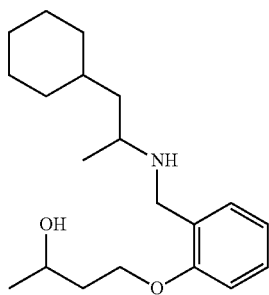 [SMILES: CC(O)CCOc1ccccc1CNC(C)CC1CCCCC1]
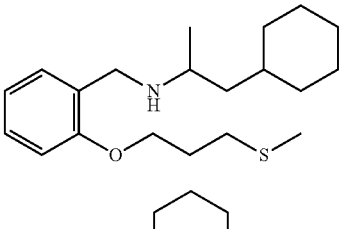
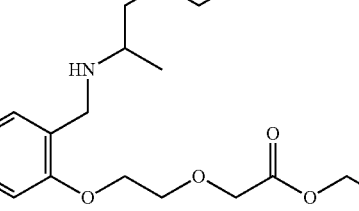
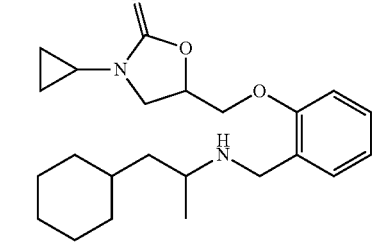
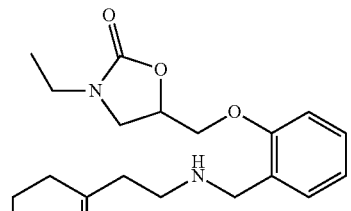
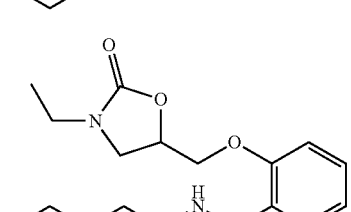
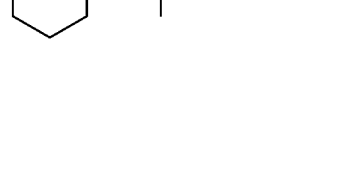

TABLE 1-continued
Compounds of the Invention
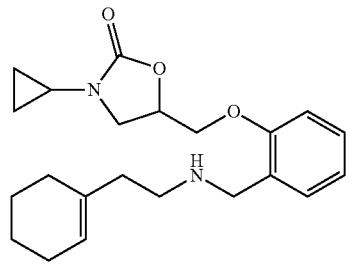 [SMILES: O=C1OC(COc2ccccc2CNCCC2=CCCCC2)CN1C1CC1]
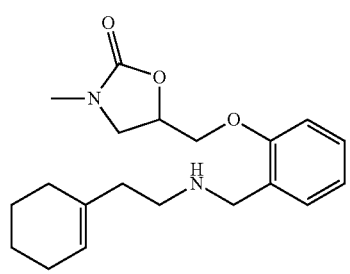 [SMILES: CN1CC(COc2ccccc2CNCCC2=CCCCC2)OC1=O]
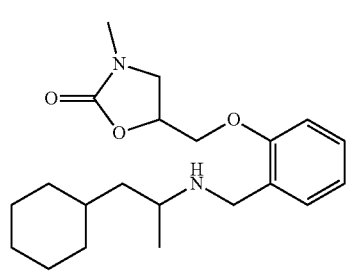 [SMILES: CC(CC1CCCCC1)NCc1ccccc1OCC1CN(C)C(=O)O1]
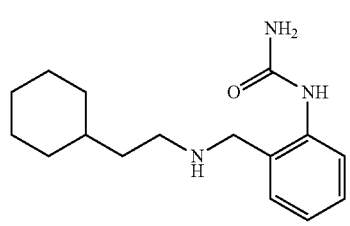
HCl
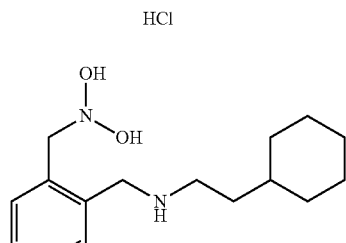
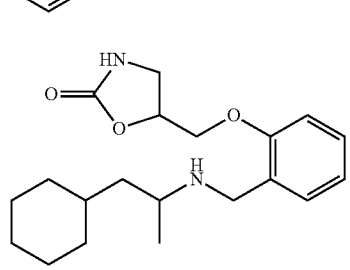
TABLE 1-continued
Compounds of the Invention
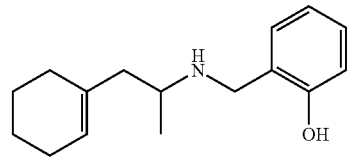 [SMILES: CC(CC1=CCCCC1)NCc1ccccc1O]
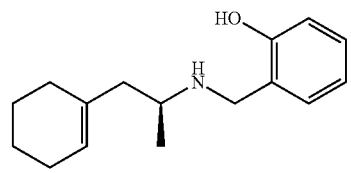 [SMILES: C[C@@H](CC1=CCCCC1)NCc1ccccc1O]
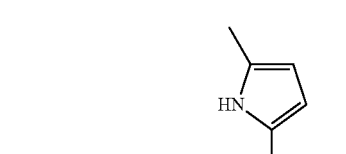
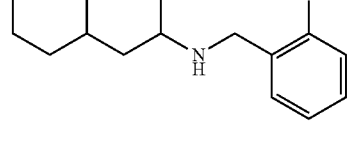
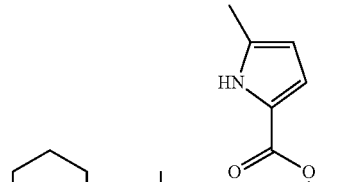
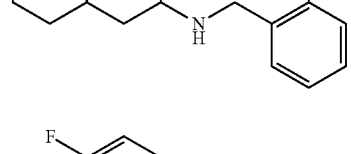

TABLE 1-continued

Compounds of the Invention

TABLE 1-continued

Compounds of the Invention

TABLE 1-continued
Compounds of the Invention
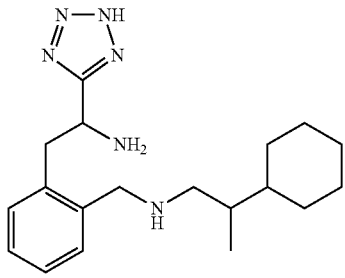 [SMILES: CC(CNCc1ccccc1CC(N)c1nn[nH]n1)C1CCCCC1]
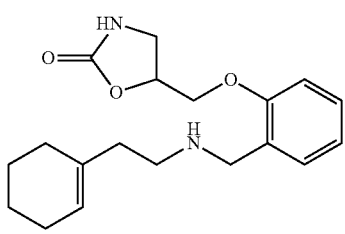 [SMILES: O=C1NCC(COc2ccccc2CNCCC2=CCCCC2)O1]
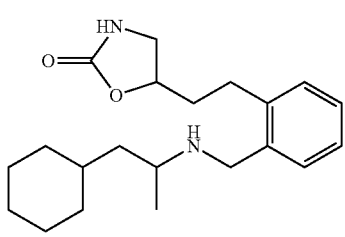 [SMILES: CC(CC1CCCCC1)NCc1ccccc1CCC1CNC(=O)O1]
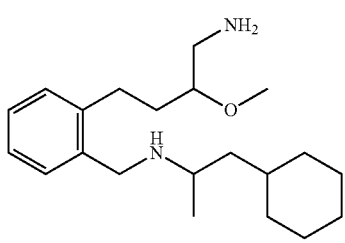 [SMILES: COC(CN)CCc1ccccc1CNC(C)CC1CCCCC1]
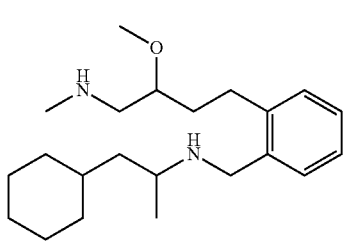 [SMILES: CNCC(CCc1ccccc1CNC(C)CC1CCCCC1)OC]
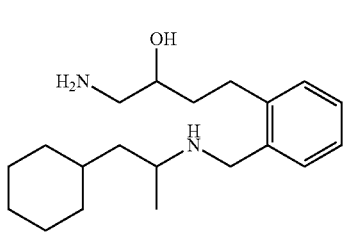 [SMILES: CC(CC1CCCCC1)NCc1ccccc1CCC(O)CN]

TABLE 1-continued
Compounds of the Invention
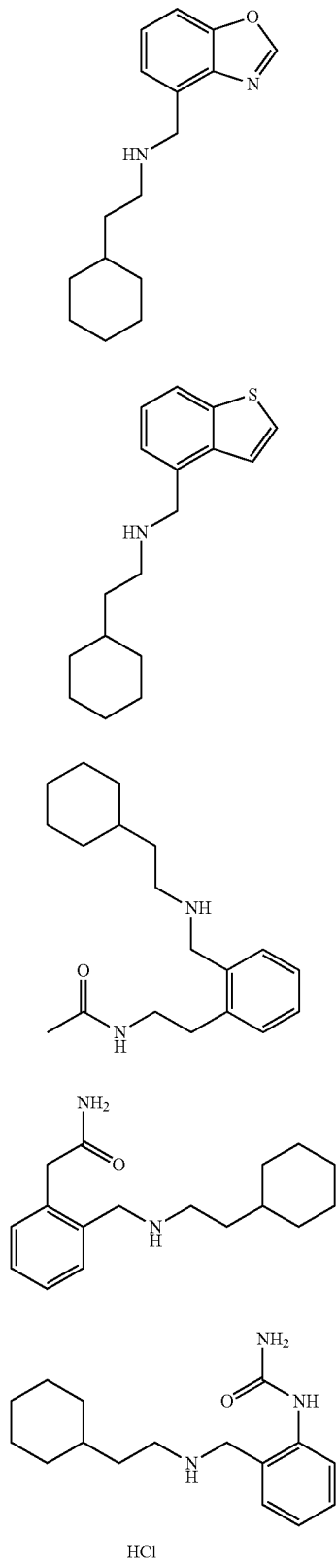
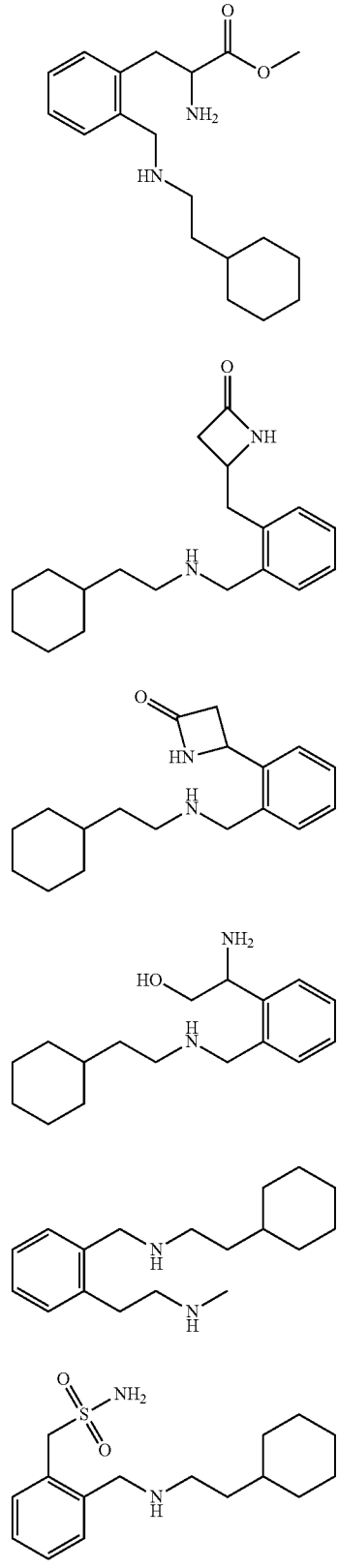

TABLE 1-continued
Compounds of the Invention
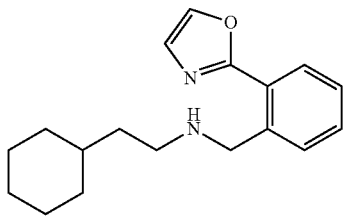 [SMILES: c1ccc(-c2ncco2)c(CNCCC2CCCCC2)c1]
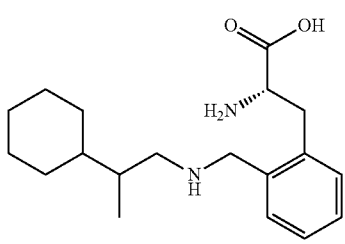 [SMILES: CC(CNCc1ccccc1C[C@H](N)C(=O)O)C1CCCCC1]
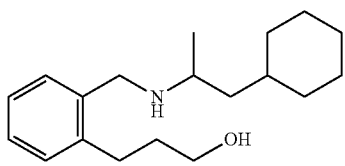 [SMILES: CC(CC1CCCCC1)NCc1ccccc1CCCO]
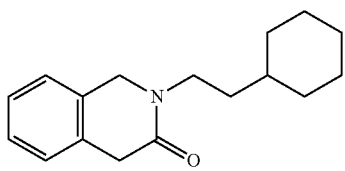
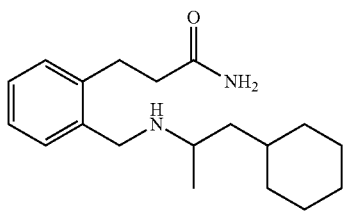 [SMILES: CC(CC1CCCCC1)NCc1ccccc1CCC(N)=O]
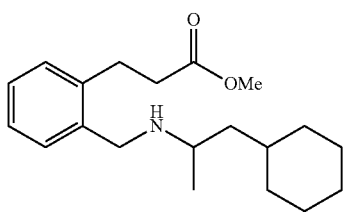 [SMILES: COC(=O)CCc1ccccc1CNC(C)CC1CCCCC1]
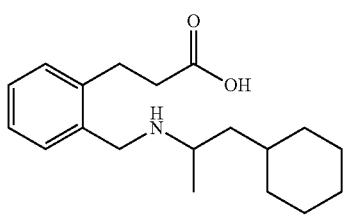 [SMILES: CC(CC1CCCCC1)NCc1ccccc1CCC(=O)O]
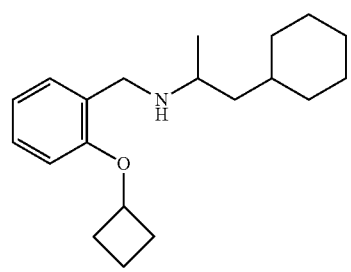 [SMILES: CC(CC1CCCCC1)NCc1ccccc1OC1CCC1]
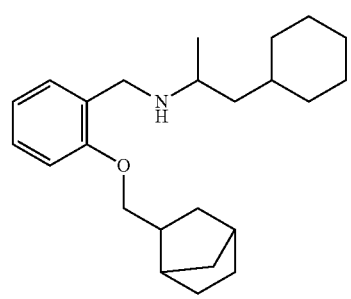 [SMILES: CC(CC1CCCCC1)NCc1ccccc1OCC1CC2CCC1C2]
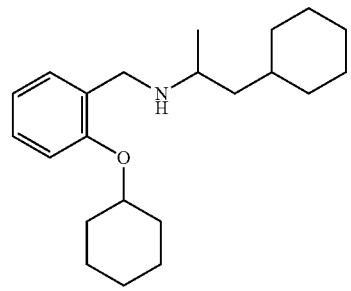 [SMILES: CC(CC1CCCCC1)NCc1ccccc1OC1CCCCC1]
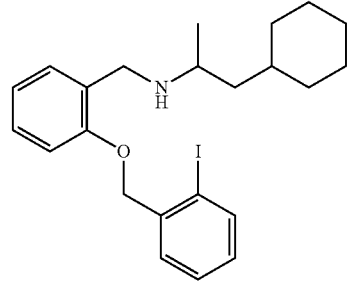 [SMILES: CC(CC1CCCCC1)NCc1ccccc1OCc1ccccc1I]
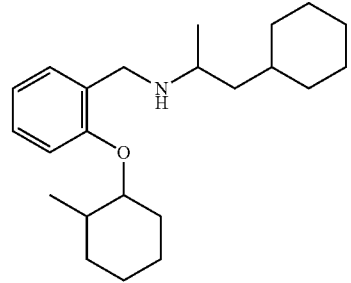 [SMILES: CC(CC1CCCCC1)NCc1ccccc1OC1CCCCC1C]

TABLE 1-continued
Compounds of the Invention
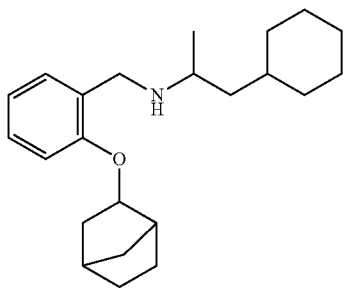 [SMILES: CC(CC1CCCCC1)NCc1ccccc1OC1CC2CCC1C2]
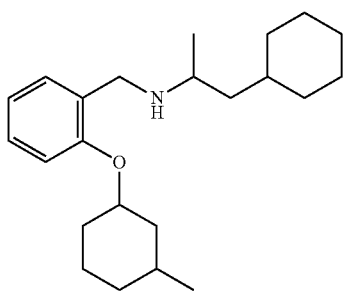 [SMILES: CC1CCCC(Oc2ccccc2CNC(C)CC2CCCCC2)C1]
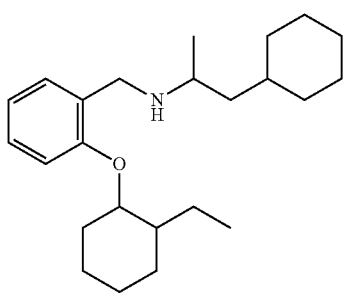 [SMILES: CCC1CCCCC1Oc1ccccc1CNC(C)CC1CCCCC1]
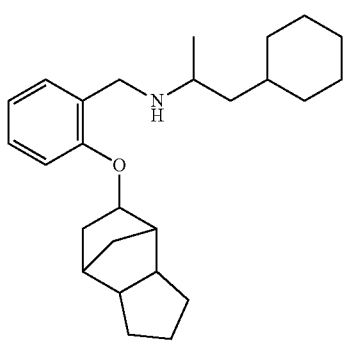 [SMILES: CC(CC1CCCCC1)NCc1ccccc1OC1CC2CC1C1CCCC21]
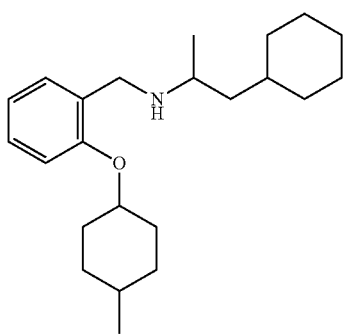 [SMILES: CC1CCC(Oc2ccccc2CNC(C)CC2CCCCC2)CC1]
TABLE 1-continued
Compounds of the Invention
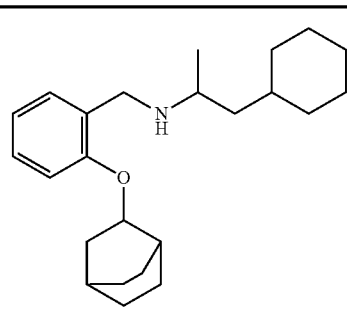
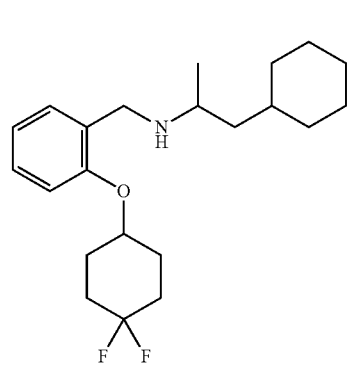 [SMILES: CC(CC1CCCCC1)NCc1ccccc1OC1CCC(F)(F)CC1]
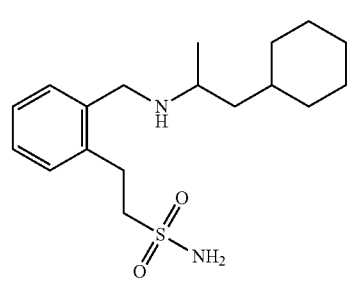 [SMILES: CC(CC1CCCCC1)NCc1ccccc1CCS(N)(=O)=O]
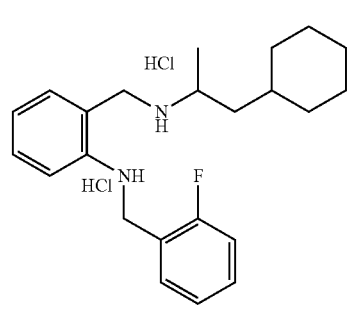 [SMILES: CC(CC1CCCCC1)NCc1ccccc1NCc1ccccc1F ; Cl ; Cl]
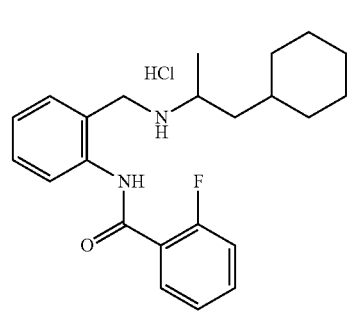 [SMILES: CC(CC1CCCCC1)NCc1ccccc1NC(=O)c1ccccc1F ; Cl]

TABLE 1-continued
Compounds of the Invention
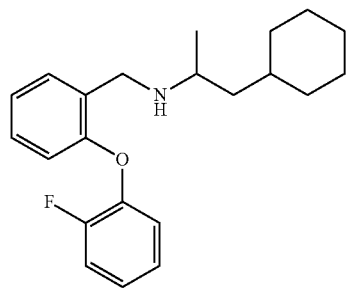 [SMILES: CC(CC1CCCCC1)NCc1ccccc1Oc1ccccc1F]
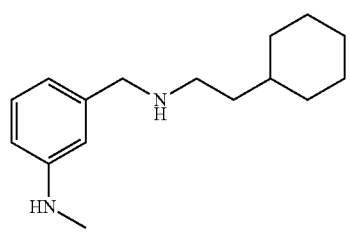 [SMILES: CNc1cccc(CNCCC2CCCCC2)c1]
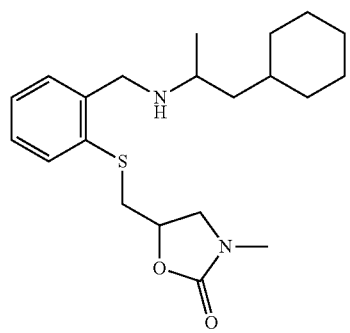 [SMILES: CC(CC1CCCCC1)NCc1ccccc1SCC1CN(C)C(=O)O1]
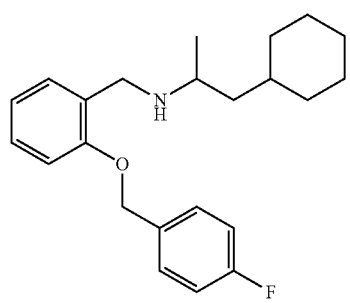 [SMILES: CC(CC1CCCCC1)NCc1ccccc1OCc1ccc(F)cc1]
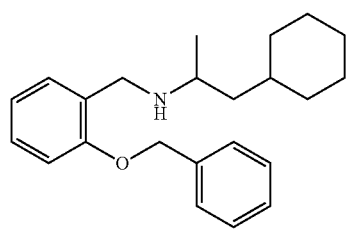 [SMILES: CC(CC1CCCCC1)NCc1ccccc1OCc1ccccc1]
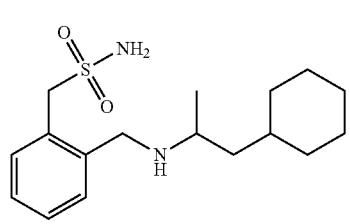 [SMILES: CC(CC1CCCCC1)NCc1ccccc1CS(N)(=O)=O]
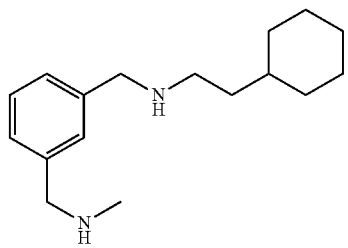 [SMILES: CNCc1cccc(CNCCC2CCCCC2)c1]
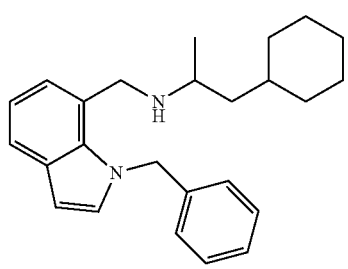 [SMILES: CC(CC1CCCCC1)NCc1cccc2ccn(Cc3ccccc3)c12]
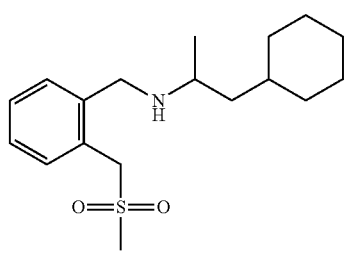 [SMILES: CC(CC1CCCCC1)NCc1ccccc1CS(C)(=O)=O]
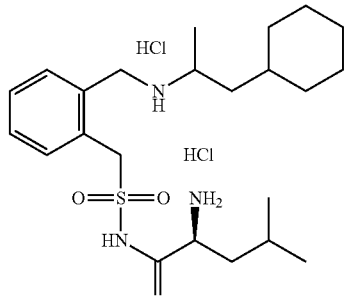
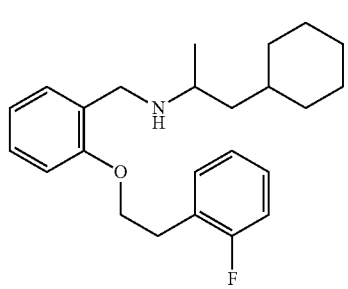 [SMILES: CC(CC1CCCCC1)NCc1ccccc1OCCc1ccccc1F]

TABLE 1-continued
Compounds of the Invention
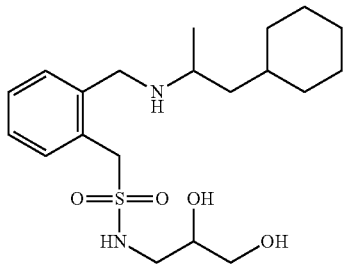 [SMILES: CC(CC1CCCCC1)NCc1ccccc1CS(=O)(=O)NCC(O)CO]
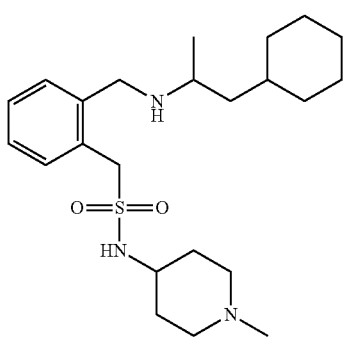 [SMILES: CC(CC1CCCCC1)NCc1ccccc1CS(=O)(=O)NC1CCN(C)CC1]
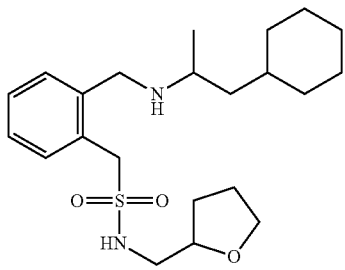 [SMILES: CC(CC1CCCCC1)NCc1ccccc1CS(=O)(=O)NCC1CCCO1]
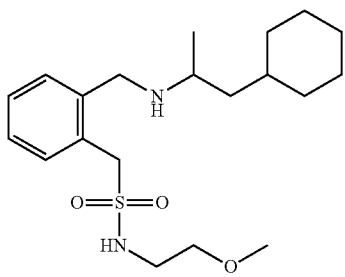 [SMILES: COCCNS(=O)(=O)Cc1ccccc1CNC(C)CC1CCCCC1]
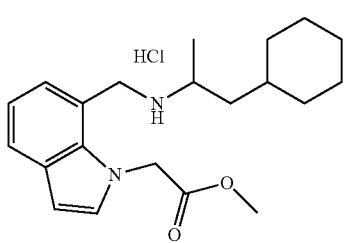 [SMILES: COC(=O)Cn1ccc2cccc(CNC(C)CC3CCCCC3)c21 ; Cl]
TABLE 1-continued
Compounds of the Invention
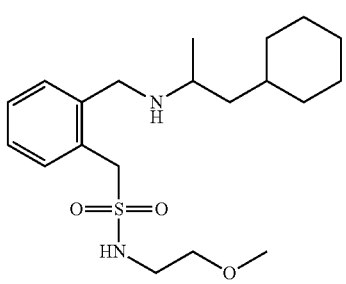 [SMILES: COCCNS(=O)(=O)Cc1ccccc1CNC(C)CC1CCCCC1]
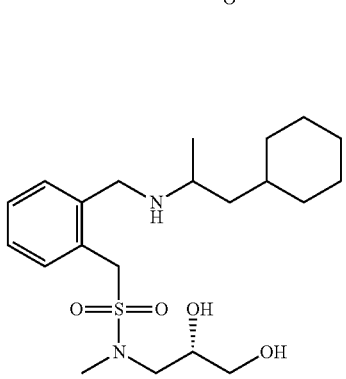
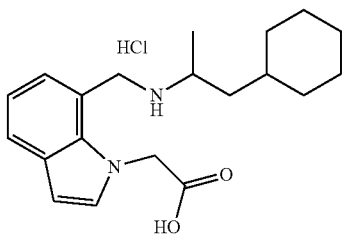 [SMILES: CC(CC1CCCCC1)NCc1cccc2ccn(CC(=O)O)c12 ; Cl]
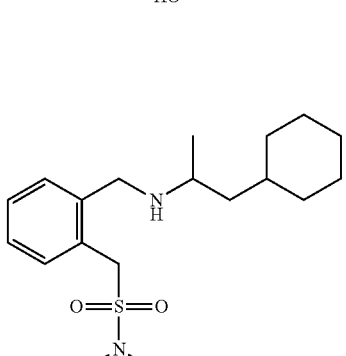
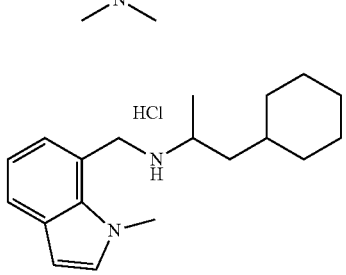

TABLE 1-continued
Compounds of the Invention
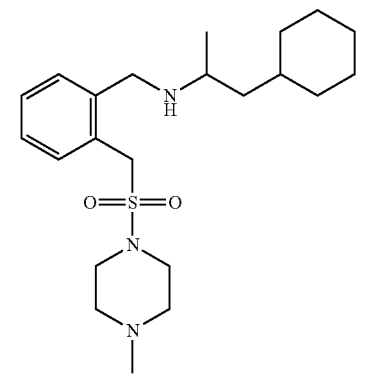 [SMILES: CC(CC1CCCCC1)NCc1ccccc1CS(=O)(=O)N1CCN(C)CC1]
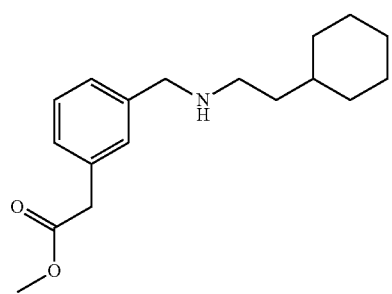 [SMILES: COC(=O)Cc1cccc(CNCCC2CCCCC2)c1]
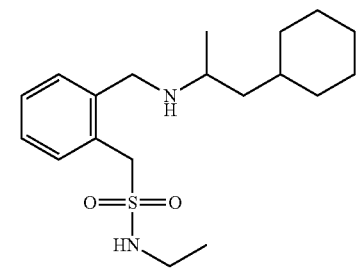 [SMILES: CCNS(=O)(=O)Cc1ccccc1CNC(C)CC1CCCCC1]
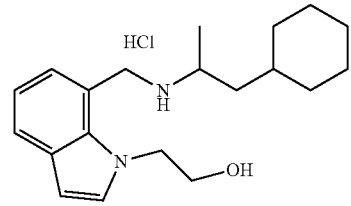 [SMILES: CC(CC1CCCCC1)NCc1cccc2ccn(CCO)c12 ; Cl]
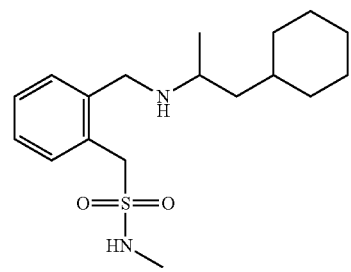 [SMILES: CNS(=O)(=O)Cc1ccccc1CNC(C)CC1CCCCC1]
TABLE 1-continued
Compounds of the Invention
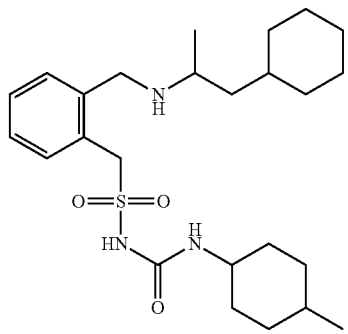 [SMILES: CC1CCC(NC(=O)NS(=O)(=O)Cc2ccccc2CNC(C)CC2CCCCC2)CC1]
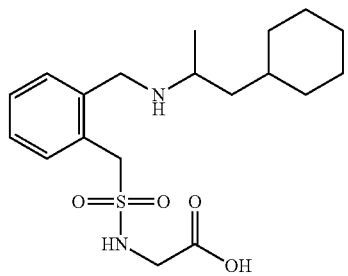 [SMILES: CC(CC1CCCCC1)NCc1ccccc1CS(=O)(=O)NCC(=O)O]
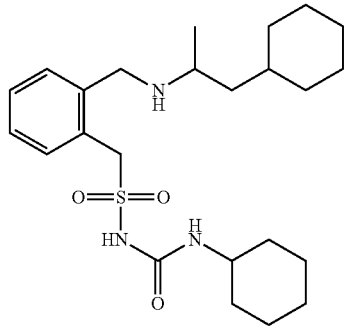 [SMILES: CC(CC1CCCCC1)NCc1ccccc1CS(=O)(=O)NC(=O)NC1CCCCC1]
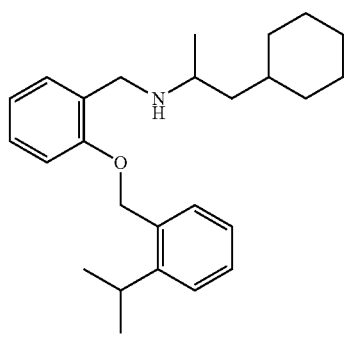 [SMILES: CC(CC1CCCCC1)NCc1ccccc1OCc1ccccc1C(C)C]
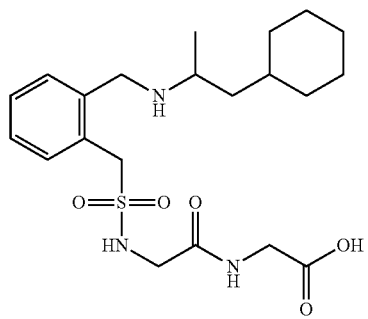 [SMILES: CC(CC1CCCCC1)NCc1ccccc1CS(=O)(=O)NCC(=O)NCC(=O)O]

TABLE 1-continued
Compounds of the Invention
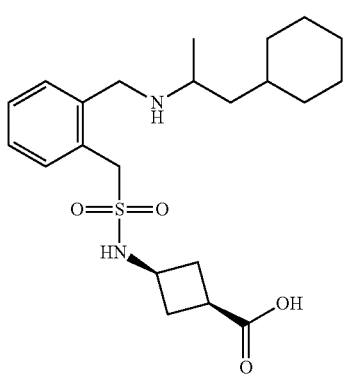 [SMILES: CC(CC1CCCCC1)NCc1ccccc1CS(=O)(=O)N[C@H]1C[C@@H](C(=O)O)C1]
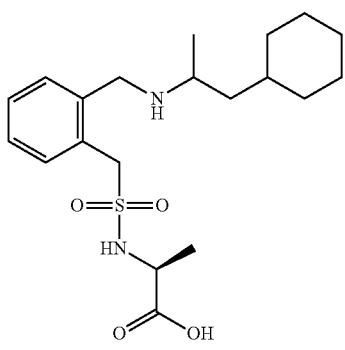 [SMILES: CC(CC1CCCCC1)NCc1ccccc1CS(=O)(=O)N[C@@H](C)C(=O)O]
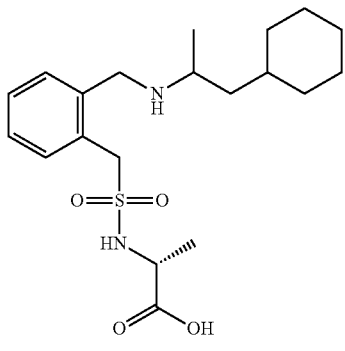 [SMILES: CC(CC1CCCCC1)NCc1ccccc1CS(=O)(=O)N[C@H](C)C(=O)O]
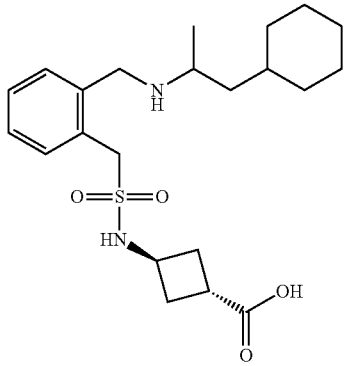 [SMILES: CC(CC1CCCCC1)NCc1ccccc1CS(=O)(=O)N[C@H]1C[C@H](C(=O)O)C1]
TABLE 1-continued
Compounds of the Invention
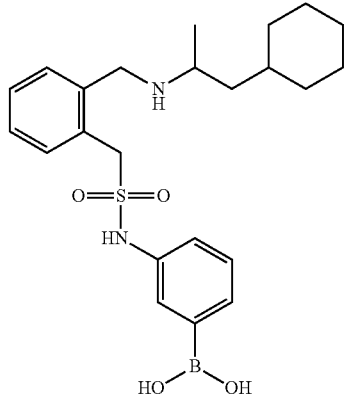 [SMILES: CC(CC1CCCCC1)NCc1ccccc1CS(=O)(=O)Nc1cccc(B(O)O)c1]
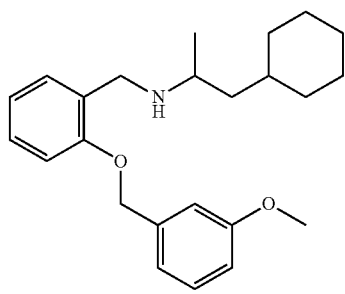 [SMILES: COc1cccc(COc2ccccc2CNC(C)CC2CCCCC2)c1]
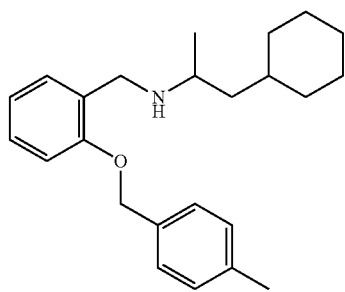 [SMILES: Cc1ccc(COc2ccccc2CNC(C)CC2CCCCC2)cc1]
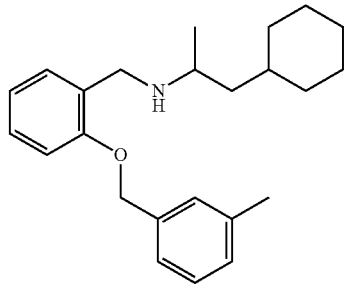 [SMILES: Cc1cccc(COc2ccccc2CNC(C)CC2CCCCC2)c1]
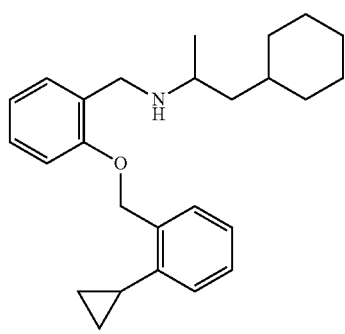 [SMILES: CC(CC1CCCCC1)NCc1ccccc1OCc1ccccc1C1CC1]

TABLE 1-continued
Compounds of the Invention
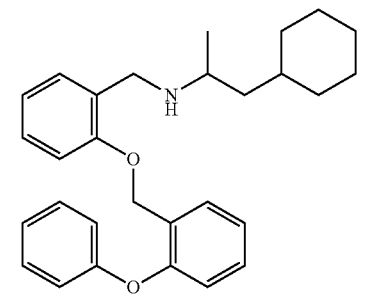 [SMILES: CC(CC1CCCCC1)NCc1ccccc1OCc1ccccc1Oc1ccccc1]
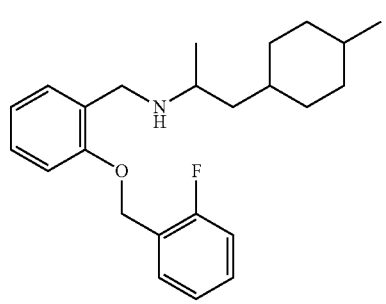 [SMILES: CC1CCC(CC(C)NCc2ccccc2OCc2ccccc2F)CC1]
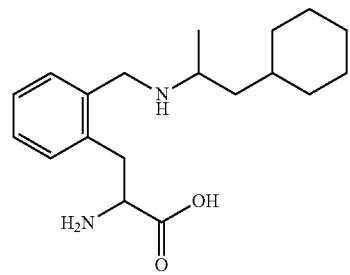 [SMILES: CC(CC1CCCCC1)NCc1ccccc1CC(N)C(=O)O]
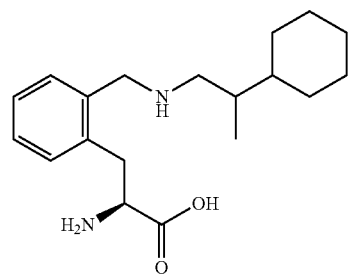 [SMILES: CC(CNCc1ccccc1C[C@H](N)C(=O)O)C1CCCCC1]
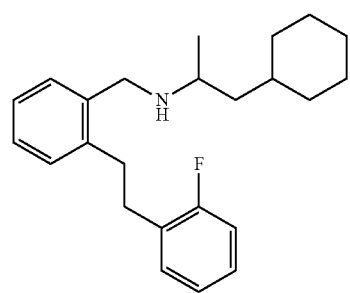 [SMILES: CC(CC1CCCCC1)NCc1ccccc1CCc1ccccc1F]
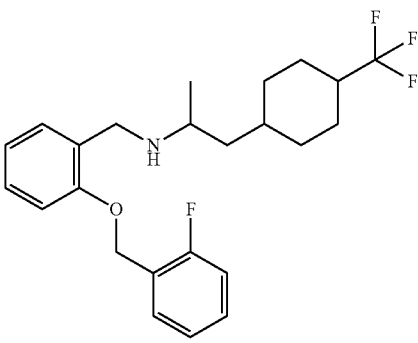 [SMILES: CC(CC1CCC(C(F)(F)F)CC1)NCc1ccccc1OCc1ccccc1F]
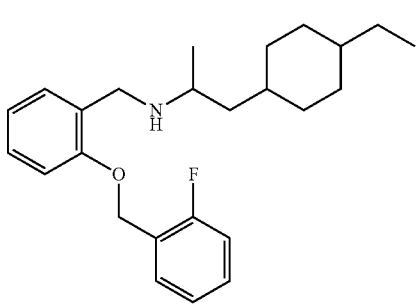 [SMILES: CCC1CCC(CC(C)NCc2ccccc2OCc2ccccc2F)CC1]
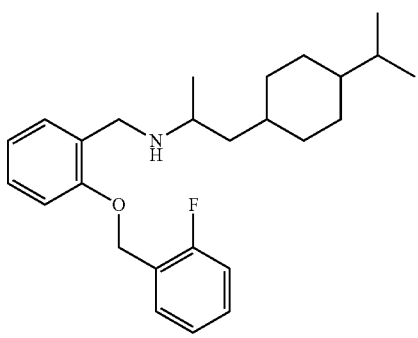 [SMILES: CC(CC1CCC(C(C)C)CC1)NCc1ccccc1OCc1ccccc1F]
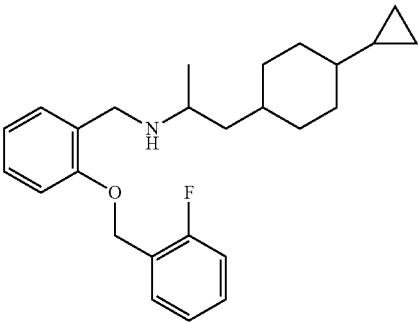 [SMILES: CC(CC1CCC(C2CC2)CC1)NCc1ccccc1OCc1ccccc1F]

TABLE 1-continued
Compounds of the Invention
TABLE 2-continued
Further compounds of the invention include, but are not limited to the following compounds in Table 2. IDC-329 TRE M
TABLE 2

TABLE 2-continued

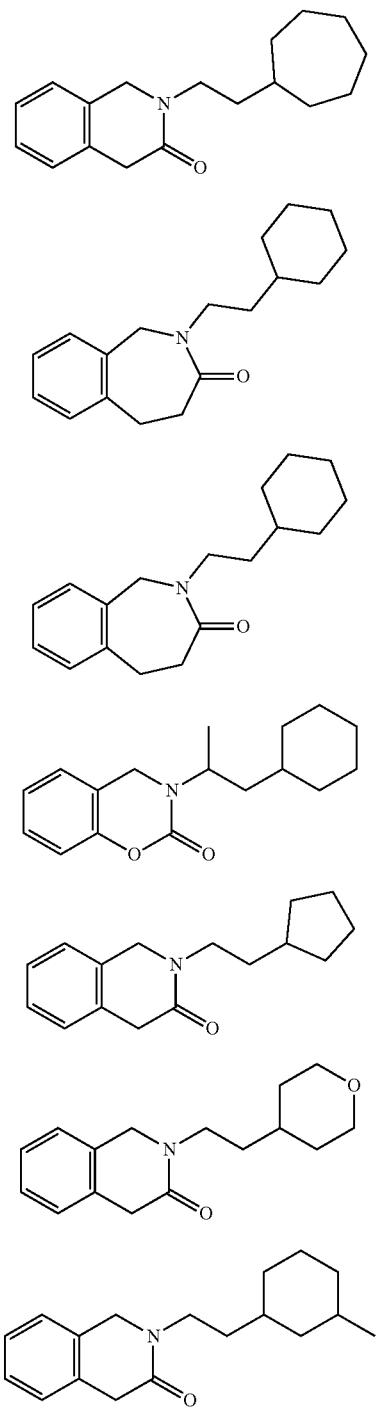

Pharmaceutical Compositions

In certain aspects, the invention also provides a pharmaceutical composition comprising a compound of the invention (e.g., a compound of formula (I)), in combination with a pharmaceutically acceptable carrier.

The invention further includes the process for making the composition comprising mixing one or more of the present compounds and an optional pharmaceutically acceptable carrier; and includes those compositions resulting from such a process, which process includes conventional pharmaceutical techniques.

The compositions of the invention include ocular, oral, nasal, transdermal, topical with or without occlusion, intravenous (both bolus and infusion), inhalable, and injection (intraperitoneally, subcutaneously, intramuscularly, intralesionally, or parenterally) formulations. The composition may be in a dosage unit such as a tablet, pill, capsule, powder, granule, liposome, ion exchange resin, sterile ocular solution, or ocular delivery device (such as a contact lens and the like facilitating immediate release, timed release, or sustained release), parenteral solution or suspension, metered aerosol or liquid spray, drop, ampoule, auto-injector device, or suppository; for administration ocularly, orally, intranasally, sublingually, parenterally, or rectally, or by inhalation or insufflation.

Compositions of the invention suitable for oral administration include solid forms such as pills, tablets, caplets, capsules (each including immediate release, timed release, and sustained release formulations), granules and powders; and, liquid forms such as solutions, syrups, elixirs, emulsions, and suspensions. Forms useful for ocular administration include sterile solutions or ocular delivery devices. Forms useful for parenteral administration include sterile solutions, emulsions, and suspensions.

The compositions of the invention may be administered in a form suitable for once-weekly or once-monthly administration. For example, an insoluble salt of the active compound may be adapted to provide a depot preparation for intramuscular injection (e.g., a decanoate salt) or to provide a solution for ophthalmic administration.

The dosage form containing the composition of the invention contains an effective amount of the active ingredient necessary to provide a therapeutic effect. The composition may contain from about 5,000 mg to about 0.5 mg (preferably, from about 1,000 mg to about 0.5 mg) of a compound of the invention or salt form thereof and may be constituted into any form suitable for the selected mode of administration. The composition may be administered about 1 to about 5 times per day. Daily administration or post-periodic dosing may be employed.

For oral administration, the composition is preferably in the form of a tablet or capsule containing, e.g., 500 to 0.5 milligrams of the active compound. Dosages will vary depending on factors associated with the particular patient being treated (e.g., age, weight, diet, and time of administration), the severity of the condition being treated, the compound being employed, the mode of administration, and the strength of the preparation.

The oral composition is preferably formulated as a homogeneous composition, wherein the active ingredient is dispersed evenly throughout the mixture, which may be readily subdivided into dosage units containing equal amounts of a compound of the invention. Preferably, the compositions are prepared by mixing a compound of the invention (or pharmaceutically acceptable salt thereof) with one or more optionally present pharmaceutical carriers (such as a starch, sugar, diluent, granulating agent, lubricant, glidant, binding agent, and disintegrating agent), one or more optionally present inert pharmaceutical excipients (such as water, glycols, oils, alcohols, flavoring agents, preservatives, coloring agents, and syrup), one or more optionally present conventional tableting ingredients (such as corn starch, lactose, sucrose, sorbitol, talc, stearic acid, magnesium stearate, dicalcium phosphate, and any of a variety of gums), and an optional diluent (such as water).

Binder agents include starch, gelatin, natural sugars (e.g., glucose and beta-lactose), corn sweeteners and natural and synthetic gums (e.g., acacia and tragacanth). Disintegrating agents include starch, methyl cellulose, agar, and bentonite.

Tablets and capsules represent an advantageous oral dosage unit form. Tablets may be sugarcoated or film-coated using standard techniques. Tablets may also be coated or otherwise compounded to provide a prolonged, control-release therapeutic effect. The dosage form may comprise an inner dosage and an outer dosage component, wherein the outer component is in the form of an envelope over the inner component. The two components may further be separated by a layer which resists disintegration in the stomach (such as an enteric layer) and permits the inner component to pass intact into the duodenum or a layer which delays or sustains release. A variety of enteric and non-enteric layer or coating materials (such as polymeric acids, shellacs, acetyl alcohol, and cellulose acetate or combinations thereof) may be used.

Compounds of the invention may also be administered via a slow release composition; wherein the composition includes a compound of the invention and a biodegradable slow release carrier (e.g., a polymeric carrier) or a pharmaceutically acceptable non-biodegradable slow release carrier (e.g., an ion exchange carrier).

Biodegradable and non-biodegradable slow release carriers are well known in the art. Biodegradable carriers are used to form particles or matrices which retain an active agent(s) and which slowly degrade/dissolve in a suitable environment (e.g., aqueous, acidic, basic and the like) to release the agent. Such particles degrade/dissolve in body fluids to release the active compound(s) therein. The particles are preferably nanoparticles or nanoemulsions (e.g., in the range of about 1 to 500 nm in diameter, preferably about 50-200 nm in diameter, and most preferably about 100 nm in diameter). In a process for preparing a slow release composition, a slow release carrier and a compound of the invention are first dissolved or dispersed in an organic solvent. The resulting mixture is added into an aqueous solution containing an optional surface-active agent(s) to produce an emulsion. The organic solvent is then evaporated from the emulsion to provide a colloidal suspension of particles containing the slow release carrier and the compound of the invention.

The compounds disclosed herein may be incorporated for administration orally or by injection in a liquid form such as aqueous solutions, suitably flavored syrups, aqueous or oil suspensions, flavored emulsions with edible oils such as cottonseed oil, sesame oil, coconut oil or peanut oil and the like, or in elixirs or similar pharmaceutical vehicles.

Suitable dispersing or suspending agents for aqueous suspensions, include synthetic and natural gums such as tragacanth, acacia, alginate, dextran, sodium carboxymethylcellulose, methylcellulose, polyvinyl-pyrrolidone, and gelatin. The liquid forms in suitably flavored suspending or dispersing agents may also include synthetic and natural gums. For parenteral administration, sterile suspensions and solutions are desired. Isotonic preparations, which generally contain suitable preservatives, are employed when intravenous administration is desired.

The compounds may be administered parenterally via injection. A parenteral formulation may consist of the active ingredient dissolved in or mixed with an appropriate inert liquid carrier. Acceptable liquid carriers usually comprise aqueous solvents and other optional ingredients for aiding solubility or preservation. Such aqueous solvents include sterile water, Ringer's solution, or an isotonic aqueous saline solution. Other optional ingredients include vegetable oils (such as peanut oil, cottonseed oil, and sesame oil), and organic solvents (such as solketal, glycerol, and formyl). A sterile, non-volatile oil may be employed as a solvent or suspending agent. The parenteral formulation is prepared by dissolving or suspending the active ingredient in the liquid carrier whereby the final dosage unit contains from 0.005 to 10% by weight of the active ingredient. Other additives include preservatives, isotonizers, solubilizers, stabilizers, and pain-soothing agents. Injectable suspensions may also be prepared, in which case appropriate liquid carriers, suspending agents and the like may be employed.

Compounds of the invention may be administered intranasally using a suitable intranasal vehicle.

In other embodiments, the compounds of this invention may be administered directly to the lungs by inhalation.

Compounds of the invention may also be administered topically or enhanced by using a suitable topical transdermal vehicle or a transdermal patch.

For ocular administration, the composition is preferably in the form of an ophthalmic composition. The ophthalmic compositions are preferably formulated as eye-drop formulations and filled in appropriate containers to facilitate administration to the eye, for example a dropper fitted with a suitable pipette. Preferably, the compositions are sterile and aqueous based, using purified water. In addition to the compound of the invention, an ophthalmic composition may contain one or more of: a) a surfactant such as a polyoxyethylene fatty acid ester; b) a thickening agents such as cellulose, cellulose derivatives, carboxyvinyl polymers, polyvinyl polymers, and polyvinylpyrrolidones, typically at a concentration n the range of about 0.05 to about 5.0% (wt/vol); c) (as an alternative to or in addition to storing the composition in a container containing nitrogen and optionally including a free oxygen absorber such as Fe), an anti-oxidant such as butylated hydroxyanisol, ascorbic acid, sodium thiosulfate, or butylated hydroxytoluene at a concentration of about 0.00005 to about 0.1% (wt/vol); d) ethanol at a concentration of about 0.01 to 0.5% (wt/vol); and e) other excipients such as an isotonic agent, buffer, preservative, and/or pH-controlling agent. The pH of the ophthalmic composition is desirably within the range of 4 to 8.

In certain embodiments, the pharmaceutical composition of the invention further comprises one or more additional agents, such as a second antibacterial agent. The other agent may be ay agent that is capable of treating, suppressing, or preventing a bacterial infection. For example, the other therapeutic agent may be an antibacterial compound.

Alternatively, the other therapeutic agent may be any agent of benefit to a patient when administered in combination with the tRNA synthetase inhibitor compound in this invention.

In certain embodiments, the second antibacterial agent in the pharmaceutical composition of the invention is a tRNA synthetase inhibitor. Exemplary tRNA synthetase inhibitors include oxaborole compounds such as AN3365.

Methods of Treatment

In certain aspects, the invention provides methods of treating a bacterial infection in a subject, comprising administering to the subject a therapeutically effective amount of a compound of the invention, i.e., a compound of formula (I), formula (II), formula (IF), formula (III), formula (III'), or a compound pictured in Table 1, or a pharmaceutical composition comprising the compound.

The invention further provides methods of treating a bacterial infection in a subject, comprising administering to the subject a therapeutically effective amount of a compound of formula (IV'):

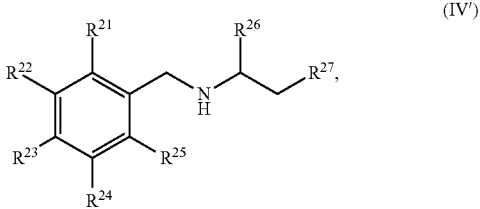

(IV')

or a pharmaceutically acceptable salt thereof;
wherein:
each of $R^{21}$, $R^{22}$, $R^{23}$, $R^{24}$, and $R^{25}$ is independently selected from H, OH, —$NH_2$, halide, sulfonamido, $(C_1-C_6)$alkylsulfonyl, —OC(O)(($C_1-C_8$)alkyl), —C(O)O(($C_1-C_8$)alkyl), —C(O)OH, optionally substituted —NHC(O)(aryl), —C(O)$NH_2$, —B(OH)$_2$, optionally substituted —S—($C_1-C_6$)alkyl; tri(($C_1-C_8$)alkyl)silyl, optionally substituted ($C_1-C_8$)alkyl, optionally substituted ($C_1-C_8$)alkoxy, optionally substituted ($C_1-C_8$)aminoalkyl, optionally substituted ($C_1-C_8$)hydroxyalkyl, optionally substituted ($C_1-C_8$)haloalkyl, optionally substituted ($C_1-C_8$)haloalkoxy, optionally substituted aryl, optionally substituted heteroaryl, optionally substituted aryloxy, optionally substituted arylalkoxy, optionally substituted heteroaryloxy, optionally substituted heteroarylalkoxy, optionally substituted ($C_3-C_{10}$)cycloalkyl, optionally substituted ($C_3-C_{10}$)cycloalkoxy, optionally substituted ($C_2-C_9$)heterocycloalkyl, optionally substituted ($C_2-C_9$)heterocycloalkoxy, ($H_3CSO_2$)($C_1-C_8$)alkylene, optionally substituted ($R^e{}_2NSO_2$)($C_1-C_8$)alkylene, optionally substituted di(($C_1-C_8$)alkyl)amino, —NH—$CH_2$—$R^{28}$, —O—$CH_2$—$R^{28}$, and —O—$CH_2CH_2$—O—$R^{29}$;
or $R^{21}$ and $R^{22}$, $R^{22}$ and $R^{23}$, $R^{23}$ and $R^{24}$, or $R^{24}$ and $R^{25}$, taken together with the intervening atoms, form an optionally substituted aryl, heteroaryl, cycloalkyl, or heterocycloalkyl group;
$R^{26}$ is H or ($C_1-C_6$)alkyl;
$R^{27}$ is optionally substituted ($C_3-C_{10}$)cycloalkyl or ($C_3-C_{10}$)cycloalkenyl;
$R^{28}$ is selected from H, —C(O)(($C_2-C_9$)heterocycloalkyl), —C(O)NH(($C_1-C_8$)alkyl), —C(O)NH(aryl($C_1-C_8$)alkyl), —C(O)NH(($C_3-C_8$)cycloalkyl), —C(O)NH(($C_3-C_8$)cycloalkyl($C_1-C_8$)alkyl), —C(O)N($CH_3$)(($C_3-C_8$)cycloalkyl), —C(O)N($CH_3$)(aryl($C_1-C_8$)alkyl), —C(O)NHC(O)NH(($C_3-C_8$)cycloalkyl), —C(O)NHC(O)NH(($C_1-C_8$)alkyl), —C(O)NHC(O)$NH_2$, optionally substituted heteroaryl, optionally substituted aryl, optionally substituted aryloxy($C_1-C_8$)alkyl, ($C_3-C_8$)cycloalkyl, ($C_2-C_9$)heterocycloalkyl, ($C_2-C_9$)heterocycloalkyl($C_2-C_8$)alkyl, heteroaryl($C_1-C_8$)alkyl, ($C_1-C_8$)alkoxy, ($C_2-C_8$)hydroxyalkyl, ($C_1-C_8$)alkoxy($C_1-C_8$)alkyl, ($C_1-C_8$)haloalkoxy($C_1-C_8$)alkyl, ($C_1-C_8$)thioalkoxy($C_1-C_8$)alkyl, ($CH_3SO_2$)($C_1-C_8$)alkyl, and (($C_1-C_8$)alkylC(O))($C_1-C_8$)alkyl;
$R^{29}$ is selected from ($C_3-C_{10}$)cycloalkyl, ($C_3-C_{10}$)cycloalkyl($C_1-C_8$)alkyl, ($C_1-C_8$)haloalkyl, ($C_1-C_8$)hydroxyalkyl, ($C_1-C_8$)alkyl, ($C_1-C_8$)alkoxy($C_1-C_8$)alkyl, and optionally substituted aryl; and
$R^e$, independently for each occurrence, is selected from H, optionally substituted —C(O)($C_1-C_8$)alkyl, optionally substituted —C(O)NH—($C_3-C_{10}$)cycloalkyl, optionally substituted ($C_1-C_8$)alkyl, optionally substituted ($C_1-C_8$)haloalkyl, optionally substituted ($C_1-C_8$)hydroxyalkyl, optionally substituted ($C_3-C_{10}$)cycloalkyl, optionally substituted heterocyclyl, optionally substituted ($C_3-C_{10}$)cycloalkyl($C_1-C_3$)alkyl, optionally substituted aryl, and optionally substituted aryl($C_1-C_8$)alkyl, or
two $R^e$ are taken together with the nitrogen atom to which they are attached to form a 5-6-membered heterocyclyl;
further wherein:
if $R^{26}$ is ($C_1-C_6$)alkyl and $R^{27}$ is ($C_6$)cycloalkyl, then $R^{21}$ and $R^{25}$ are not OH, —OC(O)(($C_1-C_8$)alkyl), optionally substituted ($C_1-C_8$)alkoxy, optionally substituted ($C_1-C_8$)haloalkoxy, optionally substituted aryloxy, optionally substituted arylalkoxy, optionally substituted heteroaryloxy, optionally substituted heteroarylalkoxy, optionally substituted ($C_3-C_{10}$)cycloalkoxy, optionally substituted ($C_2-C_9$)heterocycloalkoxy, —O—$CH_2$—$R^{28}$, or —O—$CH_2CH_2$—O—$R^{29}$.

The invention further provides methods of treating a bacterial infection in a subject, comprising administering to the subject a therapeutically effective amount of a compound of formula (IV):

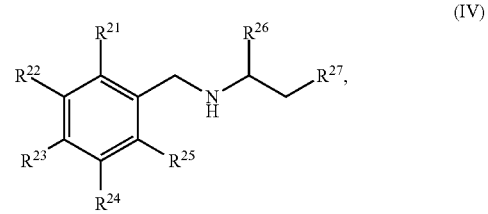

(IV)

or a pharmaceutically acceptable salt thereof;
wherein:
each of $R^{21}$, $R^{22}$, $R^{23}$, $R^{24}$, and $R^{25}$ is independently selected from H, OH, —$NH_2$, halide, sulfonamido, ($C_1-C_6$)alkylsulfonyl, —OC(O)(($C_1-C_8$)alkyl), —C(O)O(($C_1-C_8$)alkyl), —C(O)OH, optionally substituted —NHC(O)(aryl), —C(O)$NH_2$, —B(OH)$_2$, tri(($C_1-C_8$)alkyl)silyl, optionally substituted ($C_1-C_8$)alkyl, optionally substituted ($C_1-C_8$)alkoxy, optionally substituted ($C_1-C_8$)aminoalkyl, optionally substituted ($C_1-C_8$)hydroxyalkyl, optionally substituted ($C_1-C_8$)haloalkyl, optionally substituted ($C_1-C_8$)haloalkoxy, optionally substituted aryl, optionally substituted heteroaryl, optionally substituted aryloxy, optionally substituted arylalkoxy, optionally substituted heteroaryloxy, optionally substituted heteroarylalkoxy, optionally substituted ($C_3-C_{10}$)cycloalkyl, optionally substituted ($C_3-C_{10}$)cycloalkoxy, optionally substituted ($C_2-C_9$)heterocycloalkyl, optionally substituted ($C_2-C_9$)heterocycloalkoxy, ($H_3CSO_2$)($C_1-C_8$)alkylene, optionally substituted ($R^e{}_2NSO_2$)($C_1-C_8$)alkylene, optionally substituted di(($C_1-C_8$)alkyl)amino, —NH—$CH_2$—$R^{28}$, —O—$CH_2$—$R^{28}$, and —O—$CH_2CH_2$—O—$R^{29}$;
or $R^{21}$ and $R^{22}$, $R^{22}$ and $R^{23}$, $R^{23}$ and $R^{24}$, or $R^{24}$ and $R^{25}$, taken together with the intervening atoms, form an optionally substituted aryl, heteroaryl, cycloalkyl, or heterocycloalkyl group;
$R^{26}$ is H or ($C_1-C_6$)alkyl;
$R^{27}$ is optionally substituted ($C_3-C_{10}$)cycloalkyl or ($C_3-C_{10}$)cycloalkenyl;
$R^{28}$ is selected from —C(O)(($C_2-C_9$)heterocycloalkyl), —C(O)NH(($C_1-C_8$)alkyl), —C(O)NH(aryl($C_1-C_8$)alkyl), —C(O)NH(($C_3-C_8$)cycloalkyl), —C(O)NH(($C_3-C_8$)cycloalkyl($C_1-C_8$)alkyl), —C(O)N($CH_3$)(($C_3-C_8$)

cycloalkyl), —C(O)N(CH$_3$)(aryl(C$_1$-C$_8$)alkyl), —C(O)NHC(O)NH((C$_3$-C$_8$)cycloalkyl), —C(O)NHC(O)NH((C$_1$-C$_8$)alkyl), —C(O)NHC(O)NH$_2$, optionally substituted heteroaryl, optionally substituted aryl, optionally substituted aryloxy(C$_1$-C$_8$)alkyl, (C$_3$-C$_8$)cycloalkyl, (C$_2$-C$_9$)heterocycloalkyl, (C$_2$-C$_9$)heterocycloalkyl(C$_2$-C$_8$)alkyl, heteroaryl(C$_1$-C$_8$)alkyl, (C$_1$-C$_8$)alkoxy, (C$_2$-C$_8$)hydroxyalkyl, (C$_1$-C$_8$)alkoxy(C$_1$-C$_8$)alkyl, (C$_1$-C$_8$)haloalkoxy(C$_1$-C$_8$)alkyl, (C$_1$-C$_8$)thioalkoxy(C$_1$-C$_8$)alkyl, (CH$_3$SO$_2$)(C$_1$-C$_8$)alkyl, and ((C$_1$-C$_8$)alkylC(O))(C$_1$-C$_8$)alkyl;

R$^{29}$ is selected from (C$_3$-C$_{10}$)cycloalkyl, (C$_3$-C$_{10}$)cycloalkyl(C$_1$-C$_8$)alkyl, (C$_1$-C$_8$)haloalkyl, (C$_1$-C$_8$)hydroxyalkyl, (C$_1$-C$_8$)alkyl, (C$_1$-C$_8$)alkoxy(C$_1$-C$_8$)alkyl, and optionally substituted aryl; and R$^e$, independently for each occurrence, is selected from H, optionally substituted (C$_1$-C$_8$)alkyl, optionally substituted (C$_1$-C$_8$)haloalkyl, optionally substituted (C$_1$-C$_8$)hydroxyalkyl, optionally substituted (C$_3$-C$_{10}$)cycloalkyl, optionally substituted (C$_3$-C$_{10}$)cycloalkyl(C$_1$-C$_8$)alkyl, optionally substituted aryl, and optionally substituted aryl(C$_1$-C$_8$) alkyl;

further wherein:

if R$^{26}$ is (C$_1$-C$_6$)alkyl and R$^{27}$ is (C$_6$)cycloalkyl, then R$^{21}$ and R$^{25}$ are not OH, —OC(O)((C$_1$-C$_8$)alkyl), optionally substituted (C$_1$-C$_8$)alkoxy, optionally substituted (C$_1$-C$_8$)haloalkoxy, optionally substituted aryloxy, optionally substituted arylalkoxy, optionally substituted heteroaryloxy, optionally substituted heteroarylalkoxy, optionally substituted (C$_3$-C$_{10}$)cycloalkoxy, optionally substituted (C$_2$-C$_9$)heterocycloalkoxy, —O—CH$_2$—R$^{28}$, or —O—CH$_2$CH$_2$—O—R$^{29}$.

In certain embodiments of the methods of the invention, the bacterial infection is caused by Gram-negative bacteria.

Exemplary Gram-negative bacteria used with the methods of the invention include *Acidaminococcus* spp (e.g. *A. fermentans, A. intestini*), *Acinetobacter* spp (e.g. *A. baumannii, A. calcoaceticus, A. gyllenbergii, A. haemolyticus, A. junii, A. lwoffli, A. nosocomialis, A. parvus, A. pittii, A. schindleri, A. seifertii, A. soli, A. ursingii, A. variabilis*), *Aggregatibacter* spp (*A. actinomycetemcomitans, A. aphrophilus, A. segnis*), *Agrobacterium tumefaciens, Anaerobiospirillum* aka *Anaerobiospirillum thomasii, Arcobacter* spp (e.g. *A. skirrowii, A. butzleri, A. cryaerophilus*), *Bacteroides* spp, (*B. fragilis, B. ureolyticus, B. melaninogenicus*), *Bartonella* spp (e.g. *B. japonica, B. koehlerae, B. taylorii, B. alsatica, B. ancashensis, B. bacilliformis, B. capreoli, B. clarridgeiae, B. doshiae, B. elizabethae, B. grahamii, B. henselae, B. peromysci, B. quintana, B. rochalimae, B. schoenbuchensis, B. talpae, B. tamiae, B. tribocorum, B. vinsonii, B. washoensis*), *Bordetella* spp (e.g. *B. ansorpii, B. avium, B. bronchiseptica, B. hinzii, B. holmesii, B. parapertussis, B. pertussis, B. trematum*), *Borrelia* spp. (e.g. *B. burgdorferi, B. afzelii, B. garinii, B. andersonii, B. anserine, B. bissettii, B. carolinensis, B. hermsii, B. kurtenbachii, B. lusitaniae, B. miyamotoi, B. parkeri, B. recurrentis, B. sinica, B. spielmanii, B. turicatae*), *Brachyspira* spp (e.g. *B. aalborgi, B. pilosicoli, B. hyodysenteriae*), *Bradyrhizobium* spp (e.g. *B. japonicum, B. enterica*), *Burkholderia* spp (e.g. *B. mallei, B. pseudomallei, B. cepacia, B. dolosa*), *Campylobacter* spp. (e.g. *C. jejuni, C. coli, C. upsaliensis, C. fetus, C. lari, C. hyointestinalis, C. rectus*), *Cardiobacterium* spp. (e.g. *C. hominis, C. valvarum*), *Christensenella* spp (e.g. *C. minuta, C. massiliensis, C. timonensis*), *Citrobacter* spp. (e.g. *C. amalonaticus, C. braakii, C. koseri, C. sedlakii*), *Coxiella burnetii, Cytophaga* spp. (e.g. *C. columnaris, C. johnsonae, C. psychrophila*), *Dialister* spp (e.g. *D. pneumosintes*), *Eikenella corrodens, Enterobacter* spp (e.g. *E. cloacae, E. aerogenes, E. cancerogenus* aka *E. taylorae, E. cowanii*), *Escherichia* spp (e.g. *E. coli, E. fergusonii, E. hermannii, E. albertii, E. vulneris*), *Ewingella americana, Flavobacterium* spp (e.g. *F. psychrophilum, F. columnare, F. branchiophilum*), *Francisella* spp. (e.g. *F. novicida, F. tularensis, F. piscicida, F. philomiragia*), *Fusobacterium* spp (e.g *F. necrophorum, F. nucleatum, F. polymorphum*), *Haemophilus* spp (e.g *H. felis, H. haemolyticus, H. influenzae, H. parainfluenzae, H. pittmaniae, H. ducreyi*), *Helicobacter* spp (e.g. *H. pylori, H. bilis, H. canadensis, H. canis, H. cinaedi*), *Kingella* spp (e.g. *Kingella kingae* aka *Moraxella kingae, K. indologenes, K. denitrificans, K. oralis*), *Klebsiella* spp (e.g. *K. pneumoniae, K. granulomatis, K. oxytoca, K. michiganensis, K. quasipneumoniae, K. variicola*), *Kluyvera* spp (e.g. *K. intermedia, K. ascorbate, K. cryocrescens, K. intestine, K. georgiana*), *Legionella* spp (e.g *Legionella clemsonensis, Legionella pneumophila, L. wadsworthii, L. waltersii, L. anisa, L. birminghamensis, L. bozemanae, L. cardiaca, L. cherrii, L. cincinnatiensis, L. dumoffli, L. feeleii, L. gormanii, L. hackeliae, L. jordanis, L. lansingensis, L. longbeachae, L. oakridgensis, L. micdadei, L. rubrilucens, L. sainthelensi, L. steelei, L. tucsonensis*), *Leptonema illini, Leptotrichia* spp (e.g. *L. buccalis, L. amnionii, L. trevesanii, L. goodfellowii*), *Methylobacterium* spp (e.g. *M. fujisawaense, M. mesophilicum, M. thiocyanatum, M. aminovorans, M. lusitanum, M. radiotolerans*), *Moraxella* spp. (e.g. *M. lacunata* aka *Morax-Axenfeld diplobacilli, M. bovis, M. osloensis, M. atlantae, M. boevrei, M. bovoculi, M. canis, M. caprae, M. catarrhalis, M. caviae, M. cuniculi, M. equi, M. lincolnii, M. nonliquefaciens, M. oblonga, M. osloensis, M. pluranimalium, M. porci, M. saccharolytica*), *Morganella morganii, Mycoplasma* spp. (e.g *M. spumans, M. adleri, M. agalactiae, M. agassizii, M. alligatoris, M. amphoriforme, M. bovis, M. buccale, M. capricolum, M. faucium, M. fermentans, M. gallisepticum, M. genitalium, M. haemofelis, M. haemomuris, M. hominis, M. hyopneumoniae, M. hyorhinis, M. lipophilum, M. mobile, M. mycoides, M. orale, M. ovipneumoniae, M. penetrans, M. pirum, M. pneumoniae, M. primatum, M. salivarium, M. spermatophilum, M. synoviae*), *Neisseria* spp. (e.g. *N. gonorrhoeae, N. meningitides, N. cinerea, N. polysaccharea, N. sicca*), *Proteus* spp. (e.g. *P. mirabilis, P. penneri, P. hauseri, P. myxofaciens, P. vulgaris*), *Pseudomonas* spp. (e.g. *P. aeruginosa, P. oryzihabitans, P. luteola, P. floridensis, P. syringae, P. anguilliseptica, P. argentinensis, P. flavescens, P. mendocina, P. asplenii, P. corrugate, P. fragi, P. lundensis, P. taetrolens, P. azotoformans, P. blatchfordae, P. brassicacearum, P. fluorescens, P. marginalis, P. mediterranea, P. mucidolens, P. panacis, P. tolaasii, P. cremoricolorata, P. entomophila, P. monteilii, P. plecoglossicida, P. stutzeri, P. amygdali, P. avellanae, P. caricapapayae, P. cichorii, P. coronafaciens, P. ficuserectae, P. helianthin, P. meliae, P. savastanoi, P. tomato, P. viridiflava, P. asplenii, P. cannabina, P. costantinii, P. fuscovaginae, P. otitidis, P. palleroniana, P. perolens, P. reptilivora, P. salomonii, P. septica, P. simiae, P. suis, P. tremae, P. turbinellae*), *Pseudoxanthomonas* spp. (e.g. *P. broegbernensis, P. japonensis, P. mexicana*), *Rickettsia* spp. (e.g. *R. rickettsii,*

*R. asiatica, R. australis, R. conorii, R. felis, R. heilongjiangensis, R. helvetica, R. honei, R. japonica, R. massiliae, R. monacensis, R. parkeri, R. peacockii, R. prowazekii, R. akari, R. africae, R. sibirica, R. typhi*), *Rouxiella chamberiensis*, *Salmonella* spp (e.g. *S. bongori, S. enterica*), *Serratia* spp. (e.g. *S. marcescens, S. plymuthica, S. liquefaciens, S. rubidaea, S. odorifera, S. fonticola*), *Shigella* spp. (e.g. *S. dysenteriae, S. flexneri, S. boydii, S. sonnei*), *Solobacterium moorei*, *Sphingomonas* spp (*S. gei, S. paucimobilis, S. koreensis*), *Spirochaeta* spp, *Stenotrophomonas* spp (e.g. *S. nitritireducens, S. maltophilia*), *Treponema* spp. (e.g. *T. pallidum, T. carateum, T. denticola, T. lecithinolyticum, T. maltophilum, T. socranskii, T. vincentii*), *Vibrio* spp (e.g. *V. adaptatus, V. azasii, V. campbellii, V. cholera, V. alginolyticus, V. anguillarum, V. campbellii, V. fluvialis, V. furnissii, V. harveyi, V. lentus, V. mimicus, V. ordalii, V. parahaemolyticus, V. pectenicida, V. tapetis, V. tubiashii, V. vulnmficus*), *Wolbachia* spp., and *Yersinia* spp. (e.g. *Y. aldovae, Y. bercovieri, Y. enterocolitica, Y. frederiksenii, Y. pestis, Y. pseudotuberculosis, Y. ruckeri*).

In other embodiments, the bacterial infection treated by the methods of the invention is caused by *Mycobacterium kansasii, Mycobacterium marinum, Mycobacterium simiae, Mycobacterium scrofulaceum, Mycobacterium szulgai, Mycobacterium gordonae; Mycobacterium avium* complex, *Mycobacterium ulcerans, Mycobacterium xenopi, Mycobacterium malmoense, Mycobacterium terrae* complex, *Mycobacterium haemophilum, Mycobacterium genavense, Mycobacterium abscessus* complex, *Mycobacterium chelonae, Mycobacterium fortuitum* complex, or *Mycobacterium peregrinum*.

In further embodiments, the bacterial infection treated by the methods of the invention is caused by a *Nocardia* species selected from *N. concava, N. cyriacigeorgica, N. donostiensis, N. elegans, N. exalbida, N. farcinica, N. harenae, N. higoensis, N. ignorata, N. inohanensis, N. jinanensis, N. kroppenstedtii, N. kruczakiae, N. mexicana, N. mikamii, N. neocaledoniensis, N. niigatensis, N. ninae, N. niwae, N. nova, N. otitidiscaviarum, N. paucivorans, N. pneumoniae, N. pseudobrasiliensis, N. puris, N. shinanonensis, N. sienata, N. takedensis, N. terpenica, N. testaceae, N. thailandica, N. transvalensis, N. vermiculata, N. veterana, N. vulneris, N. wallacei*, and *N. yamanashiensis*.

In further embodiments, the bacterial infection treated by the methods of the invention is caused by a *Actinomyces* species selected from *A. israelii, A. viscosus, A. meyeri, A. naeslundii, A. odontolyticus, A. gerencseriae, A. neuii, A. turicensis*, and *A. radingae*.

When administered in combination with a second antibacterial agent, the compounds of the invention may be effective to overcome bacterial resistance to the second antibacterial agent. Thus, in certain embodiments, the method of treating a bacterial infection provided by the invention further comprises administering to the subject a second antibacterial agent. In some embodiments, the second antibacterial agent is a tRNA synthtase inhibitor such as AN3365.

In certain embodiments, the invention provides methods of treating tuberculosis, comprising administering to a subject in need thereof a therapeutically effective amount of a compound of the invention, i.e., a compound of formula (I), formula (II), formula (IT), formula (III), formula (III'), or a compound pictured in Table 1, or a pharmaceutical composition comprising the compound.

The invention further provides methods of treating tuberculosis, comprising administering to a subject in need thereof a therapeutically effective amount of a compound of formula (V'):

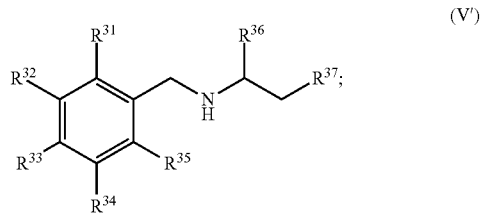

or a pharmaceutically acceptable salt thereof;
wherein:
each of $R^{31}$, $R^{32}$, $R^{33}$, $R^{34}$, and $R^{35}$ is independently selected from from H, OH, —$NH_2$, halide, sulfonamido, ($C_1$-$C_6$)alkylsulfonyl, —OC(O)(($C_1$-$C_8$)alkyl), —C(O)O(($C_1$-$C_8$)alkyl), —C(O)OH, optionally substituted —NHC(O)(aryl), —C(O)$NH_2$, —B(OH)$_2$, optionally substituted —S—($C_1$-$C_6$)alkyl; tri(($C_1$-$C_8$)alkyl)silyl, optionally substituted ($C_1$-$C_8$)alkyl, optionally substituted ($C_1$-$C_8$)alkoxy, optionally substituted ($C_1$-$C_8$)aminoalkyl, optionally substituted ($C_1$-$C_8$)hydroxyalkyl, optionally substituted ($C_1$-$C_8$)haloalkyl, optionally substituted ($C_1$-$C_8$)haloalkoxy, optionally substituted aryl, optionally substituted heteroaryl, optionally substituted aryloxy, optionally substituted arylalkoxy, optionally substituted heteroaryloxy, optionally substituted heteroarylalkoxy, optionally substituted ($C_3$-$C_{10}$)cycloalkyl, optionally substituted ($C_3$-$C_{10}$)cycloalkoxy, optionally substituted ($C_2$-$C_9$)heterocycloalkyl, optionally substituted ($C_2$-$C_9$) heterocycloalkoxy, ($H_3CSO_2$)($C_1$-$C_8$)alkylene, optionally substituted ($R^f_2NSO_2$)($C_1$-$C_8$)alkylene, optionally substituted di(($C_1$-$C_8$)alkyl)amino, —NH—$CH_2$—$R^{38}$, —O—$CH_2$—$R^{38}$, and —O—$CH_2CH_2$—O—$R^{39}$;
or $R^{31}$ and $R^{32}$, $R^{32}$ and $R^{33}$, $R^{33}$ and $R^{34}$, or $R^{34}$ and $R^{35}$, taken together with the intervening atoms, form an optionally substituted aryl, heteroaryl, cycloalkyl, or heterocycloalkyl group;
$R^{36}$ is H or ($C_1$-$C_6$)alkyl;
$R^{37}$ is optionally substituted ($C_3$-$C_{10}$)cycloalkyl or ($C_3$-$C_{10}$)cycloalkenyl;
$R^{38}$ is selected from H, —C(O)(($C_2$-$C_9$)heterocycloalkyl), —C(O)NH(($C_1$-$C_8$)alkyl), —C(O)NH(aryl($C_1$-$C_8$)alkyl), —C(O)NH(($C_3$-$C_8$)cycloalkyl), —C(O)NH(($C_3$-$C_8$)cycloalkyl($C_1$-$C_8$)alkyl), —C(O)N($CH_3$)(($C_3$-$C_8$)cycloalkyl), —C(O)N($CH_3$)(aryl($C_1$-$C_8$)alkyl), —C(O)NHC(O)NH(($C_3$-$C_8$)cycloalkyl), —C(O)NHC(O)NH(($C_1$-$C_8$)alkyl), —C(O)NHC(O)$NH_2$, optionally substituted heteroaryl, optionally substituted aryl, optionally substituted aryloxy($C_1$-$C_8$)alkyl, ($C_3$-$C_8$)cycloalkyl, ($C_2$-$C_9$)heterocycloalkyl, ($C_2$-$C_9$)heterocycloalkyl($C_2$-$C_8$)alkyl, heteroaryl($C_1$-$C_8$)alkyl, ($C_1$-$C_8$) alkoxy, ($C_2$-$C_8$)hydroxyalkyl, ($C_1$-$C_8$)alkoxy($C_1$-$C_8$) alkyl, ($C_1$-$C_8$)haloalkoxy($C_1$-$C_8$)alkyl, ($C_1$-$C_8$) thioalkoxy($C_1$-$C_8$)alkyl, ($CH_3SO_2$)($C_1$-$C_8$)alkyl, and (($C_1$-$C_8$)alkylC(O))($C_1$-$C_8$)alkyl;
$R^{39}$ is selected from ($C_3$-$C_{10}$)cycloalkyl, ($C_3$-$C_{10}$)cycloalkyl($C_1$-$C_8$)alkyl, ($C_1$-$C_8$)haloalkyl, ($C_1$-$C_8$)hydroxyalkyl, ($C_1$-$C_8$)alkyl, ($C_1$-$C_8$)alkoxy($C_1$-$C_8$)alkyl, and optionally substituted aryl; and $R^f$, independently for each occurrence, is selected from H, optionally substituted —C(O)($C_1$-$C_8$)alkyl, optionally substituted —C(O)NH—($C_3$-$C_{10}$)cycloalkyl, optionally substituted ($C_1$-$C_8$)alkyl, optionally substituted ($C_1$-$C_8$)haloalkyl, optionally substituted ($C_1$-$C_8$)hydroxyalkyl, optionally substituted ($C_3$-$C_{10}$)cycloalkyl, optionally substituted heterocyclyl, optionally substituted ($C_3$-$C_{10}$)cycloalkyl($C_1$-$C_8$)alkyl, optionally substituted aryl, and optionally substituted aryl($C_1$-$C_8$) alkyl, or two $R^f$ are taken together with the nitrogen atom to which they are attached to form a 5-6-membered heterocyclyl.

The invention further provides methods of treating tuberculosis, comprising administering to a subject in need thereof a therapeutically effective amount of a compound of formula (V):

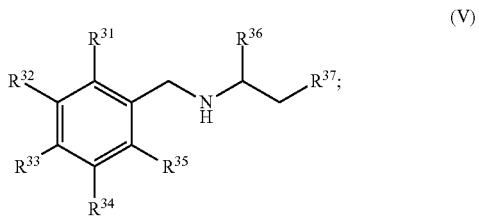

(V)

or a pharmaceutically acceptable salt thereof;
wherein:
each of $R^{31}$, $R^{32}$, $R^{33}$, $R^{34}$, and $R^{35}$ is independently selected from from H, OH, —$NH_2$, halide, sulfonamido, ($C_1$-$C_6$)alkylsulfonyl, —OC(O)(($C_1$-$C_8$)alkyl), —C(O)O(($C_1$-$C_8$)alkyl), —C(O)OH, optionally substituted —NHC(O)(aryl), —C(O)$NH_2$, —B(OH)$_2$, tri(($C_1$-$C_8$)alkyl)silyl, optionally substituted ($C_1$-$C_8$)alkyl, optionally substituted ($C_1$-$C_8$)alkoxy, optionally substituted ($C_1$-$C_8$)aminoalkyl, optionally substituted ($C_1$-$C_8$)hydroxyalkyl, optionally substituted ($C_1$-$C_8$) haloalkyl, optionally substituted ($C_1$-$C_8$)haloalkoxy, optionally substituted aryl, optionally substituted heteroaryl, optionally substituted aryloxy, optionally substituted arylalkoxy, optionally substituted heteroaryloxy, optionally substituted heteroarylalkoxy, optionally substituted ($C_3$-$C_{10}$)cycloalkyl, optionally substituted ($C_3$-$C_{10}$)cycloalkoxy, optionally substituted ($C_2$-$C_9$)heterocycloalkyl, optionally substituted ($C_2$-$C_9$)heterocycloalkoxy, ($H_3CSO_2$)($C_1$-$C_8$)alkylene, optionally substituted ($R^f_2NSO_2$)($C_1$-$C_8$)alkylene, optionally substituted di(($C_1$-$C_8$)alkyl)amino, —NH—$CH_2$—$R^{38}$, —O—$CH_2$—$R^{38}$, and —O—$CH_2CH_2$—O—$R^{39}$;

or $R^{31}$ and $R^{32}$, $R^{32}$ and $R^{33}$, $R^{33}$ and $R^{34}$, or $R^{34}$ and $R^{35}$, taken together with the intervening atoms, form an aryl, heteroaryl, cycloalkyl, or heterocycloalkyl group;

$R^{36}$ is H or ($C_1$-$C_6$)alkyl;

$R^{37}$ is optionally substituted ($C_3$-$C_{10}$)cycloalkyl or ($C_3$-$C_{10}$)cycloalkenyl;

$R^{38}$ is selected from —C(O)(($C_2$-$C_9$)heterocycloalkyl), —C(O)NH(($C_1$-$C_8$)alkyl), —C(O)NH(aryl($C_1$-$C_8$)alkyl), —C(O)NH(($C_3$-$C_8$)cycloalkyl), —C(O)NH(($C_3$-$C_8$)cycloalkyl($C_1$-$C_8$)alkyl), —C(O)N($CH_3$)(($C_3$-$C_8$)cycloalkyl), —C(O)N($CH_3$)(aryl($C_1$-$C_8$)alkyl), —C(O)NHC(O)NH(($C_3$-$C_8$)cycloalkyl), —C(O)NHC(O)NH(($C_1$-$C_8$)alkyl), —C(O)NHC(O)$NH_2$, optionally substituted heteroaryl, optionally substituted aryl, optionally substituted aryloxy($C_1$-$C_8$)alkyl, ($C_3$-$C_8$)cycloalkyl, ($C_2$-$C_9$)heterocycloalkyl, ($C_2$-$C_9$)heterocycloalkyl($C_2$-$C_8$)alkyl, heteroaryl($C_1$-$C_8$)alkyl, ($C_1$-$C_8$)alkoxy, ($C_2$-$C_8$)hydroxyalkyl, ($C_1$-$C_8$)alkoxy($C_1$-$C_8$)alkyl, ($C_1$-$C_8$)haloalkoxy ($C_1$-$C_8$)alkyl, ($C_1$-$C_8$)thioalkoxy($C_1$-$C_8$)alkyl, ($CH_3SO_2$)($C_1$-$C_8$)alkyl, and (($C_1$-$C_8$)alkylC(O))($C_1$-$C_8$)alkyl;

$R^{39}$ is selected from ($C_3$-$C_{10}$)cycloalkyl, ($C_3$-$C_{10}$)cycloalkyl($C_1$-$C_8$)alkyl, ($C_1$-$C_8$)haloalkyl, ($C_1$-$C_8$)hydroxyalkyl, ($C_1$-$C_8$)alkyl, ($C_1$-$C_8$)alkoxy($C_1$-$C_8$)alkyl, and optionally substituted aryl; and $R^f$, independently for each occurrence, is selected from H, optionally substituted ($C_1$-$C_8$)alkyl, optionally substituted ($C_1$-$C_8$)haloalkyl, optionally substituted ($C_1$-$C_8$)hydroxyalkyl, optionally substituted ($C_3$-$C_{10}$)cycloalkyl, optionally substituted ($C_3$-$C_{10}$)cycloalkyl($C_1$-$C_8$)alkyl, optionally substituted aryl, and optionally substituted aryl($C_1$-$C_8$) alkyl.

In some embodiments, at least four of $R^{31}$, $R^{32}$, $R^{33}$, $R^{34}$, and $R^{35}$ are H. For example, $R^{32}$, $R^{33}$, $R^{34}$, and $R^{35}$ may each be H.

In certain embodiments, $R^{31}$ and $R^{32}$, taken together with the intervening atoms, form an aryl, heteroaryl, cycloalkyl, or heterocycloalkyl group, preferably a heteroaryl group.

In certain embodiments, $R^{31}$ is selected from the group consisting of —OH, —OC(O)(($C_1$-$C_8$)alkyl), optionally substituted ($C_1$-$C_8$)alkoxy, optionally substituted ($C_1$-$C_8$) haloalkoxy, optionally substituted aryloxy, optionally substituted arylalkoxy, optionally substituted heteroaryloxy, optionally substituted heteroarylalkoxy, optionally substituted ($C_3$-$C_{10}$)cycloalkoxy, optionally substituted ($C_2$-$C_9$)heterocycloalkoxy, —O—$CH_2$—$R^{38}$, and —O—$CH_2CH_2$—O—$R^{39}$.

In certain embodiments, $R^{36}$ is ($C_1$-$C_6$)alkyl, e.g., methyl. Alternatively, $R^{36}$ may be H.

In certain embodiments, $R^{37}$ is optionally substituted cyclohexyl or cyclohexenyl, preferably optionally substituted cyclohexyl.

In certain embodiments, the subject is a mammal, e.g., a human.

EXAMPLES

Example 1: General Synthetic Procedures 1

Certain compounds of the invention are synthesized according to Synthetic Scheme 1:
Synthetic Scheme 1

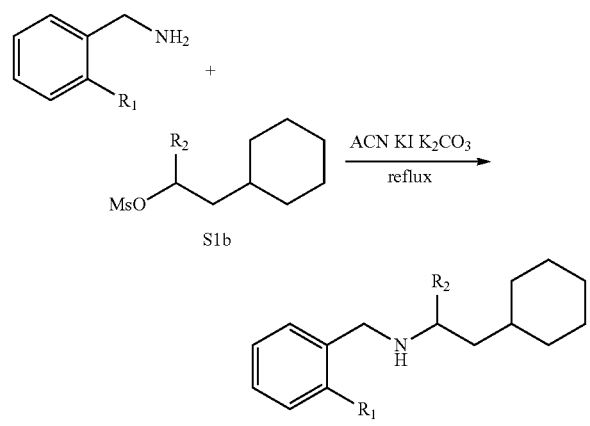

For example, N-benzyl-1-cyclohexylbutan-2-amine (B164) was synthesized as follows:

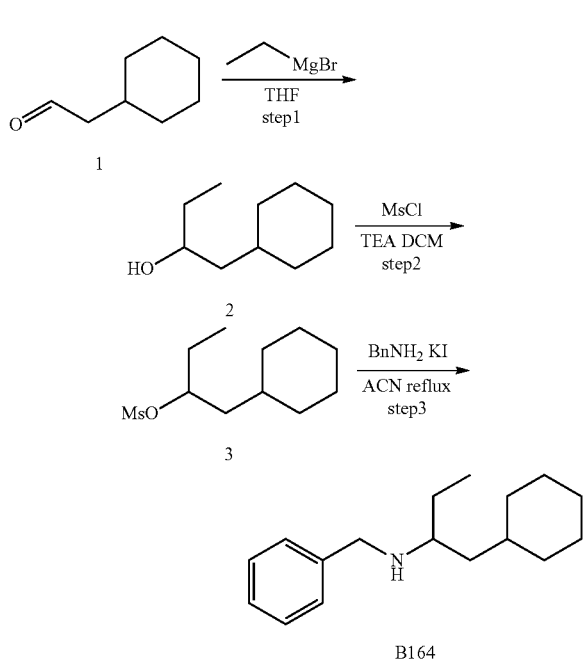

Step 1: Preparation of 2

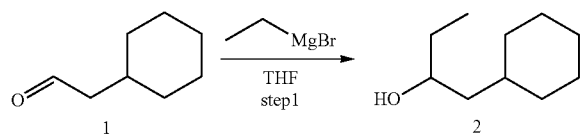

To a solution of 1 (1.5 g, 11.895 mmol, 1.0 eq) in THF (24 mL, c=0.5) was added dropwise ethylmagnesium bromide (24 mL, 1M in THF, 23.79 mmol, 2.0 eq) at 0° C. under nitrogen. After 0.5 h at 0° C., the reaction mixture was added to aq. HCl (2N, 40 mL) at 0° C. The solution was extracted with EA (3×30 mL). The combined organic phases were washed with brine, dried over Na$_2$SO$_4$, filtered and concentrated in vacuum. The residue was purified by column chromatography to give the desired product 2 (1.313 g, yield=71%) as a yellow oil.

Step 2: Preparation of 3

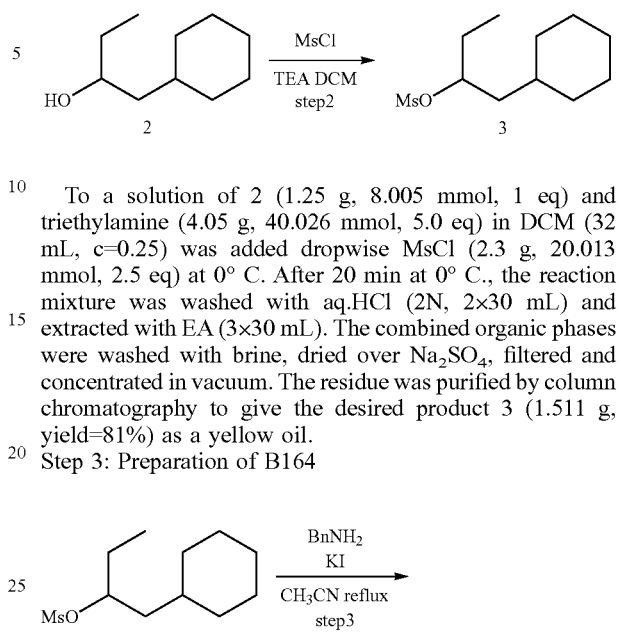

To a solution of 2 (1.25 g, 8.005 mmol, 1 eq) and triethylamine (4.05 g, 40.026 mmol, 5.0 eq) in DCM (32 mL, c=0.25) was added dropwise MsCl (2.3 g, 20.013 mmol, 2.5 eq) at 0° C. After 20 min at 0° C., the reaction mixture was washed with aq.HCl (2N, 2×30 mL) and extracted with EA (3×30 mL). The combined organic phases were washed with brine, dried over Na$_2$SO$_4$, filtered and concentrated in vacuum. The residue was purified by column chromatography to give the desired product 3 (1.511 g, yield=81%) as a yellow oil.

Step 3: Preparation of B164

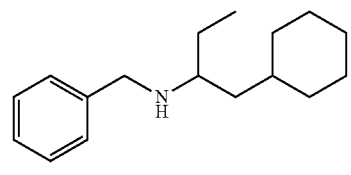

To a solution of 3 (100 mg, 0.427 mmol, 1 eq) in CH$_3$CN (2 mL, c=0.2) was added BnNH$_2$ (275 mg, 2.562 mmol, 6 eq) and KI (35 mg, 0.213 mmol, 0.5 eq) and the reaction mixture was refluxed at 80° C. for 1.5 h. After completion, the suspension was concentrated in vacuum and the residue was purified by column chromatography to give the desired product B164 (30.8 mg, yield=29%) as a yellow oil. $^1$H NMR (400 MHz, DMSO): δ 7.34-7.20 (m, 5H), 3.74-3.64 (m, 2H), 2.50-2.45 (m, 1H), 1.62-1.10 (m, 15H), 0.89-0.75 (m, 3H). Mass: m/z=246 [M+H]$^+$ The following compounds were synthesized via similar routes:

| Compound Name, ID | Structure | $^1$H NMR (400 MHz), MS |
|---|---|---|
| B165: N-benzyl-1-cyclohexylpentan-2-amine | 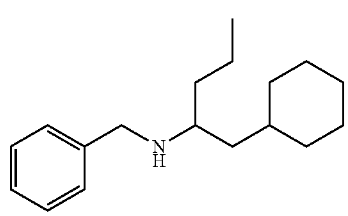 | $^1$H NMR (DMSO): δ 7.35-7.28 (m, 4H), 7.23-7.21 (m, 1H), 3.73-3.71 (m, 2H), 2.52-2.50 (m, 1H), 1.64-0.81 (m, 20H); Mass: m/z = 260 [M + H]$^+$ |

-continued

| Compound Name, ID | Structure | $^1$H NMR (400 MHz), MS |
|---|---|---|
| B166: 1-cyclohexyl-N-(2-fluorobenzyl)butan-2-amine hydrochloride | 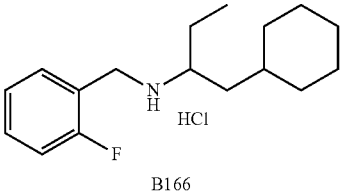 [SMILES: "B166" ; CCC(CC1CCCCC1)NCc1ccccc1F ; Cl]<br>B166 | $^1$H NMR (DMSO): δ 8.86-8.84 (m, 2H), 7.72-7.65 (m, 1H), 7.49-7.48 (m, 1H), 7.34-7.28 (m, 2H), 4.25-4.10 (m, 2H), 3.15-3.05 (m, 1H), 1.73-0.84 (m, 18H); Mass: m/z = 264 [M − HCl + H]$^+$ |
| B213: N-benzyl-1-(2,3-dihydro-1H-inden-1-yl)methanamine hydrochloride | 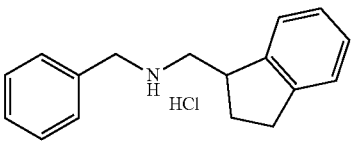<br>B213 | $^1$H NMR (DMSO): δ 9.70-9.10 (m, 2H), 7.65-7.55 (m, 2H), 7.45-7.35 (m, 3H), 7.25-7.10 (m, 4H), 4.30-4.10 (m, 2H), 3.60-3.55 (m, 1H), 3.33-3.30 (m, 1H), 3.00-2.75 (m, 3H), 2.35-2.20 (m, 1H), 2.05-1.85 (m, 1H); Mass: m/z = 238 [M − HCl + H]$^+$ |
| B214: N-benzyl-1-(1,2,3,4-tetrahydronaphthalen-1-yl)methanamine hydrochloride | 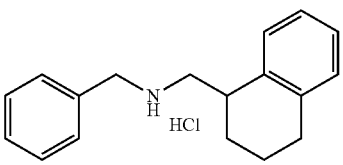<br>B214 | $^1$H NMR (DMSO): δ 9.55-9.40 (m, 1H), 9.20-9.05 (m, 1H), 7.75-7.05 (m, 9H), 4.30-4.10 (m, 2H), 3.35-3.25 (m, 1H), 3.20-3.00 (m, 2H), 2.75-2.65 (m, 2H), 2.05-0.60 (m, 4H); Mass: m/z = 252 [M − HCl + H]$^+$ |
| B215: N-benzyl-2-(piperidin-4-yl)ethanamine hydrochloride | 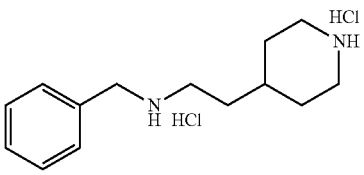<br>B215 | $^1$H NMR (DMSO): δ 9.45-9.20 (m, 2H), 8.95-8.55 (m, 2H), 7.64-7.38 (m, 5H), 4.15-4.05 (m, 2H), 3.30-3.20 (m, 2H), 3.00-2.75 (m, 4H), 1.85-1.20 (m, 7H). |
| B216: tert-butyl 4-(2-(benzylamino)ethyl)piperidine-1-carboxylate | 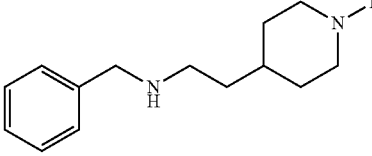<br>B216 | $^1$H NMR (DMSO): δ 7.60-7.40 (m, 5H), 4.18-4.10 (m, 2H), 3.95-3.80 (m, 2H), 2.95-2.85 (m, 2H), 2.75-2.60 (m, 2H), 1.70-0.90 (m, 16H). |
| B218: 4-(2-(benzylamino)ethyl)cyclohexanone | 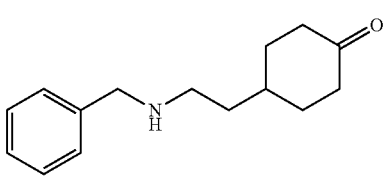<br>B218 | $^1$H NMR (DMSO): δ 7.50-7.10 (m, 5H), 4.15-4.10 (m, 2H), 3.75-3.65 (m, 2H), 2.20-1.10 (m, 11H); Mass: m/z = 232 [M + H]$^+$ |
| B219: (E)-N-benzyl-4-cyclohexylbut-3-en-2-amine | 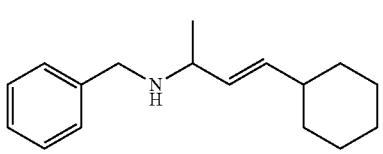<br>B219 | $^1$H NMR (DMSO): δ 7.50-7.20 (m, 5H), 3.90-3.60 (m, 2H), 3.40-3.20 (m, 1H), 2.90-2.80 (m, 1H), 1.80-0.80 (m, 15H); Mass: m/z = 244 [M + H]$^+$ |

Synthetic Scheme 2

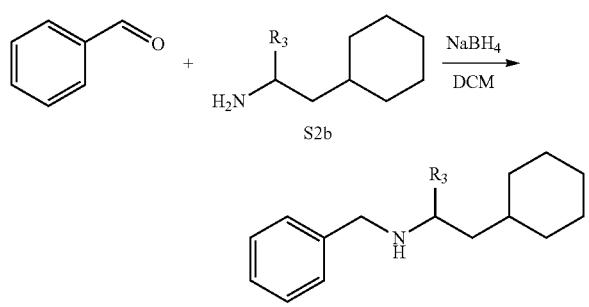

For example, N-benzyl-2-cyclohexyl-1-cyclopropyl-ethanamine (B167) was synthesized as follows: N-benzyl-2-cyclohexyl-1-cyclopropylethanamine
Synthetic Scheme 2

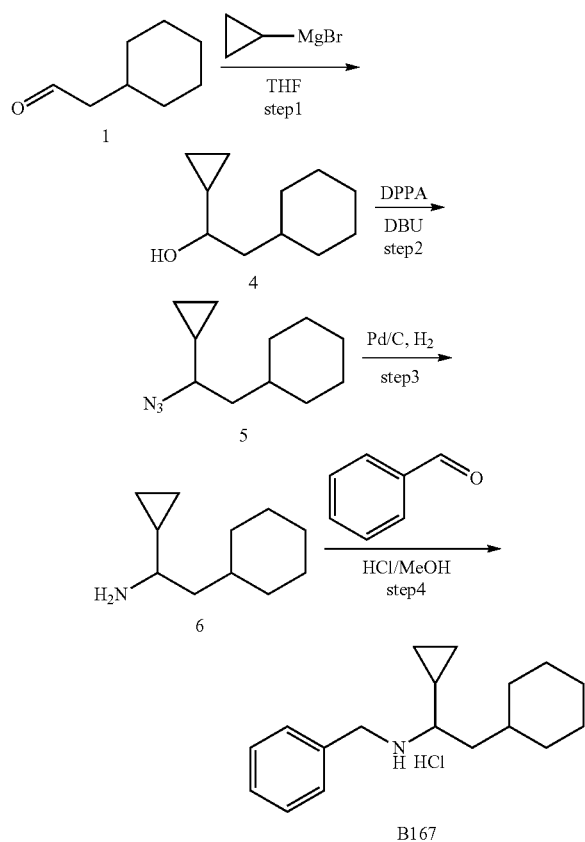

Step 1: See Scheme 1, step 1
Step 2: Preparation of 5

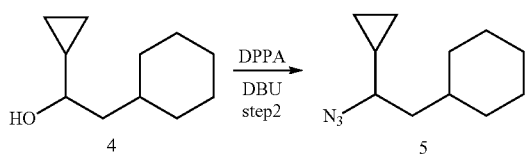

To a solution of 4 (565 mg, 8.005 mmol, 1 eq) in THF (14 mL, c=0.25) was added dropwise DPPA (1.11 g, 4.032 mmol, 1.2 eq) and DBU (614 mg, 4.032 mmol, 1.2 eq) at 0° C. and the reaction mixture was stirred at 50° C. overnight. After completion, the reaction mixture was washed with water (20 mL) and extracted with EA (2×20 mL). The combined organic phases were washed with brine, dried over $Na_2SO_4$, filtered and concentrated in vacuum. The residue was purified by column chromatography to give the desired product 5 (348.8 mg, yield=50%) as an oil.

Step 3: Preparation of 6

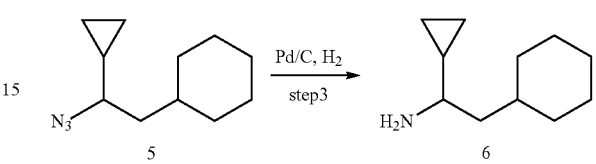

To a solution of 5 (267 mg, 1.382 mmol, 1 eq) in THF (7 mL, c=0.2) was added Pd/C (20% wt, 53 mg). $H_2$ was bubbled through the reaction mixture to saturate the solution. The reaction mixture was stirred at room temperature for 0.5 h. After completion, the reaction solution was filtered and washed with EtOH (4×30 mL). The filtrate was concentrated in vacuum and the residue was purified on a silica gel column to give the product 6 (125 mg, yield=54%) as a yellow solid.

Step 4: Preparation of B167

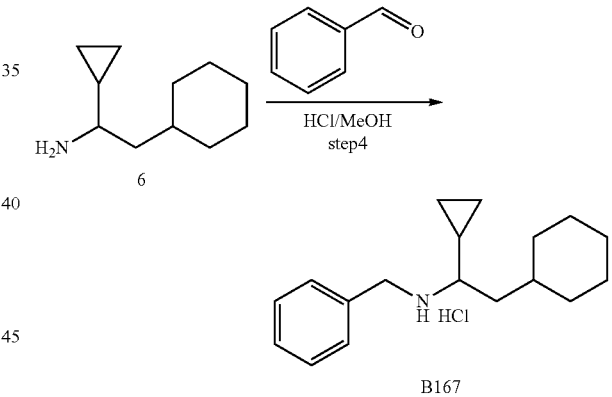

To a solution of 6 (63 mg, 0.377 mmol, 1 eq) in MeOH (3.4 mL, c=0.2) was added benzaldehyde (147 mg, 1.382 mmol, 4 eq) and $MgSO_4$ (62 mg). The reaction mixture was stirred at 40° C. for 1 h. After that, AcOH (0.1 mL) and $NaBH_3CN$ (91 mg, 1.4415 mmol, 3 eq) was added and the resulting mixture was stirred at 80° C. overnight. After completion, the suspension was concentrated in vacuum and the residue was purified by column chromatography to give the desired product (8.5 mg, yield=9%) as a yellow oil. After that, the product was dissolved in a solution of HCl/MeOH (4M, 0.5 mL) again and the resulting mixture was concentrated in vacuum to give the desired product B167 (9.5 mg, yield=95%) as a yellow oil. $^1$H NMR (400 MHz, DMSO): δ 9.00-8.70 (m, 2H), 7.60-7.35 (m, 5H), 4.23-4.10 (m, 2H), 3.30-3.25 (m, 1H), 1.90-0.65 (m, 14H), 0.55-0.50 (m, 2H), 0.28-0.25 (m, 2H). Mass: m/z=258 [M+H]$^+$ The following compounds were synthesized via a similar route:

| Compound Name, ID | Structure | Data of $^1$H NMR (400 MHz), MS |
|---|---|---|
| B169; N-benzyl-2-cyclohexyl-1-phenylethanamine hydrochloride | B169 | $^1$H NMR (DMSO): δ 9.52 (brs, 1H), 9.33 (brs, 1H), 7.54-7.31 (m, 10H), 4.31 (brs, 1H), 4.06 (brs, 1H), 3.70 (brs, 1H), 1.99-0.86 (m, 13H); Mass: m/z = 294 [M − HCl + H]$^+$ |
| B168; 2-(benzylamino)-3-cyclohexylpropan-1-ol | B168 | $^1$H NMR (DMSO): δ 8.88-8.60 (m, 2H), 7.53-7.44 (m, 2H), 7.42-7.31 (m, 3H), 4.28-4.10 (m, 2H), 3.72-3.71 (m, 1H), 3.57-3.56 (m, 1H), 3.11-3.01 (m, 1H), 1.78-0.72 (m, 13H); Mass: m/z = 248 [M + H]$^+$ |
| B202; N-benzyl-1-cyclohexyl-3-methoxypropan-2-amine hydrochloride | B202 | $^1$H NMR (DMSO): δ 8.90-8.71 (m, 2H), 7.60-7.38 (m, 5H), 4.28-4.10 (m, 2H), 3.72-3.71 (m, 2H), 3.58-3.56 (m, 1H), 3.35 (s, 3H), 1.78-0.72 (m, 13H); Mass: m/z = 262 [M − HCl + H]$^+$ |
| B203; methyl 2-(benzylamino)-3-cyclohexylpropanoate hydrochloride | B203 | $^1$H NMR (DMSO): δ 9.91 (brs, 1H), 9.64 (brs, 1H), 7.53-7.35 (m, 5H), 4.19-4.10 (m, 2H), 4.00 (brs, 1H), 3.75 (s, 3H), 1.84-0.83 (m, 13H); Mass: m/z = 276 [M − HCl + H]$^+$ |
| B204; 2-(benzylamino)-3-cyclohexylpropanoic acid | B204 | $^1$H NMR (DMSO): δ 13.92 (brs, 1H), 9.59 (brs, 1H), 7.53-7.43 (m, 5H), 4.20-4.10 (m, 2H), 3.81 (s, 1H), 3.46-3.41 (m, 1H), 1.76-0.84 (m, 13H); Mass: m/z = 262 [M + H]$^+$ |
| B205; 2-(benzylamino)-3-cyclohexylpropanamide hydrochloride | B205 | $^1$H NMR (DMSO): δ 9.30 (brs, 2H), 8.09 (s, 1H), 7.73 (s, 1H), 7.51-7.42 (m, 5H), 4.04 (s, 2H), 3.67 (s, 1H), 1.81-0.80 (m, 13H); Mass: m/z = 261 [M − HCl + H]$^+$ |
| B210; tert-butyl benzyl(1-cyclohexyl-3-oxopropan-2-yl)carbamate | B210 | $^1$H NMR (DMSO): δ 9.40 (s, 1H), 7.40-7.15 (m, 5H), 4.15-4.10 (m, 2H), 3.95-3.80 (m, 1H), 1.70-0.65 (m, 22H); Mass: m/z = 246 [M − Boc + H]$^+$ |

Synthetic Scheme 3

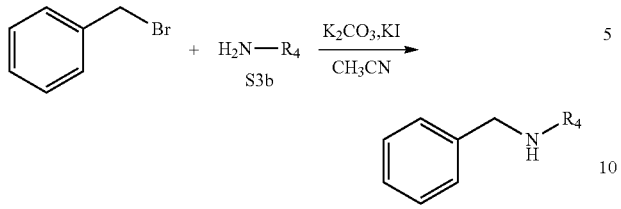

N-benzyl-2,3-dihydro-1H-inden-2-amine hydrochloride (B206) was synthesized according to Synthetic Scheme 3.

Synthetic Scheme 3

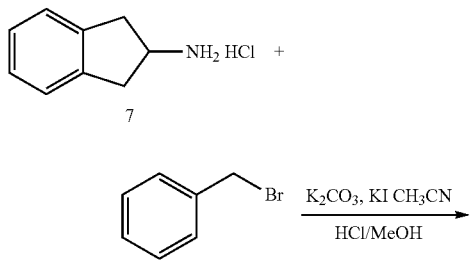

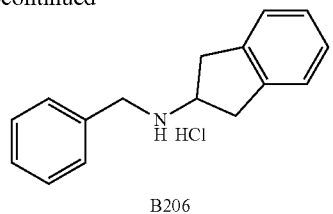

To a solution of 7 (1 g, 5.915 mmol, 1 eq) in CH₃CN (12 mL, c=0.5) was added BnBr (1.51 g, 8.87 mmol, 1.5 eq), K₂CO₃ (3.27 g, 23.66 mmol, 4 eq) and KI (295 mg, 1.775 mmol, 0.3 eq) and the reaction mixture was refluxed at room temperature for 4 h. After completion, the reaction mixture was washed with water (20 mL) and extracted with EA (2×20 mL). The combined organic phases were washed with brine, dried over Na₂SO₄, filtered and concentrated in vacuum. The residue was purified by column chromatography to give the desired product (421 mg, yield=32%) as a oil. After that, the product was dissolved in a solution of HCl/MeOH (4M, 2.0 mL) again and the resulting mixture was concentrated in vacuum to give the desired product B206 (480 mg, yield=95%) as a yellow oil. $^1$H NMR (400 MHz, DMSO): δ 9.80-9.55 (m, 1H), 7.70-7.60 (m, 2H), 7.50-7.35 (m, 3H), 7.25-7.10 (m, 4H), 4.25-4.15 (m, 2H), 4.05-3.90 (m, 1H), 3.35-3.25 (m, 2H), 3.25-3.15 (m, 2H). Mass: m/z=224 [M−HCl+H]$^+$ The following compounds were synthesized via a similar route:

| Compound Name, ID | Structure | Data of $^1$H NMR (400 MHz), MS |
|---|---|---|
| B207; (R)-N-benzyl-2-cyclohexyl-1-phenylethanamine hydrochloride | 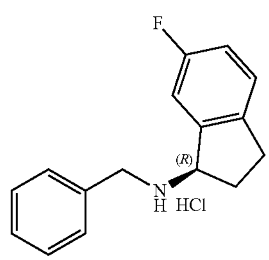 | $^1$H NMR (DMSO): δ 9.60-9.35 (m, 2H), 7.70-7.10 (m, 8H), 4.90-4.78 (m, 1H), 4.25-4.15 (m, 2H), 3.20-3.05 (m, 1H), 2.95-2.80 (m, 1H), 2.51-2.50 (m, 1H), 2.35-2.25 (m, 1H); Mass: m/z = 242 [M + H]$^+$. |
| B208; (S)-N-benzyl-6-fluoro-2,3-dihydro-1H-inden-1-amine hydrochloride | 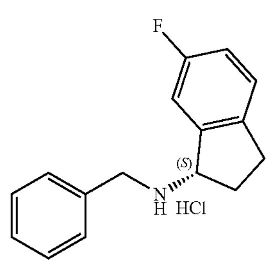 | $^1$H NMR (DMSO): δ 9.60-9.35 (m, 2H), 7.70-7.10 (m, 8H), 4.90-4.78 (m, 1H), 4.25-4.15 (m, 2H), 3.20-3.05 (m, 1H), 2.95-2.80 (m, 1H), 2.51-2.50 (m, 1H), 2.35-2.25 (m, 1H); Mass: m/z = 242 [M + H]$^+$ |

| Compound Name, ID | Structure | Data of ¹H NMR (400 MHz), MS |
|---|---|---|
| B209; (S)-N-benzyl-6-methoxy-2,3-dihydro-1H-inden-1-amine hydrochloride | B209 | ¹H NMR (DMSO): δ 9.60-9.56 (m, 2H), 7.65-7.60 (m, 2H), 7.45-7.35 (m, 4H), 7.30-7.20 (m, 1H), 7.00-6.90 (m, 1H), 4.75 (s, 1H), 4.19 (s, 2H), 3.76 (s, 3H), 3.10-3.00 (m, 1H), 2.85-2.75 (m, 1H), 2.55-2.45 (m, 1H), 2.35-2.23 (m, 1H); Mass: m/z = 254 [M − HCl + H]⁺ |
| B211; (1S,2R)-N-benzyl-2-(3,4-difluorophenyl)cyclopropanamine hydrochloride | B211 | ¹H NMR (DMSO): δ 9.88 (brs, 2H), 7.54 (s, 2H), 7.41-7.31 (m, 4H), 7.24-7.19 (m, 1H), 7.04-6.99 (m, 1H), 4.27 (s, 2H), 2.88 (s, 1H), 2.50 (s, 1H), 1.57-1.56 (m, 1H), 1.35-1.30 (m, 1H); Mass: m/z = 260 [M − HCl + H]⁺ |
| B212; N-benzyl-2-(4,4-difluorocyclohexyl)ethanamine hydrochloride | B212 | ¹H NMR (DMSO): δ 9.25-8.90 (m, 2H), 7.55-7.30 (m, 5H), 4.15-4.05 (m, 2H), 2.95-2.85 (m, 2H), 2.00-1.05 (m, 11H); Mass: m/z = 254 [M + H]⁺ |
| B220; 3-((benzylamino)methyl)-7-methoxybenzo[c][1,2]oxaborol-1(3H)-ol hydrochloride | B220 | ¹H NMR (DMSO): δ 8.18-8.05 (m, 2H), 7.75-7.65 (m, 1H), 7.40-7.25 (m, 5H), 7.05-6.85 (m, 2H), 4.70-4.65 (m, 1H), 4.40-4.30 (m, 2H), 4.15-4.05 (m, 1H), 3.77 (s, 3H), 3.15-3.00 (m, 2H); Mass: m/z = 284 [M + H]⁺ |

Compound B255 was made according to Synthetic Scheme 4:

Synthetic Scheme 4

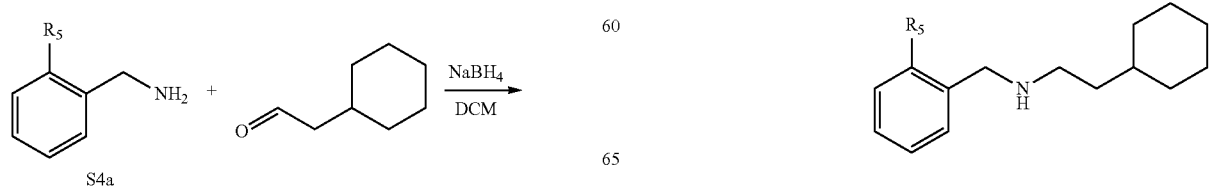

Reference: WO 2007/017267, 15 Feb. 2007.

| Compound Name | Structure | Data of $^1$H NMR (400 MHz), MS |
|---|---|---|
| B255; (2-((2-cyclohexylethylamino)methyl)phenyl)methanol hydrochloride | B255 | $^1$H NMR (DMSO): δ 8.95-8.75 (m, 2H), 7.58-7.25 (m, 4H), 5.85-5.71 (s, 1H), 4.70-4.60 (m, 2H), 4.25-4.15 (m, 2H), 3.05-2.90 (m, 2H), 1.85-0.75 (m, 13H); Mass: m/z = 248 [M + H]$^+$ |

Synthetic Scheme 5

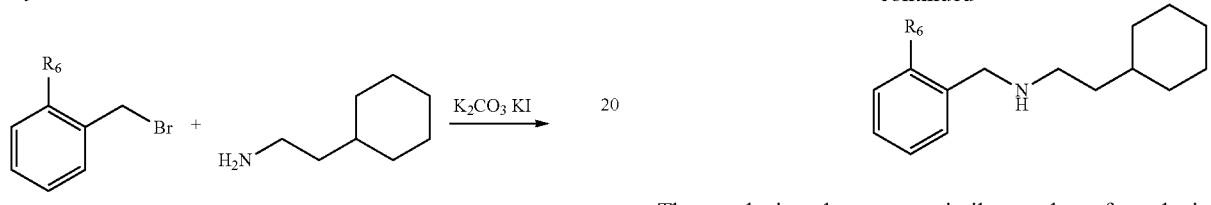

The synthetic scheme was similar to that of synthetic scheme 3 and the corresponding data were summarized as follows:

| Compound Name, ID | Structure | Data of $^1$H NMR (400 MHz); MS |
|---|---|---|
| B340; 2-((2-cyclohexylethylamino)methyl)phenylboronic acid | B340 | $^1$H NMR (DMSO): δ 7.62-7.45 (m, 1H), 7.25-7.00 (m, 3H), 4.05-3.85 (m, 2H), 2.80-2.65 (m, 2H), 1.90 (s, 2H), 1.70-0.68 (m, 13H); Mass: m/z = 262 [M + H]$^+$ |
| B376; 2-((2-cyclohexylethylamino)methyl)benzylboronic acid | B376 | $^1$H NMR (DMSO): δ 7.25-6.90 (m, 4H), 3.90-3.80 (m, 2H), 3.78-3.32 (m, 2H), 3.05-2.85 (m, 2H), 1.95-0.75 (m, 13H); Mass: m/z = 276 [M + H]$^+$ |
| B225; 2-cyclohexyl-N-(2-(trifluoromethyl)benzyl)ethanamine hydrochloride | B225 | $^1$H NMR (DMSO): δ 9.68 (brs, 2H), 8.10-7.90 (m, 1H), 7.85-7.70 (m, 2H), 7.65-7.55 (m, 1H), 4.30-4.20 (m, 2H), 2.97-2.82 (m, 2H), 1.66-0.85 (m, 13H); Mass: m/z = 286 [M − HCl + H]$^+$ |
| B228; 2-cyclohexyl-N-(2-ethylbenzyl)ethanamine hydrochloride | B228 | $^1$H NMR (DMSO): δ 9.14 (brs, 2H), 7.61-7.53 (m, 1H), 7.40-7.10 (m, 3H), 4.16-4.08 (m, 2H), 3.10-2.90 (m, 2H), 2.80-2.65 (m, 2H), 1.80-0.70 (m, 18H); Mass: m/z = 246 [M − HCl + H]$^+$ |

-continued

| Compound Name, ID | Structure | Data of $^1$H NMR (400 MHz); MS |
|---|---|---|
| B254; N-(2-(aminomethyl)benzyl)-2-cyclohexylethanamine hydrochloride | B254 | $^1$H NMR (DMSO): δ 9.17 (brs, 2H), 8.44 (brs, 2H), 7.70-7.42 (m, 4H), 4.35-4.15 (m, 4H), 3.10-2.98 (m, 2H), 1.80-0.80 (m, 13H); Mass: m/z = 247 [M − 2HCl + H]$^+$ |

Synthetic Scheme 6

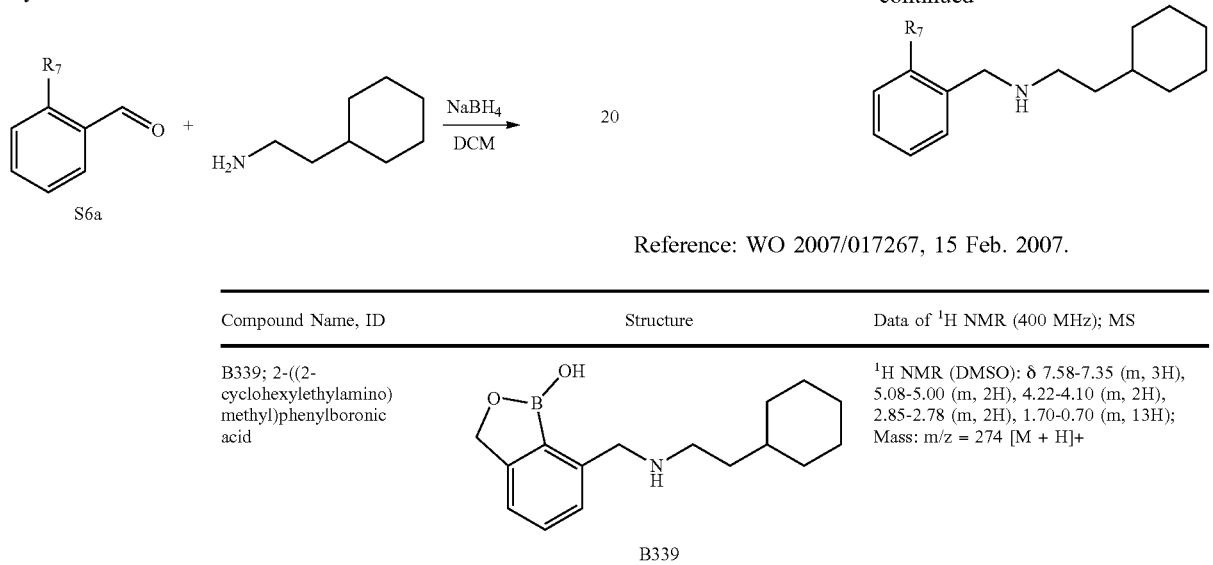

Reference: WO 2007/017267, 15 Feb. 2007.

| Compound Name, ID | Structure | Data of $^1$H NMR (400 MHz); MS |
|---|---|---|
| B339; 2-((2-cyclohexylethylamino)methyl)phenylboronic acid | B339 | $^1$H NMR (DMSO): δ 7.58-7.35 (m, 3H), 5.08-5.00 (m, 2H), 4.22-4.10 (m, 2H), 2.85-2.78 (m, 2H), 1.70-0.70 (m, 13H); Mass: m/z = 274 [M + H]+ |
| B341; 2-cyclohexyl-N-(2-(trimethylsilyl)benzyl)ethanamine hydrochloride | B341 | $^1$H NMR (DMSO): δ 9.50-8.80 (m, 2H), 7.80-7.30 (m, 4H), 4.25-4.10 (m, 2H), 3.10-2.90 (m, 2H), 1.70-0.75 (m, 13H), 0.34 (s, 9H); Mass: m/z = 290 [M + H]$^+$ |
| B226; 2-((2-cyclohexylethylamino)methyl)phenol | B226 | $^1$H NMR (DMSO): δ 7.10-6.95 (m, 2H), 6.80-6.55 (m, 2H), 3.85-3.75 (m, 2H), 2.53-2.45 (m, 2H), 1.80-0.75 (m, 13H); Mass: m/z = 234 [M + H]$^+$ |
| B227; 2-cyclohexyl-N-(2-isopropylbenzyl)ethanamine hydrochloride | B227 | $^1$H NMR (DMSO): δ 9.12 (brs, 2H), 7.60-7.15 (m, 4H), 4.15-4.05 (m, 2H), 3.05-2.95 (m, 3H), 1.75-0.80 (m, 19H); Mass: m/z = 260 [M + H]$^+$ |

-continued

| Compound Name, ID | Structure | Data of ¹H NMR (400 MHz); MS |
|---|---|---|
| B229; N-(biphenyl-2-ylmethyl)-2-cyclohexylethanamine hydrochloride | B229 | ¹H NMR (DMSO): δ 9.34 (brs, 2H), 7.89-7.86 (m, 1H), 7.51-7.31 (m, 8H), 4.10-3.95 (m, 2H), 2.80-2.65 (m, 2H), 1.83-0.65 (m, 13H); Mass: m/z = 294 [M + H]⁺ |
| B230; 2-cyclohexyl-N-(2-(thiophen-2-yl)benzyl)ethanamine hydrochloride | B230 | ¹H NMR (DMSO): δ 9.31 (brs, 2H), 7.86-7.84 (m, 1H), 7.71-7.69 (m, 1H), 7.50-7.46 (m, 3H), 7.25-7.19 (m, 2H), 4.25-4.15 (m, 2H), 2.90-2.78 (m, 2H), 1.70-0.70 (m, 13H); Mass: m/z = 300 [M − HCl + H]⁺ |
| B231; 2-cyclohexyl-N-(2-(pyridin-3-yl)benzyl)ethanamine hydrochloride | B231 | ¹H NMR (DMSO): δ 9.53 (brs, 2H), 9.04 (s, 1H), 8.96 (s, 1H), 8.58 (s, 1H), 8.09 (s, 1H), 8.08-7.99 (m, 1H), 7.63-7.55 (m, 2H), 7.45-7.43 (m, 1H), 4.20-3.90 (m, 2H), 2.85-2.75(m, 2H), 1.75-0.65 (m, 13H); Mass: m/z = 295 [M − HCl + H]⁺ |
| B232; 2-cyclohexyl-N-(2-phenoxybenzyl)ethanamine hydrochloride | B232 | ¹H NMR (DMSO): δ 9.25-9.10 (m, 2H), 7.73-7.71 (m, 1H), 7.47-7.38 (m, 3H), 7.23-7.19 (m, 2H), 7.10-7.08 (m, 2H), 6.86-6.84 (m, 1H), 4.25-4.10 (m, 2H), 3.05-2.95 (m, 2H), 1.70-0.70 (m, 13H); Mass: m/z = 310 [M − HCl + H]⁺ |
| B233; 2-cyclohexyl-N-(2-cyclopropylbenzyl)ethanamine hydrochloride | B233 | ¹H NMR (DMSO): δ 9.30-9.17 (m, 2H), 7.65-7.40 (m, 1H), 7.35-7.20 (m, 2H), 7.11-7.08 (m, 2H), 4.40-4.25 (m, 2H), 3.05-2.95 (m, 2H), 2.25-2.10 (m, 1H), 1.85-0.60 (m, 17H); Mass: m/z = 258 [M − HCl + H]⁺ |
| B234; 2-cyclohexyl-N-(2-(naphthalen-2-yl)benzyl)ethanamine hydrochloride | B234 | ¹H NMR (DMSO): δ 9.09 (brs, 2H), 8.05-7.35 (m, 11H), 4.16-4.08 (m, 2H), 2.75-2.65 (m, 2H), 1.65-0.55 (m, 13H); Mass: m/z = 344 [M − HCl + H]⁺ |

| Compound Name, ID | Structure | Data of ¹H NMR (400 MHz); MS |
|---|---|---|
| B235; 2-((2-cyclohexylethylamino)methyl)aniline hydrochloride | B235 | ¹H NMR (DMSO): δ 10.30-8.30 (m, 2H), 7.68-7.20 (m, 4H), 4.43-4.11 (m, 2H), 3.05-2.85 (m, 2H), 1.85-0.80 (m, 13H); Mass: m/z = 233 [M − HCl + H]⁺ |
| B236; 2-cyclohexyl-N-(2-(furan-2-yl)benzyl)ethanamine hydrochloride | B236 | ¹H NMR (DMSO): δ 9.31 (brs, 2H), 7.90-7.70 (m, 3H), 7.55-7.35 (m, 2H), 6.95-6.60 (m, 2H), 4.29-4.38 (m, 2H), 3.00-2.85 (m, 2H), 1.80-0.75 (m, 13H); Mass: m/z = 284 [M − HCl + H]⁺ |
| B237; 2-((2-cyclohexylethylamino)methyl)-N,N-dimethylaniline hydrochloride | B237 | ¹H NMR (DMSO): δ 9.08 (brs, 2H), 7.75-7.20 (m, 4H), 4.36-4.24 (m, 2H), 3.05-2.95 (m, 2H), 2.85 (s, 6H), 1.75-0.80 (m, 13H); Mass: m/z = 261 [M − HCl + H]⁺ |
| B238; 2-cyclohexyl-N-(2-(naphthalen-1-yl)benzyl)ethanamine hydrochloride | B238 | ¹H NMR (DMSO): δ 8.06 (brs, 1H), 8.04 (brs, 1H), 8.15-8.05 (m, 2H), 7.90-7.82 (m, 1H), 7.70-7.20 (m, 8H), 3.95-3.85 (m, 1H), 3.75-3.60 (m, 1H), 2.60-2.50 (m, 2H), 1.65-0.50 (m, 13H); Mass: m/z = 344 [M − HCl + H]⁺ |
| B253; 2-cyclohexyl-N-(2-methoxybenzyl)ethanamine hydrochloride | B253 | ¹H NMR (400 MHz, DMSO): δ 9.20-8.50 (m, 2H), 7.52-7.38 (m, 2H), 7.18-6.95 (m, 2H), 4.15-4.05 (m, 2H), 3.80 (s, 3H), 3.00-2.75 (m, 2H), 1.75-0.70 (m, 13H); Mass: m/z = 248 [M − HCl + H]⁺ |
| B256; 2-((2-cyclohexylethylamino)methyl)phenyl acetate | B256 | ¹H NMR (DMSO): δ 7.82-7.70 (m, 1H), 7.15-7.00 (m, 2H), 6.80-6.65 (m, 2H), 3.85-3.78 (m, 2H), 3.05-2.95 (m, 2H), 2.55-2.45 (s, 3H), 1.80-0.70 (m, 13H); Mass: m/z = 276 [M + H]⁺ |
| B257; 2-((2-cyclohexylethylamino)methyl)benzoic acid hydrochloride | B257 | ¹H NMR (DMSO): δ 13.50 (brs, 1H), 8.95-8.80 (m, 2H), 8.10-8.00 (m, 1H), 7.75-7.55 (m, 3H), 4.50-4.32 (m, 2H), 3.10-2.90 (m, 2H), 1.80-0.70 (m, 13H); Mass: m/z = 262 [M − HCl + H]⁺ |

| Compound Name, ID | Structure | Data of $^1$H NMR (400 MHz); MS |
|---|---|---|
| B258; methyl 2-((2-cyclohexylethylamino)methyl)benzoate hydrochloride | 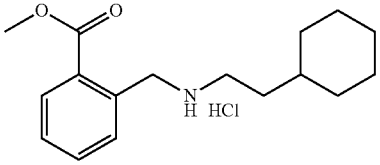<br>B258 | $^1$H NMR (DMSO): δ 8.88 (brs, 2H), 8.10-8.00 (m, 1H), 7.72-7.50 (m, 3H), 4.45-4.30 (m, 2H), 3.85 (s, 3H), 3.05-2.90 (m, 2H), 1.78-0.75 (m, 13H); Mass: m/z = 276 [M − HCl + H]$^+$ |
| B259; 2-((2-cyclohexylethylamino)methyl)benzamide trifluoroacetate | 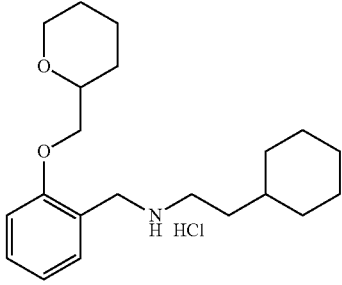<br>B259 | $^1$H NMR (DMSO): δ 8.77 (brs, 2H), 8.35 (s, 1H), 7.91 (s, 1H), 7.75-7.53 (m, 4H), 4.25-4.10 (m, 2H), 3.12-2.90 (m, 2H), 1.80-0.70 (m, 13H); Mass: m/z = 261 [M − TFA + H]$^+$ |
| B328; 2-cyclohexyl-N-(2-((tetrahydro-2H-pyran-2-yl)methoxy)benzyl)ethanamine hydrochloride | 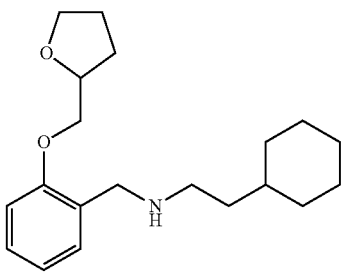<br>B328 | $^1$H NMR (400 MHz, DMSO): δ 9.15-8.90 (m, 2H), 7.49-7.32 (m, 2H), 7.15-6.90 (m, 2H), 4.10-3.90 (m, 5H), 3.76-3.65 (m, 1H), 3.48-3.30 (m, 1H), 2.95-2.80 (m, 2H), 1.90-0.70 (m, 19H); Mass: m/z = 332 [M − HCl + H]$^+$ |
| B329; 2-cyclohexyl-N-(2-((tetrahydrofuran-2-yl)methoxy)benzyl)ethanamine | 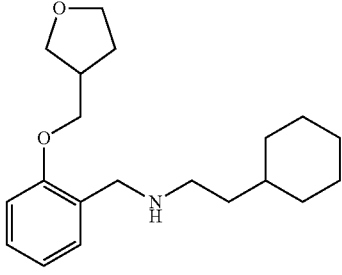<br>B329 | $^1$H NMR (DMSO): δ 7.41-7.30 (m, 2H), 7.06-6.80 (m, 2H), 4.21-4.20 (m, 1H), 4.06-3.86 (m, 2H), 3.95-3.85 (m, 2H), 3.85-3.60 (m, 2H), 2.80-2.72 (m, 2H), 2.05-0.70 (m, 17H); Mass: m/z = 318 [M + H]$^+$ |
| B330; 2-cyclohexyl-N-(2-((tetrahydrofuran-3-yl)methoxy)benzyl)ethanamine | B330 | $^1$H NMR (DMSO): δ 7.43-7.35 (m, 2H), 7.08-6.99 (m, 2H), 4.01-3.94 (m, 4H), 3.85-3.80 (m, 2H), 3.68-3.60 (m, 2H), 2.88-2.85 (m, 2H), 2.85-2.62 (m, 1H), 2.10-1.90 (m, 1H), 1.80-0.70 (m, 14H); Mass: m/z = 318 [M + H]$^+$ |

-continued

| Compound Name, ID | Structure | Data of ¹H NMR (400 MHz); MS |
|---|---|---|
| B331; 2-cyclohexyl-N-(2-((tetrahydro-2H-pyran-4-yl)methoxy)benzyl)ethanamine | B331 | ¹H NMR (DMSO): δ 7.35-7.25 (m, 2H), 6.92-6.88 (m, 2H), 3.91-3.82 (m, 6H), 3.45-3.31 (m, 2H), 2.68-2.64 (m, 2H), 2.05-1.90 (m, 1H), 1.70-0.84 (m, 17H); Mass: m/z = 332 [M + H]⁺ |
| B378; 3-(2-((1-cyclohexylpropan-2-ylamino)methyl)phenyl)propan-1-ol | B378 | ¹H NMR (DMSO): δ 7.56-7.35 (m, 1H), 7.30-7.08 (m, 3H), 3.95-3.78 (m, 2H), 3.45-3.32 (m, 2H), 3.10-2.85 (m, 1H), 2.85-2.65 (m, 2H), 1.85-0.75 (m, 18H); Mass: m/z = 290 [M + H]⁺ |
| B399; 3-(2-((1-cyclohexylpropan-2-ylamino)methyl)phenyl)propanamide trifluoroacetate | B399 | ¹H NMR (DMSO): δ 8.76 (brs, 2H), 7.63 (s, 1H), 7.43-7.00 (m, 5H), 4.30-4.08 (m, 2H), 3.29-3.22 (m, 1H), 2.85-2.78 (m, 2H), 2.60-2.52 (m, 2H), 1.70-0.75 (m, 16H); Mass: m/z = 303 [M − TFA + H]⁺ |
| B400; methyl 3-(2-((1-cyclohexylpropan-2-ylamino)methyl)phenyl)propanoate hydrochloride | B400 | ¹H NMR (DMSO): δ 8.73 (brs, 1H), 8.65 (brs, 1H), 7.60-7.05 (m, 4H), 4.45-4.16 (m, 2H), 3.75-3.50 (m, 3H), 2.95-2.85 (m, 1H), 2.60-2.55 (m, 2H), 1.85-0.65 (m, 18H); Mass: m/z = 318 [M + H]⁺ |
| B401; 3-(2-((1-cyclohexylpropan-2-ylamino)methyl)phenyl)propanoic acid trifluoroacetate | B401 | ¹H NMR (DMSO): δ 8.60 (brs, 1H), 8.54 (brs, 1H), 7.47-7.45 (m, 1H), 7.37-7.29 (m, 3H), 4.32-4.20 (m, 2H), 3.50-3.28 (m, 1H), 2.95-2.88 (m, 2H), 2.60-2.55 (m, 2H), 1.85-0.75 (m, 16H); Mass: m/z = 304 [M + H]⁺ |

The compounds listed below were synthesized according to the following general procedure:

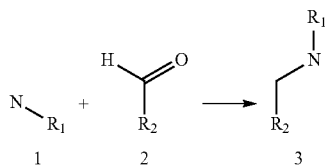

Amine 1 (0.5 mmol), aldehyde 2 (0.55 mmol) were dissolved in 0.6 ml MeOH, heated at 100° C. for 2 hours, then mixture was cooled, NaBH$_4$ (0.5 mmol) was added and stirred for 4 hours. The mixture was heated for 2 hours at 60° C., 3 ml of methanol and 0.2 g of C-18 chromatographic phase were added, stirred for 2 hours, filtered, evaporated and dissolved in 0.5 ml of DMSO. The residue was purified using HPLC. Yields: 31-67%.

Example 2: General Compound Syntheses 2

Synthesis of target compounds was carried out following the general scheme below:

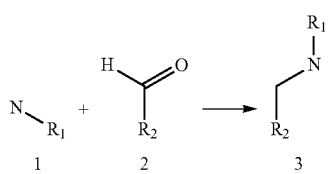

Amine 1 (0.5 mmol), aldehyde 2 (0.55 mmol) were dissolved in 0.6 ml MeOH, heated at 100° C. for 2 hours, then mixture was cooled, NaBH$_4$ (0.5 mmol) was added and stirred for 4 hours. The mixture was heated for 2 hours at 60° C., 3 ml of methanol and 0.2 g of C-18 chromatographic phase were added, stirred for 2 hours, filtered, evaporated and optionally dissolved in 0.5 ml of DMSO. The residue was purified using HPLC. Yield: 31-67%

B27

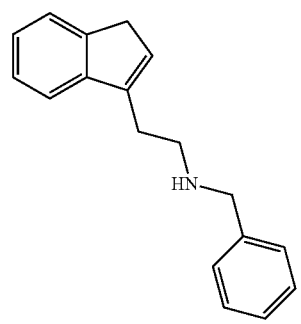

1H NMR (400 MHz, DMSO-d6) δ 7.45 (d, J=7.3 Hz, 1H), 7.29 (dtd, J=27.0, 14.5, 12.6, 7.4 Hz, 7H), 7.17 (t, J=7.5 Hz, 1H), 6.26 (s, 1H), 3.75 (s, 2H), 2.80 (t, J=7.3 Hz, 2H), 2.69 (t, J=7.7 Hz, 2H), 2.54 (s, 1H);

B36

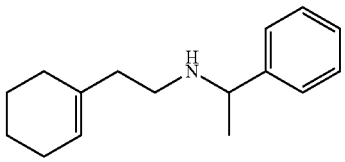

1H NMR (400 MHz, Chloroform-d) δ 9.28 (s, 1H), 8.74 (s, 1H), 7.63 (d, J=7.0 Hz, 2H), 7.45 (dd, J=8.1, 6.2 Hz, 2H), 7.44-7.36 (m, 1H), 5.37 (d, J=3.7 Hz, 1H), 4.40 (d, J=7.1 Hz, 1H), 2.82 (p, J=11.9, 10.4 Hz, 2H), 2.58 (t, J=8.0 Hz, 2H), 1.98 (d, J=6.8 Hz, 3H), 1.94-1.88 (m, 2H), 1.74 (q, J=4.9 Hz, 2H), 1.50 (ddtd, J=16.3, 10.4, 5.5, 3.0 Hz, 4H);

B39

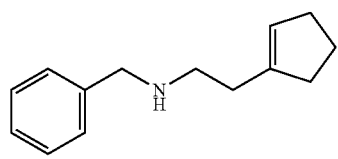

1H NMR (400 MHz, DMSO-d6) δ 7.30-7.21 (m, 4H), 7.20 (s, 1H), 7.16 (ddd, J=8.6, 5.5, 2.5 Hz, 1H), 5.32 (s, 1H), 3.70 (s, 2H), 2.63 (t, J=7.0 Hz, 2H), 2.32-2.20 (m, 3H), 2.19 (d, J=8.8 Hz, 3H), 1.83 (p, J=7.5 Hz, 2H).

B51

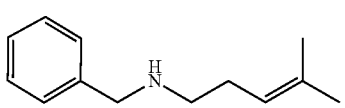

1H NMR (400 MHz, DMSO-d6) δ 7.25 (d, J=6.6 Hz, 4H), 7.17 (d, J=6.4 Hz, 1H), 5.08 (t, J=7.2 Hz, 1H), 3.70 (s, 2H), 2.52 (d, J=7.3 Hz, 2H), 2.12 (q, J=7.2 Hz, 2H), 1.68 (s, 3H), 1.61 (s, 3H).

B63

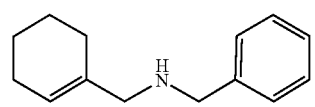

1H NMR (400 MHz, DMSO-d6) δ 7.30-7.20 (m, 4H), 7.16 (t, J=7.0 Hz, 1H), 5.52 (s, 1H), 3.64 (s, 2H), 2.01-1.94 (m, 4H), 1.67-1.51 (m, 5H).

B70

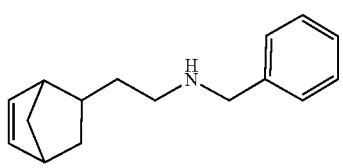

1H NMR (400 MHz, DMSO-d6) δ 7.25 (d, J=6.5 Hz, 5H), 7.16 (dd, J=8.1, 4.9 Hz, 1H), 6.08 (dd, J=5.7, 3.0 Hz, 1H), 5.88 (dd, J=5.8, 2.8 Hz, 1H), 3.68 (s, 2H), 2.73 (s, 2H), 2.50 (d, J=14.5 Hz, 1H), 2.06 (qt, J=8.0, 3.7 Hz, 1H), 1.83 (ddd, J=12.2, 8.9, 3.8 Hz, 1H), 1.40-1.32 (m, 1H), 1.26 (dd, J=13.5, 6.7 Hz, 1H), 1.21 (dd, J=7.9, 4.3 Hz, 2H), 0.49 (dt, J=11.6, 3.3 Hz, 1H).

B71

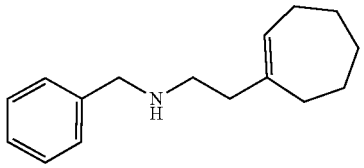

1H NMR (400 MHz, DMSO-d6) δ 7.35-7.21 (m, 4H), 7.17 (tq, J=5.7, 3.7, 3.0 Hz, 1H), 5.53 (t, J=6.4 Hz, 1H), 3.69 (s, 2H), 2.56 (t, J=7.0 Hz, 2H), 2.50 (s, 1H), 2.12 (d, J=7.0 Hz, 1H), 2.06 (dq, J=10.8, 6.1, 5.0 Hz, 5H), 1.88 (s, 6H), 1.72 (p, J=6.0 Hz, 2H), 1.44 (dt, J=10.4, 5.5 Hz, 4H).

B72

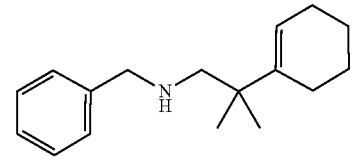

1H NMR (400 MHz, DMSO-d6) δ 7.24 (d, J=4.4 Hz, 4H), 7.16 (p, J=4.3 Hz, 1H), 5.46-5.40 (m, 1H), 3.69 (s, 2H), 2.36 (s, 2H), 2.03 (tt, J=6.2, 3.1 Hz, 2H), 1.87 (s, 1H), 1.88-1.78 (m, 1H), 1.62-1.47 (m, 5H), 1.00 (s, 6H), 0.95 (d, J=2.1 Hz, 1H).

B73

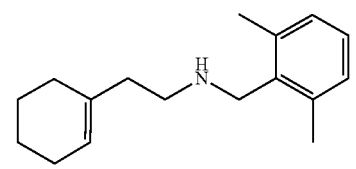

1H NMR (400 MHz, DMSO-d6) δ 6.99-6.87 (m, 3H), 5.38 (s, 1H), 3.00 (s, 2H), 2.68 (t, J=6.9 Hz, 2H), 2.34 (s, 6H), 2.09 (t, J=7.0 Hz, 2H), 1.96 (d, J=6.2 Hz, 2H), 1.90 (d, J=14.3 Hz, 0H), 1.90 (s, 2H), 1.65-1.48 (m, 4H), 0.93 (s, 1H).

B74

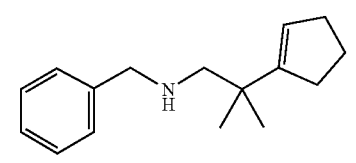

1H NMR (400 MHz, DMSO-d6) δ 7.25 (dd, J=12.9, 5.5 Hz, 4H), 7.15 (t, J=7.0 Hz, 1H), 3.00 (s, 2H), 2.71 (s, 1H), 2.49-2.41 (m, 1H), 2.27 (t, J=10.8 Hz, 1H), 2.21-2.08 (m, 2H), 1.84-1.76 (m, 1H), 1.60 (d, J=21.6 Hz, 8H).

B144

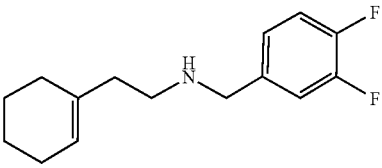

1H NMR (400 MHz, Chloroform-d) δ 7.22-7.03 (m, 2H), 7.03-6.96 (m, 1H), 5.45 (tt, J=3.7, 1.7 Hz, 1H), 3.73 (s, 2H), 2.65 (t, J=6.9 Hz, 2H), 2.14 (t, J=7.0 Hz, 2H), 1.98 (tdd, J=6.2, 3.8, 1.8 Hz, 2H), 1.92-1.84 (m, 2H), 1.66-1.49 (m, 3H), 1.35-1.29 (m, 1H).

B146

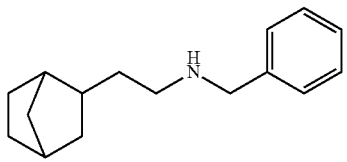

1H NMR (400 MHz, DMSO-d6) δ 7.30-7.21 (m, 4H), 7.16 (td, J=6.5, 6.1, 2.5 Hz, 1H), 3.68 (s, 2H), 2.56-2.44 (m, 3H), 2.16 (d, J=4.7 Hz, 1H), 1.93 (d, J=3.5 Hz, 1H), 1.42 (dqt, J=21.5, 8.2, 3.5 Hz, 5H), 1.30 (d, J=9.8 Hz, 1H), 1.23 (s, 1H), 1.22-0.96 (m, 4H).

B151

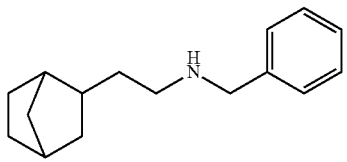

1H NMR (500 MHz, Chloroform-d) δ 7.29 (q, J=7.3, 6.8 Hz, 1H), 7.21 (d, J=7.2 Hz, 2H), 5.38 (d, J=3.9 Hz, 1H), 2.89 (t, J=6.7 Hz, 1H), 2.81 (t, J=7.0 Hz, 1H), 2.68 (t, J=7.0 Hz, 1H), 2.11 (t, J=7.0 Hz, 1H), 1.96-1.90 (m, 1H), 1.56 (ddt, J=8.6, 6.4, 4.0 Hz, 1H), 1.50 (dtt, J=9.3, 6.1, 2.8 Hz, 1H), 1.31 (s, 1H).

B152

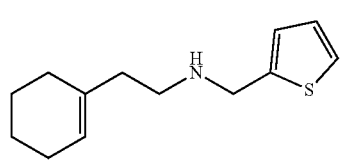

1H NMR (400 MHz, DMSO-d6) δ 7.19 (d, J=5.0 Hz, 1H), 6.92-6.83 (m, 2H), 5.38 (s, 1H), 3.89 (s, 2H), 2.62 (t, J=7.2 Hz, 2H), 2.50 (s, OH), 2.07 (t, J=7.3 Hz, 2H), 1.97 (s, 3H), 1.88 (d, J=6.9 Hz, 2H), 1.57 (dq, J=19.1, 5.2 Hz, 5H).

B153

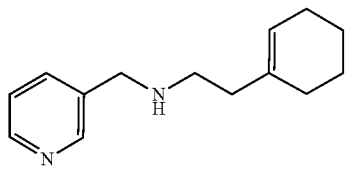

1H NMR (400 MHz, Chloroform-d) δ 8.56-8.46 (m, 2H), 7.69-7.62 (m, 1H), 7.24 (dd, J=7.6, 4.8 Hz, 1H), 5.45 (s, 1H), 3.80 (s, 2H), 2.67 (t, J=6.9 Hz, 2H), 2.14 (t, J=6.9 Hz, 2H), 1.98 (s, 2H), 1.86 (d, J=7.4 Hz, 2H), 1.56 (dq, J=11.7, 6.3 Hz, 3H), 1.22 (s, 1H).

B222

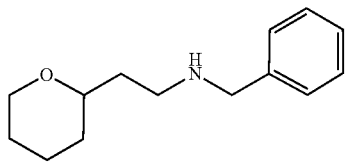

1H NMR (400 MHz, DMSO-d6) δ 7.26 (s, 3H), 7.23 (d, J=7.6 Hz, 1H), 7.16 (s, 1H), 3.84 (d, J=11.6 Hz, 1H), 3.68 (s, 1H), 3.29 (d, J=10.6 Hz, 2H), 3.20 (d, J=4.5 Hz, 1H), 2.56 (d, J=12.9 Hz, 2H), 1.79 (s, 1H), 1.58-1.49 (m, 2H), 1.46 (s, 2H).

B223

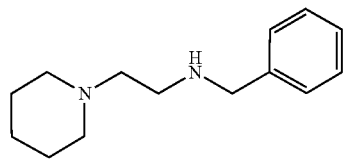

1H NMR (400 MHz, Chloroform-d) δ 7.32 (d, J=4.5 Hz, 3H), 7.28-7.20 (m, 1H), 3.80 (s, 2H), 2.70 (t, J=6.3 Hz, 2H), 2.44 (t, J=6.3 Hz, 2H), 2.33 (t, J=5.2 Hz, 4H), 1.90 (s, 1H), 1.55 (t, J=5.7 Hz, 3H), 1.41 (p, J=5.8 Hz, 2H).

B224

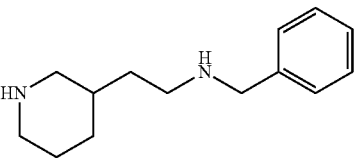

1H NMR (400 MHz, Chloroform-d) δ 7.36-7.28 (m, 3H), 7.28-7.21 (m, 1H), 3.77 (d, J=1.9 Hz, 2H), 3.00 (t, J=10.0 Hz, 2H), 2.64 (t, J=7.5 Hz, 2H), 2.52 (t, J=12.1 Hz, 1H), 2.24 (t, J=11.3 Hz, 1H), 2.05 (s, 5H), 1.79 (d, J=13.2 Hz, 1H), 1.63 (d, J=13.4 Hz, 1H), 1.41 (dtd, J=21.0, 15.1, 13.7, 5.1 Hz, 4H), 1.04 (tt, J=13.0, 6.5 Hz, 1H).

B332

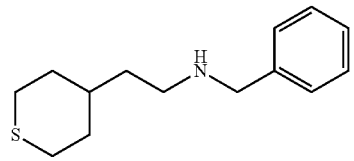

1H NMR (400 MHz, DMSO-d6) δ 7.34-7.25 (m, 2H), 3.66 (s, 1H), 2.59-2.43 (m, 3H), 1.90 (dd, J=13.0, 3.4 Hz, 1H), 1.33 (p, J=6.9 Hz, 1H), 1.27-1.13 (m, 1H).

B348

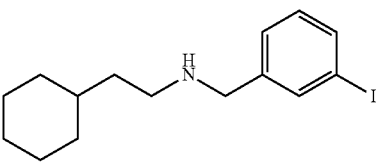

1H NMR (400 MHz, DMSO-d6) δ 7.70 (s, 1H), 7.56 (d, J=7.9 Hz, 1H), 7.31 (d, J=7.6 Hz, 1H), 7.10 (t, J=7.7 Hz, 1H), 3.62 (s, 2H), 2.44 (d, J=13.6 Hz, 1H), 2.44 (s, 2H), 2.05 (s, 1H), 1.63 (d, J=11.4 Hz, 5H), 1.29 (d, J=7.4 Hz, 3H), 1.15 (h, J=12.3 Hz, 3H), 0.83 (d, J=11.1 Hz, 2H).

B349

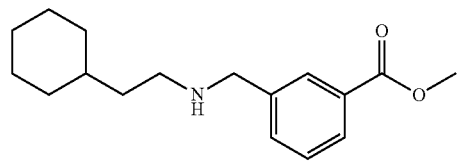

m/z: 275.23

B350

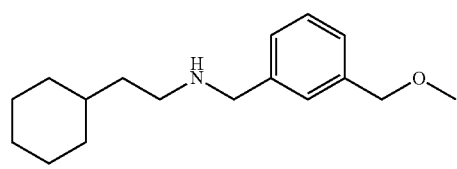

1H NMR (400 MHz, Chloroform-d) δ 7.35-7.27 (m, 1H), 7.23 (t, J=9.0 Hz, 1H), 4.45 (s, 1H), 3.79 (s, 1H), 3.39 (s, 1H), 2.64 (t, J=7.5 Hz, 1H), 1.68 (d, J=12.4 Hz, 2H), 1.40 (q, J=7.2 Hz, 1H), 1.29 (s, 1H), 1.17 (p, J=12.4 Hz, 1H), 0.90 (q, J=11.2 Hz, 1H).

B351

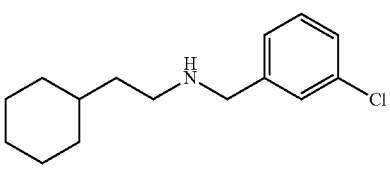

1H NMR (400 MHz, Chloroform-d) δ 7.33 (s, 1H), 7.27-7.16 (m, 3H), 3.76 (s, 2H), 2.62 (t, J=7.4 Hz, 2H), 1.72-1.60 (m, 5H), 1.40 (q, J=7.1 Hz, 2H), 1.34 (s, 2H), 1.33-1.22 (m, 1H), 1.25 (s, 1H), 1.19 (d, J=9.1 Hz, 1H), 1.20-1.09 (m, 1H), 0.93 (d, J=11.6 Hz, 1H), 0.88 (s, 1H).

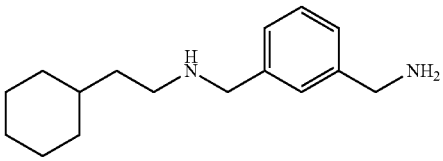
B355

1H NMR (400 MHz, DMSO-d6) δ 7.24-7.15 (m, 2H), 7.12 (d, J=12.2 Hz, 2H), 3.74 (s, 2H), 3.66 (s, 2H), 2.53 (d, J=6.7 Hz, 2H), 1.68 (d, J=13.2 Hz, 5H), 1.33 (s, 3H), 1.24 (s, 1H), 1.19 (d, J=12.4 Hz, 2H), 0.88 (s, 2H).

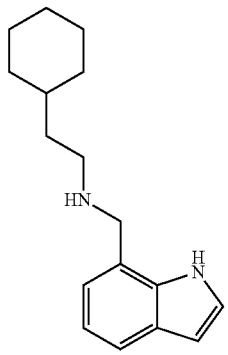
B352

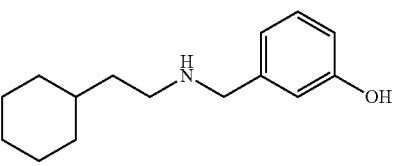
B356

1H NMR (400 MHz, DMSO-d6) δ 10.63 (s, 1H), 7.37 (d, J=7.7 Hz, 1H), 7.18 (s, 1H), 6.93 (d, J=7.2 Hz, 1H), 6.88 (td, J=7.4, 2.1 Hz, 1H), 6.36 (d, J=2.7 Hz, 1H), 4.00 (s, 2H), 2.61-2.52 (m, 2H), 2.53 (s, 1H), 2.02 (s, 2H), 1.67 (d, J=12.4 Hz, 5H), 1.37 (q, J=6.9 Hz, 3H), 1.18 (h, J=11.9, 11.2 Hz, 3H), 0.88 (t, J=11.2 Hz, 2H).

1H NMR (400 MHz, Chloroform-d) δ 7.12 (t, J=7.7 Hz, 1H), 6.75 (dd, J=18.8, 10.6 Hz, 3H), 6.02 (s, 3H), 3.71 (s, 2H), 2.70 (t, J=7.9 Hz, 2H), 1.61 (s, 1H), 1.47 (q, J=7.4 Hz, 2H), 1.31-1.06 (m, 4H), 0.94-0.80 (m, 2H).

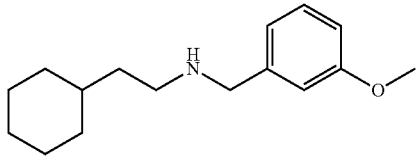
B353

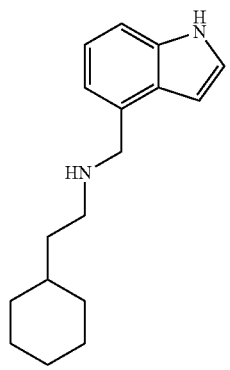
B357

1H NMR (400 MHz, DMSO-d6) δ 7.18 (t, J=7.8 Hz, 1H), 6.99 (s, 1H), 6.90 (d, J=7.5 Hz, 1H), 6.79-6.72 (m, 1H), 3.78 (d, J=3.0 Hz, 5H), 2.62 (t, J=7.5 Hz, 2H), 1.69 (d, J=12.6 Hz, 5H), 1.46-1.38 (m, 2H), 1.32 (s, 1H), 1.18 (dt, J=22.3, 12.6 Hz, 3H), 0.93 (d, J=11.5 Hz, 1H), 0.88 (s, 1H).

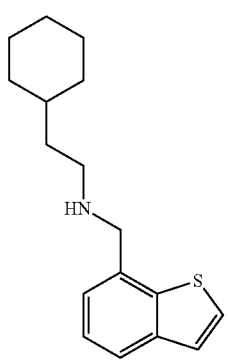
B354

1H NMR (400 MHz, DMSO-d6) δ 10.82 (s, 2H), 7.23 (d, J=7.9 Hz, 2H), 7.16 (t, J=2.9 Hz, 2H), 6.97 (dd, J=9.7, 5.6 Hz, 2H), 6.90 (d, J=7.2 Hz, 2H), 6.45 (s, 2H), 3.94 (d, J=3.6 Hz, 4H), 2.60 (t, J=7.0 Hz, 4H), 1.68 (d, J=13.5 Hz, 11H), 1.39-1.31 (m, 6H), 1.23 (s, 1H), 1.20 (s, 5H), 1.17 (s, 1H), 1.10 (d, J=10.7 Hz, 1H), 0.88 (d, J=12.1 Hz, 5H).

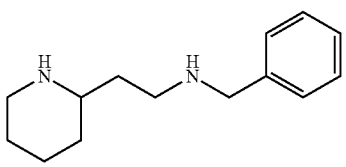
B360

1H NMR (400 MHz, Chloroform-d) δ 7.74 (d, J=7.6 Hz, 1H), 7.44 (d, J=5.4 Hz, 1H), 7.40-7.24 (m, 4H), 4.09 (s, 2H), 2.68 (t, J=7.4 Hz, 2H), 1.69 (s, 1H), 1.52 (s, 2H), 1.43 (q, J=7.3 Hz, 2H), 1.33 (s, 1H), 1.18 (h, J=12.1 Hz, 3H), 0.89 (q, J=11.8 Hz, 2H).

1H NMR (400 MHz, DMSO-d6) δ 9.62 (s, 2H), 9.35 (s, 1H), 9.19 (d, J=10.5 Hz, 1H), 7.64-7.57 (m, 2H), 7.42 (d, J=5.9 Hz, 3H), 4.11 (p, J=8.8, 7.0 Hz, 2H), 3.18 (d, J=12.0 Hz, 2H), 3.05 (s, 2H), 2.84-2.74 (m, 1H), 2.16 (dq, J=14.1, 6.5 Hz, 1H), 2.00 (dq, J=14.3, 7.2 Hz, 1H), 1.71 (td, J=30.9, 23.6, 10.6 Hz, 4H), 1.50-1.32 (m, 2H).

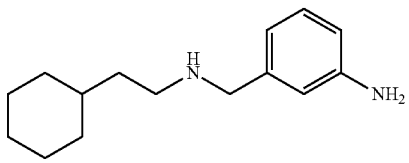
B366

1H NMR (400 MHz, Chloroform-d) δ 7.26 (s, 1H), 7.10 (t, J=7.7 Hz, 1H), 6.69 (d, J=11.1 Hz, 2H), 6.58 (d, J=8.0 Hz, 1H), 3.70 (s, 2H), 3.64 (s, 2H), 2.64 (t, J=7.6 Hz, 2H), 1.40 (q, J=7.2 Hz, 2H), 1.29 (s, 1H), 1.24 (d, J=13.0 Hz, 1H), 1.16 (dd, J=21.0, 11.6 Hz, 2H), 0.91 (t, J=11.6 Hz, 2H).

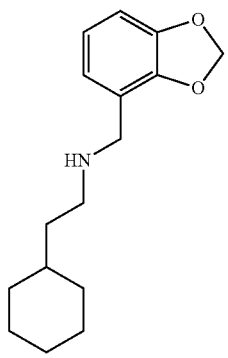
B374

1H NMR (400 MHz, DMSO-d6) δ 6.78 (d, J=7.6 Hz, 1H), 6.73 (td, J=7.6, 3.2 Hz, 1H), 6.67 (d, J=7.5 Hz, 1H), 5.94 (d, J=3.3 Hz, 2H), 3.64 (d, J=3.3 Hz, 2H), 2.51 (dd, J=8.4, 4.8 Hz, 3H), 1.67 (d, J=12.8 Hz, 5H), 1.32 (d, J=6.1 Hz, 3H), 1.23 (s, 1H), 1.21-1.09 (m, 2H), 0.89 (t, J=11.2 Hz, 2H).

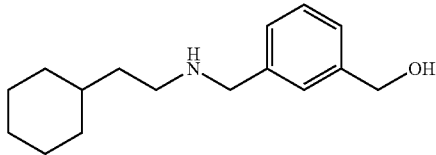
B375

1H NMR (400 MHz, Chloroform-d) δ 7.31 (d, J=10.3 Hz, 1H), 7.25 (d, J=9.0 Hz, 1H), 4.69 (s, 1H), 3.78 (s, 1H), 2.65 (t, J=7.5 Hz, 1H), 1.41 (q, J=7.3 Hz, 1H), 1.32-1.21 (m, 1H), 1.16 (dd, J=21.4, 11.5 Hz, 1H), 0.90 (q, J=11.6 Hz, 1H).

Example 3: General Compound Syntheses 3

Synthesis of target compounds was carried out following the scheme below:

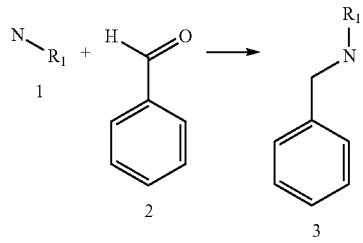

Amine 1 (0.5 mmol), benzaldehyde 2 (0.55 mmol) were dissolved in 0.6 ml MeOH, heated at 100° C. for 2 hours, then mixture was cooled, NaBH$_4$ (0.5 mmol) was added and stirred for 4 hours. The mixture was heated for 2 hours at 60° C., 3 ml of methanol and 0.2 g of C-18 chromatographic phase were added, stirred for 2 hours, filtered, evaporated and dissolved in 0.5 ml of DMSO. The residue was purified using HPLC. Yield: 31-59%.

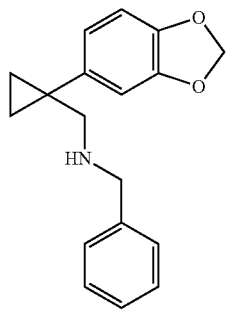
B18

1H NMR (400 MHz, DMSO-d6) δ 7.26 (p, J=6.9, 6.3 Hz, 4H), 7.18 (s, 1H), 6.90-6.85 (m, 1H), 6.82-6.73 (m, 2H), 5.95 (s, 2H), 3.66 (s, 2H), 2.61 (s, 2H), 1.83 (s, 1H), 0.74-0.63 (m, 3H).

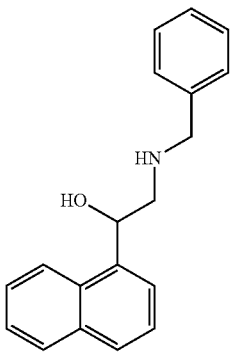
B19

1H NMR (400 MHz, DMSO-d6) δ 8.08-8.01 (m, 1H), 7.94-7.87 (m, 1H), 7.79 (d, J=8.1 Hz, 1H), 7.65 (d, J=7.1 Hz, 1H), 7.48 (dq, J=7.2, 3.6, 2.9 Hz, 3H), 7.31 (dt, J=14.8, 7.5 Hz, 4H), 7.21 (t, J=7.1 Hz, 1H), 5.45 (s, 2H), 5.43 (d, J=3.8 Hz, 0H), 3.79 (s, 2H), 2.86-2.78 (m, 1H), 2.69 (dd, J=12.2, 7.8 Hz, 1H), 2.31 (s, 1H).

B21

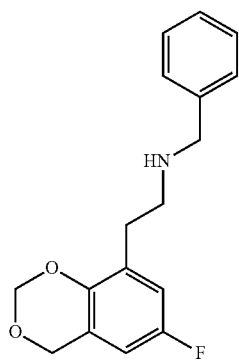

1H NMR (400 MHz, DMSO-d6) δ 7.29 (d, J=4.5 Hz, 4H), 7.20 (p, J=4.1 Hz, 1H), 6.90 (dd, J=9.6, 3.1 Hz, 1H), 6.77 (dd, J=8.7, 3.1 Hz, 1H), 5.22 (s, 2H), 4.84 (s, 2H), 3.69 (s, 2H), 2.67 (s 4H) 2.13 (s, 1H).

B22

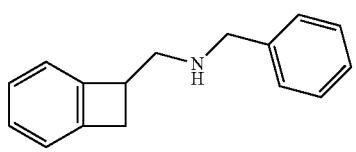

1H NMR (400 MHz, DMSO-d6) δ 7.34-7.22 (m, 4H), 7.17 (t, J=7.2 Hz, 1H), 7.16-7.03 (m, 3H), 7.00 (d, J=6.4 Hz, 1H), 3.59 (d, J=7.1 Hz, 1H), 3.26 (dd, J=14.1, 5.2 Hz, 1H), 2.99 (s, 1H), 2.90-2.77 (m, 3H), 1.73 (s, 1H).

B23

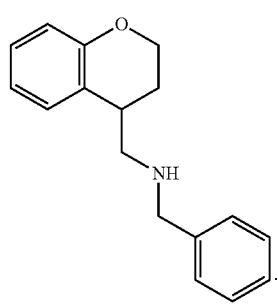

m/z 253.18

B24

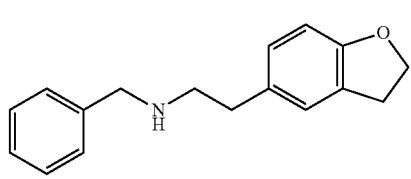

1H NMR (400 MHz, DMSO-d6) δ 7.29 (d, J=4.5 Hz, 4H), 7.20 (dt, J=8.7, 4.3 Hz, 1H), 7.03 (s, 1H), 6.88 (d, J=8.2 Hz, 1H), 6.63 (d, J=8.1 Hz, 1H), 4.46 (t, J=8.6 Hz, 2H), 3.69 (s, 2H), 3.11 (t, J=8.7 Hz, 2H), 2.68-2.59 (m, 4H).

B37

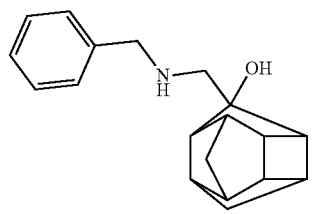

1H NMR (400 MHz, DMSO-d6) δ 7.32-7.21 (m, 4H), 7.17 (t, J=6.9 Hz, 1H), 3.74 (d, J=13.5 Hz, 1H), 3.68 (d, J=13.5 Hz, 1H), 2.99 (s, 1H), 2.64 (d, J=6.2 Hz, 1H), 2.58 (dd, J=21.1, 9.9 Hz, 2H), 2.39-2.20 (m, 5H), 2.18 (d, J=4.8 Hz, 1H), 2.18-2.09 (m, 1H), 1.99 (d, J=9.6 Hz, 1H), 1.90 (s, 1H), 1.60 (d, J=10.2 Hz, 1H), 1.11 (d, J=10.2 Hz, 1H), 0.91 (dt, J=11.3, 3.7 Hz, 1H).

B42

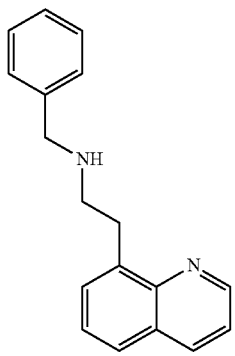

1H NMR (400 MHz, DMSO-d6) δ 8.91 (dd, J=4.1, 1.9 Hz, 1H), 8.39-8.26 (m, 2H), 8.20 (d, J=10.1 Hz, 1H), 7.81 (d, J=8.3 Hz, 2H), 7.62 (d, J=6.8 Hz, 1H), 7.52 (dq, J=8.1, 4.9, 3.5 Hz, 3H), 7.40 (s, 2H), 7.28 (q, J=7.8, 7.4 Hz, 7H), 7.23-7.15 (m, 2H), 3.74 (s, 3H), 3.38 (t, J=7.4 Hz, 3H), 2.87 (t, J=7.4 Hz, 3H), 2.54 (s, 1H).

B45

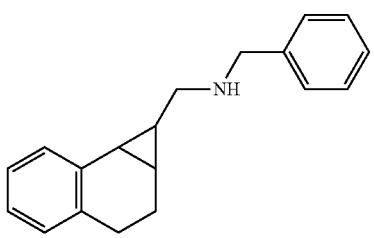

1H NMR (400 MHz, Chloroform-d) δ 7.35-7.21 (m, 4H), 7.20 (s, 11H), 7.11 (t, J=7.4 Hz, 1H), 7.05 (td, J=7.3, 1.5 Hz, 1H), 7.00 (d, J=7.3 Hz, 11H), 3.83 (s, 2H), 2.71 (dd, J=12.2, 6.7 Hz, 11H), 2.67-2.54 (m, 2H), 2.46 (td, J=15.6, 14.7, 6.2 Hz, 1H), 2.14 (ddt, J=13.3, 6.4, 2.1 Hz, 11H), 1.75-1.61 (m, 2H), 1.45 (dq, J=9.2, 3.5, 2.5 Hz, 1H), 1.42-1.35 (m, 1H).

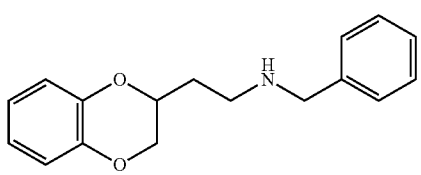
B46

1H NMR (400 MHz, DMSO-d6) δ 7.36-7.26 (m, 4H), 7.21 (t, J=6.9 Hz, 11H), 6.87-6.76 (m, 2H), 6.81 (s, 2H), 4.33-4.25 (m, 1H), 4.25 (d, J=7.1 Hz, 11H), 3.87 (dd, J=11.2, 7.4 Hz, 11H), 3.70 (s, 2H), 2.67 (t, J=7.0 Hz, 2H), 2.54 (s, OH), 2.25 (s, 1H), 1.80-1.69 (m, 2H).

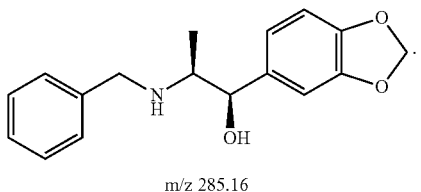
B53 m/z 285.16

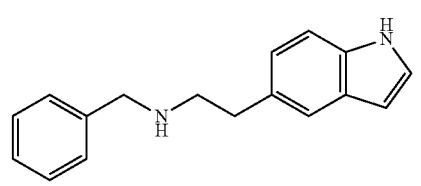
B55

1H NMR (400 MHz, DMSO-d6) δ 7.29 (d, J=4.4 Hz, 4H), 7.20 (dt, J=8.7, 4.3 Hz, 1H), 6.82 (d, J=2.1 Hz, 1H), 6.69 (d, J=2.1 Hz, 11H), 4.26 (ddd, J=20.7, 6.1, 3.1 Hz, 4H), 3.68 (s, 2H), 2.69-2.62 (m, 2H), 2.58 (s, 1H), 2.62-2.52 (m, 2H), 2.01 (s, 1H).

B56

1H NMR (400 MHz, Chloroform-d) δ 8.17 (s, 1H), 7.47 (s, 1H), 7.35-7.25 (m, 2H), 7.25 (s, 1H), 7.25-7.16 (m, 1H), 7.05 (d, J=8.3 Hz, 1H), 6.50 (s, 1H), 3.82 (s, 2H), 2.95 (s, 4H).

B58

1H NMR (400 MHz, DMSO-d6) δ 12.89 (s, 1H), 7.97 (s, 1H), 7.63 (d, J=8.3 Hz, 1H), 7.30 (t, J=6.9 Hz, 5H), 7.21 (s, 1H), 6.96 (d, J=8.3 Hz, 1H), 3.72 (s, 2H), 2.85 (t, J=7.2 Hz, 2H), 2.77 (s, 2H), 2.54 (s, 1H), 2.02 (s, 1H).

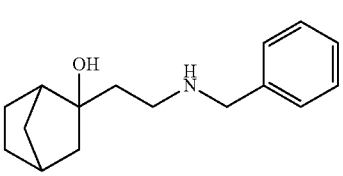
B60

1H NMR (400 MHz, Chloroform-d) δ 7.29 (dt, J=20.2, 6.9 Hz, 4H), 3.78 (d, J=2.4 Hz, 2H), 2.96-2.86 (m, 2H), 2.16 (s, 1H), 2.08 (d, J=15.8 Hz, 2H), 1.77-1.52 (m, 3H), 1.40-1.13 (m, 5H).

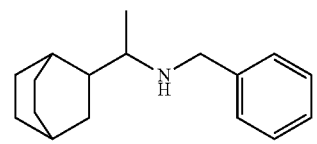
B62

1H NMR (400 MHz, Chloroform-d) δ 7.36-7.28 (m, 8H), 7.25 (d, J=6.5 Hz, 3H), 3.91 (dd, J=16.5, 12.8 Hz, 2H), 3.66 (d, J=12.8 Hz, 2H), 2.52 (tt, J=11.5, 6.2 Hz, 2H), 1.77 (s, 1H), 1.71 (s, 2H), 1.42-1.31 (m, 4H), 1.18 (dd, J=12.8, 6.3 Hz, 1H), 1.09 (dd, J=10.6, 6.1 Hz, 7H).

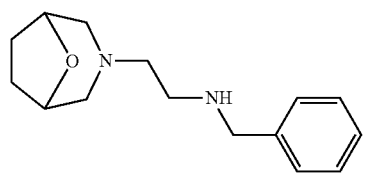
B64

1H NMR (400 MHz, Chloroform-d) δ 7.31 (p, J=6.9, 6.1 Hz, 2H), 7.25 (d, J=3.2 Hz, 1H), 4.25 (s, 1H), 3.79 (s, 1H), 2.64 (t, J=5.8 Hz, 1H), 2.54-2.41 (m, 2H), 2.27 (dd, J=11.2, 2.1 Hz, 1H), 1.90-1.79 (m, 2H).

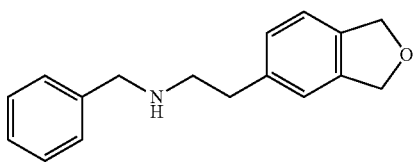
B65

1H NMR (400 MHz, DMSO-d6) δ 7.31-7.14 (m, 4H), 7.18-7.09 (m, 1H), 7.05 (d, J=6.8 Hz, 2H), 4.96 (s, 4H), 3.72 (s, 2H), 2.76 (s, 4H), 1.58 (s, 1H).

1H NMR (400 MHz, DMSO-d6) δ 7.30-7.20 (m, 3H), 7.16 (td, J=6.2, 2.9 Hz, 1H), 2.98 (s, 1H), 2.53-2.47 (m, 4H), 1.93 (s, 2H), 1.65 (q, J=12.4 Hz, 5H), 1.49 (d, J=2.9 Hz, 4H), 1.24 (t, J=8.1 Hz, 2H).

B66

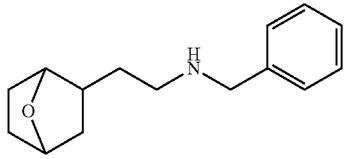

B105

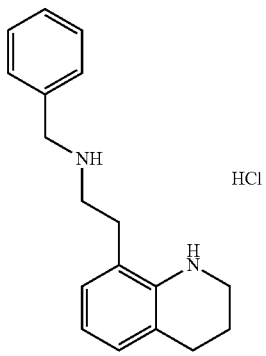

1H NMR (400 MHz, DMSO-d6) δ 7.25 (d, J=6.7 Hz, 4H), 7.16 (t, J=6.8 Hz, 1H), 4.43-4.32 (m, 1H), 4.26 (t, J=5.0 Hz, 1H), 3.69 (s, 2H), 2.04-1.94 (m, 1H), 1.85 (tdd, J=11.4, 5.7, 2.8 Hz, 1H), 1.75 (ddd, J=12.7, 9.0, 3.9 Hz, 1H), 1.65-1.53 (m, 2H), 1.48 (p, J=6.7, 6.0 Hz, 2H), 1.43 (s, 1H), 1.35 (td, J=9.7, 4.2 Hz, 1H), 0.86 (dd, J=11.4, 5.1 Hz, 1H).

1H NMR (400 MHz, DMSO-d6) δ 9.41 (s, 2H), 7.58 (d, J=6.9 Hz, 2H), 7.42 (d, J=6.9 Hz, 3H), 6.75 (t, J=7.4 Hz, 2H), 6.67 (s, 1H), 6.39 (t, J=7.4 Hz, 1H), 5.49 (s, 1H), 4.13 (s, 2H), 3.24 (t, J=5.5 Hz, 2H), 3.01-2.93 (m, 2H), 2.85 (t, J=8.0 Hz, 2H), 2.66 (d, J=6.4 Hz, 2H), 1.77 (p, J=6.0, 5.5 Hz, 2H).

B94

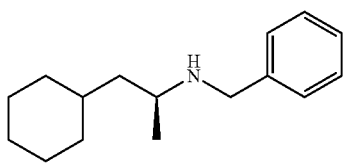

B107

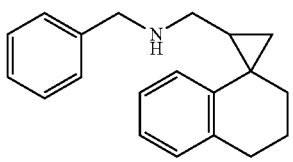

1H NMR (400 MHz, DMSO-d6) δ 7.31-7.20 (m, 4H), 7.16 (dq, J=7.0, 4.5, 3.2 Hz, 1H), 3.76 (d, J=13.4 Hz, 1H), 3.64 (d, J=13.3 Hz, 1H), 2.65 (h, J=6.4 Hz, 1H), 1.64 (q, J=10.5, 8.6 Hz, 5H), 1.35 (ddd, J=16.2, 8.2, 4.9 Hz, 1H), 1.32-1.14 (m, 2H), 1.17-1.04 (m, 1H), 1.00 (d, J=6.2 Hz, 3H), 0.91-0.76 (m, 2H).

1H NMR (400 MHz, DMSO-d6) δ 7.28 (d, J=7.5 Hz, 2H), 7.24 (t, J=7.4 Hz, 2H), 7.16 (t, J=7.0 Hz, 1H), 6.99 (td, J=7.7, 6.9, 2.6 Hz, 1H), 6.93 (d, J=6.0 Hz, 2H), 6.61 (d, J=7.8 Hz, 1H), 3.81-3.67 (m, 2H), 2.82 (t, J=6.1 Hz, 2H), 2.69 (d, J=6.9 Hz, 2H), 2.54 (s, 1H), 1.86 (s, 2H), 1.91-1.73 (m, 1H), 1.71-1.61 (m, 1H), 1.32 (dt, J=13.2, 6.5 Hz, 1H), 1.08 (dd, J=8.9, 4.6 Hz, 1H), 0.61-0.54 (m, 1H).

B95

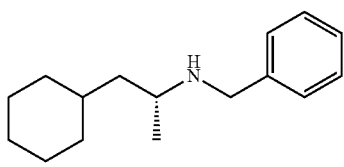

1H NMR (400 MHz, DMSO-d6) δ 7.31-7.17 (m, 4H), 7.16 (dq, J=9.6, 4.4, 3.1 Hz, 1H), 3.76 (d, J=13.3 Hz, 1H), 3.64 (d, J=13.3 Hz, 1H), 2.65 (h, J=6.3 Hz, 1H), 1.65 (t, J=6.6 Hz, 5H), 1.35 (ddd, J=15.6, 8.2, 4.9 Hz, 1H), 1.32-1.22 (m, 1H), 1.15 (ddd, J=26.6, 14.4, 4.6 Hz, 2H), 1.10-0.97 (m, 3H), 0.83 (dd, J=16.0, 6.9 Hz, 2H).

B108

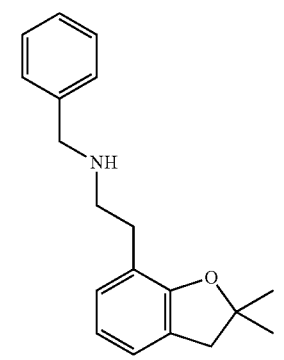

B104

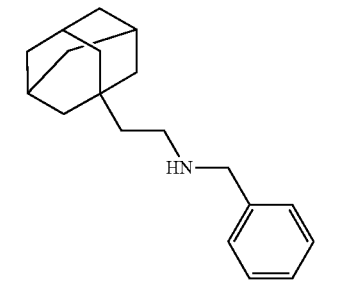

1H NMR (400 MHz, DMSO-d6) δ 7.34-7.23 (m, 4H), 7.20 (s, 1H), 6.98 (d, J=7.3 Hz, 1H), 6.90 (d, J=7.5 Hz, 1H), 6.69 (t, J=7.4 Hz, 1H), 3.69 (s, 2H), 2.96 (s, 2H), 2.63 (dt, J=11.9, 6.1 Hz, 4H), 2.54 (s, 1H), 2.01 (s, 1H), 1.36 (s, 6H).

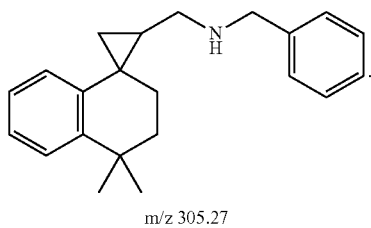

B109 m/z 305.27

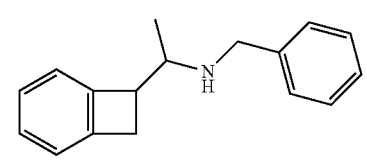

B110

1H NMR (400 MHz, DMSO-d6) δ 7.37-7.24 (m, 7H), 7.23-7.09 (m, 5H), 7.06 (d, J=6.1 Hz, 1H), 3.82 (d, J=15.7 Hz, 2H), 3.69 (d, J=13.4 Hz, 2H), 3.16 (ddd, J=20.1, 14.0, 5.6 Hz, 2H), 2.84 (d, J=14.2 Hz, 2H), 2.75 (d, J=7.5 Hz, 1H), 2.66 (s, 1H), 2.54 (s, 1H), 1.99 (s, 1H), 1.90 (s, 1H), 1.12 (d, J=6.3 Hz, 2H), 1.05 (d, J=6.3 Hz, 3H).

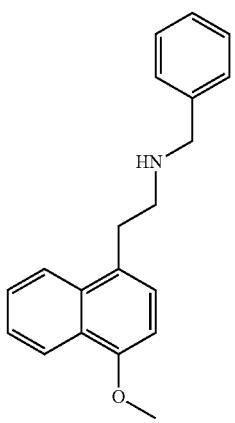

B111

1H NMR (400 MHz, DMSO-d6) δ 8.19 (dd, J=8.4, 1.5 Hz, 1H), 7.96 (d, J=8.5 Hz, 1H), 7.52-7.37 (m, 2H), 7.32-7.25 (m, 2H), 7.23 (dd, J=15.5, 7.6 Hz, 3H), 7.21-7.12 (m, 1H), 6.75 (d, J=7.8 Hz, 1H), 3.97 (s, 3H), 3.75 (s, 2H), 3.14 (t, J=7.4 Hz, 2H), 2.87 (q, J=8.0, 7.3 Hz, 2H), 1.68 (s, 1H).

B112

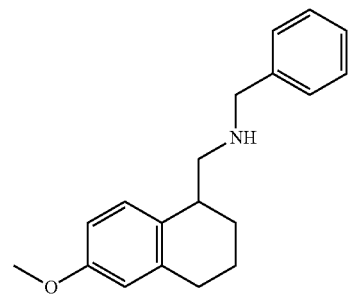

1H NMR (400 MHz, DMSO-d6) δ 7.31 (dt, J=11.4, 7.0 Hz, 4H), 7.25-7.17 (m, 1H), 7.04 (d, J=8.4 Hz, 1H), 6.65 (dd, J=8.5, 2.7 Hz, 1H), 6.58 (d, J=2.6 Hz, 1H), 3.79-3.65 (m, 5H), 2.79 (dd, J=9.4, 4.8 Hz, 1H), 2.63 (dd, J=7.8, 4.5 Hz, 3H), 2.55 (d, J=10.1 Hz, 1H), 2.07 (s, 1H), 1.88 (q, J=6.1, 5.5 Hz, 1H), 1.68 (s, 2H), 1.60 (s, 1H).

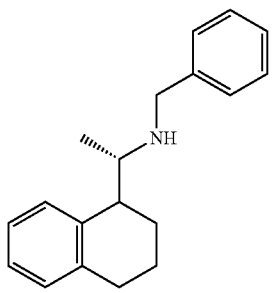

B113

1H NMR (400 MHz, DMSO-d6) δ 7.29 (t, J=6.6 Hz, 2H), 7.25 (d, J=7.7 Hz, 1H), 7.26-7.18 (m, 2H), 7.21-7.09 (m, 4H), 7.01 (ddd, J=12.0, 8.7, 5.9 Hz, 6H), 3.69 (d, J=13.5 Hz, 1H), 3.53 (d, J=13.5 Hz, 1H), 3.27-3.16 (m, 1H), 3.12 (td, J=6.5, 3.9 Hz, 1H), 3.06 (s, 1H), 2.99 (s, 2H), 2.86-2.77 (m, 1H), 2.69 (q, J=5.9 Hz, 3H), 2.54 (s, 0H), 2.01-1.79 (m, 3H), 1.77-1.52 (m, 2H), 1.46 (s, 1H), 1.16 (s, 1H), 1.07 (d, J=6.4 Hz, 3H), 0.82 (d, J=6.4 Hz, 2H).

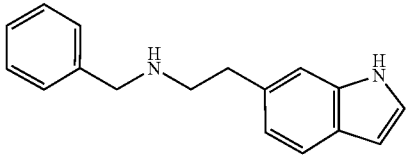

B114

1H NMR (400 MHz, Chloroform-d) δ 8.25 (s, 1H), 7.57 (d, J=8.0 Hz, 1H), 7.31 (d, J=7.6 Hz, 1H), 7.31-7.20 (m, 6H), 7.16 (t, J=2.8 Hz, 1H), 6.99 (d, J=8.1 Hz, 1H), 6.52 (t, J=2.7 Hz, 1H), 3.81 (s, 2H), 2.95 (d, J=3.2 Hz, 4H).

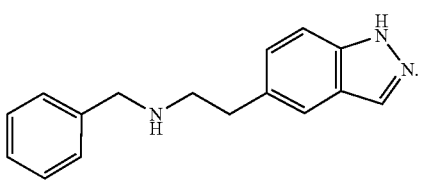

B115 m/z 251.17

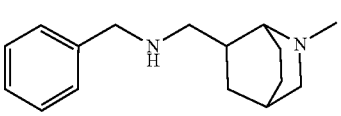

B116

1H NMR (400 MHz, Chloroform-d) δ 7.32 (d, J=2.0 Hz, 3H), 7.28-7.20 (m, 4H), 3.78 (d, J=3.0 Hz, 5H), 3.03-2.92 (m, OH), 2.74 (dt, J=9.9, 2.8 Hz, 2H), 2.62-2.49 (m, 6H), 2.46-2.39 (m, 2H), 2.36 (s, 6H), 2.37-2.30 (m, 1H), 2.28 (s, 1H), 2.21 (s, 3H), 2.00 (dd, J=20.7, 10.3 Hz, 1H), 1.86-1.74

(m, 4H), 1.63 (s, 2H), 1.58 (dd, J=5.1, 2.1 Hz, 1H), 1.57-1.49 (m, 2H), 1.45-1.37 (m, 2H), 1.16 (s, 3H), 1.07-0.96 (m, 2H).

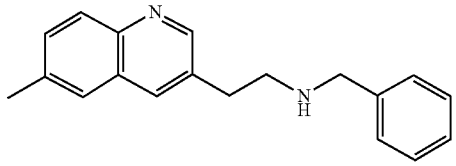
B117

1H NMR (400 MHz, DMSO-d6) δ 8.71 (d, J=2.1 Hz, 1H), 8.02 (s, 1H), 7.87 (d, J=8.5 Hz, 1H), 7.65 (s, 1H), 7.52 (d, J=8.6 Hz, 1H), 7.34-7.16 (m, 6H), 3.73 (s, 2H), 2.91 (t, J=6.9 Hz, 2H), 2.82 (t, J=7.0 Hz, 2H), 2.54 (s, OH), 2.48 (s, 3H).

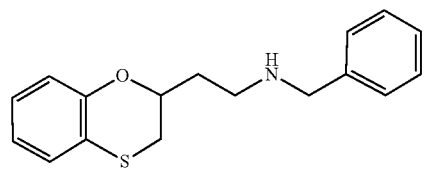
B118

1H NMR (400 MHz, DMSO-d6) δ 7.30 (d, J=7.1 Hz, 4H), 7.21 (t, J=6.8 Hz, 1H), 7.05 (d, J=7.7 Hz, 1H), 6.98 (t, J=7.7 Hz, 1H), 6.83 (t, J=7.3 Hz, 1H), 6.76 (d, J=8.1 Hz, 1H), 4.29 (d, J=7.2 Hz, 1H), 3.69 (s, 2H), 3.16 (dd, J=13.1, 2.1 Hz, 1H), 2.97 (dd, J=13.1, 8.1 Hz, 1H), 2.68 (t, J=6.8 Hz, 2H), 2.17 (s, 1H), 1.84 (dp, J=19.9, 7.1 Hz, 2H).

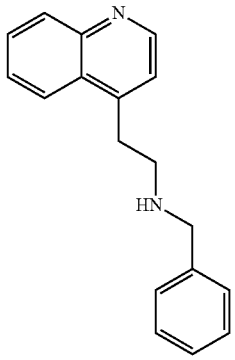
B119

1H NMR (400 MHz, DMSO-d6) δ 8.77 (d, J=4.4 Hz, 2H), 8.73 (s, 1H), 8.15 (d, J=8.4 Hz, 2H), 8.00 (d, J=8.5 Hz, 3H), 7.71 (dt, J=16.7, 7.1 Hz, 2H), 7.60 (t, J=7.8 Hz, 2H), 7.45-7.34 (m, 3H), 7.29 (q, J=7.6 Hz, 8H), 7.20 (s, 3H), 3.74 (s, 3H), 3.24 (t, J=7.4 Hz, 3H), 2.86 (q, J=7.8 Hz, 4H), 2.54 (s, 1H).

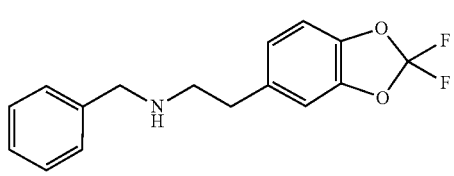
B120

1H NMR (400 MHz, DMSO-d6) δ 7.28 (t, J=5.4 Hz, 6H), 7.24-7.13 (m, 1H), 7.03 (d, J=8.3 Hz, 1H), 3.69 (s, 2H), 2.71 (dp, J=10.3, 5.1, 4.2 Hz, 4H), 2.08 (s, 1H).

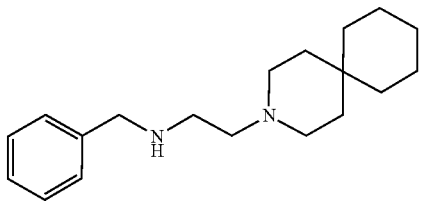
B121

1H NMR (400 MHz, Chloroform-d) δ 7.32 (d, J=4.4 Hz, 2H), 7.26 (s, 1H), 7.24 (s, 1H), 3.80 (s, 1H), 2.71 (t, J=6.3 Hz, 1H), 2.49 (t, J=6.4 Hz, 1H), 2.34 (t, J=5.7 Hz, 2H), 1.87 (s, 1H), 1.44 (t, J=5.9 Hz, 3H), 1.31 (s, 3H).

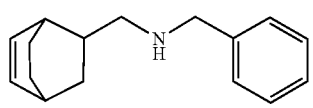
B122

1H NMR (400 MHz, DMSO-d6) δ 7.31 (d, J=14.6 Hz, 1H), 7.24 (tt, J=7.9, 3.6 Hz, 8H), 7.19-7.13 (m, 2H), 6.32 (t, J=7.4 Hz, 1H), 6.18 (t, J=7.3 Hz, 2H), 6.04 (t, J=7.5 Hz, 1H), 3.70 (t, J=5.0 Hz, 2H), 3.65 (d, J=2.6 Hz, 2H), 2.56 (d, J=15.3 Hz, 3H), 2.47 (s, 7H), 2.23 (dd, J=11.3, 8.3 Hz, 1H), 2.14 (dd, J=11.3, 6.5 Hz, 1H), 1.78 (s, 1H), 1.71-1.61 (m, 2H), 1.53-1.33 (m, 4H), 1.31-1.14 (m, 3H), 1.03 (d, J=12.8 Hz, 1H), 0.93-0.85 (m, 1H), 0.79-0.71 (m, 1H).

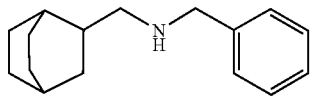
B123

1H NMR (400 MHz, DMSO-d6) δ 7.31-7.20 (m, 4H), 7.16 (t, J=6.8 Hz, 1H), 3.70 (s, 2H), 2.47 (td, J=11.3, 5.1 Hz, 3H), 1.81-1.61 (m, 2H), 1.63-1.54 (m, 1H), 1.58-1.48 (m, 6H), 1.46-1.38 (m, 2H), 1.38-1.27 (m, 1H), 1.04-0.95 (m, 1H).

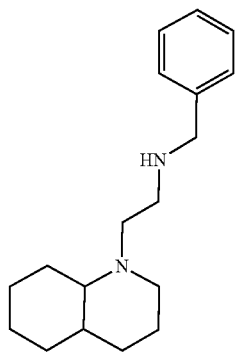
B124

1H NMR (400 MHz, DMSO-d6) δ 7.30 (d, J=4.4 Hz, 4H), 7.21 (h, J=4.4 Hz, 1H), 3.67 (s, 2H), 2.82 (d, J=7.0 Hz, 1H), 2.82-2.74 (m, 1H), 2.23 (ddd, J=12.8, 7.5, 4.9 Hz, 1H), 2.10-2.01 (m, 1H), 2.04-1.98 (m, 1H), 1.74-1.60 (m, 2H), 1.60-1.54 (m, 1H), 1.54-1.49 (m, 1H), 1.52-1.37 (m, 3H), 1.27-1.15 (m, 1H), 1.18-1.05 (m, 1H), 1.07-0.94 (m, 1H), 0.94 (d, J=6.9 Hz, 1H), 0.90 (t, J=5.9 Hz, 1H).

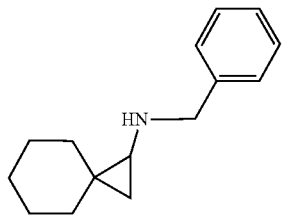

B125

1H NMR (400 MHz, DMSO-d6) δ 7.29-7.20 (m, 4H), 7.16 (dd, J=7.7, 4.6 Hz, 1H), 3.73 (s, 2H), 2.54 (s, 1H), 1.86 (dd, J=7.0, 3.9 Hz, 1H), 1.58-1.44 (m, 9H), 1.15 (s, 2H), 0.30 (dd, J=7.1, 4.3 Hz, 1H), 0.08 (t, J=4.1 Hz, 1H).

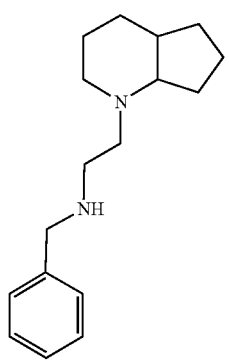

B126

1H NMR (400 MHz, DMSO-d6) δ 7.32-7.15 (m, 3H), 3.68 (s, 1H), 2.68-2.54 (m, 1H), 2.57-2.51 (m, 1H), 2.25-2.02 (m, 1H), 1.85 (q, J=6.1 Hz, 1H), 1.75-1.60 (m, 1H), 1.49 (tdt, J=14.0, 10.5, 5.0 Hz, 2H), 1.36 (tt, J=7.0, 3.6 Hz, 1H).

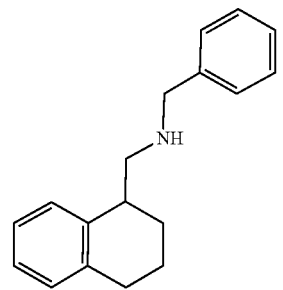

B127

1H NMR (400 MHz, DMSO-d6) δ 7.37-7.26 (m, 4H), 7.21 (t, J=7.1 Hz, 1H), 7.16-6.97 (m, 5H), 3.77 (d, J=13.7 Hz, 1H), 3.70 (d, J=13.7 Hz, 1H), 2.86 (dd, J=9.5, 4.8 Hz, 1H), 2.67 (dq, J=10.2, 5.9, 5.3 Hz, 3H), 2.62-2.52 (m, 1H), 2.18 (s, 1H), 1.98-1.88 (m, 1H), 1.76-1.61 (m, 4H).

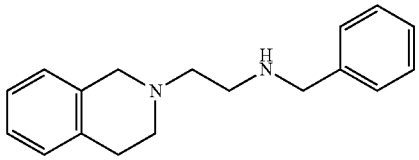

B129

1H NMR (400 MHz, DMSO-d6) δ 7.35-7.25 (m, 5H), 7.23 (dd, J=16.0, 13.7 Hz, 0H), 7.21 (s, 2H), 7.09 (d, J=4.7 Hz, 3H), 7.02 (s, 1H), 3.71 (s, 2H), 3.52 (s, 2H), 2.77 (d, J=6.1 Hz, 2H), 2.71-2.52 (m, 6H), 2.03 (s, 1H).

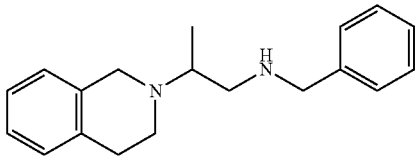

B130

1H NMR (400 MHz, DMSO-d6) δ 7.31-7.17 (m, 4H), 7.16 (ddd, J=8.8, 5.7, 3.3 Hz, 1H), 7.03 (q, J=4.4, 3.6 Hz, 3H), 6.97-6.91 (m, 1H), 3.71 (d, J=3.2 Hz, 2H), 3.58 (d, J=14.9 Hz, 1H), 3.03-2.88 (m, 3H), 2.84-2.73 (m, 3H), 2.59 (ddt, J=26.1, 12.6, 7.4 Hz, 2H), 2.43 (dd, J=11.6, 5.0 Hz, 1H), 1.88 (s, 1H), 0.99 (d, J=6.6 Hz, 3H).

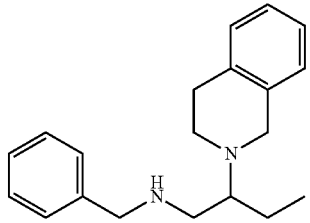

B131

1H NMR (400 MHz, Chloroform-d) δ 7.28 (dd, J=8.0, 5.7 Hz, 4H), 7.15-7.08 (m, 3H), 6.99 (d, J=5.8 Hz, 1H), 3.88 (d, J=13.6 Hz, 1H), 3.81-3.71 (m, 2H), 3.64 (d, J=14.9 Hz, 1H), 2.83 (s, 3H), 2.75 (s, 5H), 2.73-2.65 (m, 1H), 2.59 (q, J=11.0, 9.7 Hz, 1H), 1.70 (s, 1H), 1.21 (dt, J=14.0, 8.2 Hz, 1H), 0.93 (t, J=7.4 Hz, 3H).

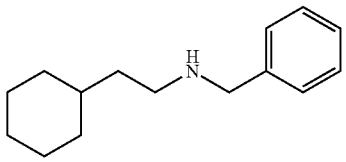

B132

1H NMR (400 MHz, DMSO-d6) δ 7.25 (d, J=6.5 Hz, 4H), 7.20-7.11 (m, 1H), 3.68 (s, 2H), 2.53 (d, J=6.5 Hz, 1H), 1.68 (d, J=12.5 Hz, 5H), 1.33 (t, J=5.8 Hz, 3H), 1.29-1.09 (m, 3H), 0.89 (t, J=11.3 Hz, 2H).

B138

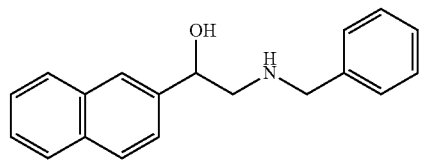

1H NMR (400 MHz, Chloroform-d) δ 7.83 (dd, J=7.6, 5.0 Hz, 4H), 7.46 (td, J=5.6, 2.5 Hz, 3H), 7.38-7.22 (m, 2H), 4.90 (dd, J=8.7, 3.6 Hz, 1H), 3.92-3.80 (m, 2H), 3.03 (dd, J=12.2, 3.7 Hz, 1H), 2.85 (dd, J=12.2, 8.7 Hz, 1H).

B139

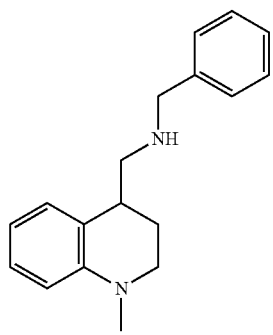

1H NMR (400 MHz, DMSO-d6) δ 7.37-7.26 (m, 4H), 7.27 (s, 1H), 7.21 (t, J=7.0 Hz, 1H), 7.01-6.89 (m, 2H), 6.57-6.46 (m, 2H), 3.76 (d, J=13.7 Hz, 1H), 3.69 (d, J=13.7 Hz, 1H), 3.17-3.05 (m, 2H), 2.82 (d, J=9.5 Hz, 1H), 2.79 (s, 3H), 2.62 (dd, J=11.9, 4.9 Hz, 1H), 2.55 (d, J=9.3 Hz, 1H), 2.16 (s, 1H), 2.08-1.99 (m, 1H), 1.83 (dt, J=12.4, 5.8 Hz, 1H).

B140

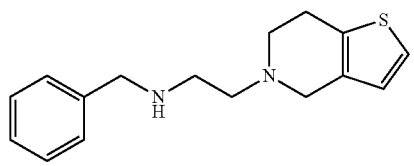

1H NMR (400 MHz, DMSO-d6) δ 7.32-7.21 (m, 4H), 7.16 (t, J=6.9 Hz, 1H), 7.06 (d, J=5.1 Hz, 1H), 6.67 (d, J=5.2 Hz, 1H), 3.74 (s, 2H), 3.47 (s, 2H), 2.85-2.59 (m, 8H), 2.54 (s, OH), 1.93 (s, 1H).

B145

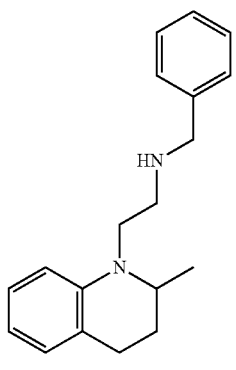

m/z 280.24.

B147

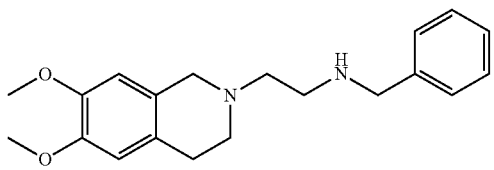

1H NMR (400 MHz, DMSO-d6) δ 7.26 (q, J=7.9 Hz, 4H), 7.18 (d, J=7.0 Hz, 1H), 6.54 (s, 1H), 6.47 (s, 1H), 3.73 (s, 3H), 3.44 (s, 2H), 3.01 (s, 7H), 2.76-2.52 (m, 7H), 1.82 (s, 1H).

B148

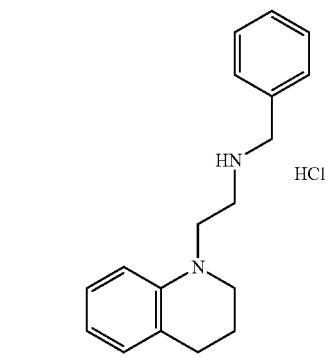

1H NMR (400 MHz, DMSO-d6) δ 9.46 (s, 2H), 7.59 (d, J=7.1 Hz, 2H), 7.48-7.36 (m, 3H), 6.96 (t, J=7.7 Hz, 1H), 6.88 (d, J=7.4 Hz, 1H), 6.71 (d, J=8.2 Hz, 1H), 6.51 (t, J=7.3 Hz, 1H), 4.17 (s, 2H), 3.62 (t, J=7.5 Hz, 2H), 3.24 (t, J=5.6 Hz, 2H), 3.04 (t, J=7.5 Hz, 2H), 2.66 (t, J=6.4 Hz, 2H), 1.85 (p, J=6.3, 5.8 Hz, 2H).

B154

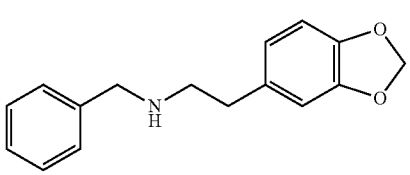

1H NMR (400 MHz, DMSO-d6) δ 7.30 (d, J=4.4 Hz, 4H), 7.21 (q, J=4.5 Hz, 1H), 6.79 (d, J=8.2 Hz, 2H), 6.64 (dd, J=7.9, 1.8 Hz, 1H), 5.94 (s, 2H), 3.70 (s, 2H), 2.72-2.59 (m, J=4.2 Hz, 4H).

B155

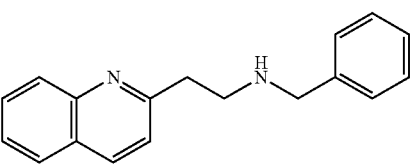

1H NMR (400 MHz, DMSO-d6) δ 8.25 (d, J=8.4 Hz, 2H), 7.90 (dd, J=12.6, 7.2 Hz, 5H), 7.71 (t, J=7.8 Hz, 3H), 7.53 (t, J=7.5 Hz, 2H), 7.44 (d, J=8.6 Hz, 1H), 7.34-7.24 (m, 8H), 7.21 (d, J=7.0 Hz, 2H), 7.13 (s, 1H), 5.16 (s, OH), 4.49 (d, J=5.4 Hz, 1H), 3.73 (d, J=4.3 Hz, 3H), 3.08 (t, J=7.1 Hz, 4H), 2.95 (q, J=9.1, 7.1 Hz, 4H), 2.54 (s, 1H), 2.33 (s, 1H).

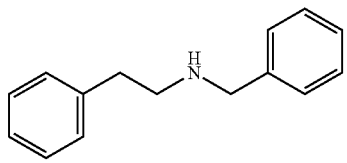
B181

1H NMR (400 MHz, DMSO-d6) δ 7.64-7.57 (m, 1H), 7.43-7.12 (m, 4H), 4.10 (s, 1H), 3.13-2.99 (m, 2H).

Example 4: General Compound Syntheses 4

Synthesis of compounds was carried out according to the scheme below:

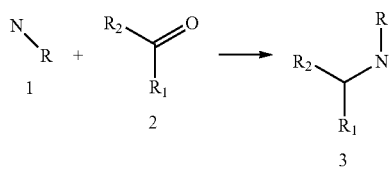

Amine 1 (0.5 mmol) and compound 2 (0.55 mmol) were dissolved in 0.6 ml MeOH, heated at 100° C. for 2 hours, then mixture was cooled, NaBH₄ (0.5 mmol) was added and stirred for 4 hours. The mixture was heated for 2 hours at 60° C., 3 ml of methanol and 0.2 g of C-18 chromatographic phase were added, stirred for 2 hours, filtered, evaporated and dissolved in 0.5 ml of DMSO. The residue was purified using HPLC. Yield: 42-74%.

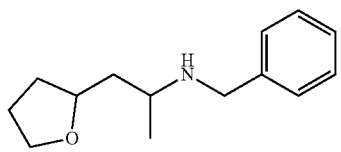
B20

1H NMR (400 MHz, DMSO-d6) δ 7.32-7.19 (m, 4H), 7.15 (t, J=7.1 Hz, 1H), 3.94-3.77 (m, 1H), 3.80-3.70 (m, 2H), 3.65 (dd, J=13.2, 7.1 Hz, 1H), 3.63-3.55 (m, 1H), 2.73 (dh, J=10.0, 3.3 Hz, 1H), 1.93 (dtd, J=11.3, 6.7, 5.6, 3.4 Hz, 1H), 1.88-1.80 (m, 1H), 1.79 (ddd, J=12.5, 6.1, 3.0 Hz, 1H), 1.68-1.31 (m, 3H), 1.05 (dd, J=10.4, 6.2 Hz, 3H).

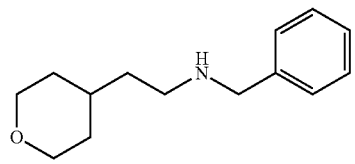
B25

1H NMR (400 MHz, Chloroform-d) δ 7.26 (s, 2H), 3.89 (d, J=15.7 Hz, 4H), 3.30 (t, J=11.7 Hz, 2H), 2.83 (t, J=7.7 Hz, 2H), 1.45 (s, 1H), 1.23 (d, J=12.8 Hz, 3H).

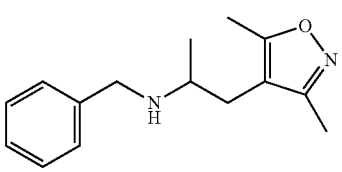
B26

1H NMR (400 MHz, DMSO-d6) δ 7.29 (d, J=4.4 Hz, 4H), 7.28-7.17 (m, 1H), 3.77 (d, J=13.8 Hz, 1H), 3.70 (d, J=13.9 Hz, 1H), 2.64-2.57 (m, 1H), 2.50-2.42 (m, 1H), 2.26-2.11 (m, 4H), 2.06 (s, 3H), 1.97 (s, 1H), 0.92 (d, J=6.2 Hz, 3H).

B28

1H NMR (400 MHz, DMSO-d6) δ 7.27 (dd, J=12.5, 5.6 Hz, 5H), 7.21 (d, J=7.2 Hz, 5H), 7.08 (t, J=6.8 Hz, 4H), 6.83 (d, J=8.1 Hz, 4H), 3.81-3.72 (m, 1H), 3.71 (s, 6H), 3.67 (s, 1H), 3.60 (d, J=14.4 Hz, 2H), 3.26 (s, 1H), 2.78-2.70 (m, 1H), 2.64 (s, 3H), 1.59 (s, 2H), 1.21 (d, J=6.8 Hz, 2H), 1.14 (d, J=7.0 Hz, 3H), 0.88 (d, J=6.2 Hz, 3H), 0.80 (d, J=6.1 Hz, 2H).

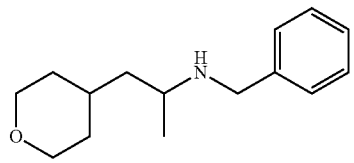
B29

1H NMR (400 MHz, DMSO-d6) δ 7.31-7.20 (m, 4H), 7.20-7.12 (m, 1H), 3.84-3.73 (m, 2H), 3.64 (d, J=13.4 Hz, 1H), 3.25 (tdd, J=11.7, 5.5, 2.2 Hz, 2H), 2.66 (h, J=6.4 Hz, 1H), 1.64 (dqd, J=11.3, 7.3, 3.4 Hz, 1H), 1.54-1.42 (m, 2H), 1.36 (dt, J=13.7, 6.8 Hz, 1H), 1.26-1.00 (m, 6H).

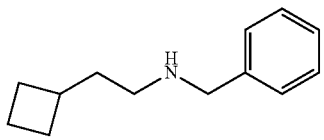
B30

1H NMR (400 MHz, DMSO-d6) δ 7.30-7.21 (m, 4H), 7.16 (ddd, J=8.7, 5.3, 2.3 Hz, 1H), 3.67 (s, 2H), 2.43 (t, J=7.2 Hz, 2H), 2.32 (h, J=7.9 Hz, 1H), 2.02 (ddt, J=15.2, 11.4, 5.1 Hz, 2H), 1.92-1.79 (m, 1H), 1.83-1.73 (m, 1H), 1.67-1.49 (m, 4H).

B31

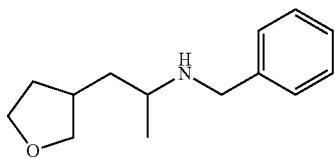

1H NMR (400 MHz, DMSO-d6) δ 7.26 (dt, J=14.8, 7.5 Hz, 4H), 7.16 (t, J=7.1 Hz, 1H), 3.82-3.54 (m, 5H), 3.15 (td, J=7.8, 5.8 Hz, 1H), 2.62-2.51 (m, 1H), 2.53 (s, 0H), 2.28 (hept, J=7.4 Hz, 1H), 1.95 (dqd, J=19.2, 7.5, 4.5 Hz, 1H), 1.57-1.18 (m, 2H), 1.05 (dd, J=6.2, 3.5 Hz, 3H).

B32

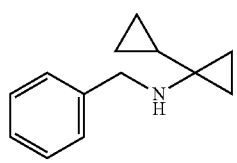

1H NMR (400 MHz, DMSO-d6) δ 7.43-7.23 (m, 4H), 7.19 (t, J=7.0 Hz, 1H), 3.85 (s, 2H), 1.28 (tt, J=8.3, 5.2 Hz, 1H), 0.38 (ddd, J=14.4, 7.4, 3.0 Hz, 3H), 0.23 (d, J=3.8 Hz, 1H), 0.22 (d, J=4.3 Hz, 1H).

B33

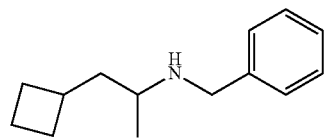

1H NMR (400 MHz, DMSO-d6) δ 7.34-7.17 (m, 4H), 7.20-7.11 (m, 1H), 2.53 (dd, J=7.6, 4.9 Hz, 1H), 2.40 (dq, J=15.7, 7.8 Hz, 1H), 2.06-1.94 (m, 2H), 1.93-1.70 (m, 2H), 1.66-1.50 (m, 3H), 1.34 (dt, J=13.7, 7.0 Hz, 1H), 0.98 (d, J 6.2 Hz, 3H).

B34

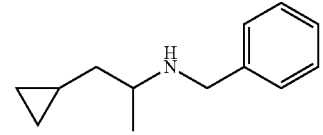

1H NMR (400 MHz, DMSO-d6) δ 7.34-7.21 (m, 4H), 7.21-7.11 (m, 1H), 3.76 (d, J=13.4 Hz, 1H), 3.68 (d, J=13.4 Hz, 1H), 2.69 (p, J=6.3 Hz, 1H), 2.30 (s, 5H), 1.36-1.17 (m, 1H), 1.07 (d, J=6.3 Hz, 3H), 0.76-0.64 (m, 1H), 0.45-0.36 (m, 2H).

B35

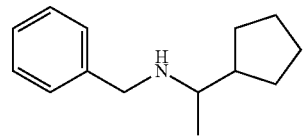

1H NMR (400 MHz, Chloroform-d) δ 7.41-7.28 (m, 4H), 7.24 (dt, J=9.0, 2.7 Hz, 1H), 3.91 (d, J=13.2 Hz, 1H), 3.70 (d, J=13.2 Hz, 1H), 2.55-2.43 (m, 1H), 1.84 (dt, J=13.6, 7.7 Hz, 2H), 1.77-1.66 (m, 1H), 1.65-1.45 (m, 4H), 1.24-1.13 (m, 2H), 1.10 (d, J=6.3 Hz, 3H).

B38

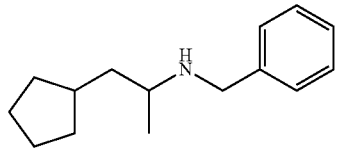

1H NMR (400 MHz, DMSO-d6) δ 7.34-7.24 (m, 2H), 7.24 (t, J=7.4 Hz, 2H), 7.16 (dq, J=9.4, 4.4, 3.1 Hz, 1H), 3.76 (d, J=13.3 Hz, 1H), 3.65 (d, J=13.3 Hz, 1H), 2.64-2.52 (m, 1H), 1.87 (dp, J=15.5, 7.7, 6.9 Hz, 1H), 1.71 (qd, J=10.1, 9.5, 3.7 Hz, 2H), 1.65-1.40 (m, 5H), 1.25 (dt, J=13.5, 6.9 Hz, 1H), 1.10-0.97 (m, 4H).

B40

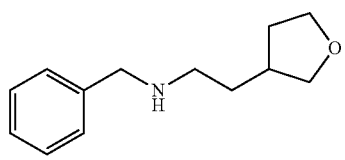

1H NMR (400 MHz, Chloroform-d) δ 7.37-7.21 (m, 3H), 3.89 (t, J=7.7 Hz, 1H), 3.84 (td, J=8.2, 4.7 Hz, 1H), 3.79 (s, 2H), 3.73 (q, J=7.8 Hz, 1H), 3.33 (t, J=7.8 Hz, 1H), 2.65 (q, J=7.1 Hz, 2H), 2.24 (p, J=7.5 Hz, 1H), 2.09-1.96 (m, 1H), 1.65-1.44 (m, 2H).

B41

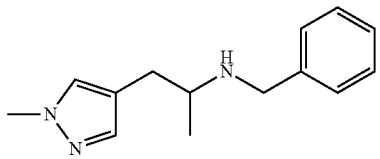

1H NMR (400 MHz, DMSO-d6) δ 7.42 (s, 1H), 7.32-7.25 (m, 4H), 7.20 (d, J=7.7 Hz, 2H), 3.75 (s, 3H), 3.72 (q, J=13.5 Hz, 2H), 2.75-2.63 (m, 1H), 2.58-2.50 (m, 2H), 2.34 (dd, J=14.1, 7.0 Hz, 1H), 0.94 (d, J=6.2 Hz, 3H).

B43

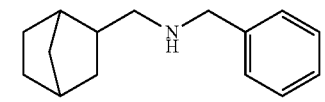

1H NMR (400 MHz, Chloroform-d) δ 7.32 (dd, J=4.4, 2.2 Hz, 6H), 7.27-7.20 (m, 2H), 3.86-3.74 (m, 1H), 3.78 (s, 2H), 2.65-2.44 (m, 2H), 2.33 (dd, J=11.5, 6.9 Hz, 1H), 2.17 (d, J=12.2 Hz, 2H), 2.05 (s, 1H), 1.65-1.59 (m, 3H), 1.45-1.35 (m, 1H), 1.34-1.10 (m, 3H), 1.04 (dd, J=22.7, 11.6 Hz, 2H), 0.66-0.57 (m, 0H).

B44

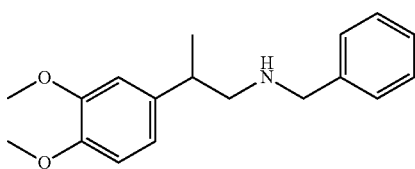

1H NMR (400 MHz, DMSO-d6) δ 7.27 (d, J=5.8 Hz, 4H), 7.23-7.17 (m, 1H), 6.84 (d, J=8.2 Hz, 1H), 6.77 (d, J=2.0 Hz, 1H), 6.70 (dd, J=8.2, 2.0 Hz, 1H), 3.74-3.64 (m, 9H), 2.80 (q, J=7.0 Hz, 1H), 2.59 (qd, J=11.4, 7.1 Hz, 2H), 2.53 (s, 1H), 1.76 (s, 1H), 1.17 (d, J=6.9 Hz, 3H).

B52

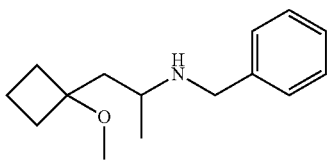

1H NMR (400 MHz, DMSO-d6) δ 7.34-7.21 (m, 4H), 7.19 (s, 1H), 7.15 (tt, J=5.6, 2.9 Hz, 1H), 3.79-3.69 (m, 1H), 3.61 (d, J=13.5 Hz, 1H), 3.07 (s, 3H), 2.76 (h, J=6.2 Hz, 1H), 2.04 (p, J=10.6 Hz, 2H), 1.88-1.77 (m, 3H), 1.77-1.63 (m, 1H), 1.62-1.48 (m, 2H), 1.04 (d, J=6.2 Hz, 3H).

B47

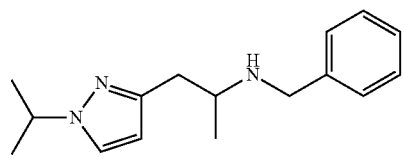

1H NMR (400 MHz, DMSO-d6) δ 7.59 (d, J=2.3 Hz, 1H), 7.27 (d, J=4.5 Hz, 4H), 7.20 (q, J=5.3, 4.7 Hz, 1H), 5.97 (d, J=2.3 Hz, 1H), 4.39 (p, J=6.7 Hz, 1H), 3.75 (d, J=13.5 Hz, 1H), 3.67 (d, J=13.5 Hz, 1H), 2.80 (q, J=6.3 Hz, 1H), 2.65 (dd, J=14.0, 6.1 Hz, 1H), 1.36 (d, J=6.7 Hz, 6H), 1.32 (s, 0H), 0.98 (d, J=6.2 Hz, 3H).

B54

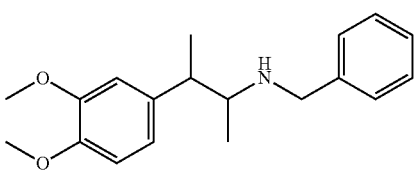

1H NMR (400 MHz, DMSO-d6) δ 7.28 (q, J=7.8, 7.3 Hz, 5H), 7.23 (d, J=13.1 Hz, 2H), 7.19 (s, 1H), 6.84 (d, J=8.3 Hz, 2H), 6.77 (s, 1H), 6.69 (d, J=8.9 Hz, 2H), 3.78 (d, J=14.0 Hz, 1H), 3.70 (d, J=6.9 Hz, 9H), 3.61 (d, J=15.6 Hz, 1H), 2.66 (s, 3H), 2.54 (s, 1H), 1.66 (s, 2H), 1.22 (d, J=5.9 Hz, 2H), 1.14 (d, J=6.9 Hz, 2H), 0.89 (t, J=7.4 Hz, 2H), 0.83 (d, J=5.3 Hz, 2H).

B49

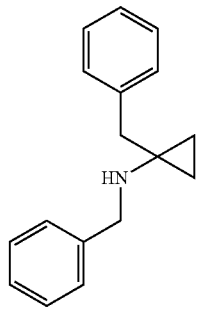

1H NMR (400 MHz, DMSO-d6) δ 7.34-7.17 (m, 10H), 7.21-7.16 (m, 1H), 3.77 (d, J=6.9 Hz, 2H), 2.79 (s, 2H), 1.81 (t, J=7.0 Hz, 1H), 0.52 (d, J=11.8 Hz, 3H).

B61

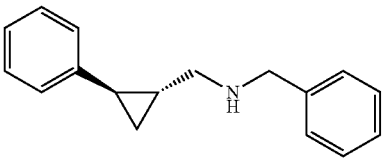

1H NMR (400 MHz, DMSO-d6) δ 7.33-7.12 (m, 8H), 7.10-6.98 (m, 4H), 3.75 (s, 2H), 2.64 (dd, J=12.2, 6.2 Hz, 1H), 2.57-2.47 (m, 2H), 1.70 (dt, J=9.2, 4.9 Hz, 1H), 1.30-1.19 (m, 1H), 0.83 (ddd, J=13.9, 9.5, 4.9 Hz, 2H).

B50

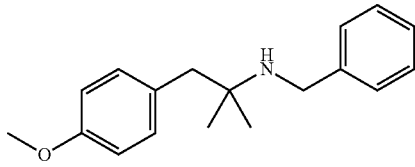

1H NMR (400 MHz, DMSO-d6) δ 7.34 (d, J=7.5 Hz, 2H), 7.29 (t, J=7.5 Hz, 2H), 7.20 (t, J=7.2 Hz, 1H), 7.10 (d, J=8.1 Hz, 2H), 6.83 (d, J=8.1 Hz, 2H), 3.73 (d, J=9.7 Hz, 5H), 2.64 (s, 2H), 1.43 (s, 1H), 1.00 (s, 5H).

B67

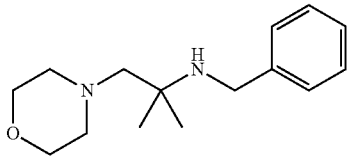

1H NMR (400 MHz, DMSO-d6) δ 7.30-7.19 (m, 4H), 7.15 (t, J=7.1 Hz, 1H), 3.56 (t, J=4.6 Hz, 4H), 3.00 (s, 2H), 2.54 (dd, J=5.6, 3.4 Hz, 4H), 2.42 (s, 1H), 2.27 (s, 2H), 1.47 (s, 1H), 1.05 (s, 5H).

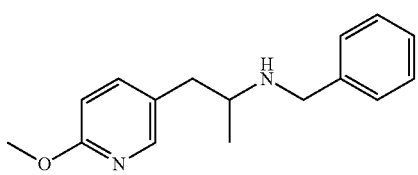

B68

1H NMR (400 MHz, DMSO-d6) δ 7.94 (d, J=2.4 Hz, 1H), 7.50 (dd, J=8.5, 2.4 Hz, 1H), 7.28 (d, J=4.5 Hz, 4H), 7.20 (q, J=4.4 Hz, 1H), 6.72 (d, J=8.4 Hz, 1H), 3.78 (d, J=23.2 Hz, 4H), 3.70 (d, J=13.6 Hz, 1H), 2.71 (ddt, J=18.8, 13.3, 6.0 Hz, 2H), 2.45 (dd, J=13.2, 6.7 Hz, 1H), 1.87 (s, 1H), 0.92 (d, J=6.1 Hz, 3H).

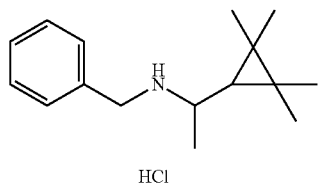

B77

1H NMR (400 MHz, DMSO-d6) δ 9.62 (s, 1H), 9.06 (s, 2H), 7.66-7.59 (m, 2H), 7.47-7.36 (m, 3H), 4.06 (d, J=13.1 Hz, 1H), 3.97 (d, J=13.0 Hz, 1H), 2.89 (dt, J=13.0, 6.4 Hz, 1H), 1.35 (d, J=6.4 Hz, 3H), 1.08 (d, J=17.4 Hz, 6H), 0.95 (s, 3H), 0.88 (s, 3H), 0.54 (d, J=10.6 Hz, 1H).

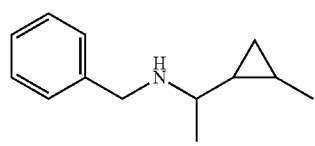

B69

1H NMR (400 MHz, DMSO-d6) δ 7.29 (ddt, J=11.3, 8.2, 5.1 Hz, 4H), 7.20 (d, J=7.5 Hz, 1H), 3.83-3.65 (m, 2H), 3.20 (t, J=6.9 Hz, 1H), 3.12 (s, 1H), 2.54 (s, 1H), 2.17-2.01 (m, 1H), 2.01-1.81 (m, 1H), 1.13-0.95 (m, 4H), 0.96 (s, 1H), 0.35 (ddq, J=26.9, 8.7, 5.1 Hz, 1H), 0.13 (dddd, J=26.6, 18.0, 8.5, 4.4 Hz, 1H).

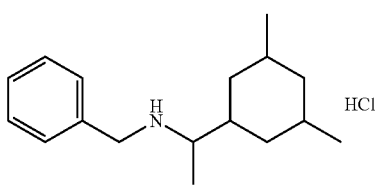

B79

1H NMR (400 MHz, DMSO-d6) δ 9.27 (s, 3H), 8.88 (s, 3H), 7.63 (dd, J=6.5, 3.2 Hz, 5H), 7.42 (d, J=6.5 Hz, 8H), 4.24-4.15 (m, 3H), 4.09 (dq, J=13.8, 7.5, 6.8 Hz, 3H), 3.16 (s, 1H), 2.97 (s, 1H), 2.54 (s, 1H), 2.04 (s, 3H), 1.87 (dt, J=11.8, 6.0 Hz, 2H), 1.69 (d, J=12.7 Hz, 2H), 1.60 (d, J=12.5 Hz, 3H), 1.48 (s, 2H), 1.41 (s, 2H), 1.41 (d, J=12.6 Hz, 2H), 1.29-1.20 (m, 1H), 1.23-1.15 (m, 7H), 1.03 (td, J=12.7, 4.7 Hz, 1H), 0.97 (s, 2H), 0.95 (s, 2H), 0.93 (d, J=6.6 Hz, 0H), 0.86 (dq, J=13.5, 6.6 Hz, 10H), 0.64 (tq, J=12.2, 7.3, 6.8 Hz, 3H), 0.50 (q, J=12.0 Hz, 1H).

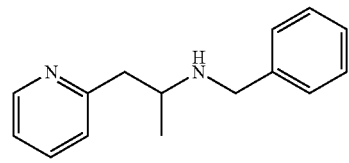

B75

1H NMR (400 MHz, DMSO-d6) δ 8.46 (d, J=4.9 Hz, 1H), 7.67 (td, J=7.6, 2.0 Hz, 1H), 7.34-7.21 (m, 5H), 7.19 (dd, J=10.7, 4.7 Hz, 3H), 3.76 (d, J=13.6 Hz, 1H), 3.68 (d, J=13.8 Hz, 1H), 3.00-2.92 (m, 2H), 2.90 (d, J=7.0 Hz, 1H), 2.64 (dd, J=12.7, 6.7 Hz, 1H), 2.07 (s, 1H), 0.96 (d, J=6.0 Hz, 3H).

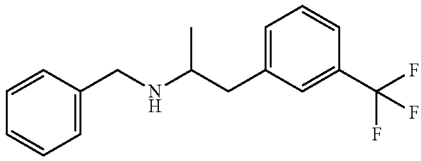

B81

1H NMR (400 MHz, DMSO-d6) δ 7.57-7.46 (m, 5H), 7.26 (d, J=4.5 Hz, 4H), 7.19 (q, J=4.5 Hz, 1H), 3.77 (d, J=13.7 Hz, 1H), 3.70 (d, J=13.8 Hz, 1H), 2.82 (ddd, J=18.5, 12.6, 6.1 Hz, 2H), 2.62 (dd, J=12.2, 5.7 Hz, 1H), 2.22 (s, 1H), 0.95 (d, J=5.8 Hz, 3H).

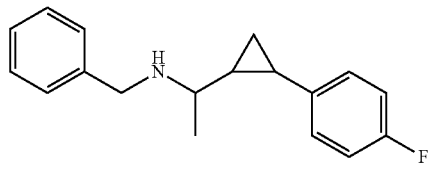

B76

1H NMR (400 MHz, DMSO-d6) δ 7.38-7.24 (m, 4H), 7.21 (t, J=7.1 Hz, 1H), 7.08 (ddd, J=14.2, 7.1, 2.8 Hz, 3H), 7.02 (d, J=8.9 Hz, 1H), 3.76 (dd, J=17.5, 3.8 Hz, 2H), 2.54 (s, 1H), 2.13 (dt, J=14.5, 7.2 Hz, 1H), 2.02 (s, 1H), 1.69 (dt, J=8.6, 5.1 Hz, 1H), 1.11 (t, J=5.8 Hz, 3H), 1.00-0.84 (m, 2H), 0.77 (ddt, J=20.2, 9.0, 5.0 Hz, 1H).

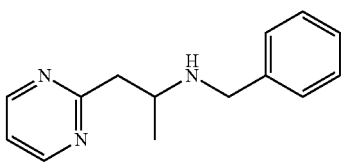

B82

1H NMR (400 MHz, DMSO-d6) δ 8.70 (d, J=4.9 Hz, 2H), 7.32 (t, J=4.9 Hz, 1H), 7.26 (d, J=5.5 Hz, 4H), 7.19 (d, J=5.5 Hz, 1H), 3.79-3.65 (m, 2H), 3.11 (ddd, J=22.8, 12.9, 6.2 Hz, 2H), 2.79 (dd, J=12.9, 6.7 Hz, 1H), 2.54 (s, 1H), 2.13 (s, 1H), 1.00 (d, J=6.1 Hz, 3H).

B83

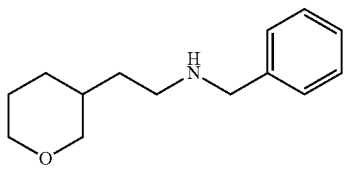

1H NMR (400 MHz, Chloroform-d) δ 7.36-7.19 (m, 6H), 3.90-3.79 (m, 4H), 3.77 (s, 4H), 3.34 (ddd, J=11.0, 9.0, 4.3 Hz, 2H), 3.05 (t, J=10.6 Hz, 2H), 2.71-2.56 (m, 4H), 1.88-1.78 (m, 2H), 1.72-1.53 (m, 4H), 1.46-1.23 (m, 3H), 1.23-1.07 (m, 1H), 1.13 (s, 1H).

B84

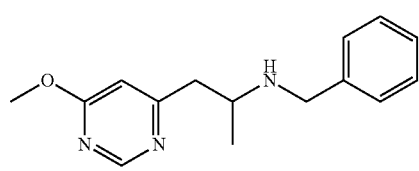

1H NMR (400 MHz, DMSO-d6) δ 8.66 (s, 1H), 7.27 (d, J=4.4 Hz, 4H), 7.19 (dt, J=8.9, 4.3 Hz, 1H), 6.78 (s, 1H), 3.89 (s, 3H), 3.75 (d, J=13.6 Hz, 1H), 3.69 (d, J=13.6 Hz, 1H), 3.00 (p, J=6.4 Hz, 1H), 2.83 (dd, J=13.2, 6.2 Hz, 1H), 2.62-2.52 (m, 1H), 2.09 (s, 1H), 0.97 (d, J=6.3 Hz, 3H).

B85

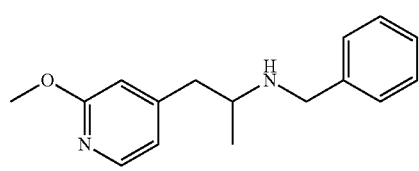

1H NMR (400 MHz, DMSO-d6) δ 8.02 (d, J=5.2 Hz, 1H), 7.28 (d, J=4.4 Hz, 4H), 7.20 (q, J=4.4 Hz, 1H), 6.82-6.76 (m, 1H), 6.60 (s, 1H), 3.81 (s, 3H), 3.76 (d, J=14.1 Hz, 1H), 3.70 (d, J=13.8 Hz, 1H), 2.83 (q, J=6.3 Hz, 1H), 2.76 (dd, J=12.9, 5.8 Hz, 1H), 2.54 (s, 1H), 2.46 (dd, J=12.8, 7.0 Hz, 1H), 1.91 (s, 1H), 0.93 (d, J=6.1 Hz, 3H).

B86

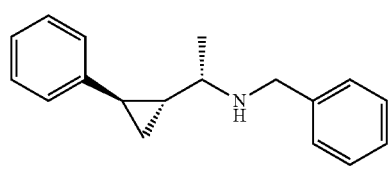

1H NMR (400 MHz, DMSO-d6) δ 7.38-7.15 (m, 7H), 7.09 (dt, J=22.5, 6.8 Hz, 3H), 3.79 (d, J=6.3 Hz, 1H), 3.74 (d, J=5.1 Hz, 1H), 2.13 (dq, J=13.9, 6.8 Hz, 1H), 2.04 (s, 1H), 1.71 (ddt, J=35.4, 9.4, 5.0 Hz, 1H), 1.11 (t, J=7.0 Hz, 3H), 1.03-0.88 (m, 1H), 0.92-0.69 (m, 1H).

B87

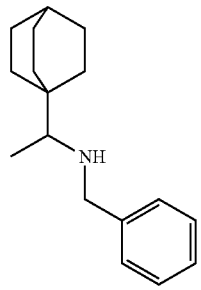

1H NMR (400 MHz, DMSO-d6) δ 7.35-7.24 (m, 4H), 7.19 (t, J=7.2 Hz, 1H), 3.81 (d, J=13.7 Hz, 1H), 3.54 (d, J=13.7 Hz, 1H), 2.54 (s, 2H), 2.03 (s, 1H), 1.51-1.43 (m, 8H), 1.40 (s, 2H), 1.31 (s, 1H), 1.26 (s, 4H), 0.86 (d, J=6.5 Hz, 3H).

B88

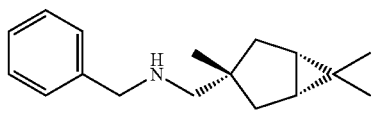

1H NMR (400 MHz, Chloroform-d) δ 7.39-7.28 (m, 4H), 7.28-7.19 (m, 1H), 5.34 (d, J=3.1 Hz, 1H), 3.89-3.77 (m, 2H), 3.17 (dd, J=5.2, 2.8 Hz, 1H), 2.16 (p, J=6.8 Hz, 1H), 2.07-1.94 (m, 2H), 1.93-1.81 (m, 1H), 1.65-1.52 (m, 2H), 1.37 (s, 2H), 0.99 (d, J=6.8 Hz, 5H), 0.98-0.83 (m, 3H).

B89

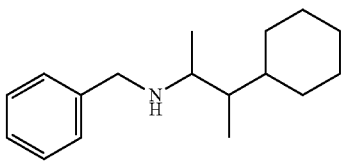

1H NMR (400 MHz, DMSO-d6) δ 7.31-7.20 (m, 8H), 7.15 (t, J=7.1 Hz, 2H), 3.81 (d, J=13.2 Hz, 1H), 3.72 (d, J=13.3 Hz, 1H), 3.61 (dd, J=27.8, 13.3 Hz, 2H), 3.00 (s, 1H), 2.72-2.58 (m, 2H), 1.73-1.62 (m, 10H), 1.54 (d, J=12.7 Hz, 1H), 1.39-1.26 (m, 2H), 1.21 (s, 3H), 1.14 (dddd, J=21.6, 16.3, 10.8, 7.7 Hz, 6H), 1.06-0.84 (m, 8H), 0.80 (dd, J=21.9, 6.6 Hz, 6H).

B90

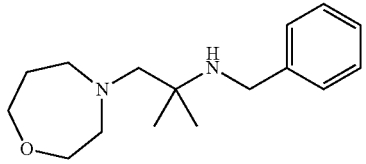

1H NMR (400 MHz, DMSO-d6) δ 7.35-7.24 (m, 2H), 3.69-3.61 (m, 2H), 3.60-3.53 (m, 1H), 2.79 (q, J=5.4, 4.5 Hz, 2H), 2.46 (s, 1H), 1.74 (p, J=5.9 Hz, 1H), 1.65 (s, 1H), 1.01 (s, 3H).

B91

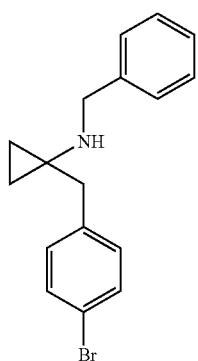

1H NMR (400 MHz, DMSO-d6) δ 7.29 (ddt, J=11.3, 8.2, 5.1 Hz, 4H), 7.20 (d, J=7.5 Hz, 1H), 3.83-3.65 (m, 2H), 3.20 (t, J=6.9 Hz, 1H), 3.12 (s, 1H), 2.54 (s, 1H), 2.17-2.01 (m, 1H), 2.01-1.81 (m, 1H), 1.13-0.95 (m, 4H), 0.96 (s, 1H), 0.35 (ddq, J=26.9, 8.7, 5.1 Hz, 1H), 0.13 (dddd, J=26.6, 18.0, 8.5, 4.4 Hz, 1H).

B92

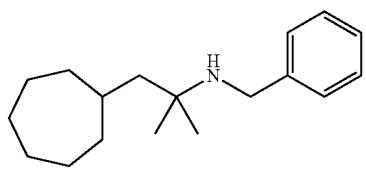

1H NMR (400 MHz, DMSO-d6) δ 7.32-7.11 (m, 3H), 3.63 (s, 1H), 1.74 (ddd, J=13.2, 7.3, 3.2 Hz, 1H), 1.70-1.52 (m, 3H), 1.45 (q, J=11.5, 10.5 Hz, 2H), 1.37-1.22 (m, 2H), 1.08 (s, 3H).

B93

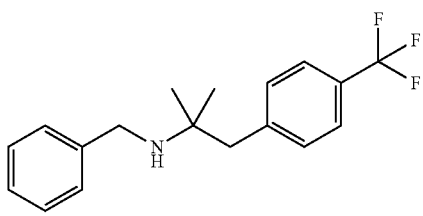

1H NMR (400 MHz, DMSO-d6) δ 7.63 (d, J=7.8 Hz, 2H), 7.44 (d, J=7.9 Hz, 2H), 7.35 (d, J=7.4 Hz, 2H), 7.29 (t, J=7.5 Hz, 2H), 7.20 (t, J=7.2 Hz, 1H), 3.76 (d, J=7.5 Hz, 2H), 2.80 (s, 2H), 1.60 (t, J=7.6 Hz, 1H), 1.03 (s, 5H).

B96

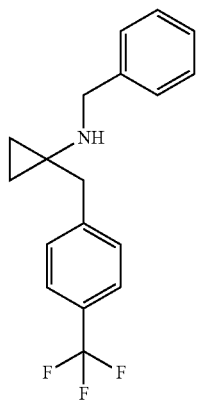

1H NMR (400 MHz, DMSO-d6) δ 7.65 (d, J=7.9 Hz, 2H), 7.52 (d, J=7.8 Hz, 2H), 7.26 (d, J=4.4 Hz, 4H), 7.19 (td, J=6.7, 5.0, 3.0 Hz, 1H), 3.77 (d, J=4.9 Hz, 2H), 2.86 (s, 2H), 1.89 (s, 1H), 0.56 (dt, J=11.5, 2.1 Hz, 3H).

B97

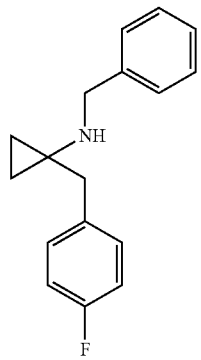

1H NMR (400 MHz, DMSO-d6) δ 7.35-7.22 (m, 6H), 7.26-7.15 (m, 1H), 7.11 (t, J=8.9 Hz, 2H), 3.75 (d, J=4.0 Hz, 2H), 2.76 (s, 2H), 2.54 (s, 0H), 1.83 (s, 1H), 0.52 (dt, J=14.7, 2.0 Hz, 3H).

B98

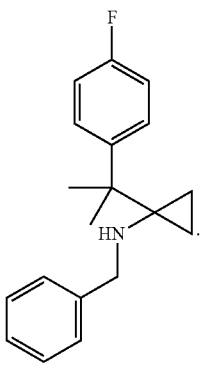

m/z 283.22

B99

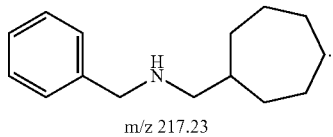

m/z 217.23

B100

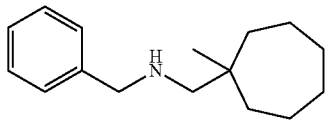

1H NMR (400 MHz, DMSO-d6) δ 7.35-7.25 (m, 4H), 7.24-7.15 (m, 1H), 3.69 (s, 2H), 2.54 (s, 0H), 2.21 (s, 2H), 1.78 (s, 1H), 1.50-1.35 (m, 6H), 1.36 (s, 3H), 1.27-1.16 (m, 2H), 0.83 (s, 2H).

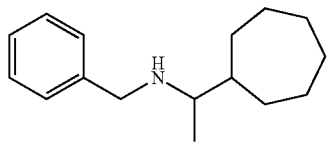

B101

1H NMR (400 MHz, DMSO-d6) δ 7.31-7.23 (m, 4H), 7.23 (d, J=7.6 Hz, 2H), 7.20-7.11 (m, 1H), 3.77-3.61 (m, 3H), 2.53 (d, J=4.2 Hz, 1H), 1.73 (s, 1H), 1.70 (dddt, J=22.8, 9.6, 6.3, 3.0 Hz, 3H), 1.62-1.39 (m, 6H), 1.42-1.33 (m, 1H), 1.36-1.12 (m, 2H), 0.92 (d, J=6.4 Hz, 4H).

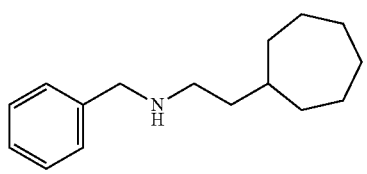

B102 m/z 231.25.

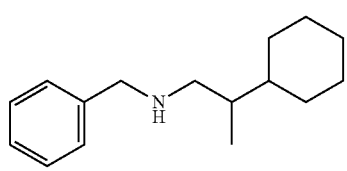

B103

1H NMR (400 MHz, DMSO-d6) δ 7.30 (d, J=6.6 Hz, 4H), 7.20 (s, 1H), 3.66 (s, 2H), 2.54 (s, 1H), 2.45 (dd, J=11.4, 5.7 Hz, 1H), 2.25 (dd, J=11.5, 7.6 Hz, 1H), 1.86 (s, 1H), 1.67 (d, J=12.4 Hz, 2H), 1.60 (d, J=11.8 Hz, 1H), 1.51 (d, J=11.9 Hz, 2H), 1.46-1.36 (m, 1H), 1.29 (dt, J=11.7, 3.8 Hz, 1H), 1.22-1.02 (m, 2H), 1.06-0.92 (m, 1H), 0.81 (d, J=6.9 Hz, 3H).

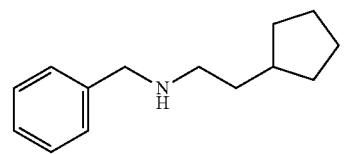

B128

1H NMR (400 MHz, DMSO-d6) δ 7.30-7.20 (m, 8H), 7.16 (t, J=6.8 Hz, 2H), 2.53 (d, J=7.0 Hz, 3H), 1.88-1.74 (m, 2H), 1.78-1.67 (m, 4H), 1.65-1.51 (m, 3H), 1.55 (s, 3H), 1.47 (dq, J=14.5, 7.3 Hz, 7H), 1.14-1.01 (m, 4H).

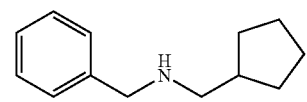

B141

1H NMR (400 MHz, Chloroform-d) δ 7.29 (s, 8H), 3.48 (s, 1H), 1.25 (s, 1H).

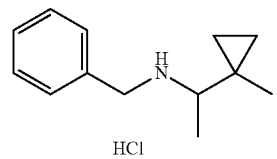

B149

1H NMR (400 MHz, DMSO-d6) δ 9.61 (s, 2H), 8.82 (s, 2H), 7.64-7.57 (m, 3H), 7.48-7.36 (m, 5H), 4.14 (d, J=16.7 Hz, 4H), 2.54 (s, 2H), 2.38 (s, 2H), 1.33 (d, J=6.7 Hz, 4H), 1.08 (s, 4H), 0.55 (ddt, J=19.4, 10.4, 5.2 Hz, 3H), 0.34 (dq, J=9.7, 5.8, 5.4 Hz, 3H).

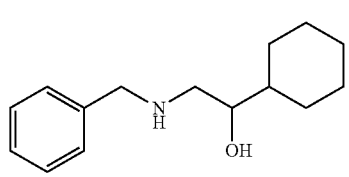

B172

1H NMR (400 MHz, DMSO-d6) δ 7.32-7.21 (m, 4H), 7.17 (t, J=6.9 Hz, 1H), 4.10-4.05 (m, 1H), 3.76-3.64 (m, 2H), 3.25 (s, 1H), 2.54 (dd, J=11.4, 3.0 Hz, 1H), 2.41 (dd, J=11.6, 8.6 Hz, 1H), 1.79 (d, J=12.7 Hz, 1H), 1.70 (s, 3H), 1.67-1.54 (m, 2H), 1.24 (s, 1H), 1.20-1.14 (m, 2H), 1.13 (d, J=9.2 Hz, 1H), 1.06-0.89 (m, 2H).

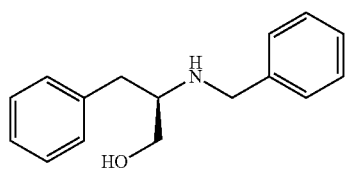

B173

1H NMR (400 MHz, DMSO-d6) δ 7.22 (dd, J=8.8, 5.7 Hz, 6H), 7.18-7.09 (m, 4H), 4.21 (d, J=5.5 Hz, 1H), 3.41-3.32 (m, 1H), 3.24 (dt, J=10.6, 5.0 Hz, 1H), 3.02 (s, 2H), 2.79-2.66 (m, 2H), 2.65 (dd, J=12.8, 7.1 Hz, 1H), 1.76 (s, 1H).

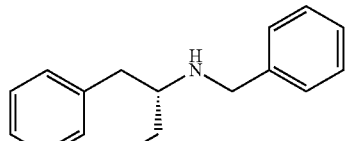

B174

1H NMR (400 MHz, DMSO-d6) δ 7.26-7.11 (m, 10H), 4.22 (s, 1H), 3.75 (s, 2H), 3.36 (s, 1H), 2.79-2.62 (m, 3H), 1.76 (s, 1H).

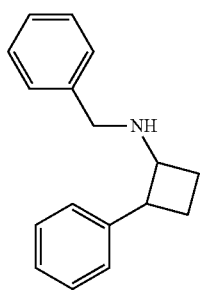

B176

1H NMR (400 MHz, DMSO-d6) δ 7.31 (d, J=4.4 Hz, 6H), 7.18 (s, 3H), 7.25-7.07 (m, 7H), 6.98 (d, J=7.2 Hz, 3H), 3.75 (d, J=7.3 Hz, 2H), 3.68-3.55 (m, 2H), 3.42-3.29 (m, 3H), 3.25 (s, 1H), 2.95 (s, 1H), 2.28 (s, 2H), 2.17 (ddd, J=21.2, 10.2, 4.2 Hz, 4H), 1.89 (t, J=9.2 Hz, 1H), 1.68 (s, 1H), 1.24 (s, 2H).

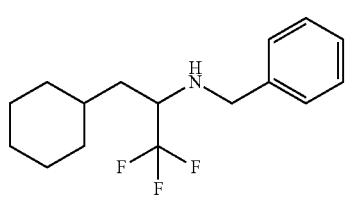

B177

1H NMR (400 MHz, Chloroform-d) δ 7.34 (s, 1H), 7.26 (s, 1H), 4.03 (d, J=13.3 Hz, 1H), 3.82 (d, J=13.3 Hz, 1H), 3.09 (s, 1H), 1.69 (d, J=13.0 Hz, 1H), 1.46 (d, J=11.4 Hz, 1H), 1.42 (s, 3H), 1.29 (s, 1H), 1.13 (d, J=10.6 Hz, 2H), 0.95 (d, J=11.6 Hz, 1H), 0.73 (s, 1H).

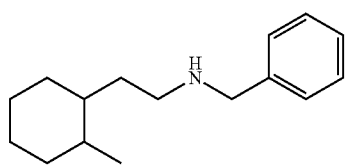

B178

1H NMR (400 MHz, DMSO-d6) δ 7.25 (d, J=6.6 Hz, 4H), 7.17 (d, J=6.9 Hz, 1H), 3.69 (s, 2H), 1.73 (s, 1H), 1.54 (s, 1H), 1.42 (s, 2H), 1.34 (q, J=8.1 Hz, 2H), 1.30-1.22 (m, 1H), 0.89 (d, J=6.2 Hz, 1H), 0.83 (d, J=7.1 Hz, 2H).

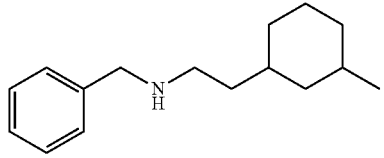

B179

1H NMR (400 MHz, Chloroform-d) δ 7.31 (s, 3H), 7.30-7.18 (m, 2H), 3.77 (s, 3H), 2.62 (q, J=7.9 Hz, 3H), 1.75-1.59 (m, 1H), 1.66 (s, 2H), 1.57-1.12 (m, 7H), 1.09 (p, J=5.8, 5.2 Hz, 1H), 0.85 (dd, J=10.5, 6.7 Hz, 4H).

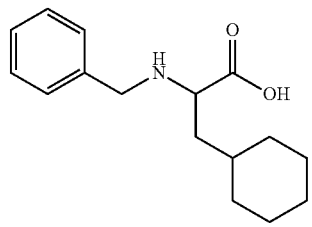

B180

1H NMR (400 MHz,) δ 11.47 (d, J=4.0 Hz, 10H), 7.48 (d, J=7.6 Hz, 2H), 7.44 (t, J=7.6 Hz, 3H), 4.52 (dd, J=13.3, 4.1 Hz, 1H), 4.44-4.36 (m, 1H), 4.25-4.19 (m, 1H), 1.93 (t, J=6.9 Hz, 2H), 1.74 (d, J=12.7 Hz, 3H), 1.68 (s, 2H), 1.61 (d, J=4.6 Hz, 0H), 1.44 (s, 2H), 1.25 (s, 1H), 1.16 (s, 3H), 0.93 (s, 2H).

Example 5: General Compound Syntheses 5

Step A

Compound 1 (0.22 ml) was added to a suspension of 2-OH-benzaldehyde 2 (0.17 g) and potassium carbonate (0.20 g) in DMF (5 ml), and the mixture was stirred at 90° C. for 1 hour. The mixture was allowed to cool to room temperature, and neutralized with 1N hydrochloric acid. After extraction with ethyl acetate, the organic layer was washed with saturated salt water, dried over anhydrous sodium sulfate, and concentrated. The concentrate was purified by silica gel column chromatography (n-hexane/ethyl acetate=4/1). Yield: 23-39%.

Step B

Amine 4 (0.5 mmol), aldehyde 3 (0.55 mmol) were dissolved in 0.6 ml MeOH, heated at 100° C. for 2 hours, then mixture was cooled, NaBH₄ (0.5 mmol) was added and stirred for 4 hours. The mixture was heated for 2 hours at 60° C., 3 ml of methanol and 0.2 g of C-18 chromatographic phase were added, stirred for 2 hours, filtered, evaporated and dissolved in 0.5 ml of DMSO. The residue 5 was purified using HPLC. Yield: 23-38%.

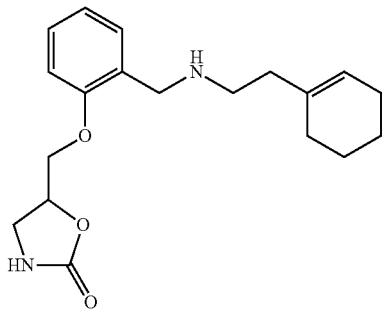

B402

1H NMR (400 MHz, Chloroform-d) δ 7.24 (d, J=17.8 Hz, 1H), 6.97 (t, J=7.5 Hz, 1H), 6.84 (d, J=8.1 Hz, 1H), 5.97 (s, 1H), 5.42 (s, 1H), 4.97 (dq, J=9.4, 4.7 Hz, 1H), 4.17 (qd, J=10.2, 4.3 Hz, 2H), 3.79 (d, J=6.2 Hz, 3H), 3.62 (dd, J=8.7, 5.6 Hz, 1H), 3.56 (s, 1H), 2.65 (t, J=7.0 Hz, 2H), 2.13 (t, J=7.2 Hz, 2H), 1.95 (s, 2H), 1.80 (d, J=6.6 Hz, 2H), 1.54 (td, J=11.6, 5.9 Hz, 4H). Compound B377 was synthesized in accord with this procedure.

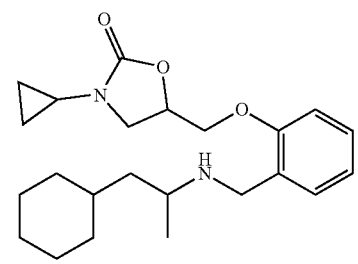

B367

1H NMR (400 MHz, DMSO-d6) δ 7.29 (d, J=7.4 Hz, 1H), 7.19 (t, J=7.8 Hz, 1H), 6.98-6.87 (m, 2H), 4.84-4.78 (m, 1H), 4.16 (dd, J=8.8, 5.0 Hz, 1H), 4.08 (dd, J=11.1, 5.2 Hz, 1H), 3.75-3.64 (m, 2H), 3.58 (dd, J=14.2, 6.6 Hz, 1H), 3.43 (t, J=7.7 Hz, 1H), 2.55 (q, J=6.3 Hz, 4H), 1.57 (d, J=11.5 Hz, 5H), 1.48 (d, J=12.9 Hz, 1H), 1.27 (d, J=12.0 Hz, 2H), 1.18-1.09 (m, 1H), 1.04 (s, 2H), 0.95 (d, J=6.1 Hz, 3H), 0.76 (s, 3H), 0.72-0.62 (m, 3H).

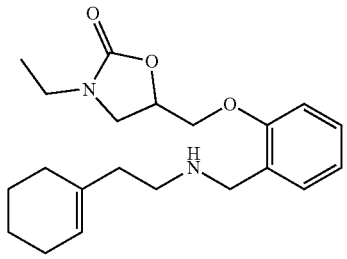

B368

1H NMR (400 MHz, DMSO-d6) δ 7.28 (d, J=7.4 Hz, 1H), 7.21 (t, J=7.8 Hz, 1H), 7.00-6.88 (m, 2H), 5.35 (s, 1H), 4.90-4.82 (m, 1H), 4.19 (dd, J=10.8, 3.0 Hz, 1H), 4.10 (dd, J=10.8, 4.4 Hz, 1H), 3.71 (t, J=9.0 Hz, 1H), 3.64 (s, 2H), 3.46 (dd, J=8.6, 6.1 Hz, 1H), 3.22 (q, J=7.2 Hz, 2H), 2.53 (d, J=6.2 Hz, 2H), 2.04 (t, J=7.2 Hz, 2H), 1.92 (s, 2H), 1.81 (d, J=6.6 Hz, 2H), 1.51 (ddt, J=19.8, 13.8, 6.5 Hz, 5H), 1.09 (t, J=7.2 Hz, 3H).

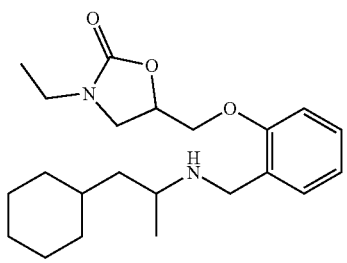

B369

1H NMR (400 MHz, DMSO-d6) δ 7.30 (d, J=7.4 Hz, 1H), 7.20 (t, J=7.8 Hz, 1H), 6.96 (d, J=8.2 Hz, 1H), 6.91 (t, J=7.4 Hz, 1H), 4.87 (d, J=7.0 Hz, 1H), 4.19 (q, J=6.4, 3.5 Hz, 1H), 4.15-4.04 (m, 1H), 3.71 (dd, J=14.0, 8.9 Hz, 2H), 3.59 (dd, J=14.3, 8.8 Hz, 1H), 3.52-3.41 (m, 1H), 3.22 (q, J=7.4 Hz, 2H), 2.55 (d, J=7.6 Hz, 2H), 1.58 (d, J=11.3 Hz, 5H), 1.47 (t, J=15.1 Hz, 1H), 1.29 (dd, J=11.2, 5.4 Hz, 2H), 1.10 (t, J=7.2 Hz, 3H), 1.07-0.92 (m, 3H), 0.77 (t, J=13.9 Hz, 2H).

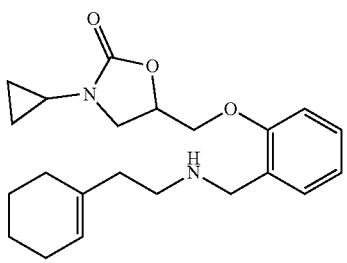

B370

1H NMR (400 MHz, DMSO-d6) δ 7.28 (d, J=7.4 Hz, 1H), 7.20 (t, J=7.8 Hz, 1H), 6.93 (dd, J=17.2, 8.3 Hz, 2H), 5.35 (s, 1H), 4.80 (dt, J=9.2, 4.5 Hz, 1H), 4.16 (dd, J=11.0, 3.0 Hz, 1H), 4.07 (dd, J=11.0, 4.5 Hz, 1H), 3.68 (t, J=9.0 Hz, 1H), 3.62 (s, 2H), 3.42 (dd, J=8.6, 6.0 Hz, 1H), 2.60-2.47 (m, 4H), 2.04 (t, J=7.4 Hz, 2H), 1.92 (s, 2H), 1.81 (d, J=6.6 Hz, 2H), 1.67 (s, 0H), 1.50 (dt, J=19.6, 6.6 Hz, 4H), 0.77-0.65 (m, 4H).

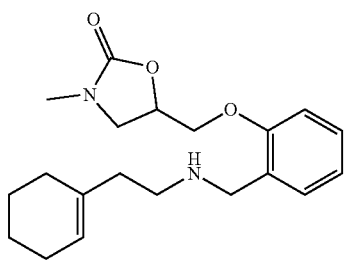
B371

1H NMR (400 MHz, Chloroform-d) δ 6.97 (t, J=7.3 Hz, 1H), 6.84 (d, J=8.2 Hz, 1H), 5.43 (s, 1H), 4.84 (s, 1H), 4.16 (s, 2H), 3.80-3.69 (m, 2H), 3.60-3.52 (m, 1H), 2.94 (s, 3H), 2.66 (t, J=7.0 Hz, 1H), 2.15 (s, 2H), 1.97 (s, 2H), 1.85 (s, 2H), 1.25 (s, 1H).

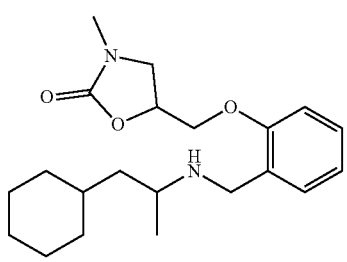
B372

1H NMR (400 MHz, Chloroform-d) δ 7.29 (s, 1H), 7.22 (d, J=8.0 Hz, 1H), 6.97 (t, J=7.3 Hz, 1H), 6.84 (d, J=8.1 Hz, 1H), 4.85 (s, 1H), 4.17 (dd, J=8.5, 5.0 Hz, 1H), 3.83 (d, J=13.3 Hz, 1H), 3.78-3.66 (m, 2H), 3.60-3.52 (m, 1H), 2.93 (s, 3H), 2.70 (d, J=6.7 Hz, 1H), 1.35 (s, 3H), 1.15 (d, J=10.5 Hz, 6H), 1.06 (d, J=6.3 Hz, 3H), 0.84 (s, 3H).

Example 6: General Compound Syntheses 6

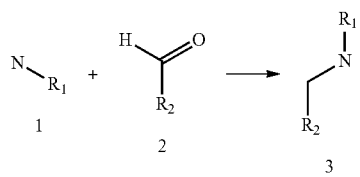

Amine 1 (0.25 mmol) and aldehyde 2 (0.23 mmol) were dissolved in 0.3 ml MeOH, heated at 100° C. for 2 hours, then mixture was cooled, NaBH₄ (0.25 mmol) was added and stirred for 4 hours. The mixture was heated for 2 hours at 60° C., 3 ml of methanol and 0.1 g of C-18 chromatographic phase were added, stirred for 2 hours, filtered, evaporated and dissolved in 0.25 ml of DMSO. The residue was purified using HPLC. Yield: 32-47%.

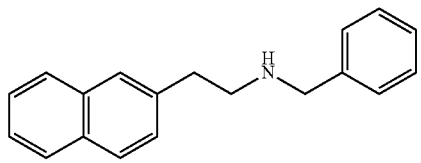
B133

1H NMR (400 MHz, DMSO-d6) δ 8.06 (d, J=8.0 Hz, 1H), 7.93-7.86 (m, 1H), 7.76 (d, J=8.0 Hz, 1H), 7.56-7.46 (m, 2H), 7.49-7.37 (m, 1H), 7.36 (d, J=6.9 Hz, 1H), 7.35-7.24 (m, 4H), 7.20 (t, J=7.0 Hz, 1H), 3.74 (s, 2H), 3.21 (t, J=7.6 Hz, 2H), 2.81 (t, J=7.6 Hz, 2H), 2.32 (s, 1H).

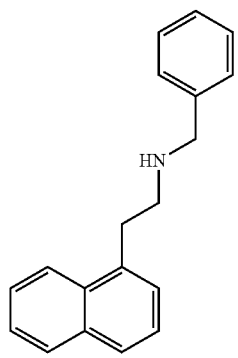
B192

1H NMR (400 MHz, Chloroform-d) δ 8.30 (d, J=8.1 Hz, 1H), 7.98 (d, J=8.2 Hz, 1H), 7.50 (p, J=6.9 Hz, 2H), 7.25 (d, J=8.3 Hz, 2H), 7.17 (d, J=7.7 Hz, 2H), 7.10 (d, J=7.7 Hz, 2H), 6.73 (d, J=7.8 Hz, 1H), 3.98 (s, 3H), 3.78 (s, 2H), 3.22 (t, J=7.2 Hz, 2H), 3.00 (t, J=7.3 Hz, 2H), 2.32 (s, 3H).

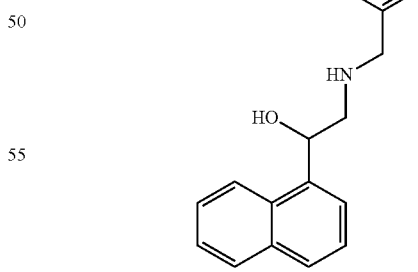
B193

1H NMR (400 MHz, DMSO-d6) δ 8.08-8.01 (m, 1H), 7.94-7.87 (m, 1H), 7.79 (d, J=8.1 Hz, 1H), 7.65 (d, J=7.1 Hz, 1H), 7.48 (dq, J=7.2, 3.6, 2.9 Hz, 3H), 7.31 (dt, J=14.8, 7.5 Hz, 4H), 7.21 (t, J=7.1 Hz, 1H), 5.45 (s, 2H), 5.43 (d, J=3.8 Hz, 0H), 3.79 (s, 2H), 2.86-2.78 (m, 1H), 2.69 (dd, J=12.2, 7.8 Hz, 1H), 2.31 (s, 1H).

B194

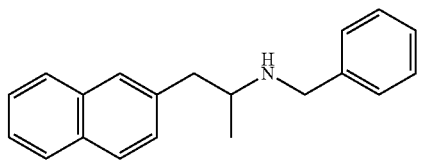

1H NMR (400 MHz, DMSO-d6) δ 7.89-7.71 (m, 4H), 7.66 (s, 1H), 7.51-7.39 (m, 3H), 7.34 (d, J=9.0 Hz, 1H), 7.27 (d, J=6.6 Hz, 4H), 7.20 (d, J=6.5 Hz, 1H), 3.80 (d, J=13.6 Hz, 1H), 3.74 (d, J=13.8 Hz, 1H), 2.94 (ddd, J=26.2, 12.3, 5.7 Hz, 2H), 2.64 (dd, J=12.7, 7.0 Hz, 1H), 1.94 (s, 1H), 0.98 (d, J=6.1 Hz, 3H).

B195

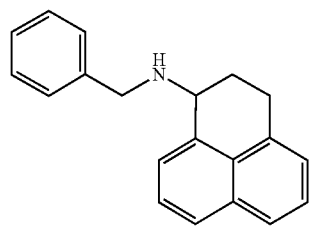

1H NMR (400 MHz, Chloroform-d) δ 7.76 (dd, J=7.4, 1.9 Hz, 1H), 7.70 (d, J=8.3 Hz, 1H), 7.48-7.23 (m, 9H), 4.13 (s, 1H), 4.02 (d, J=13.3 Hz, 1H), 3.93 (d, J=13.3 Hz, 1H), 3.04 (d, J=16.3 Hz, 1H), 2.19 (dd, J=9.8, 4.8 Hz, 1H).

Example 7: General Compound Syntheses 7

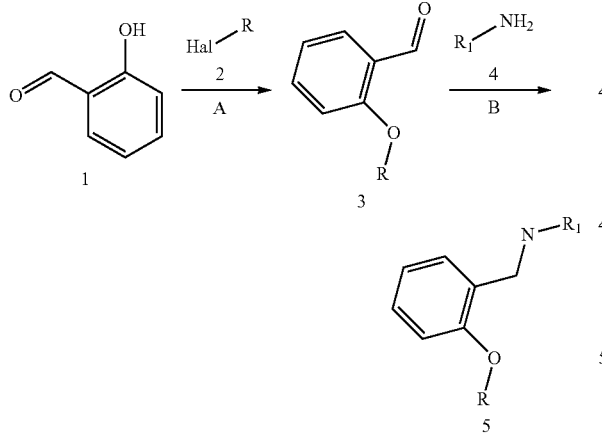

Step A:

A solution of 2-hydroxybenzaldehyde 1 (5.0 mmol, 1.0 equiv), K$_2$CO$_3$ (7.5 mmol, 1.5 equiv), compound 2 (5.0 mmol, 1.0 equiv) in CH$_3$CN (50 mL) was refluxed and monitored by TLC. After completion of the reaction, the solution was cooled; solvent was evaporated under reduced pressure. The residue was poured into water (30 mL) and extracted with ethyl acetate (3×30 mL). The organic layer was washed with brine and dried over anhydrous MgSO$_4$. Filtration of MgSO$_4$ and evaporation of solvent under vacuum gave the crude product. The residue obtained was purified by using HPLC to obtain the corresponding compound 3. Yield: 34-58%.

Step B:

Aldehyde 3 (0.55 mmol), amine 4 (0.5 mmol) were dissolved in 0.6 ml MeOH, heated at 100° C. for 2 hours, then mixture was cooled, NaBH$_4$ (0.5 mmol) was added and stirred for 4 hours. The mixture was heated for 2 hours at 60° C., 3 ml of methanol and 0.2 g of C-18 chromatographic phase were added, stirred for 2 hours, filtered, evaporated and optionally dissolved in 0.5 mL of DMSO. The residue was purified using HPLC. Yield: 24-47%.

B243

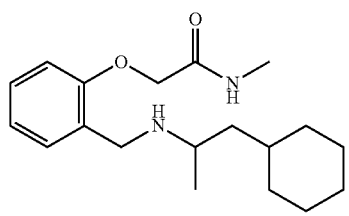

1H NMR (400 MHz, DMSO-d6) δ 8.56 (s, 1H), 7.19 (t, J=8.0 Hz, 2H), 6.93-6.84 (m, 2H), 4.51 (s, 2H), 3.78 (d, J=12.0 Hz, 1H), 3.65 (d, J=12.1 Hz, 1H), 2.71 (d, J=5.8 Hz, 2H), 2.66 (d, J=4.6 Hz, 3H), 2.54 (s, 1H), 1.67 (d, J=15.3 Hz, 5H), 1.35 (s, 1H), 1.20 (dd, J=22.0, 9.6 Hz, 2H), 1.05 (d, J=6.2 Hz, 3H), 0.86 (d, J=12.3 Hz, 2H).

B244

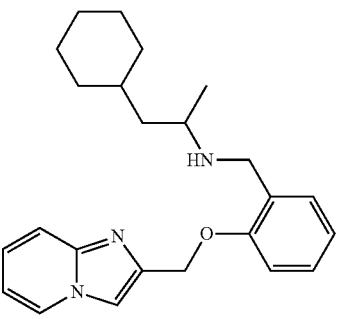

1H NMR (400 MHz, DMSO-d6) δ 8.55 (d, J=6.8 Hz, 1H), 7.98 (s, 1H), 7.51 (d, J=9.0 Hz, 1H), 7.21 (ddd, J=28.6, 15.1, 7.8 Hz, 4H), 6.88 (t, J=6.9 Hz, 2H), 5.22 (d, J=2.6 Hz, 2H), 3.73 (d, J=13.6 Hz, 1H), 3.61 (d, J=13.8 Hz, 1H), 2.54 (s, 0H), 1.71 (s, 1H), 1.50 (d, J=11.8 Hz, 4H), 1.43 (s, 1H), 1.24 (s, 2H), 1.01 (d, J=16.2 Hz, 5H), 0.91 (d, J=6.0 Hz, 2H), 0.74-0.64 (m, 2H).

B249

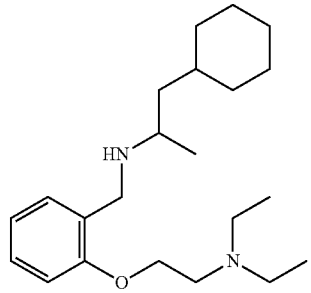

1H NMR (400 MHz, DMSO-d6) δ 7.24 (d, J=7.2 Hz, 1H), 7.17 (t, J=7.8 Hz, 11H), 6.94 (d, J=8.1 Hz, 1H), 6.86 (t, J=7.4

Hz, 1H), 4.00 (t, J=5.9 Hz, 2H), 3.71 (d, J=13.7 Hz, 1H), 3.58 (d, J=14.2 Hz, 1H), 2.79 (t, J=5.7 Hz, 2H), 2.60-2.52 (m, 4H), 1.61 (d, J=16.9 Hz, 3H), 1.56 (s, 2H), 1.49 (d, J=13.0 Hz, 1H), 1.28 (s, 2H), 1.17 (d, J=12.1 Hz, 1H), 1.12 (s, 2H), 1.07-0.92 (m, 8H), 0.81 (s, 1H), 0.80-0.71 (m, 1H).

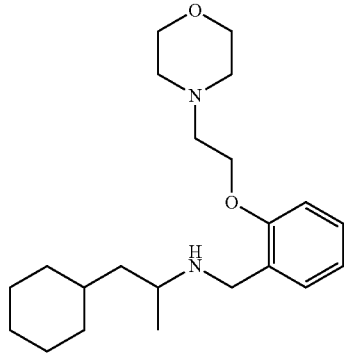

B250

1H NMR (400 MHz, DMSO-d6) δ 7.21-7.09 (m, 1H), 6.83 (s, 1H), 4.08 (t, J=5.6 Hz, 1H), 3.60 (t, J=4.7 Hz, 2H), 2.75 (t, J=5.8 Hz, 1H), 1.64 (s, 2H), 1.29 (s, 1H), 1.16 (s, 2H), 0.98 (d, J=6.1 Hz, 1H), 0.82 (s, 1H).

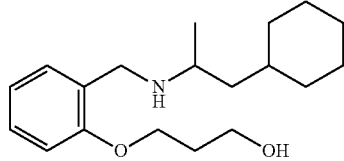

B251

1H NMR (400 MHz, DMSO-d6) δ 7.21-7.11 (m, 2H), 6.87 (d, J=8.0 Hz, 1H), 6.81 (s, 1H), 4.06 (s, 2H), 3.73 (d, J=13.4 Hz, 1H), 3.61 (s, 4H), 2.54 (s, 1H), 1.92 (s, 2H), 1.63 (s, 6H), 1.29 (s, 4H), 1.16 (s, 4H), 1.07 (s, 1H), 0.99 (d, J=6.1 Hz, 3H), 0.83 (s, 2H).

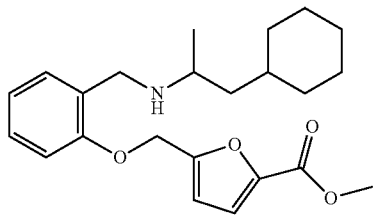

B252

1H NMR (400 MHz, DMSO-d6) δ 7.30 (dd, J=7.4, 4.9 Hz, 2H), 7.22 (t, J=7.8 Hz, 1H), 7.11 (d, J=8.2 Hz, 1H), 6.93 (t, J=7.4 Hz, 1H), 6.76 (d, J=3.5 Hz, 1H), 5.17 (d, J=3.5 Hz, 2H), 3.80 (s, 3H), 3.68 (d, J=13.8 Hz, 1H), 3.59 (d, J=13.8 Hz, 1H), 2.51 (s, 1H), 1.56 (s, 5H), 1.47 (d, J=12.7 Hz, 1H), 1.24 (s, 2H), 1.11 (q, J=10.6, 9.2 Hz, 2H), 0.91 (d, J=6.1 Hz, 3H), 0.75 (q, J=11.1 Hz, 2H).

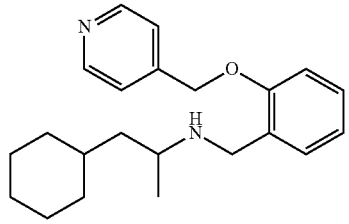

B283

1H NMR (400 MHz, DMSO-d6) δ 8.53 (d, J=5.0 Hz, 2H), 7.40 (d, J=5.4 Hz, 2H), 7.27 (d, J=7.4 Hz, 1H), 7.15 (t, J=8.2 Hz, 1H), 6.94-6.84 (m, 2H), 5.16 (s, 2H), 3.82 (d, J=13.5 Hz, 1H), 3.71 (d, J=13.5 Hz, 1H), 2.69-2.61 (m, 1H), 1.60 (q, J=14.9, 12.0 Hz, 6H), 1.28 (q, J=7.8 Hz, 3H), 1.12 (s, 5H), 1.00 (d, J=6.0 Hz, 3H), 0.86-0.75 (m, 2H).

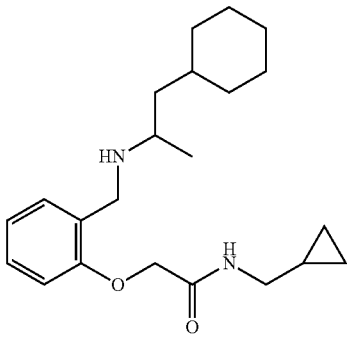

B284

1H NMR (400 MHz, Chloroform-d) δ 8.02 (s, 1H), 7.30-7.21 (m, 3H), 6.96 (t, J=7.4 Hz, 1H), 6.87 (d, J=8.2 Hz, 1H), 4.61 (s, 2H), 3.90 (d, J=12.0 Hz, 1H), 3.73 (d, J=12.0 Hz, 1H), 3.15 (q, J=5.8 Hz, 2H), 2.83-2.75 (m, 1H), 1.39 (dd, J=13.0, 6.5 Hz, 1H), 1.30 (s, 1H), 1.16 (s, 4H), 1.10 (d, J=6.1 Hz, 3H), 0.88 (s, 3H), 0.85 (d, J=2.3 Hz, 0H), 0.41 (d, J=7.7 Hz, 2H), 0.13 (d, J=5.2 Hz, 2H).

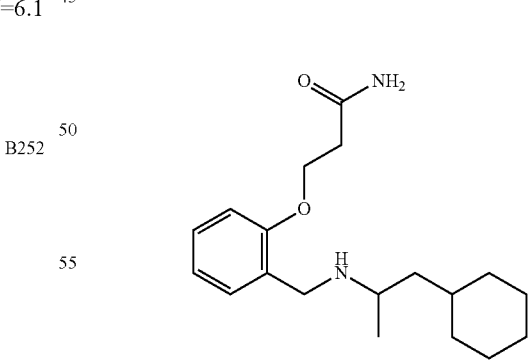

B285

1H NMR (400 MHz, Chloroform-d) δ 7.15 (t, J=7.7 Hz, 1H), 6.97 (t, J=8.5 Hz, 1H), 6.86-6.72 (m, 2H), 5.53 (s, 1H), 5.37 (s, 1H), 3.96-3.81 (m, 1H), 3.73 (d, J=14.4 Hz, 1H), 2.93 (s, 1H), 2.83 (p, J=7.0, 6.3 Hz, 2H), 2.40 (t, J=7.1 Hz, 2H), 1.67 (s, 2H), 1.61 (d, J=14.5 Hz, 4H), 1.43 (s, 2H), 1.28-1.19 (m, 2H), 1.22-1.12 (m, 4H), 1.12 (s, 1H), 1.10 (s, 1H), 1.05 (d, J=6.6 Hz, 2H), 0.87 (s, 3H).

B286

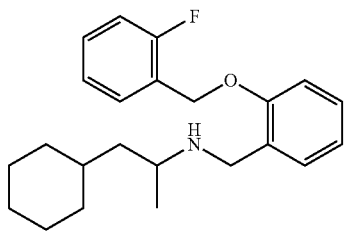

1H NMR (400 MHz, Chloroform-d) δ 7.29 (s, 1H), 7.26 (s, 1H), 7.23 (d, J=7.9 Hz, 2H), 6.99 (d, J=8.0 Hz, 4H), 5.27 (s, 4H), 3.86 (d, J=13.5 Hz, 2H), 3.74 (d, J=13.4 Hz, 2H), 2.69 (d, J=6.3 Hz, 2H), 2.57 (s, 6H), 1.35 (dd, J=12.9, 6.3 Hz, 1H), 1.28 (s, 3H), 1.15 (s, 8H), 1.12 (s, 1H), 1.05 (d, J=6.2 Hz, 6H), 0.83 (s, 6H).

B287

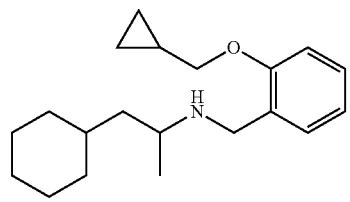

1H NMR (400 MHz, DMSO-d6) δ 7.17 (d, J=7.3 Hz, 1H), 7.11 (t, J=7.9 Hz, 1H), 6.84-6.75 (m, 2H), 3.83 (dd, J=6.8, 2.8 Hz, 2H), 3.73 (d, J=13.4 Hz, 1H), 3.60 (d, J=13.4 Hz, 1H), 1.63 (d, J=10.9 Hz, 5H), 1.56 (d, J=13.0 Hz, 1H), 1.29 (s, 6H), 1.15 (t, J=11.2 Hz, 2H), 1.08 (s, 2H), 0.99 (d, J=6.2 Hz, 3H), 0.87-0.77 (m, 2H), 0.61 (q, J=5.6 Hz, 2H), 0.37 (d, J=5.0 Hz, 2H).

B288

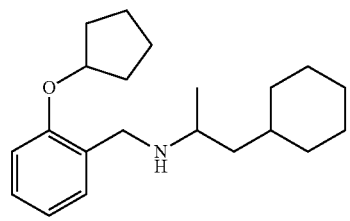

1H NMR (400 MHz, DMSO-d6) δ 7.15 (d, J=7.5 Hz, 1H), 7.10 (t, J=7.5 Hz, 1H), 6.84-6.73 (m, 2H), 4.81 (s, 1H), 3.64 (s, 1H), 3.54 (s, 1H), 2.54 (s, 0H), 1.91 (s, 2H), 1.82 (d, J=15.6 Hz, 5H), 1.64 (s, 8H), 1.25 (s, 5H), 1.15 (s, 2H), 0.97 (d, J=6.1 Hz, 3H), 0.81 (s, 2H).

B289

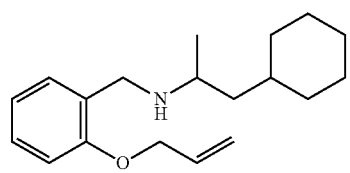

1H NMR (400 MHz, DMSO-d6) δ 7.20 (d, J=7.3 Hz, 1H), 7.13 (t, J=7.5 Hz, 1H), 6.84 (d, J=7.6 Hz, 2H), 6.06 (td, J=11.1, 5.2 Hz, 1H), 5.46-5.37 (m, 1H), 5.26 (d, J=10.4 Hz, 1H), 4.55 (d, J=4.8 Hz, 2H), 3.75 (d, J=13.6 Hz, 1H), 3.61 (d, J=13.6 Hz, 1H), 1.62 (d, J=10.9 Hz, 5H), 1.54 (s, 1H), 1.31-1.12 (m, 8H), 0.98 (d, J=6.1 Hz, 3H), 0.81 (dd, J=22.0, 11.4 Hz, 2H).

B290

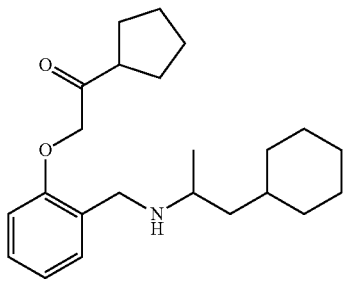

1H NMR (400 MHz, DMSO-d6) δ 7.20 (d, J=7.3 Hz, 1H), 7.13 (t, J=7.8 Hz, 1H), 6.84 (dd, J=11.9, 7.7 Hz, 2H), 4.65 (s, 2H), 3.75 (d, J=13.2 Hz, 1H), 3.63 (d, J=13.3 Hz, 1H), 3.51 (s, 2H), 3.40 (t, J=7.0 Hz, 2H), 2.61 (s, 1H), 2.54 (s, 1H), 2.02-1.94 (m, 2H), 1.86 (q, J=6.7 Hz, 2H), 1.63 (s, 6H), 1.32 (s, 2H), 1.16 (s, 5H), 1.06 (d, J=6.6 Hz, 0H), 0.98 (d, J=6.1 Hz, 3H), 0.83 (d, J=11.3 Hz, 2H).

B291

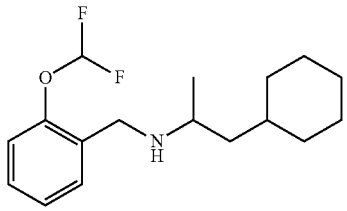

1H NMR (400 MHz, DMSO-d6) δ 7.41 (d, J=7.4 Hz, 1H), 7.24 (t, J=7.6 Hz, 1H), 7.13 (dt, J=16.6, 7.7 Hz, 2H), 6.94 (s, 0H), 3.77 (d, J=13.5 Hz, 1H), 3.67 (d, J=13.5 Hz, 1H), 2.66 (q, J=6.4 Hz, 1H), 1.64 (s, 5H), 1.33 (s, 1H), 1.25-1.18 (m, 1H), 1.16 (s, 1H), 1.05 (dd, J=30.4, 6.4 Hz, 3H), 0.84 (t, J=11.6 Hz, 2H).

B292

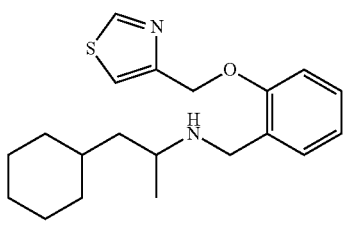

1H NMR (400 MHz, DMSO-d6) δ 8.95 (d, J=2.0 Hz, 1H), 7.54 (s, 1H), 7.23 (d, J=7.4 Hz, 1H), 7.16 (t, J=7.8 Hz, 1H), 6.99 (d, J=8.2 Hz, 1H), 6.86 (t, J=7.4 Hz, 1H), 5.24 (s, 2H), 3.78 (d, J=13.6 Hz, 1H), 3.65 (d, J=13.4 Hz, 1H), 2.62 (d, J=6.4 Hz, 1H), 1.60 (d, J=10.3 Hz, 6H), 1.53 (s, 1H), 1.27 (d, J=8.0 Hz, 2H), 1.12 (s, 4H), 1.04 (t, J=6.5 Hz, 1H), 0.97 (d, J=6.1 Hz, 3H), 0.79 (t, J=12.4 Hz, 2H).

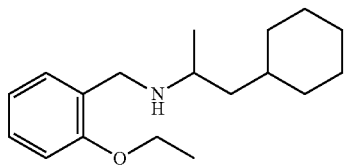
B293

1H NMR (400 MHz, DMSO-d6) δ 7.18 (d, J=7.2 Hz, 1H), 7.15-7.07 (m, 1H), 6.81 (d, J=7.7 Hz, 2H), 4.04 (q, J=7.0 Hz, 2H), 3.71 (d, J=13.5 Hz, 1H), 3.58 (d, J=13.5 Hz, 1H), 2.64-2.52 (m, 1H), 1.63 (d, J=10.8 Hz, 5H), 1.56 (d, J=13.5 Hz, 1H), 1.43 (t, J=6.9 Hz, 3H), 1.28 (d, J=6.5 Hz, 2H), 1.28-1.17 (m, 1H), 1.17-1.02 (m, 2H), 0.98 (d, J=6.1 Hz, 3H), 0.84 (d, J=12.2 Hz, 1H), 0.78 (d, J=11.9 Hz, 1H).

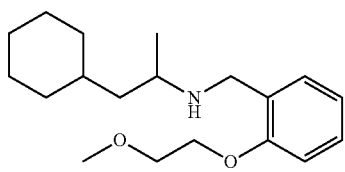
B294

1H NMR (400 MHz, DMSO-d6) δ 7.20-7.09 (m, 2H), 6.88-6.78 (m, 2H), 4.09 (q, J=3.8 Hz, 2H), 3.77-3.67 (m, 1H), 3.71 (s, 2H), 3.58 (d, J=13.5 Hz, 1H), 3.00 (s, 12H), 2.61-2.52 (m, 1H), 1.62 (d, J=11.5 Hz, 4H), 1.54 (d, J=13.4 Hz, 1H), 1.29 (s, 2H), 1.30-1.22 (m, 0H), 0.97 (d, J=6.1 Hz, 3H), 0.79 (s, 2H).

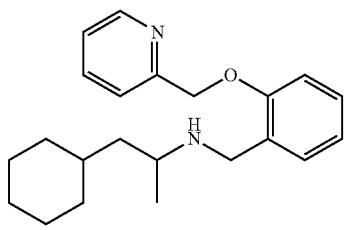
B295

1H NMR (400 MHz, DMSO-d6) δ 8.53 (d, J=4.8 Hz, 1H), 7.75 (t, J=7.6 Hz, 1H), 7.50 (d, J=7.8 Hz, 1H), 7.26 (t, J=7.1 Hz, 2H), 7.14 (t, J=7.8 Hz, 1H), 6.94-6.82 (m, 2H), 5.17 (s, 2H), 3.84 (d, J=13.5 Hz, 1H), 3.70 (d, J=13.5 Hz, 1H), 2.65 (q, J=6.3 Hz, 1H), 1.61 (s, 5H), 1.55 (s, 0H), 1.34-1.26 (m, 2H), 1.13-0.97 (m, 7H), 0.85-0.74 (m, 2H).

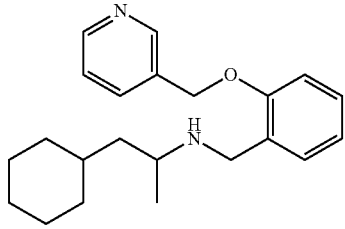
B296

1H NMR (400 MHz, DMSO-d6) δ 8.64 (s, 1H), 8.50 (d, J=4.5 Hz, 1H), 7.82 (d, J=7.9 Hz, 1H), 7.38-7.30 (m, 1H), 7.26 (d, J=7.3 Hz, 1H), 7.16 (d, J=8.1 Hz, 1H), 6.98 (d, J=8.1 Hz, 1H), 6.88 (t, J=7.4 Hz, 1H), 5.14 (s, 2H), 3.77 (d, J=13.4 Hz, 1H), 3.65 (d, J=13.3 Hz, 1H), 2.63 (d, J=7.0 Hz, 1H), 1.61 (d, J=10.6 Hz, 5H), 1.26 (d, J=9.2 Hz, 2H), 1.12 (s, 4H), 1.05 (d, J=5.5 Hz, 1H), 0.97 (d, J=6.1 Hz, 3H), 0.79 (s, 3H).

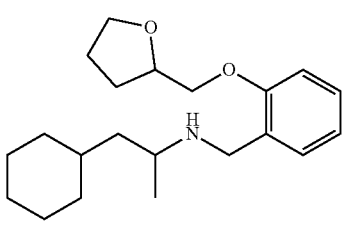
B297

1H NMR (400 MHz, DMSO-d6) δ 7.20-7.09 (m, 2H), 6.87-6.78 (m, 2H), 4.19 (q, J=6.0 Hz, 1H), 3.93 (t, J=5.7 Hz, 2H), 3.88-3.81 (m, 1H), 3.78-3.69 (m, 2H), 3.57 (d, J=13.5 Hz, 1H), 2.57 (dt, J=10.4, 5.3 Hz, 1H), 2.05 (d, J=8.4 Hz, 1H), 1.93 (dd, J=14.2, 7.1 Hz, 2H), 1.83 (ddt, J=26.4, 14.0, 6.6 Hz, 1H), 1.61 (d, J=12.3 Hz, 4H), 1.52 (d, J=13.3 Hz, 1H), 1.31-1.23 (m, 2H), 1.14 (s, 3H), 1.01 (dd, J=29.9, 6.3 Hz, 3H), 0.80 (dt, J=23.0, 11.0 Hz, 2H).

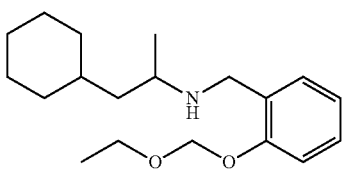
B298

1H NMR (400 MHz, DMSO-d6) δ 7.21-7.10 (m, 2H), 6.87-6.80 (m, 2H), 4.79 (t, J=5.2 Hz, 1H), 3.93 (t, J=5.7 Hz, 2H), 3.78-3.66 (m, 3H), 3.60 (q, J=10.4, 9.1 Hz, 3H), 2.59 (s, 1H), 1.61 (d, J=12.4 Hz, 4H), 1.51 (d, J=13.1 Hz, 1H), 1.26 (d, J=24.1 Hz, 4H), 1.20 (d, J=7.2 Hz, 4H), 1.14 (s, 2H), 1.05 (s, 1H), 0.98 (d, J=6.1 Hz, 2H), 0.85-0.75 (m, 1H).

B311

1H NMR (400 MHz, DMSO-d6) δ 7.23 (d, J=7.3 Hz, 1H), 7.12 (t, J=7.8 Hz, 1H), 7.02 (d, J=8.1 Hz, 1H), 6.88 (t, J=7.1 Hz, 1H), 5.21 (s, 2H), 3.71 (dd, J=9.4, 5.6 Hz, 3H), 3.61 (d, J=13.9 Hz, 1H), 2.64 (s, 1H), 2.54 (s, 1H), 1.63 (s, 5H), 1.33-1.25 (m, 1H), 1.21 (t, J=7.1 Hz, 2H), 0.99 (d, J=6.2 Hz, 3H), 0.81 (d, J=13.0 Hz, 2H).

B312

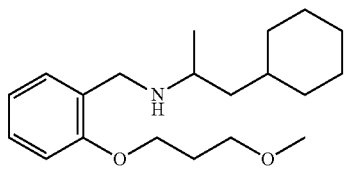

1H NMR (400 MHz, DMSO-d6) δ 7.18 (d, J=7.4 Hz, 1H), 7.11 (d, J=7.8 Hz, 1H), 6.87-6.77 (m, 2H), 4.03 (d, J=8.0 Hz, 2H), 3.72 (d, J=13.4 Hz, 1H), 3.61-3.48 (m, 3H), 3.30 (s, 3H), 2.60 (s, 2H), 2.05-1.98 (m, 2H), 1.62 (d, J=11.3 Hz, 5H), 1.54 (d, J=12.2 Hz, 1H), 1.27 (s, 3H), 1.14 (s, 4H), 0.98 (d, J=6.0 Hz, 2H).

B313

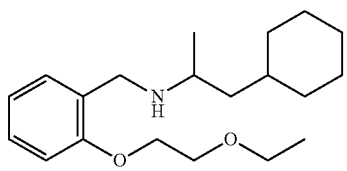

1H NMR (400 MHz, DMSO-d6) δ 7.14 (dd, J=17.4, 7.9 Hz, 2H), 6.83 (dd, J=12.1, 7.6 Hz, 2H), 4.08 (d, J=5.4 Hz, 2H), 3.77-3.70 (m, 3H), 3.61-3.50 (m, 3H), 2.52 (d, J=16.8 Hz, 2H), 1.61 (d, J=12.1 Hz, 4H), 1.52 (d, J=12.8 Hz, 1H), 1.29-1.16 (m, 3H), 1.15 (s, 1H), 0.97 (d, J=6.1 Hz, 2H), 0.82 (d, J=11.9 Hz, 1H), 0.77 (s, 1H).

B314

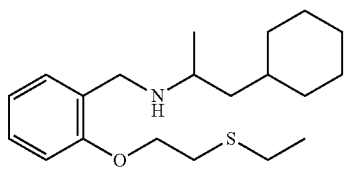

1H NMR (400 MHz, DMSO-d6) δ 7.22-7.09 (m, 2H), 6.83 (t, J=7.7 Hz, 2H), 4.12 (s, 2H), 3.72 (d, J=13.6 Hz, 1H), 3.59 (d, J=13.6 Hz, 1H), 2.89 (t, J=6.5 Hz, 2H), 2.63 (q, J=7.5 Hz, 3H), 2.54 (s, 1H), 1.63 (d, J=10.6 Hz, 5H), 1.56 (d, J=13.2 Hz, 1H), 1.28 (t, J=7.4 Hz, 3H), 1.15 (s, 2H), 0.98 (d, J=6.1 Hz, 3H), 0.81 (s, 2H).

B315

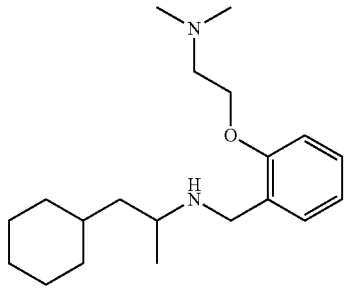

1H NMR (400 MHz, Chloroform-d) δ 7.26 (s, 1H), 7.20 (t, J=7.7 Hz, 2H), 6.94-6.81 (m, 2H), 4.10 (t, J=5.9 Hz, 2H), 3.84 (d, J=13.1 Hz, 1H), 3.71 (d, J=13.1 Hz, 1H), 2.76 (t, J=5.9 Hz, 2H), 2.68 (q, J=6.4 Hz, 1H), 2.35 (s, 6H), 1.64 (s, 5H), 1.55 (d, J=12.7 Hz, 1H), 1.36 (dt, J=13.0, 6.7 Hz, 1H), 1.16 (s, 6H), 1.05 (d, J=6.2 Hz, 3H), 0.86 (s, 1H), 0.81 (d, J=11.3 Hz, 1H).

B320

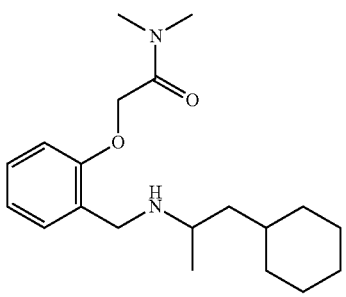

1H NMR (400 MHz, DMSO-d6) δ 7.26 (d, J=7.3 Hz, 1H), 7.15 (t, J=7.9 Hz, 1H), 6.88 (t, J=9.1 Hz, 2H), 4.89-4.76 (m, 2H), 3.74 (d, J=13.6 Hz, 1H), 3.63 (d, J=13.7 Hz, 1H), 3.00 (d, J=1.8 Hz, 3H), 2.84 (s, 3H), 2.80 (d, J=10.9 Hz, 0H), 2.55 (d, J=10.8 Hz, 2H), 1.92 (s, 1H), 1.57 (d, J=13.4 Hz, 6H), 1.31 (s, 1H), 1.11 (s, 4H), 0.95 (d, J=6.1 Hz, 2H), 0.83-0.73 (m, 2H).

B321

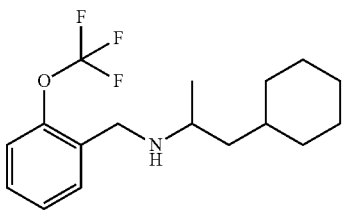

m/z 315.23.

B326

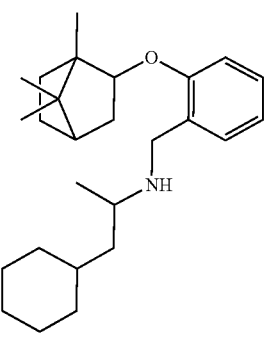

1H NMR (400 MHz, DMSO-d6) δ 7.22 (d, J=7.4 Hz, 1H), 7.14 (t, J=7.8 Hz, 1H), 6.90-6.78 (m, 2H), 4.11 (dt, J=7.3, 3.5 Hz, 1H), 3.70 (dd, J=13.7, 7.0 Hz, 1H), 3.54 (t, J=13.3 Hz, 1H), 2.59 (s, 1H), 2.56 (d, J=12.6 Hz, 1H), 2.00-1.89 (m, 1H), 1.76 (d, J=3.9 Hz, 1H), 1.70 (s, 4H), 1.57 (d, J=12.4 Hz, 7H), 1.48 (d, J=15.0 Hz, 1H), 1.28-1.20 (m, 4H), 1.15 (d, J=11.3 Hz, 1H), 1.10 (s, 1H), 1.05 (d, J=2.2 Hz, 3H), 0.99-0.92 (m, 5H), 0.86 (s, 3H), 0.77 (t, J=13.6 Hz, 1H).

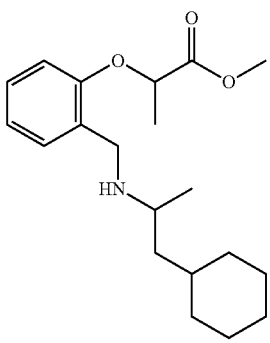

B327

1H NMR (400 MHz, DMSO-d6) δ 7.28 (s, 1H), 7.15 (t, J=7.8 Hz, 1H), 6.90 (t, J=7.4 Hz, 1H), 6.81 (dd, J=8.2, 5.4 Hz, 1H), 5.02 (q, J=6.7 Hz, 1H), 3.73 (d, J=13.5 Hz, 1H), 3.67 (d, J=3.2 Hz, 5H), 2.65-2.52 (m, 2H), 1.68 (s, 1H), 1.59 (d, J=11.1 Hz, 6H), 1.52 (dd, J=6.8, 4.6 Hz, 3H), 1.31 (s, 2H), 1.12 (s, 5H), 1.09-1.01 (m, 0H), 0.97 (dd, J=6.2, 3.2 Hz, 3H), 0.82 (s, 1H), 0.78 (d, J=12.0 Hz, 1H).

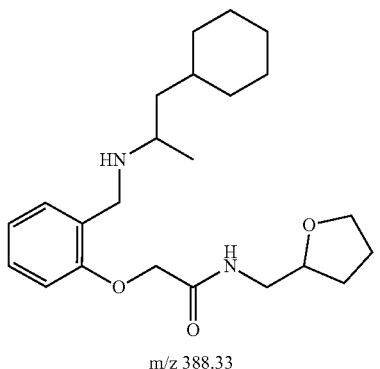

B336 m/z 388.33.

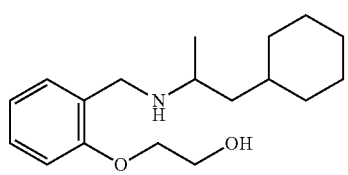

B337

1H NMR (400 MHz, Chloroform-d) δ 7.18 (d, J=7.4 Hz, 1H), 6.94 (dd, J=12.7, 7.5 Hz, 2H), 3.89 (d, J=11.0 Hz, 1H), 3.74 (s, 2H), 3.63 (d, J=10.9 Hz, 1H), 2.81 (d, J=6.9 Hz, 1H), 1.41 (dd, J=12.7, 6.2 Hz, 1H), 1.25-1.17 (m, 1H), 1.18 (s, 4H), 1.12 (d, J=6.1 Hz, 2H), 0.89 (t, J=13.5 Hz, 2H).

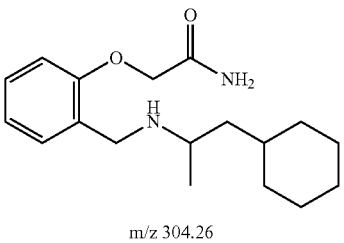

B338 m/z 304.26

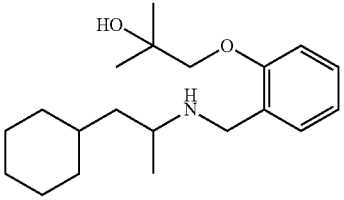

B343

1H NMR (400 MHz, Chloroform-d) δ 7.29-7.14 (m, 1H), 6.94-6.83 (m, 1H), 4.01-3.91 (m, 1H), 3.89 (s, 1H), 3.67 (d, J=11.5 Hz, 0H), 2.78 (d, J=8.7 Hz, 1H), 1.42-1.36 (m, 1H), 1.32 (d, J=13.6 Hz, 2H), 1.19 (s, 5H), 1.11 (d, J=6.1 Hz, 2H), 0.88 (d, J=12.5 Hz, 2H).

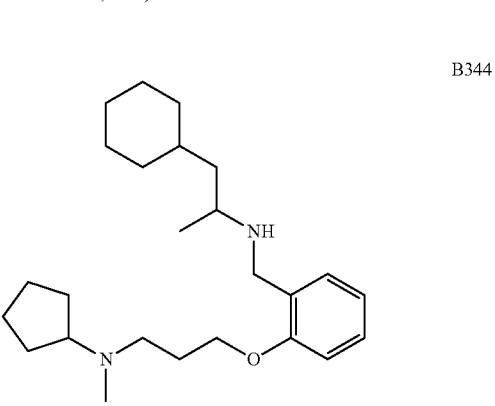

B344

1H NMR (400 MHz, DMSO-d6) δ 11.22 (s, 1H), 9.18 (s, 1H), 9.07 (s, 1H), 7.56 (d, J=7.5 Hz, 1H), 7.38 (t, J=7.8 Hz, 1H), 7.06 (d, J=8.4 Hz, 1H), 6.98 (t, J=7.5 Hz, 1H), 4.10 (dq, J=12.7, 6.1 Hz, 12H), 4.02 (s, 2H), 3.58 (q, J=8.0 Hz, 1H), 3.20 (s, 2H), 2.72 (d, J=4.9 Hz, 3H), 2.25 (s, 3H), 1.99 (s, 2H), 1.84 (s, 2H), 1.72 (s, 2H), 1.62 (t, J=14.2 Hz, 8H), 1.55 (s, 4H), 1.52 (d, J=7.8 Hz, 1H), 1.31 (d, J=6.4 Hz, 3H), 1.14 (dd, J=23.8, 13.4 Hz, 3H), 0.94 (t, J=11.5 Hz, 1H), 0.80 (d, J=11.5 Hz, 1H).

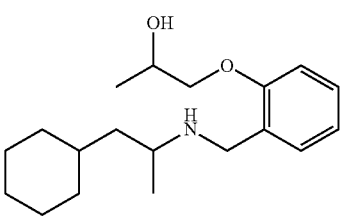

B361

1H NMR (400 MHz, DMSO-d6) δ 7.26-7.14 (m, 2H), 6.93 (d, J=8.1 Hz, 1H), 6.86 (t, J=7.3 Hz, 1H), 3.99-3.88 (m, 1H), 3.83 (q, J=5.1, 4.4 Hz, 2H), 3.73 (d, J=13.3 Hz, 1H), 3.59 (d, J=13.3 Hz, 1H), 3.33 (s, 1H), 2.57 (dd, J=13.4, 7.2 Hz, 1H), 1.58 (d, J=11.9 Hz, 5H), 1.50 (d, J=12.6 Hz, 1H), 1.27 (td, J=11.2, 10.3, 6.1 Hz, 2H), 1.16 (d, J=6.3 Hz, 3H), 1.11 (s, 4H), 0.99 (dd, J=24.3, 6.3 Hz, 3H), 0.76 (q, J=12.8, 12.2 Hz, 2H).

B362

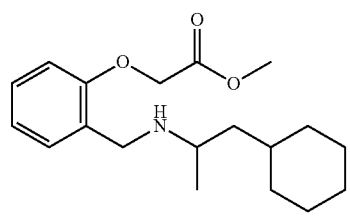

1H NMR (400 MHz, DMSO-d6) δ 7.28 (d, J=7.4 Hz, 1H), 7.16 (t, J=7.9 Hz, 1H), 6.94-6.84 (m, 2H), 4.80 (s, 2H), 3.74 (d, J=13.9 Hz, 1H), 3.69 (s, 3H), 3.64 (d, J=13.8 Hz, 1H), 2.62-2.51 (m, 1H), 1.77 (s, 1H), 1.61-1.49 (m, 5H), 1.29 (s, 2H), 1.27 (dd, J=13.7, 7.7 Hz, 0H), 1.10 (s, 3H), 0.95 (d, J=6.1 Hz, 3H), 0.79 (q, J=12.4, 11.8 Hz, 2H).

B363

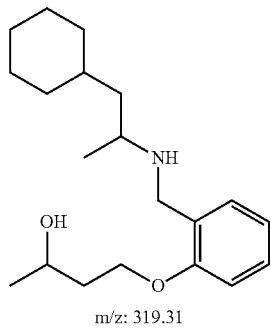

m/z: 319.31

B364

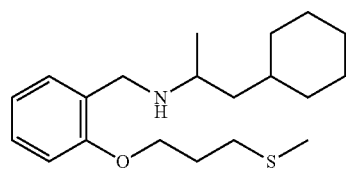

1H NMR (400 MHz, DMSO-d6) δ 7.26 (d, J=7.4 Hz, 1H), 7.18 (t, J=7.8 Hz, 1H), 6.94 (d, J=8.2 Hz, 1H), 6.87 (t, J=7.4 Hz, 1H), 4.04 (t, J=6.1 Hz, 2H), 3.71 (d, J=13.6 Hz, 1H), 3.59 (d, J=13.6 Hz, 1H), 2.69-2.52 (m, 3H), 2.07 (d, J=1.7 Hz, 2H), 2.00 (p, J=6.7 Hz, 2H), 1.58 (d, J=12.2 Hz, 5H), 1.50 (d, J=12.7 Hz, 1H), 1.26 (dd, J=13.5, 7.8 Hz, 2H), 1.21-1.11 (m, 2H), 1.05 (q, J=11.0, 6.1 Hz, 2H), 0.96 (dd, J=6.1, 1.7 Hz, 2H), 0.79 (dt, J=22.8, 11.4 Hz, 2H).

Example 8: General Compound Syntheses 8

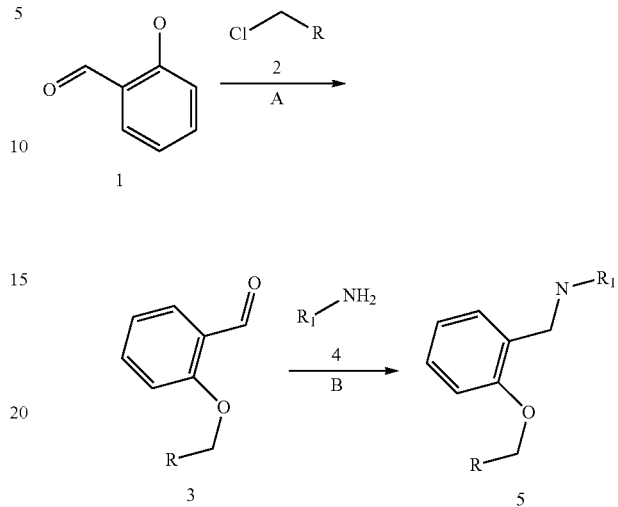

General Procedure for Preparation of Target Compounds 5:

Step A:

The solution of 2-hydroxybenzaldehyde 1 (5.0 mmol, 1.0 equiv), K$_2$CO$_3$ (7.5 mmol, 1.5 equiv), compound 2 (5.0 mmol, 1.0 equiv) in CH$_3$CN (50 mL) was refluxed and monitored by TLC. After completion of the reaction, the solution was cooled; solvent was evaporated under reduced pressure. The residue was poured into water (30 mL) and extracted with ethyl acetate (3×30 mL). The organic layer was washed with brine and dried over anhydrous MgSO$_4$. Filtration of MgSO$_4$ and evaporation of solvent under vacuum gave the crude product. The residue obtained was purified by using HPLC to obtain the corresponding compound 3. Yield: 32-53%.

Step B:

Aldehyde 3 (0.55 mmol), amine 4 (0.5 mmol) were dissolved in 0.6 ml MeOH, heated at 100° C. for 2 hours, then mixture was cooled, NaBH$_4$ (0.5 mmol) was added and stirred for 4 hours. The mixture was heated for 2 hours at 60° C., 3 ml of methanol and 0.2 g of C-18 chromatographic phase were added, stirred for 2 hours, filtered, evaporated and dissolved in 0.5 ml of DMSO, and purified using HPLC. Yield: 24-47%.

B239

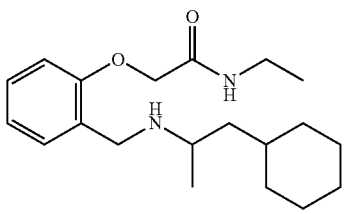

1H NMR (400 MHz, DMSO-d6) δ 8.49 (t, J=5.8 Hz, 1H), 7.26 (d, J=7.2 Hz, 1H), 7.20 (t, J=7.8 Hz, 1H), 6.96-6.87 (m, 2H), 4.52 (s, 2H), 3.77 (d, J=12.9 Hz, 1H), 3.64 (d, J=12.9 Hz, 1H), 3.12 (p, J=7.0 Hz, 2H), 2.63 (q, J=6.4 Hz, 1H), 1.82

(s, 1H), 1.61 (d, J=12.3 Hz, 5H), 1.54 (d, J=12.9 Hz, 1H), 1.33 (dd, J=11.6, 5.2 Hz, 2H), 1.14 (q, J=11.4, 9.5 Hz, 3H), 1.09-0.96 (m, 6H), 0.81 (d, J=11.0 Hz, 2H).

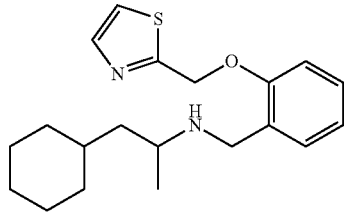

B240

1H NMR (400 MHz, DMSO-d6) δ 7.85 (d, J=3.1 Hz, 1H), 7.79 (d, J=3.3 Hz, 1H), 7.33 (d, J=7.5 Hz, 1H), 7.22 (t, J=7.8 Hz, 1H), 7.10 (d, J=8.3 Hz, 1H), 6.95 (t, J=7.3 Hz, 1H), 5.44 (d, J=2.5 Hz, 2H), 3.80 (d, J=13.8 Hz, 1H), 3.68 (d, J=14.1 Hz, 1H), 2.61-2.52 (m, 2H), 1.67 (s, 1H), 1.55 (d, J=10.9 Hz, 5H), 1.47 (s, 0H), 1.26 (q, J=7.3 Hz, 2H), 1.07 (s, 5H), 0.96 (d, J=6.1 Hz, 2H), 0.76 (s, 2H).

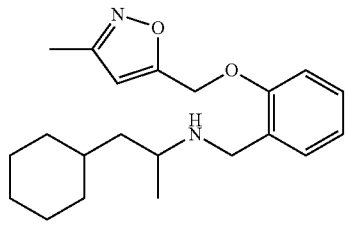

B241

1H NMR (400 MHz, DMSO-d6) δ 7.31 (d, J=7.4 Hz, 1H), 7.21 (t, J=7.9 Hz, 1H), 7.08 (d, J=8.2 Hz, 1H), 6.93 (t, J=7.5 Hz, 1H), 6.46 (s, 1H), 5.24 (d, J=2.9 Hz, 2H), 3.70 (d, J=14.0 Hz, 1H), 3.60 (d, J=13.9 Hz, 1H), 2.53 (s, 1H), 2.24 (s, 3H), 1.58 (s, 6H), 1.29-1.21 (m, 2H), 1.12 (d, J=12.5 Hz, 2H), 1.04 (s, 2H), 0.93 (d, J=6.1 Hz, 3H), 0.81-0.71 (m, 2H).

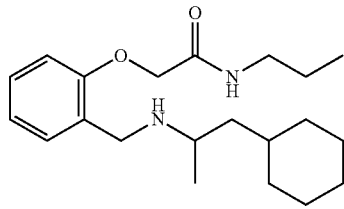

B242

1H NMR (400 MHz, DMSO-d6) δ 8.45 (s, 2H), 7.27 (d, J=7.3 Hz, 2H), 7.20 (t, J=7.9 Hz, 2H), 6.96-6.87 (m, 4H), 4.54 (s, 4H), 3.77 (d, J=12.9 Hz, 2H), 3.64 (d, J=12.8 Hz, 2H), 3.05 (q, J=6.7 Hz, 4H), 2.63 (d, J=6.4 Hz, 1H), 1.80 (s, 1H), 1.59 (s, 8H), 1.53 (s, 1H), 1.40 (d, J=7.3 Hz, 1H), 1.40-1.29 (m, 7H), 1.14 (s, 4H), 1.12 (s, 1H), 0.99 (d, J=6.1 Hz, 6H), 0.75 (t, J=7.4 Hz, 14H).

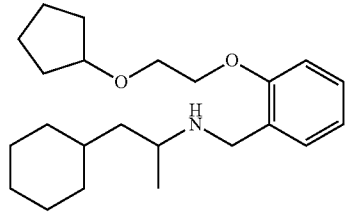

B260

1H NMR (400 MHz, DMSO-d6) δ 7.19-7.08 (m, 2H), 6.82 (t, J=8.3 Hz, 2H), 4.05 (s, 2H), 3.96 (s, 1H), 3.77-3.66 (m, 3H), 3.57 (d, J=13.8 Hz, 1H), 1.68 (s, 7H), 1.61 (d, J=11.7 Hz, 3H), 1.52 (s, 3H), 1.29-1.16 (m, 2H), 1.14 (s, 2H), 0.96 (d, J=6.1 Hz, 3H), 0.85-0.71 (m, 2H).

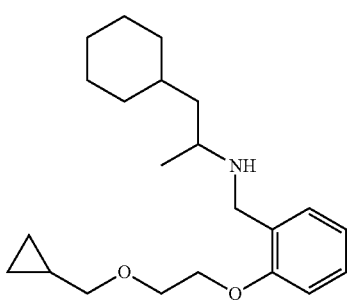

B261

1H NMR (400 MHz, DMSO-d6) δ 7.20-7.09 (m, 2H), 6.83 (dd, J=13.2, 7.4 Hz, 2H), 4.12-4.05 (m, 2H), 3.80-3.70 (m, 3H), 3.57 (d, J=13.6 Hz, 1H), 3.34 (d, J=6.7 Hz, 2H), 2.57 (dd, J=14.1, 7.7 Hz, 1H), 1.61 (d, J=11.8 Hz, 4H), 1.52 (d, J=13.2 Hz, 1H), 1.29 (s, 1H), 1.30-1.16 (m, 1H), 1.14 (s, 4H), 1.04 (d, J=6.6 Hz, 1H), 0.97 (d, J=6.1 Hz, 3H), 0.86-0.72 (m, 2H), 0.49 (t, J=6.4 Hz, 2H), 0.20 (d, J=5.1 Hz, 2H).

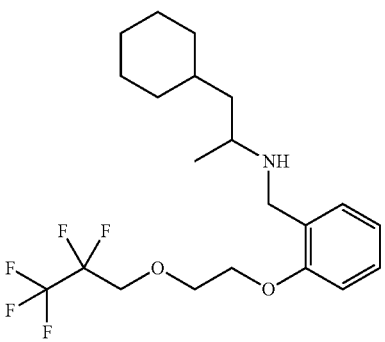

B262

1H NMR (400 MHz, DMSO-d6) δ 7.21 (d, J=7.5 Hz, 2H), 7.13 (d, J=8.1 Hz, 1H), 6.86 (d, J=7.9 Hz, 4H), 4.12 (d, J=13.6 Hz, 4H), 3.99 (t, J=4.5 Hz, 3H), 3.73 (d, J=13.6 Hz, 2H), 3.60 (d, J=13.7 Hz, 2H), 2.60 (d, J=5.7 Hz, 1H), 2.54 (s, 1H), 1.62 (d, J=10.6 Hz, 9H), 1.53 (s, 1H), 1.29 (s, 5H), 1.15 (s, 9H), 1.06 (s, 1H), 0.97 (d, J=6.1 Hz, 5H), 0.86-0.75 (m, 4H).

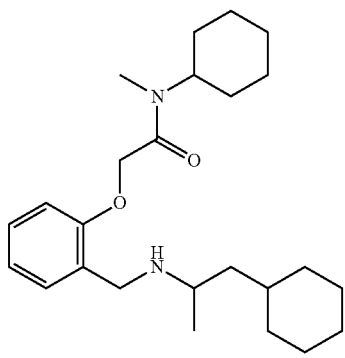

B263

1H NMR (400 MHz, DMSO-d6) δ 7.25 (t, J=8.9 Hz, 1H), 7.15 (s, 2H), 6.90 (dd, J=16.3, 8.2 Hz, 3H), 4.86-4.71 (m, 2H), 4.19 (s, 1H), 3.73 (d, J=13.8 Hz, 1H), 3.62 (d, J=13.4 Hz, 2H), 3.18 (s, 1H), 2.84 (s, 2H), 1.93 (s, 1H), 1.75 (d, J=12.6 Hz, 2H), 1.57 (s, 9H), 1.47 (s, 3H), 1.44 (d, J=13.6 Hz, 1H), 1.30 (s, 5H), 1.10 (s, 6H), 1.03 (s, 1H), 0.95 (d, J=6.1 Hz, 3H), 0.77 (s, 3H).

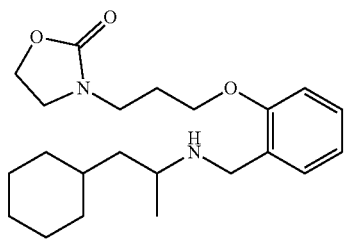

B264

1H NMR (400 MHz, DMSO-d6) δ 7.26 (d, J=7.3 Hz, 1H), 7.18 (t, J=7.7 Hz, 1H), 6.93 (d, J=8.1 Hz, 1H), 6.87 (t, J=7.4 Hz, 1H), 4.25 (t, J=8.0 Hz, 2H), 3.99 (t, J=6.2 Hz, 2H), 3.73 (d, J=13.7 Hz, 1H), 3.61 (d, J=13.8 Hz, 1H), 3.55 (t, J=7.9 Hz, 2H), 2.61-2.50 (m, 1H), 1.96 (q, J=6.7 Hz, 2H), 1.62-1.48 (m, 6H), 1.29 (s, 2H), 1.11 (td, J=22.0, 19.4, 8.9 Hz, 4H), 0.96 (d, J=6.1 Hz, 3H), 0.78 (s, 2H).

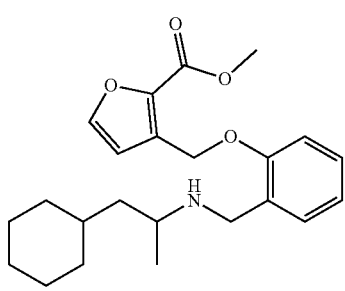

B265

1H NMR (400 MHz, DMSO-d6) δ 7.96 (s, 1H), 7.30 (d, J=7.4 Hz, 1H), 7.20 (t, J=7.8 Hz, 1H), 7.00 (d, J=8.1 Hz, 1H), 6.91 (t, J=7.3 Hz, 1H), 6.79 (d, J=1.7 Hz, 1H), 5.29 (s, 2H), 3.84 (s, 3H), 3.76 (d, J=13.8 Hz, 1H), 3.63 (d, J=13.8 Hz, 1H), 2.59-2.47 (m, 1H), 1.56 (s, 5H), 1.23 (d, J=9.7 Hz, 2H), 1.07 (s, 4H), 1.05-0.97 (m, 0H), 0.93 (d, J=6.1 Hz, 2H), 0.76 (d, J=13.7 Hz, 2H).

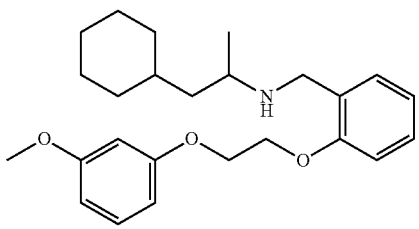

B266

1H NMR (400 MHz, DMSO-d6) δ 7.28-7.19 (m, 2H), 7.18 (d, J=8.0 Hz, 1H), 7.01 (d, J=8.2 Hz, 1H), 6.89 (t, J=7.4 Hz, 1H), 6.60-6.50 (m, 3H), 4.31 (d, J=2.4 Hz, 4H), 3.57 (d, J=13.9 Hz, 1H), 3.33 (s, 2H), 2.52 (d, J=17.3 Hz, 1H), 1.65 (s, 1H), 1.53 (s, 4H), 1.41 (d, J=13.1 Hz, 1H), 1.23 (s, 2H), 1.11-1.04 (m, 1H), 1.04 (s, 1H), 0.90 (d, J=6.1 Hz, 3H), 0.71 (dt, J=21.5, 11.1 Hz, 2H).

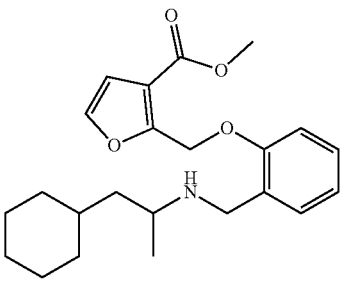

B267

1H NMR (400 MHz, DMSO-d6) δ 7.83 (d, J=2.0 Hz, 1H), 7.28 (d, J=7.3 Hz, 1H), 7.21 (t, J=7.8 Hz, 1H), 7.09 (d, J=8.2 Hz, 1H), 6.92 (t, J=7.4 Hz, 1H), 6.81 (d, J=2.0 Hz, 1H), 5.42-5.30 (m, 2H), 3.78 (s, 3H), 3.65 (d, J=13.7 Hz, 1H), 3.55 (d, J=13.8 Hz, 1H), 2.74 (s, 1H), 2.53 (d, J=7.0 Hz, 1H), 1.56 (d, J=9.1 Hz, 6H), 1.48 (d, J=13.3 Hz, 1H), 1.24 (s, 2H), 1.23-1.11 (m, 1H), 1.09 (d, J=9.0 Hz, 1H), 0.89 (d, J=6.2 Hz, 3H), 0.77 (s, 1H), 0.73 (d, J=11.7 Hz, 1H).

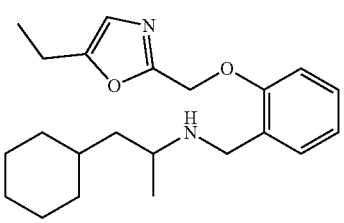

B268

1H NMR (400 MHz, DMSO-d6) δ 7.29 (d, J=7.3 Hz, 1H), 7.21 (t, J=7.9 Hz, 1H), 7.10 (d, J=8.2 Hz, 1H), 6.97-6.87 (m, 2H), 5.15 (d, J=2.7 Hz, 2H), 3.70 (d, J=13.8 Hz, 1H), 3.59 (d, J=14.0 Hz, 1H), 2.66 (q, J=7.6 Hz, 2H), 2.54 (s, 1H), 1.66 (s, 1H), 1.57 (s, 5H), 1.48 (d, J=12.4 Hz, 1H), 1.27 (s, 2H), 1.18 (t, J=7.5 Hz, 3H), 1.10 (s, 1H), 1.09-0.97 (m, 1H), 0.92 (d, J=6.1 Hz, 3H), 0.75 (t, J=15.1 Hz, 2H).

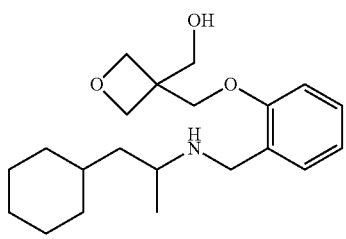

B269

1H NMR (400 MHz, DMSO-d6) δ 7.24-7.12 (m, 2H), 6.93 (d, J=8.0 Hz, 1H), 6.85 (t, J=7.3 Hz, 1H), 4.81 (s, 1H), 4.46 (d, J=5.9 Hz, 2H), 4.40 (d, J=6.0 Hz, 2H), 4.13 (s, 2H), 3.73 (d, J=15.8 Hz, 4H), 3.60 (d, J=13.3 Hz, 1H), 2.62 (s, 2H), 2.54 (s, 1H), 1.63 (s, 6H), 1.56 (d, J=12.5 Hz, 1H), 1.29 (s, 3H), 1.16 (s, 5H), 1.06 (s, 1H), 0.98 (d, J=6.1 Hz, 3H), 0.82 (s, 3H).

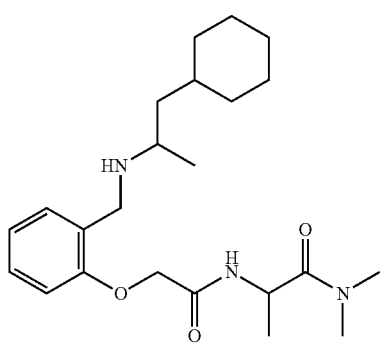

B270

1H NMR (400 MHz, Chloroform-d) δ 8.21 (d, J=10.2 Hz, 1H), 7.31-7.17 (m, 2H), 6.96 (t, J=7.4 Hz, 1H), 6.82 (d, J=8.2 Hz, 1H), 4.94 (d, J=5.8 Hz, 1H), 4.56 (s, 2H), 3.94 (dd, J=13.1, 3.1 Hz, 1H), 3.82 (dd, J=12.9, 4.1 Hz, 1H), 3.62 (s, 1H), 2.99 (d, J=2.3 Hz, 3H), 2.92 (d, J=2.1 Hz, 3H), 2.80 (d, J=7.2 Hz, 1H), 1.69-1.61 (m, 4H), 1.58 (s, 1H), 1.44-1.35 (m, 1H), 1.32 (d, J=6.8 Hz, 2H), 1.16 (s, 6H), 1.13 (dd, J=16.7, 8.8 Hz, 3H), 1.09 (s, 1H), 0.83 (t, J=12.5 Hz, 2H).

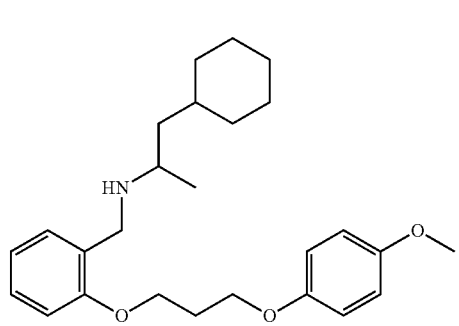

B271

1H NMR (400 MHz, Chloroform-d) δ 7.29-7.17 (m, 2H), 6.94-6.79 (m, 6H), 4.16 (dt, J=22.9, 6.0 Hz, 4H), 3.85 (d, J=13.1 Hz, 1H), 3.76 (s, 3H), 3.70 (d, J=13.1 Hz, 1H), 2.66 (q, J=6.4 Hz, 1H), 2.28 (q, J=6.1 Hz, 2H), 1.50 (d, J=12.9 Hz, 1H), 1.38-1.20 (m, 2H), 1.13 (s, 5H), 1.03 (d, J=6.2 Hz, 3H), 0.81 (q, J=13.3, 12.8 Hz, 2H).

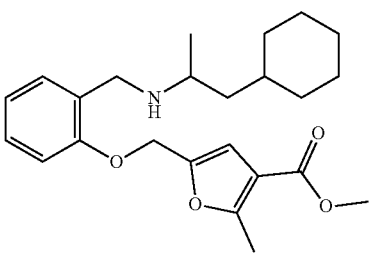

B272

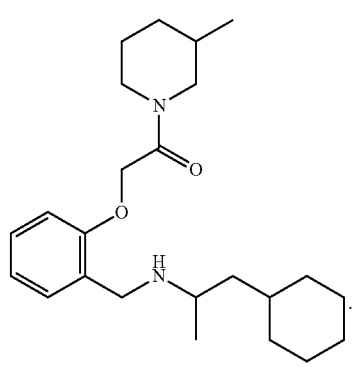

B273

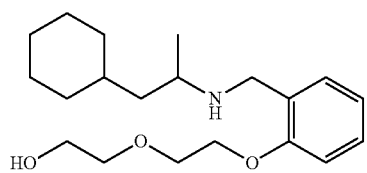

B274

1H NMR (400 MHz, DMSO-d6) δ 7.21-7.10 (m, 2H), 6.90-6.79 (m, 2H), 4.10 (p, J=5.6 Hz, 2H), 3.80 (t, J=4.8 Hz, 2H), 3.75 (d, J=13.9 Hz, 1H), 3.02 (s, 8H), 2.56 (d, J=17.3 Hz, 1H), 1.62 (d, J=12.2 Hz, 5H), 1.51 (d, J=13.1 Hz, 1H), 1.27 (d, J=8.3 Hz, 3H), 1.23-0.95 (m, 6H), 0.80 (dd, J=21.9, 11.4 Hz, 2H).

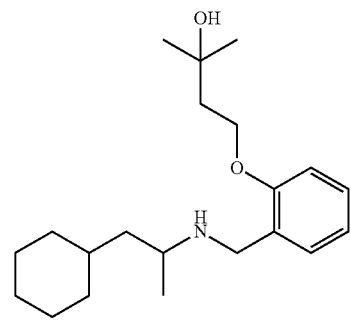

B275

1H NMR (400 MHz, DMSO-d6) δ 7.20-7.09 (m, 2H), 6.87 (d, J=8.2 Hz, 1H), 6.80 (t, J=7.4 Hz, 1H), 4.10 (q, J=10.4, 6.9 Hz, 3H), 3.70 (d, J=13.4 Hz, 1H), 3.56 (d, J=13.3 Hz, 11H), 2.64-2.52 (m, 1H), 1.89 (t, J=6.9 Hz, 2H), 1.63 (d, J=10.5 Hz, 5H), 1.55 (s, 1H), 1.30 (s, 3H), 1.27 (d, J=6.4 Hz, 0H), 1.20 (s, 6H), 1.15 (d, J=7.5 Hz, 1H), 0.97 (d, J=6.1 Hz, 3H), 0.81 (t, J=15.8 Hz, 2H).

B276

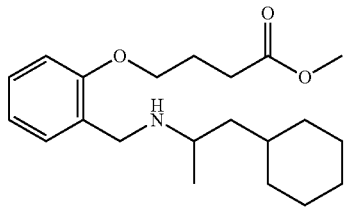

1H NMR (400 MHz, DMSO-d6) δ 7.19 (d, J=7.5 Hz, 11H), 7.13 (t, J=7.7 Hz, 1H), 6.82 (t, J=8.4 Hz, 2H), 4.01 (t, J=6.2 Hz, 2H), 3.71 (d, J=13.5 Hz, 1H), 3.64 (s, 3H), 3.59 (d, J=13.4 Hz, 1H), 2.54 (s, 11H), 2.49 (s, 1H), 2.11-2.03 (m, 2H), 1.63 (d, J=10.3 Hz, 5H), 1.56 (d, J=13.0 Hz, 1H), 1.17 (d, J=13.8 Hz, 1H), 1.07 (d, J=6.8 Hz, 1H), 0.99 (d, J=6.1 Hz, 3H), 0.81 (s, 2H).

B277

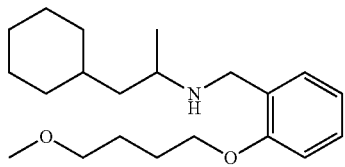

1H NMR (400 MHz, DMSO-d6) δ 7.17 (s, 1H), 7.12 (s, 1H), 6.82 (d, J=8.2 Hz, 2H), 3.98 (s, 2H), 3.72 (d, J=13.7 Hz, 1H), 3.58 (d, J=13.0 Hz, 1H), 3.39 (s, 2H), 3.27 (s, 3H), 2.60 (s, 1H), 1.84 (s, 2H), 1.72 (s, 1H), 1.63 (s, 7H), 1.28 (s, 3H), 1.15 (s, 4H), 1.06 (s, 1H), 0.98 (d, J=5.9 Hz, 3H), 0.81 (s, 2H).

B278

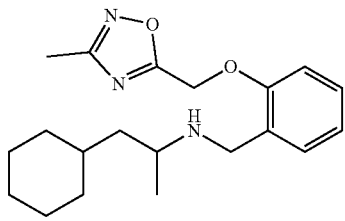

1H NMR (400 MHz, DMSO-d6) δ 7.33 (d, J=7.4 Hz, 1H), 7.21 (t, J=7.8 Hz, 1H), 7.05 (d, J=8.2 Hz, 1H), 6.96 (t, J=7.3 Hz, 1H), 5.49 (s, 2H), 3.81-3.70 (m, 1H), 3.64 (d, J=14.0 Hz, 1H), 2.36 (s, 3H), 1.69 (s, 1H), 1.58 (s, 5H), 1.52 (d, J=17.4 Hz, 1H), 1.29 (s, 2H), 1.26 (d, J=6.5 Hz, 0H), 1.08 (dd, J=19.4, 9.7 Hz, 4H), 1.02 (t, J=5.9 Hz, 1H), 0.95 (d, J=6.1 Hz, 3H), 0.81 (d, J=12.6 Hz, 1H), 0.75 (d, J=11.9 Hz, 1H).

B279

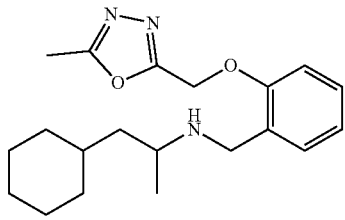

m/z 343.27

B280

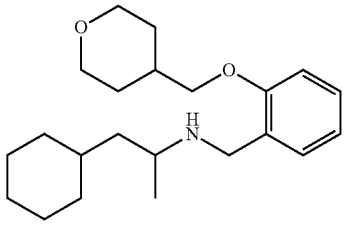

1H NMR (400 MHz, Chloroform-d) δ 8.27 (s, 1H), 7.29-7.18 (m, 3H), 6.95 (t, J=7.5 Hz, 1H), 6.84 (d, J=8.1 Hz, 1H), 4.59 (s, 2H), 3.85 (d, J=11.9 Hz, 1H), 3.70 (d, J=11.8 Hz, 1H), 2.80 (d, J=6.6 Hz, 1H), 2.64 (s, 1H), 1.42 (dd, J=13.3, 6.7 Hz, 1H), 1.19 (s, 7H), 1.11 (d, J=6.2 Hz, 3H), 0.88 (d, J=12.2 Hz, 3H), 0.74 (d, J=6.6 Hz, 2H), 0.43 (s, 2H).

B281

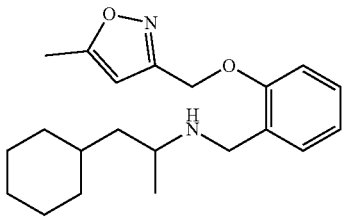

1H NMR (400 MHz, DMSO-d6) δ 7.19 (d, J=7.2 Hz, 1H), 7.12 (t, J=7.8 Hz, 1H), 6.83 (d, J=7.7 Hz, 2H), 3.95-3.87 (m, 2H), 3.82 (dd, J=6.4, 2.8 Hz, 2H), 3.72 (d, J=13.4 Hz, 1H), 3.58 (d, J=13.4 Hz, 1H), 3.36 (t, J=11.3 Hz, 2H), 2.61 (d, J=6.2 Hz, 1H), 2.05 (s, 1H), 1.73 (d, J=13.2 Hz, 2H), 1.63 (d, J=11.2 Hz, 5H), 1.54 (d, J=12.7 Hz, 1H), 1.44 (dt, J=12.5, 6.7 Hz, 1H), 1.27 (s, 3H), 1.15 (t, J=10.9 Hz, 2H), 0.98 (d, J=6.2 Hz, 3H), 0.81 (s, 2H).

B282 m/z 342.28

B316

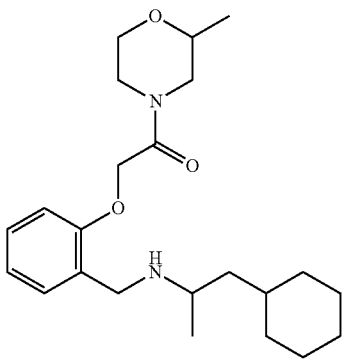

1H NMR (400 MHz, DMSO-d6) δ 7.26 (d, J=7.3 Hz, 2H), 7.16 (t, J=7.8 Hz, 2H), 6.90 (s, 3H), 6.87 (d, J=7.5 Hz, 1H), 4.89 (d, J=11.3 Hz, 2H), 4.78 (t, J=14.5 Hz, 2H), 4.19 (s,

0H), 4.10 (s, 1H), 3.79 (d, J=13.2 Hz, 3H), 3.73 (d, J=13.7 Hz, 3H), 3.62 (d, J=13.6 Hz, 2H), 3.45 (d, J=10.9 Hz, 1H), 3.14 (s, 8H), 2.81 (s, 1H), 2.69 (s, 1H), 2.55 (d, J=12.8 Hz, 1H), 2.40 (s, 7H), 1.89 (s, 2H), 1.59 (s, 7H), 1.09 (d, J=6.2 Hz, 7H), 0.95 (d, J=6.1 Hz, 5H), 0.77 (s, 5H).

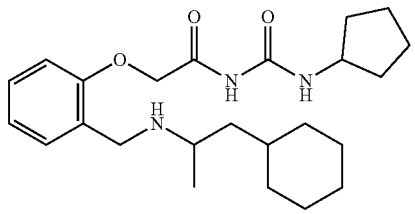

B317

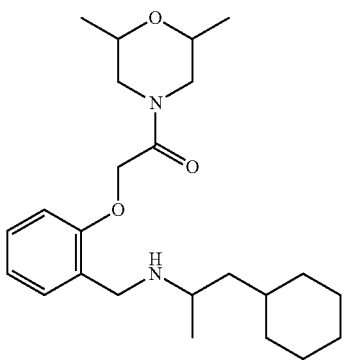

B333

1H NMR (400 MHz, DMSO-d6) δ 8.12 (s, 1H), 7.27 (d, J=7.4 Hz, 1H), 7.20 (t, J=8.0 Hz, 1H), 6.95-6.84 (m, 2H), 4.77 (d, J=3.5 Hz, 2H), 3.98 (q, J=6.8 Hz, 1H), 3.74 (d, J=13.2 Hz, 1H), 3.62 (d, J=13.3 Hz, 1H), 2.63 (s, 1H), 1.85 (dd, J=12.5, 6.2 Hz, 2H), 1.61-1.49 (m, 9H), 1.38 (s, 2H), 1.30 (s, 2H), 1.12 (d, J=12.3 Hz, 1H), 1.08 (s, 4H), 0.98 (d, J=6.2 Hz, 2H), 0.79 (d, J=16.2 Hz, 2H).

1H NMR (400 MHz, Chloroform-d) δ 7.24 (dd, J=30.2, 8.7 Hz, 2H), 6.96 (t, J=7.5 Hz, 1H), 6.88 (d, J=8.2 Hz, 1H), 4.73 (d, J=3.5 Hz, 2H), 4.40 (d, J=13.2 Hz, 1H), 3.82 (d, J=11.8 Hz, 2H), 3.79-3.70 (m, 1H), 3.51 (s, 2H), 2.84 (t, J=11.8 Hz, 1H), 2.71 (d, J=6.4 Hz, 1H), 2.38 (t, J=11.9 Hz, 1H), 1.36 (dd, J=13.1, 6.6 Hz, 1H), 1.28 (s, 2H), 1.17 (dd, J=14.3, 6.2 Hz, 9H), 1.06 (d, J=6.2 Hz, 3H), 0.84 (d, J=11.8 Hz, 2H).

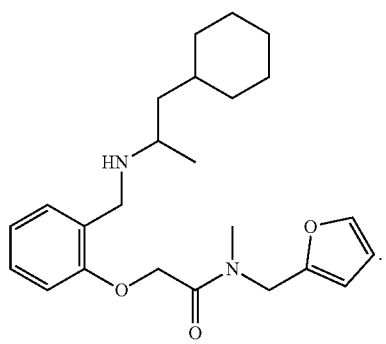

B318

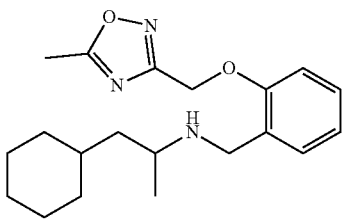

B334

1H NMR (400 MHz, Chloroform-d) δ 7.24 (dt, J=15.5, 5.9 Hz, 2H), 6.95 (dd, J=8.0, 5.4 Hz, 2H), 5.18 (d, J=2.1 Hz, 2H), 3.86 (d, J=13.2 Hz, 1H), 3.75 (d, J=13.2 Hz, 1H), 2.68 (q, J=6.4 Hz, 1H), 2.61 (s, 3H), 1.82 (s, 1H), 1.55 (d, J=13.3 Hz, 1H), 1.37 (dt, J=12.8, 6.5 Hz, 1H), 1.30 (s, 1H), 1.17-1.10 (m, 4H), 1.04 (d, J=6.2 Hz, 3H), 0.82 (s, 3H).

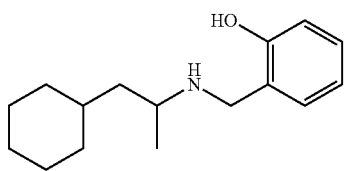

B319

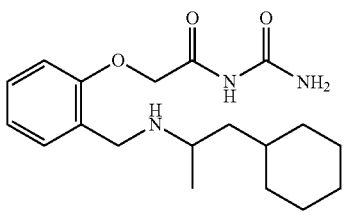

B335

1H NMR (400 MHz, Chloroform-d) δ 7.25 (d, J=8.1 Hz, 3H), 6.96 (t, J=7.4 Hz, 1H), 6.85 (d, J=8.2 Hz, 1H), 5.72 (s, 1H), 5.00 (s, 11H), 4.21 (s, 2H), 4.20-4.15 (m, 1H), 3.87 (dd, J=13.3, 6.7 Hz, 1H), 3.80 (s, 2H), 3.72 (dd, J=13.5, 8.4 Hz, 1H), 3.66 (s, 2H), 2.69 (q, J=6.4 Hz, 1H), 1.36 (s, 1H), 1.25 (s, 3H), 1.16 (d, J=12.3 Hz, 5H), 1.06 (d, J=6.1 Hz, 3H), 0.87-0.80 (m, 2H).

1H NMR (400 MHz, Chloroform-d) δ 8.12 (s, 1H), 7.30-7.23 (m, 1H), 7.21 (d, J=7.4 Hz, 1H), 6.97 (t, J=7.5 Hz, 1H), 6.87 (d, J=8.1 Hz, 1H), 5.11 (s, 2H), 4.74 (s, 2H), 3.84 (d, J=11.9 Hz, 1H), 3.76 (d, J=11.8 Hz, 1H), 2.86 (q, J=6.6 Hz, 1H), 1.49 (dt, J=13.5, 6.8 Hz, 1H), 1.26 (s, 1H), 1.12 (p, J=7.1 Hz, 7H), 0.84 (d, J=11.7 Hz, 3H).

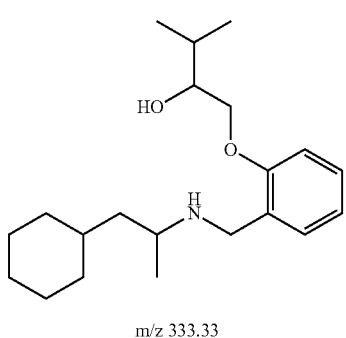

B342 m/z 333.33

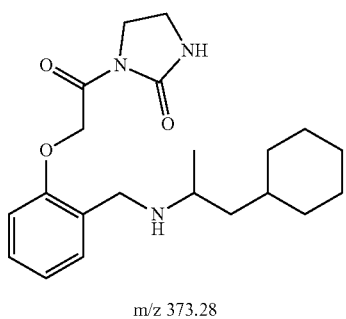

B347 m/z 373.28

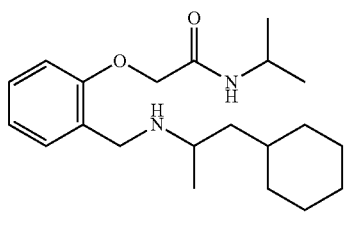

m/z 346.32

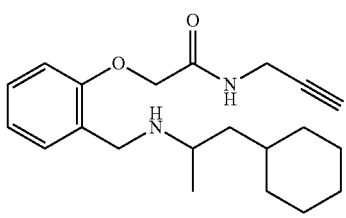

B359

1H NMR (400 MHz, Chloroform-d) δ 7.27 (q, J=14.2, 11.0 Hz, 4H), 6.96 (t, J=7.4 Hz, 1H), 6.88 (d, J=8.3 Hz, 1H), 4.65 (s, 2H), 4.00 (d, J=14.6 Hz, 3H), 3.83 (d, J=12.0 Hz, 1H), 2.96 (s, 1H), 2.13 (s, 1H), 1.52 (s, 1H), 1.30 (s, 2H), 1.19 (d, J=6.1 Hz, 4H), 0.94-0.83 (m, 2H).

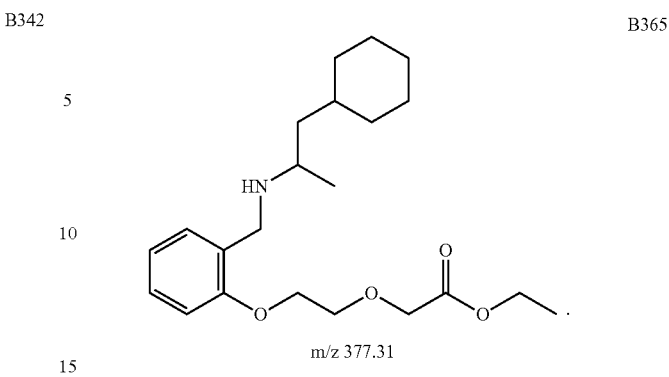

B365 m/z 377.31

Example 9: General Compound Syntheses 9

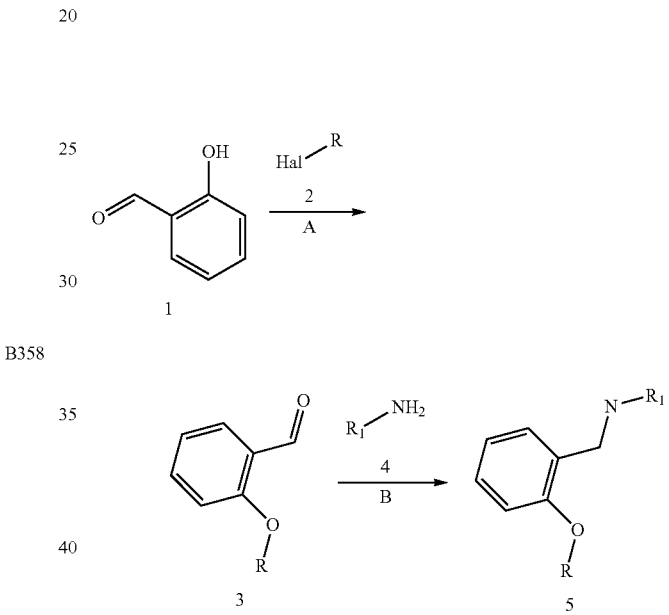

Step A:

A solution of 2-hydroxybenzaldehyde 1 (5.0 mmol, 1.0 equiv), $K_2CO_3$ (7.5 mmol, 1.5 equiv), compound 2 (5.0 mmol, 1.0 equiv) in $CH_3CN$ (50 mL) was refluxed and monitored by TLC. After completion of the reaction, the solution was cooled; solvent was evaporated under reduced pressure. The residue was poured into water (30 mL) and extracted with ethyl acetate (3×30 mL). The organic layer was washed with brine and dried over anhydrous $MgSO_4$. Filtration of $MgSO_4$ and evaporation of solvent under vacuum gave the crude product. The residue obtained was purified by using HPLC to obtain the corresponding compound 3. Yield: 29-53%.

Step B:

Aldehyde 3 (0.55 mmol), amine 4 (0.5 mmol) were dissolved in 0.6 ml MeOH, heated at 100° C. for 2 hours, then mixture was cooled, $NaBH_4$ (0.5 mmol) was added and stirred for 4 hours. The mixture was heated for 2 hours at 60° C., 3 ml of methanol and 0.2 g of C-18 chromatographic phase were added, stirred for 2 hours, filtered, evaporated. The residue was purified using HPLC. Yield: 31-48%.

B245

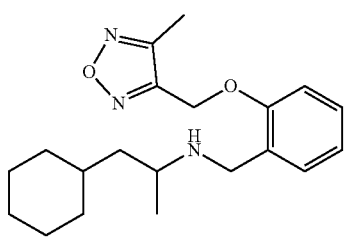

1H NMR (400 MHz, DMSO-d6) δ 7.33 (d, J=7.4 Hz, 1H), 7.23 (t, J=7.8 Hz, 1H), 7.12 (d, J=8.1 Hz, 1H), 6.96 (t, J=7.3 Hz, 1H), 5.40 (s, 2H), 3.70 (d, J=13.8 Hz, 1H), 3.60 (d, J=14.0 Hz, 1H), 2.54 (s, 1H), 2.45 (d, J=1.9 Hz, 3H), 1.57 (s, 5H), 1.48 (s, 1H), 1.28-1.20 (m, 2H), 1.09 (s, 3H), 0.92 (d, J=6.1 Hz, 3H), 0.75 (t, J=11.8 Hz, 2H).

B246

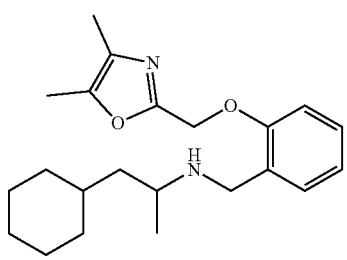

1H NMR (400 MHz, DMSO-d6) δ 7.29 (d, J=7.4 Hz, 1H), 7.20 (t, J=7.9 Hz, 1H), 7.09 (d, J=8.3 Hz, 1H), 6.92 (t, J=7.3 Hz, 1H), 5.09 (d, J=2.1 Hz, 2H), 3.69 (d, J=13.9 Hz, 1H), 3.58 (d, J=13.9 Hz, 1H), 2.58-2.47 (m, 2H), 2.23 (s, 3H), 2.02 (s, 3H), 1.57 (s, 5H), 1.49 (d, J=12.9 Hz, 1H), 1.30-1.21 (m, 2H), 1.10 (t, J=11.3 Hz, 2H), 1.02 (q, J=6.7, 6.2 Hz, 1H), 0.93 (d, J=6.1 Hz, 3H), 0.75 (s, 2H).

B247

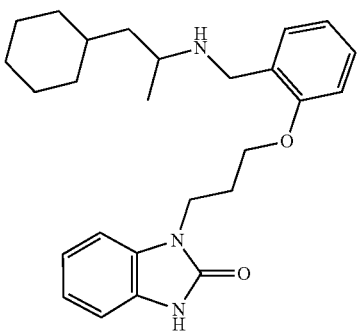

1H NMR (400 MHz, DMSO-d6) δ 7.27 (d, J=7.2 Hz, 1H), 7.16 (t, J=7.7 Hz, 1H), 7.12-7.06 (m, 1H), 6.96 (d, J=8.0 Hz, 3H), 6.87 (t, J=7.0 Hz, 2H), 3.99 (q, J=7.4, 7.0 Hz, 4H), 3.73 (d, J=13.7 Hz, 1H), 3.61 (d, J=13.6 Hz, 1H), 2.62-2.52 (m, 1H), 2.14-2.07 (m, 2H), 1.52 (q, J=16.7, 13.9 Hz, 6H), 1.27 (t, J=8.1 Hz, 2H), 1.06 (d, J=12.0 Hz, 4H), 0.96 (d, J=6.1 Hz, 3H), 0.75 (s, 2H).

B248

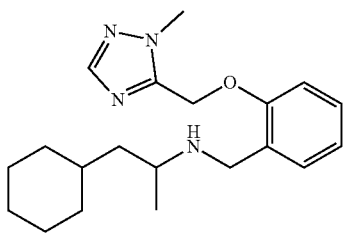

1H NMR (400 MHz, DMSO-d6) δ 7.94 (s, 1H), 7.34-7.28 (m, 1H), 7.25-7.17 (m, 1H), 7.13 (d, J=8.2 Hz, 1H), 6.94 (t, J=7.3 Hz, 1H), 5.31 (s, 2H), 3.99 (s, 1H), 3.92 (s, 3H), 3.69 (d, J=13.7 Hz, 1H), 3.59 (d, J=14.1 Hz, 1H), 1.58 (s, 7H), 1.26 (s, 2H), 1.19-0.97 (m, 3H), 0.92 (d, J=6.1 Hz, 3H), 0.81-0.70 (m, 2H).

B299

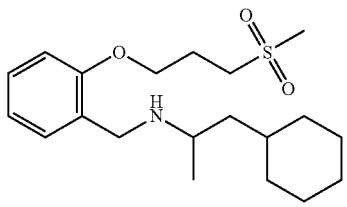

1H NMR (400 MHz, DMSO-d6) δ 7.22 (d, J=7.3 Hz, 1H), 7.15 (t, J=7.8 Hz, 1H), 6.90-6.80 (m, 2H), 4.11 (t, J=6.2 Hz, 2H), 3.75 (d, J=13.6 Hz, 1H), 3.61 (d, J=13.5 Hz, 1H), 3.26 (t, J=7.7 Hz, 2H), 2.63 (q, J=6.3 Hz, 1H), 2.50 (s, 2H), 2.24 (t, J=7.6 Hz, 2H), 1.65 (d, J=11.0 Hz, 4H), 1.59 (s, 1H), 1.34-1.20 (m, 3H), 1.16 (s, 4H), 1.15-1.03 (m, 1H), 1.00 (d, J=6.1 Hz, 3H), 0.88-0.77 (m, 2H).

B300

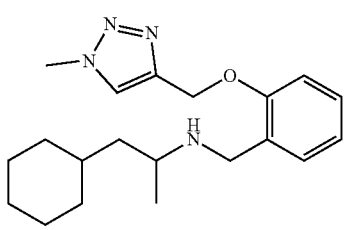

1H NMR (400 MHz, Chloroform-d) δ 7.59 (s, 1H), 7.28-7.19 (m, 3H), 7.02-6.90 (m, 2H), 5.26 (s, 2H), 4.11 (s, 3H), 3.86 (d, J=13.2 Hz, 1H), 3.72 (d, J=13.4 Hz, 11H), 2.66 (d, J=7.1 Hz, 11H), 1.50 (d, J=12.9 Hz, 11H), 1.32 (dd, J=13.0, 6.6 Hz, 1H), 1.17-1.07 (m, 3H), 1.03 (d, J=6.1 Hz, 3H), 0.85-0.75 (m, 2H).

B301

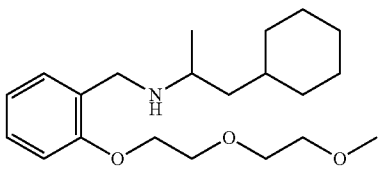

1H NMR (400 MHz, DMSO-d6) δ 7.21-7.09 (m, 2H), 6.88-6.78 (m, 2H), 4.13-4.06 (m, 2H), 3.80 (t, J=4.8 Hz,

2H), 3.73 (d, J=13.5 Hz, 1H), 3.63 (t, J=4.8 Hz, 2H), 3.58 (d, J=13.3 Hz, 1H), 3.48 (t, J=4.8 Hz, 2H), 3.30 (s, 3H), 2.56 (d, J=17.9 Hz, 1H), 1.62 (d, J=11.6 Hz, 4H), 1.53 (d, J=12.9 Hz, 1H), 1.28 (s, 11H), 1.15 (s, 5H), 1.01 (dd, J=30.7, 6.3 Hz, 3H), 0.80 (q, J=10.3 Hz, 2H).

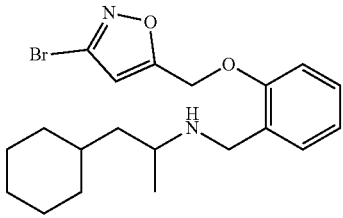

B302

1H NMR (400 MHz, DMSO-d6) δ 7.32 (d, J=7.4 Hz, 1H), 7.22 (t, J=7.9 Hz, 1H), 7.08 (d, J=8.2 Hz, 11H), 6.96 (d, J=6.5 Hz, 2H), 5.33 (s, 2H), 3.70 (d, J=13.9 Hz, 1H), 3.61 (d, J=13.7 Hz, 1H), 2.55 (d, J=8.9 Hz, 1H), 2.49 (s, 11H), 1.57 (s, 6H), 1.49 (s, 0H), 1.26 (s, 2H), 1.10 (s, 3H), 1.09-0.98 (m, 11H), 0.93 (d, J=6.1 Hz, 3H), 0.81-0.71 (m, 2H).

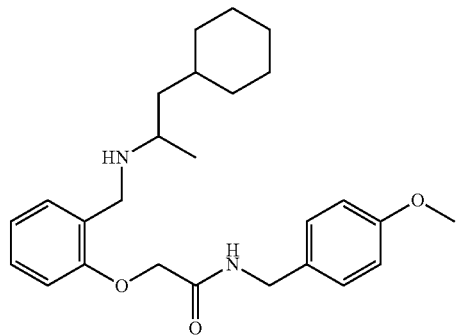

B303

1H NMR (400 MHz, Chloroform-d) δ 9.12 (s, 1H), 7.29 (d, J=7.8 Hz, 0H), 7.16 (d, J=6.9 Hz, 1H), 7.01-6.92 (m, 2H), 6.84 (d, J=8.2 Hz, 2H), 6.70 (d, J=8.1 Hz, 2H), 4.73 (d, J=4.3 Hz, 2H), 4.42 (dd, J=15.1, 5.8 Hz, 1H), 4.32 (dd, J=14.9, 5.3 Hz, 1H), 3.78 (d, J=15.2 Hz, 5H), 3.60 (d, J=11.6 Hz, 1H), 2.68-2.60 (m, 1H), 1.55 (t, J=14.7 Hz, 2H), 1.13 (d, J=11.1 Hz, 7H), 0.95 (d, J=6.3 Hz, 3H), 0.80 (d, J=13.1 Hz, 2H).

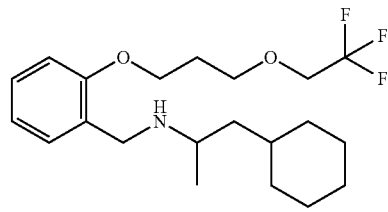

B304

1H NMR (400 MHz, DMSO-d6) δ 7.20 (d, J=7.5 Hz, 1H), 7.12 (d, J=8.0 Hz, 1H), 6.88-6.78 (m, 2H), 4.06 (t, J=6.1 Hz, 2H), 3.92 (q, J=9.2 Hz, 2H), 3.80 (t, J=6.2 Hz, 2H), 3.72 (d, J=13.7 Hz, 1H), 3.59 (d, J=13.1 Hz, 1H), 2.61 (s, 1H), 2.08 (t, J=6.3 Hz, 2H), 1.63 (d, J=10.5 Hz, 5H), 1.54 (s, 1H), 1.28 (s, 3H), 1.20 (d, J=12.1 Hz, 0H), 1.15 (s, 3H), 1.06 (s, 1H), 0.98 (d, J=6.1 Hz, 2H), 0.82 (s, 2H).

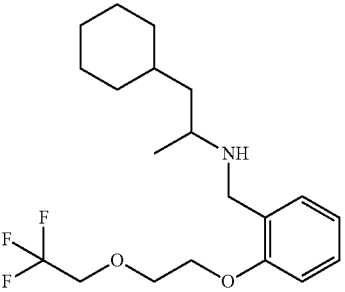

B305

1H NMR (400 MHz, DMSO-d6) δ 6.86 (d, J=9.7 Hz, 1H), 4.14 (s, 1H), 4.04 (d, J=8.8 Hz, 0H), 3.99 (s, 1H), 2.54 (s, 1H), 1.63 (s, 2H), 1.15 (s, 2H), 0.98 (d, J=5.7 Hz, 1H), 0.80 (s, 1H).

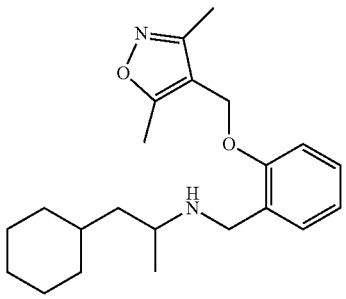

B306

1H NMR (400 MHz, DMSO-d6) δ 7.30 (d, J=7.4 Hz, 1H), 7.22 (t, J=7.4 Hz, 1H), 7.09 (d, J=8.2 Hz, 1H), 6.92 (t, J=7.4 Hz, 1H), 4.92 (s, 2H), 3.65 (d, J=13.8 Hz, 1H), 3.56 (d, J=13.9 Hz, 1H), 2.55 (d, J=6.8 Hz, 1H), 2.40 (s, 3H), 2.30 (s, 3H), 2.23 (s, 3H), 1.57 (s, 4H), 1.50 (d, J=13.8 Hz, 3H), 1.22 (dd, J=14.2, 7.5 Hz, 2H), 1.11 (d, J=12.3 Hz, 3H), 1.04-0.96 (m, 1H), 0.91 (d, J=6.1 Hz, 3H), 0.80-0.70 (m, 2H).

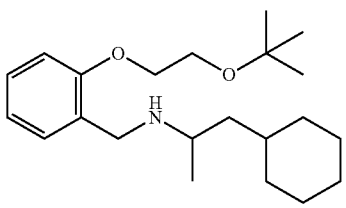

B307

1H NMR (400 MHz, DMSO-d6) δ 7.18-7.08 (m, 3H), 6.81 (dd, J=12.9, 7.4 Hz, 3H), 4.03 (hept, J=4.9 Hz, 3H), 3.74 (d, J=13.7 Hz, 1H), 3.67 (t, J=5.0 Hz, 3H), 3.56 (d, J=13.7 Hz, 2H), 2.55 (d, J=5.5 Hz, 1H), 1.60 (d, J=12.9 Hz, 7H), 1.47 (d, J=13.8 Hz, 3H), 1.28 (s, 2H), 1.25 (d, J=6.5 Hz, 1H), 1.21 (s, 12H), 1.12 (d, J=11.3 Hz, 1H), 1.06-0.93 (m, 4H), 0.77 (dd, J=28.9, 12.5 Hz, 3H).

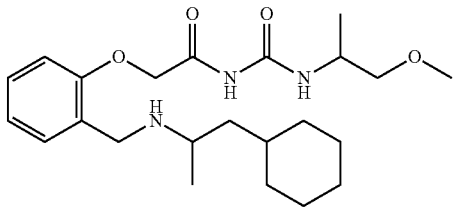

B308

1H NMR (400 MHz, DMSO-d6) δ 8.18 (s, 1H), 7.27 (d, J=7.4 Hz, 1H), 7.20 (t, J=7.7 Hz, 1H), 6.91 (dt, J=17.1, 8.1 Hz, 2H), 4.78 (d, J=3.5 Hz, 2H), 3.90 (d, J=8.7 Hz, 1H), 3.75 (d, J=13.2 Hz, 1H), 3.63 (d, J=13.3 Hz, 1H), 3.30 (s, 1H), 2.64 (s, 1H), 2.54 (s, 0H), 1.58 (s, 6H), 1.34 (d, J=7.2 Hz, 1H), 1.30 (s, 2H), 1.09 (p, J=14.1, 13.5 Hz, 8H), 0.98 (d, J=6.0 Hz, 3H), 0.81 (s, 1H), 0.76 (d, J=12.7 Hz, 1H).

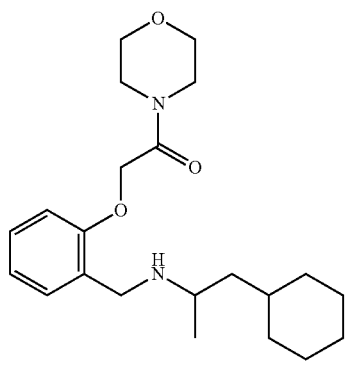

B309

1H NMR (400 MHz, DMSO-d6) δ 7.26 (d, J=7.3 Hz, 1H), 7.16 (t, J=7.7 Hz, 1H), 6.94-6.84 (m, 2H), 4.91-4.78 (m, 2H), 3.74 (d, J=13.8 Hz, 1H), 3.66-3.53 (m, 5H), 3.46 (s, 4H), 2.60-2.52 (m, 1H), 1.90 (s, 1H), 1.59 (s, 5H), 1.30 (s, 2H), 1.12 (s, 5H), 0.95 (d, J=6.0 Hz, 3H), 0.83-0.72 (m, 2H).

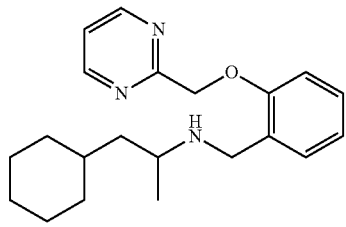

B310

1H NMR (400 MHz, DMSO-d6) δ 10.55 (s, 1H), 8.82 (d, J=4.9 Hz, 2H), 7.43 (t, J=5.0 Hz, 1H), 7.09 (t, J=8.5 Hz, 2H), 6.71 (t, J=7.2 Hz, 2H), 3.96 (d, J=16.3 Hz, 1H), 3.82-3.69 (m, 2H), 3.64 (d, J=13.8 Hz, 1H), 2.78 (q, J=6.9 Hz, 1H), 1.50 (t, J=13.8 Hz, 3H), 1.38 (dd, J=13.5, 6.8 Hz, 1H), 1.26 (d, J=12.1 Hz, 3H), 1.02 (s, 4H), 0.98 (d, J=6.6 Hz, 3H), 0.68 (d, J=10.9 Hz, 1H), 0.57 (d, J=12.3 Hz, 1H).

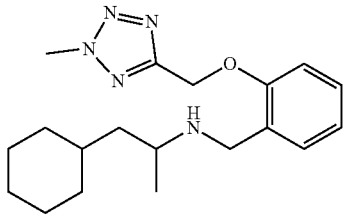

B322

1H NMR (400 MHz, Chloroform-d) δ 7.25 (d, J=11.7 Hz, 3H), 7.02 (d, J=8.2 Hz, 1H), 6.95 (t, J=7.4 Hz, 1H), 5.36 (s, 2H), 4.37 (s, 3H), 3.87 (d, J=13.2 Hz, 1H), 3.75 (d, J=13.3 Hz, 1H), 2.68 (d, J=7.1 Hz, 1H), 1.54 (d, J=13.0 Hz, 1H), 1.36 (dd, J=12.9, 6.6 Hz, 1H), 1.28 (s, 1H), 1.13 (s, 5H), 1.04 (d, J=6.1 Hz, 3H), 0.82 (s, 2H).

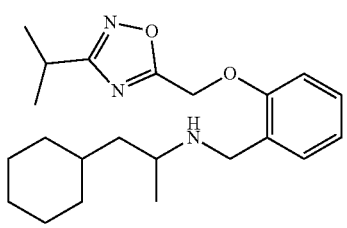

B323

1H NMR (400 MHz, DMSO-d6) δ 7.32 (d, J=7.4 Hz, 1H), 7.22 (t, J=7.7 Hz, 1H), 7.06 (d, J=8.3 Hz, 1H), 6.96 (t, J=7.4 Hz, 1H), 5.49 (d, J=2.5 Hz, 2H), 3.75 (d, J=13.8 Hz, 1H), 3.64 (d, J=13.8 Hz, 1H), 3.09 (p, J=7.0 Hz, 1H), 2.60-2.52 (m, 1H), 1.57 (s, 4H), 1.26 (d, J=7.0 Hz, 7H), 1.09 (s, 3H), 1.01 (s, 1H), 0.95 (d, J=6.1 Hz, 3H), 0.76 (t, J=12.8 Hz, 2H).

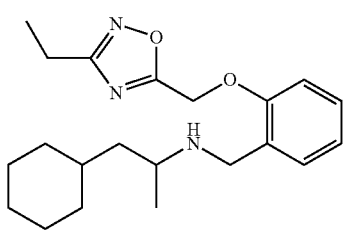

B324

1H NMR (400 MHz, DMSO-d6) δ 7.33 (d, J=7.4 Hz, 1H), 7.22 (t, J=7.8 Hz, 1H), 7.06 (d, J=8.2 Hz, 1H), 6.96 (t, J=7.3 Hz, 1H), 5.49 (s, 2H), 3.75 (d, J=13.8 Hz, 1H), 3.64 (d, J=13.9 Hz, 1H), 2.74 (q, J=7.6 Hz, 2H), 2.59-2.52 (m, 1H), 1.70 (s, 1H), 1.57 (s, 5H), 1.51 (d, J=15.5 Hz, 1H), 1.28 (s, 2H), 1.23 (t, J=7.6 Hz, 3H), 1.07 (dt, J=17.1, 8.6 Hz, 2H), 0.94 (d, J=6.1 Hz, 3H), 0.78 (q, J=11.6 Hz, 2H).

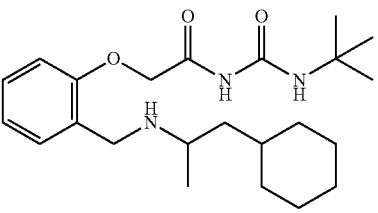

B325

1H NMR (400 MHz, DMSO-d6) δ 8.16 (s, 1H), 7.27 (d, J=7.3 Hz, 1H), 7.20 (t, J=7.9 Hz, 1H), 6.95-6.85 (m, 2H), 4.76 (d, J=3.3 Hz, 2H), 3.74 (d, J=13.1 Hz, 1H), 3.62 (d, J=13.2 Hz, 1H), 2.62 (d, J=6.8 Hz, 1H), 2.33 (s, 1H), 1.58 (s, 4H), 1.51 (s, 1H), 1.28 (s, 9H), 1.22-0.95 (m, 6H), 0.77 (s, 2H).

Example 10: General Compound Syntheses 10

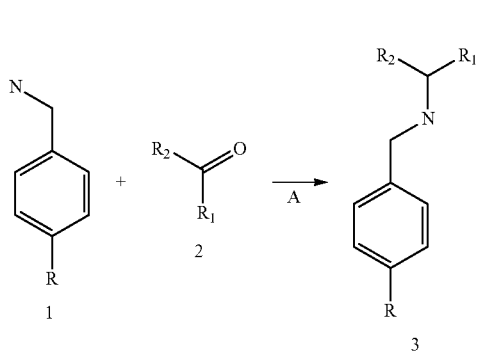

Amine 1 (0.5 mmol) and compound 2 (0.55 mmol) were dissolved in 0.6 ml MeOH, heated at 100° C. for 2 hours, then mixture was cooled, NaBH$_4$ (0.5 mmol) was added and stirred for 4 hours. The mixture was heated for 2 hours at 60° C., 3 ml of methanol and 0.2 g of C-18 chromatographic phase were added, stirred for 2 hours, filtered, evaporated. The residue was purified using HPLC. Yield: 23-58%.

The following compounds were synthesized according to the Scheme shown in Example 10 above:

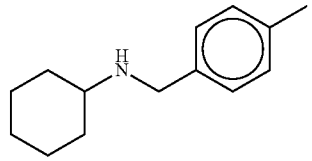
B134

1H NMR (400 MHz, DMSO-d6) δ 7.28 (dd, J=14.3, 7.3 Hz, 4H), 7.17 (t, J=7.1 Hz, 1H), 3.78 (dd, J=13.4, 3.2 Hz, 1H), 3.65 (d, J=13.1 Hz, 1H), 2.43 (p, J=5.9 Hz, 1H), 1.71 (q, J=14.0, 13.6 Hz, 5H), 1.38-1.22 (m, 1H), 1.29 (s, 1H), 1.26-1.17 (m, 1H), 1.17 (s, 1H), 1.04 (d, J=14.0 Hz, 1H), 0.98 (d, J=6.6 Hz, 3H).

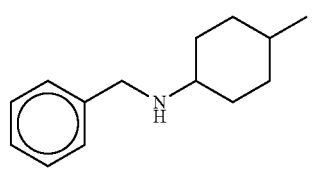
B135

1H NMR (400 MHz, DMSO-d6) δ 7.36-7.26 (m, 4H), 7.21 (td, J=6.5, 6.0, 2.5 Hz, 1H), 3.67 (s, 2H), 2.49 (s, 1H), 2.46-2.36 (m, 1H), 1.98 (pd, J=7.6, 4.1 Hz, 2H), 1.91-1.79 (m, 1H), 1.82-1.72 (m, 1H), 1.69-1.56 (m, 2H).

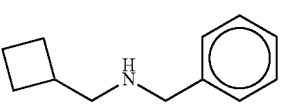
B136

1H NMR (400 MHz, DMSO-d6) δ 7.37-7.26 (m, 4H), 7.22 (d, J=6.8 Hz, 1H), 3.68 (s, 2H), 2.29 (d, J=6.7 Hz, 2H), 1.93 (s, 1H), 1.68 (dp, J=13.3, 6.7 Hz, 1H), 0.87 (d, J=6.6 Hz, 5H).

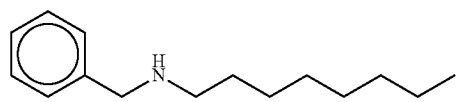
B137

1H NMR (400 MHz, DMSO-d6) δ 9.17 (s, 2H), 7.46 (d, J=7.8 Hz, 2H), 7.23 (d, J=7.6 Hz, 2H), 4.08 (s, 2H), 4.08 (d, J=12.1 Hz, 0H), 2.90 (s, 1H), 2.32 (s, 3H), 2.14-2.06 (m, 2H), 1.76 (d, J=12.8 Hz, 2H), 1.59 (d, J=12.0 Hz, 1H), 1.40 (s, 1H), 1.36 (d, J=10.8 Hz, 1H), 1.22 (d, J=12.5 Hz, 1H), 1.12 (dd, J=28.3, 13.2 Hz, 2H).

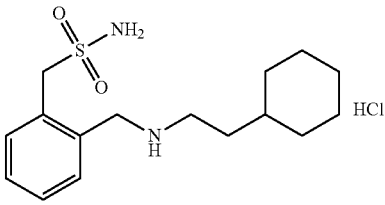
B142

1H NMR (400 MHz, DMSO-d6) δ 7.29 (dt, J=15.0, 7.5 Hz, 6H), 7.19 (t, J=7.1 Hz, 2H), 3.16 (s, 4H), 2.70-2.64 (m, 2H), 2.55 (s, 1H), 1.60 (dd, J=13.2, 5.4 Hz, 3H), 1.49 (s, 4H), 1.47 (t, J=4.3 Hz, 1H), 1.45-1.32 (m, 5H), 0.91 (d, J=6.6 Hz, 4H).

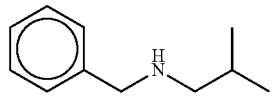
B150

1H NMR (400 MHz, DMSO-d6) δ 7.31-7.20 (m, 3H), 7.16 (t, J=7.0 Hz, 1H), 3.70 (s, 1H), 1.44 (q, J=7.0 Hz, 1H), 1.28 (s, 9H), 0.90 (t, J=6.6 Hz, 2H), 0.82 (s, 1H).

B380

1H NMR (400 MHz, DMSO-d6) δ 8.95 (s, 2H), 7.69-7.62 (m, 1H), 7.47-7.41 (m, 1H), 7.42 (s, 2H), 6.99 (s, 2H), 4.55 (s, 2H), 4.24 (t, J=5.9 Hz, 2H), 3.00 (s, 2H), 1.65 (d, J=11.9 Hz, 5H), 1.55 (q, J=7.3 Hz, 3H), 1.30 (s, 1H), 1.16 (p, J=12.0 Hz, 3H), 0.89 (q, J=11.8 Hz, 2H). Yield: 39%.

B385

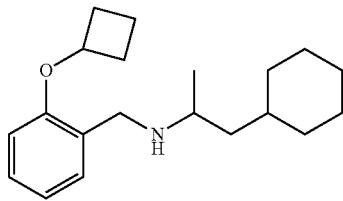

1H NMR (400 MHz, Chloroform-d) δ 7.24-7.12 (m, 2H), 6.87 (t, J=7.4 Hz, 1H), 6.69 (d, J=8.1 Hz, 1H), 4.66 (p, J=7.2 Hz, 1H), 3.83 (d, J=13.0 Hz, 1H), 3.70 (d, J=13.0 Hz, 1H), 2.69 (h, J=6.4 Hz, 1H), 2.47 (dtt, J=12.3, 6.7, 2.7 Hz, 2H), 2.19 (d, J=10.1 Hz, 1H), 2.14 (d, J=10.2 Hz, 1H), 1.87 (q, J=10.0 Hz, 2H), 1.79-1.61 (m, 5H), 1.60 (s, 1H), 1.42-1.22 (m, 2H), 1.19 (s, 3H), 1.18-1.08 (m, 2H), 1.05 (d, J=6.2 Hz, 3H), 0.86 (s, 1H), 0.81 (dd, J=12.1, 4.0 Hz, 1H). Yield: 32%.

B386

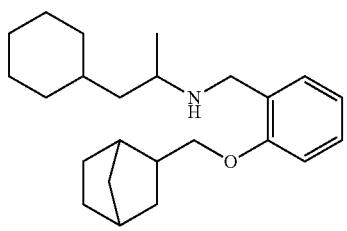

1H NMR (400 MHz, DMSO-d6) δ 7.26-7.12 (m, 3H), 7.00-6.81 (m, 3H), 3.97 (q, J=7.8 Hz, 1H), 3.82 (q, J=8.6 Hz, 1H), 3.70 (dt, J=14.5, 6.4 Hz, 3H), 3.59 (d, J=11.8 Hz, 2H), 2.56 (p, J=6.0 Hz, 2H), 2.32 (s, 1H), 2.27 (s, 1H), 2.25-2.17 (m, 2H), 1.89 (p, J=7.4 Hz, 1H), 1.73 (t, J=12.1 Hz, 1H), 1.57 (d, J=11.6 Hz, 8H), 1.53-1.43 (m, 5H), 1.37 (d, J=9.9 Hz, 2H), 1.28 (dt, J=17.8, 7.4 Hz, 5H), 1.17 (s, 2H), 1.11 (t, J=11.6 Hz, 5H), 1.04 (d, J=7.9 Hz, 2H), 0.95 (d, J=5.7 Hz, 4H), 0.80 (d, J=10.1 Hz, 2H), 0.75 (s, 2H). Yield 29%.

B387

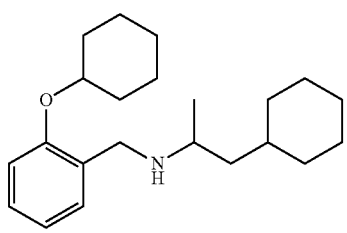

1H NMR (400 MHz, DMSO-d6) δ 7.24 (d, J=7.4 Hz, 1H), 7.15 (t, J=7.8 Hz, 1H), 6.96 (d, J=8.2 Hz, 1H), 6.83 (t, J=7.4 Hz, 1H), 4.43-4.34 (m, 1H), 3.69 (d, J=13.4 Hz, 1H), 3.58 (d, J=13.4 Hz, 1H), 2.58 (q, J=6.3 Hz, 1H), 1.87 (d, J=11.8 Hz, 2H), 1.69 (s, 2H), 1.58 (d, J=10.5 Hz, 6H), 1.50 (t, J=8.4 Hz, 4H), 1.35 (dt, J=20.6, 10.4 Hz, 4H), 1.30-1.21 (m, 1H), 1.11 (td, J=22.2, 19.3, 9.7 Hz, 4H), 0.96 (d, J=6.1 Hz, 3H), 0.83 (dd, J=18.2, 7.7 Hz, 1H), 0.75 (d, J=11.4 Hz, 1H). Yield 39%.

Example 11: General Compound Syntheses 11

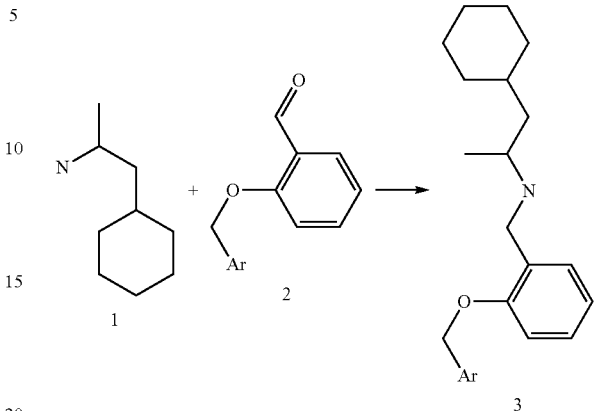

Amine 1 (0.5 mmol), aldehyde 2 (0.55 mmol) were dissolved in 0.6 ml MeOH, heated at 100° C. for 2 hours, then mixture was cooled, NaBH₄ (0.5 mmol) was added and stirred for 4 hours. The mixture was heated for 2 hours at 60° C., 3 ml of methanol and 0.2 g of C-18 chromatographic phase were added, stirred for 2 hours, filtered, evaporated. The residue was purified using HPLC. Yield: 31-54%.

The following compounds were synthesized according to the Scheme shown in Example 10 above:

B381

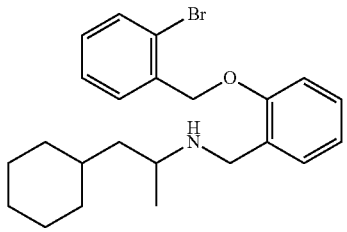

1H NMR (400 MHz, DMSO-d6) δ 7.69 (d, J=7.9 Hz, 1H), 7.61 (d, J=7.6 Hz, 1H), 7.44 (t, J=7.5 Hz, 1H), 7.32 (t, J=8.1 Hz, 2H), 7.22 (t, J=7.8 Hz, 1H), 7.05 (d, J=8.1 Hz, 1H), 6.92 (t, J=7.4 Hz, 1H), 5.13 (s, 2H), 3.75 (d, J=13.7 Hz, 1H), 3.64 (d, J=13.7 Hz, 1H), 2.56 (q, J=6.2 Hz, 1H), 1.58-1.44 (m, 6H), 1.28-1.17 (m, 2H), 1.04 (dt, J=28.1, 7.4 Hz, 5H), 0.91 (d, J=6.1 Hz, 3H), 0.73 (t, J=12.1 Hz, 2H).

B382

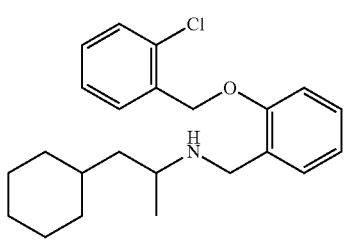

1H NMR (400 MHz, DMSO-d6) δ 7.66-7.59 (m, 1H), 7.56-7.49 (m, 1H), 7.44-7.35 (m, 2H), 7.30 (d, J=7.3 Hz, 1H), 7.22 (t, J=7.6 Hz, 1H), 7.07 (d, J=8.1 Hz, 1H), 6.92 (t, J=7.4 Hz, 1H), 5.17 (s, 2H), 3.75 (d, J=13.6 Hz, 1H), 3.63

(d, J=13.8 Hz, 1H), 2.56 (s, 1H), 1.58 (d, J=12.3 Hz, 1H), 1.57-1.43 (m, 5H), 1.27-1.17 (m, 2H), 1.08 (d, J=8.1 Hz, 2H), 1.03 (s, 1H), 1.08-0.96 (m, 1H), 0.91 (d, J=6.1 Hz, 3H), 0.74 (t, J=12.1 Hz, 2H).

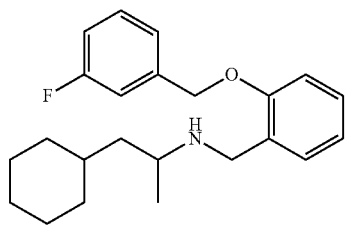

B383

1H NMR (400 MHz, DMSO-d6) δ 7.44 (td, J=8.0, 5.9 Hz, 1H), 7.30 (d, J=6.8 Hz, 3H), 7.26-7.11 (m, 2H), 7.02 (d, J=8.2 Hz, 1H), 6.91 (t, J=7.4 Hz, 1H), 5.15 (s, 2H), 3.77 (d, J=13.6 Hz, 1H), 3.66 (d, J=13.6 Hz, 1H), 2.59 (q, J=6.3 Hz, 1H), 1.55 (d, J=12.9 Hz, 6H), 1.49 (s, 1H), 1.26 (dq, J=13.0, 6.8, 6.3 Hz, 2H), 1.05 (dt, J=21.5, 7.8 Hz, 5H), 0.95 (d, J=6.1 Hz, 3H), 0.75 (dd, J=17.6, 7.0 Hz, 2H).

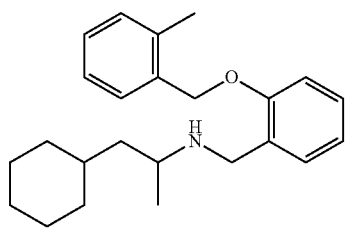

B384

1H NMR (400 MHz, DMSO-d6) δ 7.43 (d, J=7.2 Hz, 1H), 7.30 (d, J=7.4 Hz, 1H), 7.27-7.16 (m, 4H), 7.10 (d, J=8.2 Hz, 1H), 6.90 (t, J=7.3 Hz, 1H), 5.09 (s, 2H), 3.73 (d, J=13.7 Hz, 1H), 3.63 (d, J=13.8 Hz, 1H), 2.56 (q, J=6.3 Hz, 1H), 2.34 (s, 3H), 1.59-1.44 (m, 6H), 1.21 (dd, J=14.0, 7.5 Hz, 2H), 1.04 (dt, J=30.0, 7.8 Hz, 4H), 0.91 (d, J=6.1 Hz, 3H), 0.74 (t, J=12.1 Hz, 2H).

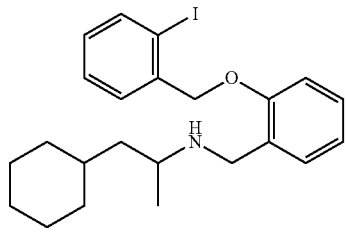

B388

1H NMR (400 MHz, Chloroform-d) δ 7.88 (d, J=7.9 Hz, 1H), 7.52 (d, J=7.6 Hz, 1H), 7.38 (t, J=7.5 Hz, 1H), 7.32-7.19 (m, 3H), 7.04 (t, J=7.7 Hz, 1H), 6.99-6.89 (m, 2H), 5.07 (s, 2H), 3.95 (d, J=13.1 Hz, 1H), 3.82 (d, J=13.1 Hz, 1H), 2.72 (q, J=6.4 Hz, 1H), 1.60 (d, J=9.5 Hz, 5H), 1.52 (d, J=13.1 Hz, 1H), 1.35 (dt, J=13.3, 6.6 Hz, 1H), 1.18-1.02 (m, 7H), 0.80 (d, J=11.4 Hz, 2H).

Example 12: Individual Compound Syntheses

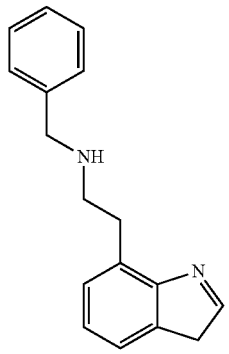

B48

2-(1H-indol-7-yl)ethan-1-amine (0.5 mmol) and benzaldehyde (0.55 mmol) were dissolved in 0.6 ml MeOH, heated at 100° C. for 2 hours, then mixture was cooled, NaBH₄ (0.5 mmol) was added and stirred for 4 hours. The mixture was heated for 2 hours at 60° C., 3 ml of methanol and 0.2 g of C-18 chromatographic phase were added, stirred for 2 hours, filtered, evaporated and dissolved in 0.5 ml of DMSO. The residue was purified using HPLC. Yield: 47%. Brown gum. 1H NMR (400 MHz, DMSO-d6) δ 11.21 (s, 1H), 7.37 (dd, J=6.7, 2.3 Hz, 1H), 7.29 (dd, J=9.1, 5.1 Hz, 5H), 7.25-7.16 (m, 1H), 7.11 (s, 1H), 6.94-6.85 (m, 2H), 6.44-6.38 (m, 1H), 3.74 (s, 2H), 3.01 (t, J=7.2 Hz, 2H), 2.83 (t, J=7.2 Hz, 2H).

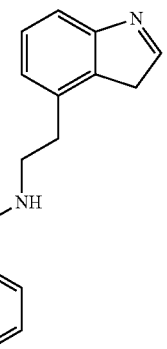

B57

2-(1H-indol-4-yl)ethan-1-amine (0.5 mmol) and benzaldehyde (0.55 mmol) were dissolved in 0.6 ml MeOH, heated at 100° C. for 2 hours, then mixture was cooled, NaBH₄ (0.5 mmol) was added and stirred for 4 hours. The mixture was heated for 2 hours at 60° C., 3 ml of methanol and 0.2 g of C-18 chromatographic phase were added, stirred for 2 hours, filtered, evaporated and dissolved in 0.5 ml of DMSO. The residue was purified using HPLC. Yield: 56%. Yellow gum. 1H NMR (400 MHz, Chloroform-d) δ 8.20 (s, 1H), 7.26 (s, 1H), 7.21 (s, 2H), 7.13 (t, J=7.7 Hz, 1H), 6.96 (d, J=7.1 Hz, 1H), 6.61 (s, 1H), 3.83 (s, 2H), 3.15 (t, J=7.2 Hz, 2H), 3.05 (t, J=7.2 Hz, 2H).

B143

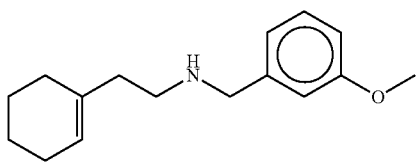

2-(cyclohex-1-en-1-yl)ethan-1-amine (0.5 mmol) and 3-methoxybenzaldehyde (0.55 mmol) were dissolved in 0.6 ml MeOH, heated at 100° C. for 2 hours, then mixture was cooled, NaBH₄ (0.5 mmol) was added and stirred for 4 hours. The mixture was heated for 2 hours at 60° C., 3 ml of methanol and 0.2 g of C-18 chromatographic phase were added, stirred for 2 hours, filtered, evaporated and dissolved in 0.5 ml of DMSO. The residue was purified using HPLC. Yield: 58%. Cream solid. ¹H NMR (400 MHz, DMSO-d6) δ 9.70 (s, 2H), 7.29 (dd, J=15.7, 7.7 Hz, 2H), 7.11 (d, J=7.4 Hz, 1H), 6.90 (dd, J=8.4, 2.6 Hz, 1H), 5.47 (s, 1H), 3.82 (s, 3H), 3.09 (s, 1H), 2.88 (t, J=8.2 Hz, 2H), 2.37 (t, J=8.4 Hz, 3H), 1.98 (s, 2H), 1.91 (d, J=6.8 Hz, 2H), 1.67-1.57 (m, 2H), 1.60-1.50 (m, 2H).

B160

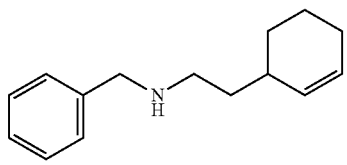

To borane tetrahydrofuran complex (1.6 ml, 1.6 mmol) was slowly added at 0° C. N-benzyl-2-(cyclohex-2-en-1-yl)acetamide (0.89 mmol) in tetrahydrofuran (3 ml). The reaction mixture was then stirred at 60° C. for 3 hours, cooled to room temperature and quenched with 6N aqueous hydrochloric acid. The solvent was removed by distillation and water (10 ml) 5 was added. The residue was purified using HPLC. Yield: 34%. 1H NMR (400 MHz, Chloroform-d) δ 7.37-7.19 (m, 3H), 5.66 (dq, J=9.8, 3.2 Hz, 1H), 5.59-5.51 (m, 1H), 3.79 (s, 2H), 2.69 (ddt, J=11.2, 6.4, 3.3 Hz, 2H), 2.14 (s, 1H), 1.96 (tp, J=5.1, 2.6 Hz, 2H), 1.82-1.66 (m, 2H), 1.62-1.41 (m, 2H), 1.29-1.16 (m, 1H).

B161

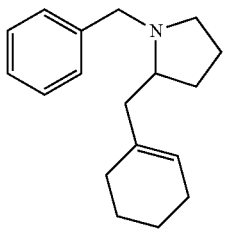

2-(cyclohex-1-en-1-ylmethyl)pyrrolidine (0.5 mmol), benzaldehyde (0.55 mmol) were dissolved in 0.6 ml of CHCl₃; NaBHAc₃ (1.5 mmol) was added and stirred for 4 hours. The mixture was heated for 12 hours at 60° C., 3 ml of methanol and 0.2 g of C-18 chromatographic phase were added, stirred for 2 hours, filtered, evaporated and dissolved in 0.5 ml of DMSO. The residue was purified using HPLC. Yield: 32%. 1H NMR (400 MHz, DMSO-d6) δ 7.28 (q, J=5.5, 4.2 Hz, 4H), 7.21 (td, J=6.0, 3.0 Hz, 1H), 5.42 (s, 1H), 4.00 (d, J=13.1 Hz, 1H), 3.16 (d, J=13.1 Hz, 1H), 2.75 (dt, J=9.5, 4.8 Hz, 1H), 2.35-2.27 (m, 1H), 2.05 (q, J=8.6 Hz, 1H), 1.92 (d, J=6.0 Hz, 4H), 1.83 (t, J=6.9 Hz, 1H), 1.80 (s, 1H), 1.54 (dddd, J=22.2, 16.9, 10.3, 5.1 Hz, 6H), 1.49-1.33 (m, 1H).

B163

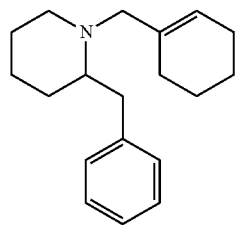

2-(cyclohex-1-en-1-ylmethyl)piperidine (0.5 mmol), benzaldehyde (0.55 mmol) were dissolved in 0.6 ml of CHCl₃; NaBHAc₃ (1.5 mmol) was added and stirred for 4 hours. The mixture was heated for 12 hours at 60° C., 3 ml of methanol and 0.2 g of C-18 chromatographic phase were added, stirred for 2 hours, filtered, evaporated and dissolved in 0.5 ml of DMSO. The residue was purified using HPLC. Yield: 48%. 1H NMR (400 MHz, Chloroform-d) δ 7.34-7.21 (m, 4H), 7.21 (dd, J=7.6, 4.8 Hz, 1H), 5.16 (d, J=8.9 Hz, 1H), 4.10 (d, J=13.4 Hz, 1H), 3.02 (d, J=13.4 Hz, 1H), 2.88 (s, 1H), 2.82 (d, J=11.8 Hz, 1H), 2.27-2.14 (m, 2H), 2.11 (d, J=5.8 Hz, 2H), 1.86 (td, J=11.8, 3.0 Hz, 1H), 1.72-1.64 (m, 1H), 1.53 (s, 1H), 1.49-1.40 (m, 1H), 1.40-1.19 (m, 1H).

B170

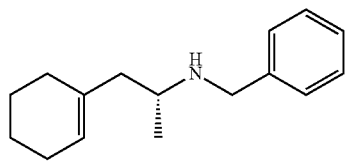

(R)-1-(cyclohex-1-en-1-yl)propan-2-amine (0.5 mmol) and benzaldehyde (0.55 mmol) were dissolved in 0.6 ml CHCl₃, NaBH(OAc)₃ (1.5 mmol) was added and stirred for 4 hours. The mixture was heated for 12 hours at 60° C., 3 ml of methanol and 0.2 g of C-18 chromatographic phase were added, stirred for 2 hours, filtered, evaporated and dissolved in 0.5 ml of DMSO. The residue was purified using HPLC. Yield: 47%. 1H NMR (400 MHz, Chloroform-d) δ 7.37-7.24 (m, 3H), 7.22 (d, J=7.3 Hz, 2H), 5.47 (s, 1H), 4.69 (ddt, J=10.7, 7.2, 3.4 Hz, 1H), 4.16 (ddq, J=14.8, 11.9, 7.3 Hz, 3H), 4.00 (h, J=6.9 Hz, 1H), 3.44 (s, 1H), 3.28 (dd, J=13.3, 3.4 Hz, 1H), 2.67 (dd, J=13.3, 9.8 Hz, 1H), 2.57 (q, J=7.3 Hz, 1H), 2.47 (dd, J=13.7, 7.0 Hz, 1H), 2.07-1.97 (m, 2H), 1.66-1.56 (m, 2H), 1.59-1.48 (m, 3H), 1.32-1.05 (m, 5H).

B171

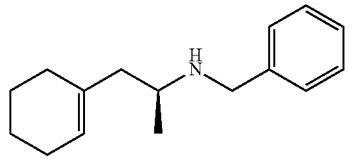

(S)-1-(cyclohex-1-en-1-yl)propan-2-amine (0.5 mmol) and benzaldehyde (0.55 mmol) were dissolved in 0.6 ml CHCl₃, NaBH(OAc)₃ (1.5 mmol) was added and stirred for 4 hours. The mixture was heated for 12 hours at 60° C., 3 ml of methanol and 0.2 g of C-18 chromatographic phase were added, stirred for 2 hours, filtered, evaporated and dissolved in 0.5 ml of DMSO. The residue was purified using HPLC. Yield: 36%. 1H NMR (400 MHz, Chloroform-d) δ 7.37-7.24 (m, 3H), 7.22 (d, J=7.3 Hz, 2H), 5.47 (s, 1H), 4.69 (ddt, J=10.7, 7.2, 3.4 Hz, 1H), 4.16 (ddq, J=14.8, 11.9, 7.3 Hz, 3H), 4.00 (h, J=6.9 Hz, 1H), 3.44 (s, 1H), 3.28 (dd, J=13.3, 3.4 Hz, 1H), 2.67 (dd, J=13.3, 9.8 Hz, 1H), 2.57 (q, J=7.3 Hz, 1H), 2.47 (dd, J=13.7, 7.0 Hz, 1H), 2.07-1.97 (m, 2H), 1.66-1.56 (m, 2H), 1.59-1.48 (m, 3H), 1.32-1.05 (m, 5H).

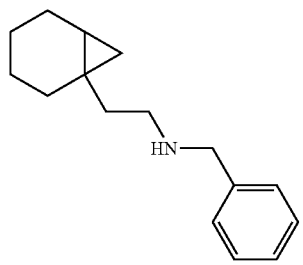

B182

To borane tetrahydrofuran complex (1.6 ml, 1.6 mmol) was slowly added at 0° C. N-(2-(bicyclo[4.1.0]heptan-1-yl)ethyl)benzamide (0.89 mmol) in tetrahydrofuran (3 ml). The reaction mixture was then stirred at 60° C. for 3 hours, cooled to room temperature and quenched with 6N aqueous hydrochloric acid. The solvent was removed by distillation and water (10 ml) was added. The residue was purified using HPLC. Yield: 37%. 1H NMR (400 MHz, DMSO-d6) δ 9.28 (s, 2H), 7.60-7.53 (m, 2H), 7.47-7.36 (m, 3H), 4.11 (s, 2H), 2.94 (t, J=8.5 Hz, 2H), 1.83 (dq, J=13.3, 6.4 Hz, 1H), 1.57 (dddd, J=34.1, 16.9, 13.1, 8.3 Hz, 5H), 1.20 (dd, J=14.8, 7.1 Hz, 1H), 1.17-1.06 (m, 3H), 0.71 (q, J=7.3 Hz, 1H), 0.38 (dd, J=9.2, 4.2 Hz, 1H), 0.20 (t, J=4.8 Hz, 1H).

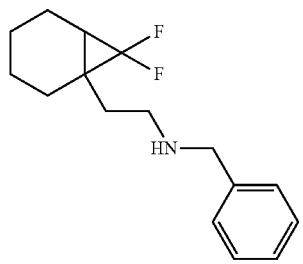

B183

To borane tetrahydrofuran complex (1.6 ml, 1.6 mmol) was slowly added at 0° C. N-(2-(7,7-difluorobicyclo[4.1.0]heptan-1-yl)ethyl)benzamide (0.89 mmol) in tetrahydrofuran (3 ml). The reaction mixture was then stirred at 60° C. for 3 hours, cooled to room temperature and quenched with 6N aqueous hydrochloric acid. The solvent was removed by distillation and water (10 ml) was added. The residue was purified using HPLC. Yield: 34%. 1H NMR (400 MHz, DMSO-d6) δ 7.30 (dd, J=8.6, 5.1 Hz, 4H), 7.25-7.17 (m, 1H), 3.68 (s, 2H), 2.57 (dd, J=15.3, 7.7 Hz, 2H), 2.00 (s, 1H), 1.63-1.50 (m, 5H), 1.33 (dd, J=15.6, 8.4 Hz, 1H), 1.20 (dd, J=20.0, 9.1 Hz, 4H).

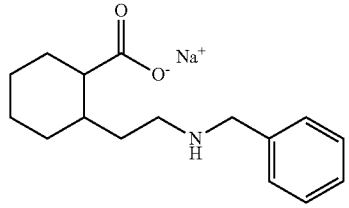

B184

2-benzyloctahydroisoquinolin-1(2H)-one (0.1 mmol) was dissolved in methanol; an excess of hydrochloric acid (0.2 mmol) was added to the reaction mixture. The mixture was refluxed for 10 h, solvent was removed. The resulting compound was purified using HPLC. Yield: 44%. 1H NMR (400 MHz, DMSO-d6) δ 9.03 (s, 2H), 7.54-7.48 (m, 2H), 7.47-7.38 (m, 3H), 4.11 (t, J=8.7 Hz, 2H), 3.01-2.91 (m, 1H), 2.83 (s, 1H), 1.95 (dd, J=12.3, 8.9 Hz, 1H), 1.82 (d, J=12.6 Hz, 1H), 1.72 (d, J=12.8 Hz, 2H), 1.66 (s, 2H), 1.56-1.46 (m, 1H), 1.45 (s, 1H), 1.32 (d, J=11.8 Hz, 1H), 1.20 (d, J=10.4 Hz, 2H), 0.89 (d, J=12.2 Hz, 1H).

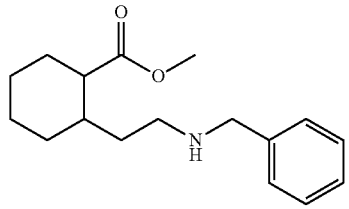

B185

To a flask was added 2-(2-(benzylamino)ethyl)cyclohexane-1-carboxylic acid (1 mmol), anhydrous DMF 10 mL, potassium carbonate (2 mmol), catalytic amount of potassium iodide, stirring 10 min, then methyl iodide (1 mmol) was added, reacted at 70° C., monitored by TLC. After the reaction was allowed to cool to room temperature, the reaction solution was poured into ice water, stirred for 30 min, extracted with ethyl acetate. The organic layers were combined, washed with saturated brine. Dried over anhydrous sodium sulfate, the solvent was distilled off under reduced pressure, dried in vacuo. The crude residue was purified by HPLC. Yield: 21%. 1H NMR (400 MHz, DMSO-d6) δ 9.04 (s, 1H), 8.97 (s, 11H), 7.50 (s, 11H), 7.42 (s, 2H), 4.10 (s, 2H), 3.59 (d, J=5.1 Hz, 2H), 2.94 (s, 1H), 2.80 (s, 11H), 2.07 (s, 1H), 1.76 (dd, J=26.2, 12.2 Hz, 11H), 1.65 (s, 3H), 1.43 (s, 1H), 1.20 (s, 2H), 0.92 (d, J=11.6 Hz, 1H).

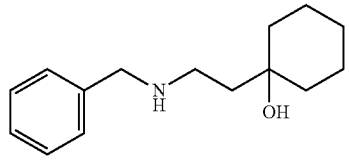

B187

To borane tetrahydrofuran complex (1.6 ml, 1.6 mmol) was slowly added at 0° C. N-benzyl-2-(1-hydroxycyclohexyl)acetamide (0.89 mmol) in tetrahydrofuran (3 ml). The reaction mixture was then stirred at 60° C. for 3 hours, cooled to room temperature and quenched with 6N aqueous hydrochloric acid. The solvent was removed by distillation and water (10 ml) 5 was added. The residue was purified using HPLC. Yield: 22%. 1H NMR (400 MHz, Chloroform-d) δ 7.36-7.22 (m, 2H), 3.77 (s, 2H), 2.94-2.87 (m, 2H), 1.69-1.58 (m, 3H), 1.35 (dt, J=22.6, 12.2 Hz, 3H), 1.26 (s, 1H).

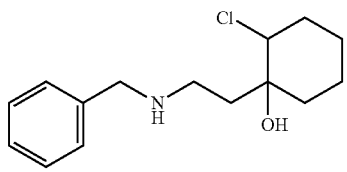

B188

To a solution of tert-butyl benzyl(2-(2-chloro-1-hydroxycyclohexyl)ethyl)carbamate (0.1 mmol) in dichloromethane (25 mL) was slowly added trifluoroacetic acid (3.4 mmol) at 0° C. The reaction solution was stirred at room temperature for 5 h, and then 1N NaOH was added. The mixture was extracted with dichloromethane, and the organic layer was washed with brine, dried (Na$_2$SO$_4$), and filtered. The solvent was evaporated under reduced pressure to give the product. The crude residue was purified by HPLC. Yield: 46%. 1H NMR (400 MHz, DMSO-d6) δ 8.89 (s, 3H), 7.53-7.37 (m, 7H), 5.07 (s, 1H), 4.19 (d, J=11.6 Hz, 3H), 4.08 (s, 1H), 4.01 (dd, J=7.1, 3.6 Hz, 1H), 3.17 (s, 2H), 3.01 (d, J=9.0 Hz, 2H), 2.11 (t, J=9.8 Hz, 1H), 1.96 (dd, J=14.8, 7.1 Hz, 1H), 1.87 (td, J=13.7, 13.2, 5.8 Hz, 1H), 1.67 (q, J=14.9, 13.5 Hz, 2H), 1.59 (s, 4H), 1.36 (d, J=9.8 Hz, 3H).

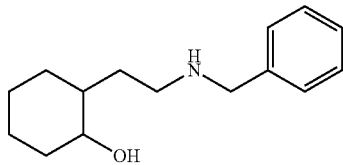

B189

2-(2-aminoethyl)cyclohexan-1-ol (0.5 mmol), benzaldehyde (0.55 mmol) were dissolved in 0.6 ml MeOH, heated at 100° C. for 2 hours, then mixture was cooled, NaBH$_4$ (0.5 mmol) was added and stirred for 4 hours. The mixture was heated for 2 hours at 60° C., 3 ml of methanol and 0.2 g of C-18 chromatographic phase were added, stirred for 2 hours, filtered, evaporated and dissolved in 0.5 ml of DMSO. The residue was purified using HPLC. Yield: 68%. 1H NMR (400 MHz, Chloroform-d) δ 7.34 (s, 1H), 7.27 (d, J=6.7 Hz, 1H), 4.53 (s, 2H), 3.80 (s, 2H), 3.79 (s, 0H), 3.13 (s, 1H), 3.01-2.89 (m, 1H), 2.63 (t, J=11.1 Hz, 1H), 2.00 (s, 1H), 1.42 (dd, J=15.6, 9.5 Hz, 1H), 1.21 (q, J=11.8, 11.0 Hz, 4H), 1.07-0.97 (m, 1H).

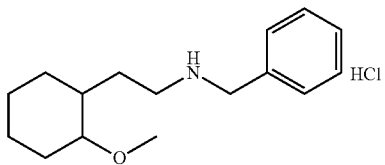

B190

To a solution of tert-butyl benzyl(2-(2-methoxycyclohexyl)ethyl)carbamate (0.1 mmol) in dichloromethane (25 mL) was slowly added trifluoroacetic acid (3.4 mmol) at 0° C. The reaction solution was stirred at room temperature for 5 h, and then 1N NaOH was added. The mixture was extracted with dichloromethane, and the organic layer was washed with brine, dried (Na$_2$SO$_4$), and filtered. The solvent was evaporated under reduced pressure to give the product. The crude residue was purified by HPLC. Yield: 57%. 1H NMR (400 MHz, DMSO-d6) δ 9.22 (s, 2H), 7.55 (d, J=7.9 Hz, 2H), 7.41 (d, J=6.6 Hz, 2H), 4.10 (s, 2H), 3.20 (s, 2H), 2.88 (s, 2H), 2.73 (td, J=9.9, 4.1 Hz, 1H), 2.05 (d, J=11.8 Hz, 1H), 1.97 (s, 1H), 1.67 (d, J=12.0 Hz, 2H), 1.55 (d, J=11.2 Hz, 1H), 1.50-1.44 (m, 1H), 1.27 (s, 1H), 1.13 (q, J=12.3 Hz, 2H), 1.01-0.89 (m, 2H).

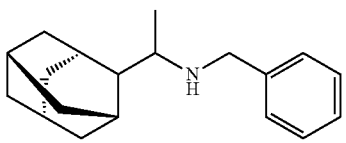

B191

Benzylamine (0.25 mmol) and 1-(adamantan-2-yl)ethan-1-one (0.3 mmol) were dissolved in 0.3 ml MeOH, heated at 100° C. for 2 hours, then mixture was cooled, NaBH$_4$ (0.25 mmol) was added and stirred for 4 hours. The mixture was heated for 2 hours at 60° C., 3 ml of methanol and 0.1 g of C-18 chromatographic phase were added, stirred for 2 hours, filtered, evaporated and dissolved in 0.25 ml of DMSO. The residue was purified using HPLC. Yield: 34%. Cream solid. 1H NMR (400 MHz, DMSO-d6) δ 9.42 (s, 1H), 8.54 (s, 1H), 7.68-7.58 (m, 2H), 7.43 (q, J=5.8 Hz, 3H), 4.20 (q, J=8.6, 7.2 Hz, 1H), 4.13 (s, 1H), 3.22 (s, 1H), 2.49 (s, 1H), 2.06 (s, 1H), 1.86-1.75 (m, 5H), 1.66 (d, J=11.0 Hz, 4H), 1.43 (s, 2H), 1.36 (s, 2H), 1.28 (d, J=6.5 Hz, 2H).

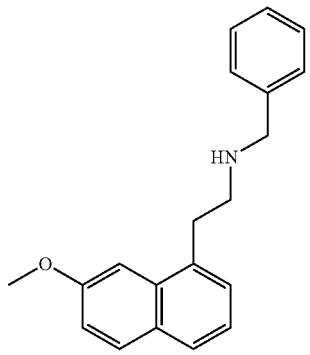

B199

To borane tetrahydrofuran complex (1.6 ml, 1.6 mmol) was slowly added at 0° C. N-benzyl-2-(7-methoxynaphthalen-1-yl)acetamide (0.89 mmol) in tetrahydrofuran (3 ml). The reaction mixture was then stirred at 60° C. for 3 hours, cooled to room temperature and quenched with 6N aqueous hydrochloric acid. The solvent was removed by distillation and water (10 ml) 5 was added. The residue was purified using HPLC. Yield: 28%. 1H NMR (400 MHz, Chloroform-d) δ 7.76 (d, J=8.9 Hz, 1H), 7.66 (d, J=8.0 Hz, 1H), 7.36-7.22 (m, 6H), 7.16 (dd, J=9.0, 2.5 Hz, 1H), 3.90 (s, 3H), 3.87 (s, 1H), 3.85 (s, 2H), 3.27 (t, J=7.3 Hz, 2H), 3.07 (t, J=7.3 Hz, 2H).

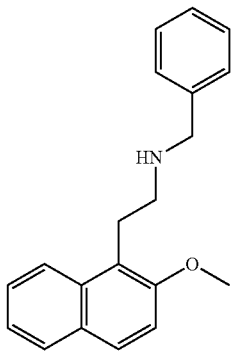

B200

2-(2-methoxynaphthalen-1-yl)ethan-1-amine (0.5 mmol) and benzaldehyde (0.55 mmol) were dissolved in 0.6 ml MeOH, heated at 100° C. for 2 hours, then mixture was cooled, NaBH₄ (0.5 mmol) was added and stirred for 4 hours. The mixture was heated for 2 hours at 60° C., 3 ml of methanol and 0.2 g of C-18 chromatographic phase were added, stirred for 2 hours, filtered, evaporated and dissolved in 0.5 ml of DMSO. The residue was purified using HPLC. Yield: 42%. 1H NMR (400 MHz, DMSO-d6) δ 9.58 (s, 1H), 8.14 (d, J=8.7 Hz, 0H), 7.94-7.86 (m, 1H), 7.61 (d, J=7.0 Hz, 1H), 7.45 (ddt, J=29.2, 22.6, 7.8 Hz, 3H), 4.22 (s, 1H), 3.51-3.43 (m, 1H), 3.34 (s, 1H), 3.00 (s, 1H).

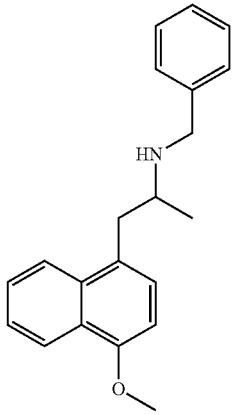

B201

Benzylamine (0.5 mmol) and 1-(4-methoxynaphthalen-1-yl)propan-2-one (0.55 mmol) were dissolved in 0.6 ml MeOH, heated at 100° C. for 2 hours, then mixture was cooled, NaBH₄ (0.5 mmol) was added and stirred for 4 hours. The mixture was heated for 2 hours at 60° C., 3 ml of methanol and 0.2 g of C-18 chromatographic phase were added, stirred for 2 hours, filtered, evaporated and dissolved in 0.5 ml of DMSO. The residue was purified using HPLC. Yield: 36%. 1H NMR (400 MHz, DMSO-d6) δ 8.19-8.13 (m, 1H), 7.95-7.88 (m, 1H), 7.47 (q, J=5.0 Hz, 2H), 7.32-7.19 (m, 5H), 7.19 (s, 1H), 6.88 (d, J=7.8 Hz, 1H), 3.94 (s, 3H), 3.84 (d, J=13.9 Hz, 1H), 3.73 (d, J=13.9 Hz, 1H), 3.26 (dd, J=13.6, 5.0 Hz, 1H), 2.88 (s, 1H), 2.75 (dd, J=13.3, 8.1 Hz, 1H), 2.54 (s, 1H), 2.17 (s, 1H), 0.95 (d, J=6.0 Hz, 3H).

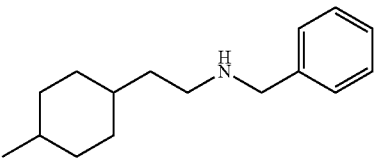

B221

To borane tetrahydrofuran complex (1.6 ml, 1.6 mmol) was slowly added at 0° C. N-benzyl-2-(4-methylcyclohexyl)acetamide (0.89 mmol) in tetrahydrofuran (3 ml). The reaction mixture was then stirred at 60° C. for 3 hours, cooled to room temperature and quenched with 6N aqueous hydrochloric acid. The solvent was removed by distillation and water (10 ml) 5 was added. The residue was purified using HPLC. Yield: 31%. 1H NMR (400 MHz, DMSO-d6) δ 9.27 (s, 1H), 7.60-7.54 (m, 1H), 7.42 (d, J=6.4 Hz, 2H), 4.10 (s, 1H), 2.87 (t, J=8.2 Hz, 1H), 1.64 (d, J=8.1 Hz, 2H), 1.55 (dt, J=11.6, 7.0 Hz, 1H), 0.86 (dd, J=15.6, 6.2 Hz, 3H).

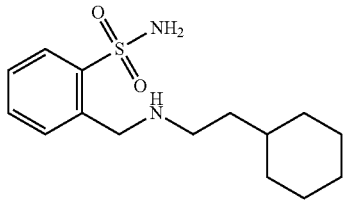

B345

2-(aminomethyl)benzenesulfonamide (0.5 mmol) and 2-cyclohexylacetaldehyde (0.55 mmol) were dissolved in 0.6 ml MeOH, heated at 100° C. for 2 hours, then mixture was cooled, NaBH₄ (0.5 mmol) was added and stirred for 4 hours. The mixture was heated for 2 hours at 60° C., 3 ml of methanol and 0.2 g of C-18 chromatographic phase were added, stirred for 2 hours, filtered, evaporated. The residue was purified using HPLC. Yield: 34%. Light brown solid. 1H NMR (400 MHz, DMSO-d6) δ 7.86 (d, J=7.8 Hz, 1H), 7.54 (d, J=6.6 Hz, 2H), 7.45 (s, 1H), 4.03 (s, 2H), 1.63 (d, J=12.2 Hz, 5H), 1.29 (t, J=7.2 Hz, 2H), 1.21-1.11 (m, 1H), 0.84 (d, J=11.4 Hz, 2H).

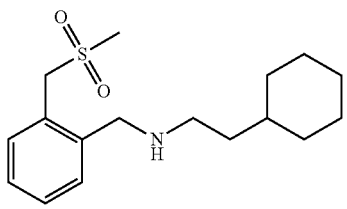

B346

(2-((methylsulfonyl)methyl)phenyl)methanamine (0.5 mmol) and 2-cyclohexylacetaldehyde (0.55 mmol) were dissolved in 0.6 ml MeOH, heated at 100° C. for 2 hours, then mixture was cooled, NaBH₄ (0.5 mmol) was added and stirred for 4 hours. The mixture was heated for 2 hours at 60° C., 3 ml of methanol and 0.2 g of C-18 chromatographic phase were added, stirred for 2 hours, filtered, evaporated. The residue was purified using HPLC. Yield: 49%. Yellow gum. m/z: 309.22

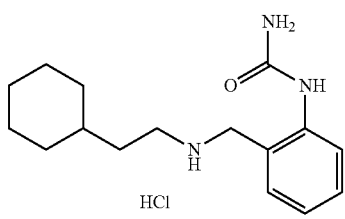

B373

To a solution of tert-butyl (2-cyclohexylethyl)(2-ureidobenzyl)carbamate (0.1 mmol) in dichloromethane (25 mL) was slowly added trifluoroacetic acid (3.4 mmol) at 0° C. The reaction solution was stirred at room temperature for 5 h, and then 1N NaOH was added. The mixture was extracted with dichloromethane, and the organic layer was washed with brine, dried ($Na_2SO_4$), and filtered. The solvent was evaporated under reduced pressure to give the product. The crude residue was purified by HPLC. Yield: 37%. 1H NMR (400 MHz, DMSO-d6) δ 8.96 (s, 2H), 8.88 (s, 1H), 7.61 (d, J=8.1 Hz, 1H), 7.51 (d, J=7.7 Hz, 1H), 7.34 (t, J=7.7 Hz, 1H), 7.12 (t, J=7.5 Hz, 1H), 6.12 (s, 5H), 4.12 (d, J=5.7 Hz, 2H), 2.99 (s, 2H), 1.66 (s, 2H), 1.61 (d, J=16.2 Hz, 3H), 1.54 (q, J=7.5 Hz, 3H), 1.30 (s, 1H), 1.17 (h, J=12.2 Hz, 3H), 0.88 (q, J=11.7 Hz, 2H).

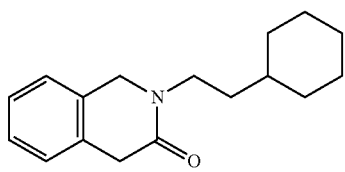

B379

Methyl 2-(2-(aminomethyl)phenyl)acetate (0.5 mmol) and 2-cyclohexylacetaldehyde (0.55 mmol) were dissolved in 0.6 ml MeOH, heated at 100° C. for 2 hours, then mixture was cooled, $NaBH_4$ (0.5 mmol) was added and stirred for 4 hours. The mixture was heated for 2 hours at 60° C., 3 ml of methanol and 0.2 g of C-18 chromatographic phase were added, stirred for 2 hours, filtered, evaporated. The residue was purified using HPLC. Yellow solid. Yield: 34%. 1H NMR (400 MHz, DMSO-d6) δ 7.27 (t, J=4.3 Hz, 1H), 7.27-7.16 (m, 3H), 4.46 (s, 2H), 3.42 (t, J=7.7 Hz, 2H), 3.33 (d, J=2.3 Hz, 1H), 1.65 (td, J=23.1, 18.8, 10.8 Hz, 5H), 1.39 (q, J=7.3 Hz, 2H), 1.20 (d, J=10.4 Hz, 1H), 1.17-1.07 (m, 3H), 0.92 (d, J=11.6 Hz, 1H), 0.86 (d, J=12.0 Hz, 1H).

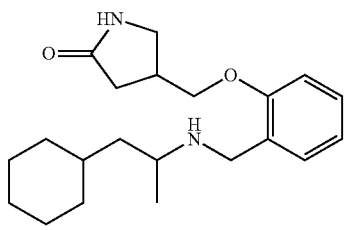

B403

1-cyclohexylpropan-2-amine (0.5 mmol) and 2-((5-oxopyrrolidin-3-yl)methoxy)benzaldehyde (0.55 mmol) were dissolved in 0.6 ml MeOH, heated at 100° C. for 2 hours, then mixture was cooled, $NaBH_4$ (0.5 mmol) was added and stirred for 4 hours. The mixture was heated for 2 hours at 60° C., 3 ml of methanol and 0.2 g of C-18 chromatographic phase were added, stirred for 2 hours, filtered, evaporated and dissolved in 0.5 ml of DMSO. The residue was purified using HPLC. Yield: 39%. 1H NMR (400 MHz, DMSO-d6) δ 7.60 (s, 1H), 7.27 (d, J=7.4 Hz, 1H), 7.19 (t, J=7.8 Hz, 1H), 6.95 (d, J=8.2 Hz, 1H), 6.88 (t, J=7.4 Hz, 1H), 4.03-3.90 (m, 2H), 3.71 (d, J=13.7 Hz, 1H), 3.59 (d, J=13.7 Hz, 1H), 3.42 (t, J=8.9 Hz, 1H), 3.13 (dd, J=9.9, 5.7 Hz, 1H), 2.90-2.80 (m, 1H), 2.62-2.52 (m, 1H), 2.33 (dd, J=16.6, 9.1 Hz, 1H), 2.07 (dd, J=16.6, 6.8 Hz, 1H), 1.58 (d, J=11.5 Hz, 4H), 1.49 (d, J=13.3 Hz, 1H), 1.27 (dt, J=13.5, 6.3 Hz, 2H), 1.20-1.00 (m, 4H), 0.96 (d, J=6.1 Hz, 3H), 0.77 (s, 2H).

Example 13: Individual Compound Syntheses 2

B156: N-benzyl-2-(cyclohex-3-enyl)ethanamine hydrochloride

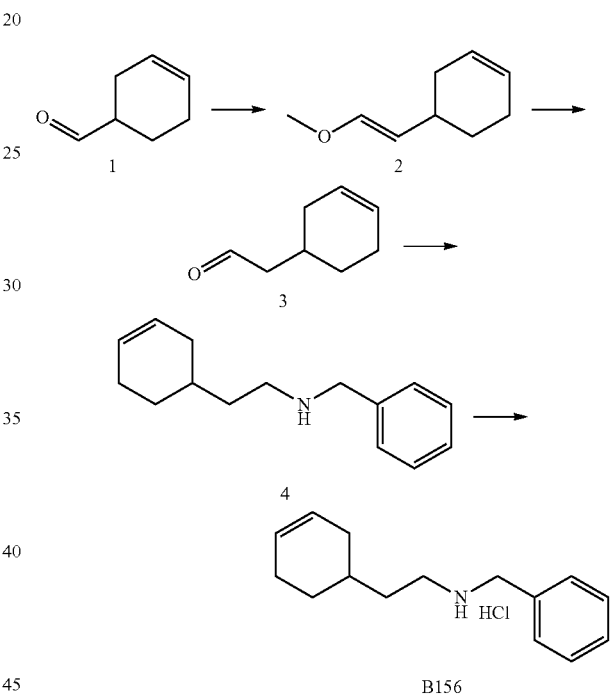

Step 1: Preparation of 2

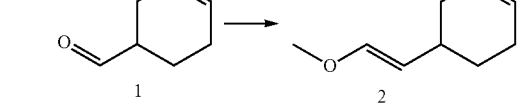

To a mixture of (methoxymethyl)triphenylphosphonium chloride (136.7 g, 399.4 mmol, 2.2 eq) in THF (450 mL) was added potassium tert-butylate (40.7 g, 363 mmol, 2.0 eq) at 0° C. for 20 min. Then, 1 (20 g, 181.6 eq, 1.0 eq) was added and the reaction mixture was stirred at room temperature. After completion, the mixture was poured into water, extracted with ethyl acetate and washed with brine. The combined organic phases were dried over $Na_2SO_4$, filtered and concentrated in vacuum. The residue was purified by column chromatography to give the product 2 (24.4 g) as an oil.

Step 2: Preparation of 3

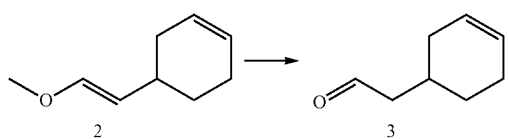

To a mixture of 2 (12 g, 86.8 mmol, 1.0 eq) in THF (347 mL, c=0.25) was added aq. HCl (6N, 72 mL, 434 mmol, 5.0 eq). The reaction mixture was stirred at room temperature for 1.5 h. After completion, water (100 mL) was added and the resulting mixture was extracted with EA (80 mL×3). The organic phases were washed with brine, dried over $Na_2SO_4$, filtered and concentrated under reduced pressure. The residue was purified by column chromatography to give the product 3 (2.6 g, yield=24.2%) as an oil. Step 3: Preparation of 4

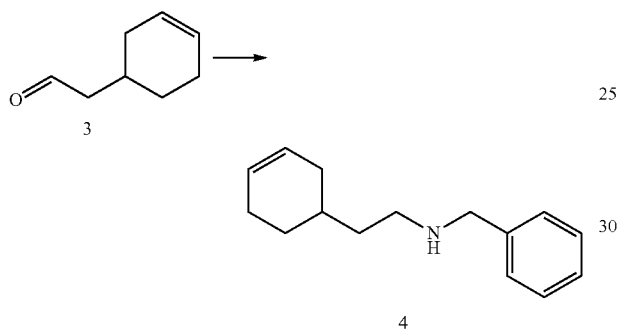

To a solution of 3 (200 mg, 1.6 mmol, 1.0 eq) in DCM (3.5 mL, c=0.46) was added benzylamine (173 mg, 1.6 mmol, 1.0 eq) and $MgSO_4$ (290 mg, 2.4 mmol, 1.5 eq). After that, AcOH (0.4 mL) and $NaBH_3CN$ (182 mg, 4.8 mmol, 3.0 eq) were added and the reaction mixture was stirred at room temperature overnight. After completion, the mixture was poured into water, extracted with ethyl acetate and washed with brine. The combined organic phases were dried over $Na_2SO_4$, filtered and concentrated in vacuum. The residue was purified by column chromatography to give the product 4 (32 mg, yield=9.3%) as a solid.

Step 4: Preparation of B156

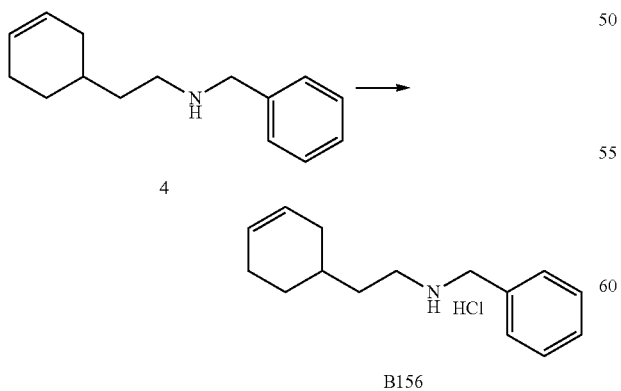

A mixture of 4 (26 mg, 0.12 mmol, 1.0 eq) in HCl/MeOH (1N, 2 mL, c=0.06) was stirred at room temperature for 1 h. After completion, the suspension was filtered and concentrated under reduced pressure to give the product B156 (31 mg, yield=100%) as a solid. $^1$H NMR (400 MHz, $D_2O$): δ 7.43-7.41 (m, 5H), 5.68-5.63 (m, 2H), 4.16 (s, 2H), 3.06-3.02 (m, 2H), 2.03-1.89 (m, 3H), 1.66-1.57 (m, 5H), 1.21-1.12 (m, 1H); Mass: m/z=216 [M−HCl+H]$^+$ B157: N-benzyl-1-(cyclohex-3-enyl)propan-2-amine

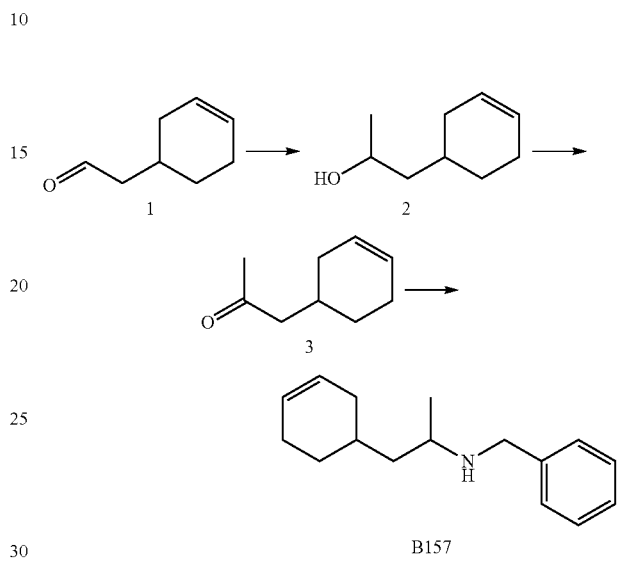

Step 1: Preparation of 2

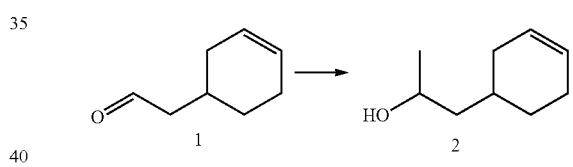

To a mixture of 1 (1.0 g, 8.07 mmol, 1.0 eq) in THF (16 mL, c=0.5) was added dropwise $CH_3MgBr$ (3N, 2.9 mL, 8.5 mmol, 1.05 eq) at −0° C. for 20 min and the mixture was stirred at room temperature for 1 h. After completion, the resulting mixture was poured into water, extracted with ethyl acetate and washed with brine. The combined organic phases were dried over $Na_2SO_4$, filtered and concentrated in vacuum. The residue was purified by column chromatography to give the product 2 (200 mg, yield=17.7%) as an oil.

Step 2: Preparation of 3

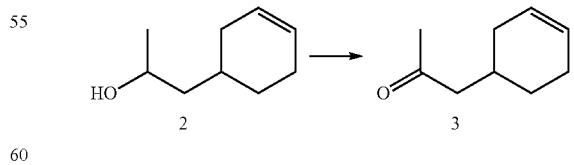

To a mixture of 2 (100 mg, 0.7 mmol, 1.0 eq) in DCM (3.5 mL, c=0.2) was added PCC (231 mg, 1.1 mmol, 1.5 eq) and the reaction mixture was stirred at room temperature overnight. After completion, the resulting mixture was filtered through celite and the filtrate was concentrated to dryness to obtain the product 3 (100 mg, yield=100%).

Step 3: Preparation of B157

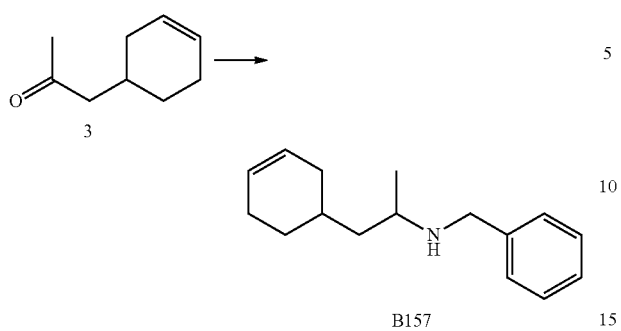

To a solution of 3 (200 mg, 1.44 mmol, 1.0 eq) in DCM (5 mL, c=0.3) was added benzylamine (150.2 mg, 1.44 mmol, 1.0 eq) and MgSO$_4$ (260 mg, 2.16 mmol, 1.5 eq). Then AcOH (0.36 mL) and NaBH$_3$CN (164 mg, 4.32 mmol, 3.0 eq) was added and the reaction mixture was stirred at room temperature overnight. After completion, the mixture was poured into water, extracted with ethyl acetate and washed with brine. The combined organic phases were dried over Na$_2$SO$_4$, filtered and concentrated in vacuum. The residue was purified by column chromatography to give the product B157 (11 mg, yield=2.9%) as a solid. $^1$H NMR (400 MHz, DMSO-d6): δ 7.34-7.19 (m, 5H), 5.61 (s, 2H), 3.79-3.66 (m, 2H), 2.66-2.65 (m, 1H), 2.00-1.00 (m, 12H); Mass: m/z=230 [M+H]$^+$ B158: 6-((benzylamino)methyl)benzo[c][1,2]oxa-borol-1(3H)-ol

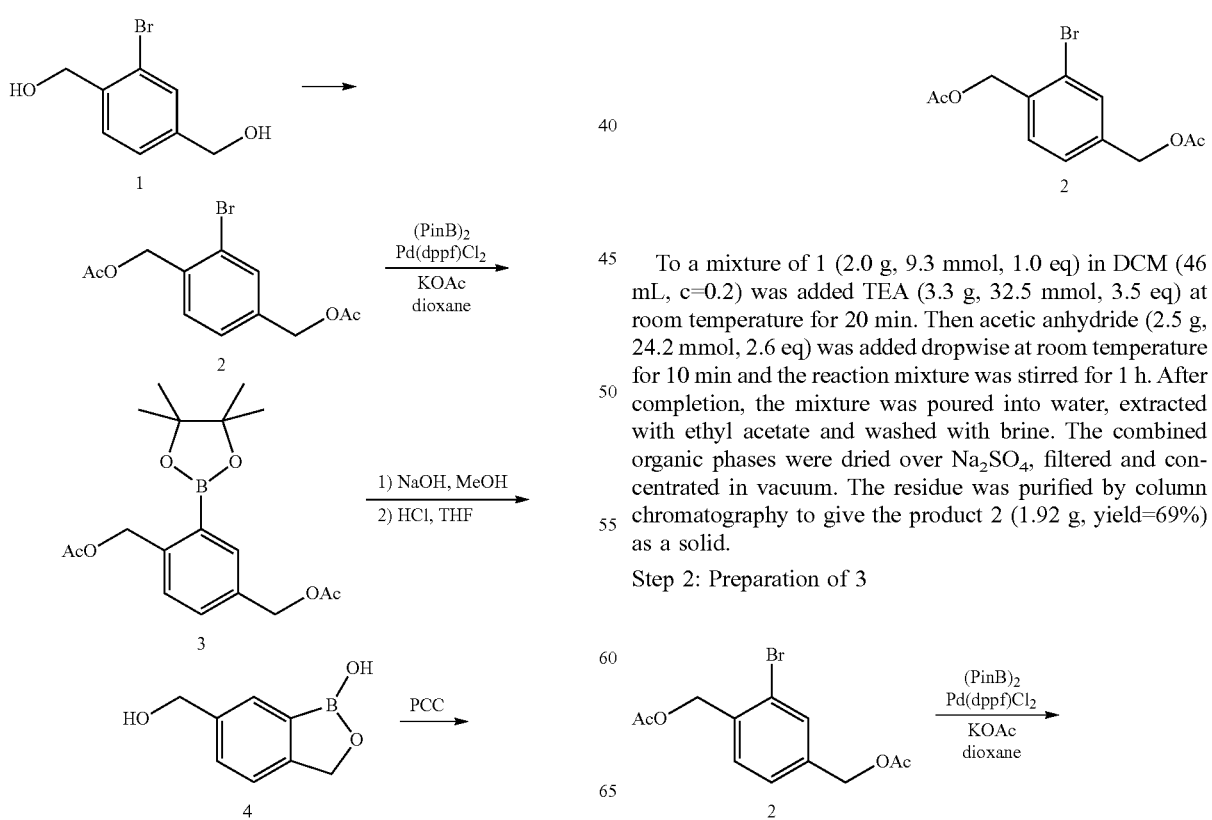

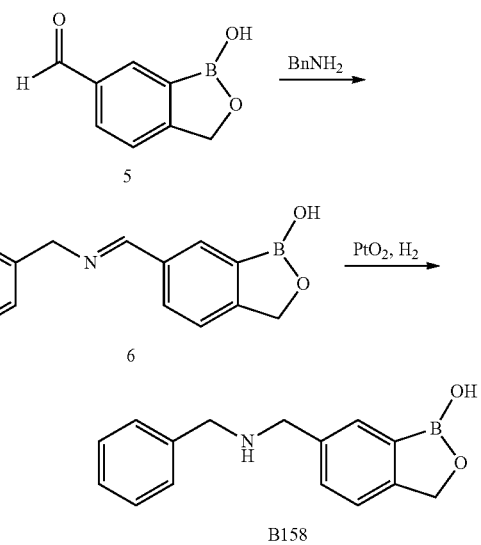

Step 1: Preparation of 2

To a mixture of 1 (2.0 g, 9.3 mmol, 1.0 eq) in DCM (46 mL, c=0.2) was added TEA (3.3 g, 32.5 mmol, 3.5 eq) at room temperature for 20 min. Then acetic anhydride (2.5 g, 24.2 mmol, 2.6 eq) was added dropwise at room temperature for 10 min and the reaction mixture was stirred for 1 h. After completion, the mixture was poured into water, extracted with ethyl acetate and washed with brine. The combined organic phases were dried over Na$_2$SO$_4$, filtered and concentrated in vacuum. The residue was purified by column chromatography to give the product 2 (1.92 g, yield=69%) as a solid.

Step 2: Preparation of 3

-continued

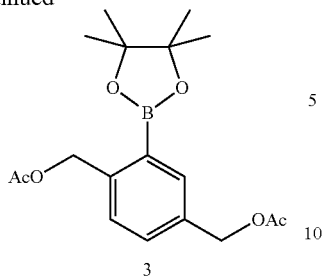

A solution of 2 (12 g, 40 mmol, 1.0 eq), bis(pinacolato)diboron (15.18 g, 60 mmol, 1.5 eq) and potassium acetate in dioxane (160 mL, c=0.25) was added trans-dichlorobis(triphenyl-phosphine)palladium(II) (3.3 g, 4 mmol, 0.1 eq) under nitrogen and the solution was heated at reflux overnight. After completion, the mixture was filtered and concentrated in vacuum. The crude was purified by column chromatography to give the product 3 (10.82 g, yield=77.7%) as a solid.

Step 3: Preparation of 4

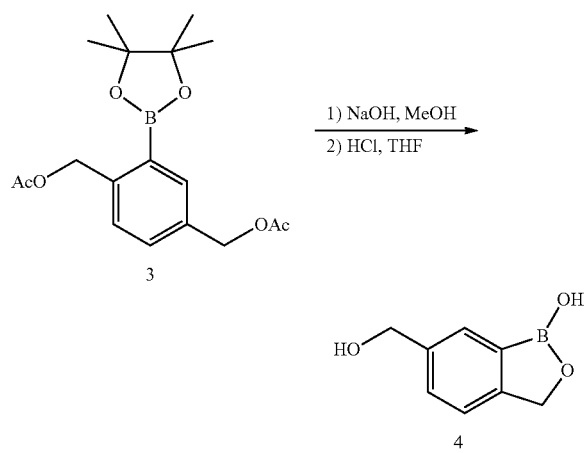

To a solution of 3 (8 g, 23 mmol, 1.0 eq) in MeOH (24 mL) was added sodium hydroxide (3.7 g, 92 mmol, 4.0 eq) in MeOH (18.4 mL) and the solution was stirred at room temperature for 4 h. After that, the reaction mixture was concentrated in vacuum. The residue was dissolved in THF again and aq.HCl (2N) was added dropwise below 15° C. with stirring and the pH of the mixture was adjusted to 1. After that, the mixture was extracted with ethyl acetate and washed with brine. The combined organic phases were dried over Na$_2$SO$_4$, filtered and concentrated in vacuum. The resulting crude was washed by 30% EA/PE to get the pure product 4 (2.8 g, yield=74.3%) as a solid.

Step 4: Preparation of 5

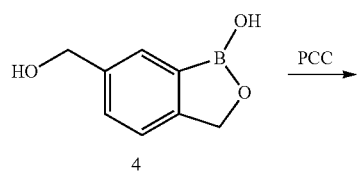

-continued

To a mixture of 4 (1.5 g, 9.14 mmol, 1.0 eq) in DCM (183 mL, c=0.05) was added PCC (3.95 g, 13.7 mmol, 1.5 eq) and the reaction solution was stirred at room temperature for 1.5 h. After completion, the mixture was filtered and the filtrate was washed with aq.HCl (2N, 50 mL×2) and aq.NaOH (2N, 40 mL×2). After that, the pH of the aqueous phase was adjusted to 1~2 by hydrochloric acid and extracted with ethyl acetate. The combined organic phases were dried over Na$_2$SO$_4$, filtered and concentrated in vacuum. The resulting crude was washed by 5% EA/PE to get the pure product 5 (786 mg, yield=53%) as a solid.

Step 5: Preparation of 6

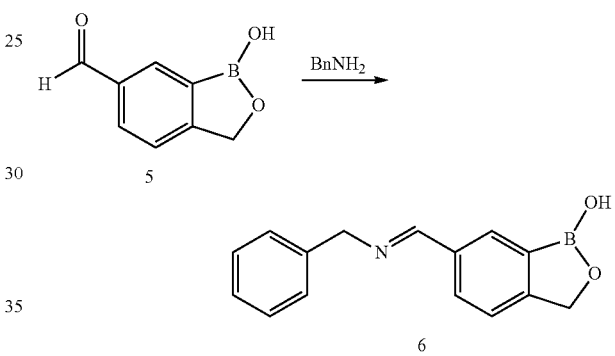

To a solution of 5 (50 mg, 0.309 mmol, 1.0 eq) and benzylamine (33.1 mg, 0.309 mmol, 1.0 eq) in DCM (1.2 mL, c=0.25) was added sodium sulfate (87.8 mg, 0.618 mmol, 2.0 eq) and the reaction mixture was stirred at room temperature under nitrogen overnight. After completion, the suspension was filtered and the filtrate was concentrated under reduced pressure to give the crude 6 (93 mg, y=122%) as a solid.

Step 6: Preparation of B158

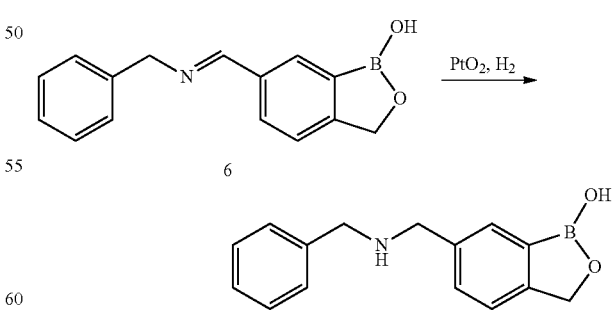

To a solution of 6 (40 mg, 0.16 mmol, 1.0 eq) in MeOH (1.6 mL, c=0.1) was added platinum(IV) oxide (3.6 mg, 0.016 mmol, 0.1 eq) and the reaction mixture was stirred at room temperature for 45 min under H$_2$. After completion, the suspension was filtered and the filtrate was concentrated under reduced pressure to give the product B158 (25 mg, y=62%) as a solid.

$^1$H NMR (400 MHz, DMSO-d6): δ 9.11 (s, 1H), 7.70-7.19 (m, 8H), 4.96 (s, 2H), 4.10 (s, 1H), 3.71 (s, 2H), 3.17 (s, 2H); Mass: m/z=254[M+H]$^+$

B159: 6-(2-(benzylamino)ethyl)benzo[c][1,2]oxaborol-1(3H)-ol

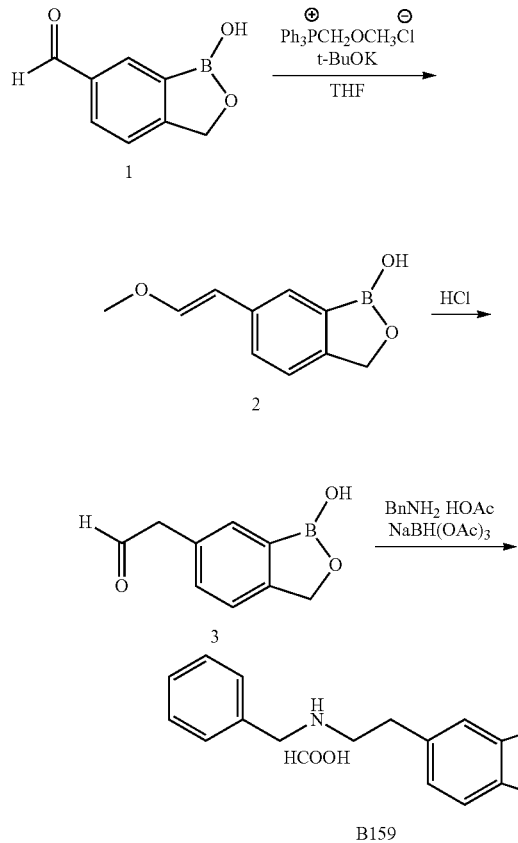

Step 1: Preparation of 2

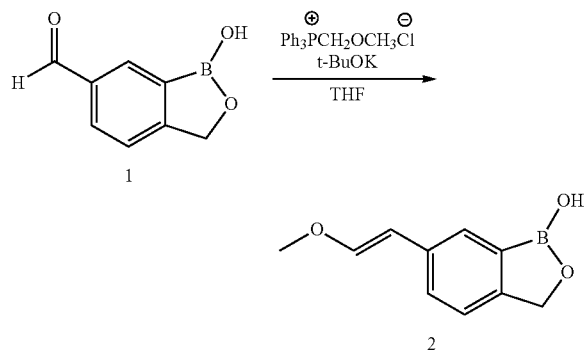

To a mixture of (Methoxymethyl)triphenylphosphonium chloride (15.5 g, 45.1 mmol, 4.87 eq) in THF (60 mL) was added potassium tert-butylate (4.78 g, 42.6 mmol, 4.6 eq) at 0° C. for 20 min. Then, a mixture of 1 (20 g, 181.6 eq, 1.0 eq) in THF (32.6 mL) was added and the reaction mixture was stirred at 0° C. After completion, the mixture was poured into water, extracted with ethyl acetate and washed with brine. The combined organic phases were dried over Na$_2$SO$_4$, filtered and concentrated in vacuum. The residue was purified by column chromatography to give the product 2 (1.2 g, yield=68%) as a solid.

Step 2: Preparation of 3

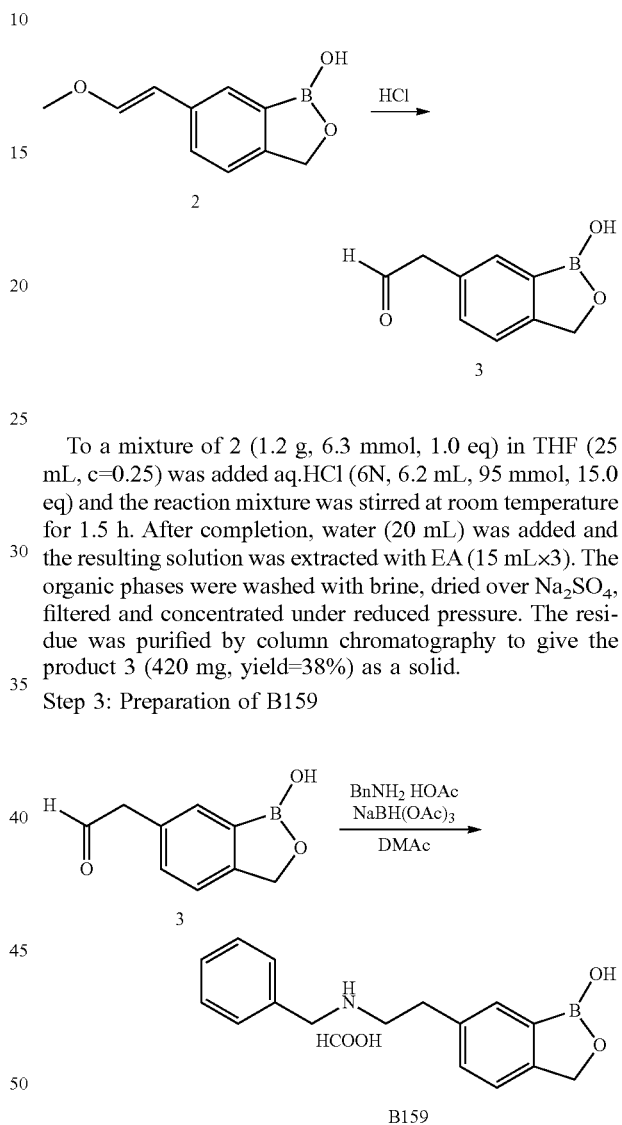

To a mixture of 2 (1.2 g, 6.3 mmol, 1.0 eq) in THF (25 mL, c=0.25) was added aq.HCl (6N, 6.2 mL, 95 mmol, 15.0 eq) and the reaction mixture was stirred at room temperature for 1.5 h. After completion, water (20 mL) was added and the resulting solution was extracted with EA (15 mL×3). The organic phases were washed with brine, dried over Na$_2$SO$_4$, filtered and concentrated under reduced pressure. The residue was purified by column chromatography to give the product 3 (420 mg, yield=38%) as a solid.

Step 3: Preparation of B159

To a solution of benzylamine acetate (142 mg, 0.85 mmol, 3.0 eq) in DMAc (1.9 mL, c=0.3) was added NaBH(OAc)$_3$ (121 mg, 0.57 mmol, 2.0 eq) and MgSO$_4$ (50.5 mg, 0.46 mmol, 1.5 eq) and the reaction mixture was stirred at room temperature for 0.5 h. Then, a mixture of 3 (50 mg, 0.28 mmol, 1.0 eq) in DMAc (0.5 mL) was added and the resulting solution was stirred at room temperature. After completion, the suspension was filtered and the filtrate was concentrated under reduced pressure. The residue was purified by C-18 reverse phase HPLC to afford the product B159 (44 mg, yield=58%) as a solid. $^1$H NMR (400 MHz, DMSO-d6): δ 9.05 (brs, 1H), 8.22 (s, 1H), 7.55 (s, 1H), 7.36-7.25 (m, 8H), 4.94 (s, 2H), 3.81 (s, 2H), 2.81 (s, 4H); Mass: m/z=268 [M+H]$^+$ B162: N-benzyl-1-(3,4-dimethylcyclohex-3-en-1-yl)propan-2-amine

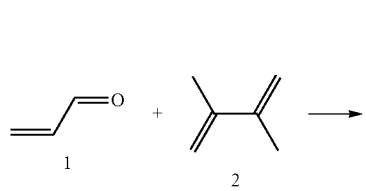

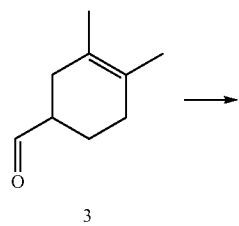

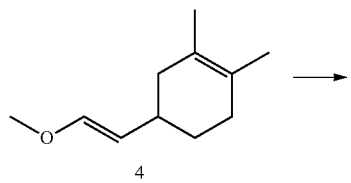

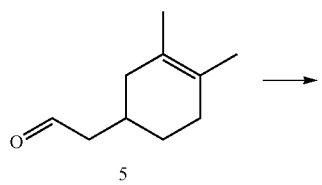

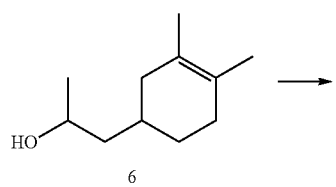

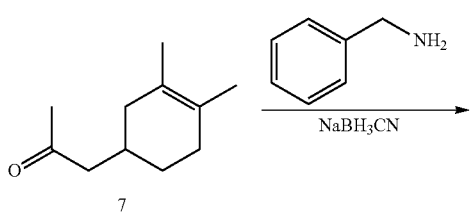

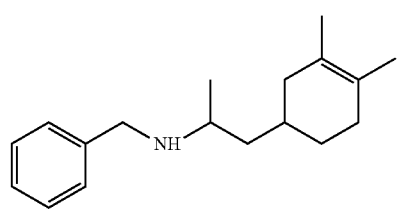

B162

Step 1: Preparation of 3

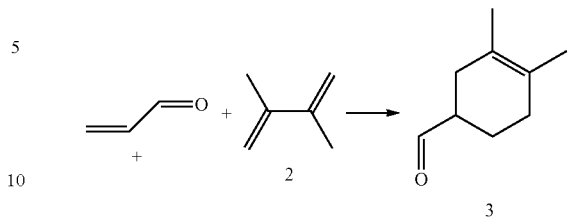

To a solution of 1 (708 mg, 12.62 mmol, 1.28 eq) in cyclohexane (1.4 mL) 2 was added (810 mg, 9.86 mmol, 1.0 eq) and the reaction mixture was stirred at 60° C. overnight. After completion, the suspension was concentrated under reduced pressure to give the product 3 (540 mg, yield=39.7%) as an oil.

Step 2: Preparation of 4

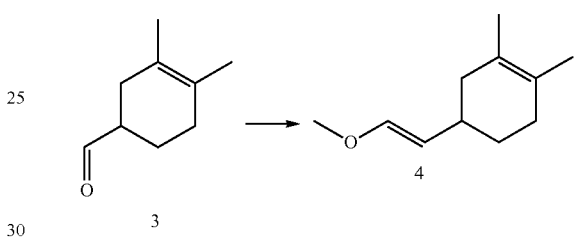

To a solution of (methoxymethyl)triphenylphosphonium chloride (6.0 g, 17.6 m mol, 4.87 eq) in THF (28 mL) was added potassium tert-butylate (1.86 g, 16.55 mmol, 4.6 eq) at 0° C. and the mixture was stirred for 20 min. Then, 3 (500 mg, 3.6 eq, 1.0 eq) in THF (8 mL) was added and the resulting mixture was stirred at room temperature. After completion, the mixture was poured into water, extracted with ethyl acetate and washed with brine. The combined organic phases were dried over $Na_2SO_4$, filtered and concentrated in vacuum. The residue was purified by column chromatography to give the product 4 (504 mg, yield=84.8%) as an oil.

Step 3: Preparation of 5

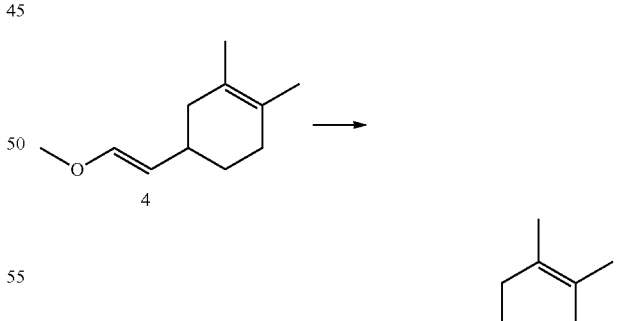

To a solution of 4 (1.0 g, 6.0 mmol, 1.0 eq) in THF (30 mL, c=0.2) was added aq.HCl (6N, 15 mL, 90 mmol, 15.0 eq) and the reaction mixture was stirred at room temperature for 1.5 h. After completion, water (25 mL) was added and the mixture was extracted by EA (20 mL×3). The combined organic phases were washed with brine, dried over $Na_2SO_4$, filtered and concentrated under reduced pressure. The residue was purified by column chromatography to give the product 5 (897 mg, yield=98%) as an oil.
Step 4: Preparation of 6

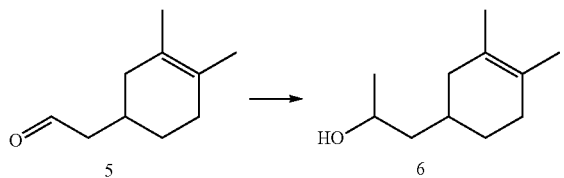

To a solution of 5 (600 mg, 3.95 mmol, 1.0 eq) in THF (8 mL, c=0.5) was added dropwise CH₃MgBr (3N, 1.4 mL, 4.14 mmol, 1.05 eq) at 0° C. for 20 min and then the mixture was stirred at room temperature for 1 h. After completion, the mixture was poured into water, extracted with ethyl acetate and washed with brine. The combined organic phases were dried over Na₂SO₄, filtered and concentrated in vacuum to give the crude product 6 (575.6 mg, yield=87.8%) as an oil.
Step 5: Preparation of 7

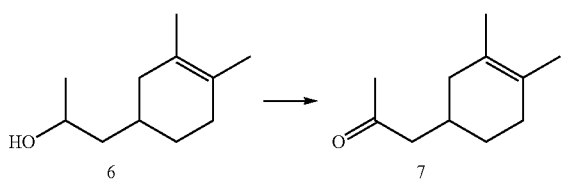

To a solution of 6 (550 mg, 3.57 mmol, 1.0 eq) in DCM (18 mL, c=0.2) was added PCC (1.15 g, 15.36 mmol, 1.5 eq) and the reaction mixture was stirred at room temperature overnight. After completion, the resulting mixture was filtered through a pad of celite and the filtrate was concentrated to dryness. The residue was purified by column chromatography to give the product 7 (150 mg, yield=27.6%) as an oil.
Step 6: Preparation of B162

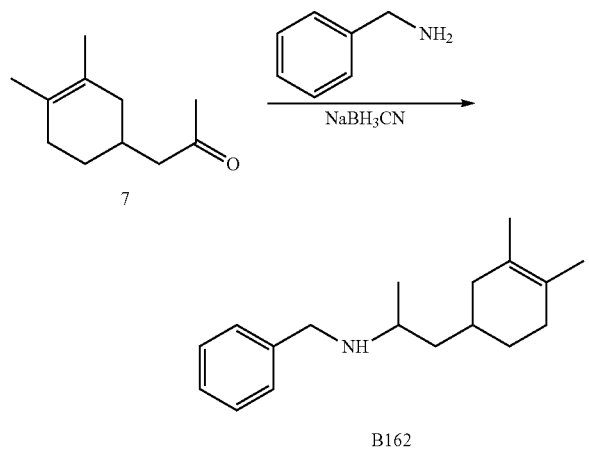

To a solution of 7 (60 mg, 0.361 mmol, 1.0 eq) in MeOH (1.8 mL, c=0.2) was added benzylamine (155 mg, 1.444 mmol, 4.0 eq) and MgSO₄ (60 mg) and the reaction mixture was stirred at 25° C. for 1 h. Then, AcOH (0.1 mL) and NaBH₃CN (68 mg, 1.083 mmol, 3.0 eq) was added and the reaction mixture was stirred at 80° C. overnight. After completion, the suspension was concentrated in vacuum and the residue was purified by column chromatography to give the desired product B162 (3.5 mg, yield=4%) as a yellow solid. ¹H NMR (400 MHz, DMSO): δ7.59-7.32 (m, 5H), 4.13-4.05 (m, 2H), 2.82-2.73 (m, 1H), 1.75-1.20 (m, 18H). Mass: m/z=258 [M+H]⁺

B385:
N-(2-cyclobutoxybenzyl)-1-cyclohexylpropan-2-amine

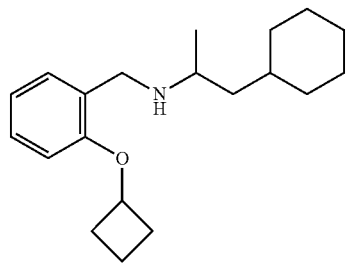 [SMILES: CC(CC1CCCCC1)NCc1ccccc1OC1CCC1]

(2-cyclobutoxyphenyl)methanamine (0.5 mmol) and 1-cyclohexylpropan-2-one (0.55 mmol) were dissolved in 0.6 ml MeOH, heated at 100° C. for 2 hours; then the mixture was cooled, NaBH₄ (0.5 mmol) was added and stirred for 4 hours. The mixture was heated for 2 hours at 60° C.; 3 ml of methanol and 0.2 g of C-18 chromatographic phase were added, stirred for 2 hours, filtered, evaporated. The residue was purified by HPLC. Yield: 39%.
1H NMR (400 MHz, Chloroform-d) δ 7.24-7.12 (m, 2H), 6.87 (t, J=7.4 Hz, 1H), 6.69 (d, J=8.1 Hz, 1H), 4.66 (p, J=7.2 Hz, 1H), 3.83 (d, J=13.0 Hz, 1H), 3.70 (d, J=13.0 Hz, 1H), 2.69 (h, J=6.4 Hz, 1H), 2.47 (dtt, J=12.3, 6.7, 2.7 Hz, 2H), 2.19 (d, J=10.1 Hz, 1H), 2.14 (d, J=10.2 Hz, 1H), 1.87 (q, J=10.0 Hz, 2H), 1.79-1.61 (m, 5H), 1.60 (s, 1H), 1.42-1.22 (m, 2H), 1.19 (s, 3H), 1.18-1.08 (m, 2H), 1.05 (d, J=6.2 Hz, 3H), 0.86 (s, 1H), 0.81 (dd, J=12.1, 4.0 Hz, 1H). m/z=302.3

B386: N-(2-(bicyclo[2.2.1]heptan-2-ylmethoxy)benzyl)-1-cyclohexylpropan-2-amine

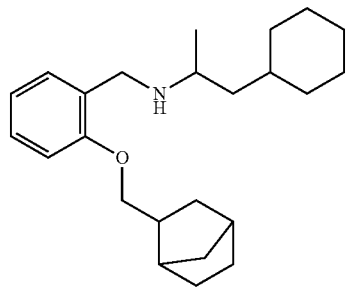 [SMILES: CC(CC1CCCCC1)NCc1ccccc1OCC1CC2CCC1C2]

1-cyclohexylpropan-2-amine (0.5 mmol) and 2-(bicyclo[2.2.1]heptan-2-ylmethoxy)benzaldehyde (0.55 mmol) were dissolved in 0.6 ml MeOH, heated at 100° C. for 2 hours; then the mixture was cooled, NaBH₄ (0.5 mmol) was added and stirred for 4 hours. The mixture was heated for 2 hours at 60° C.; 3 ml of methanol and 0.2 g of C-18 chromatographic phase were added, stirred for 2 hours, filtered, evaporated. The residue was purified by HPLC. Yield: 42%.

1H NMR (400 MHz, DMSO-d6) δ 7.26-7.12 (m, 3H), 7.00-6.81 (m, 3H), 3.97 (q, J=7.8 Hz, 1H), 3.82 (q, J=8.6 Hz, 1H), 3.70 (dt, J=14.5, 6.4 Hz, 3H), 3.59 (d, J=11.8 Hz, 2H), 2.56 (p, J=6.0 Hz, 2H), 2.32 (s, 1H), 2.27 (s, 1H), 2.25-2.17 (m, 2H), 1.89 (p, J=7.4 Hz, 1H), 1.73 (t, J=12.1 Hz, 1H), 1.57 (d, J=11.6 Hz, 8H), 1.53-1.43 (m, 5H), 1.37 (d, J=9.9 Hz, 2H), 1.28 (dt, J=17.8, 7.4 Hz, 5H), 1.17 (s, 2H), 1.11 (t, J=11.6 Hz, 5H), 1.04 (d, J=7.9 Hz, 2H), 0.95 (d, J=5.7 Hz, 4H), 0.80 (d, J=10.1 Hz, 2H), 0.75 (s, 2H). m/z=356.2

B387: 1-cyclohexyl-N-(2-(cyclohexyloxy)benzyl)propan-2-amine

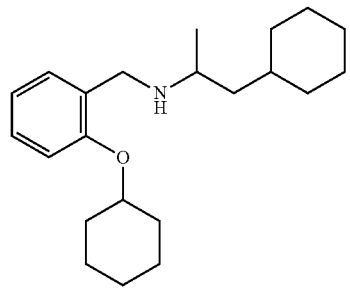 [SMILES: CC(CC1CCCCC1)NCc1ccccc1OC1CCCCC1]

(2-(cyclohexyloxy)phenyl)methanamine (0.5 mmol) and 1-cyclohexylpropan-2-one (0.55 mmol) were dissolved in 0.6 ml MeOH, heated at 100° C. for 2 hours; then the mixture was cooled, NaBH₄ (0.5 mmol) was added and stirred for 4 hours. The mixture was heated for 2 hours at 60° C.; 3 ml of methanol and 0.2 g of C-18 chromatographic phase were added, stirred for 2 hours, filtered, evaporated. The residue was purified by HPLC. Yield: 51%.

1H NMR (400 MHz, DMSO-d6) δ 7.24 (d, J=7.4 Hz, 1H), 7.15 (t, J=7.8 Hz, 1H), 6.96 (d, J=8.2 Hz, 1H), 6.83 (t, J=7.4 Hz, 1H), 4.43-4.34 (m, 1H), 3.69 (d, J=13.4 Hz, 1H), 3.58 (d, J=13.4 Hz, 1H), 2.58 (q, J=6.3 Hz, 1H), 1.87 (d, J=11.8 Hz, 2H), 1.69 (s, 2H), 1.58 (d, J=10.5 Hz, 6H), 1.50 (t, J=8.4 Hz, 4H), 1.35 (dt, J=20.6, 10.4 Hz, 4H), 1.30-1.21 (m, 1H), 1.11 (td, J=22.2, 19.3, 9.7 Hz, 4H), 0.96 (d, J=6.1 Hz, 3H), 0.83 (dd, J=18.2, 7.7 Hz, 1H), 0.75 (d, J=11.4 Hz, 1H). m/z=330.2

B388: 1-cyclohexyl-N-(2-((2-iodobenzyl)oxy)benzyl)propan-2-amine

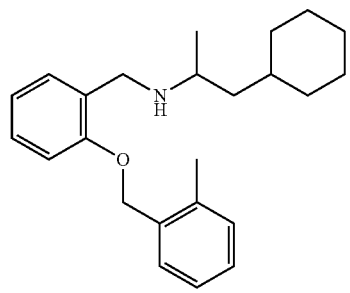

1-cyclohexylpropan-2-amine (0.5 mmol), 2-((2-iodobenzyl)oxy)benzaldehyde (0.5 mmol) were dissolved in 0.6 ml MeOH, heated at 100° C. for 2 hours; then the mixture was cooled, NaBH₄ (0.5 mmol) was added and stirred for 4 hours. The mixture was heated for 2 hours at 60° C.; then 3 ml of methanol and 0.2 g of C-18 chromatographic phase were added, stirred for 2 hours, filtered, evaporated. The residue was purified using HPLC. Yield: 39%.

1H NMR (400 MHz, Chloroform-d) δ 7.88 (d, J=7.9 Hz, 1H), 7.52 (d, J=7.6 Hz, 1H), 7.38 (t, J=7.5 Hz, 1H), 7.32-7.19 (m, 3H), 7.04 (t, J=7.7 Hz, 1H), 6.99-6.89 (m, 2H), 5.07 (s, 2H), 3.95 (d, J=13.1 Hz, 1H), 3.82 (d, J=13.1 Hz, 1H), 2.72 (q, J=6.4 Hz, 1H), 1.60 (d, J=9.5 Hz, 5H), 1.52 (d, J=13.1 Hz, 1H), 1.35 (dt, J=13.3, 6.6 Hz, 1H), 1.18-1.02 (m, 7H), 0.80 (d, J=11.4 Hz, 2H). m/z=464.2

B389: 1-cyclohexyl-N-(2-((2-methylcyclohexyl)oxy)benzyl)propan-2-amine

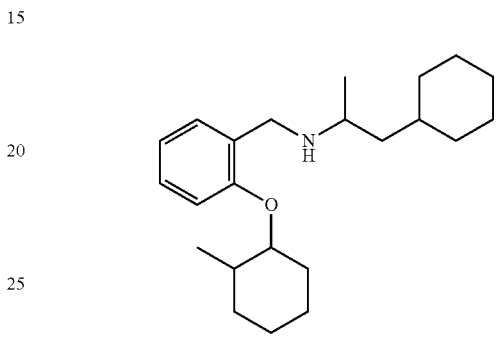

(2-((2-methylcyclohexyl)oxy)phenyl)methanamine (0.5 mmol) and 1-cyclohexylpropan-2-one (0.55 mmol) were dissolved in 0.6 ml MeOH, heated at 100° C. for 2 hours; then the mixture was cooled, NaBH₄ (0.5 mmol) was added and stirred for 4 hours. The mixture was heated for 2 hours at 60° C.; 3 ml of methanol and 0.2 g of C-18 chromatographic phase were added, stirred for 2 hours, filtered, evaporated. The residue was purified by HPLC. Yield: 38%.

1H NMR (400 MHz,) δ 7.24 (d, J=7.4 Hz, 1H), 7.15 (t, J=7.8 Hz, 1H), 6.94 (t, J=7.2 Hz, 1H), 6.82 (t, J=7.6 Hz, 1H), 3.92 (td, J=9.6, 3.8 Hz, 1H), 3.71 (ddd, J=20.0, 13.4, 4.8 Hz, 1H), 3.67-3.55 (m, 1H), 3.33 (s, 2H), 2.59 (dt, J=20.5, 9.4 Hz, 1H), 2.50 (s, 1H), 2.05 (d, J=12.5 Hz, 1H), 1.78 (s, 1H), 1.70-1.46 (m, 8H), 1.40 (dt, J=16.3, 10.6 Hz, 1H), 1.30 (s, 6H), 1.27 (d, J=8.9 Hz, 1H), 1.28-1.02 (m, 4H), 0.97 (p, J=7.6 Hz, 5H), 0.78 (t, J=14.1 Hz, 2H). m/z=344.2

B390: N-(2-(bicyclo[2.2.1]heptan-2-yloxy)benzyl)-1-cyclohexylpropan-2-amine

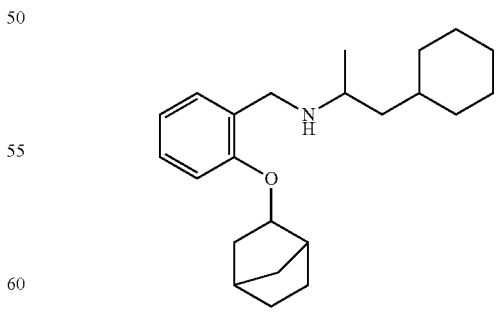

(2-(bicyclo[2.2.1]heptan-2-yloxy)phenyl)methanamine (0.5 mmol) and 1-cyclohexylpropan-2-one (0.55 mmol) were dissolved in 0.6 ml MeOH, heated at 100° C. for 2 hours; then the mixture was cooled, NaBH₄ (0.5 mmol) was added and stirred for 4 hours. The mixture was heated for 2 hours at 60° C.; 3 ml of methanol and 0.2 g of C-18 chromatographic phase were added, stirred for 2 hours, filtered, evaporated. The residue was purified by HPLC. Yield: 27%.

1H NMR (400 MHz, Chloroform-d) δ 7.23-7.13 (m, 2H), 6.86 (t, J=7.4 Hz, 1H), 6.76 (dd, J=8.2, 4.2 Hz, 1H), 4.61 (dt, J=8.8, 3.9 Hz, 1H), 3.85 (d, J=13.0 Hz, 1H), 3.70 (dd, J=13.0, 3.5 Hz, 1H), 2.68 (h, J=6.0 Hz, 1H), 2.60 (d, J=4.5 Hz, 1H), 2.29 (d, J=4.9 Hz, 1H), 2.06 (ddt, J=13.1, 7.5, 4.2 Hz, 1H), 2.02-1.91 (m, 1H), 1.80 (s, 1H), 1.63 (d, J=7.1 Hz, 4H), 1.56-1.42 (m, 1H), 1.39 (s, 1H), 1.36 (dd, J=6.4, 3.3 Hz, 1H), 1.29 (ddd, J=33.2, 8.7, 5.1 Hz, 1H), 1.14 (ddd, J=13.0, 7.2, 3.7 Hz, 3H), 1.05 (d, J=6.2 Hz, 3H), 0.91-0.72 (m, 2H). m/z=342.2

B391: 1-cyclohexyl-N-(2-((3-methylcyclohexyl)oxy)benzyl)propan-2-amine

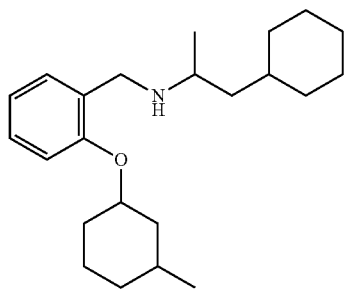 [SMILES: CC1CCCC(Oc2ccccc2CNC(C)CC2CCCCC2)C1]

(2-((3-methylcyclohexyl)oxy)phenyl)methanamine (0.5 mmol) and 1-cyclohexylpropan-2-one (0.55 mmol) were dissolved in 0.6 ml MeOH, heated at 100° C. for 2 hours; then the mixture was cooled, NaBH$_4$ (0.5 mmol) was added and stirred for 4 hours. The mixture was heated for 2 hours at 60° C.; 3 ml of methanol and 0.2 g of C-18 chromatographic phase were added, stirred for 2 hours, filtered, evaporated. The residue was purified by HPLC. Yield: 41%.

1H NMR (400 MHz,) δ 7.23 (d, J=7.2 Hz, 1H), 7.15 (t, J=7.9 Hz, 1H), 6.95 (dd, J=20.0, 8.3 Hz, 1H), 6.82 (q, J=5.6, 3.9 Hz, 1H), 4.26 (td, J=10.7, 10.0, 5.3 Hz, 1H), 3.75-3.51 (m, 2H), 3.33 (s, 1H), 2.58 (tt, J=10.9, 5.3 Hz, 1H), 2.50 (s, 1H), 2.05 (d, J=11.9 Hz, 1H), 1.87 (t, J=14.7 Hz, 1H), 1.74 (d, J=13.8 Hz, 1H), 1.58 (d, J=14.6 Hz, 7H), 1.51 (d, J=9.3 Hz, 1H), 1.44-1.25 (m, 1H), 1.28-1.03 (m, 3H), 0.91 (tdd, J=26.7, 21.1, 11.6 Hz, 6H), 0.75 (d, J=11.5 Hz, 1H). m/z=344.2

B392: 1-cyclohexyl-N-(2-((2-ethylcyclohexyl)oxy)benzyl)propan-2-amine

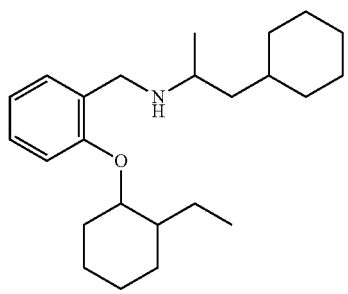 [SMILES: CCC1CCCCC1Oc1ccccc1CNC(C)CC1CCCCC1]

2-((2-ethylcyclohexyl)oxy)phenyl)methanamine (0.5 mmol) and 1-cyclohexylpropan-2-one (0.55 mmol) were dissolved in 0.6 ml MeOH, heated at 100 C for 2 hours; then the mixture was cooled, NaBH$_4$ (0.5 mmol) was added and stirred for 4 hours. The mixture was heated for 2 hours at 60° C.; 3 ml of methanol and 0.2 g of C-18 chromatographic phase were added, stirred for 2 hours, filtered, evaporated. The residue was purified by HPLC. Yield: 35%.

1H NMR (400 MHz, Chloroform-d) δ 7.24-7.13 (m, 2H), 6.85 (d, J=7.8 Hz, 2H), 4.56 (s, 1H), 3.91-3.78 (m, 1H), 3.73 (t, J=13.2 Hz, 1H), 2.77-2.64 (m, 1H), 2.10 (dq, J=8.0, 4.0 Hz, 1H), 1.86-1.70 (m, 2H), 1.67 (s, 1H), 1.65-1.57 (m, 4H), 1.60-1.51 (m, 1H), 1.47 (dt, J=14.5, 6.5 Hz, 2H), 1.34 (dhept, J=22.3, 7.5 Hz, 2H), 1.22-1.10 (m, 2H), 1.06 (d, J=6.1 Hz, 3H), 0.95-0.77 (m, 5H). m/z=358.2

B393: 1-cyclohexyl-N-(2-((octahydro-1H-4,7-methanoinden-5-yl)oxy)benzyl)propan-2-amine

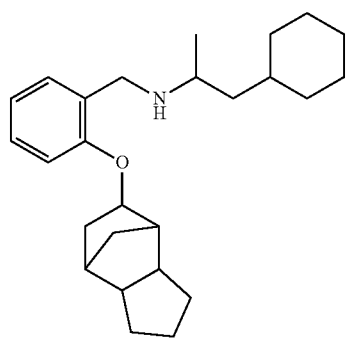 [SMILES: CC(CC1CCCCC1)NCc1ccccc1OC1CC2CC1C1CCCC21]

(2-((octahydro-1H-4,7-methanoinden-5-yl)oxy)phenyl) methanamine (0.5 mmol) and 1-cyclohexylpropan-2-one (0.55 mmol) were dissolved in 0.6 ml MeOH, heated at 100° C. for 2 hours; then the mixture was cooled, NaBH$_4$ (0.5 mmol) was added and stirred for 4 hours. The mixture was heated for 2 hours at 60° C.; 3 ml of methanol and 0.2 g of C-18 chromatographic phase were added, stirred for 2 hours, filtered, evaporated. The residue was purified by HPLC. Yield: 28%.

1H NMR (400 MHz, DMSO-d6) δ 7.23 (d, J=7.4 Hz, 1H), 7.15 (t, J=7.8 Hz, 1H), 6.91-6.79 (m, 2H), 4.64 (dt, J=8.4, 3.7 Hz, 1H), 3.72-3.64 (m, 1H), 3.58 (dd, J=13.5, 5.7 Hz, 1H), 2.63-2.50 (m, 2H), 2.33 (d, J=4.1 Hz, 1H), 2.16-2.05 (m, 1H), 1.98 (d, J=4.6 Hz, 1H), 1.95-1.73 (m, 3H), 1.60 (t, J=12.1 Hz, 6H), 1.50 (d, J=10.6 Hz, 2H), 1.42 (d, J=10.8 Hz, 1H), 1.39-1.20 (m, 2H), 1.17 (s, 1H), 1.16-1.00 (m, 3H), 0.96 (d, J=6.2 Hz, 4H), 0.82 (dp, J=28.9, 8.7 Hz, 2H). m/z=382.2

Synthesis of compounds B394, B395, B396, and B404 was performed according to the following general scheme.

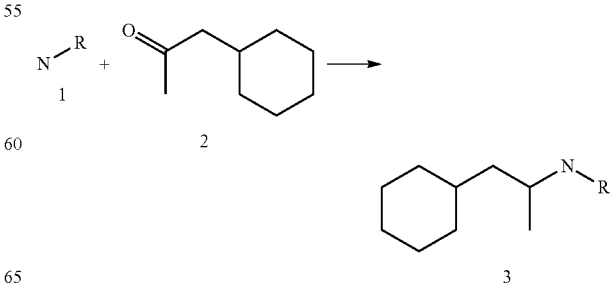

Amine 1 (0.5 mmol) and ketone 2 (0.55 mmol) were dissolved in 0.6 ml MeOH, heated at 100° C. for 2 hours; then the mixture was cooled, NaBH₄ (0.5 mmol) was added and stirred for 4 hours. The mixture was heated for 2 hours at 60° C.; 3 ml of methanol and 0.2 g of C-18 chromatographic phase were added, stirred for 2 hours, filtered, evaporated. The residue was purified by HPLC. Yields: 29-44%.

B394: 1-cyclohexyl-N-(2-((4-methylcyclohexyl)oxy)benzyl)propan-2-amine

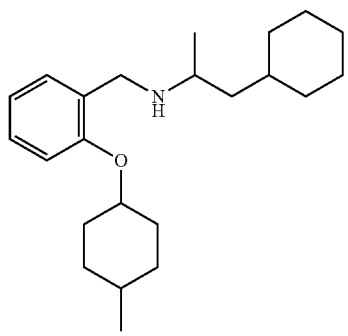 [SMILES: CC1CCC(Oc2ccccc2CNC(C)CC2CCCCC2)CC1]

1H NMR (400 MHz,) S 7.24 (t, J=6.9 Hz, 1H), 7.15 (t, J=7.8 Hz, 1H), 6.95 (dd, J=13.9, 8.2 Hz, 1H), 6.83 (t, J=7.5 Hz, 1H), 4.23 (tt, J=10.2, 4.4 Hz, 1H), 3.76-3.52 (m, 2H), 3.33 (s, 1H), 2.59 (dq, J=18.5, 6.1 Hz, 1H), 2.50 (s, 1H), 2.08-2.00 (m, 2H), 1.90 (d, J=14.0 Hz, 1H), 1.75-1.67 (m, 2H), 1.59 (s, 3H), 1.58-1.53 (m, 4H), 1.53-1.44 (m, 1H), 1.38 (t, J=11.1 Hz, 1H), 1.29 (s, 2H), 1.29-1.19 (m, 1H), 1.19-0.83 (m, 11H), 0.83-0.71 (m, 2H). m/z=344.2

B395: N-(2-(bicyclo[2.2.2]octan-2-yloxy)benzyl)-1-cyclohexylpropan-2-amine

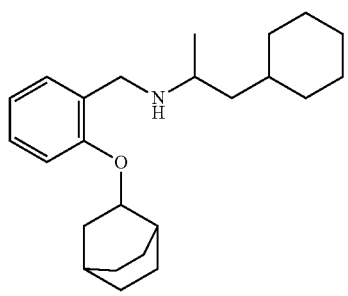 [SMILES: CC(CC1CCCCC1)NCc1ccccc1OC1CC2CCC1CC2]

1H NMR (400 MHz, DMSO-d6) δ 17.91 (s, 1H), 7.24 (d, J=7.4 Hz, 1H), 7.15 (t, J=7.8 Hz, 1H), 6.88 (d, J=8.2 Hz, 1H), 6.82 (t, J=7.4 Hz, 1H), 4.52 (d, J=9.1 Hz, 1H), 3.76-3.66 (m, 1H), 3.59 (t, J=13.2 Hz, 1H), 2.59 (p, J=6.3 Hz, 1H), 2.08 (t, J=11.7 Hz, 1H), 1.95-1.80 (m, 2H), 1.67-1.36 (m, 14H), 1.25 (tt, J=8.3, 4.5 Hz, 2H), 1.19-0.93 (m, 6H), 0.77 (dq, J=22.3, 11.0 Hz, 2H); m/z=356.2

B396: 1-cyclohexyl-N-(2-((4,4-difluorocyclohexyl)oxy)benzyl)propan-2-amine

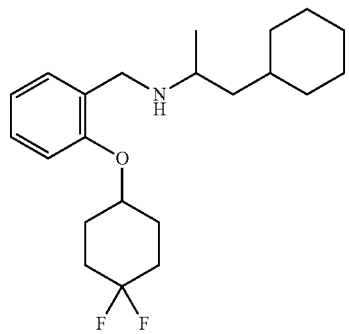 [SMILES: CC(CC1CCCCC1)NCc1ccccc1OC1CCC(F)(F)CC1]

1H NMR (400 MHz, DMSO-d6) δ 7.29 (d, J=7.4 Hz, 1H), 7.19 (t, J=7.8 Hz, 1H), 7.02 (d, J=8.2 Hz, 1H), 6.88 (t, J=7.4 Hz, 1H), 4.69-4.62 (m, 1H), 3.69 (d, J=13.3 Hz, 1H), 3.60 (d, J=13.3 Hz, 1H), 2.60 (q, J=6.3 Hz, 1H), 2.01 (s, 6H), 1.89 (dt, J=8.6, 3.9 Hz, 4H), 1.59 (d, J=10.8 Hz, 5H), 1.50 (d, J=15.8 Hz, 1H), 1.28 (dq, J=13.1, 6.6, 5.9 Hz, 2H), 1.21-1.11 (m, 2H), 1.14-1.08 (m, 1H), 1.08-1.01 (m, 1H), 0.97 (d, J=6.1 Hz, 3H), 0.79 (p, J=12.5 Hz, 2H). m/z=366.2

B404: N-(2-(((1R,3S,5r,7r)-adamantan-2-yl)oxy)benzyl)-1-cyclohexylpropan-2-amine

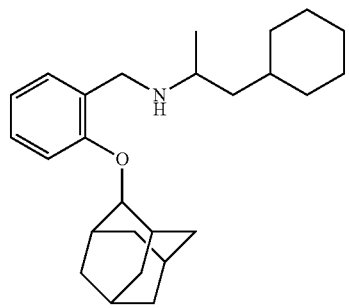 [SMILES: CC(CC1CCCCC1)NCc1ccccc1OC1C2CC3CC(C2)CC1C3]

1H NMR (400 MHz, DMSO-d6) δ 7.25 (dd, J=7.4, 1.8 Hz, 1H), 7.14 (td, J=7.8, 1.8 Hz, 1H), 6.92 (d, J=8.1 Hz, 1H), 6.82 (t, J=7.3 Hz, 1H), 4.53 (d, J=3.3 Hz, 1H), 3.75 (d, J=13.3 Hz, 1H), 3.64 (d, J=13.3 Hz, 1H), 2.61 (q, J=6.2 Hz, 1H), 2.06 (d, J=17.7 Hz, 4H), 1.82 (s, 6H), 1.71 (s, 2H), 1.57 (q, J=13.8 Hz, 8H), 1.25 (dt, J=13.1, 6.0 Hz, 2H), 1.10 (dt, J=17.7, 10.5 Hz, 3H), 1.06-0.92 (m, 3H), 0.78 (dt, J=21.3, 10.5 Hz, 2H). m/z=382.2

B397: 2-(((1-cyclohexylpropan-2-yl)amino)methyl)-N-(2-fluorobenzyl)aniline dihydrochloride

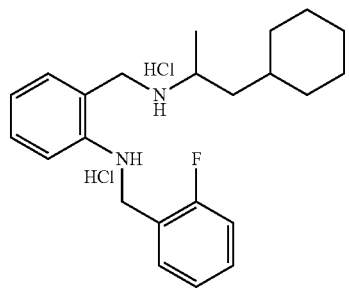 [SMILES: CC(CC1CCCCC1)NCc1ccccc1NCc1ccccc1F ; Cl ; Cl]

Step A:

tert-butyl (2-aminobenzyl)(1-cyclohexylpropan-2-yl)carbamate (1 mmol) and 2-fluorobenzaldehyde (1 mmol) were dissolved in 0.6 ml MeOH, heated at 100 C for 2 hours; then the mixture was cooled, NaBH$_4$ (1 mmol) was added and stirred for 4 hours. The mixture was heated for 2 hours at 60° C., then cooled and filtered.

Step B:

To a solution of tert-butyl (1-cyclohexylpropan-2-yl)(2-((2-fluorobenzyl)amino)benzyl)carbamate (0.5 mmol) in dichloromethane (5 mL) was slowly added trifluoroacetic acid (2.5 mmol) at 0° C. The reaction solution was stirred at room temperature for 5 h, and then 1N NaOH was added. The mixture was extracted with dichloromethane, and the organic layer was washed with brine, dried (Na$_2$SO$_4$), and filtered. The solvent was evaporated and the residue was purified by HPLC. Yield: 27%.

1H NMR (400 MHz, DMSO-d6) δ 9.16 (s, 1H), 8.97 (s, 1H), 7.46 (t, J=7.9 Hz, 1H), 7.32 (dd, J=19.2, 7.4 Hz, 2H), 7.19 (t, J=9.5 Hz, 1H), 7.13 (t, J=7.6 Hz, 2H), 6.64 (t, J=7.4 Hz, 1H), 6.54-6.45 (m, 2H), 4.39 (s, 2H), 4.14 (s, 2H), 1.73 (s, 1H), 1.62 (t, J=14.0 Hz, 5H), 1.45-1.37 (m, 2H), 1.32 (d, J=6.3 Hz, 3H), 1.22 (s, 2H), 1.18-1.11 (m, 3H), 0.92 (d, J=11.9 Hz, 1H), 0.84-0.77 (m, 2H). m/z=355.2

B398: N-(2-(((1-cyclohexylpropan-2-yl)amino)methyl)phenyl)-2-fluorobenzamide hydrochloride

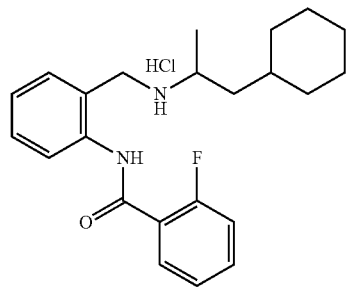 [SMILES: CC(CC1CCCCC1)NCc1ccccc1NC(=O)c1ccccc1F ; Cl]

Step A:

tert-butyl (2-aminobenzyl)(1-cyclohexylpropan-2-yl)carbamate (0.5 mmol) and CDI (1 mmol) were dissolved in 0.6 ml CH$_3$CN; the mixture was kept at a temperature of 70° C. for 1 hour, then the 2-fluorobenzoic acid (0.5 mmol) was added. The mixture was heated for 2 hours at 70° C., then filtered, evaporated. The residue was purified by HPLC.

Step B:

To a solution of tert-butyl (1-cyclohexylpropan-2-yl)(2-(2-fluorobenzamido)benzyl)carbamate (0.5 mmol) in dichloromethane (5 mL) was slowly added trifluoroacetic acid (2.5 mmol) at 0° C. The reaction solution was stirred at room temperature for 5 h; then 1N NaOH was added. The mixture was extracted with dichloromethane, and the organic layer was washed with brine, dried (Na$_2$SO$_4$), and filtered. The solvent was evaporated, and the residue was purified by HPLC. Yield: 24%.

1H NMR (400 MHz, DMSO-d6) δ 10.44 (s, 1H), 9.31 (s, 1H), 9.07 (d, J=14.5 Hz, 1H), 7.81 (t, J=7.5 Hz, 1H), 7.75 (d, J=7.7 Hz, 1H), 7.65-7.57 (m, 1H), 7.49 (s, 2H), 7.37 (t, J=9.0 Hz, 3H), 4.11 (s, 2H), 1.62 (d, J=13.4 Hz, 6H), 1.40 (s, 1H), 1.36 (d, J=11.8 Hz, 1H), 1.29 (d, J=6.3 Hz, 2H), 1.13 (dd, J=23.8, 12.8 Hz, 3H), 0.92-0.76 (m, 2H). m/z=369.2

B405: 1-cyclohexyl-N-(2-(2-fluorophenoxy)benzyl)propan-2-amine

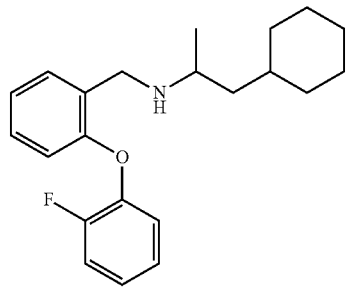 [SMILES: CC(CC1CCCCC1)NCc1ccccc1Oc1ccccc1F]

(2-(2-fluorophenoxy)phenyl)methanamine (0.5 mmol) and 1-cyclohexylpropan-2-one (0.5 mmol) were dissolved in 0.6 ml MeOH, heated at 100° C. for 3 hours; then the mixture was cooled, NaBH$_4$ (0.5 mmol) was added and stirred for 4 hours. The mixture was heated for 2 hours at 60° C.; then 3 ml of methanol and 0.2 g of C-18 chromatographic phase were added, stirred for 2 hours, filtered, evaporated. The residue was purified by HPLC. Yield: 28%. m/z=342.2

B406: 3-(((2-cyclohexylethyl)amino)methyl)-N-methylaniline

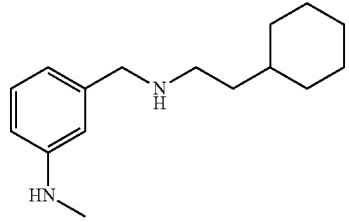 [SMILES: CNc1cccc(CNCCC2CCCCC2)c1]

Step A:

tert-butyl (3-(aminomethyl)phenyl)(methyl)carbamate (1 mmol) and 2-cyclohexylacetaldehyde (1 mmol) were dissolved in 0.6 ml MeOH, heated at 80° C. for 2 hours; then the mixture was cooled, NaBH$_4$ (1 mmol) was added and stirred for 4 hours. The mixture was heated for 2 hours at 60° C., then cooled and filtered. Yield: 43%.

Step B:

To a solution of tert-butyl (3-(((2-cyclohexylethyl)amino)methyl)phenyl)(methyl)carbamate (0.5 mmol) in dichloromethane (5 mL) was slowly added trifluoroacetic acid (2.5 mmol) at 0° C. The reaction was stirred at room temperature for 5 h, and then 1N NaOH was added. The mixture was extracted with dichloromethane, and the organic layer was washed with brine, dried (Na$_2$SO$_4$), and filtered. The solvent was evaporated, and the residue was purified by HPLC. Yield: 23%.

1H NMR (400 MHz, DMSO-d6) δ 6.98 (t, J=7.7 Hz, 1H), 6.51-6.43 (m, 2H), 6.36 (dd, J=7.9, 2.4 Hz, 1H), 5.46 (d, J=6.3 Hz, 1H), 3.54 (s, 2H), 2.64 (d, J=5.0 Hz, 3H), 2.54-2.43 (m, 3H), 1.63 (d, J=12.4 Hz, 5H), 1.29 (t, J=5.7 Hz, 3H), 1.24-1.05 (m, 3H), 0.84 (q, J=11.1 Hz, 2H). m/z=247.2

B407: 5-(((2-(((1-cyclohexylpropan-2-yl)amino)methyl)phenyl)thio)methyl)-3-methyl oxazolidin-2-one

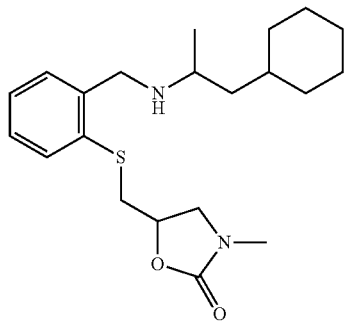 [SMILES: CC(CC1CCCCC1)NCc1ccccc1SCC1CN(C)C(=O)O1]

1-cyclohexylpropan-2-amine (0.5 mmol) and 2-(((3-methyl-2-oxooxazolidin-5-yl)methyl)thio)benzaldehyde (0.5 mmol) were dissolved in 0.6 ml MeOH, heated at 100° C. for 4 hours; then the mixture was cooled, NaBH₄ (0.5 mmol) was added and stirred for 4 hours. The mixture was heated for 2 hours at 60° C.; 3 ml of methanol and 0.2 g of C-18 chromatographic phase were added, stirred for 2 hours, filtered, evaporated. The residue was purified by HPLC. Yield: 31%.

1H NMR (400 MHz, Chloroform-d) δ 7.39 (dt, J=6.4, 1.8 Hz, 1H), 7.34 (d, J=5.7 Hz, 1H), 7.27-7.18 (m, 3H), 4.53 (ddd, J=9.2, 4.8, 2.6 Hz, 1H), 3.92 (d, J=13.0 Hz, 1H), 3.85-3.78 (m, 1H), 3.63 (t, J=8.7 Hz, 1H), 3.35 (ddd, J=9.4, 7.5, 3.9 Hz, 2H), 3.01 (ddd, J=13.5, 8.8, 4.5 Hz, 1H), 2.85 (d, J=1.7 Hz, 3H), 2.77-2.68 (m, 1H), 1.33 (s, 3H), 1.22 (d, J=11.8 Hz, 1H), 1.14 (d, J=11.0 Hz, 4H), 1.07 (dd, J=6.2, 1.7 Hz, 3H), 0.84 (s, 2H). m/z=377.2

B408: 1-cyclohexyl-N-(2-((4-fluorobenzyl)oxy)benzyl)propan-2-amine

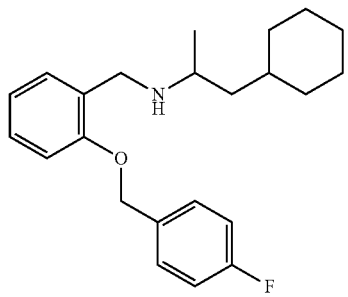 [SMILES: CC(CC1CCCCC1)NCc1ccccc1OCc1ccc(F)cc1]

1-cyclohexylpropan-2-amine (0.5 mmol) and 2-((4-fluorobenzyl)oxy)benzaldehyde (0.5 mmol) were dissolved in 0.6 ml MeOH, heated at 100° C. for 2 hours; then the mixture was cooled, NaBH₄ (0.5 mmol) was added and stirred for 4 hours. The mixture was heated for 2 hours at 60° C.; then 3 ml of methanol and 0.2 g of C-18 chromatographic phase were added, stirred for 2 hours, filtered, evaporated. The residue was purified by HPLC. Yield: 45%.

1H NMR (400 MHz, DMSO-d6) δ 7.46 (t, J=6.7 Hz, 2H), 7.24 (d, J=7.5 Hz, 1H), 7.14 (d, J=8.3 Hz, 1H), 7.09 (t, J=8.7 Hz, 2H), 6.93 (d, J=8.2 Hz, 1H), 6.86 (t, J=7.5 Hz, 1H), 5.07 (s, 2H), 3.76 (d, J=13.4 Hz, 1H), 3.65 (d, J=13.3 Hz, 1H), 2.62 (s, 1H), 1.62 (s, 4H), 1.54 (s, 1H), 1.25 (d, J=9.4 Hz, 2H), 1.12 (s, 4H), 1.05 (d, J=6.9 Hz, 1H), 0.97 (d, J=6.1 Hz, 3H), 0.78 (s, 3H). m/z=356.2

B409: N-(2-(benzyloxy)benzyl)-1-cyclohexylpropan-2-amine

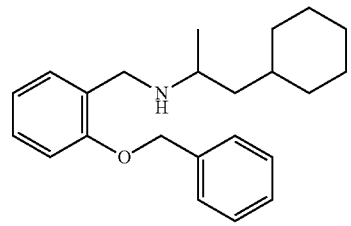 [SMILES: CC(CC1CCCCC1)NCc1ccccc1OCc1ccccc1]

1-cyclohexylpropan-2-amine (0.5 mmol) and 2-(benzyloxy)benzaldehyde (0.5 mmol) were dissolved in 0.6 ml MeOH, heated at 100° C. for 2 hours; then the mixture was cooled, NaBH₄ (0.5 mmol) was added and stirred for 4 hours. The mixture was heated for 2 hours at 60° C.; then 3 ml of methanol and 0.2 g of C-18 chromatographic phase were added, stirred for 2 hours, filtered, evaporated. The residue was purified by HPLC. Yield: 39%. 1H NMR (400 MHz, DMSO-d6) δ 7.43 (d, J=7.3 Hz, 2H), 7.36 (t, J=7.4 Hz, 2H), 7.32-7.26 (m, 1H), 7.24 (d, J=7.4 Hz, 1H), 7.15 (t, J=7.8 Hz, 1H), 6.94 (d, J=8.2 Hz, 1H), 6.86 (t, J=7.4 Hz, 1H), 5.10 (s, 2H), 3.78 (d, J=13.6 Hz, 1H), 3.66 (d, J=13.5 Hz, 1H), 2.63 (s, 1H), 1.60 (d, J=12.0 Hz, 5H), 1.26 (d, J=10.3 Hz, 2H), 1.12 (s, 5H), 0.97 (d, J=6.1 Hz, 2H), 0.80 (d, J=12.3 Hz, 2H). m/z=338.2

B410: 2-(2-(tetrahydro-2H-thiopyran-4-yl)ethyl)-1,4-dihydroisoquinolin-3(2H)-one

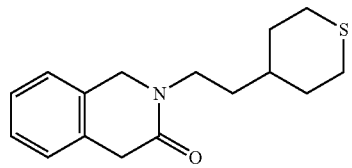 [SMILES: O=C1Cc2ccccc2CN1CCC1CCSCC1]

2-(tetrahydro-2H-thiopyran-4-yl)ethan-1-amine (0.5 mmol) and methyl 2-(2-(chloromethyl)phenyl)acetate (0.5 mmol) were mixed in 5 ml of DMF, and DIPEA (0.75 mmol) was added. The mixture was heated at 80° C. for 5 h, cooled; solvent was removed by evaporation and residue was purified by HPLC. Yield: 31%. 1H NMR (400 MHz, DMSO-d6) δ 7.23 (qd, J=10.9, 9.9, 5.4 Hz, 2H), 4.46 (s, 1H), 3.50 (s, 1H), 3.43 (t, J=7.4 Hz, 1H), 2.58-2.51 (m, 2H), 1.99 (d, J=9.9 Hz, 1H), 1.42 (s, 1H), 1.26 (s, 2H). m/z=276.0

B411: 2-(2-(cyclohex-1-en-1-yl)ethyl)-1,4-dihydroisoquinolin-3(2H)-one

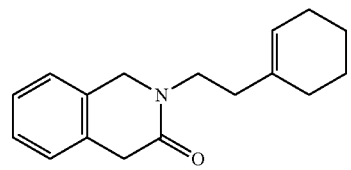 [SMILES: O=C1Cc2ccccc2CN1CCC1=CCCCC1]

2-(cyclohex-1-en-1-yl)ethan-1-amine (0.5 mmol) and methyl 2-(2-(chloromethyl)phenyl)acetate (0.5 mmol) were mixed in 5 ml of DMF, and DIPEA (0.75 mmol) was added. The mixture was heated at 80° C. for 5 h, cooled; the solvent was removed by evaporation, and the residue was purified by HPLC. Yield: 37%. 1H NMR (400 MHz, DMSO-d6) δ 7.23 (p, J=8.0 Hz, 2H), 5.32 (s, 0H), 4.46 (s, 1H), 3.32 (s, 1H), 2.12 (t, J=7.3 Hz, 1H), 1.94 (s, 1H), 1.84 (s, 1H), 1.53 (q, J=6.3, 5.7 Hz, 1H), 1.46 (d, J=6.5 Hz, 1H). m/z=256.2

B412: 2-(1-cyclohexylpropan-2-yl)-1,4-dihydroisoquinolin-3(2H)-one

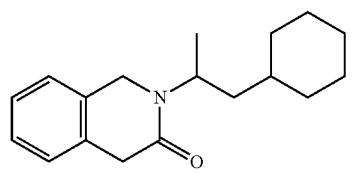 [SMILES: CC(CC1CCCCC1)N1Cc2ccccc2CC1=O]

1-cyclohexylpropan-2-amine (0.5 mmol) and methyl 2-(2-(chloromethyl)phenyl)acetate (0.5 mmol) were mixed in 5 ml of DMF; DIPEA (0.75 mmol) was added. The mixture was heated at 80° C. for 5 h, cooled; solvent was removed by evaporation and residue was purified by HPLC. Yield: 47%. Yellow gum. 1H NMR (400 MHz, DMSO-d6) δ 7.36-7.30 (m, 1H), 7.23 (p, J=4.7 Hz, 3H), 4.72 (dt, J=9.8, 6.2 Hz, 1H), 4.32 (d, J=15.5 Hz, 1H), 4.25 (d, J=15.4 Hz, 1H), 3.51 (s, 2H), 1.74 (d, J=12.8 Hz, 1H), 1.61-1.42 (m, 5H), 1.24 (ddd, J=14.0, 8.5, 5.5 Hz, 1H), 1.05 (d, J=6.8 Hz, 4H), 1.01 (s, 3H), 0.79 (dt, J=23.0, 11.9 Hz, 2H). m/z=272.2

B413: 2-(2-cyclohexylpropyl)-1,4-dihydroisoquinolin-3(2H)-one

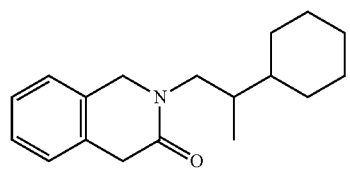 [SMILES: CC(CN1Cc2ccccc2CC1=O)C1CCCCC1]

2-cyclohexylpropan-1-amine (0.5 mmol) and methyl 2-(2-(chloromethyl)phenyl)acetate (0.5 mmol) were mixed in 5 ml of DMF; DIPEA (0.75 mmol) was added. The mixture was heated at 80° C. for 5 h, cooled; solvent was removed by evaporation, and residue was purified by HPLC. Yield: 39%. 1H NMR (400 MHz, DMSO-d6) δ 7.26 (dd, J=13.9, 6.6 Hz, 1H), 7.22 (t, J=5.3 Hz, 1H), 4.43 (d, J=2.7 Hz, 1H), 3.52 (s, 1H), 3.42-3.23 (m, 1H), 1.63 (dq, J=49.9, 12.8, 11.0 Hz, 3H), 1.16 (d, J=11.8 Hz, 1H), 1.13-1.04 (m, 1H), 0.72 (d, J=6.8 Hz, 1H). m/z=272.2

B414: (2-(((1-cyclohexylpropan-2-yl)amino)methyl)phenyl)methanesulfonamide

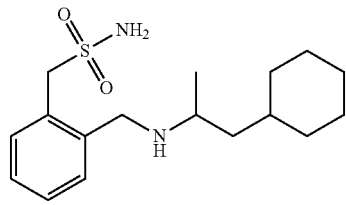

(2-(aminomethyl)phenyl)methanesulfonamide (0.5 mmol) and 1-cyclohexylpropan-2-one (0.5 mmol) were dissolved in 0.6 ml MeOH, heated at 100° C. for 2 hours; then the mixture was cooled, NaBH4 (0.5 mmol) was added and stirred for 4 hours. The mixture was heated for 2 hours at 60° C.; 3 ml of methanol and 0.2 g of C-18 chromatographic phase were added, stirred for 2 hours, filtered, evaporated. The residue was purified by HPLC. Yield: 51%.

1H NMR (400 MHz, Chloroform-d) δ 7.53-7.47 (m, 1H), 7.35 (q, J=6.3, 5.2 Hz, 3H), 4.55 (s, 2H), 3.95 (d, J=12.3 Hz, 1H), 3.82 (d, J=12.3 Hz, 1H), 2.92 (q, J=6.8 Hz, 1H), 1.69 (d, J=11.7 Hz, 4H), 1.64 (s, 1H), 1.43 (dt, J=13.0, 6.5 Hz, 1H), 1.30 (s, 1H), 1.24 (d, J=11.7 Hz, 1H), 1.22 (s, 2H), 1.18 (t, J=6.2 Hz, 4H), 0.99-0.89 (m, 1H), 0.87 (d, J=11.0 Hz, 1H). m/z=325.2

B415: 2-(2-(2-methylcyclohexyl)ethyl)-1,4-dihydroisoquinolin-3(2H)-one

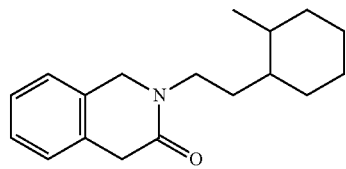 [SMILES: CC1CCCCC1CCN1Cc2ccccc2CC1=O]

2-(2-methylcyclohexyl)ethan-1-amine (0.5 mmol) and methyl 2-(2-(chloromethyl)phenyl)acetate (0.5 mmol) were mixed in 5 ml of DMF, and DIPEA (0.75 mmol) was added. The mixture was heated at 80° C. for 5 h, cooled; solvent was removed by evaporation, and the residue was purified by HPLC. Yield: 45%.

1H NMR (400 MHz, DMSO-d6) δ 7.23 (p, J=8.0 Hz, 2H), 5.32 (s, 0H), 4.46 (s, 1H), 3.32 (s, 1H), 2.12 (t, J=7.3 Hz, 1H), 1.94 (s, 1H), 1.84 (s, 1H), 1.53 (q, J=6.3, 5.7 Hz, 1H), 1.46 (d, J=6.5 Hz, 1H). m/z=272.2

B416: 2-(3-cyclohexylpropyl)-1,4-dihydroisoquinolin-3(2H)-one

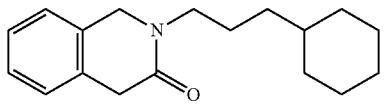 [SMILES: O=C1Cc2ccccc2CN1CCCC1CCCCC1]

2-cyclohexylethan-1-amine (0.5 mmol) and methyl 2-(2-(chloromethyl)phenyl)acetate (0.5 mmol) were mixed in 5 ml of DMF; DIPEA (0.75 mmol) was added. The mixture was heated at 80° C. for 5 h, cooled; solvent was removed by evaporation and residue was purified by HPLC. Yield: 31%.

1H NMR (400 MHz, Chloroform-d) δ 7.28-7.20 (m, 1H), 7.17 (t, J=6.5 Hz, 1H), 4.45 (s, 1H), 3.60 (s, 1H), 3.48 (t, J=7.6 Hz, 1H), 1.73-1.56 (m, 4H), 1.27-1.05 (m, 3H), 0.87 (t, J=11.3 Hz, 1H). m/z=272.2

B417: 2-(2-cyclohexylethyl)-1,2,3,4-tetrahydroiso-quinoline

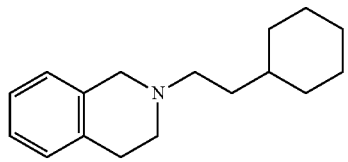 [SMILES: c1ccc2c(c1)CCN(CCC1CCCCC1)C2]

1,2,3,4-tetrahydroisoquinoline (0.5 mmol) and 2-cyclohexylacetaldehyde (0.5 mmol) were dissolved in 0.6 ml CHCl₃; NaBH(OAc)₃ (1.5 mmol) was added and stirred for 4 hours. The mixture was heated for 12 hours at 60° C.; then 3 ml of methanol and 0.2 g of C-18 chromatographic phase were added, stirred for 2 hours, filtered, evaporated and dissolved in 0.5 ml of DMSO. The residue was purified by HPLC. Yield: 51%. 1H NMR (400 MHz, Chloroform-d) δ 7.10 (dq, J=9.7, 5.6, 4.9 Hz, 3H), 7.05-6.98 (m, 1H), 3.62 (s, 2H), 2.91 (t, J=6.0 Hz, 2H), 2.72 (t, J=5.9 Hz, 2H), 2.56-2.48 (m, 2H), 1.78-1.61 (m, 5H), 1.50 (q, J=7.0 Hz, 2H), 1.36-1.12 (m, 2H), 0.95 (q, J=11.0 Hz, 2H). m/z=244.2

B418: 2-cyclohexyl-1,4-dihydroisoquinolin-3(2H)-one

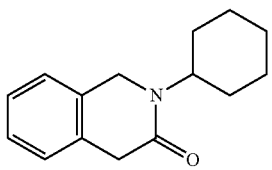 [SMILES: O=C1Cc2ccccc2CN1C1CCCCC1]

Cyclohexanamine (0.5 mmol) and methyl 2-(2-(chloromethyl)phenyl)acetate (0.5 mmol) were mixed in 5 ml of DMF; DIPEA (0.75 mmol) was added. The mixture was heated at 80° C. for 5 h, cooled; solvent was removed by evaporation, and residue was purified by HPLC. Yield: 47%.

1H NMR (400 MHz, Chloroform-d) δ 7.28-7.14 (m, 4H), 4.55 (ddq, J=11.8, 7.5, 3.8 Hz, 1H), 4.34 (s, 2H), 3.60 (s, 2H), 1.82 (d, J=10.5 Hz, 2H), 1.71 (d, J=4.1 Hz, 1H), 1.45 (hd, J=12.4, 3.2 Hz, 4H), 1.15 (tt, J=10.3, 4.6 Hz, 1H). m/z=230.2

B419: 2-(2-cyclohexylethyl)isoindolin-1-one

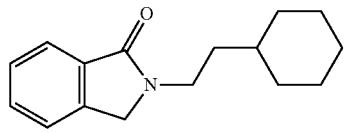 [SMILES: O=C1c2ccccc2CN1CCC1CCCCC1]

2-cyclohexylethan-1-amine (0.5 mmol) and methyl 2-formylbenzoate (0.5 mmol) were dissolved in 0.6 ml isopropanol, heated at 80° C. for 2 hours; then the mixture was cooled, NaBH₄ (0.5 mmol) was added and stirred for 4 hours. Then 0.2 g of C-18 chromatographic phase was added, stirred for 2 hours, filtered, evaporated. The residue was purified by HPLC. Yield: 41%.

1H NMR (400 MHz, DMSO-d6) δ 7.66 (d, J=7.5 Hz, 1H), 7.57 (d, J=4.2 Hz, 2H), 7.46 (dp, J=8.5, 4.2 Hz, 1H), 4.44 (s, 2H), 3.53 (t, J=7.3 Hz, 2H), 1.78-1.69 (m, 2H), 1.60 (dt, J=17.9, 6.0 Hz, 3H), 1.48 (q, J=7.1 Hz, 2H), 1.27-1.12 (m, 3H), 1.10 (dd, J=15.1, 3.6 Hz, 1H), 0.90 (tt, J=12.0, 6.0 Hz, 2H). m/z=244.2

B420: 2-cyclohexyl-N-(3-((methylamino)methyl)benzyl)ethan-1-amine

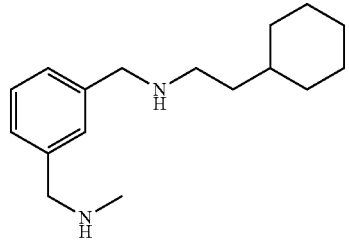 [SMILES: CNCc1cccc(CNCCC2CCCCC2)c1]

Step A:
tert-butyl (3-(aminomethyl)phenyl)(methyl)carbamate (1 mmol) and 2-cyclohexylacetaldehyde (1 mmol) were dissolved in 0.6 ml MeOH, heated at 80° C. for 2 hours; then the mixture was cooled, NaBH₄ (1 mmol) was added and stirred for 4 hours. The mixture was heated for 2 hours at 60° C.; then cooled and filtered. Yield: 51%.

Step B:
To a solution of tert-butyl (3-(((2-cyclohexylethyl)amino)methyl)phenyl)(methyl) carbamate (0.5 mmol) in dichloromethane (5 mL) was slowly added trifluoroacetic acid (2.5 mmol) at 0° C. The reaction solution was stirred at room temperature for 5 h, and then 1 N NaOH was added. The mixture was extracted with dichloromethane, and the organic layer was washed with brine, dried (Na₂SO₄), and filtered. The solvent was evaporated and the residue was purified by HPLC. Yield: 31%.

1H NMR (400 MHz, DMSO-d6) δ 7.26-7.18 (m, 2H), 7.14 (d, J=7.4 Hz, 2H), 3.62 (d, J=16.2 Hz, 4H), 2.95 (s, 1H), 2.46 (d, J=7.0 Hz, 2H), 2.24 (s, 3H), 1.63 (d, J=12.3 Hz, 5H), 1.30 (t, J=6.1 Hz, 3H), 1.18 (d, J=11.9 Hz, 1H), 1.12 (d, J=9.7 Hz, 2H), 0.90-0.80 (m, 2H). m/z=261.2

B421: 2-phenethyl-1,4-dihydroisoquinolin-3(2H)-one

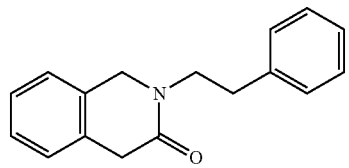 [SMILES: O=C1Cc2ccccc2CN1CCc1ccccc1]

2-phenylethan-1-amine (0.5 mmol) and methyl 2-(2-(chloromethyl)phenyl)acetate (0.5 mmol) were mixed in 5 ml of DMF; DIPEA (0.75 mmol) was added. The mixture was heated at 80° C. for 5 h, cooled; solvent was removed by evaporation and residue was purified by HPLC. Yield: 51%.

1H NMR (400 MHz, Chloroform-d) δ 7.31-7.16 (m, 6H), 7.16 (d, J=7.5 Hz, 1H), 7.04 (d, J=7.4 Hz, 1H), 4.29 (s, 2H), 3.75 (t, J=7.4 Hz, 2H), 3.60 (s, 2H), 2.92 (t, J=7.4 Hz, 2H). m/z=252.2

B422: 2-(2-cycloheptylethyl)-1,4-dihydroisoquinolin-3(2H)-one

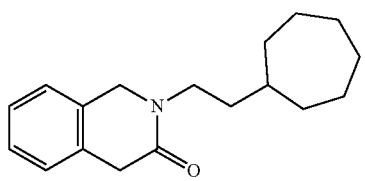 [SMILES: O=C1Cc2ccccc2CN1CCC1CCCCCC1]

Methyl 2-(2-(aminomethyl)phenyl)acetate (0.5 mmol) and 2-cycloheptylacetaldehyde (0.5 mmol) were dissolved in 0.6 ml isopropanol, heated at 80° C. for 2 hours; then the mixture was cooled, NaBH₄ (0.5 mmol) was added and stirred for 4 hours. Then 0.2 g of C-18 chromatographic phase was added, stirred for 2 hours, filtered, evaporated. The residue was purified by HPLC. Yield: 34%.

1H NMR (400 MHz, Chloroform-d) δ 7.23 (dd, J=12.7, 6.9 Hz, 1H), 7.17 (t, J=6.7 Hz, 1H), 4.45 (s, 1H), 3.60 (s, 1H), 3.52 (t, J=7.5 Hz, 1H), 1.73 (ddt, J=13.4, 6.5, 3.1 Hz, 1H), 1.64 (ddd, J=17.1, 8.6, 5.3 Hz, 1H), 1.56-1.45 (m, 1H), 1.39 (dd, J=12.4, 9.6 Hz, 0H), 1.23 (ddt, J=13.4, 9.4, 4.8 Hz, 1H). m/z=272.2

B423: N-((1-benzyl-1H-indol-7-yl)methyl)-1-cyclohexylpropan-2-amine

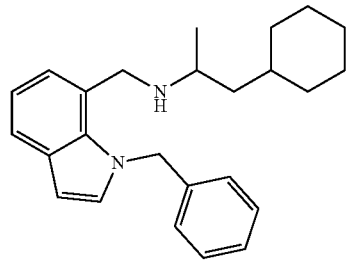 [SMILES: CC(CC1CCCCC1)NCc1cccc2ccn(Cc3ccccc3)c12]

1-cyclohexylpropan-2-amine (0.5 mmol) and 1-benzyl-1H-indole-7-carbaldehyde (0.55 mmol) were dissolved in 0.6 ml MeOH, heated at 100° C. for 2 hours; then the mixture was cooled, NaBH₄ (0.5 mmol) was added and stirred for 4 hours. The mixture was heated for 2 hours at 60° C.; 3 ml of methanol and 0.2 g of C-18 chromatographic phase were added, stirred for 2 hours, filtered, evaporated and the residue was purified by HPLC. Yield: 34%.

1H NMR (400 MHz, DMSO-d6) δ 7.50 (dd, J=6.4, 2.8 Hz, 1H), 7.37 (d, J=3.2 Hz, 1H), 7.27 (t, J=7.4 Hz, 2H), 7.20 (t, J=7.3 Hz, 1H), 6.95 (q, J=4.0, 3.4 Hz, 2H), 6.80 (d, J=7.5 Hz, 2H), 6.53 (d, J=3.1 Hz, 1H), 5.92 (d, J=17.1 Hz, 1H), 5.85 (d, J=17.1 Hz, 1H), 3.74 (d, J=11.8 Hz, 1H), 3.33 (s, 1H), 2.61 (s, 1H), 1.64-1.49 (m, 5H), 1.46 (s, 1H), 1.37 (s, 1H), 1.27 (dt, J=13.6, 6.9 Hz, 1H), 1.16 (d, J=12.3 Hz, 1H), 1.11 (s, 1H), 1.10-1.02 (m, 1H), 1.05-0.94 (m, 3H), 0.76 (p, J=11.6 Hz, 2H). m/z=361.4

B424: 1-cyclohexyl-N-(2-((methylsulfonyl)methyl)benzyl)propan-2-amine

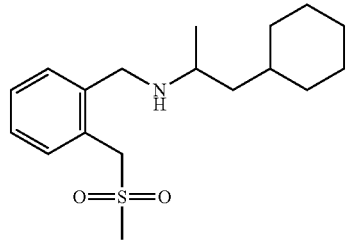 [SMILES: CC(CC1CCCCC1)NCc1ccccc1CS(C)(=O)=O]

(2-((methylsulfonyl)methyl)phenyl)methanamine (0.5 mmol) and 1-cyclohexylpropan-2-one (0.55 mmol) were dissolved in 0.6 ml MeOH, heated at 100° C. for 2 hours; then the mixture was cooled, NaBH₄ (0.5 mmol) was added and stirred for 4 hours. The mixture was heated for 2 hours at 60° C.; 3 ml of methanol and 0.2 g of C-18 chromatographic phase were added, stirred for 2 hours, filtered, evaporated. The residue was purified by HPLC. Yield: 49%.

1H NMR (400 MHz, DMSO-d6) δ 7.42-7.36 (m, 1H), 7.34 (d, J=7.1 Hz, 1H), 7.26 (p, J=7.2 Hz, 2H), 4.72 (d, J=13.8 Hz, 1H), 4.63 (d, J=13.9 Hz, 1H), 3.92 (d, J=12.6 Hz, 1H), 3.76 (d, J=12.7 Hz, 1H), 3.03 (s, 1H), 2.89 (d, J=2.3 Hz, 3H), 2.68 (s, 1H), 2.50 (s, 1H), 1.66 (d, J=11.5 Hz, 5H), 1.38-1.22 (m, 2H), 1.20 (s, 1H), 1.17 (s, 1H), 1.11 (s, 1H), 1.05 (dd, J=6.2, 2.2 Hz, 3H), 0.90-0.79 (m, 2H). m/z=324.2

B425: 2-(2-cyclohexylethyl)-1,2,4,5-tetrahydro-3H-benzo[c]azepin-3-one

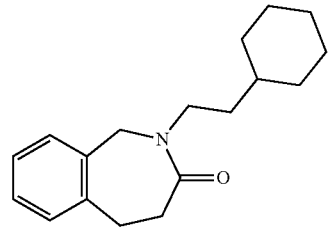 [SMILES: O=C1CCc2ccccc2CN1CCC1CCCCC1]

Under argon, into a reaction vessel of 1,2,4,5-tetrahydro-3H-benzo[c]azepin-3-one (0.5 mmol), potassium iodide 0.70 g g (0.4 mmol), potassium carbonate 0.70 g (0.5 mmol), DMF (1 mL) and (2-chloroethyl)cyclohexane (0.5 mmol) were added. The reaction vessel was heated to 80° C., and the mixture was stirred for 12 hours. The reaction vessel was cooled to room temperature, ethyl acetate 20 mL was added, the organic layer was washed with water 50 mL, saturated brine 50 mL. Product was purified by HPLC. Yield: 80%.

1H NMR (400 MHz, Chloroform-d) δ 7.27 (d, J=7.3 Hz, 1H), 7.17 (dd, J=10.5, 6.4 Hz, 3H), 3.97 (s, 2H), 3.74 (s, 0H), 2.69 (s, 2H), 2.24 (d, J=6.3 Hz, 2H), 2.14 (s, 2H), 1.65 (td, J=10.2, 4.6 Hz, 6H), 1.41 (q, J=7.6 Hz, 2H), 1.28-1.05 (m, 4H), 0.93-0.79 (m, 2H). m/z=272.2

B426: 3-(1-cyclohexylpropan-2-yl)-3,4-dihydro-2H-benzo[e][1,3]oxazin-2-one

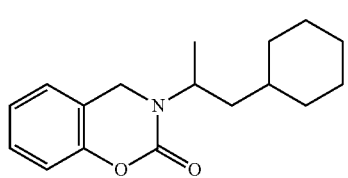 [SMILES: CC(CC1CCCCC1)N1Cc2ccccc2OC1=O]

Step A:

1-cyclohexylpropan-2-amine (1.0 mmol) and 2-hydroxybenzaldehyde (1.0 mmol) were dissolved in 1 ml MeOH, heated at 100° C. for 2 hours; then the mixture was cooled, NaBH(OAc)$_3$ (1.5 mmol) was added and stirred for 4 hours. The mixture was heated for 2 hours at 60° C.; 5 ml of methanol and 0.3 g of C-18 chromatographic phase were added, stirred for 2 hours, filtered, evaporated. The residue was purified by HPLC. Yield: 58%.

Step B:

2-(((1-cyclohexylpropan-2-yl)amino)methyl)phenol (0.5 mmol) and Boc$_2$O (0.6 mmol) in THF (1 mL) were heated for 2 h at 50° C. Then Et$_3$N (0.1 mL) was added, and the mixture was heated for 1 hour at 50° C. The solvent was evaporated, the residue was purified by LC. Yield: 41%.

1H NMR (400 MHz, DMSO-d6) δ 7.34-7.25 (m, 2H), 7.14 (t, J=7.4 Hz, 1H), 7.02 (d, J=8.3 Hz, 1H), 4.50-4.35 (m, 2H), 4.31 (d, J=15.0 Hz, 1H), 1.78 (d, J=12.8 Hz, 1H), 1.65-1.51 (m, 5H), 1.28 (ddd, J=14.0, 8.5, 5.6 Hz, 1H), 1.13 (dd, J=16.8, 7.6 Hz, 7H), 0.87 (dt, J=23.3, 12.1 Hz, 2H). m/z=274.2

B427: 2-(2-cyclopentylethyl)-1,4-dihydroisoquinolin-3(2H)-one

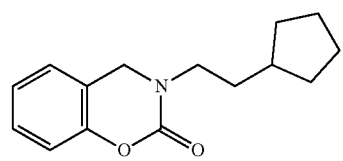 [SMILES: O=C1Oc2ccccc2CN1CCC1CCCC1]

2-cyclopentylethan-1-amine (0.5 mmol) and methyl 2-(2-(chloromethyl)phenyl)acetate (0.5 mmol) were mixed in 5 ml of DMF; DIPEA (0.75 mmol) was added. The mixture was heated at 80° C. for 5 h, cooled; solvent was removed by evaporation and residue was purified by HPLC. Yield: 29%. 1H NMR (400 MHz, Chloroform-d) δ 7.28-7.21 (m, 1H), 7.18 (q, J=9.0, 6.8 Hz, 1H), 4.46 (s, 1H), 3.60 (s, 1H), 3.52 (dd, J=8.8, 6.6 Hz, 1H), 1.79 (td, J=13.1, 11.9, 7.1 Hz, 1H), 1.66-1.53 (m, 2H), 1.52 (t, J=6.6 Hz, 1H), 1.20-1.11 (m, 1H). m/z=243

B428: (2S)-2-amino-N-((2-(((1-cyclohexylpropan-2-yl)amino)methyl)benzyl)sulfonyl)-4-methylpentanamide dihydrochloride

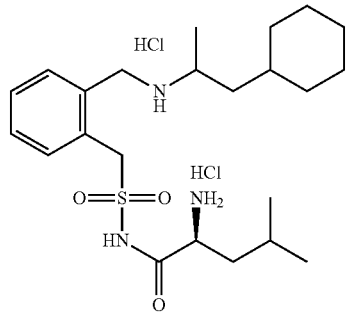 [SMILES: CC(C)C[C@H](N)C(=O)NS(=O)(=O)Cc1ccccc1CNC(C)CC1CCCCC1 ; Cl ; Cl]

Step A:

tert-butyl (1-cyclohexylpropan-2-yl)(2-(sulfamoylmethyl)benzyl)carbamate (2 mmol) and CDI (4 mmol) were dissolved in 1.2 ml CH$_3$CN; the mixture was kept at a temperature of 70° C. for 1 hour, then (tert-butoxycarbonyl)-L-leucine (2 mmol) was added. The mixture was heated for 2 hours at 70° C., then filtered, evaporated. The residue was purified by HPLC.

Step B:

To a solution of tert-butyl (2-((N-((tert-butoxycarbonyl)-L-leucyl)sulfamoyl)methyl)benzyl)(1-cyclohexylpropan-2-yl)carbamate (1 mmol) in dichloromethane (5 mL) was slowly added trifluoroacetic acid (5 mmol) at 0° C. The reaction solution was stirred at room temperature for 5 h, and then 1N NaOH was added. The mixture was extracted with dichloromethane, and the organic layer was washed with brine, dried (Na$_2$SO$_4$), and filtered. The solvent was evaporated, and the residue was purified by HPLC. Yield: 31%.

1H NMR (400 MHz, Chloroform-d) δ 7.47 (d, J=7.3 Hz, 1H), 7.33 (dt, J=24.0, 7.5 Hz, 3H), 5.20 (s, 4H), 4.48 (s, 2H), 4.08 (s, 2H), 3.39 (s, 1H), 3.24 (s, 1H), 2.56 (s, 1H), 1.63 (d, J=15.6 Hz, 6H), 1.41 (t, J=11.1 Hz, 1H), 1.27 (d, J=5.6 Hz, 3H), 1.17 (dd, J=22.8, 11.2 Hz, 2H), 0.93 (dd, J=13.7, 5.1 Hz, 5H), 0.86 (s, 3H), 0.35 (s, 1H). m/z=438.2

B429: 1-cyclohexyl-N-(2-(2-fluorophenethoxy)benzyl)propan-2-amine

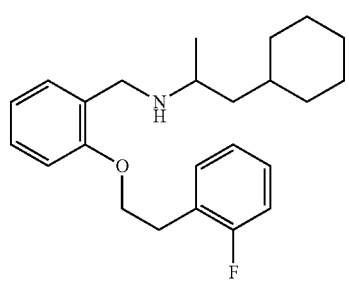 [SMILES: CC(CC1CCCCC1)NCc1ccccc1OCCc1ccccc1F]

1-cyclohexylpropan-2-amine (0.5 mmol) and 2-(2-fluorophenethoxy)benzaldehyde (0.5 mmol) were dissolved in 0.6 ml MeOH, heated at 100° C. for 2 hours; then the mixture was cooled, NaBH$_4$ (0.5 mmol) was added and stirred for 4 hours. The mixture was heated for 2 hours at 60° C.; 3 ml of methanol and 0.2 g of C-18 chromatographic phase were added, stirred for 2 hours, filtered, evaporated. The residue was purified by HPLC. Yield: 31%.

1H NMR (400 MHz, DMSO-d6) δ 7.42 (dt, J=8.9, 4.3 Hz, 1H), 7.34-7.24 (m, 1H), 7.28-7.10 (m, 4H), 6.95 (d, J=8.1 Hz, 1H), 6.85 (t, J=7.4 Hz, 1H), 4.26-4.12 (m, 2H), 3.63 (d, J=14.0 Hz, 1H), 3.48 (d, J=14.0 Hz, 1H), 3.09 (t, J=6.3 Hz, 2H), 2.54 (s, 1H), 2.49-2.42 (m, 1H), 1.56 (d, J=12.7 Hz, 4H), 1.49 (s, 1H), 1.40 (d, J=13.1 Hz, 1H), 1.16 (dd, J=9.4, 6.4 Hz, 1H), 1.14 (s, 2H), 1.08 (t, J=8.1 Hz, 3H), 0.95 (p, J=3.8 Hz, 1H), 0.88 (d, J=6.1 Hz, 3H), 0.73 (dt, J=23.4, 11.2 Hz, 2H). m/z=370.2

B430: 2-(2-(tetrahydro-2H-pyran-4-yl)ethyl)-1,4-dihydroisoquinolin-3(2H)-one

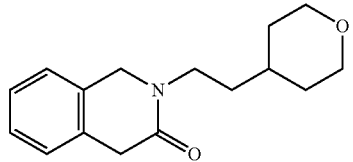 [SMILES: O=C1Cc2ccccc2CN1CCC1CCOCC1]

2-(tetrahydro-2H-pyran-4-yl)ethan-1-amine (0.5 mmol) and methyl 2-(2-(chloromethyl)phenyl)acetate (0.5 mmol) were mixed in 5 ml of DMF; DIPEA (0.75 mmol) was added. The mixture was heated at 80° C. for 5 h, cooled; solvent was removed by evaporation and residue was purified by HPLC. Yield: 41%.

1H NMR (400 MHz, Chloroform-d) δ 7.62 (ddt, J=16.3, 11.9, 5.3 Hz, 3H), 4.87 (s, 2H), 4.27-4.18 (m, 2H), 3.88 (d, J=8.7 Hz, 4H), 3.66 (td, J=11.7, 2.0 Hz, 2H), 3.56 (s, 2H), 2.91 (dd, J=3.8, 1.9 Hz, 1H), 2.05 (d, J=12.9 Hz, 2H), 1.88 (t, J=6.4 Hz, 3H), 1.68-1.57 (m, 2H). m/z=260.2

B431: 1-(2-(((1-cyclohexylpropan-2-yl)amino)methyl)phenyl)-N-(2,3-dihydroxypropyl) methanesulfonamide

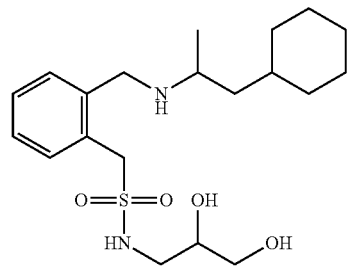 [SMILES: CC(CC1CCCCC1)NCc1ccccc1CS(=O)(=O)NCC(O)CO]

1-(2-(aminomethyl)phenyl)-N-(2,3-dihydroxypropyl) methanesulfonamide (0.5 mmol) and 1-cyclohexylpropan-2-one (0.5 mmol) were dissolved in 0.6 ml MeOH, heated at 100° C. for 3 hours; then the mixture was cooled, NaBH4 (0.5 mmol) was added and stirred for 5 hours. The mixture was heated for 2 hours at 60° C.; 3 ml of methanol and 0.2 g of C-18 chromatographic phase were added, stirred for 2 hours, filtered, evaporated. The residue was purified by HPLC. Yield: 38%.

1H NMR (400 MHz, DMSO-d6) δ 7.34 (t, J=7.5 Hz, 2H), 7.27 (q, J=7.6, 7.1 Hz, 2H), 7.04 (s, 1H), 4.80 (d, J=4.9 Hz, 1H), 4.61 (dd, J=13.9, 10.8 Hz, 1H), 4.52 (dd, J=18.3, 9.2 Hz, 2H), 3.88 (d, J=13.0 Hz, 1H), 3.74 (d, J=12.8 Hz, 1H), 3.48 (s, 1H), 2.99 (s, 1H), 2.83 (d, J=5.8 Hz, 1H), 2.63 (s, 1H), 2.54 (s, 2H), 1.60 (s, 6H), 1.32 (d, J=16.0 Hz, 2H), 1.22-1.11 (m, 1H), 1.09-0.98 (m, 3H), 0.81 (t, J=12.2 Hz, 2H). m/z=399.1

B432: 1-(2-(((1-cyclohexylpropan-2-yl)amino)methyl)phenyl)-N-(1-methylpiperidin-4-yl)methanesulfonamide

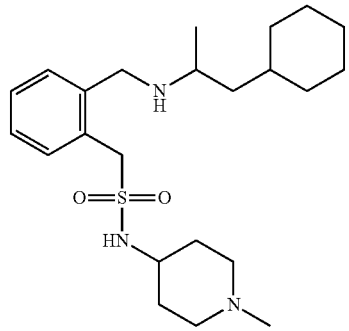 [SMILES: CC(CC1CCCCC1)NCc1ccccc1CS(=O)(=O)NC1CCN(C)CC1]

1-(2-(aminomethyl)phenyl)-N-(1-methylpiperidin-4-yl) methanesulfonamide (0.5 mmol), 1-cyclohexylpropan-2-one (0.5 mmol) were dissolved in 0.6 ml MeOH, heated at 100° C. for 3 hours; then the mixture was cooled, NaBH4 (0.5 mmol) was added and stirred for 5 hours. The mixture was heated for 2 hours at 60° C.; 3 ml of methanol and 0.2 g of C-18 chromatographic phase were added, stirred for 2 hours, filtered, evaporated. The residue was purified using HPLC. Yield: 42%.

1H NMR (400 MHz, DMSO-d6) δ 7.37-7.23 (m, 3H), 7.23 (s, 1H), 7.27-7.17 (m, 1H), 4.60 (d, J=13.8 Hz, 1H), 4.46 (d, J=13.7 Hz, 1H), 3.88 (d, J=12.8 Hz, 1H), 3.76 (d, J=12.7 Hz, 1H), 2.95 (s, 1H), 2.65 (t, J=11.7 Hz, 3H), 2.54 (s, 1H), 2.09 (d, J=11.7 Hz, 3H), 1.81 (dd, J=24.7, 13.5 Hz, 3H), 1.73 (s, 1H), 1.62 (d, J=13.7 Hz, 5H), 1.50-1.27 (m, 3H), 1.25-1.09 (m, 2H), 1.09-0.98 (m, 3H), 0.87-0.77 (m, 2H). m/z=422.1

B433: 1-(2-(((1-cyclohexylpropan-2-yl)amino)methyl)phenyl)-N-((tetrahydrofuran-2-yl)methyl)methanesulfonamide

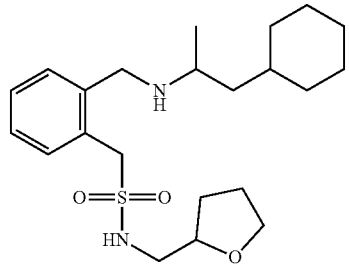 [SMILES: CC(CC1CCCCC1)NCc1ccccc1CS(=O)(=O)NCC1CCCO1]

1-(2-(aminomethyl)phenyl)-N-((tetrahydrofuran-2-yl)methyl)methanesulfonamide (0.5 mmol) and 1-cyclohexylpropan-2-one (0.5 mmol) were dissolved in 0.6 ml MeOH, heated at 100° C. for 3 hours; then the mixture was cooled, NaBH4 (0.5 mmol) was added and stirred for 5 hours. The mixture was heated for 2 hours at 60° C.; 3 ml of methanol and 0.2 g of C-18 chromatographic phase were added, stirred for 2 hours, filtered, evaporated. The residue was purified by HPLC. Yield: 34%.

1H NMR (400 MHz, DMSO-d6) δ 7.29 (dddd, J=28.1, 14.5, 7.5, 3.9 Hz, 5H), 4.61 (dd, J=13.9, 10.2 Hz, 1H), 4.50 (dd, J=13.8, 7.9 Hz, 1H), 3.88 (dd, J=12.9, 3.0 Hz, 1H), 3.81 (p, J=6.1 Hz, 1H), 3.79-3.69 (m, 2H), 3.61 (q, J=7.2 Hz, 1H), 2.89 (t, J=5.9 Hz, 2H), 2.63 (q, J=6.4 Hz, 1H), 2.54 (s, 1H), 1.86 (dq, J=11.7, 7.0 Hz, 1H), 1.84-1.73 (m, 2H), 1.65-1.57 (m, 4H), 1.54 (dt, J=10.5, 7.1 Hz, 2H), 1.33 (tt, J=13.5, 6.0 Hz, 2H), 1.14 (ddd, J=26.0, 19.5, 8.8 Hz, 4H), 1.01 (d, J=6.1 Hz, 3H), 0.83 (s, 1H), 0.79 (d, J=11.8 Hz, 1H). m/z=409.2

B434: 1-(2-(((1-cyclohexylpropan-2-yl)amino)methyl)phenyl)-N-(2-methoxyethyl) methanesulfonamide

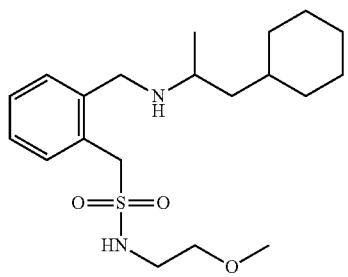 [SMILES: COCCNS(=O)(=O)Cc1ccccc1CNC(C)CC1CCCCC1]

1-(2-(aminomethyl)phenyl)-N-(2-methoxyethyl)methanesulfonamide (0.5 mmol) and 1-cyclohexylpropan-2-one (0.5 mmol) were dissolved in 0.6 ml MeOH, heated at 100° C. for 3 hours; then the mixture was cooled, NaBH$_4$ (0.5 mmol) was added and stirred for 5 hours. The mixture was heated for 2 hours at 60° C.; 3 ml of methanol and 0.2 g of C-18 chromatographic phase were added, stirred for 2 hours, filtered, evaporated. The residue was purified by HPLC. Yield: 39%.

1H NMR (400 MHz, DMSO-d6) δ 7.38-7.20 (m, 4H), 7.30 (s, 2H), 4.61 (d, J=13.9 Hz, 1H), 4.50 (d, J=13.8 Hz, 1H), 3.88 (d, J=12.9 Hz, 1H), 3.75 (d, J=12.9 Hz, 1H), 3.33 (t, J=5.8 Hz, 2H), 3.25 (s, 3H), 3.02 (t, J=5.9 Hz, 2H), 2.63 (q, J=6.4 Hz, 1H), 2.54 (s, 1H), 1.61 (d, J=17.1 Hz, 1H), 1.61 (s, 4H), 1.38-1.26 (m, 2H), 1.18 (d, J=12.9 Hz, 1H), 1.15-1.05 (m, 1H), 1.01 (d, J=6.2 Hz, 3H), 0.86-0.75 (m, 2H). m/z=383.1

B435: methyl 2-(7-(((1-cyclohexylpropan-2-yl)amino)methyl)-1H-indol-1-yl)acetate hydrochloride

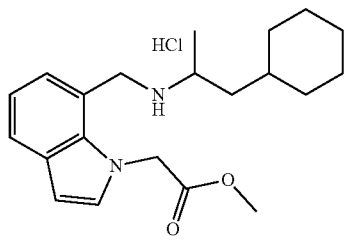 [SMILES: COC(=O)Cn1ccc2cccc(CNC(C)CC3CCCCC3)c21 ; Cl]

Step A:

tert-butyl ((1H-indol-7-yl)methyl)(1-cyclohexylpropan-2-yl)carbamate (1 mmol) was added to 10 mL of DMF. NaH (1.1 mmol) was added to the stirring solution at 0° C., and the mixture was allowed to reach r.t stirring for 20 min. Then, methyl 2-bromoacetate (1.1 mmol) was added. The reaction mixture was allowed to stir under argon for 5 h at 50° C. The reaction was quenched with water (10 mL) and extracted twice with EtOAc (20 mL). The combined organic layers were washed with brine, dried over Na$_2$SO$_4$ and concentrated under reduced pressure. The crude methyl 2-(7-(((tert-butoxycarbonyl)(I-cyclohexylpropan-2-yl)amino)methyl)-1H-indol-1-yl)acetate was purified by chromatography. Yield: 71%.

Step B:

To a solution of methyl 2-(7-(((tert-butoxycarbonyl)(1-cyclohexylpropan-2-yl)amino)methyl)-1H-indol-1-yl)acetate (0.5 mmol) in dichloromethane (5 mL) was slowly added trifluoroacetic acid (2.5 mmol) at 0° C. The reaction solution was stirred at room temperature for 5 h, and then 1N NaOH was added. The mixture was extracted with dichloromethane, and the organic layer was washed with brine, dried (Na$_2$SO$_4$), and filtered. The solvent was evaporated, and the residue was purified by HPLC. Yield: 58%.

1H NMR (400 MHz, DMSO-d6) δ 9.37 (s, 1H), 9.29 (s, 1H), 7.62 (d, J=7.8 Hz, 1H), 7.40-7.30 (m, 2H), 7.11 (t, J=7.6 Hz, 1H), 6.54 (d, J=3.2 Hz, 1H), 5.38 (s, 2H), 4.31 (s, 2H), 3.72 (s, 2H), 1.75 (t, J=9.0 Hz, 1H), 1.68 (d, J=13.2 Hz, 2H), 1.64 (s, 1H), 1.48 (td, J=12.8, 12.0, 7.1 Hz, 1H), 1.34 (d, J=6.4 Hz, 2H), 1.20 (s, 2H), 0.97 (q, J=11.3 Hz, 1H), 0.87 (s, 1H). m/z=343.2

B436: 2-(7-(((1-cyclohexylpropan-2-yl)amino)methyl)-1H-indol-1-yl)acetic acid hydrochloride

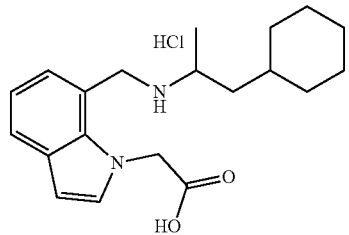 [SMILES: CC(CC1CCCCC1)NCc1cccc2ccn(CC(=O)O)c12 ; Cl]

Methyl 2-(7-(((1-cyclohexylpropan-2-yl)amino)methyl)-1H-indol-1-yl)acetate (0.5 mmol) was dissolved in HCl (5 mmol). The reaction stirred at 50° C. overnight. The reaction was poured into water and extracted (2x) with dichloromethane. Reaction mixture was concentrated under reduced pressure. The crude residue was purified by HPLC. Yield: 26%.

1H NMR (400 MHz, DMSO-d6) δ 9.66 (s, 2H), 7.58 (d, J=7.8 Hz, 1H), 7.25 (d, J=3.2 Hz, 1H), 7.11 (d, J=7.1 Hz, 1H), 7.00 (t, J=7.5 Hz, 1H), 6.45 (d, J=3.2 Hz, 1H), 4.85 (d, J=2.4 Hz, 2H), 4.44 (d, J=13.2 Hz, 1H), 4.33 (d, J=13.2 Hz, 1H), 3.16 (s, 1H), 2.54 (s, 1H), 1.67 (d, J=12.3 Hz, 4H), 1.60 (d, J=12.0 Hz, 4H), 1.23 (t, J=8.1 Hz, 4H), 1.17 (s, 7H), 0.89 (dt, J=37.0, 11.3 Hz, 3H). m/z=329.2

B437: 1-(2-(((1-cyclohexylpropan-2-yl)amino)methyl)phenyl)-N,N-dimethylmethane sulfonamide

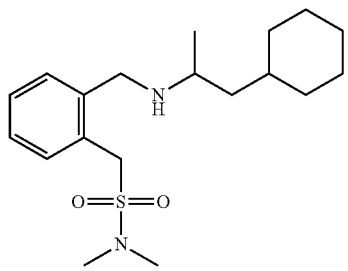 [SMILES: CC(CC1CCCCC1)NCc1ccccc1CS(=O)(=O)N(C)C]

1-(2-(aminomethyl)phenyl)-N,N-dimethylmethanesulfonamide (0.5 mmol) and 1-cyclohexylpropan-2-one (0.5 mmol) were dissolved in 0.6 ml MeOH, heated at 100° C. for 3 hours, then the mixture was cooled, NaBH$_4$ (0.5 mmol) was added and stirred for 5 hours. The mixture was heated for 2 hours at 60° C.; 3 ml of methanol and 0.2 g of C-18 chromatographic phase were added, stirred for 2 hours, filtered. The residue was purified by HPLC. Yield: 33%.

1H NMR (400 MHz, DMSO-d6) δ 7.30 (dtd, J=27.2, 7.0, 6.5, 1.9 Hz, 4H), 4.64 (d, J=13.6 Hz, 1H), 4.56 (d, J=13.7 Hz, 1H), 3.88 (d, J=12.8 Hz, 1H), 3.75 (d, J=12.8 Hz, 1H), 2.79 (s, 6H), 2.64 (q, J=5.9, 5.4 Hz, 1H), 1.62 (d, J=12.5 Hz, 6H), 1.38-1.27 (m, 2H), 1.25-1.03 (m, 3H), 1.01 (d, J=6.1 Hz, 3H), 0.81 (s, 2H). m/z=353.2

B438: 1-(2-(((1-cyclohexylpropan-2-yl)amino)methyl)phenyl)-N-((S)-2,3-dihydroxypropyl)-N-methylmethanesulfonamide

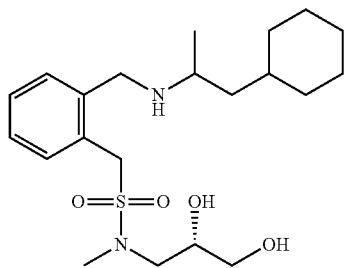 [SMILES: CC(CC1CCCCC1)NCc1ccccc1CS(=O)(=O)N(C)C[C@H](O)CO]

(S)-1-(2-(aminomethyl)phenyl)-N-(2,3-dihydroxypropyl)-N-methylmethanesulfonamide (0.5 mmol), 1-cyclohexylpropan-2-one (0.5 mmol) were dissolved in 0.6 ml MeOH, heated at 100° C. for 3 hours; then the mixture was cooled, NaBH$_4$ (0.5 mmol) was added and stirred for 5 hours. The mixture was heated for 2 hours at 60° C.; 3 ml of methanol and 0.2 g of C-18 chromatographic phase were added, stirred for 2 hours, filtered. The residue was purified by HPLC. Yield: 27%.

1H NMR (400 MHz, DMSO-d6) δ 7.34 (s, 2H), 7.34-7.22 (m, 2H), 4.88 (d, J=5.3 Hz, 1H), 4.71-4.53 (m, 3H), 3.88 (d, J=13.0 Hz, 1H), 3.77 (s, 1H), 3.63 (s, 1H), 3.19 (d, J=13.5 Hz, 1H), 3.04-2.97 (m, 1H), 2.85 (s, 2H), 2.54 (s, 3H), 2.49 (s, 1H), 1.60 (s, 6H), 1.35 (s, 2H), 1.22-1.11 (m, 2H), 1.07 (s, 3H), 1.01 (d, J=6.1 Hz, 2H), 0.86-0.76 (m, 2H). m/z=413.3

B439: 1-cyclohexyl-N-(2-(((4-methylpiperazin-1-yl)sulfonyl)methyl)benzyl)propan-2-amine

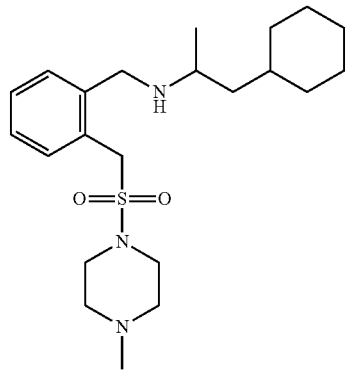 [SMILES: CC(CC1CCCCC1)NCc1ccccc1CS(=O)(=O)N1CCN(C)CC1]

(2-(((4-methylpiperazin-1-yl)sulfonyl)methyl)phenyl)methanamine (0.5 mmol), 1-cyclohexylpropan-2-one (0.5 mmol) were dissolved in 0.6 ml MeOH, heated at 100° C. for 3 hours; then the mixture was cooled, NaBH$_4$ (0.5 mmol) was added and stirred for 5 hours. The mixture was heated for 2 hours at 60° C.; 3 ml of methanol and 0.2 g of C-18 chromatographic phase were added, stirred for 2 hours, filtered. The residue was purified by HPLC. Yield: 38%.

1H NMR (400 MHz, DMSO-d6) δ 7.38-7.22 (m, 4H), 4.66 (d, J=13.7 Hz, 1H), 4.57 (d, J=13.7 Hz, 1H), 3.88 (d, J=12.7 Hz, 1H), 3.76 (d, J=12.7 Hz, 1H), 3.18 (d, J=5.1 Hz, 4H), 2.65 (t, J=6.4 Hz, 1H), 2.54 (s, 2H), 2.36 (t, J=5.0 Hz, 4H), 2.20 (s, 3H), 1.66-1.57 (m, 5H), 1.33 (dd, J=14.9, 7.9 Hz, 2H), 1.25-0.98 (m, 6H), 0.83 (d, J=10.5 Hz, 2H). m/z=408.1

B440: methyl 2-(3-(((2-cyclohexylethyl)amino)methyl)phenyl)acetate

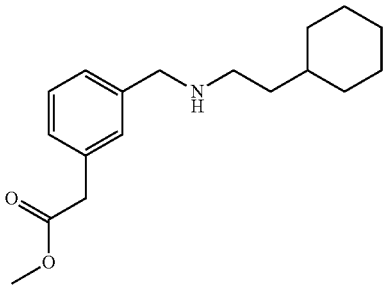 [SMILES: COC(=O)Cc1cccc(CNCCC2CCCCC2)c1]

Methyl 2-(3-(aminomethyl)phenyl)acetate (0.5 mmol) and 2-cyclohexylacetaldehyde (0.55 mmol) were dissolved in 0.6 ml MeOH, heated at 100° C. for 2 hours; then the mixture was cooled, NaBH$_4$ (0.5 mmol) was added and stirred for 4 hours. The mixture was heated for 2 hours at 60° C.; 3 ml of methanol and 0.2 g of C-18 chromatographic phase were added, stirred for 2 hours, filtered, evaporated. The residue was purified by HPLC. Yield: 41%.

1H NMR (400 MHz, DMSO-d6) δ 7.26-7.15 (m, 1H), 3.62 (t, J=12.3 Hz, 2H), 1.66 (d, J=12.6 Hz, 1H), 1.32 (d, J=7.5 Hz, 1H), 1.16 (dt, J=22.6, 12.5 Hz, 1H), 0.86 (d, J=10.3 Hz, 1H). m/z=290.1

B441: 1-cyclohexyl-N-((1-methyl-1H-indol-7-yl)methyl)propan-2-amine hydrochloride

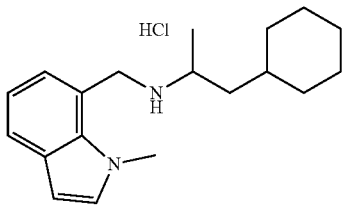 [SMILES: CC(CC1CCCCC1)NCc1cccc2ccn(C)c12 ; Cl]

Step A:

tert-butyl ((1H-indol-7-yl)methyl)(I-cyclohexylpropan-2-yl)carbamate (1 mmol) was dissolved in 10 mL of DMF. NaH (1.1 mmol) was added to the stirring solution at 0° C., and the mixture was allowed to reach r.t. stirring for 20 min. Then CH₃I (1.1 mmol) was added. The reaction mixture was allowed to stir under argon for 5 h at 50° C. The reaction was quenched with water (10 mL) and extracted twice with EtOAc (20 mL). The combined organic layers were washed with brine, dried over Na₂SO₄ and concentrated under reduced pressure. The crude product was purified by chromatography. Yield: 54%.

Step B:

To a solution of tert-butyl (1-cyclohexylpropan-2-yl)((1-methyl-1H-indol-7-yl)methyl)carbamate (0.5 mmol) in dichloromethane (5 mL) was slowly added trifluoroacetic acid (2.5 mmol) at 0° C. The reaction solution was stirred at room temperature for 5 h, and then 1N NaOH was added. The mixture was extracted with dichloromethane, and the organic layer was washed with brine, dried (Na₂SO₄), and filtered. The solvent was evaporated and the residue was purified by HPLC. Yield: 31%.

1H NMR (400 MHz, DMSO-d6) δ 7.42 (d, J=7.8 Hz, 1H), 7.21 (d, J=3.1 Hz, 1H), 6.95 (d, J=6.9 Hz, 1H), 6.91 (s, 0H), 6.89 (t, J=7.4 Hz, 1H), 6.37 (d, J=3.2 Hz, 1H), 4.12 (d, J=21.9 Hz, 4H), 3.93 (d, J=12.0 Hz, 1H), 2.73 (q, J=6.4 Hz, 1H), 1.60 (d, J=14.0 Hz, 4H), 1.52 (d, J=13.7 Hz, 1H), 1.37 (s, 2H), 1.33 (q, J=6.7, 6.1 Hz, 1H), 1.08 (dd, J=13.3, 7.8 Hz, 7H), 0.79 (dd, J=25.2, 12.5 Hz, 2H). m/z=285.2

B442: 2-(7-(((1-cyclohexylpropan-2-yl)amino)methyl)-1H-indol-1-yl)ethan-1-ol hydrochloride

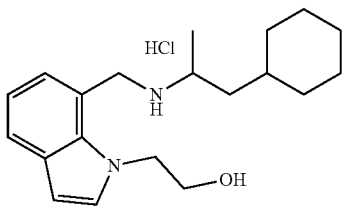 [SMILES: CC(CC1CCCCC1)NCc1cccc2ccn(CCO)c12 ; Cl]

Step A:

tert-butyl ((1H-indol-7-yl)methyl)(1-cyclohexylpropan-2-yl)carbamate (1 mmol) was dissolved in 10 mL of DMF. NaH (1.1 mmol) was added to the stirring solution at 0° C., and the mixture was allowed to reach r.t. stirring for 20 min. Then 2-chloroethanol (1.1 mmol) was added. The reaction mixture was allowed to stir under argon for 5 h at 50° C. The reaction was quenched with water (10 mL) and extracted twice with EtOAc (20 mL). The combined organic layers were washed with brine, dried over Na₂SO₄ and concentrated under reduced pressure. The crude tert-butyl (1-cyclohexylpropan-2-yl)((1-(2-hydroxyethyl)-1H-indol-7-yl)methyl)carbamate was purified by chromatography. Yield: 51%.

Step B:

To a solution of tert-butyl (1-cyclohexylpropan-2-yl)((1-(2-hydroxyethyl)-1H-indol-7-yl)methyl)carbamate (0.5 mmol) in dichloromethane (5 mL) was slowly added trifluoroacetic acid (2.5 mmol) at 0° C. The reaction solution was stirred at room temperature for 5 h, and then 1 N NaOH was added. The mixture was extracted with dichloromethane, and the organic layer was washed with brine, dried (Na₂SO₄), and filtered. The solvent was evaporated and the residue was purified by HPLC. Yield: 27%.

1H NMR (400 MHz, DMSO-d6) δ 7.44 (d, J=7.7 Hz, 1H), 7.29 (dd, J=6.7, 3.2 Hz, 1H), 6.96 (d, J=6.5 Hz, 1H), 6.90 (dd, J=8.8, 6.0 Hz, 1H), 6.42 (d, J=3.2 Hz, 1H), 4.68-4.52 (m, 2H), 4.06 (t, J=11.0 Hz, 1H), 3.90 (d, J=11.8 Hz, 1H), 3.71 (dt, J=11.4, 5.6 Hz, 2H), 3.49-3.42 (m, 0H), 2.72 (s, 1H), 2.54 (s, 1H), 1.59 (q, J=14.2, 13.0 Hz, 6H), 1.39-1.28 (m, 3H), 1.21-1.08 (m, 3H), 1.06 (d, J=6.0 Hz, 4H), 0.83 (d, J=11.0 Hz, 1H), 0.78 (d, J=10.8 Hz, 1H). m/z=315.2

B445: 1-(2-(((1-cyclohexylpropan-2-yl)amino)methyl)phenyl)-N-methylmethanesulfonamide

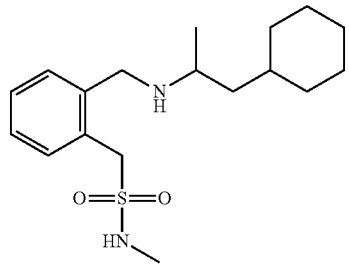 [SMILES: CNS(=O)(=O)Cc1ccccc1CNC(C)CC1CCCCC1]

1-(2-(aminomethyl)phenyl)-N-methylmethanesulfonamide (0.5 mmol) and 1-cyclohexylpropan-2-one (0.5 mmol) were dissolved in 0.6 ml MeOH, heated at 100° C. for 3 hours; then the mixture was cooled, NaBH₄ (0.5 mmol) was added and stirred for 5 hours. The mixture was heated for 2 hours at 60° C.; 3 ml of methanol and 0.2 g of C-18 chromatographic phase were added, stirred for 2 hours, filtered, evaporated. The residue was purified by HPLC. Yield: 31%.

1H NMR (400 MHz, DMSO-d6) δ 7.38-7.21 (m, 4H), 7.03 (d, J=6.0 Hz, 1H), 4.59 (d, J=13.9 Hz, 1H), 4.49 (d, J=13.9 Hz, 1H), 3.88 (d, J=12.9 Hz, 1H), 3.75 (d, J=12.8 Hz, 1H), 2.64 (dd, J=13.0, 6.6 Hz, 1H), 2.63-2.52 (m, 4H), 1.65-1.55 (m, 6H), 1.34 (tt, J=13.5, 8.1 Hz, 2H), 1.18 (dd, J=25.1, 12.9 Hz, 3H), 1.12-1.03 (m, 1H), 1.01 (d, J=6.2 Hz, 3H), 0.80 (td, J=13.1, 6.4 Hz, 2H). m/z=339.2

B446: 1-(2-(((1-cyclohexylpropan-2-yl)amino)methyl)phenyl)-N-ethylmethanesulfonamide

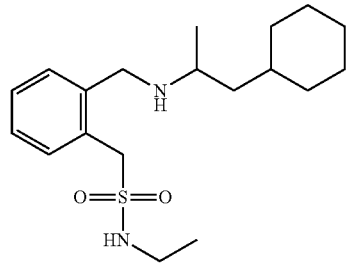 [SMILES: CCNS(=O)(=O)Cc1ccccc1CNC(C)CC1CCCCC1]

1-(2-(aminomethyl)phenyl)-N-ethylmethanesulfonamide (0.5 mmol) and 1-cyclohexylpropan-2-one (0.5 mmol) were dissolved in 0.6 ml MeOH, heated at 100° C. for 3 hours; then the mixture was cooled, NaBH$_4$ (0.5 mmol) was added and stirred for 5 hours. The mixture was heated for 2 hours at 60° C.; 3 ml of methanol and 0.2 g of C-18 chromatographic phase were added, stirred for 2 hours, filtered, evaporated. The residue was purified by HPLC. Yield: 28%.

1H NMR (400 MHz, DMSO-d6) δ 7.38-7.20 (m, 4H), 7.15 (t, J=5.6 Hz, 1H), 4.58 (d, J=13.8 Hz, 1H), 4.48 (d, J=13.8 Hz, 1H), 3.88 (d, J=12.8 Hz, 1H), 3.75 (d, J=12.9 Hz, 1H), 2.98-2.87 (m, 2H), 2.62 (q, J=6.4 Hz, 1H), 2.54 (s, 1H), 1.65-1.54 (m, 7H), 1.34 (ddt, J=19.8, 13.5, 7.2 Hz, 2H), 1.25-1.11 (m, 2H), 1.15-0.98 (m, 6H), 0.86-0.73 (m, 2H). m/z=353.2

B448: ((2-(((1-cyclohexylpropan-2-yl)amino)methyl)benzyl)sulfonyl)glycine

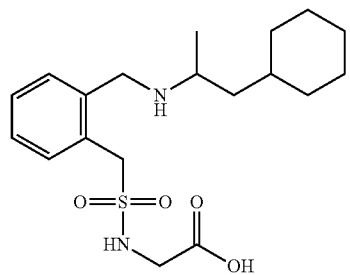 [SMILES: CC(CC1CCCCC1)NCc1ccccc1CS(=O)(=O)NCC(=O)O]

((2-(aminomethyl)benzyl)sulfonyl)glycine (0.5 mmol), 1-cyclohexylpropan-2-one (0.5 mmol) were dissolved in 0.6 ml MeOH, heated at 100° C. for 3 hours; then the mixture was cooled, NaBH$_4$ (0.5 mmol) was added and stirred for 5 hours. The mixture was heated for 2 hours at 60° C.; 3 ml of methanol and 0.2 g of C-18 chromatographic phase were added, stirred for 2 hours, filtered. The residue was purified by HPLC. Yield: 29%.

1H NMR (400 MHz, DMSO-d6) δ 7.47 (d, J=6.8 Hz, 1H), 7.45-7.33 (m, 3H), 4.67 (t, J=9.8 Hz, 2H), 4.15 (d, J=13.3 Hz, 1H), 4.07 (d, J=13.5 Hz, 1H), 3.06 (s, 1H), 1.64 (d, J=17.3 Hz, 4H), 1.56 (d, J=15.4 Hz, 2H), 1.38-1.31 (m, 1H), 1.25 (s, 1H), 1.18 (d, J=6.4 Hz, 3H), 1.15 (s, 3H), 0.86 (q, J=12.7, 12.0 Hz, 2H). m/z=383.2

B449: N-(cyclohexylcarbamoyl)-1-(2-(((1-cyclohexylpropan-2-yl)amino)methyl)phenyl) methanesulfonamide

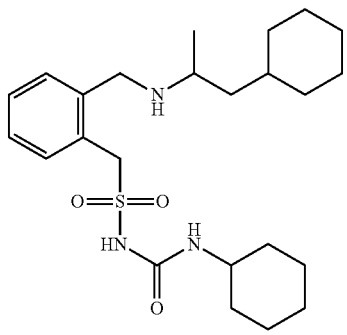 [SMILES: CC(CC1CCCCC1)NCc1ccccc1CS(=O)(=O)NC(=O)NC1CCCCC1]

1-(2-(aminomethyl)phenyl)-N-(cyclohexylcarbamoyl)methanesulfonamide (0.5 mmol) and 1-cyclohexylpropan-2-one (0.5 mmol) were dissolved in 0.6 ml MeOH, heated at 100° C. for 3 hours; then mixture was cooled, NaBH$_4$ (0.5 mmol) was added and stirred for 5 hours. The mixture was heated for 2 hours at 60° C.; 3 ml of methanol and 0.2 g of C-18 chromatographic phase were added, stirred for 2 hours, filtered. The residue was purified by HPLC. Yield: 37%.

1H NMR (400 MHz, DMSO-d6) δ 8.35 (s, 2H), 7.42 (d, J=7.2 Hz, 1H), 7.37-7.25 (m, 3H), 5.90 (s, 1H), 4.51 (d, J=13.5 Hz, 1H), 4.30 (d, J=13.3 Hz, 1H), 4.18-4.06 (m, 2H), 3.34 (d, J=9.5 Hz, 2H), 1.73 (d, J=10.8 Hz, 2H), 1.69-1.57 (m, 8H), 1.53 (d, J=12.3 Hz, 1H), 1.38-1.29 (m, 1H), 1.21 (dd, J=17.7, 5.4 Hz, 5H), 1.15 (s, 6H), 1.09 (t, J=11.1 Hz, 2H), 0.91 (d, J=11.9 Hz, 1H), 0.85 (d, J=11.3 Hz, 1H). m/z=450.2

B450: 1-(2-(((1-cyclohexylpropan-2-yl)amino)methyl)phenyl)-N-((4-methylcyclohexyl)carbamoyl)methanesulfonamide

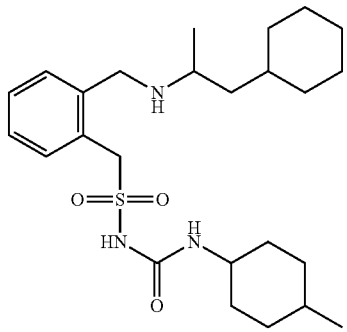 [SMILES: CC1CCC(NC(=O)NS(=O)(=O)Cc2ccccc2CNC(C)CC2CCCCC2)CC1]

1-(2-(aminomethyl)phenyl)-N-((4-methylcyclohexyl)carbamoyl)methanesulfonamide (0.5 mmol) and 1-cyclohexylpropan-2-one (0.5 mmol) were dissolved in 0.6 ml MeOH, heated at 100° C. for 3 hours; then the mixture was cooled, NaBH$_4$ (0.5 mmol) was added and stirred for 5 hours. The mixture was heated for 2 hours at 60° C.; 3 ml of methanol and 0.2 g of C-18 chromatographic phase were added, stirred for 2 hours, filtered. The residue was purified by HPLC. Yield: 28%. 1H NMR (400 MHz, DMSO-d6) δ 7.43 (s, 0H), 7.36 (s, 1H), 7.32 (s, 1H), 4.17 (s, 1H), 2.54 (s, 9H), 1.75 (s, 2H), 1.64 (s, 5H), 1.36 (s, 1H), 1.27 (s, 3H), 1.13 (s, 3H), 0.91 (s, 2H), 0.85 (d, J=6.3 Hz, 2H). m/z=464.2

B451: 2-(2-(((1-cyclohexylpropan-2-yl)amino)methyl)phenyl)ethane-1-sulfonamide

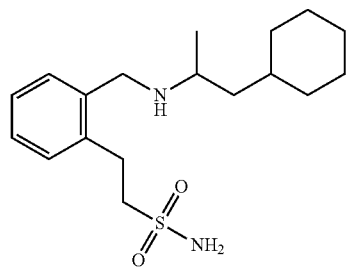 [SMILES: CC(CC1CCCCC1)NCc1ccccc1CCS(N)(=O)=O]

Step A:
1-cyclohexylpropan-2-amine (1 mmol), N-(tert-butyl)-2-(2-formylphenyl)ethane-1-sulfonamide (1 mmol) were dissolved in 0.6 ml MeOH, heated at 100° C. for 2 hours; then the mixture was cooled; NaBH₄ (1 mmol) was added and stirred for 4 hours. The mixture was heated for 2 hours at 60° C.; 3 ml of methanol and 0.4 g of C-18 chromatographic phase were added, stirred for 2 hours, filtered, evaporated. The residue was purified by HPLC. Yield: 54%.

Step B:
N-(tert-butyl)-2-(2-(((1-cyclohexylpropan-2-yl)amino)methyl)phenyl)ethane-1-sulfonamide (0.5 mmol) was dissolved in 2 ml MeOH; HCl (5 mmol) was added in the mixture. The reaction stirred at 60° C. for 2 hours. The reaction mixture was concentrated under reduced pressure. The crude residue was purified by HPLC. Yield: 29%. 1H NMR (400 MHz, DMSO-d6) δ 8.66 (s, 2H), 7.49 (d, J=7.0 Hz, 1H), 7.36 (s, 3H), 6.94 (s, 2H), 4.15 (s, 2H), 3.10 (d, J=7.9 Hz, 2H), 1.67 (d, J=16.6 Hz, 6H), 1.38 (s, 2H), 1.30 (d, J=6.3 Hz, 2H), 1.20 (s, 3H), 0.96 (d, J=12.3 Hz, 1H), 0.85 (d, J=12.1 Hz, 1H). m/z=339.2

B452: ((2-(((1-cyclohexylpropan-2-yl)amino)methyl)benzyl)sulfonyl)glycylglycine

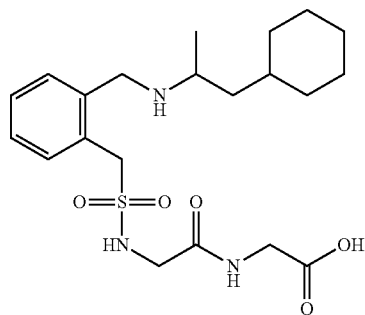 [SMILES: CC(CC1CCCCC1)NCc1ccccc1CS(=O)(=O)NCC(=O)NCC(=O)O]

Step A:
Methyl ((2-(aminomethyl)benzyl)sulfonyl)glycylglycinate (1.5 mmol) and 1-cyclohexylpropan-2-one (1.5 mmol) were dissolved in 0.8 ml MeOH, heated at 100° C. for 3 hours; then the mixture was cooled, NaBH₄ (1.5 mmol) was added and stirred for 5 hours. The mixture was heated for 2 hours at 60° C.; 3 ml of methanol and 0.4 g of C-18 chromatographic phase were added, stirred for 2 hours, filtered. The residue was purified by HPLC. Yield: 34%.

Step B:
Methyl ((2-(((1-cyclohexylpropan-2-yl)amino)methyl)benzyl)sulfonyl) glycylglycinate (0.5 mmol) was dissolved in HCl (5 mmol). The reaction was stirred at 50° C. overnight. The reaction was poured into water and extracted (2×) with dichloromethane. Reaction mixture was concentrated under reduced pressure. The crude residue was purified by HPLC. Yield: 26%.

1H NMR (500 MHz, DMSO-d6) δ 8.09 (s, 1H), 7.89 (s, 1H), 7.63 (d, J=6.9 Hz, 1H), 7.55 (s, 1H), 7.42 (d, J=6.8 Hz, 1H), 7.37-7.32 (m, 2H), 4.75-4.65 (m, 2H), 4.13 (d, J=13.5 Hz, 1H), 4.09 (d, J=13.6 Hz, 1H), 3.15 (s, 1H), 2.05 (s, 1H), 1.60 (dd, J=21.8, 11.2 Hz, 7H), 1.39-1.31 (m, 2H), 1.22 (d, J=6.5 Hz, 3H), 1.17 (s, 2H), 1.11 (dd, J=20.9, 10.8 Hz, 2H), 0.84 (dq, J=35.4, 11.0 Hz, 2H). m/z=440.2

B453: (1S,3S)-3-(((2-(((1-cyclohexylpropan-2-yl)amino)methyl)phenyl)methyl) sulfonamido)cyclobutane-1-carboxylic acid

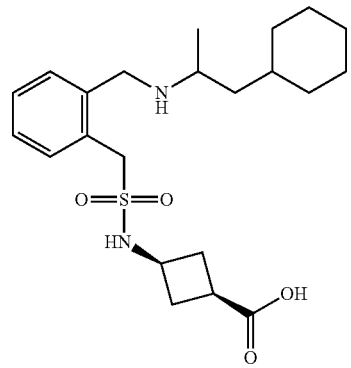 [SMILES: CC(CC1CCCCC1)NCc1ccccc1CS(=O)(=O)N[C@H]1C[C@@H](C(=O)O)C1]

Step A:
Methyl (1s,3s)-3-(((2-(aminomethyl)phenyl)methyl) sulfonamido)cyclobutane-1-carboxylate (1.5 mmol) and 1-cyclohexylpropan-2-one (1.5 mmol) were dissolved in 0.8 ml MeOH, heated at 100° C. for 3 hours; then the mixture was cooled, NaBH₄ (1.5 mmol) was added and stirred for 5 hours. The mixture was heated for 2 hours at 60° C.; 3 ml of methanol and 0.4 g of C-18 chromatographic phase were added, stirred for 2 hours, filtered. The residue was purified by HPLC. Yield: 41%.

Step B:
Methyl (1s,3s)-3-(((2-(((1-cyclohexylpropan-2-yl)amino)methyl)phenyl)methyl) sulfonamido)cyclobutane-1-carboxylate (0.5 mmol) was dissolved in HCl (5 mmol). The reaction was stirred at 50° C. overnight. The reaction was poured into water and extracted (2×) with dichloromethane. Reaction mixture was concentrated under reduced pressure. The crude residue was purified by HPLC. Yield: 34%.

1H NMR (500 MHz, DMSO-d6) δ 7.63 (s, 1H), 7.35 (s, 1H), 7.27 (s, 4H), 4.54 (s, 1H), 4.40 (d, J=14.2 Hz, 1H), 4.32 (s, 2H), 3.93-3.87 (m, 1H), 3.77 (s, 1H), 2.65 (s, 1H), 2.56 (s, 1H), 2.34 (s, 3H), 2.06 (s, 2H), 1.59 (s, 6H), 1.34 (s, 2H), 1.16 (s, 3H), 1.08 (s, 2H), 1.02 (s, 4H), 0.80 (s, 3H), 0.56 (s, 1H). m/z=423.2

B454: ((2-(((1-cyclohexylpropan-2-yl)amino)methyl)benzyl)sulfonyl)-L-alanine

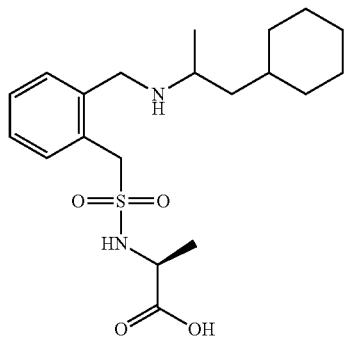 [SMILES: CC(CC1CCCCC1)NCc1ccccc1CS(=O)(=O)N[C@@H](C)C(=O)O]

Step A:
Methyl ((2-(aminomethyl)benzyl)sulfonyl)-L-alaninate (1.5 mmol) and 1-cyclohexylpropan-2-one (1.5 mmol) were dissolved in 0.8 ml MeOH, heated at 100° C. for 3 hours; then the mixture was cooled, NaBH₄ (1.5 mmol) was added and stirred for 5 hours. The mixture was heated for 2 hours at 60° C.; 3 ml of methanol and 0.4 g of C-18 chromatographic phase were added, stirred for 2 hours, filtered. The residue was purified by HPLC. Yield: 34%.
Step B:
Methyl ((2-(((1-cyclohexylpropan-2-yl)amino)methyl)benzyl)sulfonyl)-L-alaninate (0.5 mmol) was dissolved in HCl (5 mmol). The reaction was stirred at 50° C. overnight. The reaction was poured into water and extracted (2×) with dichloromethane. Reaction mixture was concentrated under reduced pressure. The crude residue was purified by HPLC. Yield: 27%.
1H NMR (400 MHz, Methanol-d4) δ 7.52 (d, J=7.1 Hz, 2H), 7.45 (d, J=4.7 Hz, 2H), 4.73 (d, J=14.2 Hz, 1H), 4.51 (dd, J=14.1, 8.9 Hz, 1H), 4.35 (dd, J=17.6, 10.1 Hz, 2H), 3.82 (s, 1H), 3.48 (s, 1H), 3.29 (s, 2H), 1.75 (s, 0H), 1.69 (s, 5H), 1.43 (s, 2H), 1.38 (d, J=6.9 Hz, 5H), 1.30 (d, J=14.6 Hz, 1H), 1.21 (dd, J=20.3, 11.3 Hz, 1H), 1.06-0.89 (m, 2H). m/z=397.2

B455: ((2-(((1-cyclohexylpropan-2-yl)amino)methyl)benzyl)sulfonyl)-D-alanine

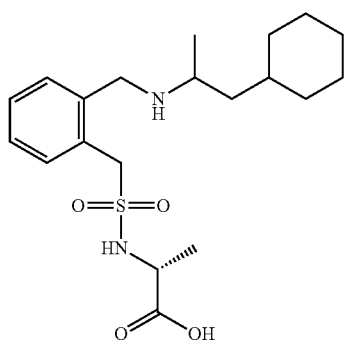 [SMILES: CC(CC1CCCCC1)NCc1ccccc1CS(=O)(=O)N[C@H](C)C(=O)O]

Step A:
Methyl ((2-(aminomethyl)benzyl)sulfonyl)-D-alaninate (1.5 mmol) and 1-cyclohexylpropan-2-one (1.5 mmol) were dissolved in 0.8 ml MeOH, heated at 100° C. for 3 hours; then the mixture was cooled, NaBH₄ (1.5 mmol) was added and stirred for 5 hours. The mixture was heated for 2 hours at 60° C.; 3 ml of methanol and 0.4 g of C-18 chromatographic phase were added, stirred for 2 hours, filtered. The residue was purified by HPLC. Yield: 39%.
Step B:
Methyl ((2-(((1-cyclohexylpropan-2-yl)amino)methyl)benzyl)sulfonyl)-D-alaninate (0.5 mmol) was dissolved in HCl (5 mmol). The reaction stirred at 50° C. overnight. The reaction was poured into water and extracted (2×) with dichloromethane. Reaction mixture was concentrated under reduced pressure. The crude residue was purified by HPLC. Yield: 24%. m/z=397.2

B456: (1S,3S)-3-(((2-(((1-cyclohexylpropan-2-yl)amino)methyl) phenyl)methyl)sulfonamido)cyclobutane-1-carboxylic acid

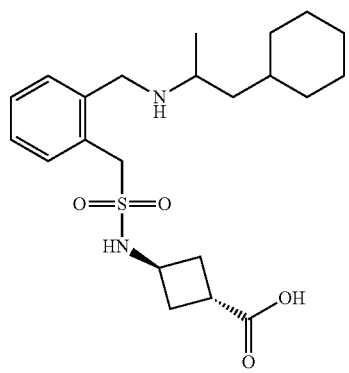 [SMILES: CC(CC1CCCCC1)NCc1ccccc1CS(=O)(=O)N[C@H]1C[C@H](C(=O)O)C1]

Synthetic Procedure 1
Step A:
Methyl (1r,3r)-3-(((2-(aminomethyl)phenyl)methyl)sulfonamido)cyclobutane-1-carboxylate (1.5 mmol) and 1-cyclohexylpropan-2-one (1.5 mmol) were dissolved in 0.8 ml MeOH, heated at 100° C. for 3 hours; then the mixture was cooled, NaBH₄ (1.5 mmol) was added and stirred for 5 hours. The mixture was heated for 2 hours at 60° C.; 3 ml of methanol and 0.4 g of C-18 chromatographic phase were added, stirred for 2 hours, filtered. The residue was purified by HPLC. Yield: 44%.
Step B:
Methyl (1r,3r)-3-(((2-(((1-cyclohexylpropan-2-yl)amino)methyl)phenyl)methyl) sulfonamido) cyclobutane-1-carboxylate (0.5 mmol) was dissolved in HCl (5 mmol). The reaction was stirred at 50° C. overnight. The reaction was poured into water and extracted (2×) with dichloromethane. Reaction mixture was concentrated under reduced pressure. The crude residue was purified by HPLC. Yield: 31%.
Synthetic Procedure 2
Step A:
Methyl (1r,3r)-3-((2-((2-(aminomethyl)phenoxy)methyl)phenyl)sulfonamido) cyclobutane-1-carboxylate (1 mmol), and 1-cyclohexylpropan-2-one (I mmol) were dissolved in 0.6 ml MeOH, heated at 100° C. for 2 hours; then the mixture was cooled, NaBH₄ (1 mmol) was added and stirred for 4 hours. The mixture was heated for 2 hours at 60° C.; 3 ml of methanol and 0.2 g of C-18 chromatographic phase were added, stirred for 2 hours, filtered, evaporated. The residue was purified by HPLC. Yield: 54%.

Step B:

To a solution of methyl (1r,3r)-3-((2-(((1-cyclohexyl-propan-2-yl)amino)methyl)phenoxy)methyl)phenyl)sulfonamido)cyclobutane-1-carboxylate (0.5 mmol) in EtOH/H$_2$O (5.0/2.5 ml) was added NaOH (1.5 mmol). The reaction stirred at room temperature overnight. To the reaction was added CH$_3$COOH (1.5 mmol) and it was extracted (2×) with dichloromethane. The organic layers were dried over magnesium sulfate, filtered and concentrated. The crude residue was purified by HPLC. Yield: 38%.

1H NMR (500 MHz, DMSO-d6) δ 7.65 (s, 1H), 7.33 (d, J=7.3 Hz, 1H), 7.25 (q, J=8.2, 7.5 Hz, 3H), 4.53 (d, J=13.8 Hz, 1H), 4.39 (d, J=13.8 Hz, 1H), 4.32 (s, 1H), 3.87 (d, J=12.3 Hz, 2H), 3.72 (d, J=12.9 Hz, 1H), 2.78 (t, J=9.8 Hz, 1H), 2.67-2.60 (m, 1H), 2.38-2.30 (m, 2H), 2.16 (q, J=10.2 Hz, 2H), 1.61 (s, 2H), 1.56 (d, J=14.8 Hz, 3H), 1.37-1.26 (m, 2H), 1.16 (d, J=12.2 Hz, 1H), 1.14-0.99 (m, 3H), 1.00 (s, 1H), 0.81 (q, J=12.1 Hz, 2H). m/z=423.2

B457: (3-(((2-(((1-cyclohexylpropan-2-yl)amino)methyl)phenyl)methyl)sulfonamido) phenyl)boronic acid

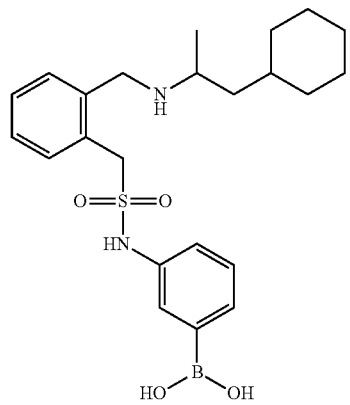 [SMILES: CC(CC1CCCCC1)NCc1ccccc1CS(=O)(=O)Nc1cccc(B(O)O)c1]

(4-(((2-(aminomethyl)phenyl)methyl)sulfonamido)phenyl)boronic acid (0.5 mmol) and 1-cyclohexylpropan-2-one (0.5 mmol) were dissolved in 0.6 ml MeOH, heated at 100° C. for 3 hours; then the mixture was cooled, NaBH$_4$ (0.5 mmol) was added and stirred for 5 hours. The mixture was heated for 2 hours at 60° C.; 3 ml of methanol and 0.2 g of C-18 chromatographic phase were added, stirred for 2 hours, filtered. The residue was purified by HPLC. Yield: 24%.

1H NMR (500 MHz, Methanol-d4) δ 7.47 (d, J=6.7 Hz, 1H), 7.47-7.34 (m, 5H), 7.24 (t, J=7.6 Hz, 1H), 7.15 (d, J=7.9 Hz, 1H), 4.61 (d, J=14.4 Hz, 1H), 4.57 (d, J=14.4 Hz, 1H), 4.11 (d, J=13.3 Hz, 1H), 4.04 (d, J=13.3 Hz, 1H), 3.15 (s, 1H), 2.66 (s, 1H), 1.71 (dd, J=27.8, 12.8 Hz, 6H), 1.56 (ddd, J=13.2, 8.5, 4.4 Hz, 1H), 1.39-1.15 (m, 6H), 1.00 (dd, J=13.4, 10.4 Hz, 2H), 0.92 (td, J=13.5, 12.3, 6.7 Hz, 1H). m/z=445.2

B458: 1-cyclohexyl-N-(2-((2-isopropylbenzyl)oxy)benzyl)propan-2-amine

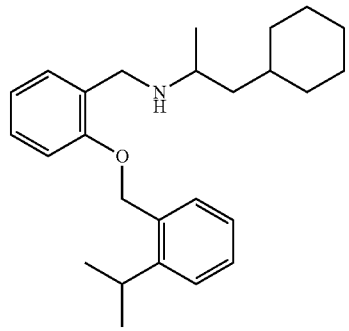 [SMILES: CC(CC1CCCCC1)NCc1ccccc1OCc1ccccc1C(C)C]

(2-((2-isopropylbenzyl)oxy)phenyl)methanamine (0.5 mmol) and 1-cyclohexylpropan-2-one (0.55 mmol) were dissolved in 0.6 ml MeOH, heated at 100° C. for 2 hours; then the mixture was cooled, NaBH$_4$ (0.5 mmol) was added and stirred for 4 hours. The mixture was heated for 2 hours at 60° C.; 3 ml of methanol and 0.2 g of C-18 chromatographic phase were added, stirred for 2 hours, filtered, evaporated. The residue was purified by HPLC. Yield: 39%.

1H NMR (400 MHz, Chloroform-d) δ 9.43 (s, 1H), 9.10 (s, 1H), 7.74 (d, J=7.6 Hz, 1H), 7.46 (d, J=7.6 Hz, 1H), 7.38 (s, 1H), 7.36-7.26 (m, 2H), 7.25 (d, J=8.4 Hz, 1H), 7.21-7.13 (m, 1H), 7.00-6.88 (m, 2H), 5.16 (s, 2H), 3.97 (d, J=13.2 Hz, 1H), 3.91 (d, J=13.9 Hz, 1H), 3.16 (hept, J=6.8 Hz, 1H), 2.93 (s, 1H), 1.58 (d, J=5.8 Hz, 2H), 1.40 (d, J=10.4 Hz, 1H), 1.37 (d, J=11.2 Hz, 2H), 1.23 (d, J=6.8 Hz, 6H), 1.17 (d, J=6.5 Hz, 4H), 1.04 (s, 1H), 1.00 (s, 1H), 0.76-0.63 (m, 1H), 0.60 (d, J=11.9 Hz, 1H). m/z=380.2

13C NMR (126 MHz, Chloroform-d) δ 157.23, 147.47, 132.71, 132.48, 130.65, 129.97, 128.94, 125.95, 125.48, 121.08, 119.45, 111.62, 68.21, 51.03, 41.87, 39.77, 33.94, 33.81, 31.54, 28.83, 26.29, 26.10, 25.88, 24.11, 24.03, 16.29.

1-cyclohexyl-N-(2-((3-methoxybenzyl)oxy)benzyl)propan-2-amine

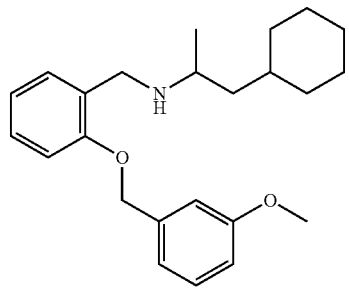 [SMILES: COc1cccc(COc2ccccc2CNC(C)CC2CCCCC2)c1]

(2-((3-methoxybenzyl)oxy)phenyl)methanamine (1 mmol), 1-cyclohexylpropan-2-one (1 mmol) were dissolved in 0.6 ml MeOH, heated at 100° C. for 2 hours; then mixture was cooled, NaBH$_4$ (1 mmol) was added and stirred for 4 hours. The mixture was heated for 2 hours at 60° C.; 3 ml of methanol and 0.2 g of C-18 chromatographic phase were added, stirred for 2 hours, filtered, evaporated. The residue was purified by HPLC. Yield: 44%. 1H NMR (500 MHz, Chloroform-d) δ 9.48 (s, 1H), 9.12 (s, 1H), 7.76-7.70 (m, 1H), 7.32-7.23 (m, 1H), 7.05 (t, J=5.8 Hz, 2H), 6.97-6.90 (m, 2H), 6.87 (dd, J=8.5, 2.6 Hz, 1H), 5.11 (d, J=2.2 Hz, 2H), 3.99 (p, J=7.4, 6.6 Hz, 2H), 3.82 (s, 3H), 3.00 (tt, J=10.2, 5.1 Hz, 1H), 1.68 (ddd, J=13.4, 9.5, 4.0 Hz, 1H), 1.63-1.56 (m, 3H), 1.50-1.39 (m, 3H), 1.26 (d, J=6.5 Hz, 3H), 1.21 (s, 2H), 1.17 (s, 1H), 1.09 (p, J=12.6, 12.0 Hz, 2H), 0.76 (qd, J=12.3, 3.2 Hz, 1H), 0.66 (tt, J=12.1, 6.0 Hz, 1H). m/z=368.2

B460: 1-cyclohexyl-N-(2-((4-methylbenzyl)oxy)benzyl)propan-2-amine

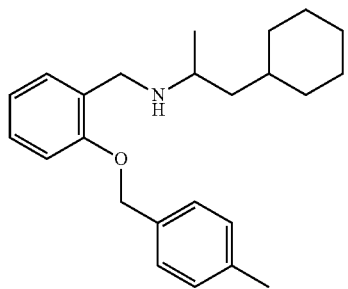 [SMILES: Cc1ccc(COc2ccccc2CNC(C)CC2CCCCC2)cc1]

(2-((4-methylbenzyl)oxy)phenyl)methanamine (1 mmol) and 1-cyclohexylpropan-2-one (1 mmol) were dissolved in 0.6 ml MeOH, heated at 100° C. for 2 hours; then the mixture was cooled, NaBH$_4$ (1 mmol) was added and stirred for 4 hours. The mixture was heated for 2 hours at 60° C.; 3 ml of methanol and 0.2 g of C-18 chromatographic phase were added, stirred for 2 hours, filtered, evaporated. The residue was purified by HPLC. Yield: 38%.

1H NMR (400 MHz, Chloroform-d) δ 9.42 (s, 1H), 9.04 (s, 1H), 7.69 (d, J=7.5 Hz, 1H), 7.35 (d, J=7.5 Hz, 2H), 7.24 (dd, J=9.9, 5.8 Hz, 1H), 7.15 (d, J=7.6 Hz, 2H), 6.92 (p, J=8.5, 7.4 Hz, 2H), 5.05 (s, 2H), 3.95 (q, J=4.9 Hz, 2H), 2.94 (dt, J=11.0, 5.7 Hz, 1H), 2.32 (s, 3H), 1.58 (dd, J=14.4, 8.8 Hz, 4H), 1.39 (tt, J=13.7, 5.2 Hz, 3H), 1.21 (d, J=6.5 Hz, 3H), 1.10 (dq, J=34.3, 9.4, 8.8 Hz, 4H), 0.71 (t, J=11.7 Hz, 1H), 0.62 (t, J=11.8 Hz, 1H). m/z=352.4

B461: 1-cyclohexyl-N-(2-((3-methylbenzyl)oxy)benzyl)propan-2-amine

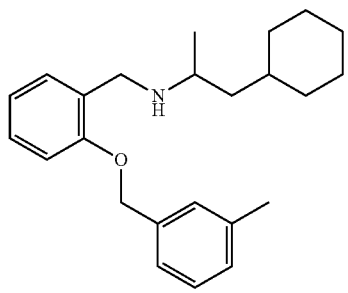 [SMILES: Cc1cccc(COc2ccccc2CNC(C)CC2CCCCC2)c1]

(2-((3-methylbenzyl)oxy)phenyl)methanamine (1 mmol) and 1-cyclohexylpropan-2-one (1 mmol) were dissolved in 0.6 ml MeOH, heated at 100° C. for 2 hours; then the mixture was cooled, NaBH$_4$ (1 mmol) was added and stirred for 4 hours. The mixture was heated for 2 hours at 60° C.; 3 ml of methanol and 0.2 g of C-18 chromatographic phase were added, stirred for 2 hours, filtered, evaporated. The residue was purified by HPLC. Yield: 32%.

1H NMR (500 MHz, Chloroform-d) δ 9.50 (s, 1H), 9.18 (s, 1H), 7.75 (dd, J=7.5, 1.7 Hz, 1H), 7.31-7.21 (m, 4H), 7.16-7.11 (m, 1H), 6.93 (t, J=8.1 Hz, 2H), 5.09 (s, 2H), 4.00 (q, J=4.5 Hz, 2H), 2.98 (dt, J=11.1, 5.5 Hz, 1H), 2.36 (s, 3H), 1.67 (ddd, J=13.5, 9.6, 4.0 Hz, 1H), 1.59 (dd, J=12.0, 6.5 Hz, 2H), 1.49-1.37 (m, 3H), 1.25 (d, J=6.5 Hz, 3H), 1.19 (s, 2H), 1.19-1.00 (m, 2H), 0.74 (qd, J=12.3, 3.3 Hz, 1H), 0.64 (qd, J=12.0, 3.0 Hz, 1H), −1.15 (s, 1H). m/z=352.4

B462: 1-cyclohexyl-N-(2-((2-cyclopropylbenzyl)oxy)benzyl)propan-2-amine

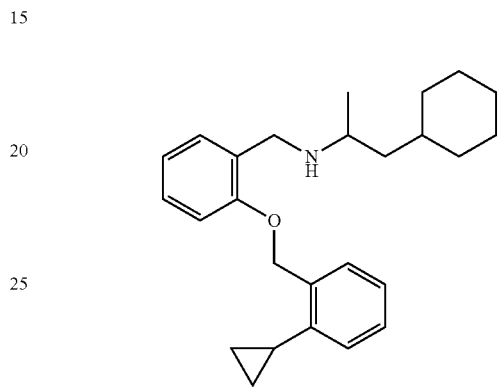

(2-((2-cyclopropylbenzyl)oxy)phenyl)methanamine (1 mmol) and 1-cyclohexylpropan-2-one (1 mmol) were dissolved in 0.6 ml MeOH, heated at 100° C. for 2 hours; then the mixture was cooled, NaBH$_4$ (1 mmol) was added and stirred for 4 hours. The mixture was heated for 2 hours at 60° C.; 3 ml of methanol and 0.2 g of C-18 chromatographic phase were added, stirred for 2 hours, filtered, evaporated. The residue was purified by HPLC. Yield: 37%.

1H NMR (500 MHz, Chloroform-d) δ 17.10 (s, 1H), 9.50 (s, 1H), 9.17 (s, 1H), 7.78 (d, J=7.4 Hz, 1H), 7.45 (d, J=7.4 Hz, 1H), 7.27 (dt, J=15.5, 7.7 Hz, 2H), 7.18 (t, J=7.4 Hz, 1H), 7.01 (dd, J=16.7, 8.0 Hz, 2H), 6.95 (t, J=7.5 Hz, 1H), 5.32 (s, 2H), 4.04 (d, J=5.9 Hz, 1H), 4.01 (d, J=5.8 Hz, 1H), 2.98 (dt, J=11.6, 5.6 Hz, 1H), 1.98 (tt, J=8.5, 5.3 Hz, 1H), 1.65 (ddd, J=13.6, 9.6, 3.9 Hz, 1H), 1.57 (d, J=8.5 Hz, 3H), 1.47-1.37 (m, 3H), 1.24-1.13 (m, 4H), 1.07 (dt, J=25.2, 13.9 Hz, 2H), 0.94 (dq, J=6.2, 3.8 Hz, 2H), 0.78-0.67 (m, 3H), 0.70-0.57 (m, 1H). m/z=378.2

B463: 1-cyclohexyl-N-(2-((2-phenoxybenzyl)oxy)benzyl)propan-2-amine

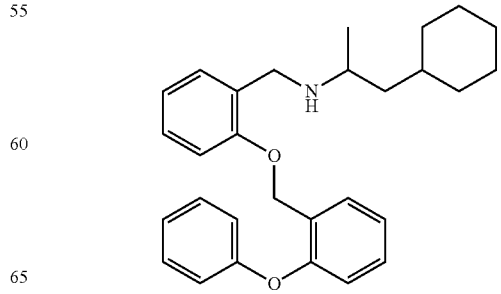

(2-((2-phenoxybenzyl)oxy)phenyl)methanamine (1 mmol) and 1-cyclohexylpropan-2-one (1 mmol) were dissolved in 0.6 ml MeOH, heated at 100° C. for 2 hours; then the mixture was cooled, NaBH$_4$ (1 mmol) was added and stirred for 4 hours. The mixture was heated for 2 hours at 60° C.; 3 ml of methanol and 0.2 g of C-18 chromatographic phase were added, stirred for 2 hours, filtered, evaporated. The residue was purified by HPLC. Yield: 39%.

1H NMR (400 MHz, DMSO-d6) δ 7.63 (d, J=7.5 Hz, 1H), 7.39 (d, J=7.7 Hz, 2H), 7.34 (d, J=13.0 Hz, 2H), 7.30-7.17 (m, 2H), 7.13 (t, J=7.4 Hz, 1H), 7.08 (d, J=8.2 Hz, 1H), 6.95 (dd, J=22.4, 8.0 Hz, 4H), 5.15 (s, 2H), 3.81 (d, J=2H), 2.79 (s, 1H), 1.56 (s, 3H), 1.49 (d, J=15.3 Hz, 2H), 1.34 (s, 1H), 1.24 (s, 1H), 1.09 (s, 5H), 1.01 (s, 2H), 0.74 (s, 2H). m/z=430.2

B464: 2-(2-(3-methylcyclohexyl)ethyl)-1,4-dihydroisoquinolin-3(2H)-one

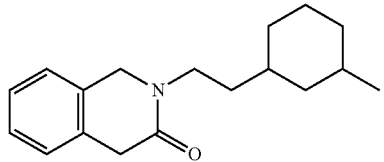 [SMILES: CC1CCCC(CCN2Cc3ccccc3CC2=O)C1]

2-(3-methylcyclohexyl)ethan-1-amine (0.5 mmol) and methyl 2-(2-(chloromethyl)phenyl)acetate (0.5 mmol) were mixed in 5 ml of DMF; DIPEA (0.75 mmol) was added. The mixture was heated at 80° C. for 5 h, cooled; solvent was removed by evaporation and residue was purified by HPLC. Yield: 32%.

1H NMR (400 MHz, Chloroform-d) δ 7.26-7.10 (m, 4H), 4.42 (s, 2H), 3.57 (s, 2H), 3.50 (p, J=7.4, 6.4 Hz, 2H), 3.44 (s, 1H), 1.73 (dq, J=11.1, 4.0 Hz, 1H), 1.72-1.58 (m, 1H), 1.62-1.37 (m, 4H), 1.37-1.17 (m, 1H), 1.09 (td, J=10.2, 7.9, 4.7 Hz, 1H), 0.85 (t, J=6.5 Hz, 3H), 0.84-0.71 (m, 1H). m/z=272.2

B465: N-(2-((2-fluorobenzyl)oxy)benzyl)-1-(4-methylcyclohexyl)propan-2-amine

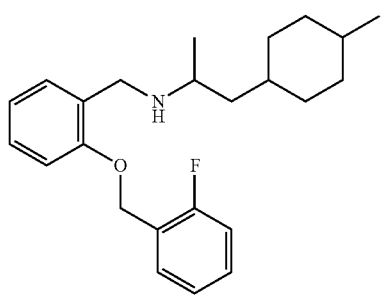 [SMILES: CC1CCC(CC(C)NCc2ccccc2OCc2ccccc2F)CC1]

1-(4-methylcyclohexyl)propan-2-amine (1 mmol) and 2-((2-fluorobenzyl)oxy)benzaldehyde (1 mmol) were dissolved in 0.6 ml MeOH, heated at 100° C. for 2 hours; then the mixture was cooled, NaBH$_4$ (1 mmol) was added and stirred for 4 hours. The mixture was heated for 2 hours at 60° C.; 3 ml of methanol and 0.2 g of C-18 chromatographic phase were added, stirred for 2 hours, filtered, the solvent was evaporated. The residue was purified by HPLC. Yield: 57%.

1H NMR (400 MHz, DMSO-d6) δ 7.61-7.53 (m, 1H), 7.41 (tdd, J=7.6, 5.4, 1.8 Hz, 1H), 7.32-7.22 (m, 2H), 7.25-7.16 (m, 2H), 7.09 (d, J=8.1 Hz, 1H), 6.90 (t, J=7.3 Hz, 1H), 5.15 (s, 2H), 3.76-3.67 (m, 1H), 3.60 (d, J=13.7 Hz, 1H), 2.60-2.47 (m, 1H), 1.54 (dd, J=13.2, 8.3 Hz, 3H), 1.50-1.43 (m, 1H), 1.22-1.09 (m, 3H), 1.04-0.90 (m, 1H), 0.90 (d, J=6.1 Hz, 2H), 0.82 (dd, J=13.9, 6.7 Hz, 2H), 0.78-0.68 (m, 3H). m/z=370.2

B466: 2-amino-3-(2-(((1-cyclohexylpropan-2-yl)amino)methyl)phenyl)propanoic acid

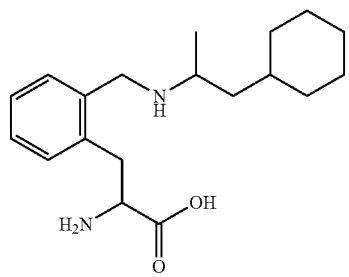 [SMILES: CC(CC1CCCCC1)NCc1ccccc1CC(N)C(=O)O]

Step A:
diethyl 2-acetamido-2-(2-(aminomethyl)benzyl)malonate (1 mmol) and 1-cyclohexylpropan-2-one (1 mmol) were dissolved in 0.6 ml MeOH, heated at 100° C. for 2 hours; then the mixture was cooled, NaBH$_4$ (1 mmol) was added and stirred for 4 hours. The mixture was heated for 2 hours at 60° C. Water (5 ml) were added, the organic layer was extracted with EtOAc (3*10 ml) and concentrated in vacuo. The residue was purified by HPLC. Yield: 57%.

Step B:
Diethyl 2-acetamido-2-(2-(((1-cyclohexylpropan-2-yl)amino)methyl)benzyl)malonate (0.05 mmol) was dissolved in 0.5 ml MeCOH; 0.1 ml HCl was added. The mixture was refluxed for 1 hour. The precipitate was filtered and was purified by LC. Yield: 39%.

1H NMR (500 MHz, Chloroform-d) δ 7.38 (d, J=7.5 Hz, 1H), 7.24 (d, J=8.0 Hz, 2H), 7.15 (d, J=7.5 Hz, 1H), 6.71 (s, 4H), 4.00 (t, J=11.5 Hz, 1H), 3.79 (d, J=12.1 Hz, 1H), 3.55 (s, 1H), 3.20 (t, J=9.9 Hz, 1H), 3.00 (s, 2H), 1.66 (q, J=11.7, 10.9 Hz, 6H), 1.40-1.34 (m, 1H), 1.32-1.27 (m, 2H), 1.27-1.19 (m, 4H), 1.14 (dt, J=22.2, 11.8 Hz, 2H), 0.89 (dp, J=40.3, 11.5, 10.8 Hz, 2H). m/z=319.2

B467: (2S)-2-amino-3-(2-(((2-cyclohexylpropyl)amino)methyl)phenyl)propanoic acid

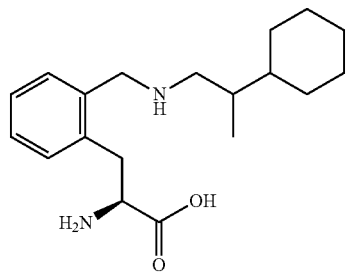 [SMILES: CC(CNCc1ccccc1C[C@H](N)C(=O)O)C1CCCCC1]

Step A:
diethyl 2-acetamido-2-(2-(aminomethyl)benzyl)malonate (5 mmol) and 2-cyclohexylpropanal (5 mmol) were dissolved in 1.5 ml MeOH, heated at 100° C. for 2 hours; then the mixture was cooled, NaBH$_4$ (5 mmol) was added and stirred for 1 hours at r.t. Thereafter, water (15 ml) was added, the organic layer was extracted with EtOAc (3×15 ml), and concentrated in vacuo. The residue was purified using HPLC. Yield: 54%.

Step B:
To a solution of diethyl 2-acetamido-2-(2-(((2-cyclohexylpropyl)amino)methyl)benzyl)malonate (2.5 mmol) in ethanol (10 ml) was added potassium hydroxide (2.5 mmol). The reaction was allowed to stir at reflux for 8 h and was then concentrated. The residue was dissolved in water and extracted with EtOAc. The aqueous layer was cooled to 0° C., carefully acidified to pH 2-3 using HCl, and extracted with EtOAc. The combined organics were dried over sodium sulfate, filtered, concentrated and purified by chiral chromatographic purification. Yield: 41%.

Step C:
(2S)-2-acetamido-3-(2-(((2-cyclohexylpropyl)amino)methyl)phenyl)propanoic acid (1 mmol) was dissolved in 0.5 ml AcOH; 0.2 ml HCl was added and was stirred for 2 hours. The precipitate was filtered and was purified using LC. Yield: 51%.

1H NMR (500 MHz, DMSO-d6) δ 7.04-6.89 (m, 3H), 6.90 (s, 1H), 4.28 (d, J=8.2 Hz, 8H), 3.83 (td, J=15.8, 15.4, 12.0 Hz, 2H), 3.65 (dd, J=9.0, 6.2 Hz, 1H), 2.96-2.88 (m, 1H), 2.78 (d, J=14.3 Hz, 1H), 2.66 (s, 1H), 2.46 (d, J=9.6 Hz, 1H), 1.28 (s, 1H), 1.21 (s, 2H), 1.19 (d, J=3.8 Hz, 1H), 1.12 (d, J=12.8 Hz, 1H), 1.05 (d, J=12.3 Hz, 2H), 0.74-0.65 (m, 1H), 0.63-0.49 (m, 1H), 0.47 (s, 2H), 0.45 (dd, J=7.1, 2.8 Hz, 2H). m/z=317.1

B468: 1-cyclohexyl-N-(2-(2-fluorophenethyl)benzyl)propan-2-amine

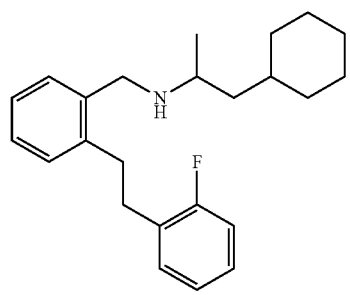

1-cyclohexylpropan-2-one (1 mmol) and (2-(2-fluorophenethyl)phenyl)methanamine (1 mmol) were dissolved in 0.6 ml MeOH, heated at 100° C. for 2 hours; then the mixture was cooled, NaBH$_4$ (1 mmol) was added and stirred for 4 hours. The mixture was heated for 2 hours at 60° C., 3 ml of methanol and 0.2 g of C-18 chromatographic phase were added, stirred for 2 hours, filtered, the solvent was evaporated. The residue was purified using HPLC. Yield: 31%. 1H NMR (400 MHz, Chloroform-d) δ 7.30 (d, J=4.4 Hz, 1H), 7.20-7.10 (m, 5H), 7.02 (q, J=8.4, 7.8 Hz, 2H), 3.80 (d, J=12.5 Hz, 1H), 3.67 (d, J=12.5 Hz, 1H), 2.99-2.90 (m, 4H), 2.77 (q, J=6.7 Hz, 1H), 1.62 (d, J=10.3 Hz, 5H), 1.39-1.30 (m, 1H), 1.10 (dd, J=23.7, 6.7 Hz, 5H), 0.84 (d, J=11.7 Hz, 2H). m/z=354.2

B469: N-(2-((2-fluorobenzyl)oxy)benzyl)-1-(4-(trifluoromethyl)cyclohexyl)propan-2-amine

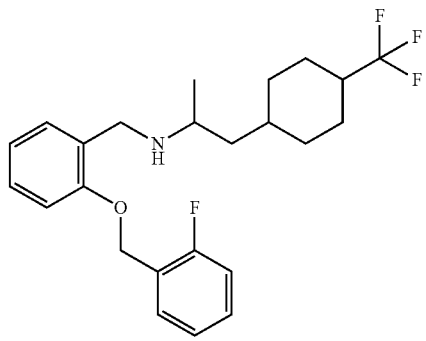 [SMILES: CC(CC1CCC(C(F)(F)F)CC1)NCc1ccccc1OCc1ccccc1F]

1-(4-(trifluoromethyl)cyclohexyl)propan-2-one (1 mmol) and (2-((2-fluorobenzyl)oxy)phenyl)methanamine (1 mmol) were dissolved in 0.6 ml MeOH, heated at 100° C. for 2 hours; then the mixture was cooled, NaBH$_4$ (1 mmol) was added and stirred for 4 hours. The mixture was heated for 2 hours at 60° C., 3 ml of methanol and 0.2 g of C-18 chromatographic phase were added, stirred for 2 hours, filtered, the solvent was evaporated. The residue was purified using HPLC. Yield: 28%.

1H NMR (400 MHz, Chloroform-d) δ 7.48 (s, 1H), 7.31 (d, J=7.1 Hz, 1H), 7.22 (t, J=9.4 Hz, 2H), 7.14 (t, J=7.5 Hz, 1H), 7.08 (t, J=9.2 Hz, 1H), 6.99-6.88 (m, 2H), 5.13 (s, 2H), 3.86 (dd, J=13.1, 8.6 Hz, 1H), 3.73 (dd, J=13.0, 8.8 Hz, 1H), 2.67-2.53 (m, 1H), 1.82 (t, J=13.7 Hz, 1H), 1.51 (s, 1H), 1.41 (s, 1H), 1.34 (ddd, J=25.5, 12.2, 6.1 Hz, 1H), 1.27-1.07 (m, 2H), 1.01 (td, J=6.6, 2.5 Hz, 3H), 0.84-0.73 (m, 1H). m/z=424.2

B470: 1-(4-ethylcyclohexyl)-N-(2-((2-fluorobenzyl)oxy)benzyl)propan-2-amine

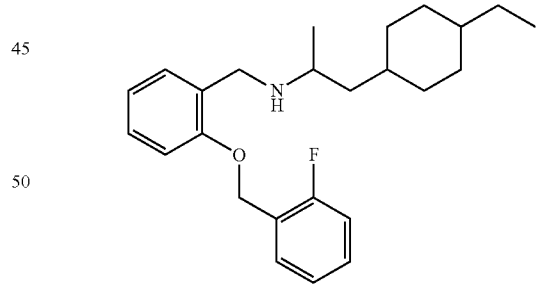

1-(4-ethylcyclohexyl)propan-2-amine (1 mmol) and 2-((2-fluorobenzyl)oxy)benzaldehyde (1 mmol) were dissolved in 0.6 ml MeOH, heated at 100° C. for 2 hours; then the mixture was cooled, NaBH$_4$ (1 mmol) was added and stirred for 4 hours. The mixture was heated for 2 hours at 60° C., 3 ml of methanol and 0.2 g of C-18 chromatographic phase were added, stirred for 2 hours, filtered, the solvent was evaporated. The residue was purified using HPLC. Yield: 38%.

1H NMR (400 MHz, Chloroform-d) δ 7.50 (t, J=7.5 Hz, 1H), 7.35-7.23 (m, 1H), 7.22 (d, J=7.6 Hz, 1H), 7.21-7.11 (m, 1H), 7.07 (dd, J=10.2, 8.1 Hz, 1H), 6.97-6.91 (m, 1H), 6.91 (d, J=7.3 Hz, 1H), 5.14 (s, 2H), 3.87 (dd, J=13.1, 6.2 Hz, 1H), 3.74 (dd, J=13.0, 4.3 Hz, 1H), 2.70-2.57 (m, 1H), 1.73 (s, 1H), 1.63 (s, 2H), 1.44-1.25 (m, 1H), 1.23 (d, J=6.5 Hz, 1H), 1.17 (dd, J=15.3, 8.6 Hz, 1H), 1.12-0.98 (m, 2H), 0.99 (s, 1H), 0.87-0.67 (m, 4H). m/z=384.2.

B471: N-(2-((2-fluorobenzyl)oxy)benzyl)-1-(4-isopropylcyclohexyl)propan-2-amine

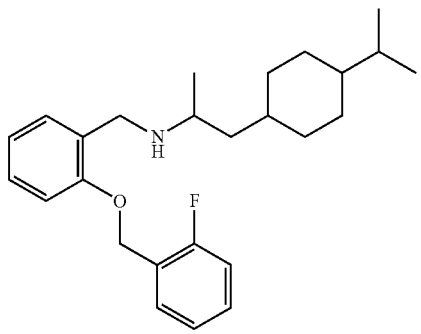 [SMILES: CC(CC1CCC(C(C)C)CC1)NCc1ccccc1OCc1ccccc1F]

1-(4-isopropylcyclohexyl)propan-2-amine (1 mmol) and 2-((2-fluorobenzyl)oxy)benzaldehyde (1 mmol) were dissolved in 0.6 ml MeOH, heated at 100° C. for 2 hours; then mixture was cooled, NaBH₄ (1 mmol) was added and stirred for 4 hours. The mixture was heated for 2 hours at 60° C., 3 ml of methanol and 0.2 g of C-18 chromatographic phase were added, stirred for 2 hours, filtered, the solvent was evaporated. The residue was purified using HPLC. Yield: 41%.

1H NMR (400 MHz, Chloroform-d) δ 7.50 (t, J=7.7 Hz, 1H), 7.30 (d, J=7.0 Hz, 1H), 7.18 (dt, J=26.1, 6.7 Hz, 2H), 7.07 (t, J=9.2 Hz, 1H), 6.93 (dd, J=12.3, 7.6 Hz, 2H), 5.15 (s, 2H), 3.88 (d, J=13.1 Hz, 1H), 3.74 (d, J=13.1 Hz, 1H), 2.65 (d, J=6.4 Hz, 1H), 1.58 (dt, J=27.6, 12.6 Hz, 4H), 1.30 (dq, J=13.2, 6.6 Hz, 1H), 1.08 (dd, J=12.8, 6.3 Hz, 1H), 1.00 (d, J=6.2 Hz, 3H), 0.80 (d, J=6.9 Hz, 7H), 0.74 (d, J=11.6 Hz, 1H). m/z=398.2

B472: 1-(4-cyclopropylcyclohexyl)-N-(2-((2-fluorobenzyl)oxy)benzyl)propan-2-amine

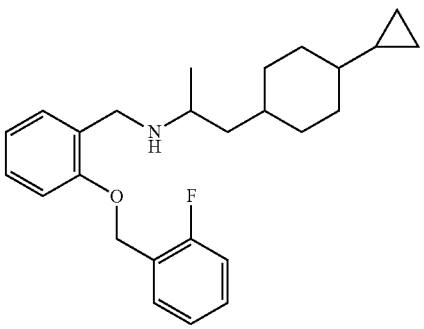 [SMILES: CC(CC1CCC(C2CC2)CC1)NCc1ccccc1OCc1ccccc1F]

1-(4-cyclopropylcyclohexyl)propan-2-amine (1 mmol) and 2-((2-fluorobenzyl)oxy)benzaldehyde (1 mmol) were dissolved in 0.6 ml MeOH, heated at 100° C. for 2 hours; then mixture was cooled, NaBH₄ (1 mmol) was added and stirred for 4 hours. The mixture was heated for 2 hours at 60° C., 3 ml of methanol and 0.2 g of C-18 chromatographic phase were added, stirred for 2 hours, filtered, the solvent was evaporated. The residue was purified using HPLC. Yield: 32%.

1H NMR (400 MHz, Chloroform-d) δ 7.50 (t, J=7.7 Hz, 2H), 7.30 (d, J=7.0 Hz, 1H), 7.26-7.03 (m, 6H), 6.97-6.88 (m, 3H), 5.14 (s, 3H), 3.88 (d, J=13.4 Hz, 2H), 3.75 (dd, J=13.2, 8.5 Hz, 2H), 2.65 (s, 2H), 1.70 (s, 4H), 1.61 (d, J=13.1 Hz, 1H), 1.40 (s, 7H), 1.31-1.16 (m, 1H), 1.20 (s, 6H), 1.13-0.98 (m, 5H), 0.94 (d, J=12.2 Hz, 1H), 0.90 (s, 1H), 0.76-0.66 (m, 2H), 0.53 (s, 1H), 0.33 (dd, J=15.5, 7.8 Hz, 5H). m/z=396.2

B473: 1-(4,4-difluorocyclohexyl)-N-(2-((2-fluorobenzyl)oxy)benzyl)propan-2-amine

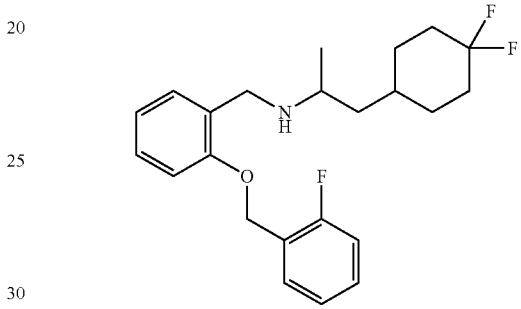

1-(4,4-difluorocyclohexyl)propan-2-amine (1 mmol) and 2-((2-fluorobenzyl)oxy)benzaldehyde (1 mmol) were dissolved in 0.6 ml MeOH, heated at 100° C. for 2 hours; then the mixture was cooled, NaBH₄ (1 mmol) was added and stirred for 4 hours. The mixture was heated for 2 hours at 60° C., 3 ml of methanol and 0.2 g of C-18 chromatographic phase were added, stirred for 2 hours, filtered, the solvent was evaporated. The residue was purified using HPLC. Yield: 39%.

1H NMR (400 MHz, Chloroform-d) δ 7.48 (dd, J=8.4, 6.6 Hz, 1H), 7.32 (d, J=7.2 Hz, 1H), 7.24 (d, J=1.7 Hz, 1H), 7.23 (s, 1H), 7.22-7.13 (m, 1H), 7.10 (dd, J=18.8, 9.4 Hz, 1H), 6.99-6.89 (m, 2H), 5.13 (s, 2H), 3.87 (d, J=13.1 Hz, 1H), 3.73 (d, J=13.1 Hz, 1H), 2.62 (dt, J=11.7, 5.7 Hz, 1H), 1.62 (d, J=12.5 Hz, 2H), 1.58-1.46 (m, 2H), 1.36 (q, J=6.2, 5.6 Hz, 1H), 1.32 (s, 2H), 1.18-1.07 (m, 3H), 1.02 (d, J=6.2 Hz, 3H). m/z=392.3

B1: N-benzyl-2-(cyclohex-1-en-1-yl)ethan-1-amine

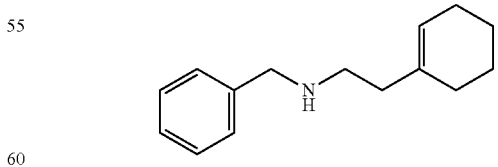

2-(cyclohex-1-en-1-yl)ethan-1-amine (0.5 mmol) and benzaldehyde (0.55 mmol) were dissolved in 0.6 ml MeOH, heated at 100° C. for 2 hours; then the mixture was cooled, NaBH₄ (0.5 mmol) was added and stirred for 4 hours. The mixture was heated for 2 hours at 60° C.; 3 ml of methanol and 0.2 g of C-18 chromatographic phase were added, stirred for 2 hours, filtered, evaporated and dissolved in 0.5 ml of DMSO. The residue was purified by HPLC. Yield: 41%.

1H NMR (400 MHz, DMSO-d6) δ 9.73 (s, 2H), 7.61 (d, J=7.6 Hz, 2H), 7.39 (d, J=6.4 Hz, 3H), 5.46 (s, 1H), 4.07 (t, J=5.6 Hz, 2H), 3.11 (s, 2H), 2.88 (d, J=9.0 Hz, 2H), 2.36 (t, J=8.3 Hz, 2H), 1.98 (s, 2H), 1.90 (d, J=7.4 Hz, 2H), 1.60 (q, J=5.7 Hz, 2H), 1.55 (q, J=5.9 Hz, 2H). m/z=216.2

B10: 2-(cyclohex-1-en-1-yl)-N-(4-methylbenzyl)ethan-1-amine

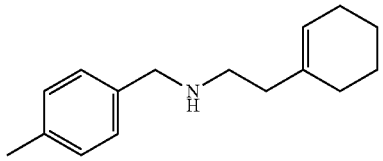 [SMILES: Cc1ccc(CNCCC2=CCCCC2)cc1]

2-(cyclohex-1-en-1-yl)ethan-1-amine (0.5 mmol) and 4-methylbenzaldehyde (0.5 mmol) were dissolved in 0.6 ml MeOH, heated at 100° C. for 2 hours; then the mixture was cooled, NaBH₄ (0.5 mmol) was added and stirred for 4 hours. The mixture was heated for 2 hours at 60° C.; 3 ml of methanol and 0.2 g of C-18 chromatographic phase were added, stirred for 2 hours, filtered, evaporated. The residue was purified by HPLC. Yield: 39%. 1H NMR (400 MHz, DMSO-d6) δ 9.34 (s, 1H), 7.45 (d, J=7.7 Hz, 1H), 7.22 (d, J=7.7 Hz, 1H), 5.43 (s, 0H), 4.06 (t, J=5.6 Hz, 1H), 2.88 (dq, J=11.3, 6.0 Hz, 1H), 2.31 (s, 3H), 1.94 (s, 1H), 1.85 (d, J=6.7 Hz, 1H), 1.59-1.53 (m, 1H), 1.53-1.43 (m, 1H). m/z=230.4

B11: 2-(cyclohex-1-en-1-yl)-N-(3-methylbenzyl)ethan-1-amine

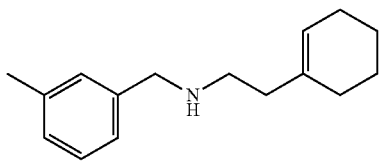 [SMILES: Cc1cccc(CNCCC2=CCCCC2)c1]

2-(cyclohex-1-en-1-yl)ethan-1-amine (0.5 mmol) and 3-methylbenzaldehyde (0.5 mmol) were dissolved in 0.6 ml MeOH, heated at 100° C. for 2 hours; then the mixture was cooled, NaBH₄ (0.5 mmol) was added and stirred for 4 hours. The mixture was heated for 2 hours at 60° C.; 3 ml of methanol and 0.2 g of C-18 chromatographic phase were added, stirred for 2 hours, filtered, evaporated and the residue was purified by HPLC. Yield: 41%. 1H NMR (400 MHz, DMSO-d6) δ 8.95 (s, 2H), 7.36-7.26 (m, 3H), 7.21 (d, J=6.5 Hz, 1H), 5.44 (s, 1H), 4.05 (s, 2H), 2.94-2.86 (m, 2H), 2.30 (d, J=18.1 Hz, 6H), 1.94 (s, 2H), 1.87 (s, 2H), 1.61-1.53 (m, 2H), 1.49 (dd, J=6.7, 4.5 Hz, 1H). m/z=230.2

B13: 2-(cyclohex-1-en-1-yl)-N-(2-methylbenzyl)ethan-1-amine

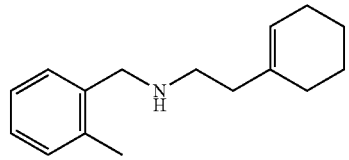 [SMILES: Cc1ccccc1CNCCC1=CCCCC1]

2-(cyclohex-1-en-1-yl)ethan-1-amine (0.5 mmol) and 2-methylbenzaldehyde (0.5 mmol) were dissolved in 0.6 ml MeOH, heated at 100° C. for 2 hours; then the mixture was cooled, NaBH₄ (0.5 mmol) was added and stirred for 4 hours. The mixture was heated for 2 hours at 60° C.; 3 ml of methanol and 0.2 g of C-18 chromatographic phase were added, stirred for 2 hours, filtered, evaporated. The residue was purified by HPLC. Yield: 43%. 1H NMR (400 MHz, DMSO-d6) δ 9.24 (s, 2H), 7.57-7.51 (m, 1H), 7.34-7.21 (m, 3H), 5.47 (s, 1H), 4.11 (t, J=6.1 Hz, 2H), 3.03 (dq, J=11.3, 5.9 Hz, 2H), 2.56-2.47 (m, 2H), 2.37 (d, J=10.0 Hz, 5H), 1.96 (s, 2H), 1.91 (s, 1H), 1.58 (dd, J=10.7, 6.0 Hz, 2H), 1.52 (p, J=5.9 Hz, 2H). m/z=230.2

Example 14: Gram Negative (*E. coli* and *A. baumannii*) MIC protocol

Overnight bacterial cultures were grown in LB with no added antibiotics at 37° C. with shaking. A 1:1000 dilution of these cultures into LB was exposed to concentration gradients of compounds in 96-well plates (100 μL per well assay volume). Resulting plates were incubated at 37° C. for 24 h without shaking, and OD600 was measured at the end of the incubation. MICs were determined as the lowest concentrations at which OD600 remained at baseline.

Antibacterial activity of the compounds of the invention is shown in Table 3.

Example 15: Tuberculosis Assay

A luminescence assay was carried out via the following steps. The strain used in the luminescence assay was H37RvMA with the LuxCDABE operon integrated at the L5 site on a Kanamycin marked plasmid (pMV306hsp+LuxG13):
1. Inoculate −80 stock into 7H9 OADC+Kan (25 ug/mL)
2. When bacteria reach mid-log phase, passage cells in 7H9 OADC+Kan25
3. When cells reach mid log phase dilute to OD=0.05 in 7H9 OADC
4. Add 100 uL of cells to each well of the plate
5. Seal the plate with an optical film and read luminescence using the following protocol:
   a. Plate reader: Biotek Synergy H1
   b. Double orbital shaking (10 s); frequency: 282 cpm (3 mm)
   c. Luminescence endpoint parameters: is integration time, gain 200, read height 1 mm
6. Remove optical film, seal with a breathable film, and incubate shaking at 37 C
7. Read luminescence at day 0, 1, 4, and 7

An Alamar Blue/Resazurin assay was carried out via the following steps. The strain used in the Alamar Blue/Resazurin assay was H37RvMA:

1. Inoculate −80 stocks into 7H9 OADC
2. When cells reach mid-log phase passage in 7H9 OADC
3. When cells reach mid log phase, dilute to OD=0.006
4. Add 100 uL of cells (diluted to OD=0.006) to the plate (making final OD in plate 0.003)
5. Seal the plate with breathable film, place in a ziplock, and put the plate in a box
   a. Incubate shaking at 37° C. for 4 days
6. After incubation, add 20 uL of Resazurin/alamar blue (0.02%) to every well (not including water wells
7. Re-seal the plates and incubate at 37° C., check the plates after 24 and 48 hours
   a. Purple=no growth, pink=growth
   b. MIC recorded as the well with the lowest concentration of drug that there is killing (purple color).

Example 16: Antibacterial and Anti-Tuberculosis Activities

TABLE 3

Antimicrobial Activity

| FRS-ID | Structure | MIC WT *E. coli* LB Media (μM) | MIC *E. coli* delta-TolC LB Media (μM) | MIC *A. baumannii* LB Media (μM) | WT H37Rv MTB Activity (μM) |
|---|---|---|---|---|---|
| B1 | benzyl-NH-CH2CH2-cyclohexenyl · HCl | 60 | 46 | 150 | >150 |
| B2 | isopentyl-NH-CH2-phenyl | >150 | >150 | >150 | >150 |
| B3 | cyclohexenyl-CH2CH2-NH-CH2-(4-pyridyl) · HCl | >150 | >150 | >150 | >150 |
| B4 | cyclohexenyl-CH2CH2-NH-CH2-(3-pyridyl) | >150 | >150 | >150 | >150 |
| B5 | benzyl-NH-CH2-CH(CH3)-cyclopentyl | >150 | >150 | >150 | >150 |
| B6 | benzyl-NH-hexyl | >150 | >150 | >150 | >150 |
| B7 | cyclohexyl-NH-CH2-phenyl | >150 | >150 | >150 | >150 | ns
TABLE 3-continued
| | Antimicrobial Activity | | | |
|---|---|---|---|---|
| FRS-ID | MIC WT *E. coli* LB Media (μM) | MIC *E. coli* delta-TolC LB Media (μM) | MIC *A. baumannii* LB Media (μM) | WT H37Rv MTB Activity (μM) |
| B8 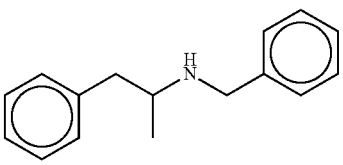 | >150 | >150 | >150 | >150 |
| B9 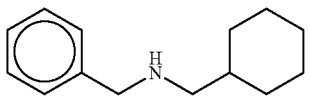 | >150 | >150 | >150 | >150 |
| B10 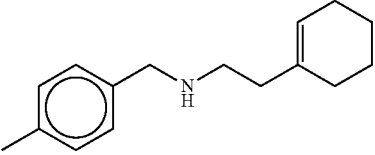 | >150 | >150 | >150 | >150 |
| B11 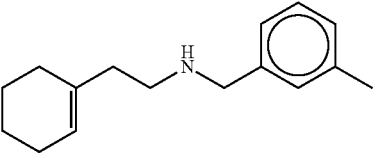 | >150 | >150 | >150 | >150 |
| B12 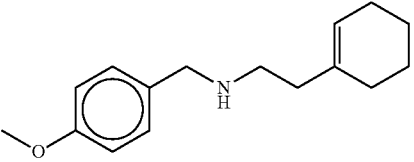 | >150 | >150 | >150 | >150 |
| B13 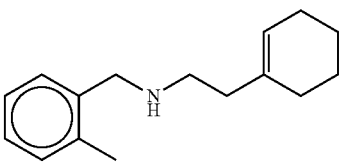 | 90 | 55 | 150 | >150 |
| B14 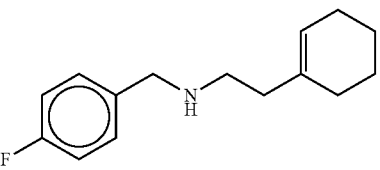 | >150 | >150 | >150 | >150 |
| B15 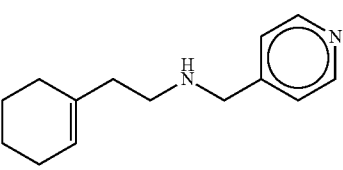 | >150 | >150 | >150 | >150 |

TABLE 3-continued

Antimicrobial Activity

| FRS-ID | Structure | MIC WT E. coli LB Media (μM) | MIC E. coli delta-TolC LB Media (μM) | MIC A. baumannii LB Media (μM) | WT H37Rv MTB Activity (μM) |
|---|---|---|---|---|---|
| B16 | | >150 | >150 | >150 | >150 |
| B17 | | >150 | >150 | >150 | >150 |
| B18 | | >150 | >150 | >150 | >150 |
| B19 | | >150 | >150 | >150 | 150 |
| B20 | | >150 | >150 | >150 | >150 |
| B21 | | >150 | >150 | >150 | >150 |

TABLE 3-continued

| | Antimicrobial Activity | | | |
|---|---|---|---|---|
| FRS-ID | MIC WT *E. coli* LB Media (μM) | MIC *E. coli* delta-TolC LB Media (μM) | MIC *A. baumannii* LB Media (μM) | WT H37Rv MTB Activity (μM) |
| B22 | >150 | >150 | >150 | >150 |
| B23 | >150 | >150 | >150 | >150 |
| B24 | >150 | >150 | >150 | >150 |
| B25 | >150 | >150 | >150 | >150 |
| B26 | >150 | >150 | >150 | >150 |
| B27 | >150 | >150 | >150 | 91 |

TABLE 3-continued
| | Antimicrobial Activity | | | |
|---|---|---|---|---|
| FRS-ID | MIC WT E. coli LB Media (μM) | MIC E. coli delta-TolC LB Media (μM) | MIC A. baumannii LB Media (μM) | WT H37Rv MTB Activity (μM) |
| B28 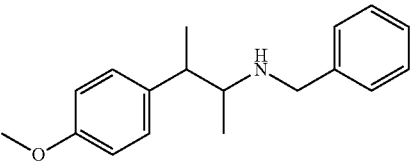 [SMILES: COc1ccc(C(C)C(C)NCc2ccccc2)cc1] | >150 | >150 | >150 | >150 |
| B29 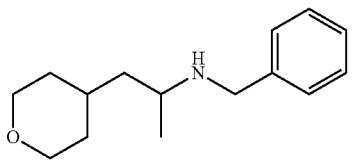 [SMILES: CC(CC1CCOCC1)NCc1ccccc1] | >150 | >150 | >150 | >150 |
| B30 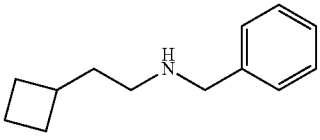 [SMILES: c1ccc(CNCCC2CCC2)cc1] | >150 | >150 | >150 | >150 |
| B31 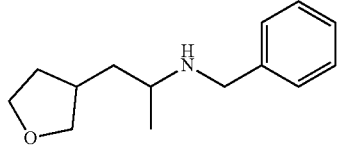 [SMILES: CC(CC1CCOC1)NCc1ccccc1] | >150 | >150 | >150 | >150 |
| B32 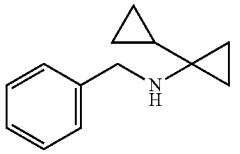 [SMILES: c1ccc(CNC2(C3CC3)CC2)cc1] | >150 | >150 | >150 | >150 |
| B33 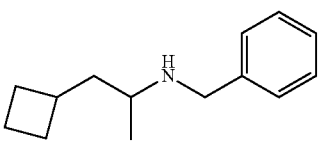 | >150 | >150 | >150 | >150 |
| B34 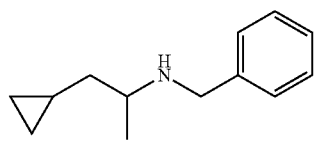 | >150 | >150 | >150 | >150 |
| B35 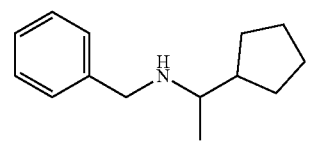 | >150 | >150 | >150 | >150 |
| B36 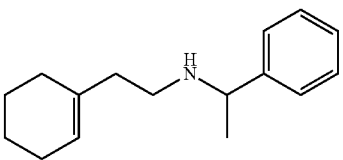 [SMILES: CC(NCCC1=CCCCC1)c1ccccc1] | >150 | >150 | >150 | >150 |

TABLE 3-continued

| | Antimicrobial Activity | | | |
|---|---|---|---|---|
| FRS-ID | MIC WT *E. coli* LB Media (μM) | MIC *E. coli* delta-TolC LB Media (μM) | MIC *A. baumannii* LB Media (μM) | WT H37Rv MTB Activity (μM) |
| B37 | >150 | >150 | >150 | 150 |
| B38 | 91 | 90 | 150 | >150 |
| B39 | >150 | >150 | >150 | >150 |
| B40 | >150 | >150 | >150 | >150 |
| B41 | >150 | >150 | >150 | >150 |
| B42 | >150 | >150 | >150 | >150 |
| B43 | >150 | >150 | >150 | >150 |

TABLE 3-continued
| | | Antimicrobial Activity | | | |
|---|---|---|---|---|---|
| FRS-ID | | MIC WT E. coli LB Media (μM) | MIC E. coli delta-TolC LB Media (μM) | MIC A. baumannii LB Media (μM) | WT H37Rv MTB Activity (μM) |
| B44 | 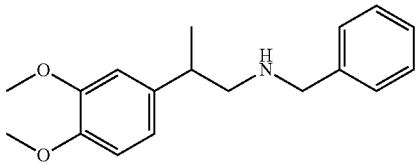 [SMILES: COc1ccc(C(C)CNCc2ccccc2)cc1OC] | >150 | >150 | >150 | >150 |
| B45 | 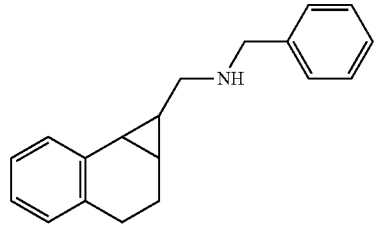 | >150 | >150 | >150 | 91 |
| B46 | 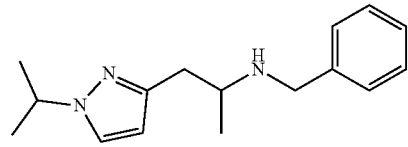 [SMILES: CC(Cc1ccn(C(C)C)n1)NCc1ccccc1] | >150 | >150 | >150 | >150 |
| B47 | 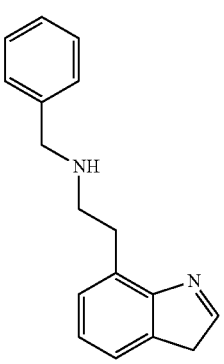 [SMILES: C1=Nc2c(cccc2CCNCc2ccccc2)C1] | >150 | >150 | >150 | >150 |
| B48 | | >150 | >150 | 150 | 150 |
| B49 | 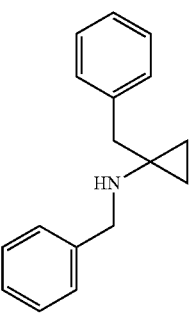 [SMILES: c1ccc(CNC2(Cc3ccccc3)CC2)cc1] | >150 | >150 | >150 | >150 |

TABLE 3-continued
| | | MIC WT E. coli LB Media (μM) | MIC E. coli delta-TolC LB Media (μM) | MIC A. baumannii LB Media (μM) | WT H37Rv MTB Activity (μM) |
|---|---|---|---|---|---|
| FRS-ID | | | | | |
| B50 | 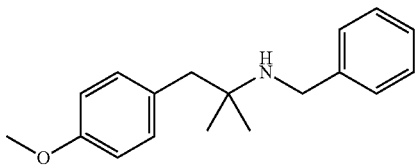 [SMILES: COc1ccc(CC(C)(C)NCc2ccccc2)cc1] | >150 | >150 | >150 | >150 |
| B51 | 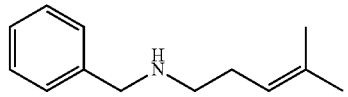 | >150 | >150 | >150 | >150 |
| B52 | 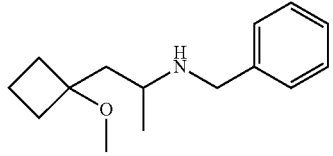 [SMILES: COC1(CC(C)NCc2ccccc2)CCC1] | >150 | >150 | >150 | >150 |
| B53 | 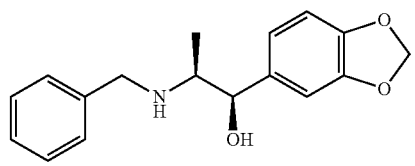 [SMILES: C[C@H](NCc1ccccc1)[C@H](O)c1ccc2c(c1)OCO2] | >150 | >150 | >150 | >150 |
| B54 | 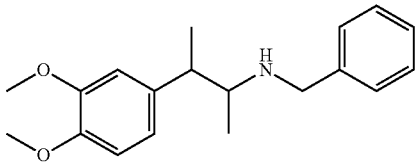 [SMILES: COc1ccc(C(C)C(C)NCc2ccccc2)cc1OC] | >150 | >150 | >150 | >150 |
| B55 | 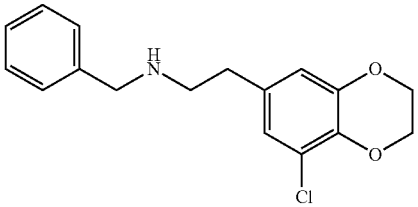 [SMILES: Clc1cc(CCNCc2ccccc2)cc2c1OCCO2] | >150 | >150 | >150 | 150 |
| B56 | 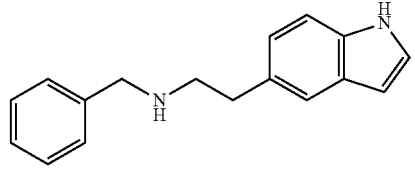 [SMILES: c1ccc(CNCCc2ccc3[nH]ccc3c2)cc1] | >150 | >150 | >150 | >150 |

TABLE 3-continued
| | | Antimicrobial Activity | | | |
|---|---|---|---|---|---|
| FRS-ID | | MIC WT E. coli LB Media (μM) | MIC E. coli delta-TolC LB Media (μM) | MIC A. baumannii LB Media (μM) | WT H37Rv MTB Activity (μM) |
| B57 | 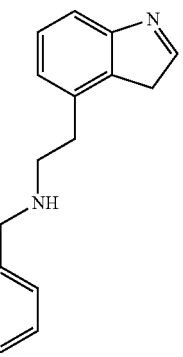 | >150 | >150 | >150 | >150 |
| B58 | 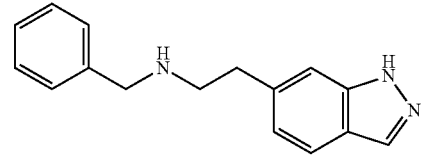 [SMILES: c1ccc(CNCCc2ccc3cn[nH]c3c2)cc1] | >150 | >150 | >150 | >150 |
| B59 | 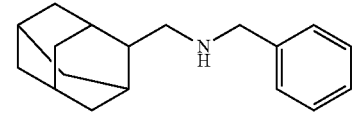 [SMILES: c1ccc(CNCC2C3CC4CC(C3)CC2C4)cc1] | >150 | >150 | >150 | 33 |
| B60 | 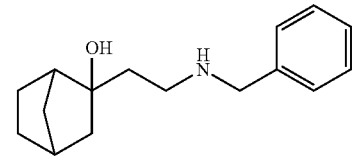 [SMILES: OC1(CCNCc2ccccc2)CC2CCC1C2] | >150 | >150 | >150 | >150 |
| B61 | 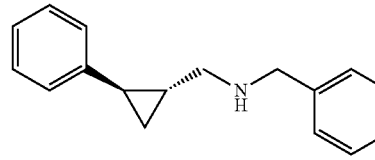 | >150 | >150 | >150 | >150 |
| B62 | 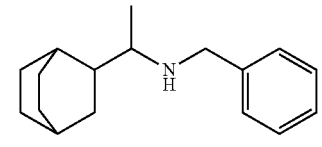 [SMILES: CC(NCc1ccccc1)C1CC2CCC1CC2] | >150 | >150 | >150 | >150 |
| B63 | 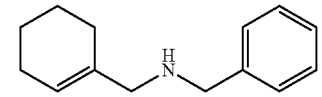 [SMILES: C1=C(CNCc2ccccc2)CCCC1] | >150 | >150 | >150 | >150 |
| B64 | 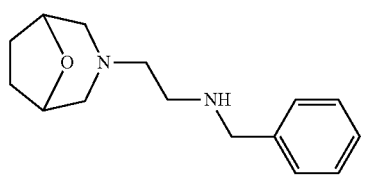 [SMILES: c1ccc(CNCCN2CC3CCC(C2)O3)cc1] | >150 | >150 | >150 | >150 |

TABLE 3-continued
| | Antimicrobial Activity | | | |
|---|---|---|---|---|
| FRS-ID | MIC WT *E. coli* LB Media (μM) | MIC *E. coli* delta-TolC LB Media (μM) | MIC *A. baumannii* LB Media (μM) | WT H37Rv MTB Activity (μM) |
| B65 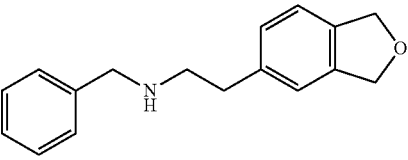 [SMILES: c1ccc(CNCCc2ccc3c(c2)COC3)cc1] | >150 | >150 | >150 | >150 |
| B66 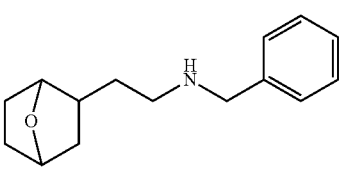 [SMILES: c1ccc(CNCCC2CC3CCC2O3)cc1] | >150 | >150 | >150 | >150 |
| B67 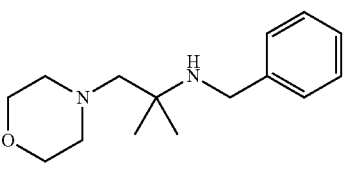 [SMILES: CC(C)(CN1CCOCC1)NCc1ccccc1] | >150 | >150 | >150 | >150 |
| B68 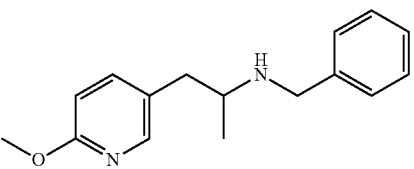 [SMILES: COc1ccc(CC(C)NCc2ccccc2)cn1] | >150 | >150 | >150 | >150 |
| B69 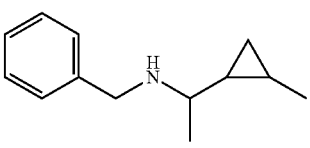 | >150 | >150 | >150 | >150 |
| B70 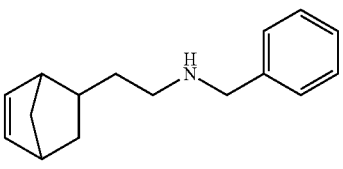 [SMILES: C1=CC2CC1CC2CCNCc1ccccc1] | >150 | >150 | >150 | >150 |
| B71 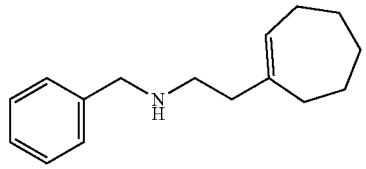 [SMILES: C1=C(CCNCc2ccccc2)CCCCC1] | 150 | 90 | >150 | 91 |
| B72 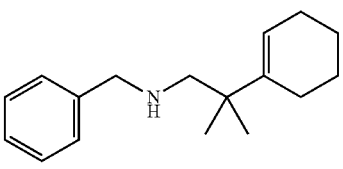 [SMILES: CC(C)(CNCc1ccccc1)C1=CCCCC1] | >150 | >150 | >150 | >150 |

TABLE 3-continued
Antimicrobial Activity
| FRS-ID | | MIC WT E. coli LB Media (μM) | MIC E. coli delta-TolC LB Media (μM) | MIC A. baumannii LB Media (μM) | WT H37Rv MTB Activity (μM) |
|---|---|---|---|---|---|
| B73 | 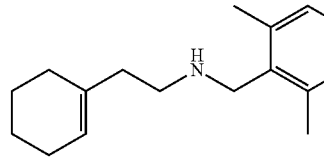 | >150 | >150 | >150 | >150 |
| B74 | 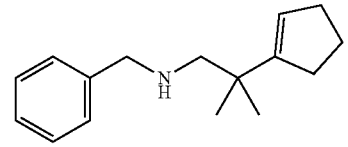 [SMILES: CC(C)(CNCc1ccccc1)C1=CCCC1] | >150 | >150 | >150 | >150 |
| B75 | 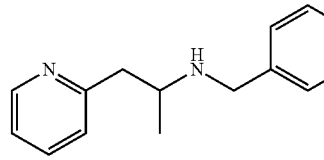 | >150 | >150 | >150 | >150 |
| B76 | 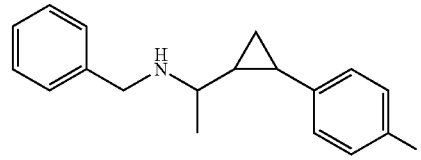 | >150 | >150 | >150 | >150 |
| B77 | 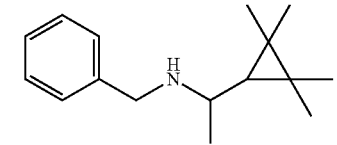 | >150 | >150 | >150 | >150 |
| B78 | 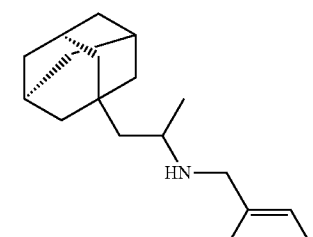 | 250 | 150 | >150 | 55 |
| B79 | 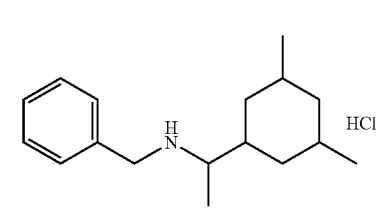 [SMILES: CC1CC(C)CC(C(C)NCc2ccccc2)C1 ; Cl] | >150 | >150 | >150 | 91 |

TABLE 3-continued

| | Antimicrobial Activity | | | |
|---|---|---|---|---|
| FRS-ID | MIC WT E. coli LB Media (μM) | MIC E. coli delta-TolC LB Media (μM) | MIC A. baumannii LB Media (μM) | WT H37Rv MTB Activity (μM) |
| B80 | 250 | 90 | >150 | >150 |
| B81 | >150 | >150 | >150 | >150 |
| B82 | >150 | >150 | >150 | >150 |
| B83 | >150 | >150 | >150 | >150 |
| B84 | >150 | >150 | >150 | >150 |
| B85 | >150 | >150 | >150 | >150 |
| B86 | >150 | >150 | >150 | >150 |

TABLE 3-continued

| | Antimicrobial Activity | | | |
|---|---|---|---|---|
| FRS-ID | MIC WT *E. coli* LB Media (μM) | MIC *E. coli* delta-TolC LB Media (μM) | MIC *A. baumannii* LB Media (μM) | WT H37Rv MTB Activity (μM) |
| B87 | 300 | >150 | >150 | >150 |
| B88 | >150 | >150 | >150 | >150 |
| B89 | 300 | >150 | >150 | 91 |
| B90 | >150 | >150 | >150 | >150 |
| B91 | >150 | 90 | >150 | >150 |
| B92 | >150 | >150 | >150 | >150 |

TABLE 3-continued
| | Antimicrobial Activity | | | |
|---|---|---|---|---|
| FRS-ID | MIC WT E. coli LB Media (μM) | MIC E. coli delta-TolC LB Media (μM) | MIC A. baumannii LB Media (μM) | WT H37Rv MTB Activity (μM) |
| B93 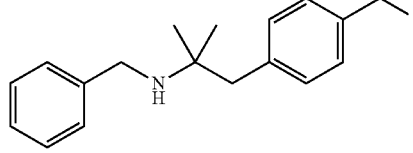 | >150 | >150 | >150 | >150 |
| B94 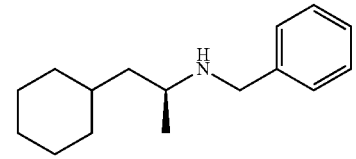 [SMILES: C[C@@H](CC1CCCCC1)NCc1ccccc1] | 17 | 7 | 91 | >150 |
| B95 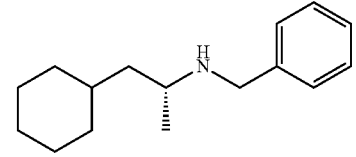 [SMILES: C[C@H](CC1CCCCC1)NCc1ccccc1] | >150 | >150 | >150 | 55 |
| B96 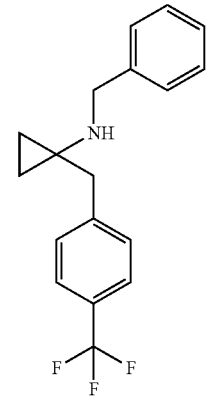 [SMILES: FC(F)(F)c1ccc(CC2(NCc3ccccc3)CC2)cc1] | >150 | 90 | >150 | >150 |
| B97 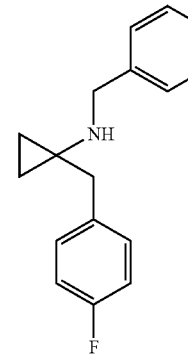 | >150 | >150 | >150 | >150 |

TABLE 3-continued

| | Antimicrobial Activity | | | |
|---|---|---|---|---|
| FRS-ID | MIC WT *E. coli* LB Media (μM) | MIC *E. coli* delta-TolC LB Media (μM) | MIC *A. baumannii* LB Media (μM) | WT H37Rv MTB Activity (μM) |
| B98 | >150 | 150 | >150 | >150 |
| B99 | >150 | >150 | >150 | 55 |
| B100 | >150 | >150 | >150 | >150 |
| B101 | 70 | 40 | 150 | >150 |
| B102 | 120 | 90 | 150 | 91 |
| B103 | 150 | 150 | >150 | >150 |
| B104 | >150 | 91 | >150 | 55 |

TABLE 3-continued
| | Antimicrobial Activity | | | |
|---|---|---|---|---|
| FRS-ID | MIC WT *E. coli* LB Media (μM) | MIC *E. coli* delta-TolC LB Media (μM) | MIC *A. baumannii* LB Media (μM) | WT H37Rv MTB Activity (μM) |
| B105 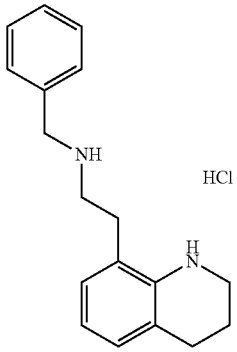 [SMILES: c1ccc(CNCCc2cccc3c2NCCC3)cc1 ; Cl] | >150 | >150 | >150 | 91 |
| B106 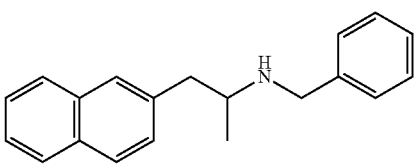 [SMILES: CC(Cc1ccc2ccccc2c1)NCc1ccccc1] | >150 | >150 | >150 | 150 |
| B107 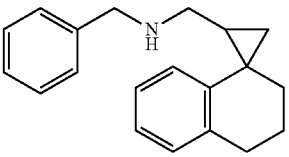 [SMILES: c1ccc(CNCC2CC23CCCc2ccccc23)cc1] | >150 | >150 | >150 | >150 |
| B108 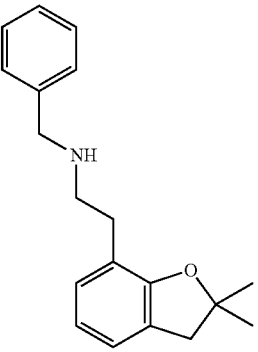 [SMILES: CC1(C)Cc2cccc(CCNCc3ccccc3)c2O1] | >150 | >150 | >150 | >150 |
| B109 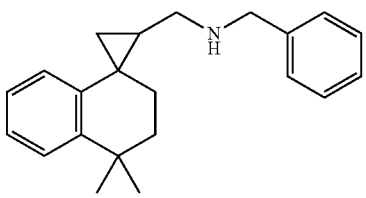 [SMILES: CC1(C)CCC2(CC2CNCc2ccccc2)c2ccccc21] | >150 | 91 | 150 | 55 |
| B110 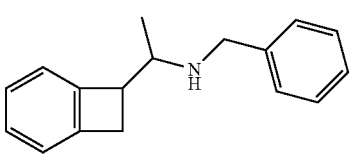 [SMILES: CC(NCc1ccccc1)C1Cc2ccccc21] | >150 | >150 | >150 | >150 |

TABLE 3-continued

Antimicrobial Activity

| FRS-ID | Structure | MIC WT *E. coli* LB Media (μM) | MIC *E. coli* delta-TolC LB Media (μM) | MIC *A. baumannii* LB Media (μM) | WT H37Rv MTB Activity (μM) |
|---|---|---|---|---|---|
| B111 | (structure: N-benzyl-2-(4-methoxynaphthalen-1-yl)ethanamine) | >150 | 150 | 150 | 33 |
| B112 | (structure: N-benzyl-1-(6-methoxy-1,2,3,4-tetrahydronaphthalen-1-yl)methanamine) | >150 | >150 | >150 | >150 |
| B113 | (structure: N-benzyl-1-(1,2,3,4-tetrahydronaphthalen-1-yl)ethanamine) | >150 | >150 | >150 | >150 |
| B114 | (structure: N-benzyl-2-(1H-indol-6-yl)ethanamine) | >150 | >150 | >150 | >150 |
| B115 | (structure: N-benzyl-2-(1H-indazol-5-yl)ethanamine) | >150 | >150 | >150 | >150 |

TABLE 3-continued
| | Antimicrobial Activity | | | |
|---|---|---|---|---|
| FRS-ID | MIC WT *E. coli* LB Media (μM) | MIC *E. coli* delta-TolC LB Media (μM) | MIC *A. baumannii* LB Media (μM) | WT H37Rv MTB Activity (μM) |
| B116 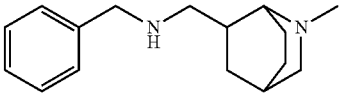 [SMILES: CN1CC2CCC1C(CNCc1ccccc1)C2] | >150 | >150 | >150 | >150 |
| B117 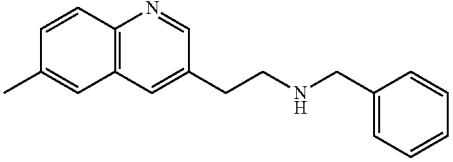 [SMILES: Cc1ccc2ncc(CCNCc3ccccc3)cc2c1] | >150 | >150 | >150 | >150 |
| B118 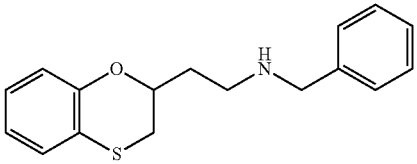 [SMILES: c1ccc(CNCCC2CSc3ccccc3O2)cc1] | >150 | >150 | >150 | >150 |
| B119 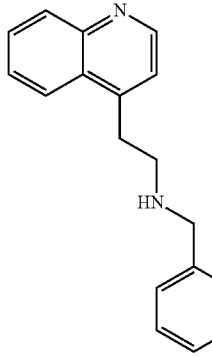 | >150 | >150 | >150 | >150 |
| B120 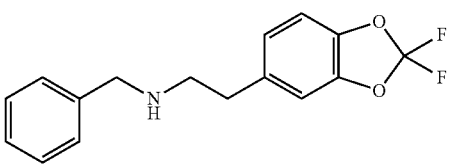 [SMILES: FC1(F)Oc2ccc(CCNCc3ccccc3)cc2O1] | >150 | >150 | >150 | >150 |
| B121 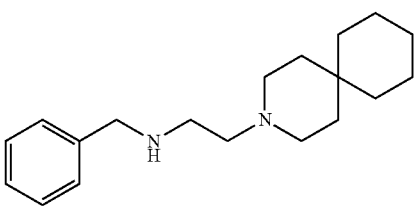 [SMILES: c1ccc(CNCCN2CCC3(CCCCC3)CC2)cc1] | >150 | >150 | >150 | >150 |
| B122 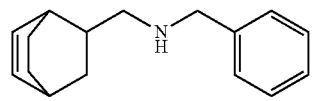 [SMILES: C1=CC2CCC1CC2CNCc1ccccc1] | >150 | >150 | >150 | 150 |
| B123 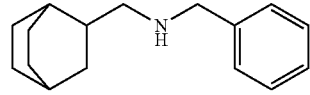 [SMILES: c1ccc(CNCC2CC3CCC2CC3)cc1] | >150 | >150 | >150 | 150 |

TABLE 3-continued

Antimicrobial Activity

| FRS-ID | MIC WT *E. coli* LB Media (μM) | MIC *E. coli* delta-TolC LB Media (μM) | MIC *A. baumannii* LB Media (μM) | WT H37Rv MTB Activity (μM) |
| --- | --- | --- | --- | --- |
| B124 | >150 | >150 | >150 | >150 |
| B125 | >150 | >150 | >150 | >150 |
| B126 | >150 | >150 | >150 | >150 |
| B127 | >150 | >150 | >150 | 150 |
| B128 | >150 | >150 | >150 | >150 |

TABLE 3-continued

| | Antimicrobial Activity | | | |
|---|---|---|---|---|
| FRS-ID | MIC WT E. coli LB Media (μM) | MIC E. coli delta-TolC LB Media (μM) | MIC A. baumannii LB Media (μM) | WT H37Rv MTB Activity (μM) |
| B129 | >150 | >150 | >150 | >150 |
| B130 | >150 | >150 | >150 | >150 |
| B131 | >150 | >150 | >150 | >150 |
| B132 | 124 | 85 | 150 | >150 |
| B133 | >150 | >150 | >150 | 55 |
| B134 | 120 | >150 | >150 | >150 |
| B135 | >150 | >150 | >150 | >150 |
| B136 | >150 | >150 | >150 | >150 |
| B137 | >150 | >150 | >150 | >150 |

TABLE 3-continued

| | Antimicrobial Activity | | | |
|---|---|---|---|---|
| FRS-ID | MIC WT E. coli LB Media (μM) | MIC E. coli delta-TolC LB Media (μM) | MIC A. baumannii LB Media (μM) | WT H37Rv MTB Activity (μM) |
| B138 | >150 | >150 | >150 | >150 |
| B139 | >150 | >150 | >150 | >150 |
| B140 | >150 | >150 | >150 | >150 |
| B141 | >150 | >150 | >150 | >150 |
| B142 | >150 | >150 | >150 | >150 |
| B143 | >150 | >150 | >150 | >150 |
| B144 | >150 | >150 | >150 | >150 |

TABLE 3-continued

| | Antimicrobial Activity | | | |
|---|---|---|---|---|
| FRS-ID | MIC WT *E. coli* LB Media (µM) | MIC *E. coli* delta-TolC LB Media (µM) | MIC *A. baumannii* LB Media (µM) | WT H37Rv MTB Activity (µM) |
| B145 | >150, res | >150 | >150 | 91 |
| B146 | 150 | 90 | 150 | >150 |
| B147 | >150 | >150 | >150 | >150 |
| B148 | >150 | >150 | >150 | 150 |
| B149 | >150 | >150 | >150 | >150 |
| B150 | >150 | >150 | >150 | >150 |
| B151 | >150 | >150 | >150 | >150 |

TABLE 3-continued
Antimicrobial Activity
| FRS-ID | | MIC WT E. coli LB Media (μM) | MIC E. coli delta-TolC LB Media (μM) | MIC A. baumannii LB Media (μM) | WT H37Rv MTB Activity (μM) |
|---|---|---|---|---|---|
| B152 | 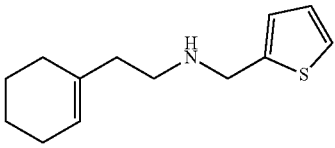 [SMILES: C1=C(CCNCc2cccs2)CCCC1] | >150 | >150 | >150 | >150 |
| B153 | 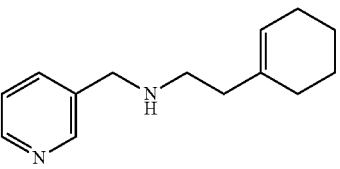 [SMILES: C1=C(CCNCc2cccnc2)CCCC1] | >150 | >150 | >150 | >150 |
| B154 | 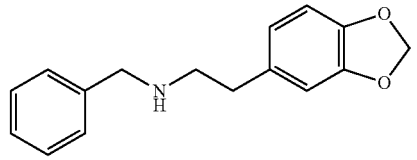 [SMILES: c1ccc(CNCCc2ccc3c(c2)OCO3)cc1] | >150 | >150 | >150 | >150 |
| B155 | 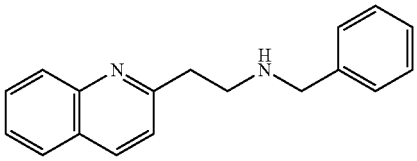 [SMILES: c1ccc(CNCCc2ccc3ccccc3n2)cc1] | >150 | >150 | >150 | >150 |
| B156 | 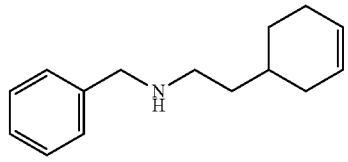 [SMILES: C1=CCC(CCNCc2ccccc2)CC1] | 150 | 150 | 150 | >150 |
| B157 | 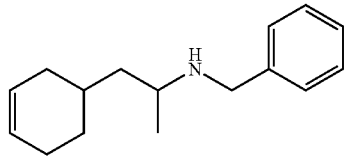 [SMILES: CC(CC1CC=CCC1)NCc1ccccc1] | 20 | 11 | 55 | 91 |
| B158 | 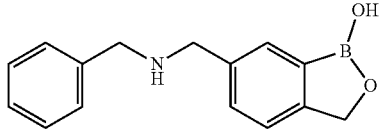 [SMILES: OB1OCc2ccc(CNCc3ccccc3)cc21] | >150 | >150 | >150 | >150 |
| B159 | 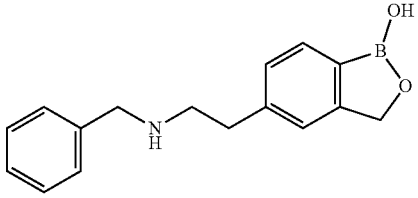 [SMILES: OB1OCc2cc(CCNCc3ccccc3)ccc21] | 500 | 250 | >150 | >150 |

TABLE 3-continued

| | Antimicrobial Activity | | | |
|---|---|---|---|---|
| FRS-ID | MIC WT *E. coli* LB Media (μM) | MIC *E. coli* delta-TolC LB Media (μM) | MIC *A. baumannii* LB Media (μM) | WT H37Rv MTB Activity (μM) |
| B160 | >150 | >150 | >150 | >150 |
| B161 | >300 | >300 | >150 | >150 |
| B162 | >500 | 300 | >150 | >150 |
| B163 | >300 | 300 | >150 | >150 |
| B164 | >300 | 60 | >150 | >150 |
| B165 | >300 | 60 | >150 | >150 |
| B166 | >300 | 250 | 300 | >150 |

TABLE 3-continued

| | Antimicrobial Activity | | | |
|---|---|---|---|---|
| FRS-ID | MIC WT *E. coli* LB Media (μM) | MIC *E. coli* delta-TolC LB Media (μM) | MIC *A. baumannii* LB Media (μM) | WT H37Rv MTB Activity (μM) |
| B167 | >300 | >300 | >300 | >150 |
| B168 | 170 | 182 | 410 | >150 |
| B169 | >300 | 74 | >300 | >150 |
| B170 | >300 | >300 | >300 | >150 |
| B171 | 41 | 19 | 110 | >150 |
| B172 | 170 | 96 | >300 | >150 |
| B173 | >300 | >300 | >300 | >150 |

TABLE 3-continued

| | Antimicrobial Activity | | | |
|---|---|---|---|---|
| FRS-ID | MIC WT *E. coli* LB Media (µM) | MIC *E. coli* delta-TolC LB Media (µM) | MIC *A. baumannii* LB Media (µM) | WT H37Rv MTB Activity (µM) |
| B174 | >300 | >300 | >300 | >150 |
| B176 | >300 | >300 | >300 | >150 |
| B177 | >300 | >300 | >300 | >150 |
| B178 | >300 | >300 | >300 | 55 |
| B179 | >300 | 230 | >300 | 150 |
| B180 | >300 | >300 | >300 | >150 |
| B181 | >300 | >300 | >300 | >150 |

TABLE 3-continued
| | | Antimicrobial Activity | | | |
|---|---|---|---|---|---|
| FRS-ID | | MIC WT *E. coli* LB Media (μM) | MIC *E. coli* delta-TolC LB Media (μM) | MIC *A. baumannii* LB Media (μM) | WT H37Rv MTB Activity (μM) |
| B182 | 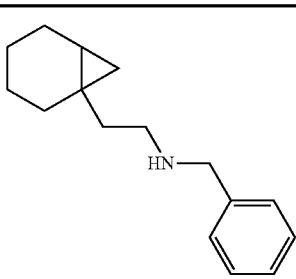 | >300 | >300 | >300 | 91 |
| B183 | 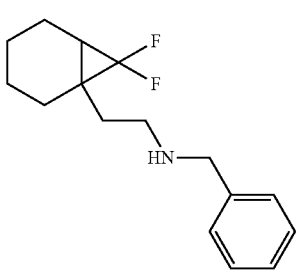 [SMILES: FC1(F)C2CCCCC21CCNCc1ccccc1] | >300 | >300 | >300 | >150 |
| B184 | 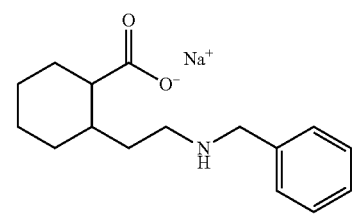 [SMILES: O=C([O-])C1CCCCC1CCNCc1ccccc1 ; [Na+]] | >300 | >300 | >300 | >150 |
| B185 | 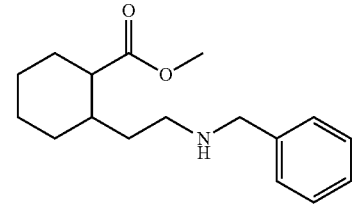 [SMILES: COC(=O)C1CCCCC1CCNCc1ccccc1] | >300 | >300 | >300 | >150 |
| B187 | 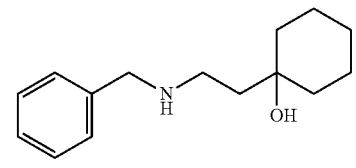 [SMILES: OC1(CCNCc2ccccc2)CCCCC1] | >300 | >300 | >300 | >150 |
| B188 | 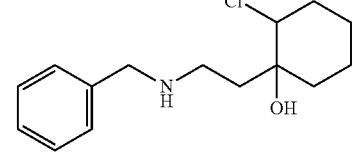 | >300 | >300 | >300 | >150 |

TABLE 3-continued
| | | Antimicrobial Activity | | | |
|---|---|---|---|---|---|
| FRS-ID | | MIC WT E. coli LB Media (μM) | MIC E. coli delta-TolC LB Media (μM) | MIC A. baumannii LB Media (μM) | WT H37Rv MTB Activity (μM) |
| B189 | 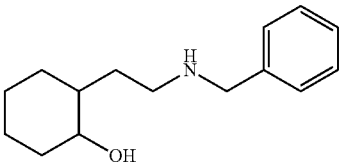 [SMILES: OC1CCCCC1CCNCc1ccccc1] | >300 | >300 | >300 | >150 |
| B190 | 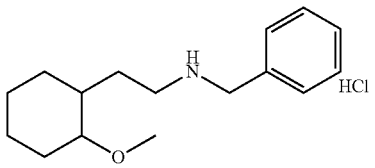 [SMILES: COC1CCCCC1CCNCc1ccccc1 ; Cl] | >300 | >300 | >300 | >150 |
| B191 | 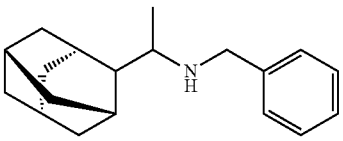 [SMILES: CC(NCc1ccccc1)C1[C@H]2C[C@@H]3C[C@@H](C[C@H]1C3)C2] | >300 | 300 | 300 | >150 |
| B192 | 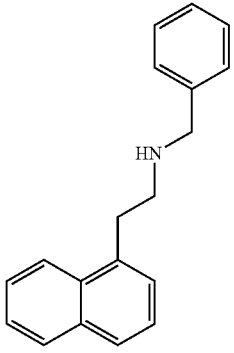 [SMILES: c1ccc(CNCCc2cccc3ccccc23)cc1] | 300 | 96 | 300 | 33 |
| B193 | 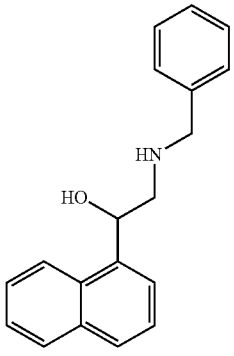 [SMILES: OC(CNCc1ccccc1)c1cccc2ccccc12] | >300 | 300 | 300 | 150 |
| B194 | 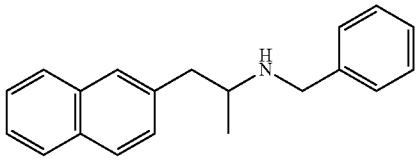 [SMILES: CC(Cc1ccc2ccccc2c1)NCc1ccccc1] | >300 | 170 | 300 | 150 |

TABLE 3-continued

| | Antimicrobial Activity | | | |
|---|---|---|---|---|
| FRS-ID | MIC WT *E. coli* LB Media (μM) | MIC *E. coli* delta-TolC LB Media (μM) | MIC *A. baumannii* LB Media (μM) | WT H37Rv MTB Activity (μM) |
| B195 | >300 | 300 | >300 | >150 |
| B196 | >300 | 300 | >300 | 55 |
| B197 | 170 | 96 | 300 | >150 |
| B198 | >300 | 170 | 170 | 91 |
| B199 | >300 | 170 | 170 | 150 |

TABLE 3-continued

| | Antimicrobial Activity | | | |
|---|---|---|---|---|
| FRS-ID | MIC WT E. coli LB Media (μM) | MIC E. coli delta-TolC LB Media (μM) | MIC A. baumannii LB Media (μM) | WT H37Rv MTB Activity (μM) |
| B200 | >300 | 170 | 300 | 91 |
| B201 | >300 | 96 | 170 | 91 |
| B202 | >300 | >300 | >300 | >150 |
| B203 | >300 | 170 | >300 | >150 |

TABLE 3-continued

| | Antimicrobial Activity | | | |
|---|---|---|---|---|
| FRS-ID | MIC WT *E. coli* LB Media (μM) | MIC *E. coli* delta-TolC LB Media (μM) | MIC *A. baumannii* LB Media (μM) | WT H37Rv MTB Activity (μM) |
| B204 | >300 | >300 | >300 | >150 |
| B205 | >300 | >300 | >300 | >150 |
| B206 | >300 | >300 | >300 | >150 |
| B207 | >300 | >300 | >300 | >150 |
| B208 | >300 | >300 | >300 | >150 |
| B209 | >300 | >300 | >300 | >150 |

TABLE 3-continued

| | Antimicrobial Activity | | | |
|---|---|---|---|---|
| FRS-ID | MIC WT *E. coli* LB Media (μM) | MIC *E. coli* delta-TolC LB Media (μM) | MIC *A. baumannii* LB Media (μM) | WT H37Rv MTB Activity (μM) |
| B210 | >300 | >300 | >300 | >150 |
| B211 | >300 | 300 | 300 | >150 |
| B212 | >300 | >300 | >300 | >150 |
| B213 | >300 | >300 | >300 | >150 |
| B214 | >300 | >300 | >300 | >150 |
| B215 | >300 | >300 | >300 | >150 |

TABLE 3-continued

Antimicrobial Activity

| FRS-ID | Structure | MIC WT *E. coli* LB Media (μM) | MIC *E. coli* delta-TolC LB Media (μM) | MIC *A. baumannii* LB Media (μM) | WT H37Rv MTB Activity (μM) |
|---|---|---|---|---|---|
| B216 | | >300 | >300 | >300 | >150 |
| B217 | | >300 | >300 | >300 | >150 |
| B218 | | >300 | >300 | >300 | >150 |
| B219 | | >300 | >300 | >300 | >150 |
| B220 | | >300 | >300 | >300 | >150 |
| B221 | | 300 | 150 | 220 | 150 |
| B222 | | >300 | >150 | >300 | >150 |

TABLE 3-continued

Antimicrobial Activity

| FRS-ID | Structure | MIC WT E. coli LB Media (μM) | MIC E. coli delta-TolC LB Media (μM) | MIC A. baumannii LB Media (μM) | WT H37Rv MTB Activity (μM) |
|---|---|---|---|---|---|
| B223 | | >300 | >150 | >300 | >150 |
| B224 | | >300 | >150 | >300 | >150 |
| B225 | | >300 | >150 | 300 | >150 |
| B226 | | 54 | 33 | 54 | 33 |
| B227 | | 170 | 12 | 170 | 150 |
| B228 | | 170 | 20 | 300 | 91 |
| B229 | | 170 | 7 | 96 | 33 |

TABLE 3-continued
| | Antimicrobial Activity | | | |
|---|---|---|---|---|
| FRS-ID | MIC WT *E. coli* LB Media (μM) | MIC *E. coli* delta-TolC LB Media (μM) | MIC *A. baumannii* LB Media (μM) | WT H37Rv MTB Activity (μM) |
| B230 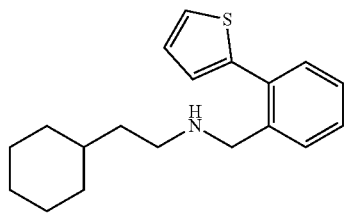 [SMILES: c1csc(-c2ccccc2CNCCC2CCCCC2)c1] | 96 | 4 | 96 | 55 |
| B231 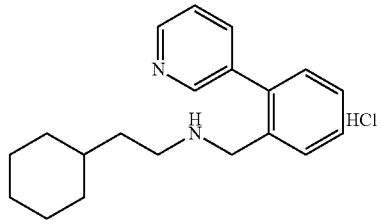 [SMILES: c1cncc(-c2ccccc2CNCCC2CCCCC2)c1 ; Cl] | 300 | 54 | >300 | >150 |
| B232 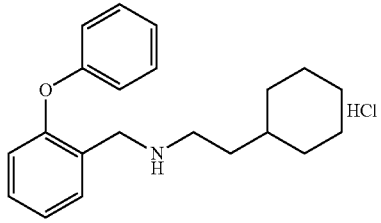 [SMILES: c1ccc(Oc2ccccc2CNCCC2CCCCC2)cc1 ; Cl] | 170 | 17 | 96 | 91 |
| B233 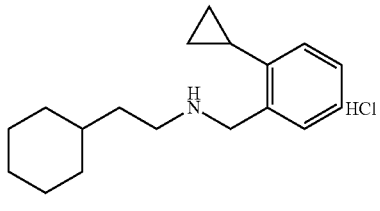 [SMILES: c1ccc(C2CC2)c(CNCCC2CCCCC2)c1 ; Cl] | 300 | 10 | 170 | 91 |
| B234 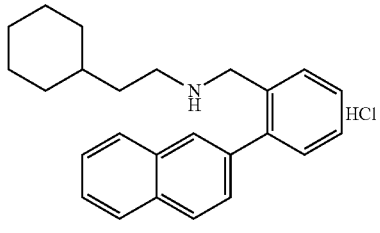 [SMILES: c1ccc(-c2ccc3ccccc3c2)c(CNCCC2CCCCC2)c1 ; Cl] | >300 | 10 | 31 | 55 |
| B235 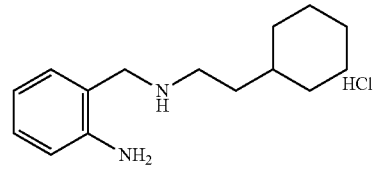 [SMILES: Nc1ccccc1CNCCC1CCCCC1 ; Cl] | 96 | 96 | >300 | >150 |

TABLE 3-continued
| | Antimicrobial Activity | | | | |
|---|---|---|---|---|---|
| FRS-ID | | MIC WT *E. coli* LB Media (μM) | MIC *E. coli* delta-TolC LB Media (μM) | MIC *A. baumannii* LB Media (μM) | WT H37Rv MTB Activity (μM) |
| B236 |  | 54 | 17 | 300 | 150 |
| B237 | 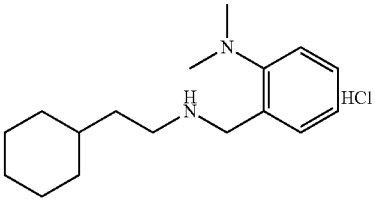 [SMILES: CN(C)c1ccccc1CNCCC1CCCCC1 ; Cl] | >300 | 170 | >300 | >150 |
| B238 | 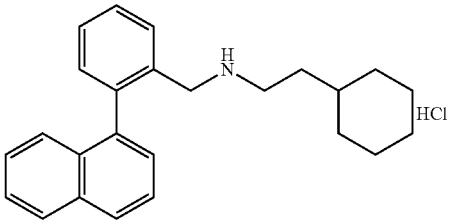 [SMILES: c1ccc(-c2cccc3ccccc23)c(CNCCC2CCCCC2)c1 ; Cl] | >300 | 10 | 54 | 55 |
| B239 | 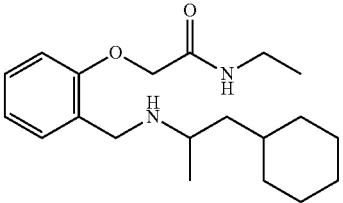 [SMILES: CCNC(=O)COc1ccccc1CNC(C)CC1CCCCC1] | >150 | 20 | >150 | >150 |
| B240 | 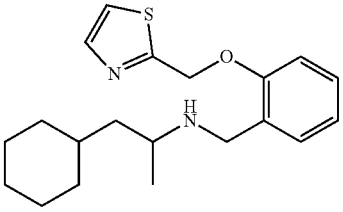 [SMILES: CC(CC1CCCCC1)NCc1ccccc1OCc1nccs1] | >150 | 7 | >150 | 150 |
| B241 | 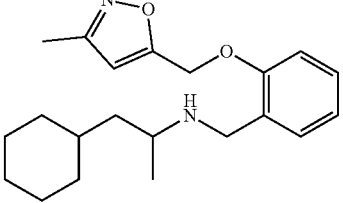 | 150 | 4 | >150 | >150 |

TABLE 3-continued
| | Antimicrobial Activity | | | |
|---|---|---|---|---|
| FRS-ID | MIC WT E. coli LB Media (μM) | MIC WT E. coli delta-TolC LB Media (μM) | MIC A. baumannii LB Media (μM) | WT H37Rv MTB Activity (μM) |
| B242 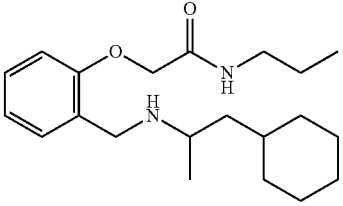 [SMILES: CCCNC(=O)COc1ccccc1CNC(C)CC1CCCCC1] | >150 | 12 | >150 | >150 |
| B243 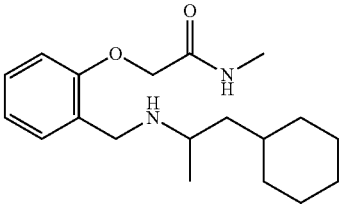 [SMILES: CNC(=O)COc1ccccc1CNC(C)CC1CCCCC1] | >150 | 12 | >150 | >150 |
| B244 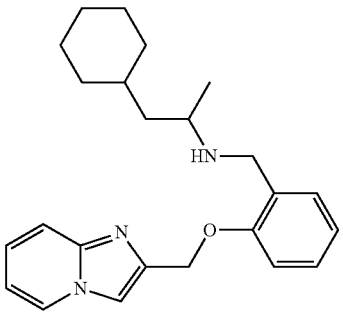 [SMILES: CC(CC1CCCCC1)NCc1ccccc1OCc1cn2ccccc2n1] | 91 | 3 | 150 | 150 |
| B245 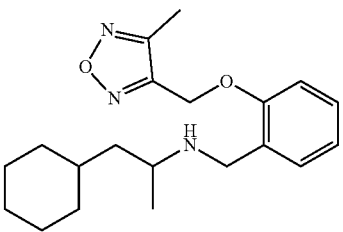 [SMILES: Cc1nonc1COc1ccccc1CNC(C)CC1CCCCC1] | 150 | 4 | 150 | 150 |
| B246 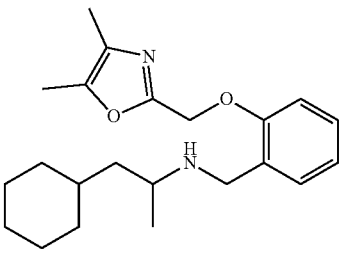 [SMILES: Cc1nc(COc2ccccc2CNC(C)CC2CCCCC2)oc1C] | >150 | 12 | >150 | 91 |

TABLE 3-continued
Antimicrobial Activity
| FRS-ID | Structure | MIC WT E. coli LB Media (μM) | MIC E. coli delta-TolC LB Media (μM) | MIC A. baumannii LB Media (μM) | WT H37Rv MTB Activity (μM) |
|---|---|---|---|---|---|
| B247 | 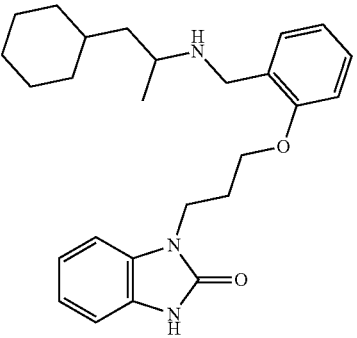 [SMILES: CC(CC1CCCCC1)NCc1ccccc1OCCCn1c(=O)[nH]c2ccccc21] | 150 | 2 | 91 | >150 |
| B248 | 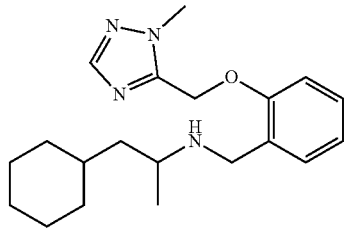 [SMILES: CC(CC1CCCCC1)NCc1ccccc1OCc1ncnn1C] | >150 | 20 | >150 | >150 |
| B249 | 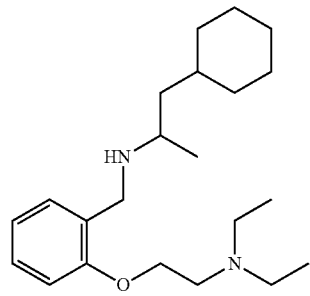 [SMILES: CCN(CC)CCOc1ccccc1CNC(C)CC1CCCCC1] | >150 | >150 | >150 | >150 |
| B250 | 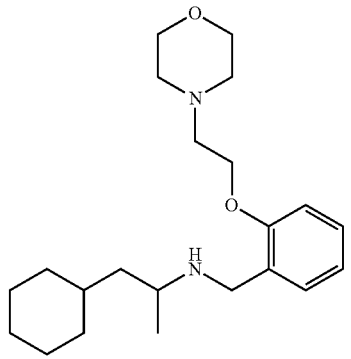 [SMILES: CC(CC1CCCCC1)NCc1ccccc1OCCN1CCOCC1] | >150 | 12 | >150 | >150 |
| B251 | 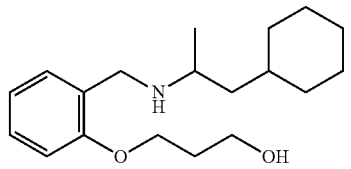 [SMILES: CC(CC1CCCCC1)NCc1ccccc1OCCCO] | 91 | 7 | 91 | >150 |

TABLE 3-continued

| | Antimicrobial Activity | | | |
|---|---|---|---|---|
| FRS-ID | MIC WT E. coli LB Media (μM) | MIC E. coli delta-TolC LB Media (μM) | MIC A. baumannii LB Media (μM) | WT H37Rv MTB Activity (μM) |
| B252 | >150 | 4 | 150 | 150 |
| B253 | 150 | 37 | >150 | >150 |
| B254 | >150 | >150 | >150 | >150 |
| B255 | >150 | 84 | >150 | >150 |
| B256 | >150 | 150 | >150 | >150 |
| B257 | >150 | 67 | >150 | >150 |
| B258 | >150 | 100 | >150 | >150 |

TABLE 3-continued
| | Antimicrobial Activity | | | |
|---|---|---|---|---|
| FRS-ID | MIC WT E. coli LB Media (μM) | MIC E. coli delta-TolC LB Media (μM) | MIC A. baumannii LB Media (μM) | WT H37Rv MTB Activity (μM) |
| B259 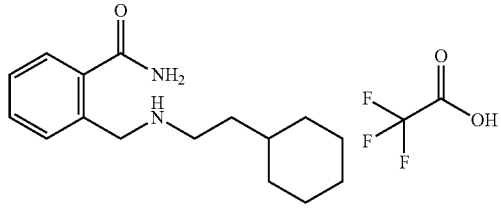 | >150 | 125 | >150 | >150 |
| B260 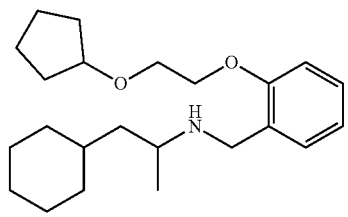 [SMILES: CC(CC1CCCCC1)NCc1ccccc1OCCOC1CCCC1] | >150 | 7 | >150 | 91 |
| B261 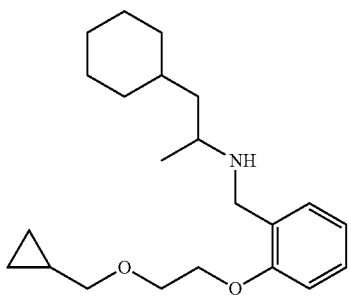 [SMILES: CC(CC1CCCCC1)NCc1ccccc1OCCOCC1CC1] | >150 | 4 | >150 | 150 |
| B262 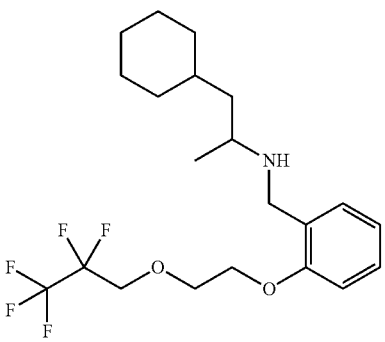 [SMILES: CC(CC1CCCCC1)NCc1ccccc1OCCOCC(F)(F)C(F)(F)F] | 150 | 12 | 91 | 55 |
| B263 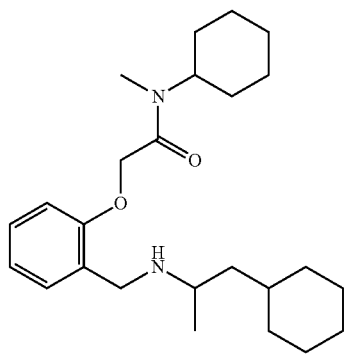 [SMILES: CC(CC1CCCCC1)NCc1ccccc1OCC(=O)N(C)C1CCCCC1] | >150 | 3 | >150 | 91 |

TABLE 3-continued
| | Antimicrobial Activity | | | | |
|---|---|---|---|---|---|
| FRS-ID | | MIC WT E. coli LB Media (μM) | MIC E. coli delta-TolC LB Media (μM) | MIC A. baumannii LB Media (μM) | WT H37Rv MTB Activity (μM) |
| B264 | 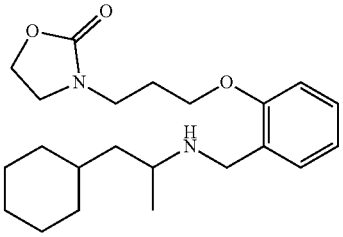 [SMILES: CC(CC1CCCCC1)NCc1ccccc1OCCCN1CCOC1=O] | 150 | 3 | 150 | >150 |
| B265 | 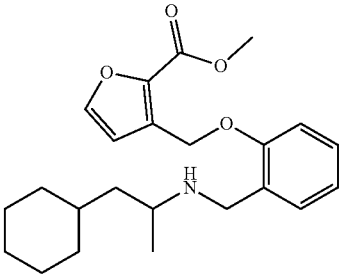 [SMILES: COC(=O)c1occc1COc1ccccc1CNC(C)CC1CCCCC1] | 150 | 3 | 91 | 91 |
| B266 | 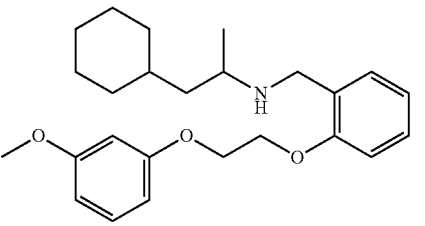 [SMILES: COc1cccc(OCCOc2ccccc2CNC(C)CC2CCCCC2)c1] | 150 | 2 | 33 | 55 |
| B267 | 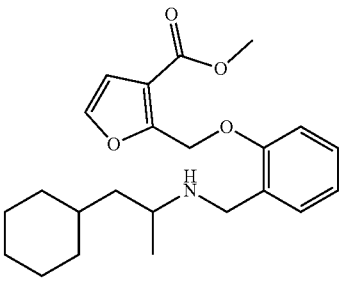 [SMILES: COC(=O)c1ccoc1COc1ccccc1CNC(C)CC1CCCCC1] | >150 | 7 | >150 | 91 |
| B268 | 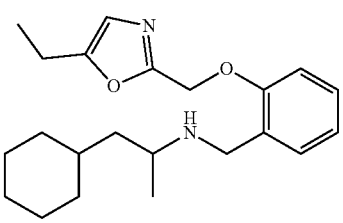 [SMILES: CCc1cnc(COc2ccccc2CNC(C)CC2CCCCC2)o1] | >150 | 7 | >150 | 91 |

TABLE 3-continued
| | Antimicrobial Activity | | | |
|---|---|---|---|---|
| FRS-ID | MIC WT E. coli LB Media (μM) | MIC E. coli delta-TolC LB Media (μM) | MIC A. baumannii LB Media (μM) | WT H37Rv MTB Activity (μM) |
| B269 | >150 | 7 | 55 | >150 |
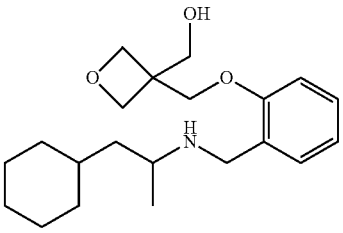 [SMILES: CC(CC1CCCCC1)NCc1ccccc1OCC1(CO)COC1]
| | | | | |
|---|---|---|---|---|
| B270 | >150 | 20 | >150 | >150 |
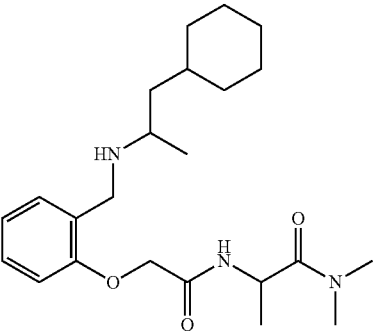 [SMILES: CC(CC1CCCCC1)NCc1ccccc1OCC(=O)NC(C)C(=O)N(C)C]
| | | | | |
|---|---|---|---|---|
| B271 | 150 | 3 | 55 | 55 |
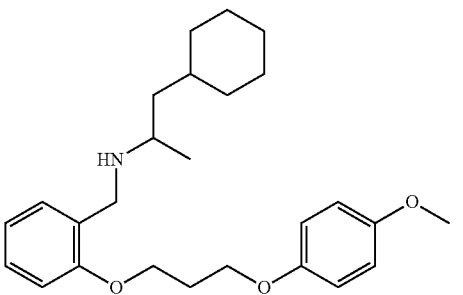 [SMILES: COc1ccc(OCCCOc2ccccc2CNC(C)CC2CCCCC2)cc1]
| | | | | |
|---|---|---|---|---|
| B272 | >150 | 12 | >150 | 150 |
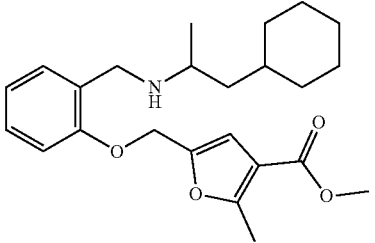 [SMILES: COC(=O)c1cc(COc2ccccc2CNC(C)CC2CCCCC2)oc1C]

TABLE 3-continued
Antimicrobial Activity
| FRS-ID | | MIC WT E. coli LB Media (μM) | MIC E. coli delta-TolC LB Media (μM) | MIC A. baumannii LB Media (μM) | WT H37Rv MTB Activity (μM) |
|---|---|---|---|---|---|
| B273 | 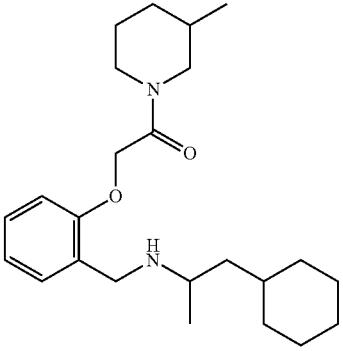 [SMILES: CC1CCCN(C(=O)COc2ccccc2CNC(C)CC2CCCCC2)C1] | >150 | 4 | >150 | 150 |
| B274 | 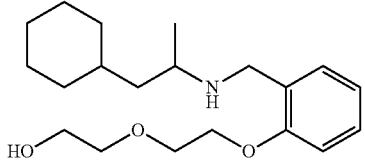 [SMILES: CC(CC1CCCCC1)NCc1ccccc1OCCOCCO] | 150 | 7 | 150 | >150 |
| B275 | 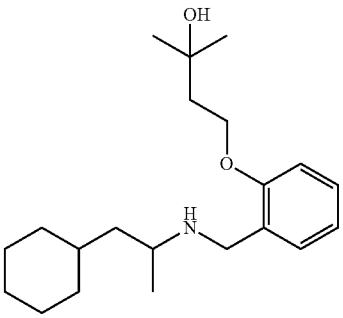 [SMILES: CC(CC1CCCCC1)NCc1ccccc1OCCC(C)(C)O] | 150 | 4 | 91 | >150 |
| B276 | 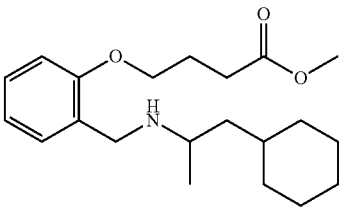 [SMILES: COC(=O)CCCOc1ccccc1CNC(C)CC1CCCCC1] | >150 | 4 | >150 | >150 |
| B277 | 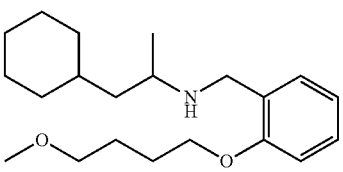 [SMILES: COCCCCOc1ccccc1CNC(C)CC1CCCCC1] | >150 | 4 | >150 | >150 |
| B278 | 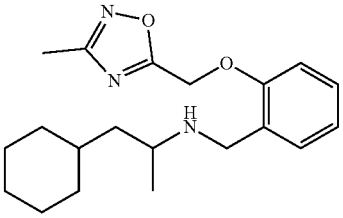 [SMILES: Cc1noc(COc2ccccc2CNC(C)CC2CCCCC2)n1] | >150 | 12 | >150 | >150 |

TABLE 3-continued

Antimicrobial Activity

| FRS-ID | Structure | MIC WT *E. coli* LB Media (μM) | MIC *E. coli* delta-TolC LB Media (μM) | MIC *A. baumannii* LB Media (μM) | WT H37Rv MTB Activity (μM) |
|---|---|---|---|---|---|
| B279 | | >150 | 12 | >150 | >150 |
| B280 | | 150 | 12 | 150 | >150 |
| B281 | | >150 | 4 | 91 | 91 |
| B282 | | >150 | 3 | >150 | 150 |
| B283 | | 91 | 7 | 91 | 150 |

TABLE 3-continued
Antimicrobial Activity
| FRS-ID | | MIC WT E. coli LB Media (µM) | MIC E. coli delta-TolC LB Media (µM) | MIC A. baumannii LB Media (µM) | WT H37Rv MTB Activity (µM) |
|---|---|---|---|---|---|
| B284 | 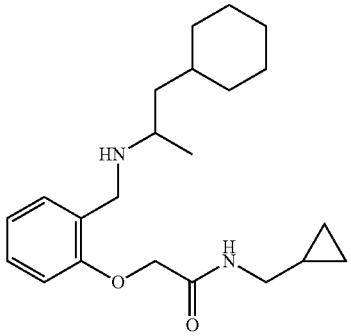 [SMILES: CC(CC1CCCCC1)NCc1ccccc1OCC(=O)NCC1CC1] | >150 | 7 | >150 | >150 |
| B285 | 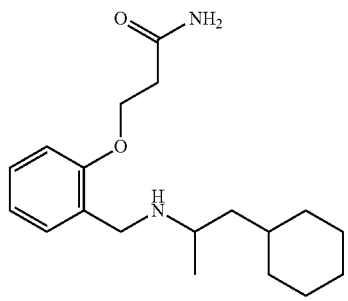 [SMILES: CC(CC1CCCCC1)NCc1ccccc1OCCC(N)=O] | 91 | 55 | >150 | >150 |
| B286 | 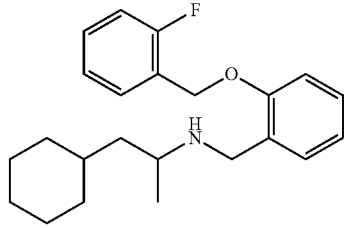 | 91 | 3 | 91 | 33 |
| B287 | 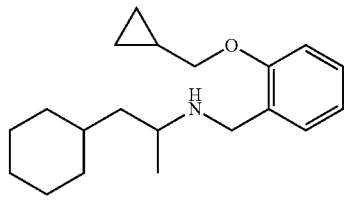 [SMILES: CC(CC1CCCCC1)NCc1ccccc1OCC1CC1] | 150 | 3 | 91 | 150 |
| B288 | 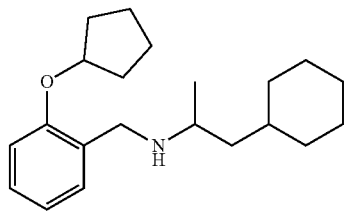 [SMILES: CC(CC1CCCCC1)NCc1ccccc1OC1CCCC1] | >150 | 3 | 150 | 91 |

TABLE 3-continued

| | Antimicrobial Activity | | | | |
|---|---|---|---|---|---|
| FRS-ID | | MIC WT *E. coli* LB Media (µM) | MIC WT *E. coli* delta-TolC LB Media (µM) | MIC *A. baumannii* LB Media (µM) | WT H37Rv MTB Activity (µM) |
| B289 | | 91 | 3 | 150 | 150 |
| B290 | | >150 | 33 | >150 | >150 |
| B291 | | 91 | 12 | >150 | >150 |
| B292 | | >150 | 4 | >150 | 150 |
| B293 | | 150 | 4 | >150 | >150 |
| B294 | | >150 | 7 | >150 | >150 |

TABLE 3-continued

Antimicrobial Activity

| FRS-ID | | MIC WT *E. coli* LB Media (μM) | MIC *E. coli* delta-TolC LB Media (μM) | MIC *A. baumannii* LB Media (μM) | WT H37Rv MTB Activity (μM) |
|---|---|---|---|---|---|
| B295 | (structure) | >150 | 4 | >150 | 150 |
| B296 | (structure) | 91 | 7 | >150 | >150 |
| B297 | (structure) | >150 | 7 | 150 | >150 |
| B298 | (structure) | >150 | 12 | >150 | >150 |
| B299 | (structure) | 150 | 4 | 150 | >150 |
| B300 | (structure) | >150 | 12 | >150 | >150 |

TABLE 3-continued

| | Antimicrobial Activity | | | |
|---|---|---|---|---|
| FRS-ID | MIC WT *E. coli* LB Media (μM) | MIC WT *E. coli* delta-TolC LB Media (μM) | MIC *A. baumannii* LB Media (μM) | WT H37Rv MTB Activity (μM) |
| B301 | >150 | 12 | >150 | >150 |
| B302 | 150 | <1 | 150 | 55 |
| B303 | >150 | 7 | >150 | 91 |
| B304 | >150 | 3 | >150 | 91 |
| B305 | >150 | 3 | 91 | 150 |

TABLE 3-continued

| | Antimicrobial Activity | | | |
|---|---|---|---|---|
| FRS-ID | MIC WT *E. coli* LB Media (μM) | MIC *E. coli* delta-TolC LB Media (μM) | MIC *A. baumannii* LB Media (μM) | WT H37Rv MTB Activity (μM) |
| B306 | >150 | 12 | >150 | >150 |
| B307 | >150 | 20 | >150 | 150 |
| B308 | >150 | 4 | 150 | >150 |
| B309 | >150 | 33 | >150 | >150 |
| B310 | >150 | 55 | >150 | >150 |

TABLE 3-continued
| | Antimicrobial Activity | | | |
|---|---|---|---|---|
| FRS-ID | MIC WT E. coli LB Media (μM) | MIC E. coli delta-TolC LB Media (μM) | MIC A. baumannii LB Media (μM) | WT H37Rv MTB Activity (μM) |
| B311 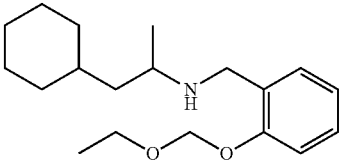 [SMILES: CCOCOc1ccccc1CNC(C)CC1CCCCC1] | >150 | 7 | >150 | >150 |
| B312 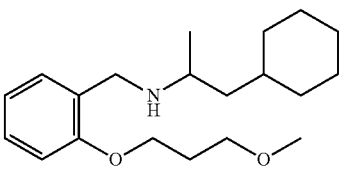 | >150 | 7 | >150 | >150 |
| B313 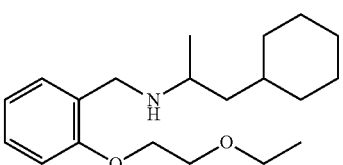 | >150 | 7 | >150 | >150 |
| B314 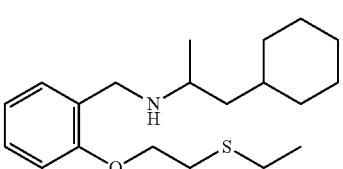 | 150 | 4 | 91 | 150 |
| B315 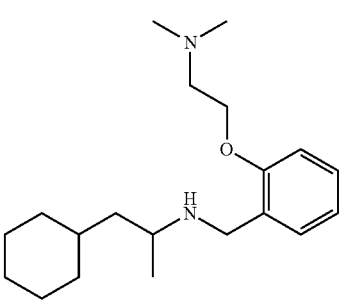 [SMILES: CC(CC1CCCCC1)NCc1ccccc1OCCN(C)C] | 91 | 150 | 150 | >150 |
| B316 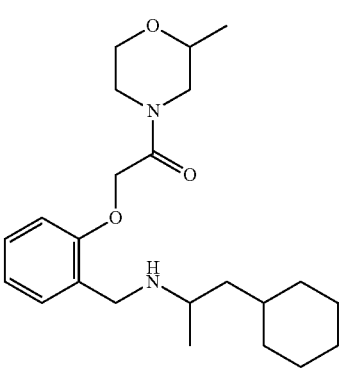 [SMILES: CC(CC1CCCCC1)NCc1ccccc1OCC(=O)N1CCOC(C)C1] | >150 | 7 | >150 | >150 |

TABLE 3-continued
Antimicrobial Activity
| FRS-ID | | MIC WT *E. coli* LB Media (μM) | MIC *E. coli* delta-TolC LB Media (μM) | MIC *A. baumannii* LB Media (μM) | WT H37Rv MTB Activity (μM) |
|---|---|---|---|---|---|
| B317 | 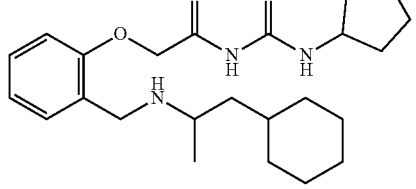 | 91 | 3 | 91 | 55 |
| B318 | 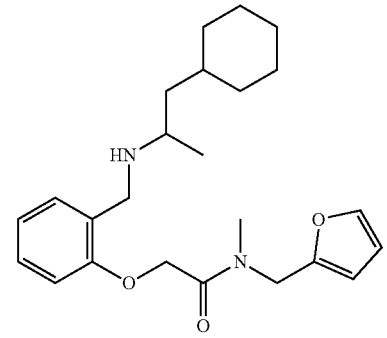 [SMILES: CC(CC1CCCCC1)NCc1ccccc1OCC(=O)N(C)Cc1ccco1] | >150 | 7 | >150 | 150 |
| B319 | 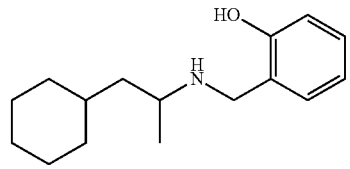 [SMILES: CC(CC1CCCCC1)NCc1ccccc1O] | 33 | 12 | >150 | 150 |
| B320 | 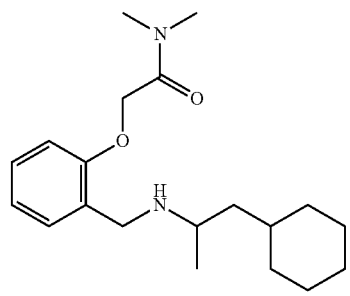 [SMILES: CC(CC1CCCCC1)NCc1ccccc1OCC(=O)N(C)C] | >150 | 20 | >150 | >150 |
| B321 | 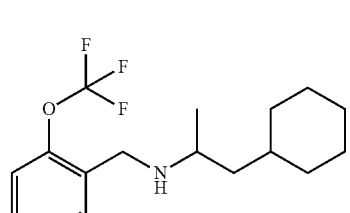 | >150 | 55 | >150 | >150 |

TABLE 3-continued
| | Antimicrobial Activity | | | |
|---|---|---|---|---|
| FRS-ID | MIC WT *E. coli* LB Media (µM) | MIC *E. coli* delta-TolC LB Media (µM) | MIC *A. baumannii* LB Media (µM) | WT H37Rv MTB Activity (µM) |
| B322 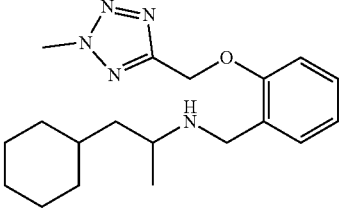 [SMILES: CC(CC1CCCCC1)NCc1ccccc1OCc1nnn(C)n1] | 150 | 4 | 150 | >150 |
| B323 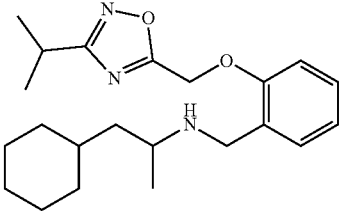 [SMILES: CC(CC1CCCCC1)NCc1ccccc1OCc1nc(C(C)C)no1] | >150 | 4 | >150 | 150 |
| B324 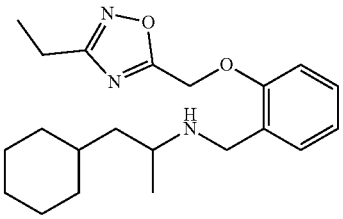 [SMILES: CCc1noc(COc2ccccc2CNC(C)CC2CCCCC2)n1] | >150 | 7 | >150 | >150 |
| B325 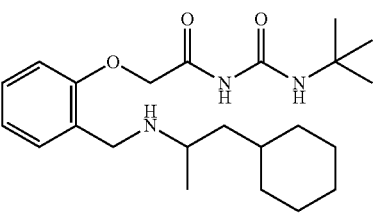 [SMILES: CC(CC1CCCCC1)NCc1ccccc1OCC(=O)NC(=O)NC(C)(C)C] | >150 | 4 | 150 | 91 |
| B326 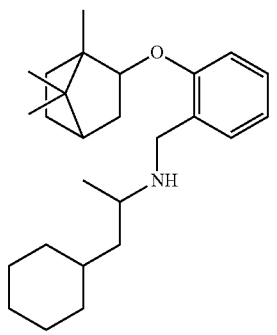 [SMILES: CC(CC1CCCCC1)NCc1ccccc1OC1CC2CCC1(C)C2(C)C] | >150 | 12 | >150 | 55 |

TABLE 3-continued

| | Antimicrobial Activity | | | |
|---|---|---|---|---|
| FRS-ID | MIC WT E. coli LB Media (μM) | MIC E. coli delta-TolC LB Media (μM) | MIC A. baumannii LB Media (μM) | WT H37Rv MTB Activity (μM) |
| B327 | >150 | 7 | >150 | >150 |
| B328 | >150 | 55 | >150 | 150 |
| B329 | >150 | 33 | >150 | >150 |
| B330 | >150 | 33 | >150 | >150 |
| B331 | >150 | 33 | >150 | >150 |
| B332 | >150 | >150 | >150 | ND |

TABLE 3-continued
| | Antimicrobial Activity | | | | |
|---|---|---|---|---|---|
| FRS-ID | | MIC WT *E. coli* LB Media (µM) | MIC *E. coli* delta-TolC LB Media (µM) | MIC *A. baumannii* LB Media (µM) | WT H37Rv MTB Activity (µM) |
| B333 | 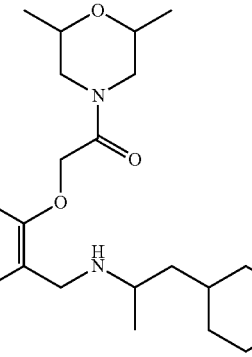 | >150 | 7 | >150 | >150 |
| B334 | 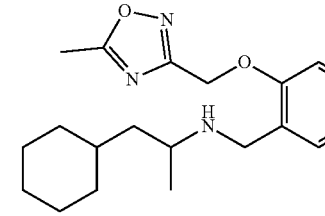 | >150 | 7 | >150 | >150 |
| B335 | 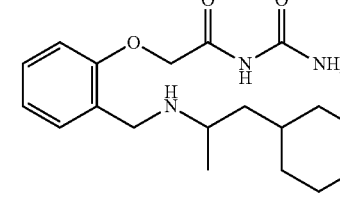 | 55 | 4 | 150 | >150 |
| B336 | 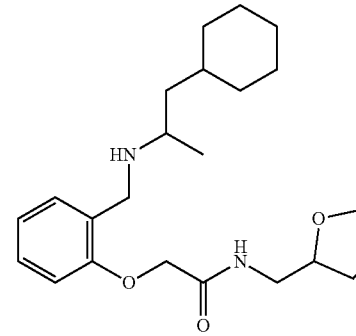 | >150 | 33 | >150 | >150 |
| B337 | 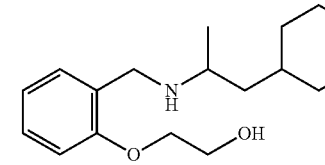 | 55 | 4 | 150 | >150 |

TABLE 3-continued

| | Antimicrobial Activity | | | |
|---|---|---|---|---|
| FRS-ID | MIC WT *E. coli* LB Media (μM) | MIC *E. coli* delta-TolC LB Media (μM) | MIC *A. baumannii* LB Media (μM) | WT H37Rv MTB Activity (μM) |
| B338 | 91 | 12 | >150 | >150 |
| B339 | >300 | 200 | >300 | >150 |
| B340 | >150 | 55 | >150 | >150 |
| B341 | >150 | 7 | >150 | 150 |
| B342 | 150 | 4 | 150 | 91 |

TABLE 3-continued
| | | Antimicrobial Activity | | | |
|---|---|---|---|---|---|
| FRS-ID | | MIC WT E. coli LB Media (µM) | MIC E. coli delta-TolC LB Media (µM) | MIC A. baumannii LB Media (µM) | WT H37Rv MTB Activity (µM) |
| B343 | 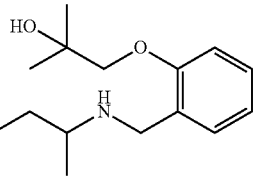 | 150 | 4 | 150 | >150 |
| B344 | 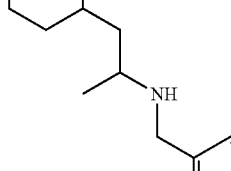 | 150 | 91 | 91 | 150 |
| B345 | 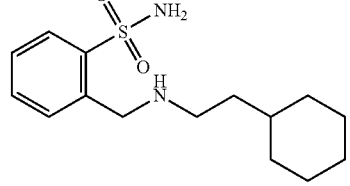 | >150 | 20 | 33 | >150 |
| B346 | 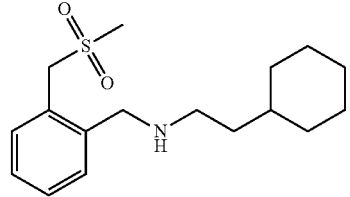 [SMILES: CS(=O)(=O)Cc1ccccc1CNCCC1CCCCC1] | >150 | 4 | 12 | >150 |
| B347 | 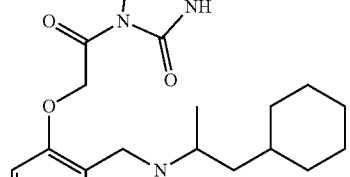 | 150 | 4 | >150 | >150 |
| B348 | 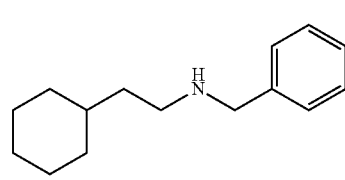 | >150 | >150 | >150 | 150 |

TABLE 3-continued
| | Antimicrobial Activity | | | |
|---|---|---|---|---|
| FRS-ID | MIC WT *E. coli* LB Media (μM) | MIC *E. coli* delta-TolC LB Media (μM) | MIC *A. baumannii* LB Media (μM) | WT H37Rv MTB Activity (μM) |
| B349 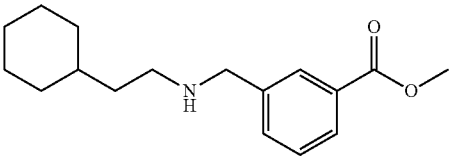 [SMILES: COC(=O)c1cccc(CNCCC2CCCCC2)c1] | >150 | >150 | >150 | >150 |
| B350 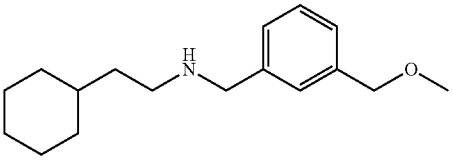 [SMILES: COCc1cccc(CNCCC2CCCCC2)c1] | >150 | >150 | >150 | >150 |
| B351 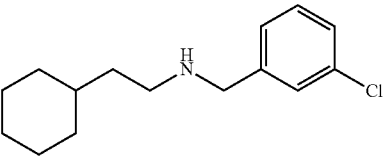 [SMILES: Clc1cccc(CNCCC2CCCCC2)c1] | >150 | >150 | >150 | >150 |
| B352 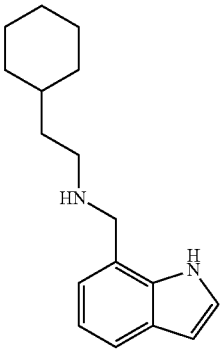 [SMILES: c1cc(CNCCC2CCCCC2)c2[nH]ccc2c1] | 91 | 91 | 150 | 91 |
| B353 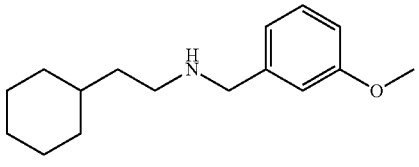 [SMILES: COc1cccc(CNCCC2CCCCC2)c1] | >150 | >150 | >150 | >150 |
| B354 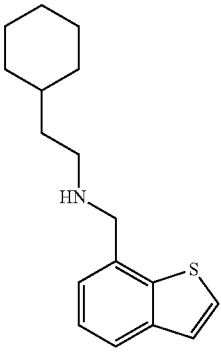 [SMILES: c1cc(CNCCC2CCCCC2)c2sccc2c1] | >150 | 150 | >150 | 150 |

TABLE 3-continued

| | Antimicrobial Activity | | | |
|---|---|---|---|---|
| FRS-ID | MIC WT *E. coli* LB Media (μM) | MIC *E. coli* delta-TolC LB Media (μM) | MIC *A. baumannii* LB Media (μM) | WT H37Rv MTB Activity (μM) |
| B355 | >150 | >150 | >150 | >150 |
| B356 | >150 | >150 | >150 | >150 |
| B357 | 150 | 20 | 91 | 91 |
| B358 | >150 | 20 | >150 | >150 |
| B359 | >150 | 12 | 150 | >150 |
| B360 | >150 | >150 | >150 | >150 |

TABLE 3-continued

| | Antimicrobial Activity | | | | |
|---|---|---|---|---|---|
| FRS-ID | | MIC WT E. coli LB Media (μM) | MIC E. coli delta-TolC LB Media (μM) | MIC A. baumannii LB Media (μM) | WT H37Rv MTB Activity (μM) |
| B361 | | 91 | 4 | 91 | >150 |
| B362 | | 150 | 7 | 150 | >150 |
| B363 | | 150 | 3 | 150 | >150 |
| B364 | | 150 | 3 | 150 | 91 |
| B365 | | >150 | 5 | >150 | >150 |
| B366 | | 150 | 150 | >150 | >150 |

TABLE 3-continued

| | Antimicrobial Activity | | | |
|---|---|---|---|---|
| FRS-ID | MIC WT *E. coli* LB Media (µM) | MIC *E. coli* delta-TolC LB Media (µM) | MIC *A. baumannii* LB Media (µM) | WT H37Rv MTB Activity (µM) |
| B367 | 150 | 5 | 150 | >150 |
| B368 | >150 | 20 | >150 | >150 |
| B369 | >150 | 3 | >150 | >150 |
| B370 | >150 | 12 | >150 | >150 |
| B371 | >150 | 33 | >150 | >150 |

TABLE 3-continued
Antimicrobial Activity
| FRS-ID | | MIC WT E. coli LB Media (μM) | MIC E. coli delta-TolC LB Media (μM) | MIC A. baumannii LB Media (μM) | WT H37Rv MTB Activity (μM) |
|---|---|---|---|---|---|
| B372 | 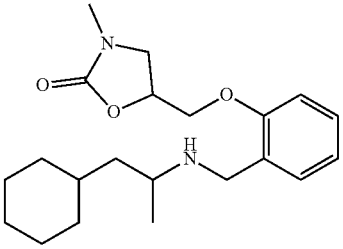 | 150 | 5 | >150 | >150 |
| B373 | 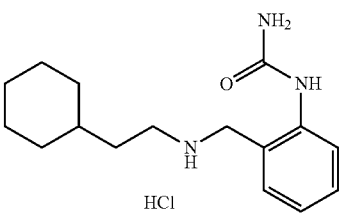 [SMILES: NC(=O)Nc1ccccc1CNCCC1CCCCC1 ; Cl] | >150 | 150 | >150 | >150 |
| B374 | 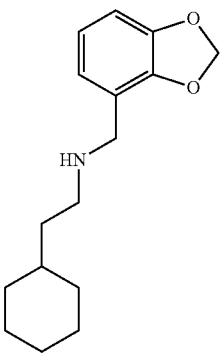 [SMILES: c1cc(CNCCC2CCCCC2)c2c(c1)OCO2] | >150 | >150 | >150 | 150 |
| B375 | 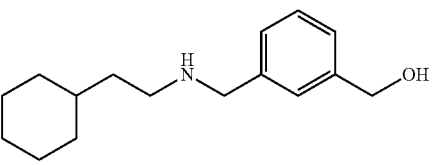 [SMILES: OCc1cccc(CNCCC2CCCCC2)c1] | >150 | >150 | >150 | >150 |
| B376 | 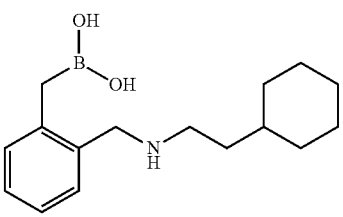 [SMILES: OB(O)Cc1ccccc1CNCCC1CCCCC1] | 150 | 91 | >150 | >150 |
| B377 | 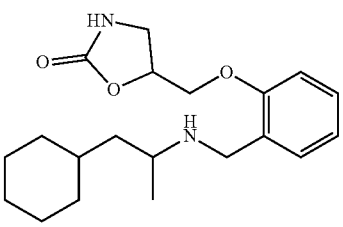 | 75 | 2.3 | 150 | >150 |

TABLE 3-continued
| | | Antimicrobial Activity | | | |
|---|---|---|---|---|---|
| FRS-ID | | MIC WT *E. coli* LB Media (μM) | MIC *E. coli* delta-TolC LB Media (μM) | MIC *A. baumannii* LB Media (μM) | WT H37Rv MTB Activity (μM) |
| B378 | 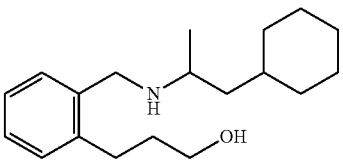 [SMILES: CC(CC1CCCCC1)NCc1ccccc1CCCO] | 91 | 7 | 150 | 150 |
| B379 | 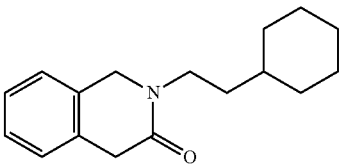 | >150 | 150 | >150 | TBD |
| B380 | 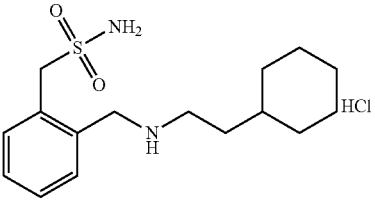 [SMILES: NS(=O)(=O)Cc1ccccc1CNCCC1CCCCC1 ; Cl] | 33 | 12 | >150 | >150 |
| B381 | 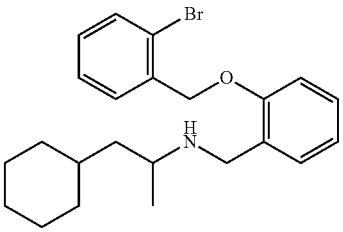 [SMILES: CC(CC1CCCCC1)NCc1ccccc1OCc1ccccc1Br] | 55 | 4 | 55 | 20.2 |
| B382 | 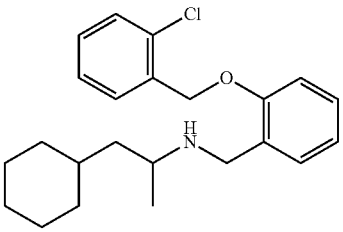 [SMILES: CC(CC1CCCCC1)NCc1ccccc1OCc1ccccc1Cl] | 55 | 3 | 55 | 12.2 |
| B383 | 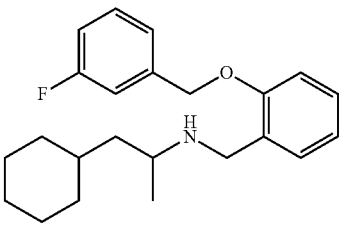 [SMILES: CC(CC1CCCCC1)NCc1ccccc1OCc1cccc(F)c1] | 55 | 2 | 91 | 12.2 |

TABLE 3-continued
Antimicrobial Activity
| FRS-ID | | MIC WT E. coli LB Media (μM) | MIC E. coli delta-TolC LB Media (μM) | MIC A. baumannii LB Media (μM) | WT H37Rv MTB Activity (μM) |
|---|---|---|---|---|---|
| B384 | 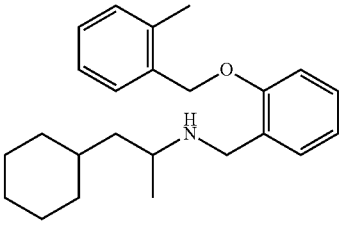 [SMILES: Cc1ccccc1COc1ccccc1CNC(C)CC1CCCCC1] | 91 | 4 | 55 | 20.2 |
| B385 | 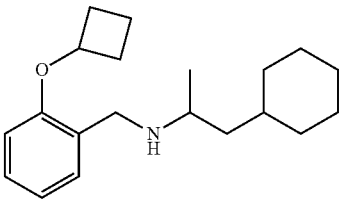 [SMILES: CC(CC1CCCCC1)NCc1ccccc1OC1CCC1] | 91 | 2 | 150 | 90.9 |
| B386 | 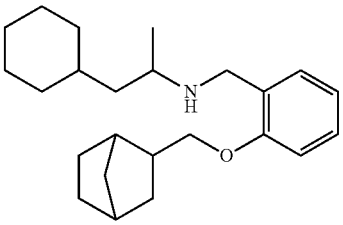 [SMILES: CC(CC1CCCCC1)NCc1ccccc1OCC1CC2CCC1C2] | >150 | 5 | 55 | 20.2 |
| B387 | 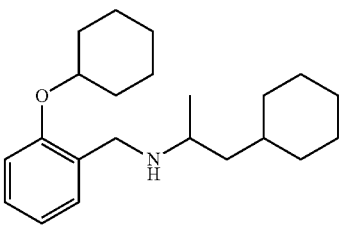 [SMILES: CC(CC1CCCCC1)NCc1ccccc1OC1CCCCC1] | 91 | 3 | 55 | 33.4 |
| B388 | 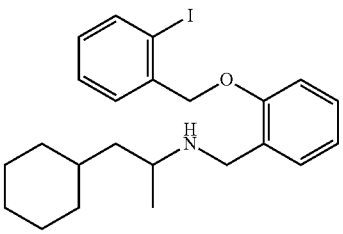 [SMILES: CC(CC1CCCCC1)NCc1ccccc1OCc1ccccc1I] | 150 | 7 | 33 | 33.4 |
| B389 | 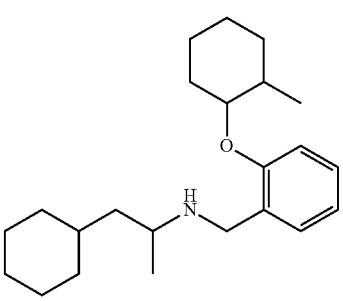 [SMILES: CC(CC1CCCCC1)NCc1ccccc1OC1CCCCC1C] | >150 | 3 | 91 | 33.4 |

TABLE 3-continued

| | Antimicrobial Activity | | | |
|---|---|---|---|---|
| FRS-ID | MIC WT *E. coli* LB Media (μM) | MIC *E. coli* delta-TolC LB Media (μM) | MIC *A. baumannii* LB Media (μM) | WT H37Rv MTB Activity (μM) |
| B390 | 150 | 3 | 55 | 20.2 |
| B391 | 150 | 3 | 91 | 20.2 |
| B392 | >150 | 7 | 150 | 33.4 |
| B393 | >150 | 7 | 150 | 20.2 |

TABLE 3-continued

| | Antimicrobial Activity | | | |
|---|---|---|---|---|
| FRS-ID | MIC WT E. coli LB Media (μM) | MIC E. coli delta-TolC LB Media (μM) | MIC A. baumannii LB Media (μM) | WT H37Rv MTB Activity (μM) |
| B394 | 150 | 3 | 55 | 20.2 |
| B395 | >150 | 3 | 33 | 20.2 |
| B396 | 150 | 3 | 150 | 55.1 |
| B397 | >150 | 5 | >150 | 12.2 |

TABLE 3-continued

Antimicrobial Activity

| FRS-ID | Structure | MIC WT E. coli LB Media (μM) | MIC E. coli delta-TolC LB Media (μM) | MIC A. baumannii LB Media (μM) | WT H37Rv MTB Activity (μM) |
|---|---|---|---|---|---|
| B398 | | >150 | 91 | >150 | 150 |
| B399 | | 150 | 20 | >150 | >150 |
| B400 | | >150 | 55 | >150 | >150 |
| B401 | | >150 | 33 | >150 | >150 |
| B402 | | 150 | 33 | >150 | >150 |
| B403 | | >150 | 7 | >150 | >150 |

TABLE 3-continued
Antimicrobial Activity
| FRS-ID | | MIC WT E. coli LB Media (μM) | MIC E. coli delta-TolC LB Media (μM) | MIC A. baumannii LB Media (μM) | WT H37Rv MTB Activity (μM) |
|---|---|---|---|---|---|
| B404 | 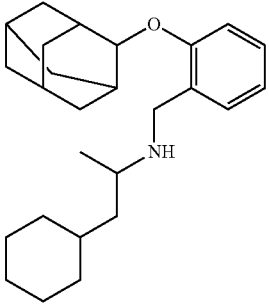 [SMILES: CC(CC1CCCCC1)NCc1ccccc1OC1C2CC3CC(C2)CC1C3] | >150 | 7 | 150 | 20.2 |
| B405 | 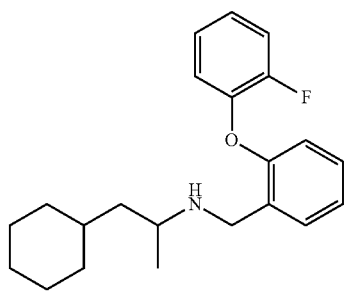 [SMILES: CC(CC1CCCCC1)NCc1ccccc1Oc1ccccc1F] | 91 | 5 | 150 | 33.4 |
| B406 | 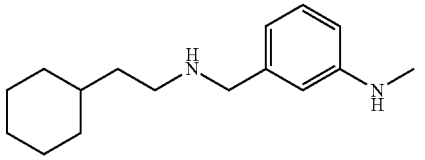 [SMILES: CNc1cccc(CNCCC2CCCCC2)c1] | >150 | >150 | >150 | 150 |
| B407 | 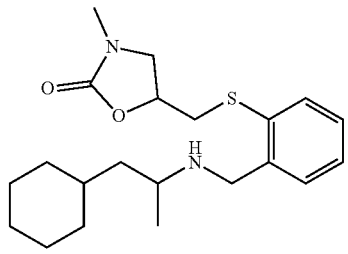 [SMILES: CC(CC1CCCCC1)NCc1ccccc1SCC1CN(C)C(=O)O1] | 150 | 7 | >150 | >150 |
| B408 | 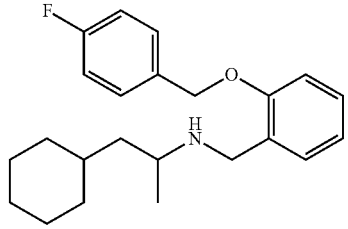 [SMILES: CC(CC1CCCCC1)NCc1ccccc1OCc1ccc(F)cc1] | 55 | 2 | 55 | 12.2 |

TABLE 3-continued
| | | Antimicrobial Activity | | | |
|---|---|---|---|---|---|
| FRS-ID | | MIC WT E. coli LB Media (μM) | MIC E. coli delta-TolC LB Media (μM) | MIC A. baumannii LB Media (μM) | WT H37Rv MTB Activity (μM) |
| B409 | 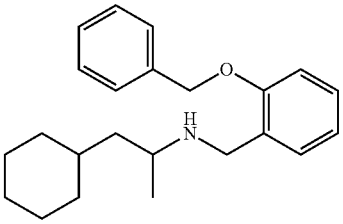 [SMILES: CC(CC1CCCCC1)NCc1ccccc1OCc1ccccc1] | 55 | 3 | 55 | 12.2 |
| B410 | 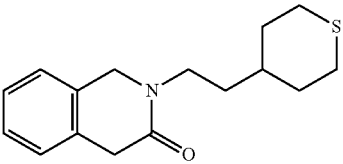 [SMILES: O=C1Cc2ccccc2CN1CCC1CCSCC1] | >150 | >150 | >150 | >150 |
| B411 | 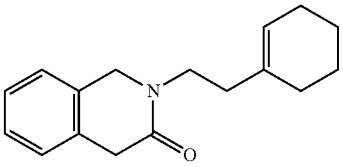 [SMILES: O=C1Cc2ccccc2CN1CCC1=CCCCC1] | >150 | 150 | >150 | 7.4 |
| B412 | 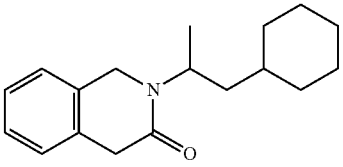 [SMILES: CC(CC1CCCCC1)N1Cc2ccccc2CC1=O] | >150 | 55 | >150 | 7.4 |
| B413 | 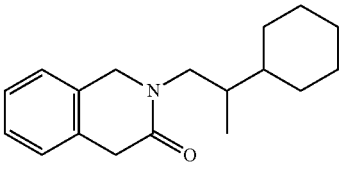 [SMILES: CC(CN1Cc2ccccc2CC1=O)C1CCCCC1] | >150 | 55 | >150 | 7.4 |
| B414 | 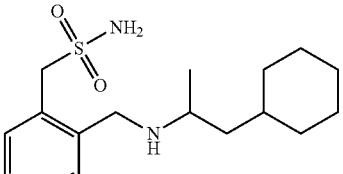 | 20 | 4 | 150 | >150 |
| B415 | 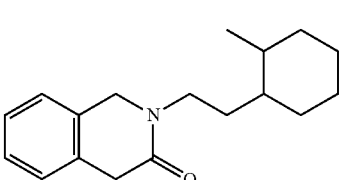 | >150 | 55 | >150 | 1.257 |
| B416 | 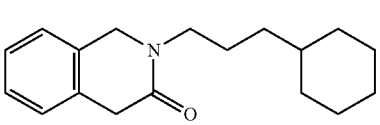 [SMILES: O=C1Cc2ccccc2CN1CCCC1CCCCC1] | >150 | 55 | >150 | 2.5 |

TABLE 3-continued
Antimicrobial Activity
| FRS-ID | | MIC WT E. coli LB Media (µM) | MIC E. coli delta-TolC LB Media (µM) | MIC A. baumannii LB Media (µM) | WT H37Rv MTB Activity (µM) |
|---|---|---|---|---|---|
| B417 | 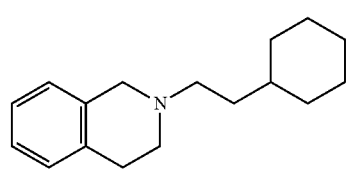 [SMILES: c1ccc2c(c1)CCN(CCC1CCCCC1)C2] | >150 | >150 | >150 | >150 |
| B418 | 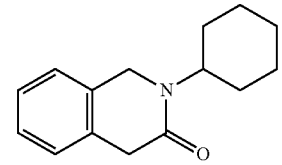 [SMILES: O=C1Cc2ccccc2CN1C1CCCCC1] | >150 | >150 | >150 | >150 |
| B419 | 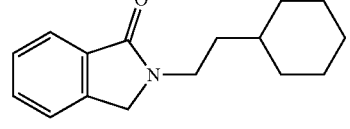 | >150 | 150 | >150 | 0.6 |
| B420 | 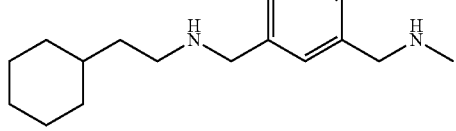 | >150 | >150 | >150 | >150 |
| B421 | 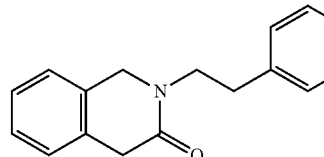 | >150 | >150 | >150 | 55.1 |
| B422 | 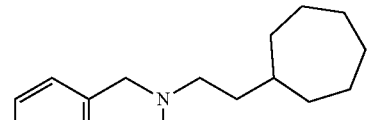 | >150 | 150 | >150 | 2.5 |
| B423 |  | >150 | 55 | >150 | 150 |

TABLE 3-continued

Antimicrobial Activity

| FRS-ID | Structure | MIC WT *E. coli* LB Media (µM) | MIC *E. coli* delta-TolC LB Media (µM) | MIC *A. baumannii* LB Media (µM) | WT H37Rv MTB Activity (µM) |
|---|---|---|---|---|---|
| B424 | | 33 | 3 | 150 | >150 |
| B425 | | >150 | 33 | >150 | >150 |
| B426 | | >150 | 55 | >150 | 1.7 |
| B427 | | >150 | >150 | >150 | 2.7 |
| B428 | | >150 | 55 | >150 | >150 |
| B429 | | 55 | 2 | 33 | 20.2 |

TABLE 3-continued

Antimicrobial Activity

| FRS-ID | MIC WT E. coli LB Media (μM) | MIC E. coli delta-TolC LB Media (μM) | MIC A. baumannii LB Media (μM) | WT H37Rv MTB Activity (μM) |
|---|---|---|---|---|
| B430 | >150 | >150 | >150 | 55.1 |
| B431 | 150 | 4 | >150 | >150 |
| B432 | 150 | 33 | >150 | >150 |
| B433 | 150 | 3 | 150 | >150 |
| B434 | 150 | 4 | 150 | >150 |

TABLE 3-continued
| | Antimicrobial Activity | | | |
|---|---|---|---|---|
| FRS-ID | MIC WT *E. coli* LB Media (μM) | MIC WT *E. coli* delta-TolC LB Media (μM) | MIC *A. baumannii* LB Media (μM) | WT H37Rv MTB Activity (μM) |
| B435 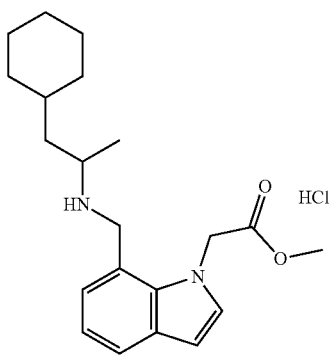 [SMILES: COC(=O)Cn1ccc2cccc(CNC(C)CC3CCCCC3)c21 ; Cl] | >150 | 150 | >150 | >150 |
| B436 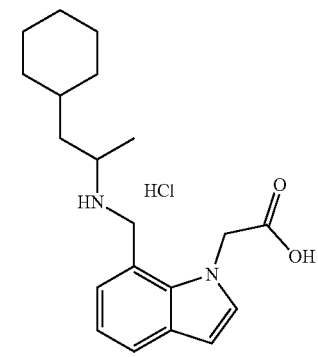 [SMILES: CC(CC1CCCCC1)NCc1cccc2ccn(CC(=O)O)c12 ; Cl] | >150 | 91 | >150 | >150 |
| B437 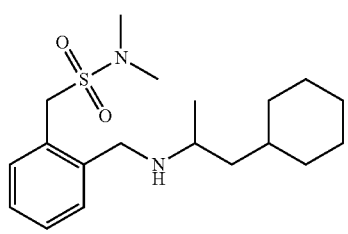 [SMILES: CC(CC1CCCCC1)NCc1ccccc1CS(=O)(=O)N(C)C] | 150 | 4 | >150 | >150 |
| B438 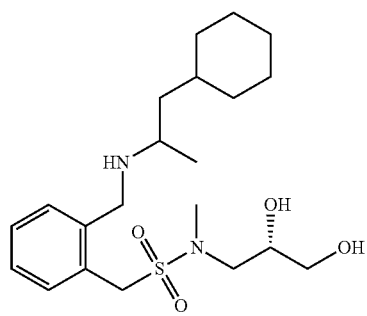 [SMILES: CC(CC1CCCCC1)NCc1ccccc1CS(=O)(=O)N(C)C[C@H](O)CO] | 150 | 7 | >150 | >150 |

TABLE 3-continued

| | Antimicrobial Activity | | | |
|---|---|---|---|---|
| FRS-ID | MIC WT E. coli LB Media (µM) | MIC E. coli delta-TolC LB Media (µM) | MIC A. baumannii LB Media (µM) | WT H37Rv MTB Activity (µM) |
| B439 | 91 | 12 | 150 | >150 |
| B440 | >150 | >150 | >150 | 150 |
| B441 | >150 | 91 | >150 | 33.4 |
| B442 | >150 | 150 | >150 | 150 |
| B445 | 55 | 4 | 150 | >150 |

TABLE 3-continued

| | Antimicrobial Activity | | | |
|---|---|---|---|---|
| FRS-ID | MIC WT *E. coli* LB Media (μM) | MIC *E. coli* delta-TolC LB Media (μM) | MIC *A. baumannii* LB Media (μM) | WT H37Rv MTB Activity (μM) |
| B446 | 91 | 7 | >150 | >150 |
| B448 | >150 | >150 | >150 | >150 |
| B449 | >150 | 12 | >150 | >150 |
| B450 | >150 | 150 | >150 | 150 |

TABLE 3-continued

| | Antimicrobial Activity | | | |
|---|---|---|---|---|
| FRS-ID | MIC WT *E. coli* LB Media (μM) | MIC WT *E. coli* delta-TolC LB Media (μM) | MIC *A. baumannii* LB Media (μM) | WT H37Rv MTB Activity (μM) |
| B451 | 55 | 4 | 150 | >150 |
| B452 | >150 | >150 | >150 | >150 |
| B453 | >150 | 20 | >150 | >150 |
| B454 | >150 | 91 | >150 | >150 |

TABLE 3-continued

| | Antimicrobial Activity | | | |
|---|---|---|---|---|
| FRS-ID | MIC WT *E. coli* LB Media (μM) | MIC *E. coli* delta-TolC LB Media (μM) | MIC *A. baumannii* LB Media (μM) | WT H37Rv MTB Activity (μM) |
| B455 | >150 | 91 | >150 | >150 |
| B456 | >150 | 33 | >150 | >150 |
| B457 | 33 | <1 | 33 | >55 |
| B458 | >150 | 4 | 20 | 10 |

TABLE 3-continued

Antimicrobial Activity

| FRS-ID | Structure | MIC WT *E. coli* LB Media (μM) | MIC *E. coli* delta-TolC LB Media (μM) | MIC *A. baumannii* LB Media (μM) | WT H37Rv MTB Activity (μM) |
|---|---|---|---|---|---|
| B459 | | 55 | 2 | 91 | 17 |
| B460 | | 33 | <1 | 33 | 10 |
| B461 | | 33 | <1 | 33 | 10 |
| B462 | | >150 | 4 | 33 | 10 |
| B463 | | >150 | 4 | >150 | 17 |

TABLE 3-continued

Antimicrobial Activity

| FRS-ID | Structure | MIC WT E. coli LB Media (μM) | MIC E. coli delta-TolC LB Media (μM) | MIC A. baumannii LB Media (μM) | WT H37Rv MTB Activity (μM) |
|---|---|---|---|---|---|
| B464 | | >150 | 90 | >150 | 2 |
| B465 | | >150 | 7 | 90 | 20 |
| B466 | | >150 | >150 | >150 | >55 |
| B467 | | ND | ND | ND | ND |
| B468 | | ND | ND | ND | ND |
| B469 | | ND | ND | ND | ND |

TABLE 3-continued

Antimicrobial Activity

| FRS-ID | | MIC WT E. coli LB Media (µM) | MIC E. coli delta-TolC LB Media (µM) | MIC A. baumannii LB Media (µM) | WT H37Rv MTB Activity (µM) |
|---|---|---|---|---|---|
| B470 | | ND | ND | ND | ND |
| B471 | | ND | ND | ND | ND |
| B472 | | ND | ND | ND | ND |
| B473 | | ND | ND | ND | ND |
| B474 | | ND | ND | ND | ND |

TABLE 3-continued

| | Antimicrobial Activity | | | |
|---|---|---|---|---|
| FRS-ID | MIC WT E. coli LB Media (µM) | MIC E. coli delta-TolC LB Media (µM) | MIC A. baumannii LB Media (µM) | WT H37Rv MTB Activity (µM) |
| B475 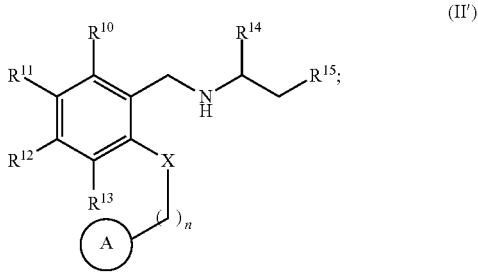 | ND | ND | ND | ND |

ND = not determined

Example 17: Combination Therapies

A serious problem for antibacterial use of tRNA synthetase inhibitors as antibiotics is high frequency of resistance. Recently, Anacor's Anti-LeuS AN3365 failed in clinical trials due to a high frequency of resistance. The problem of resistance may be overcome by employing a combination of molecules targeting different tRNA synthetases in order to decrease the frequency of resistance down to the product of two independent resistance frequencies. *E. coli* did not develop resistance to a combination of anti-LeuS Tavaborole with our dialkylamine B1 in multiple independent experiments, as shown in FIG. 1. Experimental details: Cultures of *E. coli* K-12 were started from single colonies on LB-agar plates and were grown in LB for 36 hours with shaking at 37° C. Following that, $10^8$ cells were plated on LB-agar plates containing B1 or Tavaborole alone or in combination adjusted for dose equivalence and incubated at 37° C. for 24 hours.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A compound having the structure of formula (II'):

(II')

[structure with $R^{10}$, $R^{11}$, $R^{12}$, $R^{13}$, $R^{14}$, $R^{15}$, X, NH, and ring A with $()_n$]

or a pharmaceutically acceptable salt thereof;
wherein:
X is O or S;
each of $R^{10}$, $R^{11}$, $R^{12}$, and $R^{13}$ is independently selected from H, OH, —NH$_2$, halide, sulfonamido, ($C_1$-$C_6$)alkylsulfonyl, —OC(O)(($C_1$-$C_8$)alkyl), —C(O)O(($C_1$-$C_8$)alkyl), —C(O)OH, optionally substituted —NHC(O)(aryl), —C(O)NH$_2$, —B(OH)$_2$, tri(($C_1$-$C_8$)alkyl)silyl, optionally substituted ($C_1$-$C_8$)alkyl, optionally substituted ($C_1$-$C_8$)alkoxy, optionally substituted ($C_1$-$C_8$)aminoalkyl, optionally substituted ($C_1$-$C_8$)hydroxyalkyl, optionally substituted ($C_1$-$C_8$)haloalkyl, optionally substituted ($C_1$-$C_8$)haloalkoxy, optionally substituted aryl, optionally substituted heteroaryl, optionally substituted aryloxy, optionally substituted arylalkoxy, optionally substituted heteroaryloxy, optionally substituted heteroarylalkoxy, optionally substituted ($C_3$-$C_{10}$)cycloalkyl, optionally substituted ($C_3$-$C_{10}$)cycloalkoxy, optionally substituted ($C_2$-$C_9$)heterocycloalkyl, optionally substituted ($C_2$-$C_9$)heterocycloalkoxy, (H$_3$CSO$_2$)($C_1$-$C_8$)alkylene, (H$_2$NSO$_2$)($C_1$-$C_8$)alkylene, optionally substituted di(($C_1$-$C_8$)alkyl)amino;

or $R^{10}$ and $R^{11}$, $R^{11}$ and $R^{12}$, or $R^{12}$ and $R^{13}$, taken together with the intervening atoms, form an aryl, heteroaryl, cycloalkyl, or heterocycloalkyl group;

$R^{14}$ is H or ($C_1$-$C_6$)alkyl;

$R^{15}$ is optionally substituted ($C_3$-$C_{10}$)cycloalkyl or ($C_3$-$C_{10}$)cycloalkenyl;

(A)

represents a heterocyclic group substituted by oxo (=O) and optionally substituted by one or more additional substituents; and n is an integer from 1-3.

2. The compound of claim 1, wherein $R^{15}$ is optionally substituted cyclohexyl or cyclohexenyl.

3. The compound of claim 1, wherein (A)

represents a heterocyclic group substituted by oxo (=O) and optionally substituted by one or more additional substituents; and wherein the heterocyclic group substituted by oxo (=O) and optionally substituted by one or more additional substituents is optionally substituted oxazolidinone.
4. The compound of claim 1, or a pharmaceutically acceptable salt thereof, selected from the following table:
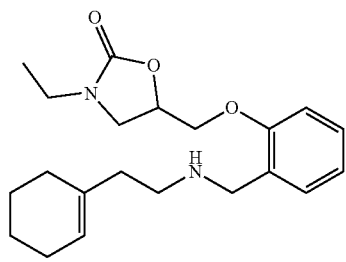 [SMILES: CCN1CC(COc2ccccc2CNCCC2=CCCCC2)OC1=O]
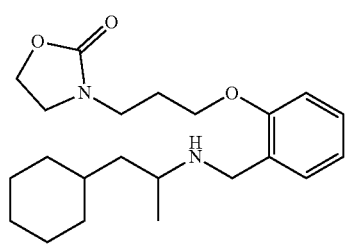 [SMILES: CC(CC1CCCCC1)NCc1ccccc1OCCCN1CCOC1=O]
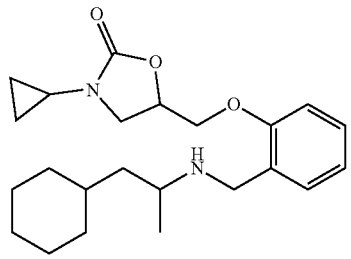 [SMILES: CC(CC1CCCCC1)NCc1ccccc1OCC1CN(C2CC2)C(=O)O1]
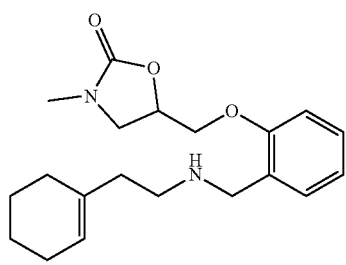 [SMILES: CN1CC(COc2ccccc2CNCCC2=CCCCC2)OC1=O]
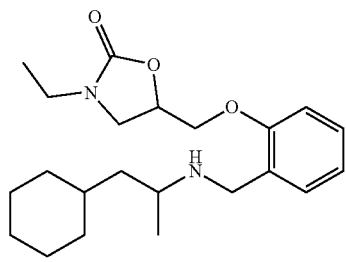 [SMILES: CCN1CC(COc2ccccc2CNC(C)CC2CCCCC2)OC1=O]
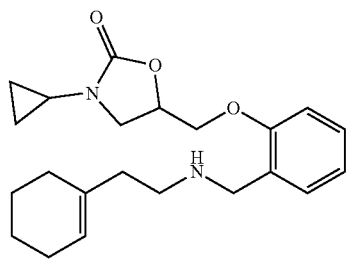 [SMILES: O=C1OC(COc2ccccc2CNCCC2=CCCCC2)CN1C1CC1]
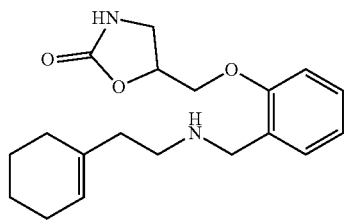 [SMILES: O=C1NCC(COc2ccccc2CNCCC2=CCCCC2)O1]
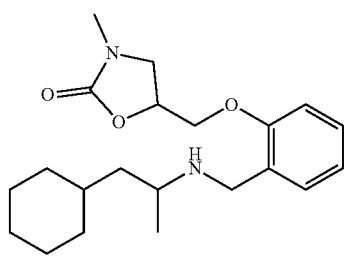 [SMILES: CC(CC1CCCCC1)NCc1ccccc1OCC1CN(C)C(=O)O1]
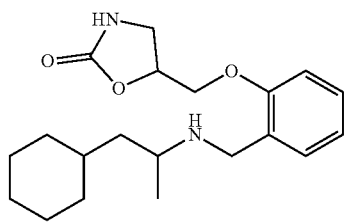 [SMILES: CC(CC1CCCCC1)NCc1ccccc1OCC1CNC(=O)O1]
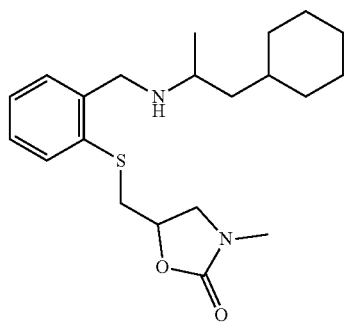 [SMILES: CC(CC1CCCCC1)NCc1ccccc1SCC1CN(C)C(=O)O1]
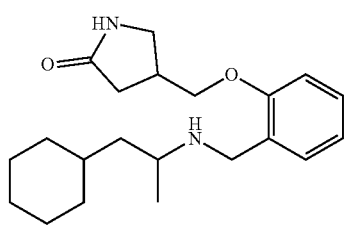

-continued

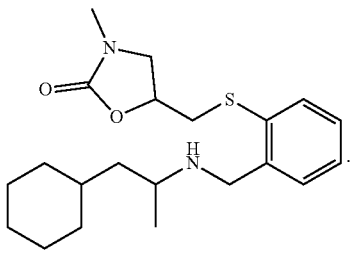 [SMILES: CC(CC1CCCCC1)NCc1ccccc1SCC1CN(C)C(=O)O1]

5. A compound having the structure of formula (III'):

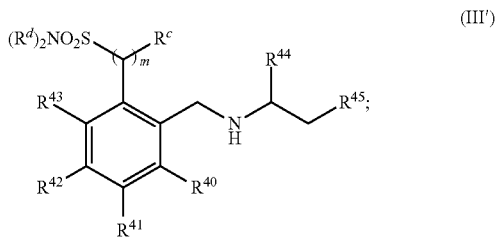

or a pharmaceutically acceptable salt thereof;
wherein:
each of $R^{40}$, $R^{41}$, $R^{42}$, and $R^{43}$ is independently selected from H, OH, —$NH_2$, halide, sulfonamido, ($C_1$-$C_6$) alkylsulfonyl, —OC(O)(($C_1$-$C_8$)alkyl), —C(O)O(($C_1$-$C_8$)alkyl), —C(O)OH, optionally substituted —NHC(O)(aryl), —C(O)$NH_2$, —B(OH)$_2$, tri(($C_1$-$C_8$)alkyl)silyl, optionally substituted ($C_1$-$C_8$)alkyl, optionally substituted ($C_1$-$C_8$)alkoxy, optionally substituted ($C_1$-$C_8$)aminoalkyl, optionally substituted ($C_1$-$C_8$)hydroxyalkyl, optionally substituted ($C_1$-$C_8$)haloalkyl, optionally substituted ($C_1$-$C_8$)haloalkoxy, optionally substituted aryl, optionally substituted heteroaryl, optionally substituted aryloxy, optionally substituted arylalkoxy, optionally substituted heteroaryloxy, optionally substituted heteroarylalkoxy, optionally substituted ($C_3$-$C_{10}$)cycloalkyl, optionally substituted ($C_3$-$C_{10}$)cycloalkoxy, optionally substituted ($C_2$-$C_9$)heterocycloalkyl, optionally substituted ($C_2$-$C_9$)heterocycloalkoxy, ($H_3CSO_2$)($C_1$-$C_8$)alkylene, ($H_2NSO_2$)($C_1$-$C_8$)alkylene, optionally substituted di(($C_1$-$C_8$)alkyl)amino;
or $R^{40}$ and $R^{41}$, $R^{41}$ and $R^{42}$, or $R^{42}$ and $R^{43}$, taken together with the intervening atoms, form an aryl, heteroaryl, cycloalkyl, or heterocycloalkyl group;
$R^{44}$ is H or ($C_1$-$C_6$)alkyl;
$R^{45}$ is optionally substituted ($C_3$-$C_{10}$)cycloalkyl or ($C_3$-$C_{10}$)cycloalkenyl;
$R^c$, independently for each occurrence, is selected from H, ($C_1$-$C_8$)alkyl, ($C_1$-$C_8$)haloalkyl, ($C_1$-$C_8$)alkoxyl, ($C_1$-$C_8$)hydroxyalkyl, ($C_3$-$C_{10}$)cycloalkyl, ($C_3$-$C_{10}$)cycloalkyl($C_1$-$C_8$)alkyl, aryl, and aryl($C_1$-$C_8$) alkyl;
$R^d$, independently for each occurrence, is selected from H, optionally substituted —C(O)($C_1$-$C_8$)alkyl, optionally substituted —C(O)NH—($C_3$-$C_{10}$)cycloalkyl, optionally substituted ($C_1$-$C_8$)alkyl, optionally substituted ($C_1$-$C_8$)haloalkyl, optionally substituted ($C_1$-$C_8$)hydroxyalkyl, optionally substituted ($C_3$-$C_{10}$)cycloalkyl, optionally substituted heterocyclyl, optionally substituted ($C_3$-$C_{10}$)cycloalkyl($C_1$-$C_8$)alkyl, optionally substituted aryl, and optionally substituted aryl($C_1$-$C_8$)alkyl, or two $R^d$ are taken together with the nitrogen atom to which they are attached to form an optionally substituted 5-6-membered heterocyclyl; and m is an integer from 1-3.

6. The compound of claim 5 wherein at least three of $R^{40}$, $R^{41}$, $R^{42}$, and $R^{43}$ are H.

7. The compound of claim 5, wherein $R^{40}$, $R^{41}$, $R^{42}$, and $R^{43}$ are each H.

8. The compound of claim 5, wherein $R^{44}$ is H.

9. The compound of claim 5, wherein $R^{44}$ is ($C_1$-$C_6$)alkyl.

10. The compound of claim 5, wherein $R^{45}$ is optionally substituted cyclohexyl or cyclohexenyl.

11. The compound of claim 5, wherein $R^{45}$ is optionally substituted cyclohexyl.

12. The compound of claim 5, wherein $R^c$ is H.

13. The compound of claim 5, wherein $R^d$, independently for each occurrence, is selected from H and ($C_1$-$C_8$)alkyl.

14. The compound of claim 5, wherein each occurrence of $R^d$ is H.

15. The compound of claim 5, wherein each occurrence of $R^d$ is methyl, or one $R^d$ is methyl or ethyl, and the other $R^d$ is H.

16. The compound of claim 7, wherein one $R^d$ is selected from one of (a)-(d):
(a) optionally substituted —C(O)alkyl;
(b) optionally substituted —C(O)NH—($C_3$-$C_{10}$)cycloalkyl;
(c) optionally substituted ($C_1$-$C_8$)alkyl; or
(d) optionally substituted cycloalkyl, optionally substituted aryl, or optionally substituted heterocyclyl.

17. The compound of claim 16, wherein one $R^d$ is —C(O)CH($NH_2$)$CH_2$CHMe$_2$.

18. The compound of claim 16, wherein one $R^d$ is —C(O)NH— cyclohexyl, optionally substituted with methyl.

19. The compound of claim 16, wherein one $R^d$ is selected from —$CH_2$CH(OH)$CH_2$OH, —$CH_2$C(O)NHCH$_2$COOH, —$CH_2$C(O)NHCH$_2$COOH, —$CH_2CH_2$OMe, —$CH_2$COOH, —CH(Me)COOH, and —$CH_2$-furanyl.

20. The compound of claim 16, wherein one $R^d$ is selected from 3-COOHcyclobutyl, 3-(B(OH)$_3$))-phenyl, and N-methylpiperidinyl.

21. The compound of claim 5, wherein both $R^d$ are taken together with the nitrogen atom to which they are attached to form an N-methylpiperizinyl.

22. The compound of claim 5, or a pharmaceutically acceptable salt thereof, selected from the following table:

| 417 | | 418 |
|---|---|---|
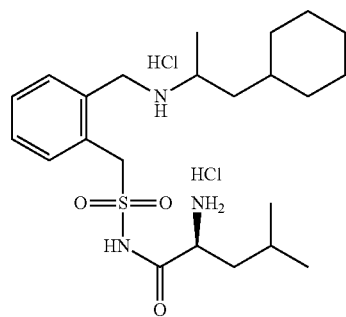 [SMILES: CC(C)C[C@H](N)C(=O)NS(=O)(=O)Cc1ccccc1CNC(C)CC1CCCCC1 ; Cl ; Cl]
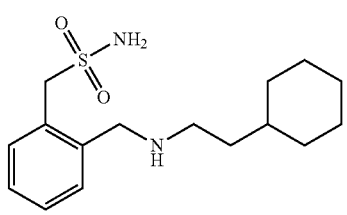
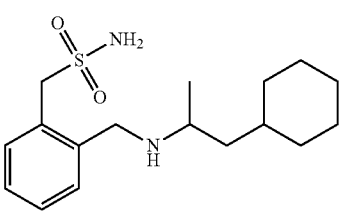 [SMILES: CC(CC1CCCCC1)NCc1ccccc1CS(N)(=O)=O]
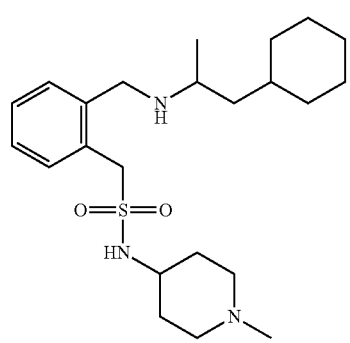 [SMILES: CC(CC1CCCCC1)NCc1ccccc1CS(=O)(=O)NC1CCN(C)CC1]
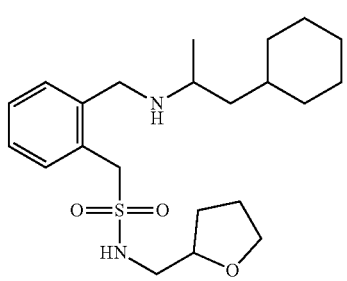 [SMILES: CC(CC1CCCCC1)NCc1ccccc1CS(=O)(=O)NCC1CCCO1]
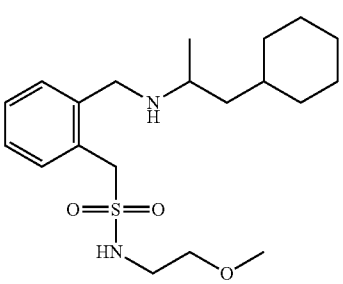 [SMILES: COCCNS(=O)(=O)Cc1ccccc1CNC(C)CC1CCCCC1]
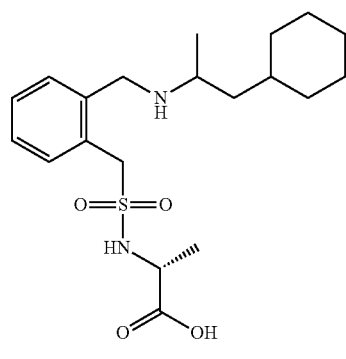 [SMILES: CC(CC1CCCCC1)NCc1ccccc1CS(=O)(=O)N[C@H](C)C(=O)O]
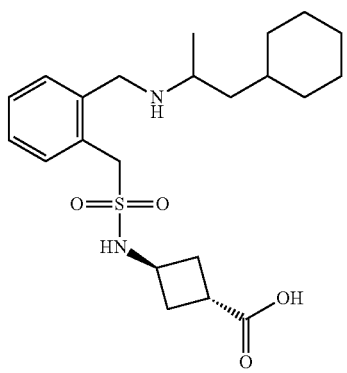 [SMILES: CC(CC1CCCCC1)NCc1ccccc1CS(=O)(=O)N[C@H]1C[C@H](C(=O)O)C1]
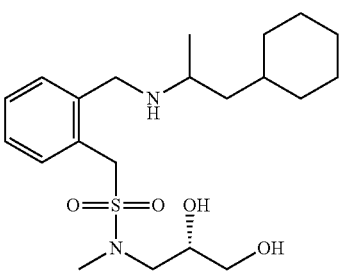 [SMILES: CC(CC1CCCCC1)NCc1ccccc1CS(=O)(=O)N(C)C[C@H](O)CO]
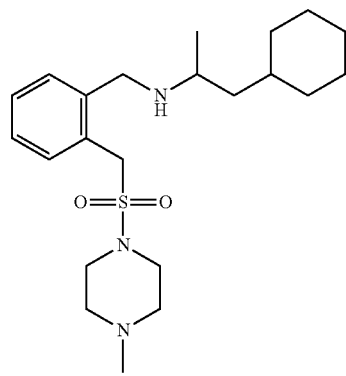 [SMILES: CC(CC1CCCCC1)NCc1ccccc1CS(=O)(=O)N1CCN(C)CC1]
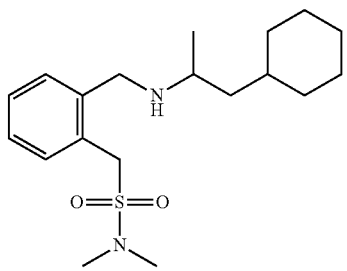 [SMILES: CC(CC1CCCCC1)NCc1ccccc1CS(=O)(=O)N(C)C]
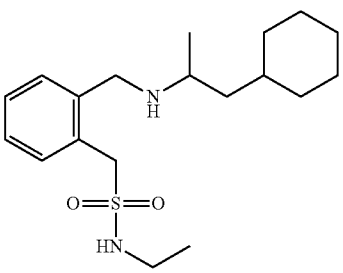 [SMILES: CCNS(=O)(=O)Cc1ccccc1CNC(C)CC1CCCCC1]

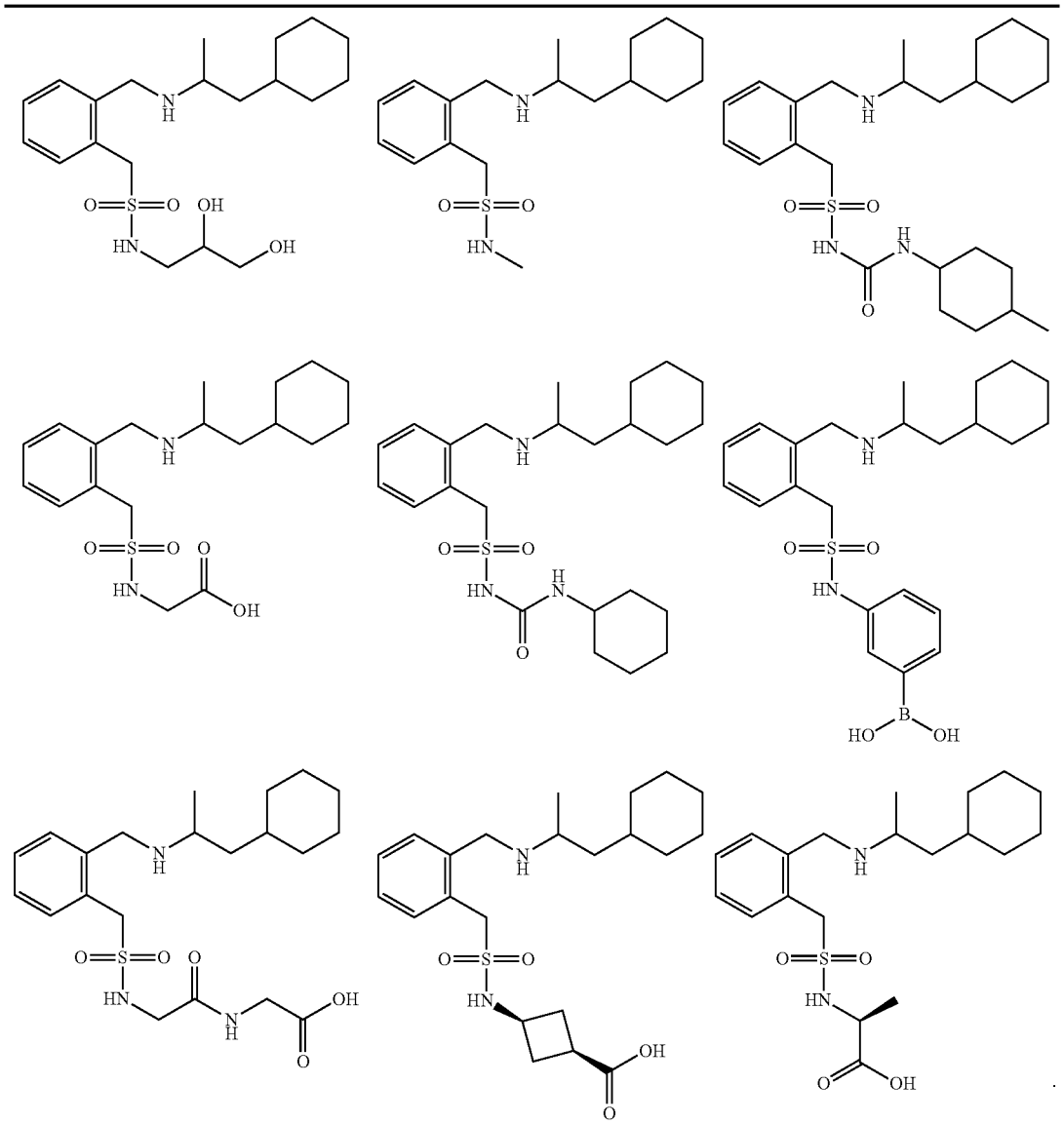

23. A pharmaceutical composition comprising a compound of claim 7, in combination with a pharmaceutically acceptable carrier.

24. A method of treating a bacterial infection in a subject, comprising administering to the subject a therapeutically effective amount of a compound of claim 7.

25. The method of claim 2, wherein the bacterial infection is caused by Gram-negative bacteria.

26. The method of claim 25, wherein the Gram-negative bacteria is selected from the group consisting of *Acidaminococcus* spp., *Acinetobacter* spp., *Aggregatibacter* spp., *Agrobacterium tumefaciens*, *Anaerobiospirillum* aka *Anaerobiospirillum thomasii*, *Arcobacter* spp., *Bacteroides* spp., *Bartonella* spp., *Bordetella* spp., *Borrelia* spp., *Brachyspira* spp., *Bradyrhizobium* spp., *Burkholderia* spp., *Campylobacter* spp., *Cardiobacterium* spp., *Christensenella* spp., *Citrobacter* spp., *Coxiella burnetii*, *Cytophaga* spp., *Dialister* spp., *Eikenella corrodens*, *Enterobacter* spp., *Escherichia* spp., *Ewingella americana*, *Flavobacterium* spp., *Francisella* spp., *Fusobacterium* spp., *Haemophilus* spp., *Helicobacter* spp., *Kingella* spp., *Klebsiella* spp., *Kluyvera* spp., *Legionella* spp., *Leptonema illini*, *Leptotrichia* spp., *Methylobacterium* spp., *Moraxella* spp., *Morganella morganii*, *Mycoplasma* spp., *Neisseria* spp., *Proteus* spp., *Pseudomonas* spp., *Pseudoxanthomonas* spp., *Rickettsia* spp., *Rouxiella chamberiensis*, *Salmonella* spp., *Serratia* spp., *Shigella* spp., *Solobacterium moorei*, *Sphingomonas* spp., *Spirochaeta* spp., *Stenotrophomonas* spp., *Treponema* spp., *Vibrio* spp., *Wolbachia* spp., and *Yersinia* spp.

27. A method of treating tuberculosis, comprising administering to a subject in need thereof a therapeutically effective amount of a compound of claim 5.

* * * * *

UNITED STATES PATENT AND TRADEMARK OFFICE
CERTIFICATE OF CORRECTION

PATENT NO. : 11,261,201 B2
APPLICATION NO. : 16/961516
DATED : March 1, 2022
INVENTOR(S) : Daniel E. Kahne et al.

It is certified that error appears in the above-identified patent and that said Letters Patent is hereby corrected as shown below:

In the Specification

Column 1, Lines 16-19, following "GOVERNMENT SUPPORT":
"This invention was made with government support under U19 AI109764 from the National Institute of Allergy and Infectious Disease. The government has certain rights in the invention."

Should read:
-- This invention was made with government support under AI057159 and AI109764 awarded by National Institutes of Health (NIH). The government has certain rights in this invention. --

Signed and Sealed this
Twenty-fifth Day of October, 2022

*Katherine Kelly Vidal*

Katherine Kelly Vidal
*Director of the United States Patent and Trademark Office*